(12) United States Patent
Dorrell et al.

(10) Patent No.: US 12,064,477 B2
(45) Date of Patent: Aug. 20, 2024

(54) HPV VACCINE

(71) Applicant: Oxford University Innovation Limited, Oxford (GB)

(72) Inventors: Lucy Dorrell, Oxford (GB); Joshua Blight, Oxford (GB); Arturo Reyes-Sandoval, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 17/532,177

(22) Filed: Nov. 22, 2021

(65) Prior Publication Data

US 2022/0152189 A1 May 19, 2022

Related U.S. Application Data

(63) Continuation of application No. 16/639,144, filed as application No. PCT/GB2018/052335 on Aug. 16, 2018, now Pat. No. 11,179,456.

(30) Foreign Application Priority Data

Aug. 16, 2017 (GB) ...................... 1713163

(51) Int. Cl.
*A61K 39/12* (2006.01)
*A61K 39/39* (2006.01)
*C07K 14/005* (2006.01)
*C12N 7/00* (2006.01)

(52) U.S. Cl.
CPC .............. *A61K 39/12* (2013.01); *A61K 39/39* (2013.01); *C07K 14/005* (2013.01); *C12N 7/00* (2013.01); *C07K 2319/00* (2013.01); *C12N 2710/20022* (2013.01); *C12N 2710/20034* (2013.01)

(58) Field of Classification Search
None
See application file for complete search history.

(56) References Cited

U.S. PATENT DOCUMENTS

2007/0014810 A1* 1/2007 Baker .................. C07K 14/005
435/235.1
2020/0306358 A1 10/2020 Dorrell et al.

FOREIGN PATENT DOCUMENTS

| JP | 2004-512814 A | 4/2004 |
| JP | 2011-512486 A | 4/2011 |
| WO | 2005/089164 A2 | 9/2005 |
| WO | 2009/059325 A2 | 5/2009 |
| WO | 2010/123561 A1 | 10/2010 |
| WO | 2014/103608 A1 | 7/2014 |
| WO | 2014/165291 A1 | 10/2014 |
| WO | 2018/060288 A1 | 4/2018 |

OTHER PUBLICATIONS

Gan et al. Fusion of CTLA-4 with HPV16 E7 and E6 Enhanced the Potency of Therapeutic HPV DNA Vaccine. PLoS One, 2014, 9(9): e108892.*
GenBank: K02718.1 Human papillomavirus type 16 (HPV16), complete genome. Dated Mar. 18, 1994.*
Qian et al. Immunology Letters 102 (2006) 191-201.*
International Search Report and Written Opinion for PCT/GB2018/052335, dated Nov. 26, 2018, pp. 1-14.
UK Search Report for GB 1713163.2, dated May 14, 2018, pp. 1-4.
Brazilian J. Biol., vol. 73, 2013, Gabriel, J. E. et al., "Revealing highly conserved regions in the E6 protein among distinct human papillomavirus types using comparative analysis of multiple sequence alignments", pp. 4549-450, May 31, 2013.
Krishna P. Singh et al: "Sequence-based approach for rapid identification of cross-clade CD8+ T-cell vaccine candidates from all high-risk HPV strains", 3 BIOTECH, vol. 6, No. 1, Jan. 27, 2016 (Jan. 27, 2016).
Yan J et al: "Induction of antitumor immunity in vivo following delivery of a novel HPV-16 DNA vaccine encoding an E6/E7 fusion antigen", Vaccine, Elsevier, Amsterdam, NL, vol. 27, No. 3, Jan. 14, 2009 (Jan. 14, 2009), pp. 431-440.
Chen et al. Fusion protein linkers: Property, design and functionality. Advanced Drug Delivery Reviews 65 (2013) 1357-1369.
Qian et al. Prophylactic, therapeutic and anti-metastatic effects of an HPV-16 mE6/mE7/TBhsp70 fusion protein vaccine in an animal model. Immunology Letters 102 (2006) 191-201.
Gan et al. usion ofCTLA-4with HPV16 E7 and E6 Enhanced the PotencyofTherapeutic HPV DNA Vaccine. PLoS One, 2014, 9(9 ): e108892.
Japanese Office Action for Patent Application No. 2020-508007, dated Sep. 28, 2022, pp. 1-8 (Translation Included).
Japanese Office Action for Patent Application No. 2020-508007, dated May 10, 2023, pp. 1-8 (Translation Included).

* cited by examiner

*Primary Examiner* — Nianxiang Zou
(74) *Attorney, Agent, or Firm* — Thomas|Horstemeyer, LLP

(57) ABSTRACT

The invention relates to a nucleic acid encoding a polypeptide comprising a plurality of conserved peptide sequences, or variants thereof, wherein the conserved sequences are conserved across one or more HPV genotypes 16, 18, 31, 52, 53, and 58; and wherein the polypeptide comprises a conserved peptide sequence of each of the HPV proteins E1, E2, E4, E5, E6, and E7; and associated vaccines, viral vectors, treatment and prophylaxis.

Figure 1:
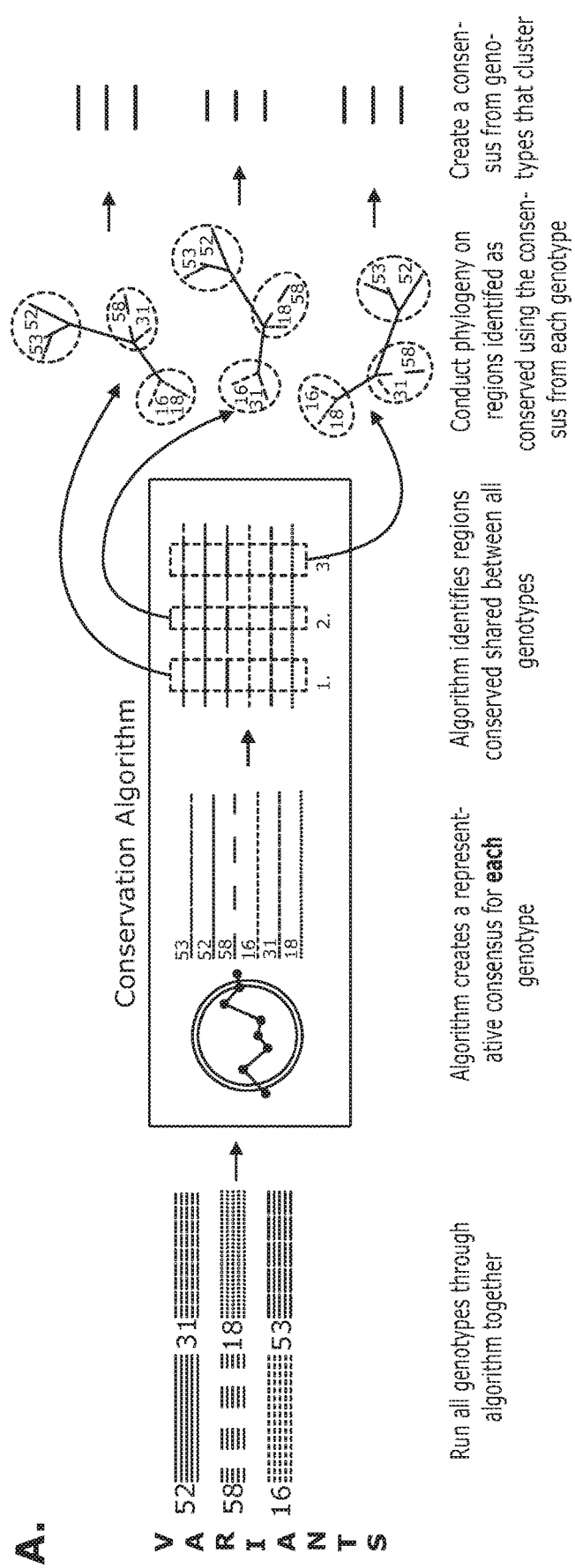
Figure 1:
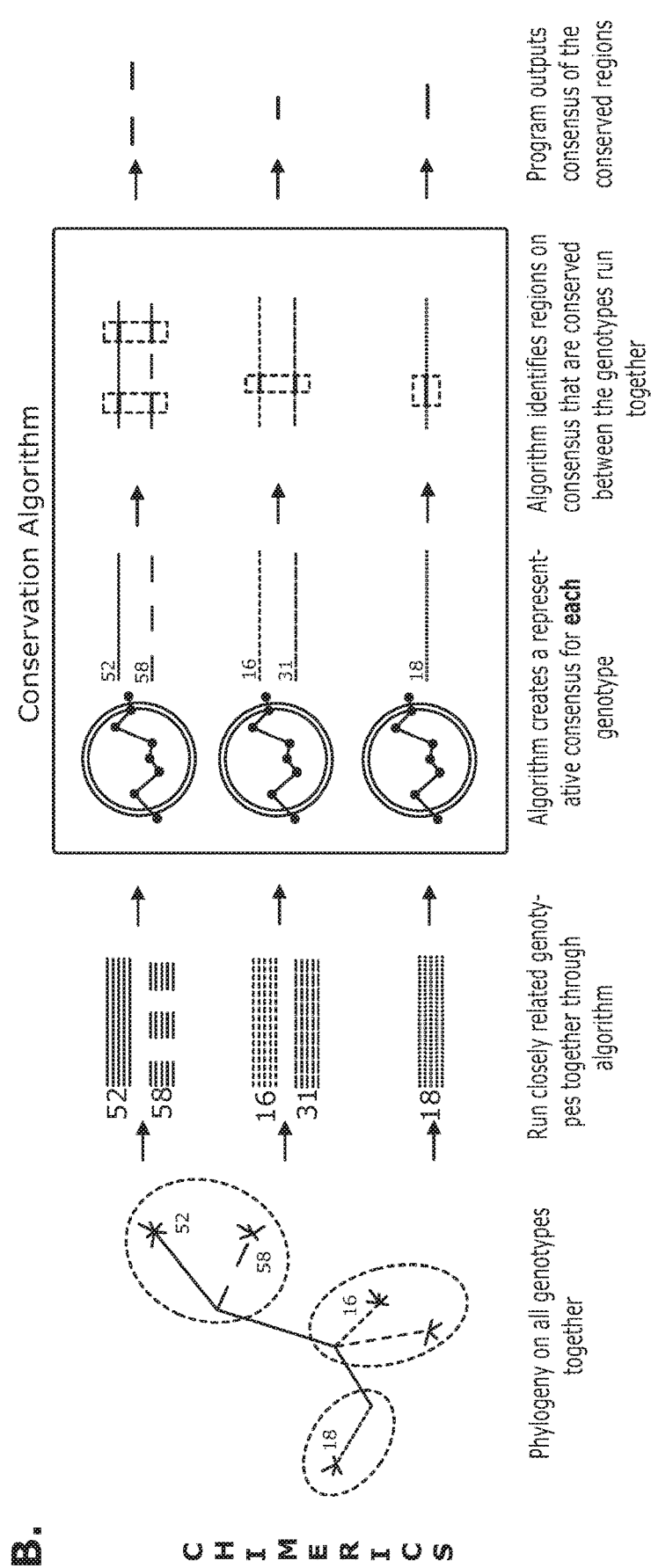

11 Claims, 23 Drawing Sheets
Specification includes a Sequence Listing.

HPV VACCINE

CROSS-REFERENCE TO RELATED APPLICATIONS

This application is a continuation of U.S. patent application Ser. No. 16/639,144, filed Feb. 14, 2020, now U.S. Pat. No. 11,179,456, issued Nov. 23, 2021, which is the National Stage of International Application No. PCT/GB2018/052335, filed Aug. 16, 2018, which claims priority to GB 1713163.2, filed Aug. 16, 2017, which are all entirely incorporated herein by reference.

SEQUENCE LISTING

This application contains a sequence listing filed in electronic form as an 15 ASCII.txt file entitled "820926_1180 Sequence Listing_ST25.txt", created on Feb. 22, 2021 and having a size of 489 kb. The content of the sequence listing is incorporated herein in its entirety.

This invention relates to viral-vectored vaccines for use in a vaccination against HPV infection.

Human papillomavirus infection is an infection by human papillomavirus (HPV). Most HPV infections cause no symptoms and resolve spontaneously. However, in some cases they persist and this can result in the development of warts or precancerous lesions. The precancerous lesions increase the risk of cancer of the cervix, vulva, vagina, penis, anus, mouth, or throat.

There are approximately 0.5 million cases of HPV-attributable cervical cancer that occur annually worldwide, and over half of these are fatal. About 85% of cases occur in low/middle income countries where there is limited or no treatment available. Women who have not received a prophylactic vaccine require 3-yearly screening to identify and treat cervical intra-epithelial neoplasia (CIN). Screening costs the UK National Health Service approximately £175 million annually.

Current therapy for CIN is ablation of abnormal cervical tissue by electrocautery or surgery. There is no current therapy available that eliminates HPV viral infection. Women require multiple follow-up visits after treatment to ensure that there is no recurrence. Therapy is also associated with increased risk of pre-term birth.

HPV vaccines that have been developed for therapy of existing HPV infection include Inovio—VGX-3100 (DNA encoding E6, E7) similarly Genexine (GX-188E); Janssen—Ad26/Ad35+/−MVA encoding E2, E6, E7 fusion protein; Synthetic long peptides (E6, E7) and similar eg. PepCan, GTL001; Advaxis—ADXS-HPV; and *L. monocytogenes* encoding E7. However, such developed vaccines have been targeted to HPV16 and 18 only, have safety concerns, and/or are low efficiency. For example, the net efficacy of VGX-3100 was 18% in a phase IIb randomised controlled trial (48% in vaccine arm vs. 30% in placebo arm).

What is needed is a vaccine that is safe, easy to deliver and to have greater efficacy than the therapeutic vaccine candidates tested to date. Therefore, an aim of the present invention is to provide an improved vaccine for HPV infection.

According to a first aspect of the invention, there is provided a nucleic acid encoding a polypeptide comprising a plurality of conserved peptide sequences, or variants thereof,
    wherein the conserved sequences are conserved across one or more HPV genotypes 16, 18, 31, 52, 53, and 58; and
    wherein the polypeptide comprises a conserved peptide sequence of each of the HPV proteins E1, E2, E4, E5, E6, and E7.

The invention advantageously provides a novel alternative and safer approach to vaccination whereby T cells can be induced to the relatively conserved antigens of the virion. The use of specially designed conserved viral segments from the non-structural proteins can provide protection against multiple important genotypes.

In one embodiment, the polypeptide is a fusion polypeptide. The polypeptide may not be a wild-type polypeptide. The polypeptide may be synthetic/artificial, for example, the polypeptide may not exist in nature. In one embodiment, the polypeptide may not comprise a complete gene sequence. The polypeptide may consist essentially of conserved peptide sequences. In another embodiment, the polypeptide may consist essentially of conserved peptide sequences and a peptide adjuvant sequence. In another embodiment, the polypeptide may consist essentially of conserved peptide sequences and one or more linkers therebetween. In another embodiment, the polypeptide may consist essentially of conserved peptide sequences, a peptide adjuvant sequence and one or more linkers therebetween. In one embodiment, the polypeptide is a recombinant polypeptide, such as a recombinant fusion polypeptide.

The term "fusion polypeptide" used herein is understood to mean a polypeptide comprising a combination of sequences derived from different gene products (for example different HPV proteins) or combinations of sequences from the same gene product (for example a single HPV protein), wherein the sequences are from distinct/separate regions of the wild-type gene product. For example the fusion polypeptide may comprise combinations of sequences which are normally separated by other sequence segments in wild-type, and the separating sequence(s) have been removed.

The term "conserved peptide sequence" or "conserved segment" used herein is defined as a sequence that is conserved in one or more genotypes, as defined below. Prior to assessment of conservation all available full-length sequences for HPV proteins E1, E2, E4, E5, E6 and E7 from genotypes 16, 18, 31, 52, 53 and 58 were collected from the NCBI Protein database (accessed 2014) and used as input for the approach of the invention. All available sequences were used to ensure the selected conserved peptide sequences would equally represent the whole environmental population (See Table 1). Conserved peptide sequences were identified using the 'variant' approach (FIG. 1A); all genotypes were aligned and sequences within each genotype weighted prior to conservation assessment to ensure equal representation of genotype diversity and thus ensure the vaccine candidates were representative of the whole environmental population. Conservation within genotypes (intra-genotype conservation) was then assessed using a 15 amino acid sliding window, whereby for each window a conservation value was determined based on combining the amino acid prevalence within the window and weighting value of each sequence to identify fragments conserved within each genotype, and a normalised intra-genotype consensus created for each window. 'Normalised consensus' meaning an amino acid sequence that represented the weighted set of genotype sequence, not the most common amino acid at each position. To be classed as conserved the window must have a conservation value within the first quartile of all window conservation values for the protein. Subsequently, conserved intra-genotype windows at the same position across all genotypes were identified independent of the percentage identity of shared intra-genotype normalised consensus between genotypes (inter-genotype conservation). A phylogeny was then created of the resultant regions and tree ingroup sequences combined to create an inter-genotype consensus with a high level of shared consensus identity. In this case 'inter-genotype consensus' refers to a consensus created using the normalised consensus created from each genotype. In some scenarios, a 'modified variant' was created where conserved intra-genotype windows at the same position across all proteins were identified which shared greater than 60% shared intra-genotype normalised consensus percentage identity between genotypes.

If the identified inter-serotype fragments from tree ingroups had a percentage identity less than 60%, the sequences were classed as "highly divergent", in contrast to "less divergent" sequences used in the variant approach. For proteins highly divergent between genotypes a 'chimeric' approach was used to identify conserved peptide sequences (FIG. 1B); a phylogeny was created and only genotype ingroups were aligned together and intra-genotype conserved assessed. Therefore, inter-genotype conservation was only assessed between ingroups and intra-serotype conserved windows with greater than 60% shared consensus identity across genotypes selected. In some cases genotypes were run as 'chimerics' but inter-genotype conservation was not assessed ('chimeric-variants').

The plurality of conserved peptide sequences may comprise 10 or more conserved peptide sequences. In another embodiment, the plurality of conserved peptide sequences may comprise 15 or more conserved peptide sequences. In another embodiment, the plurality of conserved peptide sequences may comprise 20 or more conserved peptide sequences. In another embodiment, the plurality of conserved peptide sequences may comprise 25 or more conserved peptide sequences. In another embodiment, the plurality of conserved peptide sequences may comprise 30 or more conserved peptide sequences. The plurality of conserved sequences may comprise 35 or more conserved peptide sequences. In another embodiment, the plurality of conserved peptide sequences may comprise 40 or more conserved peptide sequences. The plurality of conserved peptide sequences may comprise 45 or more conserved peptide sequences. In another embodiment, the plurality of conserved peptide sequences may comprise 50 or more conserved peptide sequences. In another embodiment, the plurality of conserved peptide sequences may comprise 55 or more conserved peptide sequences. In one embodiment, the plurality of conserved peptide sequences consists of about 56 or more conserved peptide sequences. In one embodiment, the plurality of conserved peptide sequences consists of about 57 or more conserved peptide sequences. In one embodiment, the plurality of conserved peptide sequences consists of about 58 or more conserved peptide sequences. In one embodiment, the plurality of conserved peptide sequences consists of about 59 or more conserved peptide sequences. In one embodiment, the plurality of conserved peptide sequences consists of about 59 conserved peptide sequences.

The encoded polypeptide may comprise at least 3 different conserved peptide sequences of each of the HPV proteins E1, E2, E4, E5, E6, and E7. The encoded polypeptide may comprise at least 3 different conserved peptide sequences of HPV protein E1. The encoded polypeptide may comprise at least 3 different conserved peptide sequences of HPV protein E2. The encoded polypeptide may comprise at least 3 different conserved peptide sequences of HPV protein E4. The encoded polypeptide may comprise at least 3 different conserved peptide sequences of HPV protein E5. The encoded polypeptide may comprise at least 3 different conserved peptide sequences of HPV protein E6. The encoded polypeptide may comprise at least 3 different conserved peptide sequences of HPV protein E7.

The encoded polypeptide may comprise at least 4 different conserved peptide sequences of HPV protein E1. The encoded polypeptide may comprise at least 4 different conserved peptide sequences of HPV protein E2. The encoded polypeptide may comprise at least 4 different conserved peptide sequences of HPV protein E4. The encoded polypeptide may comprise at least 4 different conserved peptide sequences of HPV protein E6. The encoded polypeptide may comprise at least 4 different conserved peptide sequences of HPV protein E7.

The encoded polypeptide may comprise at least 5 different conserved peptide sequences of HPV protein E1. The encoded polypeptide may comprise at least 5 different conserved peptide sequences of HPV protein E2. The encoded polypeptide may comprise at least 5 different conserved peptide sequences of HPV protein E4. The encoded polypeptide may comprise at least 5 different conserved peptide sequences of HPV protein E6.

The encoded polypeptide may comprise at least 6 different conserved peptide sequences of HPV protein E1. The encoded polypeptide may comprise at least 6 different conserved peptide sequences of HPV protein E2. The encoded polypeptide may comprise at least 6 different conserved peptide sequences of HPV protein E4. The encoded polypeptide may comprise at least 6 different conserved peptide sequences of HPV protein E6.

The encoded polypeptide may comprise at least 7 different conserved peptide sequences of HPV protein E1. The encoded polypeptide may comprise at least 7 different conserved peptide sequences of HPV protein E2. The encoded polypeptide may comprise at least 7 different conserved peptide sequences of HPV protein E4. The encoded polypeptide may comprise at least 7 different conserved peptide sequences of HPV protein E6.

The encoded polypeptide may comprise at least 8 different conserved peptide sequences of HPV protein E1. The encoded polypeptide may comprise at least 8 different conserved peptide sequences of HPV protein E2. The encoded polypeptide may comprise at least 8 different conserved peptide sequences of HPV protein E4. The encoded polypeptide may comprise at least 8 different conserved peptide sequences of HPV protein E6.

The encoded polypeptide may comprise at least 9 different conserved peptide sequences of HPV protein E1. The encoded polypeptide may comprise at least 9 different conserved peptide sequences of HPV protein E2. The encoded polypeptide may comprise at least 9 different conserved peptide sequences of HPV protein E4.

The encoded polypeptide may comprise at least 10 different conserved peptide sequences of HPV protein E1. The encoded polypeptide may comprise at least 10 different conserved peptide sequences of HPV protein E2.

The encoded polypeptide may comprise at least 11 different conserved peptide sequences of HPV protein E1. The encoded polypeptide may comprise at least 11 different conserved peptide sequences of HPV protein E2.

The encoded polypeptide may comprise at least 12, 13, 14, 15, 16, 17, 18, 19, 20, 21, 22, 23, or 24 different conserved peptide sequences of HPV protein E2.

The encoded polypeptide may comprise or consist of 11 or more different conserved peptide sequences of HPV protein E1, 24 or more different conserved peptide sequences of HPV protein E2, 9 or more different conserved peptide sequences of HPV protein E4, 3 or more different conserved peptide sequences of HPV protein E5, 8 or more different conserved peptide sequences of HPV protein E6, and 4 or more different conserved peptide sequences of HPV protein E7.

The plurality of conserved peptide sequences may be derived from distinct regions of sequence relative to each other (i.e. not-naturally concurrent). For example, reference to "different conserved peptide sequences" may comprise sequences that are derived from distinct regions of wild-type sequence relative to each other (i.e. not-naturally concurrent). For example, in the wild-type genotype the conserved sequences may be separated in the wild-type genotypes by variable/non-conserved sequences. The plurality of conserved peptide sequences may not, or may not significantly, overlap with each other. Two or more, or all, of the plurality of conserved peptide sequences may be directly joined together in the polypeptide, for example not comprising any non-conserved/variable residues therebetween. The polypeptide sequence may not be found in nature. The polypeptide may not comprise non-conserved sequences or residues. The conserved peptide sequences may not be distanced apart by more than 1, 2, 3, 4, or 5 residues in the polypeptide sequence, for example in embodiments where there are linker/junction residues between the conserved peptide sequences. Alternatively, the conserved peptide sequences may not be distanced apart by more than 6, 7, 8, 9, or 10 residues in the polypeptide sequence, for example in embodiments where there are linker/junction residues between the conserved peptide sequences. The polypeptide may not comprise non-conserved sequences longer than 2, 3, 4, 5, 6, 7, 8, 9, or 10 amino acids.

In one embodiment, linker residues may be provided between one or more, or all, conserved peptide sequences (e.g. providing junctions between the conserved peptide sequences in the polypeptide). The linker residues may comprise random amino acid sequences, or amino acids that have been selected to be non-immunogenic based on epitope prediction computer programs or experiments in animal models. For example, a linker may not be considered if it is predicted or known to be an epitope (i.e. in order to avoid an immune response to epitopes, e.g. artificial epitopes, not found in HPV. The linker may be flexible. The linker may comprise or consist of K, G, P, A or S amino acid residues, or combinations thereof. In one embodiment, the linker may comprise or consist of G and/or P amino acid residues. In one embodiment, the linker may comprise or consist of one or more alanine (A) amino acid residues. The linker residues may be between 1 and 10 amino acids in length. In another embodiment, the linker residues may be between 2 and 8 residues in length. In another embodiment, the linker residues may be between 1 and 6 residues in length. The conserved peptide sequences may be distanced apart by between 1 and 10 residues in the polypeptide sequence, for example in embodiments where there are linker/junction residues between the conserved peptide sequences.

In one embodiment, the polypeptide may consist essentially of conserved peptide sequences and one or more linkers, optionally wherein the one or more linkers are disposed between adjacent conserved peptide sequence.

The conserved peptide sequences may be selected from any of the group comprising SEQ ID NOs: 1 to 59; variants thereof or combinations thereof. In another embodiment, the conserved peptide sequences may be selected from any of the group comprising SEQ ID NOs: 1 to 59; variants thereof or combinations thereof, in any order. In one embodiment, the conserved peptide sequences may consist of the group comprising SEQ ID NOs: 1 to 59.

The polypeptide may comprise one or more conserved E1 sequence(s) selected from any one of SEQ ID NOs: 1-11; one or more conserved E2 sequence(s) selected from any one of SEQ ID NOs: 12-35; one or more conserved E4 sequence(s) selected from any one of SEQ ID NOs: 36-44; one or more conserved E5 sequence(s) selected from any one of SEQ ID NOs: 45-47; one or more conserved E6 sequence(s) selected from any one of SEQ ID NOs: 48-55; and one or more conserved E7 sequence(s) selected from any one of SEQ ID NOs: 56-59.

The polypeptide may comprise two or more conserved E1 sequence(s) selected from any of SEQ ID NOs: 1-11; two or more conserved E2 sequence(s) selected from any of SEQ ID NOs: 12-35; two or more conserved E4 sequence(s) selected from any of SEQ ID NOs: 36-44; two or more conserved E5 sequence(s) selected from any of SEQ ID NOs: 45-47; two or more conserved E6 sequence(s) selected from any of SEQ ID NOs: 48-55; and two or more conserved E7 sequence(s) selected from any of SEQ ID NOs: 56-59.

The polypeptide may comprise three or more conserved E1 sequence(s) selected from any of SEQ ID NOs: 1-11; three or more conserved E2 sequence(s) selected from any of SEQ ID NOs: 12-35; three or more conserved E4 sequence(s) selected from any of SEQ ID NOs: 36-44; three or more conserved E5 sequence(s) selected from any of SEQ ID NOs: 45-47; three or more conserved E6 sequence(s) selected from any of SEQ ID NOs: 48-55; and three or more conserved E7 sequence(s) selected from any of SEQ ID NOs: 56-59.

The conserved sequences are conserved across one or more of HPV genotypes 16, 18, 31, 52, and 58. The conserved sequences are conserved across all of HPV genotypes 16, 18, 31, 52, and 58.

The polypeptide may comprise:
one or more conserved E1 sequence(s) selected from any one of SEQ ID NOs: 1-11, wherein each of the genotypes 16, 18, 31, 52, 53, and 58 are represented by at least one conserved E1 sequence;
one or more conserved E2 sequence(s) selected from any one of SEQ ID NOs: 12-35, wherein each of the genotypes 16, 18, 31, 52, 53, and 58 are represented by at least one conserved E2 sequence;
one or more conserved E4 sequence(s) selected from any one of SEQ ID NOs: 36-44, wherein each of the genotypes 16, 18, 31, 52, 53, and 58 are represented by at least one conserved E4 sequence;
one or more conserved E5 sequence(s) selected from any one of SEQ ID NOs: 45-47, wherein each of the genotypes 16, 18, 31, 52, 53, and 58 are represented by at least one conserved E5 sequence;
one or more conserved E6 sequence(s) selected from any one of SEQ ID NOs: 48-55, wherein each of the genotypes 16, 18, 31, 52, 53, and 58 are represented by at least one conserved E6 sequence; and
one or more conserved E7 sequence(s) selected from any one of SEQ ID NOs: 56-59, wherein each of the genotypes 16, 18, 31, 52, 53, and 58 are represented by at least one conserved E7 sequence.

The polypeptide may comprise:
one or more conserved E1 sequence(s) selected from any one of SEQ ID NOs: 1-11, wherein each of the genotypes 16, 18, 31, 52, and 58 are represented by at least one conserved E1 sequence;
one or more conserved E2 sequence(s) selected from any one of SEQ ID NOs: 12-35, wherein each of the genotypes 16, 18, 31, 52, and 58 are represented by at least one conserved E2 sequence;
one or more conserved E4 sequence(s) selected from any one of SEQ ID NOs: 36-44, wherein each of the genotypes 16, 18, 31, 52, and 58 are represented by at least one conserved E4 sequence;
one or more conserved E5 sequence(s) selected from any one of SEQ ID NOs: 45-47, wherein each of the genotypes 16, 18, 31, 52, and 58 are represented by at least one conserved E5 sequence;
one or more conserved E6 sequence(s) selected from any one of SEQ ID NOs: 48-55, wherein each of the genotypes 16, 18, 31, 52, and 58 are represented by at least one conserved E6 sequence; and
one or more conserved E7 sequence(s) selected from any one of SEQ ID NOs: 56-59, wherein each of the genotypes 16, 18, 31, 52, and 58 are represented by at least one conserved E7 sequence.

The polypeptide may comprise:
two or more conserved E1 sequence(s) selected from any of SEQ ID NOs: 1-11, wherein each of the genotypes 16, 18, 31, 52, 53, and 58 are represented in the group of conserved E1 sequences;
two or more conserved E2 sequence(s) selected from any of SEQ ID NOs: 12-35, wherein each of the genotypes 16, 18, 31, 52, 53, and 58 are represented in the group of conserved E2 sequences;
two or more conserved E4 sequence(s) selected from any of SEQ ID NOs: 36-44, wherein each of the genotypes 16, 18, 31, 52, 53, and 58 are represented in the group of conserved E4 sequences;
two or more conserved E5 sequence(s) selected from any of SEQ ID NOs: 45-47, wherein each of the genotypes 16, 18, 31, 52, 53, and 58 are represented in the group of conserved E5 sequences;
two or more conserved E6 sequence(s) selected from any of SEQ ID NOs: 48-55, wherein each of the genotypes 16, 18, 31, 52, 53, and 58 are represented in the group of conserved E6 sequences; and
two or more conserved E7 sequence(s) selected from any of SEQ ID NOs: 56-59, wherein each of the genotypes 16, 18, 31, 52, 53, and 58 are represented in the group of conserved E7 sequences.

The polypeptide may comprise:
two or more conserved E1 sequence(s) selected from any of SEQ ID NOs: 1-11, wherein each of the genotypes 16, 18, 31, 52, and 58 are represented in the group of conserved E1 sequences;
two or more conserved E2 sequence(s) selected from any of SEQ ID NOs: 12-35, wherein each of the genotypes 16, 18, 31, 52, and 58 are represented in the group of conserved E2 sequences;
two or more conserved E4 sequence(s) selected from any of SEQ ID NOs: 36-44, wherein each of the genotypes 16, 18, 31, 52, and 58 are represented in the group of conserved E4 sequences;
two or more conserved E5 sequence(s) selected from any of SEQ ID NOs: 45-47, wherein each of the genotypes 16, 18, 31, 52, and 58 are represented in the group of conserved E5 sequences;
two or more conserved E6 sequence(s) selected from any of SEQ ID NOs: 48-55, wherein each of the genotypes 16, 18, 31, 52, and 58 are represented in the group of conserved E6 sequences; and
two or more conserved E7 sequence(s) selected from any of SEQ ID NOs: 56-59, wherein each of the genotypes 16, 18, 31, 52, and 58 are represented in the group of conserved E7 sequences.

The polypeptide may comprise:
three or more conserved E1 sequence(s) selected from any of SEQ ID NOs: 1-11, wherein each of the genotypes 16, 18, 31, 52, 53, and 58 are represented in the group of conserved E1 sequences;
three or more conserved E2 sequence(s) selected from any of SEQ ID NOs: 12-35, wherein each of the genotypes 16, 18, 31, 52, 53, and 58 are represented in the group of conserved E2 sequences;
three or more conserved E4 sequence(s) selected from any of SEQ ID NOs: 36-44, wherein each of the genotypes 16, 18, 31, 52, 53, and 58 are represented in the group of conserved E4 sequences;
three conserved E5 sequence(s) selected from SEQ ID NOs: 45-47, wherein each of the genotypes 16, 18, 31, 52, 53, and 58 are represented in the group of conserved E5 sequences;
three or more conserved E6 sequence(s) selected from any of SEQ ID NOs: 48-55, wherein each of the genotypes 16, 18, 31, 52, 53, and 58 are represented in the group of conserved E6 sequences; and
three or more conserved E7 sequence(s) selected from any of SEQ ID NOs: 56-59, wherein each of the genotypes 16, 18, 31, 52, 53, and 58 are represented in the group of conserved E7 sequences.

The polypeptide may comprise:
three or more conserved E1 sequence(s) selected from any of SEQ ID NOs: 1-11, wherein each of the genotypes 16, 18, 31, 52, and 58 are represented in the group of conserved E1 sequences;
three or more conserved E2 sequence(s) selected from any of SEQ ID NOs: 12-35, wherein each of the genotypes 16, 18, 31, 52, and 58 are represented in the group of conserved E2 sequences;
three or more conserved E4 sequence(s) selected from any of SEQ ID NOs: 36-44, wherein each of the genotypes 16, 18, 31, 52, and 58 are represented in the group of conserved E4 sequences;
three conserved E5 sequence(s) selected from SEQ ID NOs: 45-47, wherein each of the genotypes 16, 18, 31, 52, and 58 are represented in the group of conserved E5 sequences;
three or more conserved E6 sequence(s) selected from any of SEQ ID NOs: 48-55, wherein each of the genotypes 16, 18, 31, 52, and 58 are represented in the group of conserved E6 sequences; and
three or more conserved E7 sequence(s) selected from any of SEQ ID NOs: 56-59, wherein each of the genotypes 16, 18, 31, 52, and 58 are represented in the group of conserved E7 sequences.

Reference to "each of the genotypes 16, 18, 31, 52, 53, and 58 are represented" or "each of the genotypes 16, 18, 31, 52, and 58 are represented" is intended to mean that each of the identified genotypes has been used to define at least one consensus sequence of a conserved peptide sequence. Therefore, a given group may comprise a conserved peptide from each genotype, or a conserved peptide may be derived from a consensus of two or more genotypes. If sequence identities are sufficiently similar, all the genotypes 16, 18, 31, 52, 53, and 58 or 16, 18, 31, 52, and 58 could be represented by a single conserved peptide sequence, which may be a consensus of all the genotypes 16, 18, 31, 52, 53, and 58 or 16, 18, 31, 52, and 58 respectively. However, due to differences in sequence identities, a single conserved peptide may not be able to represent a consensus sequence from all genotypes 16, 18, 31, 52, 53, and 58 or 16, 18, 31, 52, and 58 and instead two or more conserved peptide sequences are required to cover/represent all the genotypes 16, 18, 31, 52, 53, and 58 or 16, 18, 31, 52, and 58. For example (for illustrative purposes only), one conserved E6 peptide sequence may represent E6 genotypes 16 and 18, another may represent E6 genotype 52, and a third may represent E6 genotypes 53 and 58, such that all three conserved E6 peptide sequences in a group represent all E6 genotypes 16, 18, 31, 52, 53, and 58 or 16, 18, 31, 52, and 58.

The nucleic acid may comprise or consist of the sequence of SEQ ID NO: 60, or variants thereof. In another embodiment, the nucleic acid may comprise or consist of the sequence of SEQ ID NO: 60, or variants thereof, and without encoding the TPA lead sequence. In another embodiment, the nucleic acid may comprise or consist of the sequence of SEQ ID NO: 60, or variants thereof, with a different/alternative peptide adjuvant encoded than the TPA lead sequence. In another embodiment, the nucleic acid may comprise or consist of the sequence of SEQ ID NO: 65, or variants thereof.

Variants of the nucleic acid may comprise or consist of a sequence having at least 80% identity with SEQ ID NO: 60 or 65. Alternatively, variants of the nucleic acid may comprise or consist of a sequence having at least 85% identity with SEQ ID NO: 60 or 65. Variants of the nucleic acid may comprise or consist of a sequence having at least 90% identity with SEQ ID NO: 60 or 65. Variants of the nucleic acid may comprise or consist of a sequence having at least 95% identity with SEQ ID NO: 60 or 65. Variants of the nucleic acid may comprise or consist of a sequence having at least 98% identity with SEQ ID NO: 60 or 65. Variants of the nucleic acid may comprise or consist of a sequence having at least 99% identity with SEQ ID NO: 60 or 65. The skilled person will understand that a variant of the nucleic acid may include redundant codon variants that encode the same peptide as SEQ ID NO: 60 or 65.

The nucleic acid may comprise or consist of the sequence of SEQ ID NO: 62, or variants thereof. In another embodiment, the nucleic acid may comprise or consist of the sequence of SEQ ID NO: 62, or variants thereof, and without encoding the TPA lead sequence. In another embodiment, the nucleic acid may comprise or consist of the sequence of SEQ ID NO: 62, or variants thereof, with a different/alternative peptide adjuvant encoded than the TPA lead sequence.

Variants of the nucleic acid may comprise or consist of a sequence having at least 80% identity with SEQ ID NO: 62. Alternatively, variants of the nucleic acid may comprise or consist of a sequence having at least 85% identity with SEQ ID NO: 62. Variants of the nucleic acid may comprise or consist of a sequence having at least 90% identity with SEQ ID NO: 62. Variants of the nucleic acid may comprise or consist of a sequence having at least 95% identity with SEQ ID NO: 62. Variants of the nucleic acid may comprise or consist of a sequence having at least 98% identity with SEQ ID NO: 62. Variants of the nucleic acid may comprise or consist of a sequence having at least 99% identity with SEQ ID NO: 62. Variants of the nucleic acid may comprise or consist of a sequence having at least 99.5% identity with SEQ ID NO: 62. Variants of the nucleic acid may comprise or consist of a sequence having at least 99.9% identity with SEQ ID NO: 62. The skilled person will understand that a variant of the nucleic acid may include redundant codon variants that encode the same viral vector and/or peptide as SEQ ID NO: 62.

The nucleic acid may comprise or consist of the sequence of SEQ ID NO: 71, 73 or 75, or variants thereof. In another embodiment, the nucleic acid may comprise or consist of the sequence of SEQ ID NO: 71, 73 or 75, or variants thereof, and without encoding the TPA lead sequence. In another embodiment, the nucleic acid may comprise or consist of the sequence of SEQ ID NO: 71, 73 or 75, or variants thereof, with a different/alternative peptide adjuvant encoded than the TPA lead sequence.

Variants of the nucleic acid may comprise or consist of a sequence having at least 80% identity with SEQ ID NO: 71, 73 or 75. Alternatively, variants of the nucleic acid may comprise or consist of a sequence having at least 85% identity with SEQ ID NO: 71, 73 or 75. Variants of the nucleic acid may comprise or consist of a sequence having at least 90% identity with SEQ ID NO: 71, 73 or 75. Variants of the nucleic acid may comprise or consist of a sequence having at least 95% identity with SEQ ID NO: 71, 73 or 75. Variants of the nucleic acid may comprise or consist of a sequence having at least 98% identity with SEQ ID NO: 71, 73 or 75. Variants of the nucleic acid may comprise or consist of a sequence having at least 99% identity with SEQ ID NO: 71, 73 or 75. Variants of the nucleic acid may comprise or consist of a sequence having at least 99.5% identity with SEQ ID NO: 71, 73 or 75. Variants of the nucleic acid may comprise or consist of a sequence having at least 99.9% identity with SEQ ID NO: 71, 73 or 75. The skilled person will understand that a variant of the nucleic acid may include redundant codon variants that encode the same viral vector and/or peptide as SEQ ID NO: 71, 73 or 75.

The polypeptide may comprise or consist of the sequence of SEQ ID NO: 61, or variants thereof. In another embodiment, the polypeptide may comprise or consist of the sequence of SEQ ID NO: 61, or variants thereof, and without the TPA lead sequence. In another embodiment, the polypeptide may comprise or consist of the sequence of SEQ ID NO: 61, or variants thereof, with a different/alternative peptide adjuvant than the TPA lead sequence. In another embodiment, the polypeptide may comprise or consist of the sequence of SEQ ID NO: 66, or variants thereof.

The polypeptide may comprise or consist of the sequence of SEQ ID NO: 72, 74 or 76, or variants thereof. In another embodiment, the polypeptide may comprise or consist of the sequence of SEQ ID NO: 72, 74 or 76, or variants thereof, and without the TPA lead sequence. In another embodiment, the polypeptide may comprise or consist of the sequence of SEQ ID NO: 72, 74 or 76, or variants thereof, with a different/alternative peptide adjuvant than the TPA lead sequence. In another embodiment, the polypeptide may comprise or consist of the sequence of SEQ ID NO: 72, 74 or 76, or variants thereof.

In one embodiment, the polypeptide may consist essentially of conserved peptide sequences and a peptide adjuvant. In one embodiment, the polypeptide may consist essentially of conserved peptide sequences, one or more linkers, and a peptide adjuvant. The one or more linkers may be disposed between adjacent conserved peptide sequence. The peptide adjuvant may be N-terminal.

Variants of the polypeptide may comprise or consist of a sequence having at least 80% identity with SEQ ID NO: 61, 66, 72, 74 or 76. Alternatively, variants of the polypeptide may comprise or consist of a sequence having at least 85% identity with SEQ ID NO: 61, 66, 72, 74 or 76. Variants of the polypeptide may comprise or consist of a sequence having at least 90% identity with SEQ ID NO: 61, 66, 72, 74 or 76. Variants of the polypeptide may comprise or consist of a sequence having at least 95% identity with SEQ ID NO: 61, 66, 72, 74 or 76. Variants of the polypeptide may comprise or consist of a sequence having at least 98% identity with SEQ ID NO: 61, 66, 72, 74 or 76. Variants of the polypeptide may comprise or consist of a sequence having at least 99% identity with SEQ ID NO: 61, 66, 72, 74 or 76.

Variants of conserved peptide sequences may comprise or consist of a truncated sequence of the conserved peptide sequences. For example, any one or more of the sequences of SEQ ID NOs: 1 to 59, herein may be truncated and still provide immunogenicity in the polypeptide. The truncated sequence may comprise a sufficient number of amino acids to form a recognisable epitope (e.g. at least the minimum number of residues for specific T cell recognition) from a sequence within any one of the sequences of SEQ ID NOs: 1 to 59. The truncated sequence may comprise at least 7 amino acids of the sequences of SEQ ID NOs: 1 to 59. Alternatively, the truncated sequence may comprise at least 8 amino acids of the sequences of SEQ ID NOs: 1 to 59. Alternatively, the truncated sequence may comprise at least 9, 10, 11 or 12 amino acids of the sequences of SEQ ID NOs: 1 to 59. Multiple truncated sequences may be provided within one of the conserved peptide sequences of SEQ ID NOs: 1 to 59.

In one embodiment, any one of the conserved peptide sequences of SEQ ID NOs: 1 to 59 may be varied, for example by residue substitution, addition or deletion. In another embodiment, some or all of the conserved peptide sequences of SEQ ID NOs: 1 to 59 may be varied, for example by residue substitution, addition or deletion. The variant conserved peptide sequences may still function to provide recognisable HPV epitopes. The skilled person will understand that natural variation exists in any given population and that these variants may have some sequence variation with the consensus sequence, or example patient sequences provided in SEQ ID NOs: 1 to 59. Therefore, a variant conserved peptide sequence may have at least 70% sequence identity with any one of SEQ ID NOs: 1 to 59. In another embodiment, a variant conserved peptide sequence may have at least 74% sequence identity with any one of SEQ ID NOs: 1 to 59. In another embodiment, a variant conserved peptide sequence may have at least 75% sequence identity with any one of SEQ ID NOs: 1 to 59. In another embodiment, a variant conserved peptide sequence may have at least 79% sequence identity with any one of SEQ ID NOs: 1 to 59. In another embodiment, a variant conserved peptide sequence may have at least 80% sequence identity with any one of SEQ ID NOs: 1 to 59. In another embodiment, a variant conserved peptide sequence may have at least 82% sequence identity with any one of SEQ ID NOs: 1 to 59. In another embodiment, a variant conserved peptide sequence may have at least 83% sequence identity with any one of SEQ ID NOs: 1 to 59. In another embodiment, a variant conserved peptide sequence may have at least 85% sequence identity with any one of SEQ ID NOs: 1 to 59. In another embodiment, a variant conserved peptide sequence may have at least 88% sequence identity with any one of SEQ ID NOs: 1 to 59. In another embodiment, a variant conserved peptide sequence may have at least 90% sequence identity with any one of SEQ ID NOs: 1 to 59. In another embodiment, a variant conserved peptide sequence may have at least 92% sequence identity with any one of SEQ ID NOs: 1 to 59. In another embodiment, a variant conserved peptide sequence may have at least 95% sequence identity with any one of SEQ ID NOs: 1 to 59. In another embodiment, a variant conserved peptide sequence may have at least 98% sequence identity with any one of SEQ ID NOs: 1 to 59. In another embodiment, a variant conserved peptide sequence may have at least 99% sequence identity with any one of SEQ ID NOs: 1 to 59. In another embodiment, a variant conserved peptide sequence may have at least 99.5% sequence identity with any one of SEQ ID NOs: 1 to 59.

Reference to sequence "identity" used herein may refer to the percentage identity between two aligned sequences using standard NCBI BLASTp parameters (http://blast.ncbi.nlm.nih.gov).

The conserved peptide sequences may vary in length, with the minimum length being defined as the minimum number of residues required to form a recognisable epitope. Therefore, the conserved peptide sequence may be from about 7 to 250 amino acids in length, or more. For example, at least one conserved peptide sequence may be at least about 7 amino acids in length. In another embodiment, at least one conserved peptide sequence may be at least about 8 amino acids in length. In another embodiment, at least one conserved peptide sequence may be at least about 10 amino acids in length. In another embodiment, at least one conserved peptide sequence may be at least about 15 amino acids in length. In another embodiment, at least one conserved peptide sequence may be at least about 20 amino acids in length. In another embodiment, at least one conserved peptide sequence may be at least about 30 amino acids in length. In one embodiment, at least one conserved peptide sequence may be between about 20 and about 220 amino acids in length. In one embodiment, at least one conserved peptide sequence may be no more than about 300 amino acids in length. In another embodiment, at least one conserved peptide sequence may be no more than about 250 amino acids in length. In another embodiment, at least one conserved peptide sequence may be no more than about 200 amino acids in length. In another embodiment, at least one conserved peptide sequence may be no more than about 150 amino acids in length. In another embodiment, at least one conserved peptide sequence may be no more than about 100 amino acids in length. In another embodiment, at least one conserved peptide sequence may be no more than about 55 amino acids in length. In another embodiment, at least one conserved peptide sequence may be no more than about 54 amino acids in length.

The conserved peptide sequences may be an average length of between about 15 and about 50 amino acids in a population of conserved peptide sequences.

In some embodiments of the invention, the polypeptide may further comprise a peptide adjuvant, such as a TPA (tissue plasminogen activator) sequence, or functional variants thereof. The TPA may comprise or consist of the sequence: MDAMKRGLCCVLLLCGAVFVSPSQEIHARFRR (SEQ ID NO: 63), or a functional variant thereof. In one embodiment, the peptide adjuvant may comprise a Shark invariant chain, for example of the sequence SLLWGGVTVLAAMLIAGQVASSVVFLV (SEQ ID NO: 64), or a functional variant thereof. The peptide adjuvant may be N-terminal on the polypeptide of the invention. A functional variant of a peptide adjuvant may be a truncated or mutated peptide variant, which can still function as an adjuvant, for example a truncated or mutated variant of the TPA or shark invariant chain, which still function as an adjuvant. The skilled person will appreciate that 1, 2, 3, 4, 5 or more amino acid residues may be substituted, added or removed without affecting function. For example, conservative substitutions may be considered. In embodiments, where a peptide adjuvant is provided (or encoded as appropriate), there may additionally be provided a linker sequence provided (or encoded) between the peptide adjuvant and the first conserved peptide sequence. In embodiments without the peptide adjuvant, the first linker sequence may not be provided.

Combinations of nucleic acids may encode different polypeptides according to the invention may be provided as a vaccine. For example, a prime and/or boost vaccine formulation may comprise nucleic acid or viral vector encoding two or more polypeptides of the invention, which may be different relative to each other.

The nucleic acid may be used in a vaccine in combination with another therapeutically or prophylactically active ingredient. The nucleic acid may be used in a vaccine in combination with an adjuvant.

According to another aspect of the invention there is provided a composition comprising a plurality of different nucleic acids according to the invention, optionally wherein the composition is a pharmaceutically acceptable composition.

According to another aspect of the invention there is provided a polypeptide encoded by the nucleic acid according to the invention herein.

In one embodiment the polypeptide is an isolated polypeptide. The polypeptide, nucleic acid encoding the polypeptide, or associated viral particle may be provided in a pharmaceutically acceptable carrier.

The nucleic acid may be a plasmid vector for vaccination. The nucleic acid may comprise viral vector sequences.

According to another aspect of the invention there is provided a viral vector comprising the nucleic acid according to the invention herein.

The viral vector may comprise a virus. The viral vector may comprise an adenovirus, such as a human or simian adenovirus. The viral vector may comprise an adenovirus when used in a prime vaccine of a prime boost regime. The viral vector may comprise ChAdOx1 (a group E simian adenovirus, like the AdCh63 vector used safely in malaria trials) or ChAdOx2 (as described in Morris et al 2016. Future Virol 11(9), pp. 649-659). The ChAdOx2 sequence may comprise or consist of the sequence described herein (e.g. SEQ ID NOs: 67+68). The viral vector may comprise AdCh63. The viral vector may comprise AdC3 or AdH6. The viral vector may be a human serotype. The viral vector may comprise Modified Vaccinia Ankara (MVA). The viral vector may comprise F11 MVA (e.g. MVA with the nucleic acid construct insert at the F11 locus). The nucleic acid of the invention (the HPV vaccine construct insert) may be inserted at the TK locus of parental MVA virus under the control of the p7.5 promoter, for example through recombination with the p7.5 MVA shuttle plasmid (SEQ ID NO: 158). The nucleic acid may comprise the sequence of SEQ ID NO: 158 with the nucleic acid vaccine construct insert as provided in SEQ ID NO: 158 (underlined), or with an alternative nucleic acid vaccine construct in accordance with the invention herein. In another embodiment, the nucleic acid of the invention (the HPV vaccine construct insert) may be inserted at the F11 locus of parental MVA virus under the control of the F11 promoter, for example through recombination with the F11 shuttle plasmid (SEQ ID NO: 159). The nucleic acid may comprise the sequence of SEQ ID NO: 159 with the nucleic acid vaccine construct insert as provided in SEQ ID NO: 159 (underlined), or with an alternative nucleic acid vaccine construct in accordance with the invention herein. The MVA sequence may comprise or consist of the sequence described herein (e.g. SEQ ID NOs: 69+70). The viral vector may comprise MVA when used as a vaccine boost in a prime boost regime. The viral vector may comprise Adeno-associated virus (AAV) or lentivirus. The viral vector may be an attenuated viral vector. The polypeptide sequence of the invention may be cloned into any suitable viral vector that is known to elicit good immune response. Suitable viral vectors have been described in Dicks et al (Vaccine. 2015 Feb. 25; 33(9):1121-8. doi: 10.1016/j.vaccine.2015.01.042. Epub 2015 Jan. 25), Antrobus et al (Mol Ther. 2014 March; 22(3):668-74. doi: 10.1038/mt.2013.284. Epub 2013 Dec. 30), and (Warimwe et al. (Virol J. 2013 Dec. 5; 10:349. doi: 10.1186/1743-422X-10-349), which are incorporated herein by reference.

According to another aspect of the invention there is provided a composition comprising one or more of:
the polypeptide according to the invention;
the nucleic acid according to the invention; and
the viral vector according to the invention.

The composition may be immunogenic, for example in a mammal, such as a human. The composition may comprise a pharmaceutically acceptable carrier. The composition may be a pharmaceutical composition comprising a pharmaceutically acceptable carrier. The composition may be for use in the prophylaxis or treatment of HPV infection.

According to another aspect of the invention there is provided a method of treatment or prophylaxis of HPV infection comprising the administration of:
the polypeptide according to the invention;
the nucleic acid according to the invention;
the composition according to the invention or
the viral vector according to the invention.

The method of treatment or prophylaxis of HPV infection may be a method of vaccination.

According to another aspect of the invention there is provided an agent for use in the prophylaxis or treatment of HPV infection, the agent comprising or consisting of:
the polypeptide according to the invention;
the composition according to the invention;
the nucleic acid according to the invention; or
the viral vector according to the invention.

In one embodiment, the treatment or prophylaxis of HPV infection comprises the treatment or prophylaxis of an anogenital HPV-driven lesion, such as anal, vulval, vaginal, or penile intraepithelial neoplasia. Additionally or alternatively, the treatment or prophylaxis of HPV infection comprises the treatment or prophylaxis of an oropharyngeal lesion that is caused by HPV.

According to another aspect of the invention there is provided the polypeptide according to the invention; the composition according to the invention; the nucleic acid according to the invention; or the viral vector according to the invention; for use in, or as, a vaccine.

According to another aspect of the invention there is provided a vaccine comprising the nucleic acid of the invention; the polypeptide according to the invention; the composition according to the invention; or the viral vector according to the invention.

The vaccine may be a prime vaccine. The vaccine may be a boost vaccine. Where a boost vaccine is provided following a prime vaccine, the polypeptide may be different. For example, the polypeptide may comprise a re-ordered sequence of conserved peptide sequences. The conserved peptide sequences may be identical, but the order in which they are provided in the polypeptide may be changed. Therefore, the invention herein provides any of the sequences/embodiments of the invention wherein the order in which conserved peptide sequences are provided may be changed. Such embodiments may also include re-ordered or differed linker/junction sequences.

Advantageously, the re-ordering of the conserved peptide sequences of the polypeptide between prime and boost vaccines can avoid the provision of "false" epitopes formed across junctions of one conserved peptide sequence with another conserved peptide sequence. i.e. the same junction may not occur in the re-ordered polypeptide.

According to another aspect of the invention, there is provided a nucleic acid or polypeptide according to the invention for use in, or as, a vaccine.

According to another aspect of the invention, there is provided a prime boost vaccination kit comprising
a prime vaccination according to the invention;
a boost vaccination according to the invention.

The prime and boost vaccinations may be different. The prime and boost vaccination may differ in the polypeptide sequence. The prime and boost vaccination may comprise different viral vectors (i.e. from different virus families such as MVA vs adenovirus).

According to another aspect of the invention, there is provided a composition comprising a nucleic acid according to the invention herein, and a pharmaceutically acceptable carrier.

The composition may not comprise wild-type HPV. The composition may not comprise full length HPV protein sequence. The viral vector or nucleic acid may not encode non-conserved protein/peptide sequence of HPV.

The use may be with a pharmaceutically acceptable carrier. Additionally or alternatively, the use may be with an adjuvant.

The term "immunogenic", when applied to the nucleic acid, polypeptide or composition of the present invention means capable of eliciting an immune response in a human or animal body. The immune response may be protective.

The term "protective" means prevention of a disease, a reduced risk of disease infection, transmission and/or progression, reduced severity of disease, a cure of a condition or disease, an alleviation of symptoms, or a reduction in severity of a disease or disease symptoms.

The term "prophylaxis" means prevention of or protective treatment for a disease. The prophylaxis may include a reduced risk of disease infection, transmission and/or progression, or reduced severity of disease.

The term "treatment", means a cure of a condition or disease, an alleviation of symptoms, or a reduction in severity of a disease or disease symptoms.

The skilled person will understand that optional features of one embodiment or aspect of the invention may be applicable, where appropriate, to other embodiments or aspects of the invention.

Embodiments of the invention will now be described in more detail, by way of example only, with reference to the accompanying drawings.

FIG. 1—Chimeric and Variant methods used to create HPV candidates.

Figure 2:
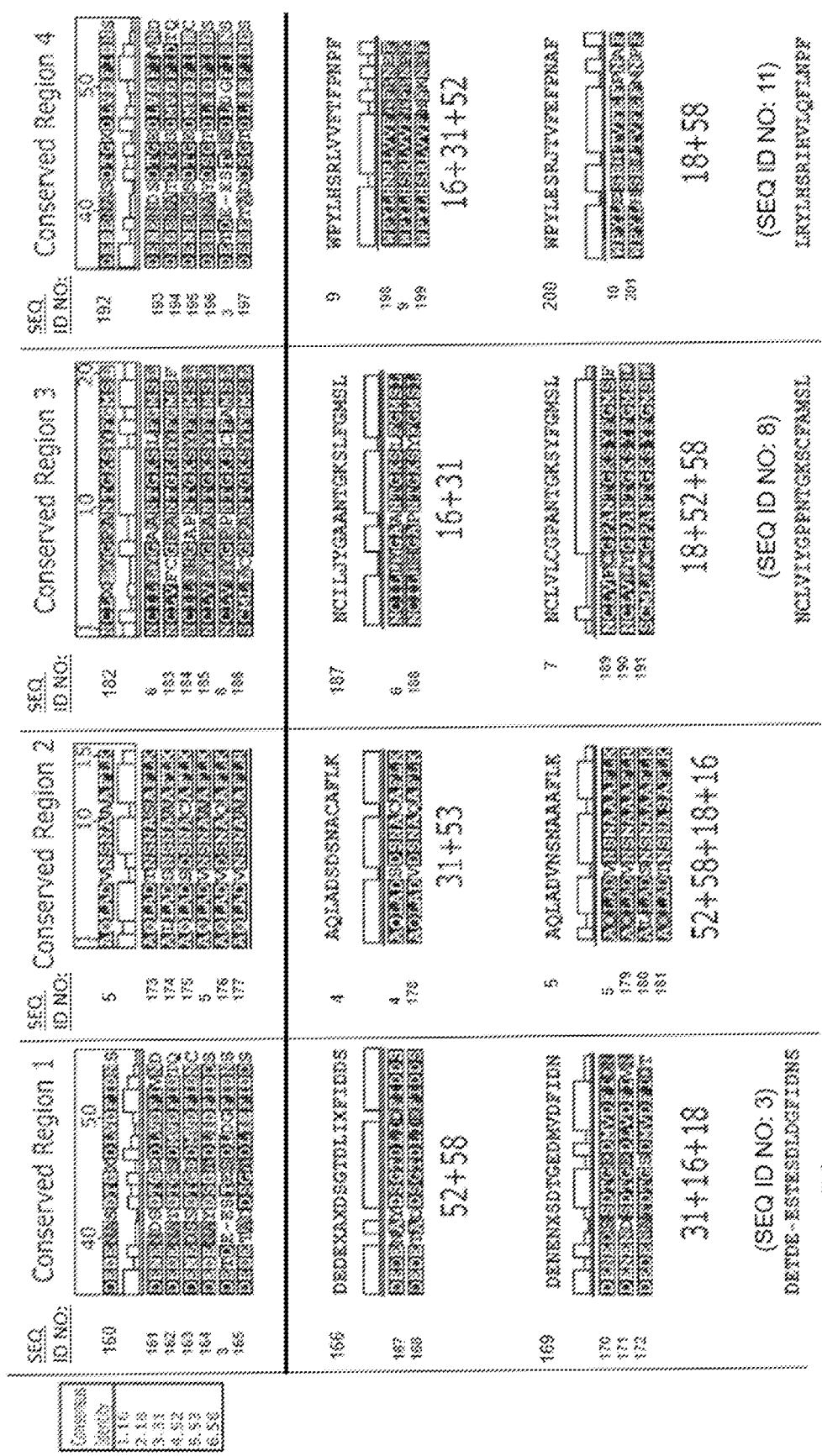

FIG. 2—Conserved regions with resultant variants below. See Table 9 for sequences and associated SEQ ID NO identifiers.

Figure 3:
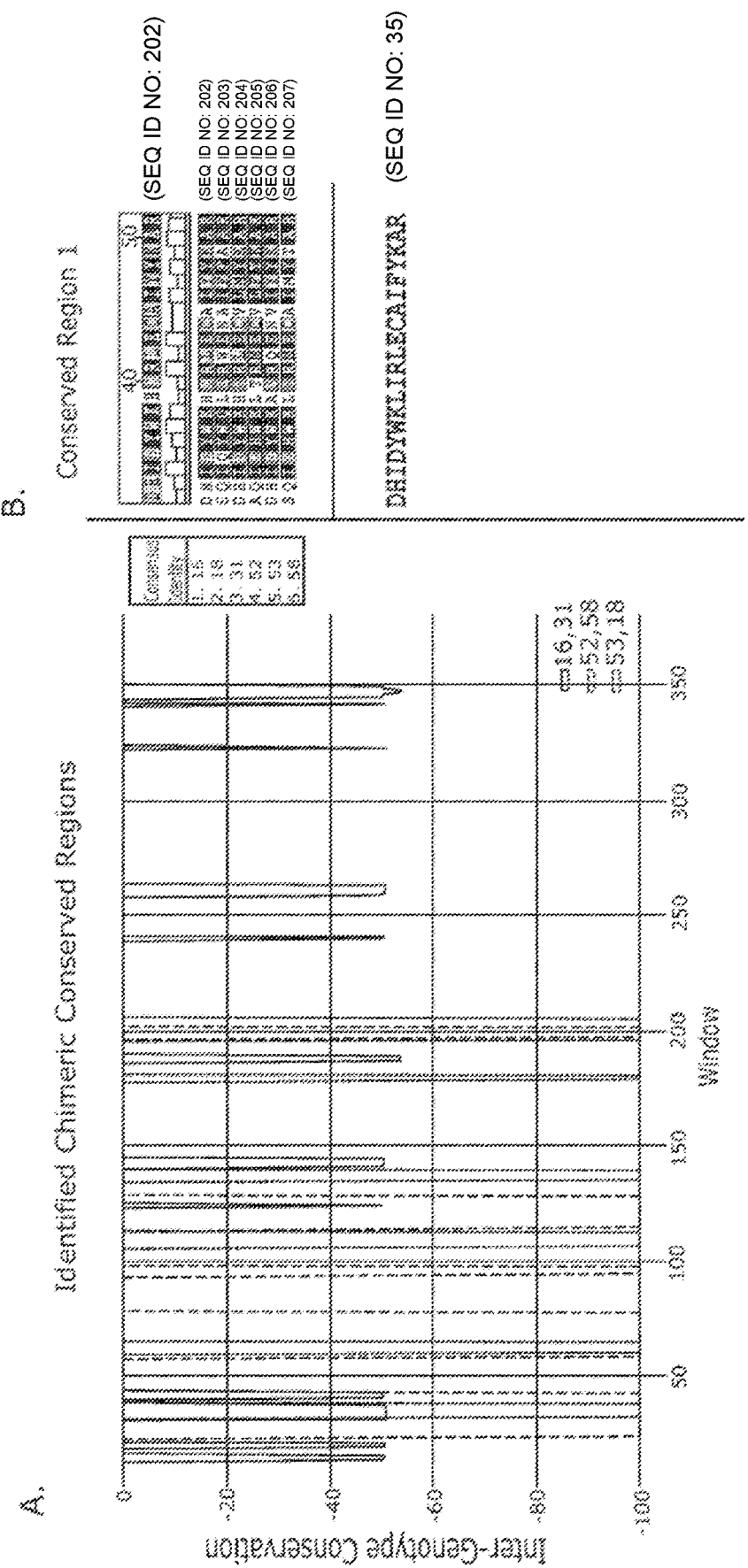

FIG. 3—A) Regions identified as conserved in the two genotypes used to form chimerics. B) Conservation plot of Modified variant. See Table 9 for sequences and associated SEQ ID NO identifiers.

Figure 4:
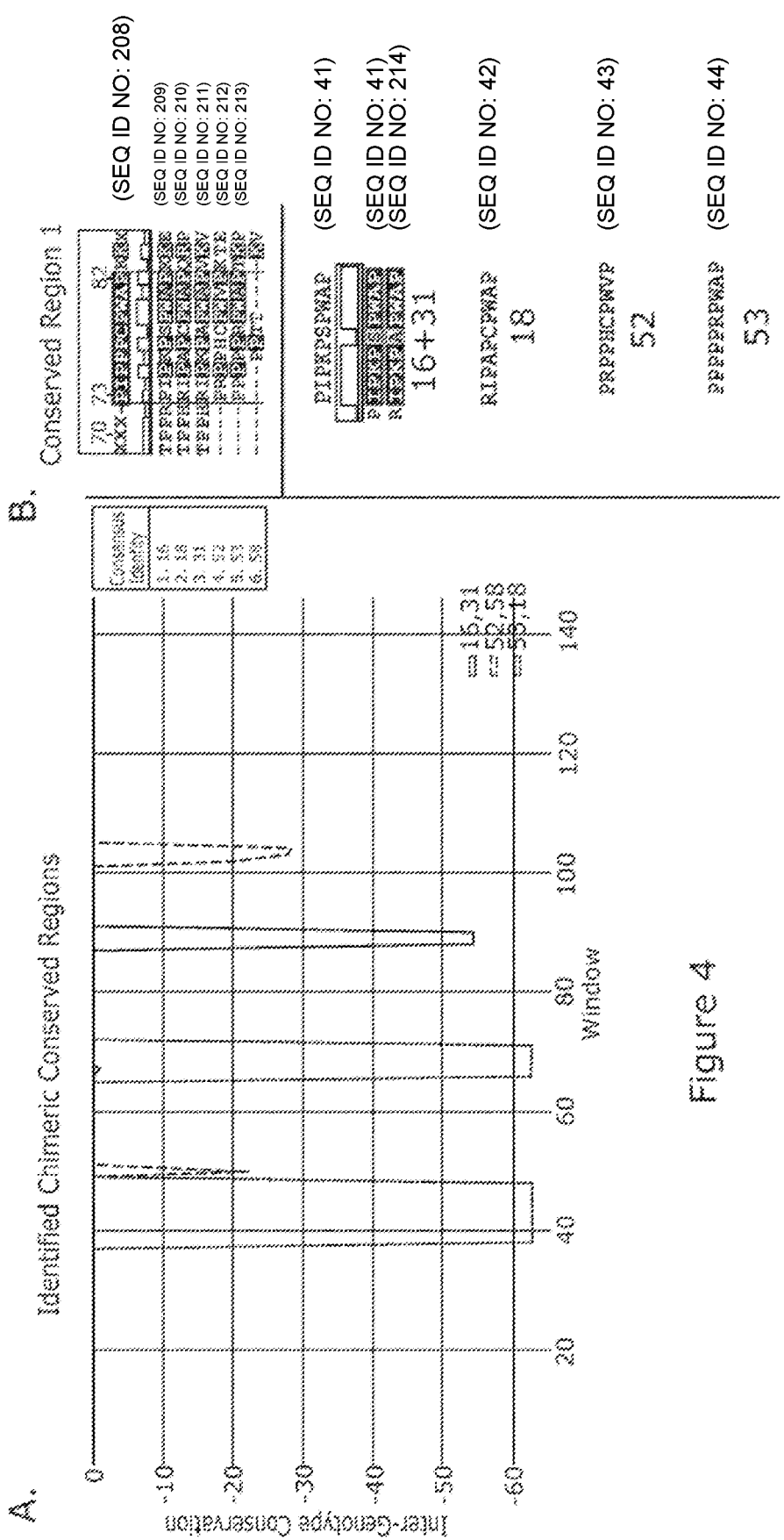

FIG. 4—A) Regions identified as conserved in the two genotypes used to form chimerics. B) Conservation plot of variants, See Table 9 for sequences and associated SEQ ID NO identifiers.

Figure 5:
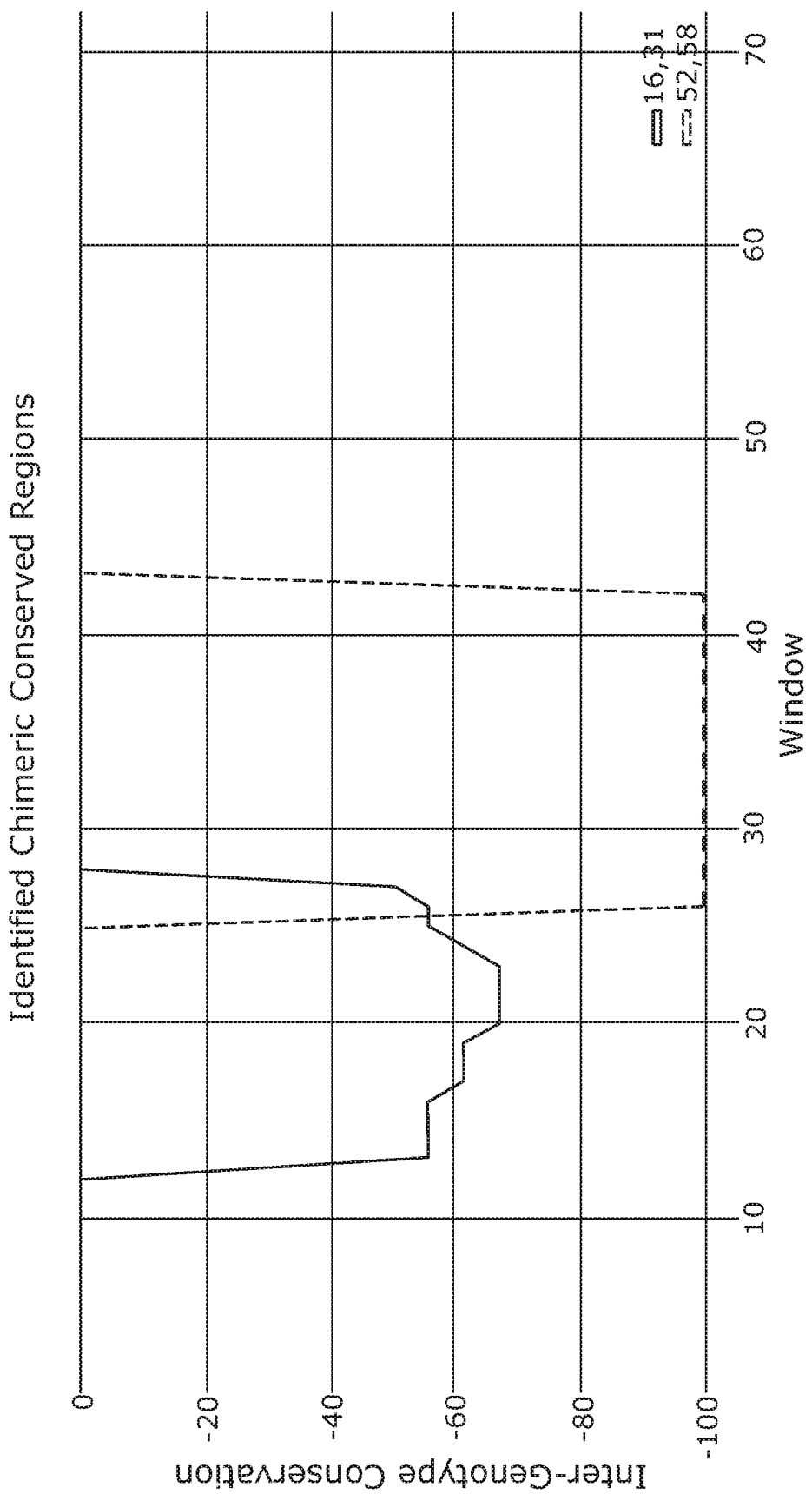
Figure 6:
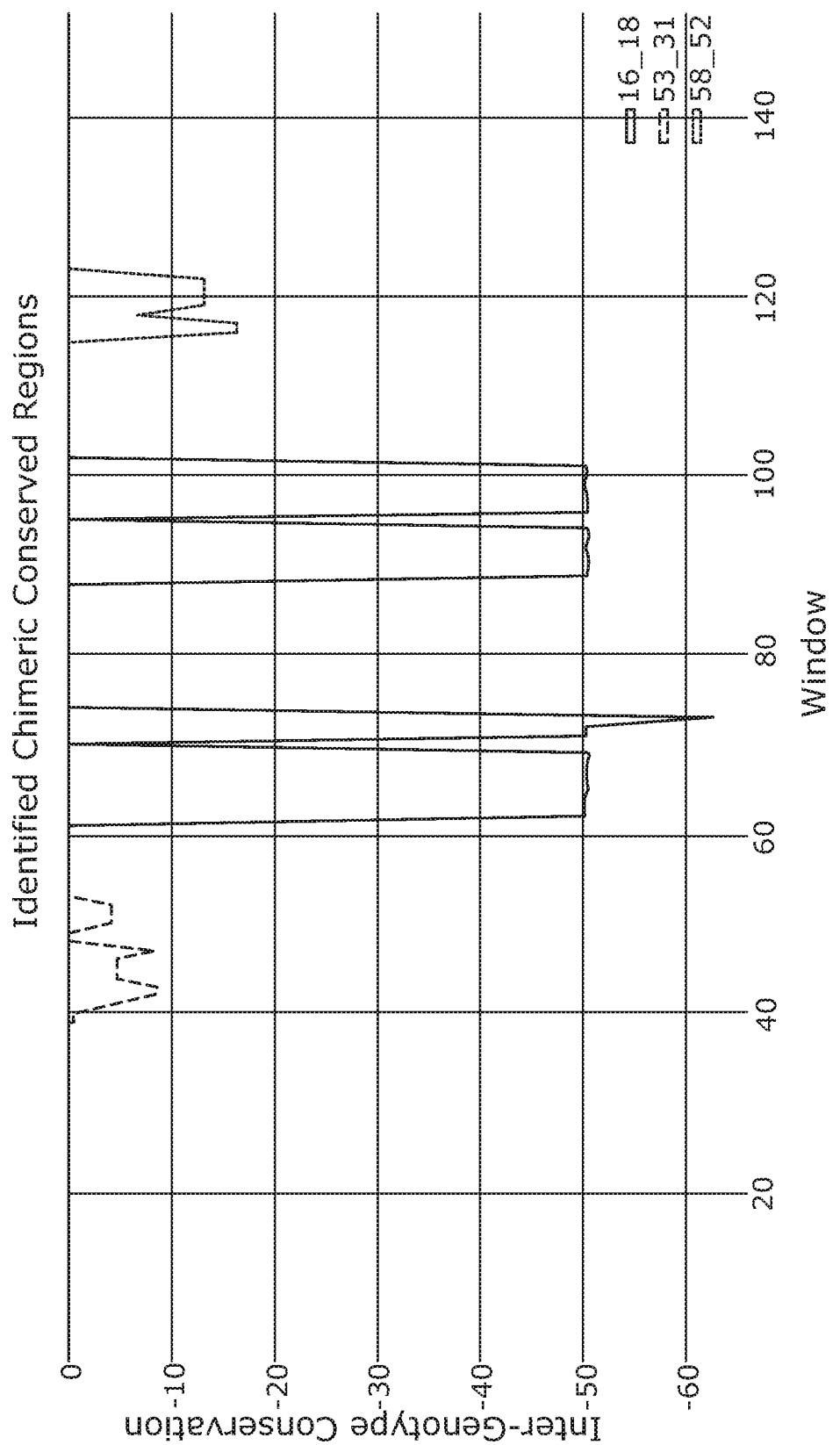
Figure 7:
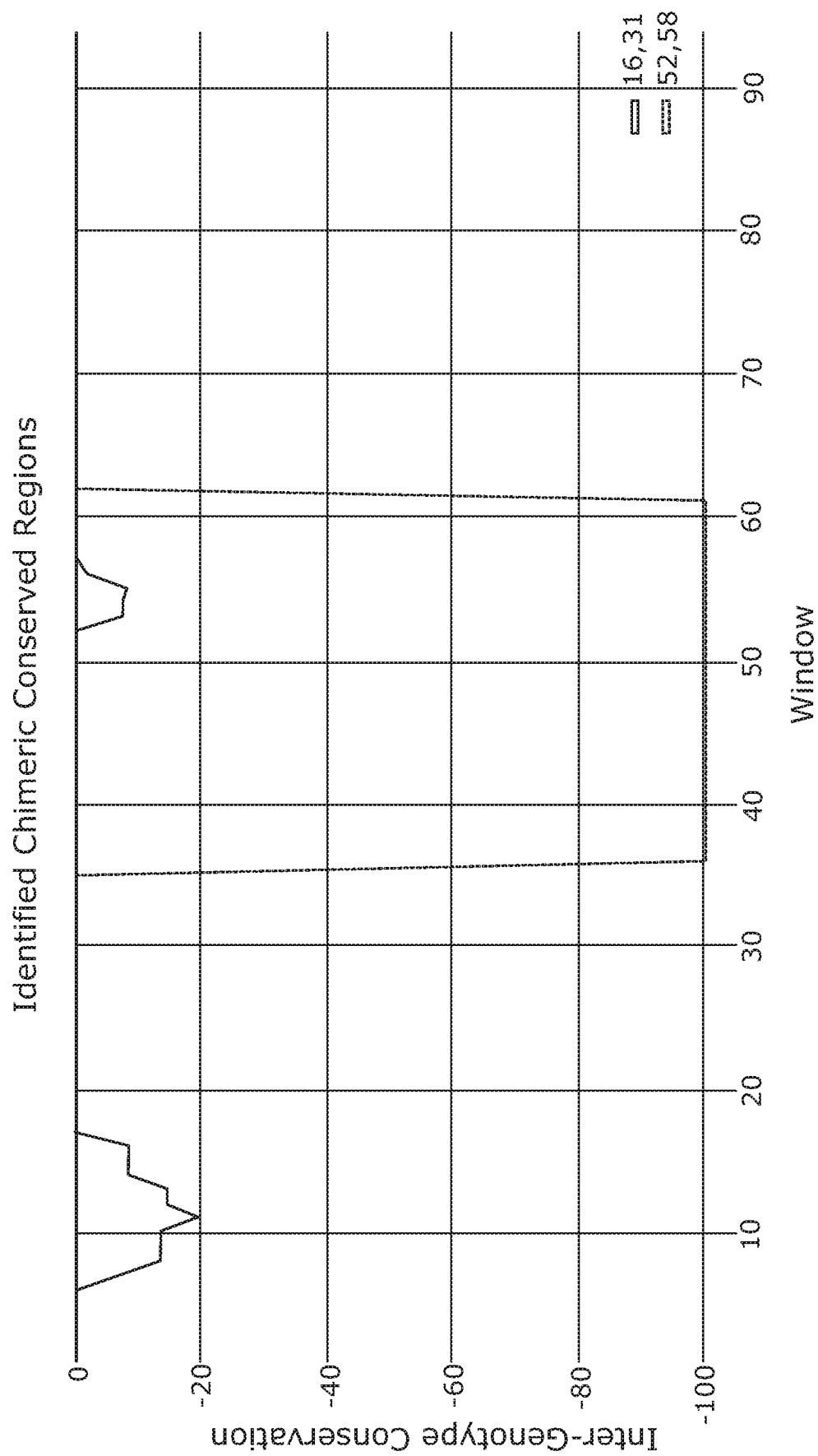
Figure 8:
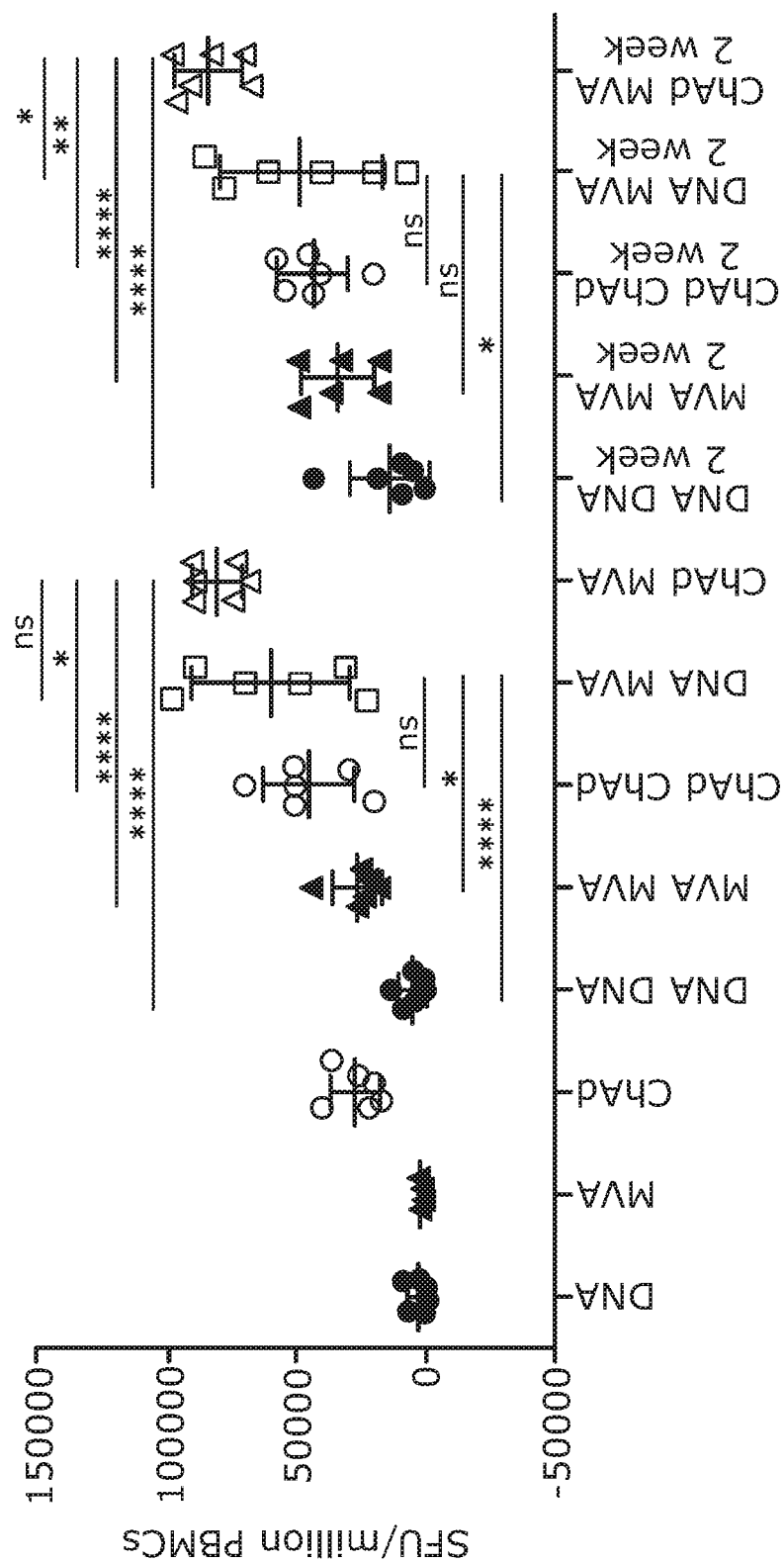

FIG. 5—Regions identified as conserved in the two genotypes used to form chimerics FIG. 6—Regions identified as conserved in the two genotypes used to form chimeric-variants FIG. 7—Regions identified as conserved in the two genotypes used to form chimeric FIG. 8—High frequencies of vaccine-specific T cells are induced following prime boost vaccination. IFNγ Elispot performed on PBMCs from C57BL/6 mice (six/group) primed intramuscularly with DNA-HPV, MVA-HPV or ChAdOx1-5GHPV3 and then boosted intramuscularly with a heterologous or homologous vaccine two weeks later. PBMCs were collected by tail vein bleed two weeks post prime and one and two weeks post boost.

Figure 9:
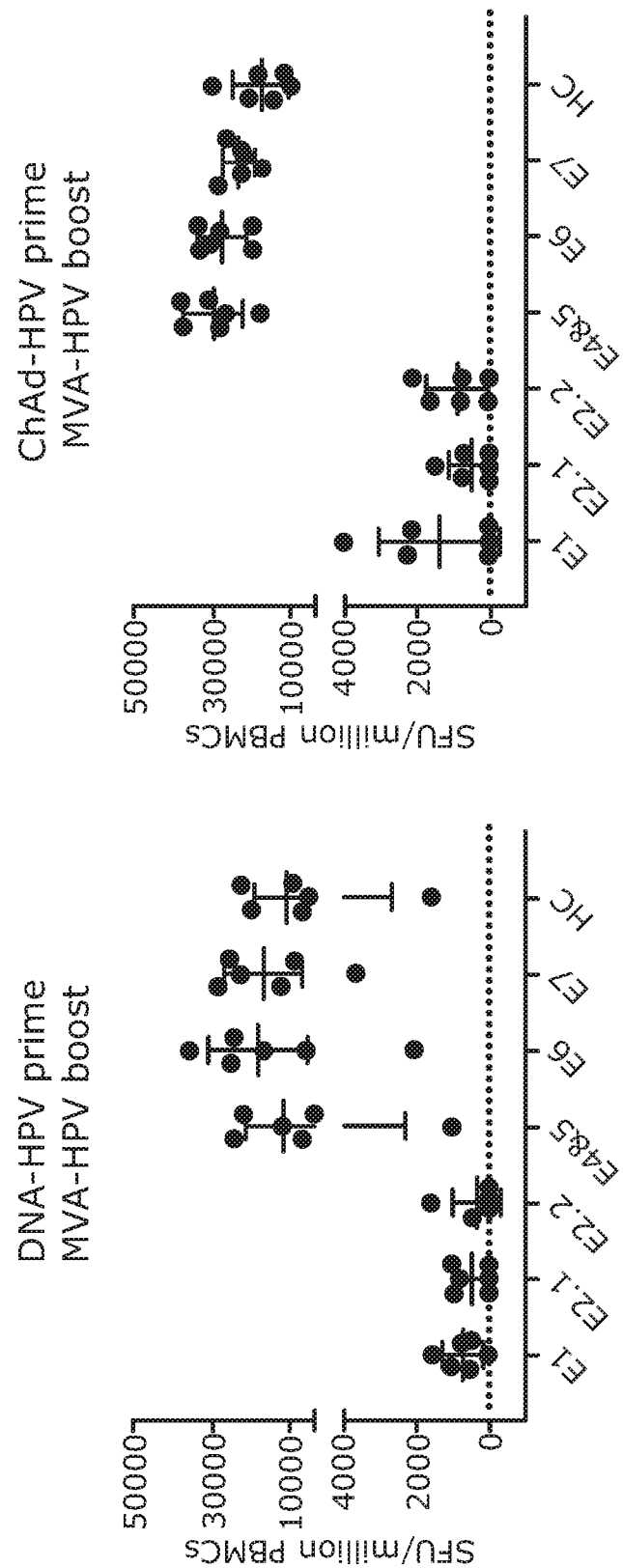

FIG. 9—Prime boost vaccination is capable of inducing responses to all antigens encoded in the immunogen. PBMCs were collected at two weeks boost and used in an IFNγ Elispot with peptides spanning the entire immunogen sequence, pooled according to protein source. Peptides spanning the E2 region of the immunogen were split into two pools because of the large number of peptides and peptides for regions spanning E4 and E5 were combined into one pool.

Figure 10A:
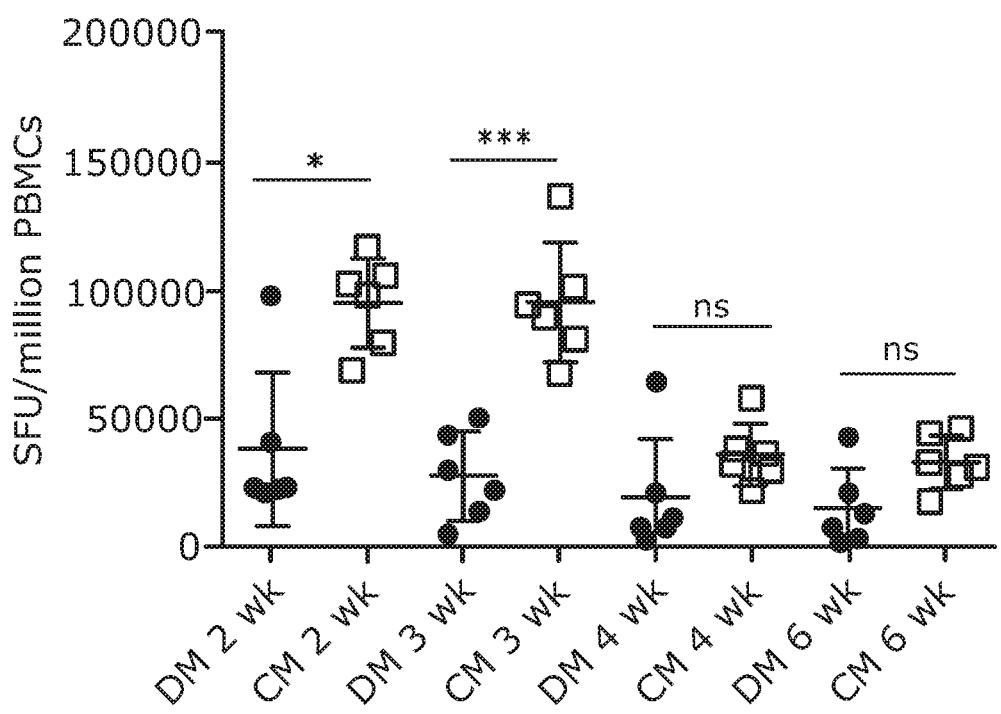
Figure 10B:
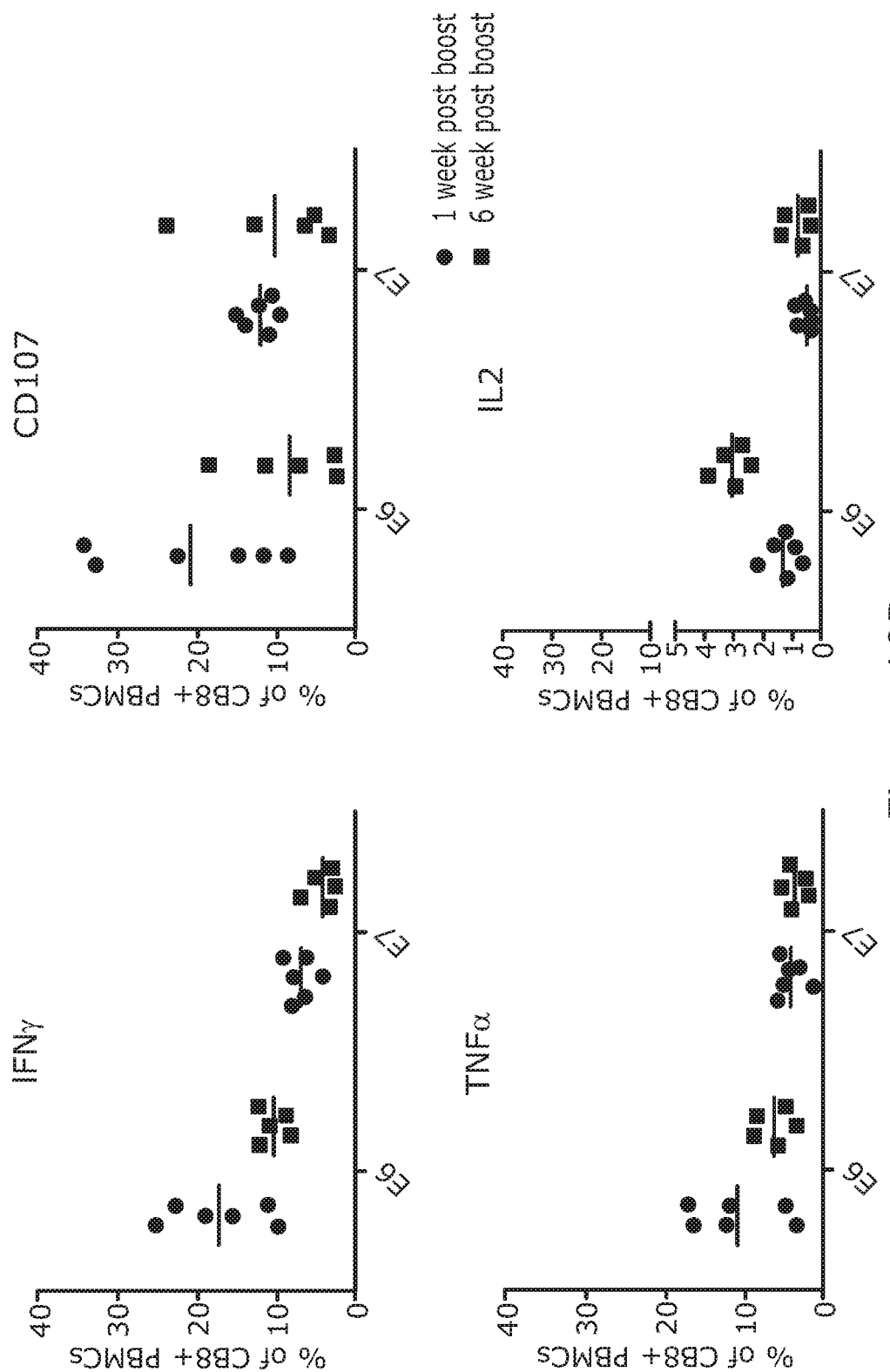

FIGS. 10A and 10B—Vaccine-specific CD8+ T cells can be detected at high frequencies six weeks after ChAdOx1-5GHPV3 prime MVA-SGHPV3 boost. FIG. 10A IFNγ Elispot using PBMCs collected by tail vein bleed two, three, four and six weeks post boost (DM; DNA-SGHPV3 prime MVA-SGHPV3 boost, CM; ChAdOx1-SGHPV3 prime MVA-SGHPV3 boost). FIG. 10B ICS performed on PBMCs obtained one week and six weeks post ChAdOx1-5GHPV3 prime, MVA-5GHPV3 boost. PBMCs stimulated with E6 and E7 peptide pools. Measured IFN-γ, CD107, TNF-α and IL2.

Figure 11:
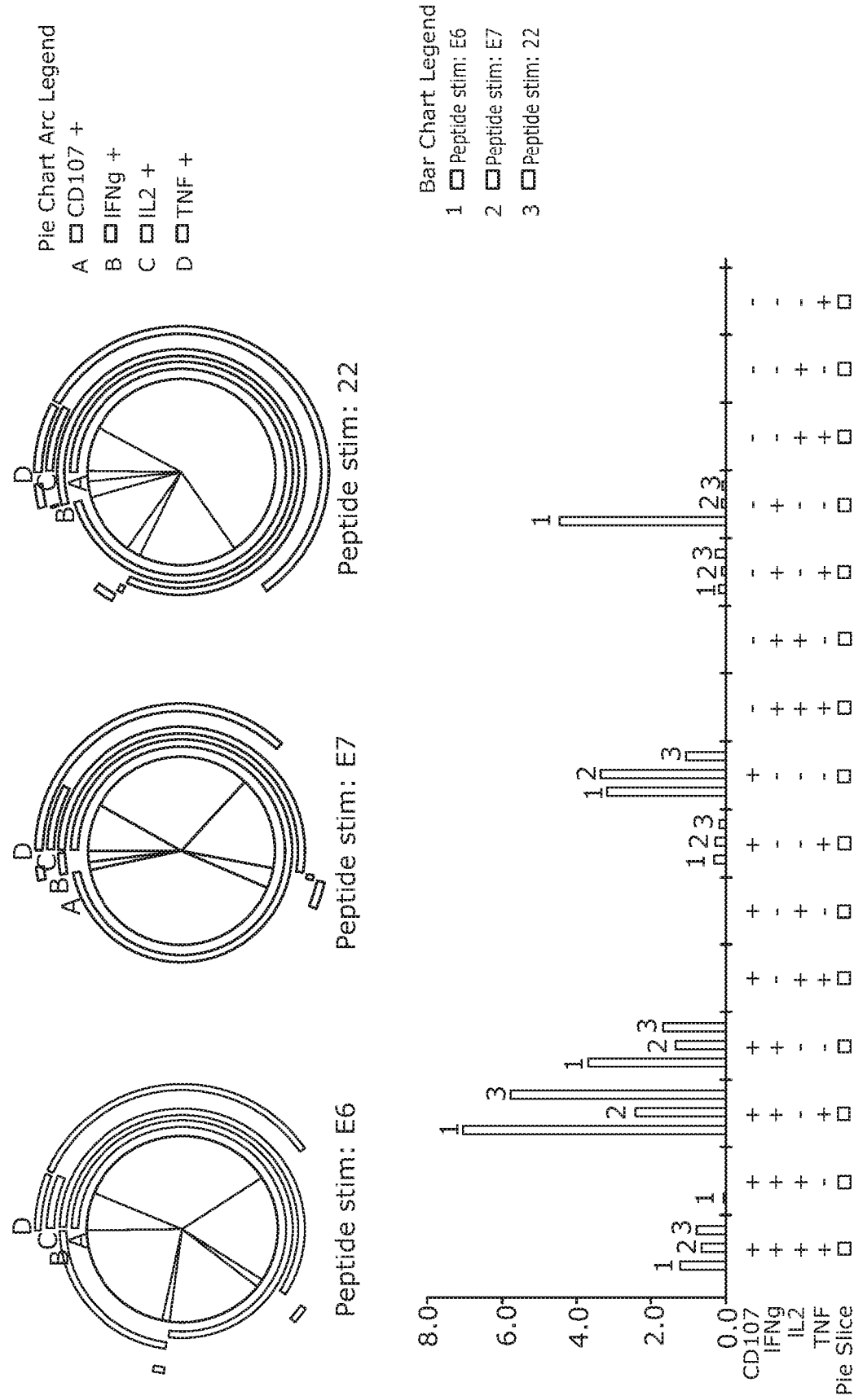

FIG. 11—HPV E6- and E7-specific CD8+ T cell responses are polyfunctional and have cytotoxic potential. PBMCs from a tail vein bleed collected one week post ChAdOx1-5GHPV3 prime MVA-5GHPV3 boost were stimulated with immunodominant peptide pools E6 and E7 and sub pool 22 which is the dominant sub pool within E6. Responding CD8+ T cells predominantly express three functions (CD107, IFNγ and TNFα).

Figure 12:
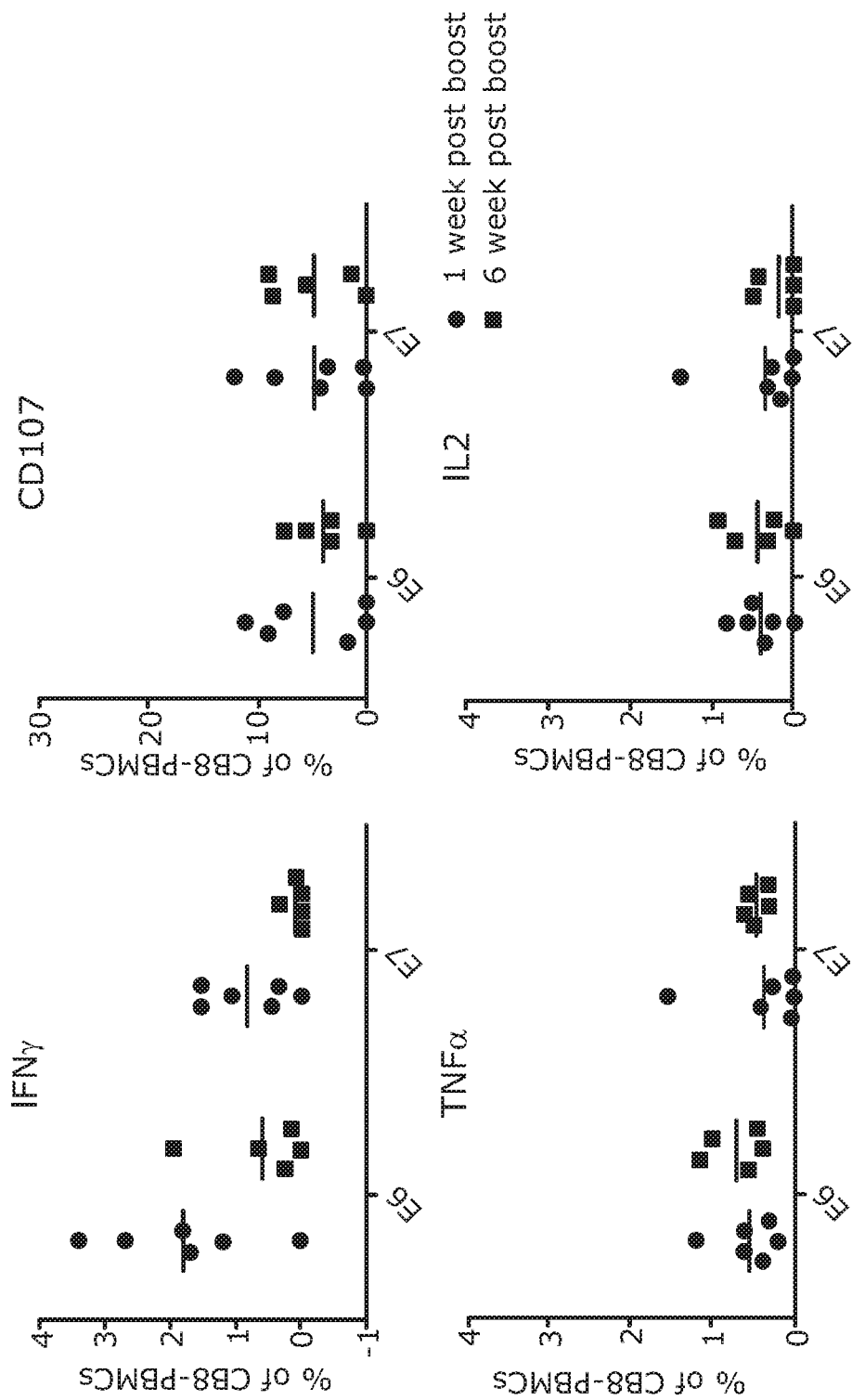

FIG. 12—ChAdOx1-5GHPV3 prime MVA-5GHPV3 boost also primes HPV E6- and E7-specific CD4+ T cell responses that are still detectable six weeks post boost. ICS performed on PBMCs obtained one week and six weeks post ChAdOx1-5GHPV3 prime, MVA-5GHPV3 boost. PBMCs stimulated with E6 and E7 peptide pools. Measured IFN-γ, CD107, TNF-α and IL2.

Figure 13:
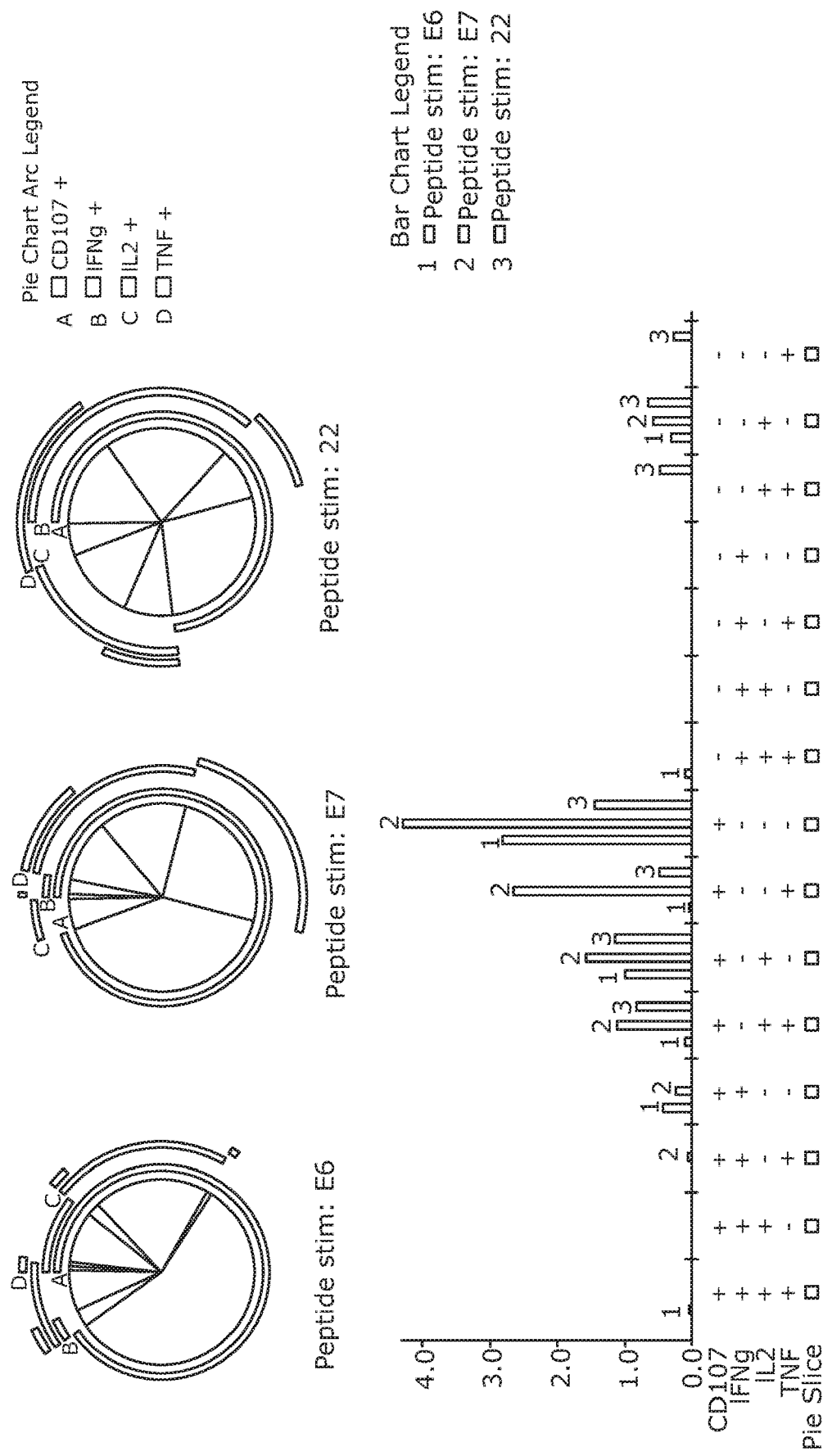

FIG. 13—Most E6 and E7-specific CD4+ T cells express two functions. PBMCs from a tail vein bleed collected one week post ChAdOx1-5GHPV3 prime MVA-5GHPV3 boost were stimulated with immunodominant peptide pools E6 and E7 and sub pool 22 which is the dominant sub pool within E6. Responding CD4+ T cells predominantly express two functions (Discounting CD107+ monofunctional cells).

Figure 14:
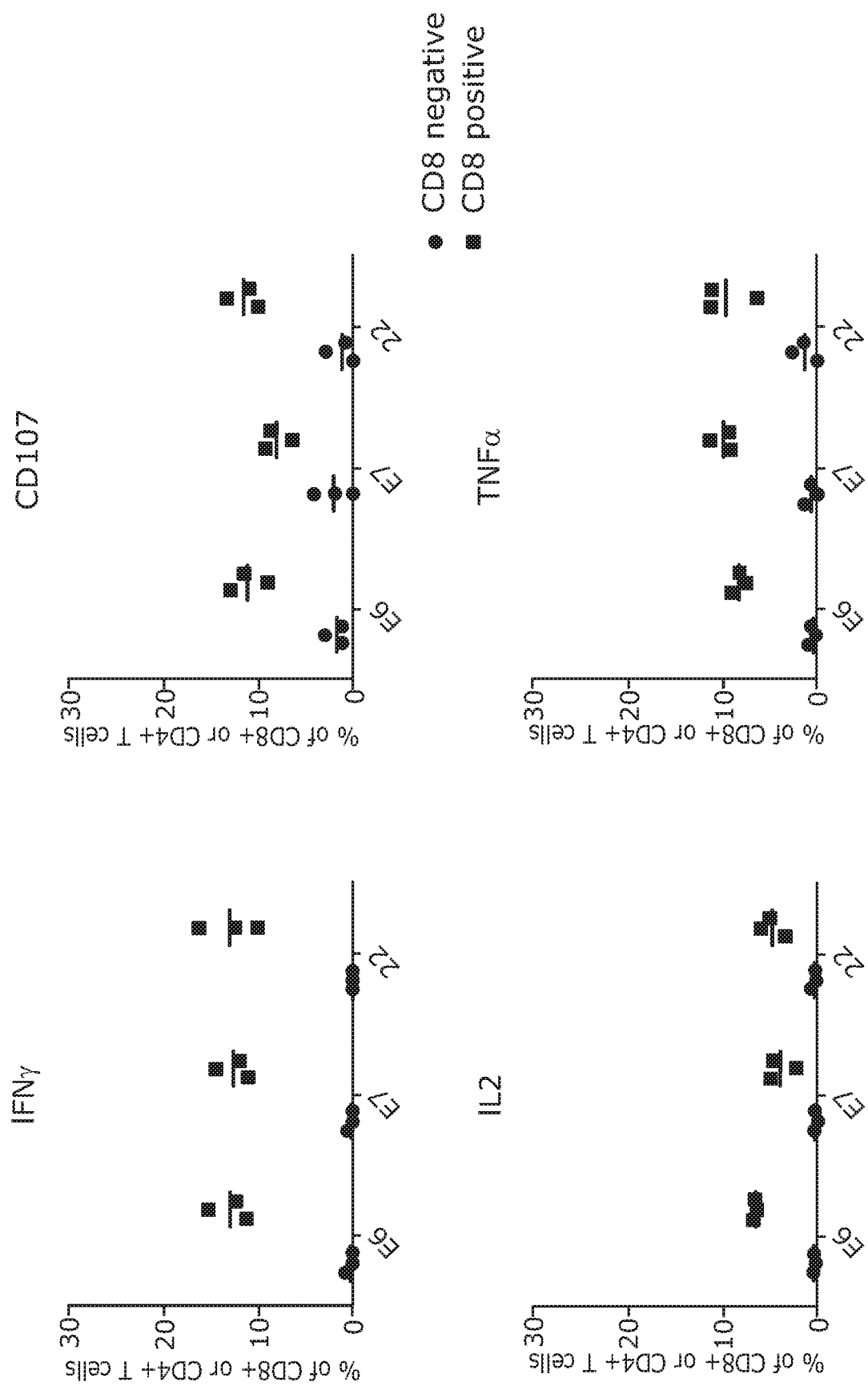

FIG. 14—HPV E6- and E7-specific CD8+ T cells can be detected in the cervix. ICS was performed on cervicovaginal lymphocytes isolated from mice two weeks post ChAdOx1-5GHPV3 prime MVA-5GHPV3 boost and stimulated with immunodominant peptide pools E6 and E7 and sub pool 22. Measured IFN-γ, CD107, TNF-α and IL2.

Figure 15:
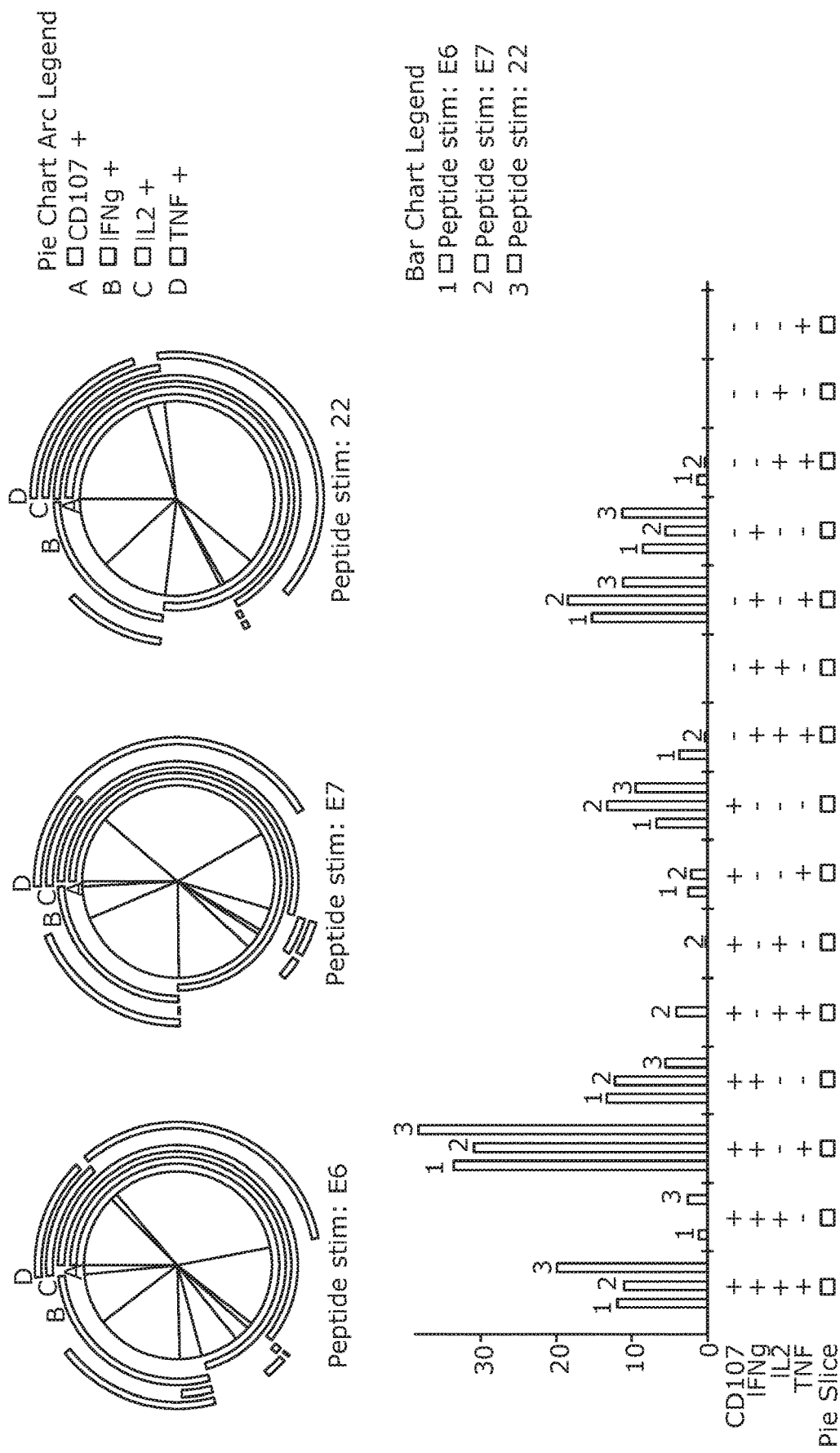

FIG. 15—Cervicovaginal HPV E6- and E7-specific CD8+ T cell responses are polyfunctional. Cervicovaginal lymphocytes collected one week post ChAdOx1-5GHPV3 prime MVA-5GHPV3 boost were stimulated with immunodominant peptide pools E6 and E7 and sub pool 22 which is the dominant sub pool within E6. Responding CD8+ T cells predominantly express three functions (CD107, IFNγ and TNFα).

Figure 16:
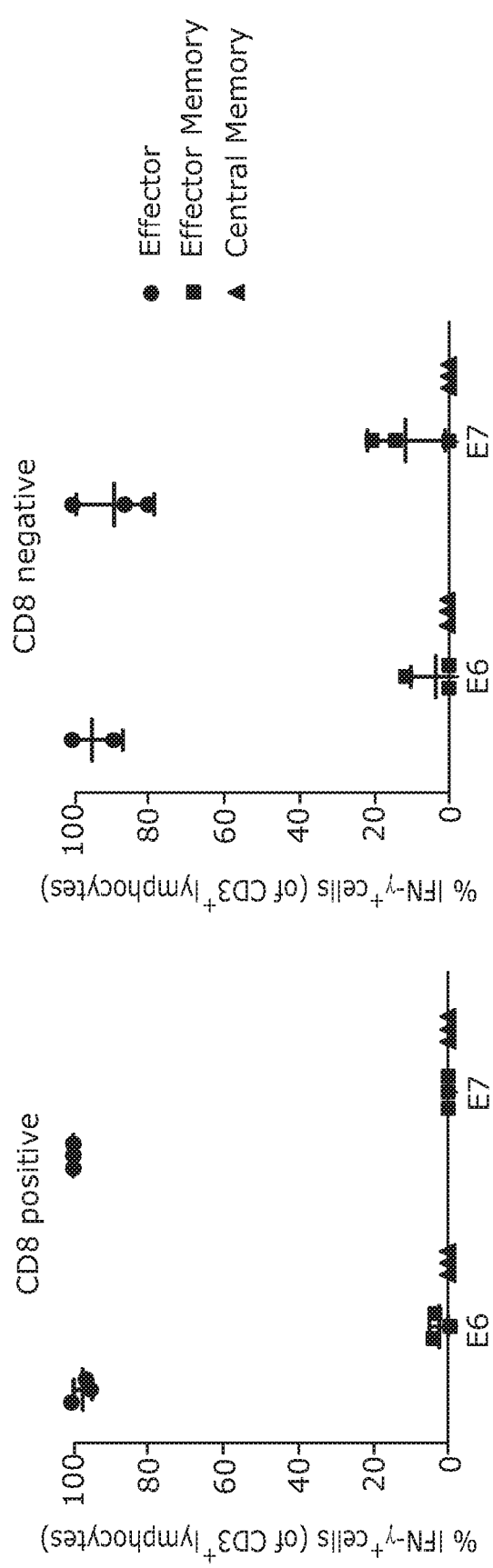
Figure 17:
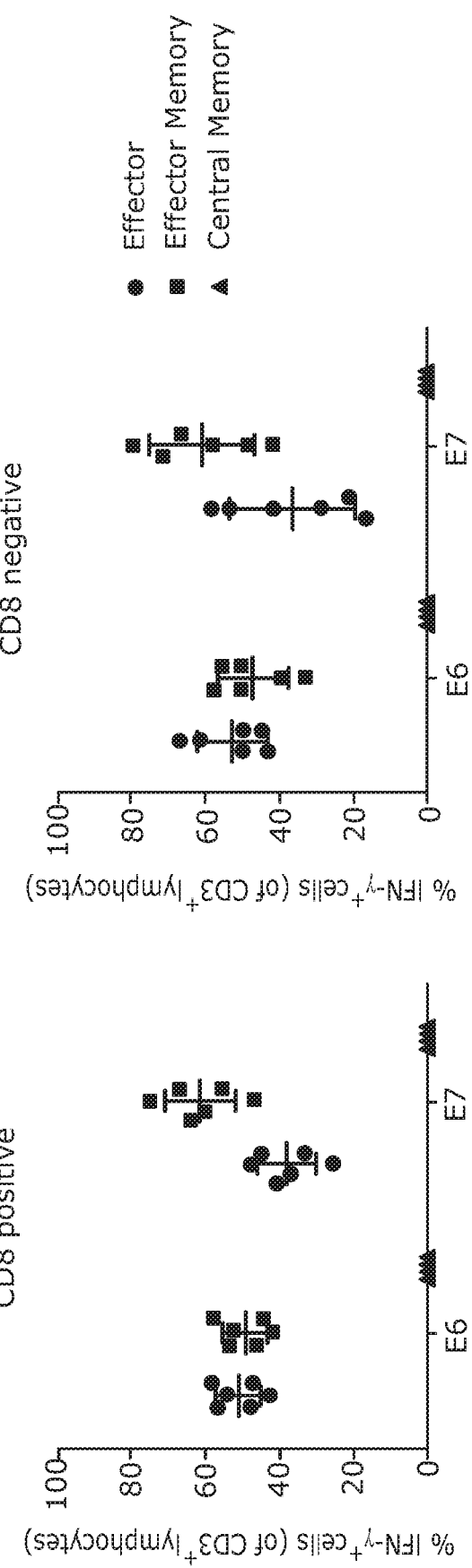

FIG. 16—Vaccine-induced E6 and E7-specific CD8+ and CD4+ T cells in the cervix are almost exclusively of effector phenotype. Naïve: CD44-CD62L+. Antigen-experienced: Central memory—CD62L+, CD127+; Effector memory—CD62L-, CD127+; Effector—CD62L-, CD127-. Cervical lymphocytes from six mice pooled into three pairs, due to low lymphocyte numbers FIG. 17—In contrast to cervix, vaccine-induced E6 and E7-specific CD8+ and CD4+ T cells in the spleen comprise effector and effector memory populations.

Figure 18:
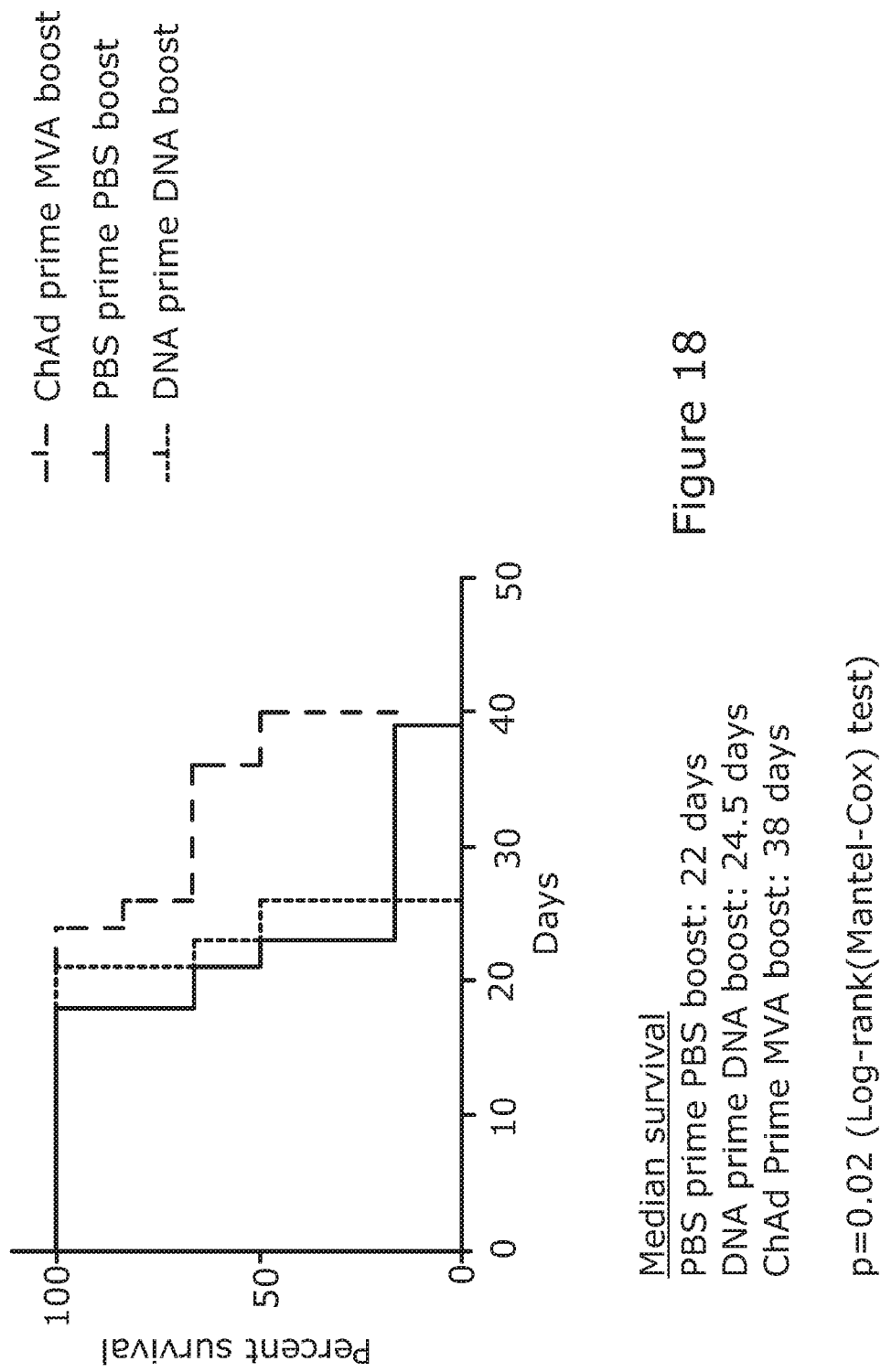

FIG. 18—Mice vaccinated with ChAdOx1-5GHPV3 prime, MVA-5GHPV3 boost show increased survival over control mice. Mice were inoculated with $5 \times 10^4$ TC-1 cells on day 0 and then primed on day 3 and boosted on day 17. Tumours were measured with digital callipers every two days and mice culled when tumours reached 10 mm in any one direction.

Figure 19:
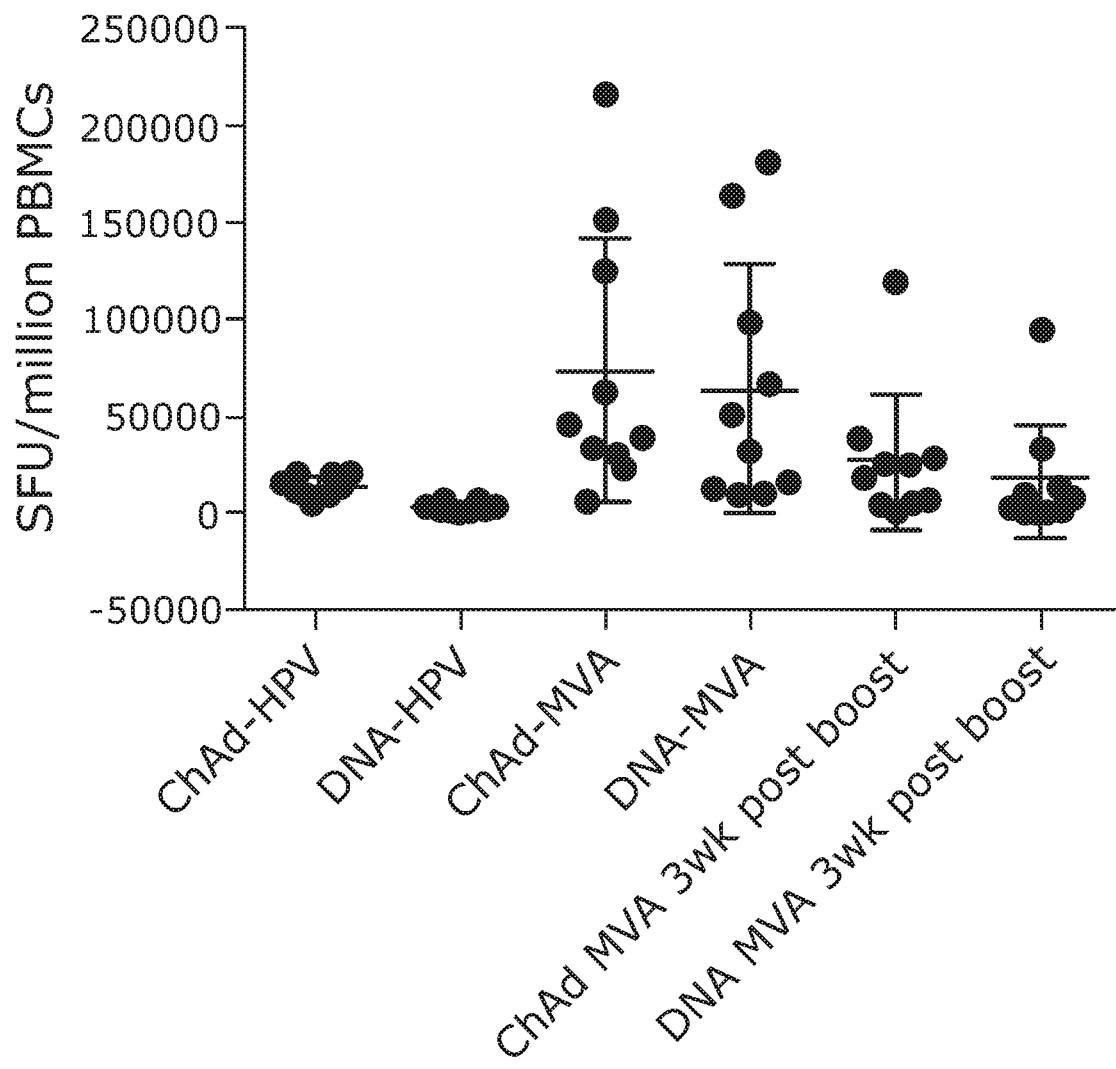

FIG. 19—Vaccination of outbred CD1 mice induces high frequency T cell responses. IFNγ Elispot performed on PBMCs from CD1 mice (ten/group) primed intramuscularly with DNA-5GHPV3, MVA-5GHPV3 or ChAdOx1-5GHPV3 and then boosted intramuscularly with a heterologous or homologous vaccine two weeks later. PBMCs were collected by tail vein bleed two weeks post prime and two and three weeks post boost.

Figure 20:
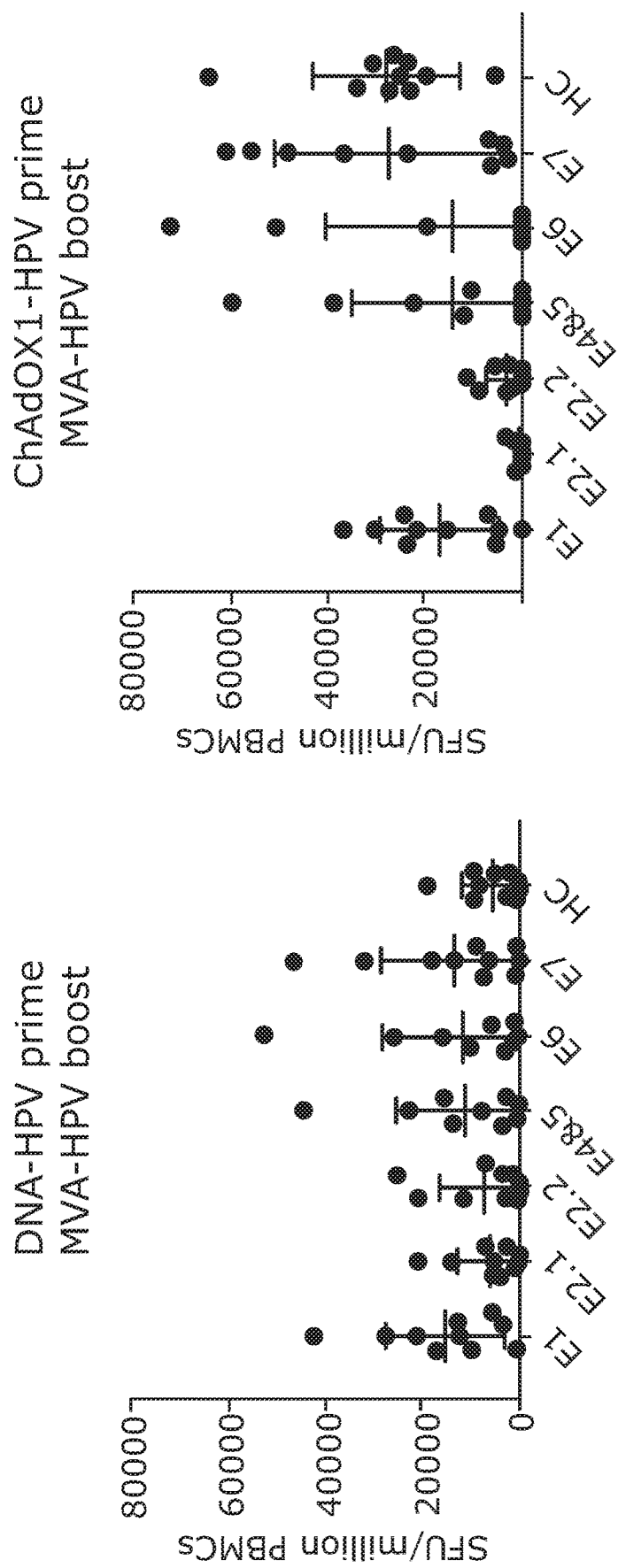

FIG. 20—T cell responses in vaccinated CD1 mice are directed across the entire immunogen. PBMCs were collected at two weeks boost and used in an IFNγ Elispot with peptides spanning the entire immunogen sequence, pooled according to protein source. Peptides spanning the E2 region of the immunogen were split into two pools because of the large number of peptides and peptides for regions spanning E4 and E5 were combined into one pool.

Figure 21:
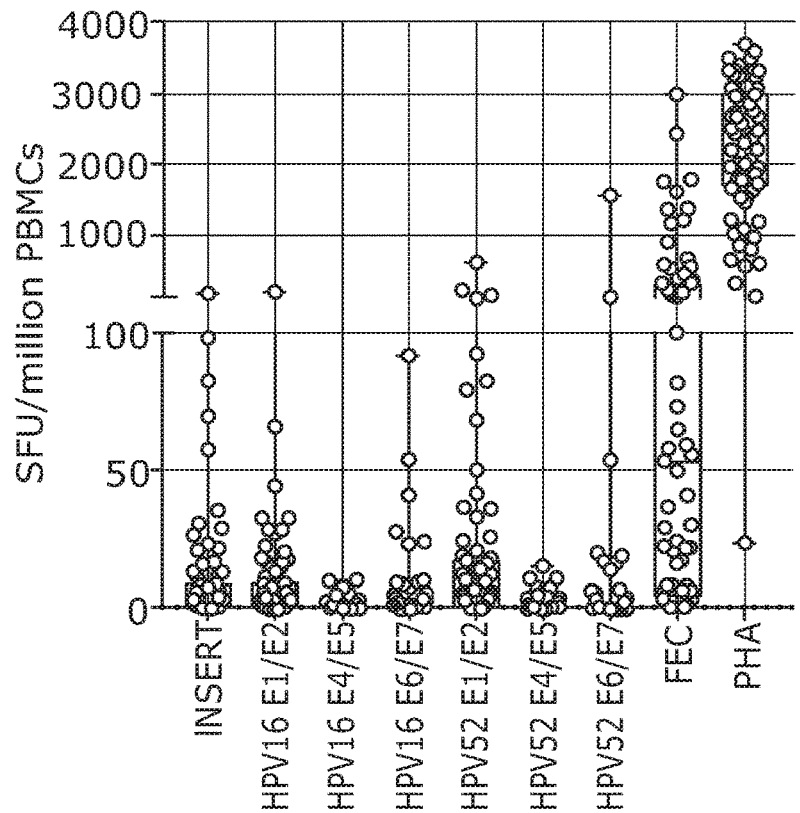
Figure 21:
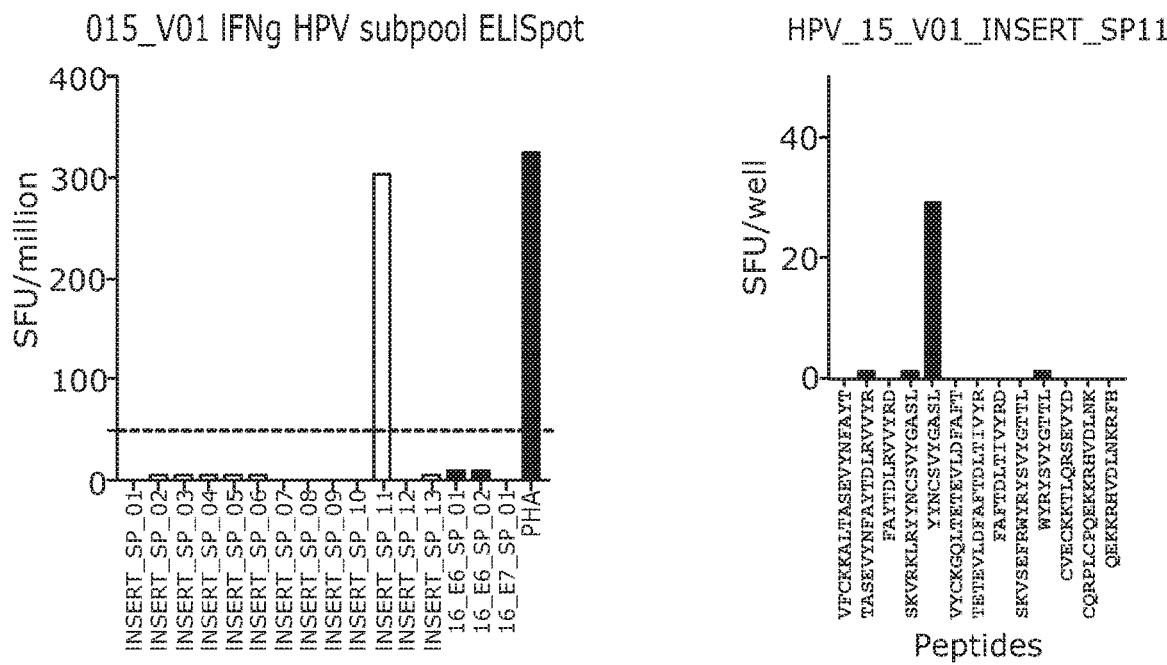

FIG. 21—Top panel: Peripheral blood mononuclear cells (PBMC) from 76 women aged 16-24 years were tested for recognition of peptides based on early proteins from high risk HPV (hrHPV) in ex vivo IFN-γ Elispot assays. 'Insert' is a pool of 15-mer peptides overlapping by 11 amino acid spanning the hrHPV transgene. 'Reference' peptides were pools of peptides based on early proteins from HPV16 and HPV52, which were combined as follows: E1/E2, E4/E5 and E6/E7. TEC' (flu, EBV and CMV) peptides and PHA (phytohaemaglutinnin) were used as positive controls. The data shown are the spot-forming units (SFU) obtained from peptide-stimulated wells after subtraction of negative control values (mock-stimulated cells). The cut-off for a positive response was set at 25 SFU/million PBMC (derived from the mean of mock-stimulated values from all donors+2 standard deviations). Women were tested concurrently for hrHPV DNA on vaginal sampling: 26% tested positive. The data show that 9/76 women with current hrHPV infection or prior exposure recognised HPV sequences encoded in the transgene. Bottom panel: Responses to the insert pool were interrogated further in one responding donor by testing PBMC with sub-pools of the insert pool (left, SFU per million PBMC), followed by individual peptides within the pools (right, SFU per well), thus confirming the presence of a true HPV-specific response. SFU—spot-forming units reported as either per well, which contains 200,000 PBMC or per million PBMC).

Figure 22:
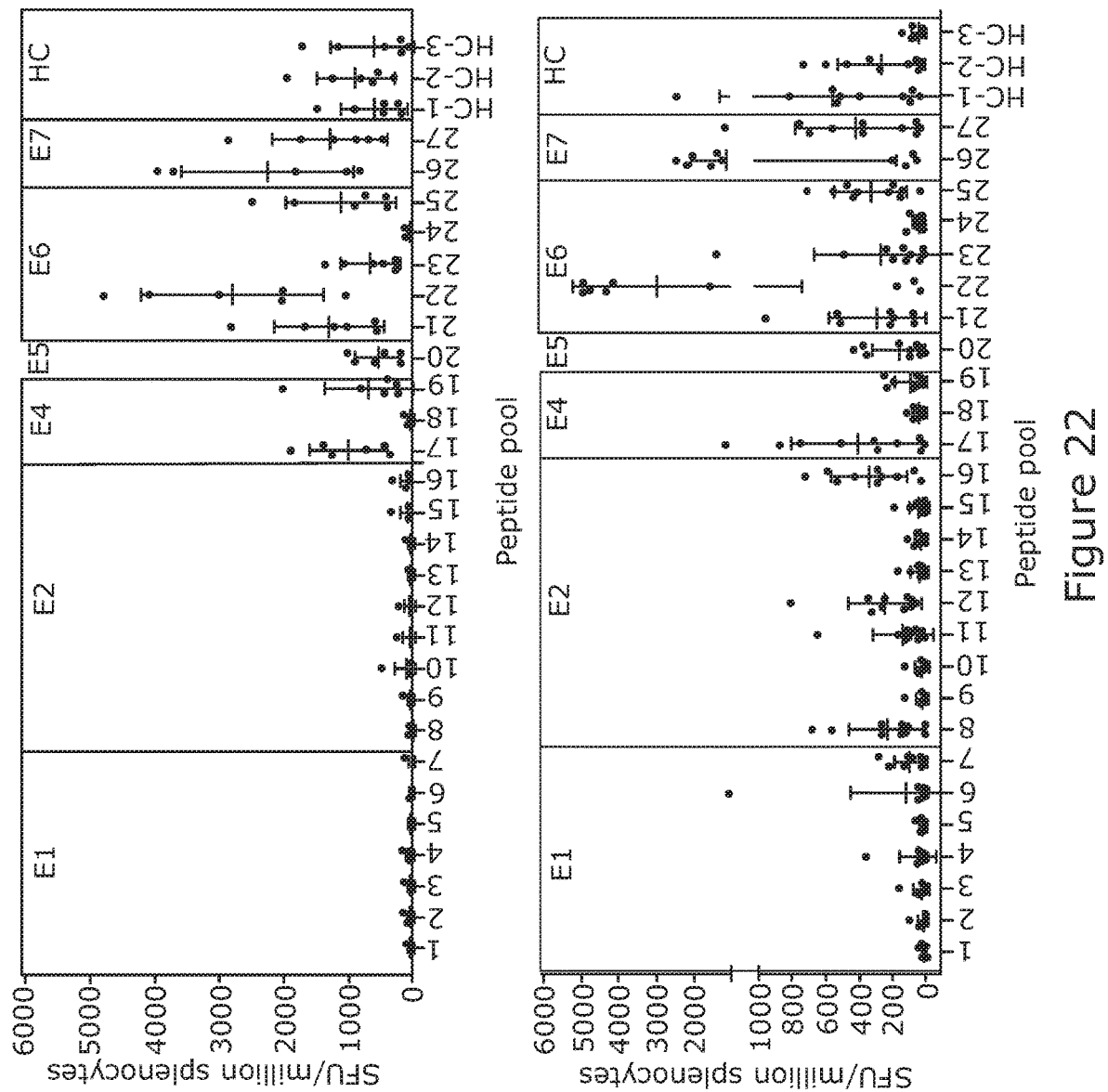

FIG. 22—Subpool mapping in C57BL/6 mice (top panel) and CD1 mice (bottom panel) following ChAdOX1-5G-HPV3 prime MVA-SGHPV3 boost. Mice were culled two weeks post boost and splenocytes isolated. Splenocytes used in an IFNγ Elispot assay using subpools that cover the immunogen sequence. Subpools 21, 25 and 26 (for example) contain no HPV53 sequences and still get high magnitude responses, thus providing evidence that a sequence without the HPV53 segments would still be immunogenic.

HPV IMMUNOGEN DESIGN

The HPV immunogen is composed of amino acid fragments conserved and geographically representative of the global HPV population at a protein level. Each fragment is created using a conservation algorithm which has been utilised to create either Chimeric or Variant based fragments. The choice being dependent on characteristics of each HPV protein used.

The core conservation algorithm uses a sliding window approach in combination with a normalisation method that accounts for collection bias to identify windows which are conserved both within (intra-genotype) and between (inter-genotype) genotypes. Intra-genotype conserved windows are classed as windows with a conservation value less than one quartile of the sum of all window conservation values for the whole sequence. A normalised representative consensus sequence is created for each genotype during this process. Subsequently inter-genotype windows are identified as windows at the same position in each genotype which are conserved and have a shared consensus identity of >60%.

A key challenge in creating sequences which represent all the selected genotypes for a region of each protein was that many genotypes showed unique phylogenetic clustering. There is a critical balance between the identification of regions conserved across genotypes and the level of shared % consensus identity between these regions. In many cases the inter-genotype diversity was so extreme that you sacrifice shared % consensus identity. Meaning some genotypes were so distinct from one another it was impossible to create a representative sequence. To solve this, raw sequences were inputted into the core algorithm in one of two ways (FIG. 1). (i) Variants; Sequences for all genotypes are input into the algorithm and regions of inter-genotype conservation are identified independent of shared % consensus identity. A phylogeny was created from the resultant regions and ingroup sequences combined to create a consensus with a high level of shared consensus identity (FIG. 1b). (ii) Chimerics; in some instances the distance between genotypes is so significant that genotypes do not align suitably. Therefore, only genotype ingroups are inputted together into the algorithm, and regions conserved between ingroups with >60% shared consensus identity are identified (FIG. 1a).

HPV Candidates

Candidate sequences were created for six HPV proteins (E1-2, E4-7) using input sequences collected from the NCBI protein database, aligned and manually audited to remove incomplete and poor quality sequences (Table 1).

TABLE 1

Number of sequences used as input post audit.

| Protein | Genotype | | | | | |
| --- | --- | --- | --- | --- | --- | --- |
| | 16 | 18 | 31 | 52 | 53 | 58 |
| E1 | 126 | 49 | 24 | 27 | 15 | 53 |
| E2 | 195 | 56 | 26 | 32 | 18 | 54 |
| E4 | 161 | 48 | 24 | 24 | 14 | 52 |
| E5 | 197 | 48 | 24 | 24 | — | 60 |

TABLE 1-continued

Number of sequences used as input post audit.

| | Genotype | | | | | |
|---|---|---|---|---|---|---|
| Protein | 16 | 18 | 31 | 52 | 53 | 58 |
| E6 | 1205 | 78 | 90 | 218 | 131 | 185 |
| E7 | 566 | 70 | 85 | 193 | 114 | 199 |

TABLE 2

_E1 Candidate

| Approach: | | Variants |
|---|---|---|
| Fragments: | 1 | E1_V1_52 + 58: DEDETAYDSGTDLIDFIDDS (SEQ ID NO: 1)<br>E1_V1_31 + 16 + 18: DENENDSDTGEDMVDFIDN (SEQ ID NO: 2)<br>E1_V1_53: DETDEESTESDLDGFIDNS (SEQ ID NO: 3) |
| | 2 | Excluded |

TABLE 2-continued

_E1 Candidate

| Approach: | | Variants |
|---|---|---|
| | 3 | E1_V3_31 + 53: AQLADSDSNACAFLK (SEQ ID NO: 4)<br>E1_V3 52 + 58 + 18 + 16: AQLADVNSNAAAFLK (SEQ ID NO: 5) |
| | 4 | E1_V4_16 + 31: NCILLYGAANTGKSLFGMSL (SEQ ID NO: 6)<br>E1_V4_18 + 52 + 58: NCLVLCGPANTGKSYFGMSL (SEQ ID NO: 7)<br>E1_V4_53: NCLVIYGPPNTGKSCFAMSL (SEQ ID NO: 8) |
| | 5 | E1_V5_16 + 31 + 52: WPYLHSRLVVFTFPNPF (SEQ ID NO: 9)<br>E1_V5_18 + 58: WPYLESRITVFEFPNAF (SEQ ID NO: 10)<br>E1_V5_53: LRYLHSRIHVLQFLNPF (SEQ ID NO: 11) |

Identified 5 fragments within the E1 protein with windows conserved at the same position within their respective genotypes. Cladistics identified the most suitable genotype combinations providing high level shared consensus identity (FIG. 2).

TABLE 3

_E2 Candidate

| Approach: | | Chimerics |
|---|---|---|
| Fragments: | 1 (16 + 31) | E2_C1-1_16 + 31 NVCQDKILEHYENDSKD (SEQ ID NO: 12)<br>E2_C1-2_16 + 31 ILEHYENDSKDLCDHI (SEQ ID NO: 13)<br>E2_C1-3_16 + 31 CDHIDYWKHIRLECAIMYKAR (SEQ ID NO: 14)<br>E2_C1-4_16 + 31 IRLECAIMYKAREMGFH (SEQ ID NO: 15)<br>E2_C1-5_16 + 31 QFDGDICNTMHYTNW (SEQ ID NO: 16)<br>E2_C1-6_16 + 31 IYICEDAQCTVVEGQVD (SEQ ID NO: 17)<br>E2_C1-7_16 + 31 KKWEVHAGGQVILCPES (SEQ ID NO: 18)<br>E2_C1-8_16 + 31 GQRRIKRPRSE (SEQ ID NO: 19)<br>E2_C1-9_16 + 31 NCHPNKLL (SEQ ID NO: 20)<br>E2_C1-10_16 + 31 ILKCLRYRFKKHCKL (SEQ ID NO: 21)<br>E2_C1-11_16 + 31 SSTWHWTCHDGKHK (SEQ ID NO: 22)<br>E2_C1-12_16 + 31 WHWTCHDGKHKNAIVTLTY (SEQ ID NO: 23) |
| | 2 (52 + 58) | E2_C1-1_52 + 58 YEADKNDLNAQIEHWKLIRMECAIFYKAKELGIS (SEQ ID NO: 24)<br>E2_C1-2_52 + 58 ICHQVVPPLAASKAKACQAIELQLALEALNASPY (SEQ ID NO: 25)<br>E2_C1-3_52 + 58 DEWTLQQTSLEMWLAEPQ (SEQ ID NO: 26)<br>E2_C1-4_52 + 58 FKKHGITITVQYDNDKANTMDYTNWKEIY (SEQ ID NO: 27)<br>E2_C1-5_52 + 58 VIVCPASIPSDEISTEEA (SEQ ID NO: 28) |
| | 3 (53 + 18) | E2_C1-1_53 + 18 DHIDYWKAIRQENAIFFAAR (SEQ ID NO: 29)<br>E2_C1-2_53 + 18 HQVVPALNICKAKACKAIE (SEQ ID NO: 30)<br>E2_C1-3_53 + 18 WNTEPKHCFKKGGQHIEVWFD (SEQ ID NO: 31) |

TABLE 3-continued

| E2 Candidate | |
|---|---|
| | E2_C1-4_53 + 18 YVAWDSVYYCGDDGWCKT (SEQ ID NO: 32) |
| | E2_C1-5_53 + 18 EAEKYGCKGTWEVHFG (SEQ ID NO: 33) |
| | E2_C1-6_53 + 18 NSIDCNDSMCSTFDDNVSATELVK (SEQ ID NO: 34) |
| Approach: | Modified Variant |
| Fragments: 1 | E2_FC1_All DHIDYWKLIRLECAIFYKAR (SEQ ID NO: 35) |

Due to alignment inconsistencies three chimerics were created based on phylogeny (16 & 31, 52 & 58, 53 & 18) (FIG. 3a). Additionally all genotypes were inputted into the algorithm in a similar fashion to creation of variants but the programs filter for only selecting conserved windows from each genotype with a shared % consensus identity of greater than 60% was not disabled. This identified one fragment, referred to as 'modified variant' (FIG. 3b).

TABLE 4

| E4 Candidate | | |
|---|---|---|
| Approach: | | Chimerics |
| Fragments: | 1 (16 + 31) | E4_C1-1_16 + 31 RRLSSDQDQSQ (SEQ ID NO: 36) |
| | 2 (52 + 58) | E4_C1-1_52 + 58 LVTKYPLLKLLS (SEQ ID NO: 37) |
| | 3 (53) | E4_C1-1_53 RPPNMGVKAHGKCIWENKVFIVPTLCPVPLDPTYPLLKLLT (SEQ ID NO: 38) |
| | | E4_C1-2_53 TQTTTPENTSLVELRVTTPKSTVVIRLHL (SEQ ID NO: 39) |
| | 4 (18) | E4_C1-1_18 TTRYPLLSLLNSYSTPPHRIPAPCPWAPQRP (SEQ ID NO: 40) |
| Approach: | | Variants |
| Fragments: | 1 | E4_V1_16 + 31 PIPKPSPWAP (SEQ ID NO: 41) |
| | | E4_V1_18 RIPAPCPWAP (SEQ ID NO: 42) |
| | | E4_V1_52 PRPPHCPWVP (SEQ ID NO: 43) |
| | | E4_V1_53 PPPPPRPWAP (SEQ ID NO: 44) |
| | | E4_V1_58 Excluded |

Four chimerics were created, two of the fragments are genotype specific (FIG. 4a). Additionally, variant analysis identified one region (FIG. 4b).

TABLE 5

| E5 Candidate | | |
|---|---|---|
| Approach: | | Chimerics |
| Fragments: | 1 (16 + 31) | E5_C1_16_31 CFLLCFCVLLCVCLLIRPLLLSVSTY (SEQ ID NO: 45) |
| | 2 (52 + 58) | E5_C1_52 + 58 LRPLLLSISVYAQVLVLVLLLWVSIGS (SEQ ID NO: 46) |
| | 3 (18) | E5_C1_18 LLPSVCMCAYAWVLVFVYIVVITSPATA (SEQ ID NO: 47) |

Three chimerics were created (FIG. 5).

TABLE 6

| E6 Candidate | | |
|---|---|---|
| Approach: | | Chimeric-Variants |
| Fragments: | 1 (16 + 18) | E6_CV1_16 IVYRDGNPYAVCDKCLKFYSKISEYRHYCYSLYGTTLEQQ YNKPLCDLLIRCIN (SEQ ID NO: 48) |

TABLE 6-continued

| | | E6 Candidate |
|---|---|---|
| Approach: | | Chimeric-Variants |
| | | E6_CV1_18 VVYRDSIPHAACHKCIDFYSRIRELRHYSDSVYGDTLEKLT NTGLYNLLIRCLR (SEQ ID NO: 49) |
| | 2 | E6_CV2-1_53 VFCKKALTASEVYNFAYTDLRVVYRD (SEQ ID NO: 50) |
| | (53 + 31) | E6_CV2-2_53 SKVRKLRYYNCSVYGASL (SEQ ID NO: 51) |
| | | E6_CV2-1_31 VYCKGQLTETEVLDFAFTDLTIVYRD (SEQ ID NO: 52) |
| | | E6_CV2-2_31 SKVSEFRWYRYSVYGTTL (SEQ ID NO:_53) |
| | 3 | E6_CV3-1_52 + 58 CVECKKTLQRSEVYD (SEQ ID NO: 54) |
| | (52_58) | E6_CV3-2_52 + 58 CQRPLCPQEKKRHVDLNKRFH (SEQ ID NO: 55) |

The E6 protein showed very limited conservation across genotypes. Instead ingroups were processed to produce chimerics without the shared % consensus identity filter, but the conserved windows were not combined to produce a consensus, except for genotypes 52 and 58. (FIG. 6)

TABLE 7

| | | E7 Candidate |
|---|---|---|
| Approach: | | Chimerics |
| Fragments: | 1 (16 + 31) | E7_C1_16 + 31 TLHEYMLDLQPETTDLYCYEQ (SEQ ID NO: 56) |
| | 2 (52 + 58) | E7_C1_58_52 PETTDLHCYEQLGDSSDEEDTGGLDG (SEQ ID NO: 57) |
| | 3 (53 + 18) | Excluded |
| Approach: | | Chimeric-Variants |
| Fragments: | 1 | E7_V1_53 DEDEDEVDHLQEQPQQARRDEQHPCYLIETQCC RCESLV (SEQ ID NO: 58) E7_V1_18 EENDEIDGVNHQHLPARRAEPQRH TABLE 8-continued Summary of Vaccine Fragments with SEQ ID NOs.

| SEQ ID NO: | Protein | Fragment |
|---|---|---|
| 10 | E1_V5_18 + 58 | WPYLESRITVFEFPNAF |
| 11 | E1_V5_53 | LRYLHSRIHVLQFLNPF |
| 12 | E2_C1-1_16 + 31 | NVCQDKILEHYENDSKD |
| 13 | E2_C1-2_16 + 31 | ILEHYENDSKDLCDHI |
| 14 | E2_C1-3_16 + 31 | CDHIDYWKHIRLECAIMYKAR |
| 15 | E2_C1-4_16 + 31 | IRLECAIMYKAREMGFH |
| 16 | E2_C1-5_16 + 31 | QFDGDICNTMHYTNW |
| 17 | E2_C1-6_16 + 31 | IYICEDAQCTVVEGQVD |
| 18 | E2_C1-7_16 + 31 | KKWEVHAGGQVILCPES |
| 19 | E2_C1-8_16 + 31 | GQRRIKRPRSE |
| 20 | E2_C1-9_16 + 31 | NCHPNKLL |
| 21 | E2_C1-10_16 + 31 | ILKCLRYRFKKHCKL |
| 22 | E2_C1-11_16 + 31 | SSTWHWTCHDGKHK |
| 23 | E2_C1-12_16 + 31 | WHWTCHDGKHKNAIVTLTY |
| 24 | E2_C1-1_52 + 58 | YEADKNDLNAQIEHWKLIRMECAIFYKAKELGIS |
| 25 | E2_C1-2_52 + 58 | ICHQVVPPLAASKAKACQAIELQLALEALNASPY |
| 26 | E2_C1-3_52 + 58 | DEWTLQQTSLEMWLAEPQ |
| 27 | E2_C1-4_52 + 58 | FKKHGITITVQYDNDKANTMDYTNWKEIY |
| 28 | E2_C1-5_52 + 58 | VIVCPASIPSDEISTEEA |
| 29 | E2_C1-1_53 + 18 | DHIDYWKAIRQENAIFFAAR |
| 30 | E2_C1-2_53 + 18 | HQVVPALNICKAKACKAIE |
| 31 | E2_C1-3_53 + 18 | WNTEPKHCFKKGGQHIEVWFD |
| 32 | E2_C1-4_53 + 18 | YVAWDSVYYCGDDGWCKT |
| 33 | E2_C1-5_53 + 18 | EAEKYGCKGTWEVHFG |
| 34 | E2_C1-6_53 + 18 | NSIDCNDSMCSTFDDNVSATELVK |
| 35 | E2_FC1_All | DHIDYWKLIRLECAIFYKAR |
| 36 | E4_C1-1_16 + 31 | RRLSSDQDQSQ |
| 37 | E4_C1-1_52 + 58 | LVTKYPLLKLLS |
| 38 | E4_C1-1_53 | RPPNMGVKAHGKCIWENKVFIVPTLCPVPLDPTYPLLKLLT |
| 39 | E4_C1-2_53 | TQTTTPENTSLVELRVTTPKSTVVIRLHL |
| 40 | E4_C1-1_18 | TTRYPLLSLLNSYSTPPHRIPAPCPWAPQRP |
| 41 | E4_V1_16 + 31 | PIPKPSPWAP |
| 42 | E4_V1_18 | RIPAPCPWAP |
| 43 | E4_V1_52 | PRPPHCPWVP |
| 44 | E4_V1_53 | PPPPPRPWAP |
| 45 | E5_C1_16_31 | CFLLCFCVLLCVCLLIRPLLLSVSTY |
| 46 | E5_C1_52 + 58 | LRPLLLSISVYAQVLVLVLLLWVSIGS |

TABLE 8-continued

Summary of Vaccine Fragments with SEQ ID NOs.

| SEQ ID NO: | Protein | Fragment |
|---|---|---|
| 47 | E5_C1_18 | LLPSVCMCAYAWVLVFVYIVVITSPATA |
| 48 | E6_CV1_16 | IVYRDGNPYAVCDKCLKFYSKISEYRHYCYSLYGTTLEQQY NKPLCDLLIRCIN |
| 49 | E6_CV1_18 | VVYRDSIPHAACHKCIDFYSRIRELRHYSDSVYGDTLEKLT NTGLYNLLIRCLR |
| 50 | E6_CV2-1_53 | VFCKKALTASEVYNFAYTDLRVVYRD |
| 51 | E6_CV2-2_53 | SKVRKLRYYNCSVYGASL |
| 52 | E6_CV2-1_31 | VYCKGQLTETEVLDFAFTDLTIVYRD |
| 53 | E6_CV2-2_31 | SKVSEFRWYRYSVYGTTL |
| 54 | E6_CV3-1_52 + 58 | CVECKKTLQRSEVYD |
| 55 | E6_CV3-2_52 + 58 | CQRPLCPQEKKRHVDLNKRFH |
| 56 | E7_C1_16 + 31 | TLHEYMLDLQPETTDLYCYEQ |
| 57 | E7_C1_58_52 | PETTDLHCYEQLGDSSDEEDTGGLDG |
| 58 | E7_V1_53 | DEDEDEVDHLQEQPQQARRDEQHPCYLIETQCCRCESLV |
| 59 | E7_V1_18 | EENDEIDGVNHQHLPARRAEPQRHTMLCMCCKCEARI |

HPV3 Nucleotide Sequence (SEQ ID NO: 60)

From Start codon, starting with the TPA leading sequence encoded with an additional linker (TPA and linker are bold and underlined).

ATGGATGCTATGAAGAGGGGCCTGTGCTGCGTGCTGCTGCTGTGTGGCGC
CGTGTTTGTGTCCCCCAGCCAGGAAATCCACGCCCGGTTCAGAAGAGGCA
GCAAGCTGGCCGACGAGGACGAGACAGCCTACGACAGCGGCACCGACCTG
ATCGACTTCATCGACGACAGCGACGAGAATGAGAACGACTCCGACACCGG
CGAGGACATGGTGGATTTCATCGACAACGACGAAACCGACGAAGAGAGCA
CCGAGAGCGACCTGGACGGCTTTATCGACAACTCCGCCCAGCTGGCTGAC
AGCGACAGCAATGCCTGCGCCTTCCTGAAGGCTCAGCTGGCAGACGTGAA
CAGCAACGCCGCTGCTTTTCTGAAGAACTGCATCCTGCTGTACGGCGCTG
CCAACACCGGCAAGAGCCTGTTCGGCATGAGCCTGAACTGCCTGGTGCTG
TGCGGCCCAGCCAATACCGGAAAGTCCTACTTCGGCATGTCCCTGAATTG
TCTCGTGATCTACGGCCCACCTAACACAGGCAAGTCCTGCTTTGCCATGT
CTCTGTGGCCCTACCTGCACAGCAGACTGGTGGTGTTTACCTTCCCCAAC
CCCTTCTGGCCTTACCTGGAAAGCCGGATCACCGTGTTCGAGTTCCCCAA
TGCCTTTCTGAGATACCTGCACTCCCGGATCCACGTGCTGCAGTTTCTGA
ACCCCTTCAACGTGTGCCAGGACAAGATCCTGGAACACTACGAGAACGAC
AGCAAGGACATTCTGGAACATTATGAGAATGATTCCAAGGACCTGTGCGA
CCACATCTGCGATCACATCGACTACTGGAAGCACATCCGGCTGGAATGCG
CCATCATGTACAAGGCCCGGATCAGACTGGAATGTGCTATTATGTATAAG

-continued

GCTCGCGAGATGGGCTTCCACCAGTTCGACGGCGACATCTGCAACACCAT
GCACTACACCAACTGGATCTATATCTGCGAGGACGCCCAGTGCACCGTGG
TGGAAGGCCAGGTGGACAAGAAATGGGAGGTGCACGCTGGCGGCCAAGTG
ATCCTGTGTCCTGAGAGCGGCCAGCGGCGGATCAAGAGGCCCAGAAGCGA
GAACTGCCACCCCAACAAGCTGCTGATCCTGAAGTGCCTGCGGTACAGAT
TCAAGAAGCACTGCAAGCTGAGCAGCACCTGGCACTGGACCTGCCACGAC
GGCAAGCACAAGTGGCATTGGACATGTCACGATGGGAAACACAAGAACGC
CATTGTGACCCTGACCTACTACGAGGCCGACAAGAACGACCTGAACGCCC
AGATCGAGCACTGGAAACTGATCCGGATGGAATGTGCAATCTTCTATAAG
GCCAAAGAGCTGGGCATCAGCATCTGCCACCAGGTGGTGCCTCCACTGGC
CGCCTCTAAAGCCAAAGCCTGCCAGGCCATCGAACTGCAGCTGGCCCTGG
AAGCCCTGAATGCCAGCCCCTACGATGAGTGGACCCTGCAGCAGACCAGC
CTGGAAATGTGGCTGCCGAGCCCCAGTTTAAGAAGCACGGCATCACCAT
CACCGTGCAGTACGACAATGACAAGGCCAATACCATGGATTACACAAATT
GGAAAGAAATCTACGTGATCGTGTGCCCCGCCAGCATCCCCTCCGATGAG
ATCAGCACCGAGGAAGCCGACCACATTGATTATTGGAAAGCCATCAGGCA
GGAAAACGCCATCTTCTTCGCCGCCAGACACCAGGTGGTGCCCGCCCTGA
ATATCTGCAAGGCCAAGGCCTGTAAAGCCATCGAGTGGAACACCGAGCCC
AAGCACTGCTTCAAGAAGGGCGGCCAGCACATCGAAGTGTGGTTCGACTA
CGTGGCCTGGGACAGCGTGTACTACTGCGGCGACGATGGCTGGTGCAAGA

-continued

CCGAGGCCGAGAAGTACGGCTGCAAGGGCACCTGGGAAGTGCATTTCGGC
AACAGCATCGACTGCAACGACTCCATGTGCAGCACCTTCGACGACAACGT
GTCCGCCACCGAGCTCGTGAAGGACCATATCGACTATTGGAAGCTGATTC
GCCTGGAATGTGCCATTTTTTACAAGGCCAGACGGCGGCTGTCCAGCGAC
CAGGATCAGTCTCAGCTCGTGACCAAGTACCCCCTGCTGAAGCTGCTGTC
CAGACCCCCCAACATGGGCGTGAAGGCCCACGGCAAGTGCATCTGGGAGA
ACAAGGTGTTCATCGTGCCCACCCTGTGCCCCGTGCCTCTGGATCCAACA
TATCCTCTGCTGAAACTGCTGACCACCCAGACCACCACCCCCGAGAATAC
CTCCCTGGTGGAACTGAGAGTGACCACCCCCAAGAGCACAGTCGTGATCA
GGCTGCACCTGACCACCAGATACCCACTGCTGTCACTGCTGAACAGCTAC
AGCACCCCCCCTCACCGGATCCCTGCTCCATGTCCTTGGGCTCCTCAGAG
GCCCCCCATCCCTAAGCTTCTCCATGGGCCCCTAGAATCCCTGCCCCTT
GCCCCTGGGCACCTCCTAGACCTCCACACTGTCCATGGGTGCCCCCTCCA
CCTCCTCCAAGACCTTGGGCCCCTTGCTTCCTGCTGTGCTTTTGTGTGCT
GCTGTGCGTGTGCCTGCTGATCAGACCCCTGCTGCTGAGTGTGTCCACCT
ACCTGAGGCCTCTGCTGCTGTCTATCAGCGTGTACGCTCAGGTGCTGGTG
CTGGTGCTGCTGCTGTGGGTGTCCATCGGAAGCCTGCTGCCCAGCGTGTG
CATGTGTGCCTATGCCTGGGTGCTGGTGTTCGTGTACATCGTCGTGATTA
CCAGCCCCGCCACCGCCATCGTGTACCGGGATGGCAATCCTTACGCCGTG
TGCGACAAGTGCCTGAAGTTCTACAGCAAGATCAGCGAGTACCGGCACTA
CTGCTACAGCCTGTACGGCACCACCCTGGAACAGCAGTACAACAAGCCCC
TGTGCGATCTGCTGATTCGGTGCATCAACTGTGGTGTACAGAGACTCCATC
CCCCACGCCGCCTGCCACAAGTGTATCGACTTCTACTCCAGAATCAGAGA
GCTGCGGCACTACAGCGACTCCGTGTACGGCGATACCCTGGAAAAGCTGA
CCAACACTGGCCTGTACAACCTGCTGATTAGATGCCTGCGGGTGTTCTGC
AAGAAGGCCCTGACAGCCAGCGAGGTGTACAACTTCGCCTACACCGATCT
GCGGGTGGTGTATCGGGACAGCAAAGTGCGGAAGCTGAGGTACTACAACT
GCTCTGTGTATGGCGCCAGCCTGGTGTATTGCAAGGGACAGCTGACCGAG
ACAGAGGTGCTGGATTTCGCCTTCACAGACCTGACAATCGTGTATCGCGA
CTCCAAGGTGTCCGAGTTCCGGTGGTACAGATATTCCGTGTATGGCACCA
CACTGTGCGTGGAATGCAAGAAAACCCTGCAGAGATCTGAGGTGTACGAC
TGCCAGCGGCCACTGTGTCCGCAGGAAAAGAAAAGACACGTGGACCTGAA
CAAGCGGTTCCACACCCTGCACGAGTACATGCTGGATCTGCAGCCCGAGA
CAACCGACCTGTACTGCTACGAGCAGCTGAAACCACTGATCTGCACTGT
TATGAGCAGCTGGGAGACAGCTCCGATGAAGAGGACACTGGCGGCCTGGA
TGGGGACGAGGATGAGGACGAAGTGGACCATCTGCAGGAACAGCCCCAGC
AGGCTAGACGGGACGAACAGCACCCTTGCTATCTGATCGAGACACAGTGC
TGCAGATGCGAATCTCTGGTGGAAGAGAACGACGAGATCGACGGCGTGAA
CCACCAGCATCTGCCCGCTAGAAGGGCCGAGCCTCAGAGACACACCATGC
TGTGTATGTGCTGCAAGTGCGAGGCCAGAATCGCCGGCTCTGGACCTGGC

-continued

GCCTCTGGCAAGCCTATCCCCAATCCACTGCTGGGCCTGGACTCCACCCG
GACCTGATAA

HPV3 Nucleotide sequence without encoding a
peptide adjuvant/TPA (SEQ ID NO: 65)
GACGAGGACGAGACAGCCTACGACAGCGGCACCGACCTG
ATCGACTTCATCGACGACAGCGACGAGAATGAGAACGACTCCGACACCGG
CGAGGACATGGTGGATTTCATCGACAACGACGAAACCGACGAAGAGAGCA
CCGAGAGCGACCTGGACGGCTTTATCGACAACTCCGCCCAGCTGGCTGAC
AGCGACAGCAATGCCTGCGCCTTCCTGAAGGCTCAGCTGGCAGACGTGAA
CAGCAACGCCGCTGCTTTTCTGAAGAACTGCATCCTGCTGTACGGCGCTG
CCAACACCGGCAAGAGCCTGTTCGGCATGAGCCTGAACTGCCTGGTGCTG
TGCGGCCCAGCCAATACCGGAAAGTCCTACTTCGGCATGTCCCTGAATTG
TCTCGTGATCTACGGCCCCACCTAACACAGGCAAGTCCTGCTTTGCCATGT
CTCTGTGGCCCTACCTGCACAGCAGACTGGTGGTGTTTACCTTCCCCAAC
CCCTTCTGGCCTTACCTGGAAAGCCGGATCACCGTGTTCGAGTTCCCCAA
TGCCTTTCTGAGATACCTGCACTCCCGGATCCACGTGCTGCAGTTTCTGA
ACCCCTTCAACGTGTGCCAGGACAAGATCCTGGAACACTACGAGAACGAC
AGCAAGGACATTCTGGAACATTATGAGAATGATTCCAAGGACCTGTGCGA
CCACATCTGCGATCACATCGACTACTGGAAGCACATCCGGCTGGAATGCG
CCATCATGTACAAGGCCCGGATCAGACTGGAATGTGCTATTATGTATAAG
GCTCGCGAGATGGCTTCCACCAGTTCGACGGCGACATCTGCAACACCAT
GCACTACACCAACTGGATCTATATCTGCGAGGACGCCCAGTGCACCGTGG
TGGAAGGCCAGGTGGACAAGAAATGGAGGTGCACGCTGGCGGCCAAGTG
ATCCTGTGTCCTGAGAGCGGCCAGCGGCGGATCAAGAGGCCCAGAAGCGA
GAACTGCCACCCCAACAAGCTGCTGATCCTGAAGTGCCTGCGGTACAGAT
TCAAGAAGCACTGCAAGCTGAGCAGCACCTGGCACTGGACCTGCCACGAC
GGCAAGCACAAGTGGCATTGGACATGTCACGATGGGAAACACAAGAACGC
CATTGTGACCCTGACCTACTACGAGGCCGACAAGAACGACCTGAACGCCC
AGATCGAGCACTGGAAACTGATCCGGATGGAATGTGCAATCTTCTATAAG
GCCAAAGAGCTGGGCATCAGCATCTGCCACCAGGTGGTGCCTCCACTGGC
CGCCTCTAAAGCCAAAGCCTGCCAGGCCATCGAACTGCAGCTGGCCCTGG
AAGCCCTGAATGCCAGCCCCTACGATGAGTGGACCCTGCAGCAGACCAGC
CTGGAAATGTGGCTGGCCGAGCCCCAGTTTAAGAAGCACGGCATCACCAT
CACCGTGCAGTACGACAATGACAAGGCCAATACCATGGATTACACAAATT
GGAAAGAAATCTACGTGATCGTGTGCCCCGCCAGCATCCCCTCCGATGAG
ATCAGCACCGAGGAAGCCGACCACATTGATTATTGGAAAGCCATCAGGCA
GGAAAACGCCATCTTCTTCGCCGCCAGACACCAGGTGGTGCCCGCCCTGA
ATATCTGCAAGGCCAAGGCCTGTAAAGCCATCGAGTGGAACACCGAGCCC
AAGCACTGCTTCAAGAAGGGCGGCCAGCACATCGAAGTGTGGTTCGACTA
CGTTGGCCTGGGACAGCGTGTACTACTGCGGCGACGATGGCTGGTGCAAGA

```
CCGAGGCCGAGAAGTACGGCTGCAAGGGCACCTGGGAAGTGCATTTCGGC
AACAGCATCGACTGCAACGACTCCATGTGCAGCACCTTCGACGACAACGT
GTCCGCCACCGAGCTCGTGAAGGACCATATCGACTATTGGAAGCTGATTC
GCCTGGAATGTGCCATTTTTTACAAGGCCAGACGGCGGCTGTCCAGCGAC
CAGGATCAGTCTCAGCTCGTGACCAAGTACCCCCTGCTGAAGCTGCTGTC
CAGACCCCCCAACATGGGCGTGAAGGCCCACGGCAAGTGCATCTGGGAGA
ACAAGGTGTTCATCGTGCCCACCCTGTGCCCCGTGCCTCTGGATCCAACA
TATCCTCTGCTGAAACTGCTGACCACCCAGACCACCACCCCCGAGAATAC
CTCCCTGGTGGAACTGAGAGTGACCACCCCCAAGAGCACAGTCGTGATCA
GGCTGCACCTGACCACCAGATACCCACTGCTGTCACTGCTGAACAGCTAC
AGCACCCCCCCTCACCGGATCCCTGCTCCATGTCCTTGGGCTCCTCAGAG
GCCCCCCATCCCTAAGCTTCTCCATGGGCCCCTAGAATCCCTGCCCCTT
GCCCCTGGGCACCTCCTAGACCTCCACACTGTCCATGGGTGCCCCCTCCA
CCTCCTCCAAGACCTTGGGCCCCTTGCTTCCTGCTGTGCTTTTGTGTGCT
GCTGTGCGTGTGCCTGCTGATCAGACCCCTGCTGCTGAGTGTGTCCACCT
ACCTGAGGCCTCTGCTGCTGTCTATCAGCGTGTACGCTCAGGTGCTGGTG
CTGGTGCTGCTGCTGTGGGTGTCCATCGGAAGCCTGCTGCCCAGCGTGTG
CATGTGTGCCTATGCCTGGGTGCTGGTGTTCGTGTACATCGTCGTGATTA
CCAGCCCCGCCACCGCCATCGTGTACCGGGATGGCAATCCTTACGCCGTG
TGCGACAAGTGCCTGAAGTTCTACAGCAAGATCAGCGAGTACCGGCACTA
CTGCTACAGCCTGTACGGCACCACCCTGGAACAGCAGTACAACAAGCCCC
TGTGCGATCTGCTGATTCGGTGCATCAACGTGGTGTACAGAGACTCCATC
CCCCACGCCGCCTGCCACAAGTGTATCGACTTCTACTCCAGAATCAGAGA
GCTGCGGCACTACAGCGACTCCGTGTACGGCGATACCCTGGAAAAGCTGA
CCAACACTGGCCTGTACAACCTGCTGATTAGATGCCTGCGGGTGTTCTGC
AAGAAGGCCCTGACAGCCAGCGAGGTGTACAACTTCGCCTACACCGATCT
GCGGGTGGTGTATCGGGACAGCAAAGTGCGGAAGCTGAGGTACTACAACT
GCTCTGTGTATGGCGCCAGCCTGGTGTATTGCAAGGGACAGCTGACCGAG
ACAGAGGTGCTGGATTTCGCCTTCACAGACCTGACAATCGTGTATCGCGA
CTCCAAGGTGTCCGAGTTCCGGTGGTACAGATATTCCGTGTATGGCACCA
CACTGTGCGTGGAATGCAAGAAAACCCTGCAGAGATCTGAGGTGTACGAC
TGCCAGCGGCCACTGTGTCCGCAGGAAAAGAAAAGACACGTGGACCTGAA
CAAGCGGTTCCACACCCTGCACGAGTACATGCTGGATCTGCAGCCCGAGA
CAACCGACCTGTACTGCTACGAGCAGCCTGAAACCACTGATCTGCACTGT
TATGAGCAGCTGGGAGACAGCTCCGATGAAGAGGACACTGGCGGCCTGGA
TGGGGACGAGGATGAGGACGAAGTGGACCATCTGCAGGAACAGCCCCAGC
AGGCTAGACGGGACGAACAGCACCCCTTGCTATCTGATCGAGACACAGTGC
TGCAGATGCGAATCTCTGGTGGAAGAGAACGACGAGATCGACGGCGTGAA
CCACCAGCATCTGCCCGCTAGAAGGGCCGAGCCTCAGAGACACACCATGC
TGTGTATGTGCTGCAAGTGCGAGGCCAGAATCGCCGGCTCTGGACCTGGC
```

```
GCCTCTGGCAAGCCTATCCCCAATCCACTGCTGGGCCTGGACTCCACCCG
GACCTGATAA
```

HPV3 Polypeptide Sequence (SEQ ID NO: 61)
From Start codon, starting with the TPA leading sequence.

MDAMKRGLCCVLLLCGAVEVSPSQEIHARFRRGSKLADEDETAYDSGTDL
IDFIDDSDENENDSDTGEDMVDFIDNDETDEESTESDLDGFIDNSAQLAD
SDSNACAFLKAQLADVNSNAAAFLKNCILLYGAANTGKSLFGMSLNCLVL
CGPANTGKSYEGMSLNCLVIYGPPNIGKSCFAMSLWPYLHSRLVVETFPN
PFWPYLESRITVFEFPNAFLRYLHSRIHVLQFLNPFNVCQDKILEHYEND
SKDILEHYENDSKDLCDHICDHIDYWKHIRLECAIMYKARIRLECAIMYK
AREMGFHQFDGDICNTMHYTNWIYICEDAQCTVVEGQVDKKWEVHAGGQV
ILCPESGQRRIKRPRSENCHPNKLLILKCLRYRFKKHCKLSSTWHWTCHD
GKHKWHWTCHDGKHKNAIVTLTYYEADKNDLNAQIEHWKLIRMECAIFYK
AKELGISICHQVVPPLAASKAKACQAIELQLALEALNASPYDEWTLQQTS
LEMWLAEPQFKKHGITITVQYDNDKANTMDYTNWKEIYVIVCPASIPSDE
ISTEEADHIDYWKAIRQENAIFFAARHQVVPALNICKAKACKAIEWNTEP
KHCFKKGGQHIEVWFDYVAWDSVYYCGDDGWCKTEAEKYGCKGTWEVHFG
NSIDCNDSMCSTFDDNVSATELVKDHIDYWKLIRLECAIFYKARRRLSSD
QDQSQLVTKYPLLKLLSRPPNMGVKAHGKCIWENKVFIVPTLCPVPLDPT
YPLLKLLTTQTTTPENTSLVELRVTTPKSTVVIRLHLTTRYPLLSLLNSY
STPPHRIPAPCPWAPQRPPIPKPSPWAPRIPAPCPWAPPRPPHCPWVPPP
PPPRPWAPCFLLCFCVLLCVCLLIRPLLLSVSTYLRPLLLSISVYAQVLV
LVLLLWVSIGSLLPSVCMCAYAWVLVFVYIVVITSPATAIVYRDGNPYAV
CDKCLKFYSKISEYRHYCYSLYGTTLEQQYNKPLCDLLIRCINVVYRDSI
PHAACHKCIDFYSRIRELRHYSDSVYGDTLEKLTNTGLYNLLIRCLRVFC
KKALTASEVYNFAYTDLRVVYRDSKVRKLRYYNCSVYGASLVYCKGQLTE
TEVLDFAFTDLTIVYRDSKVSEFRWYRYSVYGTTLCVECKKTLQRSEVYD
CQRPLCPQEKKRHVDLNKRFHTLHEYMLDLQPETTDLYCYEQPETTDLHC
YEQLGDSSDEEDTGGLDGDEDEDEVDHLQEQPQQARRDEQHPCYLIETQC
CRCESLVEENDEIDGVNHQHLPARRAEPQRHTMLCMCCKCEARIAGSGPG
ASGKPIPNPLLGLDSTRT**

HPV3 polypeptide sequence without the TPA/peptide adjuvant sequence
(SEQ ID NO: 66)

DEDETAYDSGTDL
IDFIDDSDENENDSDTGEDMVDFIDNDETDEESTESDLDGFIDNSAQLAD
SDSNACAFLKAQLADVNSNAAAFLKNCILLYGAANTGKSLFGMSLNCLVL
CGPANTGKSYEGMSLNCLVIYGPPNIGKSCFAMSLWPYLHSRLVVETFPN
PFWPYLESRITVFEFPNAFLRYLHSRIHVLQFLNPFNVCQDKILEHYEND
SKDILEHYENDSKDLCDHICDHIDYWKHIRLECAIMYKARIRLECAIMYK
AREMGFHQFDGDICNTMHYTNWIYICEDAQCTVVEGQVDKKWEVHAGGQV
ILCPESGQRRIKRPRSENCHPNKLLILKCLRYRFKKHCKLSSTWHWTCHD

```
GKHKWHWTCHDGKHKNAIVTLTYYEADKNDLNAQIEHWKLIRMECAIFYK
AKELGISICHQVVPPLAASKAKACQAIELQLALEALNASPYDEWTLQQTS
LEMWLAEPQFKKHGITITVQYDNDKANTMDYTNWKEIYVIVCPASIPSDE
ISTEEADHIDYWKAIRQENAIFFAARHQVVPALNICKAKACKAIEWNTEP
KHCFKKGGQHIEVWFDYVAWDSVYYCGDDGWCKTEAEKYGCKGTWEVHFG
NSIDCNDSMCSTFDDNVSATELVKDHIDYWKLIRLECAIFYKARRRLSSD
QDQSQLVTKYPLLKLLSRPPNMGVKAHGKCIWENKVFIVPTLCPVPLDPT
YPLLKLLTTQTTTPENTSLVELRVTTPKSTVVIRLHLTTRYPLLSLLNSY
STPPHRIPAPCPWAPQRPPIPKPSPWAPRIPAPCPWAPPRPPHCPWVPPP
PPPRPWAPCFLLCFCVLLCVCLLIRPLLLSVSTYLRPLLLSISVYAQVLV
LVLLLWVSIGSLLPSVCMCAYAWVLVFVYIVVITSPATAIVYRDGNPYAV
CDKCLKFYSKISEYRHYCYSLYGTTLEQQYNKPLCDLLIRCINVVYRDSI
PHAACHKCIDFYSRIRELRHYSDSVYGDTLEKLTNTGLYNLLIRCLRVFC
KKALTASEVYNFAYTDLRVVYRDSKVRKLRYYNCSVYGASLVYCKGQLTE
TEVLDFAFTDLTIVYRDSKVSEFRWYRYSVYGTTLCVECKKTL

-continued

```
AGTGACTGGCGATGCTGTCGGAATGGACGATATCCCGCAAGAGGCCCGGCAGTACCGGCATAACC

AAGCCTATGCCTACAGCATCCAGGGTGACGGTGCCGAGGATGACGATGAGCGCATTGTTAGATTT

CATACACGGTGCCTGACTGCGTTAGCAATTTAACTGTGATAAACTACCGCATTAAAGCTTATCGA

TGATAAGCTGTCAAACATGAGAATTGATCCGGAACCCTTAATATAACTTCGTATAATGTATGCTA

TACGAAGTTATTAGGTCCCTCGACTATAGGGTCACCGTCGACAGCGACACACTTGCATCGGATGC

AGCCCGGTTAACGTGCCGGCACGGCCTGGGTAACCAGGTATTTTGTCCACATAACCGTGCGCAAA

ATGTTGTGGATAAGCAGGACACAGCAGCAATCCACAGCAGGCATACAACCGCACACCGAGGTTAC

TCCGTTCTACAGGTTACGACGACATGTCAATACTTGCCCTTGACAGGCATTGATGGAATCGTAGT

CTCACGCTGATAGTCTGATCGACAATACAAGTGGGACCGTGGTCCCAGACCGATAATCAGACCGA

CRAYACGAGTGGGAYCGTGGTCCCAGACTAATAATCAGACCGACGATACGAGTGGGACCGTGGTC

CCAGACTAATAATCAGACCGACGATACGAGTGGGACCGTGGTYCCAGWCTRATWATCAGACCGAC

GATACRAGTGGGRACMGTGGKCCCAGASAKAATAWTCAGRCCgAGWTAYGcWKTCKGGCCTGTAAC

AAAGGACATTAAGTAAAGACAGATAMRMGTgRGACtaaaaCGTGGTCCCAGTCTGATTATCAGAC

CGACGATACGAGTGGGACCGTGGTCCCAGACTAATAATCAGACCGACGATACGAGTGGGACCGTG

GTCCCAGACTAATAATCAGACCGACGATACGAGTGGGACCGTGGTCCCAGTCTGATTATCAGACC

GACGATACAAGTGGAACAGTGGGCCCAGAGAGAATATTCAGGCCAGTTATGCTTTCTGGCCTGTA

ACAAAGGACATTAAGTAAAGACAGATAAACGTAGACTAAAACGTGGTCGCATCAGGGTGCTGGCT

TTTCAAGTTCCTTAAGAATGGCCTCAATTTTCTCTATACACTCAGTTGGAACACGAGACCTGTCC

AGGTTAAGCACCATTTTATCGCCCTTATACAATACTGTCGCTCCAGGAGCAAACTGATGTCGTGA

GCTTAAACTAGTTCTTGATGCAGATGACGTTTTAAGCACAGAAGTTAAAAGAGTGATAACTTCTT

CAGCTTCAAATATCACCCCAGCTTTTTTCTGCTCATGAAGGTTAGATGCCTGCTGCTTAAGTAAT

TCCTCTTTATCTGTAAAGGCTTTTTGAAGTGCATCACCTGACCGGGCAGATAGTTCACCGGGGTG

AGAAAAAGAGCAACAACTGATTTAGGCAATTTGGCGGTGTTGATACAGCGGGTAATAATCTTAC

GTGAAATATTTTCCGCATCAGCCAGCGCAGAAATATTTCCAGCAAATTCATTCTGCAATCGGCTT

GCATAACGCTGACCACGTTCATAAGCACTTGTTGGGCGATAATCGTTACCCAATCTGGATAATGC

AGCCATCTGCTCATCATCCAGCTCGCCAACCAGAACACGATAATCACTTTCGGTAAGTGCAGCAG

CTTTACGACGGCGACTCCCATCGGCAATTTCTATGACACCAGATACTCTTCGACCGAACGCCGGT

GTCTGTTGACCAGTCAGTAGAAAAGAAGGGATGAGATCATCCAGTGCGTCCTCAGTAAGCAGCTC

CTGGTCACGTTCATTACCTGACCATACCCGAGAGGTCTTCTCAACACTATCACCCCGGAGCACTT

CAAGAGTAAACTTCACATCCCGACCACATACAGGCAAAGTAATGGCATTACCGCGAGCCATTACT

CCTACGCGCGCAATTAACGAATCCACCATCGGGGCAGCTGGTGTCGATAACGAAGTATCTTCAAC

CGGTTGAGTATTGAGCGTATGTTTTGGAATAACAGGCGCACGCTTCATTATCTAATCTCCCAGCG

TGGTTTAATCAGACGATCGAAAATTTCATTGCAGACAGGTTCCCAAATAGAAAGAGCATTTCTCC

AGGCACCAGTTGAAGAGCGTTGATCAATGGCCTGTTCAAAAACAGTTCTCATCCGGATCTGACCT

TTACCAACTTCATCCGTTTCACGTACAACATTTTTTAGAACCATGCTTCCCCAGGCATCCCGAAT

TTGCTCCTCCATCCACGGGGACTGAGAGCCATTACTATTGCTGTATTTGGTAAGCAAAATACGTA

CATCAGGCTCGAACCCTTTAAGATCAACGTTCTTGAGCAGATCACGAAGCATATCGAAAAACTGC

AGTGCGGAGGTGTAGTCAAACAACTCAGCAGGCGTGGGAACAATCAGCACATCAGCAGCACATAC

GACATTAATCGTGCCGATACCCAGGTTAGGCGCGCTGTCAATAACTATGACATCATAGTCATGAG

CAACAGTTTCAATGGCCAGTCGGAGCATCAGGTGTGGATCGGTGGGCAGTTTACCTTCATCAAAT

TTGCCCATTAACTCAGTTTCAATACGGTGCAGAGCCAGACAGGAAGGAATAATGTCAAGCCCCGG
```

-continued

```
CCAGCAAGTGGGCTTTATTGCATAAGTGACATCGTCCTTTTCCCCAAGATAGAAAGGCAGGAGAG
TGTCTTCTGCATGAATATGAAGATCTGGTACCCATCCGTGATACATTGAGGCTGTTCCCTGGGGG
TCGTTACCTTCCACGAGCAAAACACGTAGCCCCTTCAGAGCCAGATCCTGAGCAAGATGAACAGA
AACTGAGGTTTTGTAAACGCCACCTTTATGGGCAGCAACCCCGATCACCGGTGGAAATACGTCTT
CAGCACGTCGCAATCGCGTACCAAACACATCACGCATATGATTAATTTGTTCAATTGTATAACCA
ACACGTTGCTCAACCCGTCCTCGAATTTCCATATCCGGGTGCGGTAGTCGCCCTGCTTTCTCGGC
ATCTCTGATAGCCTGAGAAGAAACCCCAACTAAATCCGCTGCTTCACCTATTCTCCAGCGCCGGG
TTATTTTCCTCGCTTCCGGGCTGTCATCATTAAACTGTGCAATGGCGATAGCCTTCGTCATTTCA
TGACCAGCGTTTATGCACTGGTTAAGTGTTTCCATGAGTTTCATTCTGAACATCCTTTAATCATT
GCTTTGCGTTTTTTTATTAAATCTTGCAATTTACTGCAAAGCAACAACAAAATCGCAAAGTCATC
AAAAAACCGCAAAGTTGTTTAAAATAAGAGCAACACTACAAAAGGAGATAAGAAGAGCACATACC
TCAGTCACTTATTATCACTAGCGCTCGCCGCAGCCGTGTAACCGAGCATAGCGAGCGAACTGGCG
AGGAAGCAAAGAAGAACTGTTCTGTCAGATAGCTCTTACGCTCAGCGCAAGAAGAAATATCCACC
GTGGGAAAAACTCCAGGTAGAGGTACACACGCGGATAGCCAATTCAGAGTAATAAACTGTGATAA
TCAACCCTCATCAATGATGACGAACTAACCCCCGATATCAGGTCACATGACGAAGGGAAAGAGAA
GGAAATCAACTGTGACAAACTGCCCTCAAATTTGGCTTCCTTAAAAATTACAGTTCAAAAAGTAT
GAGAAAATCCATGCAGGCTGAAGGAAACAGCAAAACTGTGACAAATTACCCTCAGTAGGTCAGAA
CAAATGTGACGAACCACCCTCAAATCTGTGACAGATAACCCTCAGACTATCCTGTCGTCATGGAA
GTGATATCGCGGAAGGAAAATACGATATGAGTCGTCTGGCGGCCTTTCTTTTTCTCAATGTATGA
GAGGCGCATTGGAGTTCTGCTGTTGATCTCATTAACACAGACCTGCAGGAAGCGGCGGCGGAAGT
CAGGCATACGCTGGTAACTTTGAGGCAGCTGGTAACGCTCTATGATCCAGTCGATTTTCAGAGAG
ACGATGCCTGAGCCATCCGGCTTACGATACTGACACAGGGATTCGTATAAACGCATGGCATACGG
ATTGGTGATTTCTTTTGTTTCACTAAGCCGAAACTGCGTAAACCGGTTCTGTAACCCGATAAAGA
AGGGAATGAGATATGGGTTGATATGTACACTGTAAAGCCCTCTGGATGGACTGTGCGCACGTTTG
ATAAACCAAGGAAAAGATTCATAGCCTTTTTCATCGCCGGCATCCTCTTCAGGGCGATaAAAAAC
CACTTCCTTCCCCGCGAAACTCTTCAATGCCTGCCGTATATCCTTACTGGCTTCCGCAGAGGTCA
ATCCGAATATTTCAGCATATTTAGCAACATGGATCTCGCAGATACCGTCATGTTCCTGTAGGGTG
CCATCAGATTTTCTGATCTGGTCAACGAACAGATACAGCATACGTTTTTGATCCCGGGAGAGACT
ATATGCCGCCTCAGTGAGGTCGTTTGACTGGACGATTCGCGGGCTATTTTTACGTTTCTTGTGAT
TGATAACCGCTGTTTCCGCCATGACAGATCCATGTGAAGTGTGACAAGTTTTTAGATTGTCACAC
TAAATAAAAAAGAGTCAATAAGCAGGGATAACTTTGTGAAAAAACAGCTTCTTCTGAGGGCAATT
TGTCACAGGGTTAAGGGCAATTTGTCACAGACAGGACTGTCATTTGAGGGTGATTTGTCACACTG
AAAGGGCAATTTGTCACAACACCTTCTCTAGAACCAGCATGGATAAAGGCCTACAAGGCGCTCTA
AAAAAGAAGATCTAAAAACTATaAAAAAAATAATTATAAAAATATCCCCGTGGATAAGTGGATAA
CCCCAAGGGAAGTTTTTtCAGGCATCGTGTGTAAGCAGAATATATAAGTGCTGTTCCCTGGTGCT
TCCTCGCTCACTCGAGGGCTTCGCCCTGTCGCTCAACTGCGGCGAGCACTACTGGCTGTAAAAGG
ACAGACCACATCATGGTTCTGTGTTCATTAGGTTGTTCTGTCCATTGCTGACATAATCCGCTCCA
CTTCAACGTAACACCGCACGAAGATTTCTATTGTTCCTGAAGGCATATTCAAATCGTTTTCGTTA
CCGCTTGCAGGCATCATGACAGAACACTACTTCCTATAAACGCTACACAGGCTCCTGAGATTAAT
AATGCGGATCTCTACGATAATGGGAGATTTTCCCGACTGTTTCGTTCGCTTCTCAGTGGATAACA
```

-continued

```
GCCAGCTTCTCTGTTTAACAGACAAAAACAGCATATCCACTCAGTTCCACATTTCCATATAAAGG
CCAAGGCATTTATTCTCAGGATAATTGTTTCAGCATCGCAACCGCATCAGACTCCGGCATCGCAA
ACTGCACCCGGTGCCGGGCAGCCACATCCAGCGCAAAAACCTTCGTGTAGACTTCCGTTGAACTG
ATGGACTTATGTCCCATCAGGCTTTGCAGAACTTTCAGCGGTATACCGGCATACAGCATGTGCAT
CGCATAGGAATGGCGGAACGTATGTGGTGTGACCGGAACAGAGAACGTCACACCGTCAGCAGCAG
CGGCGGCAACCGCCTCCCCAATCCAGGTCCTGACCGTTCTGTCCGTCACTTCCCAGATCCGCGCT
TTCTCTGTCCTTCCTGTGCGACGGTTACGCCGCTCCATGAGCTTATCGCGAATAAATACCTGTGA
CGGAAGATCACTTCGCAGAATAAATAAATCCTGGTGTCCCTGTTGATACCGGGAAGCCCTGGGCC
AACTTTTGGCGAAAATGAGACGTTGATCGGCACGTAAGAGGTTCCAACTTTCACCATAATGAAAT
AAGATCACTACCGGGCGTATTTTTTGAGTTATCGAGATTTTCAGGAGCTAAGGAAGCTAAAATGG
AGAAAAAAATCACTGGATATACCACCGTTGATATATCCCAATGGCATCGTAAAGAACATTTTGAG
GCATTTCAGTCAGTTGCTCAATGTACCTATAACCAGACCGTTCAGCTGGATATTACGGCCTTTTT
AAAGACCGTAAAGAAAAATAAGCACAAGTTTTATCCGGCCTTTATTCACATTCTTGCCCGCCTGA
TGAATGCTCATCCGGAGTTCCGTATGGCAATGAAAGACGGTGAGCTGGTGATATGGGATAGTGTT
CACCCTTGTTACACCGTTTTCCATGAGCAAACTGAAACGTTTTCATCGCTCTGGAGTGAATACCA
CGACGATTTCCGGCAGTTTCTACACATATATTCGCAAGATGTGGCGTGTTACGGTGAAAACCTGG
CCTATTTCCCTAAAGGGTTTATTGAGAATATGTTTTTCGTCTCAGCCAATCCCTGGGTGAGTTTC
ACCAGTTTTGATTTAAACGTGGCCAATATGGACAACTTCTTCGCCCCCGTTTTCACCATGGGCAA
ATATTATACGCAAGGCGACAAGGTGCTGATGCCGCTGGCGATTCAGGTTCATCATGCCGTTTGTG
ATGGCTTCCATGTCGGCAGAATGCTTAATGAATTACAACAGTACTGCGATGAGTGGCAGGGCGGG
GCGTAAtTTTTTTAAGGCAGTTATTGGTGCCCTTAAACGCCTGGTTGCTACGCCTGAATAAGTGA
TAATAAGCGGATGAATGGCAGAAATTCGATGATAAGCTGTCAAACATGAGAATTGGTCGACGGCG
CGCCAAAGCTTGCATGCCTGCAGCCGCGTAACCTGGCAAAATCGGTTACGGTTGAGTAATAAATG
GATGCCCTGCGTAAGCGGGGCACATTTCATTACCTCTTTCTCCGCACCCGACATAGATAATAACT
TCGTATAGTATACATTATACGAAGTTATCTAGTAGACTTAATCGCGTTTAAACCCATCATCAATA
ATATACCTCAAACTTTTTGTGCGCGTTAATATGCAAATGAGGCGTTTGAATTTGGGAAGGGAGGA
AGGTGATTGGCCGAGAGAAGGGCGACCGTTAGGGGCGGGGCGAGTGACGTTTTGATGACGTGACC
GCGAGGAGGAGCCAGTTTGCAAGTTCTCGTGGGAAAAGTGACGTCAAACGAGGTGTGGTTTGAAC
ACGGAAATACTCAATTTTCCCGCGCTCTCTGACAGGAAATGAGGTGTTTCTAGGCGGATGCAAGT
GAAAACGGGCCATTTTCGCGCGAAAACTGAATGAGGAAGTGAAAATCTGAGTAATTTCGCGTTTA
TGACAGGGAGGAGTATTTGCCGAGGGCCGAGTAGACTTTGACCGATTACGTGGGGGTTTCGATTA
CCGTGTTTTTCACCTAAATTTCCGCGTACGGTGTCAAAGTCCGGTGTTTTTACGTAGGTGTCAGC
TGATCGCCAGGGTATTTAAACCTGCGCTCTCCAGTCAAGAGGCCACTCTTGAGTGCCAGCGAGAA
GAGTTTTCTCCTCCGCGCGCGAGTCAGATCTACACTTTGAAAGGCGATCGCTAGCGACATCGATC
ACAAGTTTGTACAAAAAAGCAGGCTCCACCATGGGAACCAATTCAgTCGAGCCTTTCACTCATTA
GATGCATGTCGTTACATAACTTACGGTAAATGGCCCGCCTGGCTGACCGCCCAACGACCCCCGCC
CATTGACGTCAATAATGACGTATGTTCCCATAGTAACGCCAATAGGGACTTTCCATTGACGTCAA
TGGGTGGAGTATTTACGGTAAACTGCCCACTTGGCAGTACATCAAGTGTATCATATGCCAAGTAC
GCCCCCTATTGACGTCAATGACGGTAAATGGCCCGCCTGGCATTATGCCCAGTACATGACCTTAT
GGGACTTTCCTACTTGGCAGTACATCTACGTATTAGTCATCGCTATTACCATGGTGATGCGGTTT
TGGCAGTACATCAATGGGCGTGGATAGCGGTTTGACTCACGGGGATTTCCAAGTCTCCACCCCAT
```

-continued

TGACGTCAATGGGAGTTTGTTTTGGCACCAAAATCAACGGGACTTTCCAAAATGTCGTAACAACT

CCGCCCCATTGACGCAAATGGGCGGTAGGCGTGTACGGTGGGAGGTCTATATAAGCAGAGCTCTC

CCTATCAGTGATAGAGATCTCCCTATCAGTGATAGAGATCGTCGACGAGCTCGTTTAGTGAACCG

TCAGATCGCCTGGAGACGCCATCCACGCTGTTTTGACCTCCATAGAAGACACCGGGACCGATCCA

GCCTCCGGTTAAGCTcGgtacCGCTAGCCGCGCCGCCACCATGGATGCTATGAAGAGGGCCTGT

GCTGCGTGCTGCTGCTGTGTGGCGCCGTGTTTGTGTCCCCCAGCCAGGAAATCCACGCCCGGTTC

AGAAGAGGCAGCAAGCTGGCC<u>GAC</u>GAGGACGAGACAGCCTACGACAGCGGCACCGACCTGATCGA

CTTCATCGACGACAGCGACGAGAATGAGAACGACTCCGACACCGGCGAGGACATGGTGGATTTCA

TCGACAACGACGAAACCGACGAAGAGAGCACCGAGAGCGACCTGGACGGCTTTATCGACAACTCC

GCCCAGCTGGCTGACAGCGACAGCAATGCCTGCGCCTTCCTGAAGGCTCAGCTGGCAGACGTGAA

CAGCAACGCCGCTGCTTTTCTGAAGAACTGCATCCTGCTGTACGGCGCTGCCAACACCGGCAAGA

GCCTGTTCGGCATGAGCCTGAACTGCCTGGTGCTGTGCGGCCCAGCCAATACCGGAAAGTCCTAC

TTCGGCATGTCCCTGAATTGTCTCGTGATCTACGGCCCACCTAACACAGGCAAGTCCTGCTTTGC

CATGTCTCTGTGGCCCTACCTGCACAGCAGACTGGTGGTGTTTACCTTCCCCAACCCCTTCTGGC

CTTACCTGGAAAGCCGGATCACCGTGTTCGAGTTCCCCAATGCCTTTCTGAGATACCTGCACTCC

CGGATCCACGTGCTGCAGTTTCTGAACCCCTTCAACGTGTGCCAGGACAAGATCCTGGAACACTA

CGAGAACGACAGCAAGGACATTCTGGAACATTATGAGAATGATTCCAAGGACCTGTGCGACCACA

TCTGCGATCACATCGACTACTGGAAGCACATCCGGCTGGAATGCGCCATCATGTACAAGGCCCGG

ATCAGACTGGAATGTGCTATTATGTATAAGGCTCGCGAGATGGGCTTCCACCAGTTCGACGGCGA

CATCTGCAACACCATGCACTACACCAACTGGATCTATATCTGCGAGGACGCCCAGTGCACCGTGG

TGGAAGGCCAGGTGGACAAGAAATGGGAGGTGCACGCTGGCGGCCAAGTGATCCTGTGTCCTGAG

AGCGGCCAGCGGCGGATCAAGAGGCCCAGAAGCGAGAACTGCCACCCCAACAAGCTGCTGATCCT

GAAGTGCCTGCGGTACAGATTCAAGAAGCACTGCAAGCTGAGCAGCACCTGGCACTGGACCTGCC

ACGACGGCAAGCACAAGTGGCATTGGACATGTCACGATGGGAAACACAAGAACGCCATTGTGACC

CTGACCTACTACGAGGCCGACAAGAACGACCTGAACGCCCAGATCGAGCACTGGAAACTGATCCG

GATGGAATGTGCAATCTTCTATAAGGCCAAAGAGCTGGGCATCAGCATCTGCCACCAGGTGGTGC

CTCCACTGGCCGCCTCTAAAGCCAAAGCCTGCCAGGCCATCGAACTGCAGCTGGCCCTGGAAGCC

CTGAATGCCAGCCCCTACGATGAGTGGACCCTGCAGCAGACCAGCCTGGAAATGTGGCTGGCCGA

GCCCCAGTTTAAGAAGCACGGCATCACCATCACCGTGCAGTACGACAATGACAAGGCCAATACCA

TGGATTACACAAATTGGAAAGAAATCTACGTGATCGTGTGCCCCGCCAGCATCCCCTCCGATGAG

ATCAGCACCGAGGAAGCCGACCACATTGATTATTGGAAAGCCATCAGGCAGGAAAACGCCATCTT

CTTCGCCGCCAGACACCAGGTGGTGCCCGCCCTGAATATCTGCAAGGCCAAGGCCTGTAAAGCCA

TCGAGTGGAACACCGAGCCCAAGCACTGCTTCAAGAAGGGCGGCCAGCACATCGAAGTGTGGTTC

GACTACGTGGCCTGGGACAGCGTGTACTACTGCGGCGACGATGGCTGGTGCAAGACCGAGGCCGA

GAAGTACGGCTGCAAGGGCACCTGGGAAGTGCATTTCGGCAACAGCATCGACTGCAACGACTCCA

TGTGCAGCACCTTCGACGACAACGTGTCCGCCACCGAGCTCGTGAAGGACCATATCGACTATTGG

AAGCTGATTCGCCTGGAATGTGCCATTTTTTACAAGGCCAGACGGCGGCTGTCCAGCGACCAGGA

TCAGTCTCAGCTCGTGACCAAGTACCCCCTGCTGAAGCTGCTGTCCAGACCCCCCAACATGGGCG

TGAAGGCCCACGGCAAGTGCATCTGGGAGAACAAGGTGTTCATCGTGCCCACCCTGTGCCCCGTG

CCTCTGGATCCAACATATCCTCTGCTGAAACTGCTGACCACCCAGACCACCACCCCCGAGAATAC

-continued

```
CTCCCTGGTGGAACTGAGAGTGACCACCCCCAAGAGCACAGTCGTGATCAGGCTGCACCTGACCA

CCAGATACCCACTGCTGTCACTGCTGAACAGCTACAGCACCCCCCCTCACCGGATCCCTGCTCCA

TGTCCTTGGGCTCCTCAGAGGCCCCCCATCCCTAAGCCTTCTCCATGGGCCCCTAGAATCCCTGC

CCCTTGCCCCTGGGCACCTCCTAGACCTCCACACTGTCCATGGGTGCCCCCTCCACCTCCTCCAA

GACCTTGGGCCCCTTGCTTCCTGCTGTGCTTTTGTGTGCTGCTGTGCGTGTGCCTGCTGATCAGA

CCCCTGCTGCTGAGTGTGTCCACCTACCTGAGGCCTCTGCTGCTGTCTATCAGCGTGTACGCTCA

GGTGCTGGTGCTGGTGCTGCTGCTGTGGGTGTCCATCGGAAGCCTGCTGCCCAGCGTGTGCATGT

GTGCCTATGCCTGGGTGCTGGTGTTCGTGTACATCGTCGTGATTACCAGCCCCGCCACCGCCATC

GTGTACCGGGATGGCAATCCTTACGCCGTGTGCGACAAGTGCCTGAAGTTCTACAGCAAGATCAG

CGAGTACCGGCACTACTGCTACAGCCTGTACGGCACCACCCTGGAACAGCAGTACAACAAGCCCC

TGTGCGATCTGCTGATTCGGTGCATCAACGTGGTGTACAGAGACTCCATCCCCCACGCCGCCTGC

CACAAGTGTATCGACTTCTACTCCAGAATCAGAGAGCTGCGGCACTACAGCGACTCCGTGTACGG

CGATACCCTGGAAAAGCTGACCAACACTGGCCTGTACAACCTGCTGATTAGATGCCTGCGGGTGT

TCTGCAAGAAGGCCCTGACAGCCAGCGAGGTGTACAACTTCGCCTACACCGATCTGCGGGTGGTG

TATCGGGACAGCAAAGTGCGGAAGCTGAGGTACTACAACTGCTCTGTGTATGGCGCCAGCCTGGT

GTATTGCAAGGGACAGCTGACCGAGACAGAGGTGCTGGATTTCGCCTTCACAGACCTGACAATCG

TGTATCGCGACTCCAAGGTGTCCGAGTTCCGGTGGTACAGATATTCCGTGTATGGCACCACACTG

TGCGTGGAATGCAAGAAAACCCTGCAGAGATCTGAGGTGTACGACTGCCAGCGGCCACTGTGTCC

GCAGGAAAAGAAAAGACACGTGGACCTGAACAAGCGGTTCCACACCCTGCACGAGTACATGCTGG

ATCTGCAGCCCGAGACAACCGACCTGTACTGCTACGAGCAGCCTGAAACCACTGATCTGCACTGT

TATGAGCAGCTGGGAGACAGCTCCGATGAAGAGGACACTGGCGGCCTGGATGGGACGAGGATGA

GGACGAAGTGGACCATCTGCAGGAACAGCCCCAGCAGGCTAGACGGGACGAACAGCACCCTTGCT

ATCTGATCGAGACACAGTGCTGCAGATGCGAATCTCTGGTGGAAGAGAACGACGAGATCGACGGC

GTGAACCACCAGCATCTGCCCGCTAGAAGGGCCGAGCCTCAGAGACACACCATGCTGTGTATGTG

CTGCAAGTGCGAGGCCAGAATCGCCGGCTCTGGACCTGGCGCCTCTGGCAAGCCTATCCCCAATC

CACTGCTGGGCCTGGACTCCACCCGGACCTGATAAGcggccgctcgagcatgcatctagagggcc ctattctatagtgtcacctaaatgctagagctcgctgatcagcctcgactgtgccttctagttgc cagccatctgttgtttgccccccccgtgccttccttgaccctggaaggtgccactcccactgt cctttcctaataaaatgaggaaattgcatcgcattgtctgagtaggtgtcattctattctggggg gtggggtggggcaggacagcaaggggggaggattgggaagacaatagcaggcatgctggggatgcg gtgggctctatggcttctgaggcggaaagaaccagctggggctcgagggggatcgatcccgtcG

AGATATCTAGACCCAGCTTTCTTGTACAAAGTGGTGATCGATTCGACAGATCGCGATCGCAGTGA

GTAGTGTTCTGGGGCGGGGGAGGACCTGCATGAGGGCCAGAATGACTGAAATCTGTGCTTTTCTG

TGTGTTGCAGCATCATGAGCGGAAGCGGCTCCTTTGAGGGAGGGGTATTCAGCCCTTATCTGACG

GGGCGTCTCCCCTCCTGGGCGGGAGTGCGTCAGAATGTGATGGGATCCACGGTGGACGGCCGGCC

CGTGCAGCCCGCGAACTCTTCAACCCTGACCTATGCAACCCTGAGCTCTTCGTCGGTGGACGCAG

CTGCCGCCGCAGCTGCTGCATCCGCCGCCAGCGCCGTGCGCGGAATGGCCATGGGCGCCGGCTAC

TACGGCACTCTGGTGGCCAACTCGAGTTCCACCAATAATCCCGCCAGCCTGAACGAGGAGAAGCT

GCTGCTGCTGATGGCCCAGCTTGAGGCCTTGACCCAGCGCCTGGGCGAGCTGACCCAGCAGGTGG

CTCAGCTGCAGGAGCAGACGCGGGCCGCGGTTGCCACGGTGAAATCCAAATAAAAAATGAATCAA

TAAATAAACGGAGACGGTTGTTGATTTTAACACAGAGTCTGAATCTTTATTTGATTTTTCGCGCG
```

-continued

```
CGGTAGGCCCTGGACCACCGGTCTCGATCATTGAGCACCCGGTGGATCTTTTCCAGGACCCGGTA

GAGGTGGGCTTGGATGTTGAGGTACATGGGCATGAGCCCGTCCCGGGGGTGGAGGTAGCTCCATT

GCAGGGCCTCGTGCTCGGGGGTGGTGTTGTAAATCACCCAGTCATAGCAGGGGCGCAGGGCGTGG

TGTTGCACAATATCTTTGAGGAGGAGACTGATGGCCACGGGCAGCCCTTTGGTGTAGGTGTTTAC

AAATCTGTTGAGCTGGGAGGGATGCATGCGGGGGGAGATGAGGTGCATCTTGGCCTGGATCTTGA

GATTGGCGATGTTACCGCCCAGATCCCGCCTGGGGTTCATGTTGTGCAGGACCACCAGCACGGTG

TATCCGGTGCACTTGGGGAATTTATCATGCAACTTGGAAGGGAAGGCGTGAAAGAATTTGGCGAC

GCCCTTGTGTCCGCCCAGGTTTTCCATGCACTCATCCATGATGATGGCAATGGGCCCGTGGGCGG

CGGCCTGGGCAAAGACGTTTCGGGGGTCGGACACATCATAGTTGTGGTCCTGGGTGAGGTCATCA

TAGGCCATTTTAATGAATTTGGGGCGGAGGGTGCCGGACTGGGGGACAAAGGTACCCTCGATCCC

GGGGGCGTAGTTCCCCTCACAGATCTGCATCTCCCAGGCTTTGAGCTCAGAGGGGGGATCATGT

CCACCTGCGGGGCGATAAAGAACACGGTTTCCGGGGCGGGGGAGATGAGCTGGGCCGAAAGCAAG

TTCCGGAGCAGCTGGGACTTGCCGCAGCCGGTGGGGCCGTAAATGACCCCGATGACCGGCTGCAG

GTGGTAGTTGAGGGAGAGACAGCTGCCGTCCTCCCGGAGGAGGGGGGCCACCTCGTTCATCATCT

CGCGCACGTGCATGTTCTCGCGCACCAGTTCCGCCAGGAGGCGCTCTCCCCCCAGAGATAGGAGC

TCCTGGAGCGAGGCGAAGTTTTTCAGCGGCTTGAGTCCGTCGGCCATGGGCATTTTGGAGAGGGT

CTGTTGCAAGAGTTCCAAGCGGTCCCAGAGCTCGGTGATGTGCTCTACGGCATCTCGATCCAGCA

GACCTCCTCGTTTCGCGGGTTGGGACGACTGCGGGAGTAGGGCACCAGACGATGGGCGTCCAGCG

CAGCCAGGGTCCGGTCCTTCCAGGGCCGCAGCGTCCGCGTCAGGGTGGTCTCCGTCACGGTGAAG

GGGTGCGCGCCGGGCTGGGCGCTTGCGAGGGTGCGCTTCAGGCTCATCCGGCTGGTCGAAAACCG

CTCCCGATCGGCGCCCTGCGCGTCGGCCAGGTAGCAATTGACCATGAGTTCGTAGTTGAGCGCCT

CGGCCGCGTGGCCTTTGGCGCGGAGCTTACCTTTGGAAGTCTGCCCGCAGGCGGGACAGAGGAGG

GACTTGAGGGCGTAGAGCTTGGGGGCGAGGAAGACGGAATCGGGGGCGTAGGCGTCCGCGCCGCA

GTGGGCGCAGACGGTCTCGCACTCCACGAGCCAGGTGAGGTCGGGCTGGTCGGGGTCAAAAACCA

GTTTCCCGCCGTTCTTTTTGATGCGTTTCTTACCTTTGGTCTCCATGAGCTCGTGTCCCGCTGG

GTGACAAAGAGGCTGTCCGTGTCCCCGTAGACCGACTTTATGGGCCGGTCCTCGAGCGGTGTGCC

GCGGTCCTCCTCGTAGAGGAACCCCGCCCACTCCGAGACGAAAGCCCGGGTCCAGGCCAGCACGA

AGGAGGCCACGTGGGACGGGTAGCGGTCGTTGTCCACCAGCGGGTCCACTTTTTCCAGGGTATGC

AAACACATGTCCCCCTCGTCCACATCAGGAAGGTGATTGGCTTGTAAGTGTAGGCCACGTGACC

GGGGGTCCCGGCCGGGGGGTATAAAAGGGGCGGGCCCCTGCTCGTCCTCACTGTCTTCCGGAT

CGCTGTCCAGGAGCGCCAGCTGTTGGGGTAGGTATTCCCTCTCGAAGGCGGGCATGACCTCGGCA

CTCAGGTTGTCAGTTTCTAGAAACGAGGAGGATTTGATATTGACGGTGCCAGCGGAGATGCCTTT

CAAGAGCCCCTCGTCCATCTGGTCAGAAAAGACGAtTTTTTTGTTGTCGAGCTTGGTGGCGAAGG

AGCCGTAGAGGGCGTTGGAAAGGAGCTTGGCGATGGAGCGCATGGTCTGGTTTTTTtCCTtGTCG

GCGCGCTCCTTGGCCGCGATGTTGAGCTGCACGTACTCGCGCGCCACGCACTTCCATTCGGGGAA

GACGGTGGTCATCTCGTCGGGCACGATTCTGACCTGCCAACCTCGATTATGCAGGGTGATGAGGT

CCACACTGGTGGCCACCTCGCCGCGCAGGGGCTCGTTGGTCCAGCAGAGGCGGCCGCCCTTGCGC

GAGCAGAAGGGGGGCAGAGGGTCCAGCATGACCTCGTCGGGGGGTCGGCATCGATGGTGAAGAT

GCCGGGCAGGAGATCGGGGTCGAAGTAGCTGATGGAAGTGGCCAGATCGTCCAGGGAAGCTTGCC

ATTCGCGCACGGCCAGCGCGCGCTCGTAGGGACTGAGGGGCGTGCCCCAGGGCATGGGGTGGGTG
```

-continued

```
AGCGCGGAGGCGTACATGCCGCAGATGTCGTAGACGTAGAGGGGCTCCTCGAGGATGCCGATGTA
GGTGGGGTAGCAGCGCCCCCCGCGGATGCTGGCGCGCACGTAGTCATACAGCTCGTGCGAGGGCG
CGAGGAGCCCCGGGCCCAGGTTGGTGCGACTGGGCTTTTCGGCGCGGTAGACGATCTGGCGAAAG
ATGGCATGCGAGTTGGAGGAGATGGTGGGCCTTTGGAAGATGTTGAAGTGGGCGTGGGGGAGGCC
GACCGAGTCGCGGATGAAGTGGGCGTAGGAGTCTTGCAGTTTGGCGACGAGCTCGGCGGTGACGA
GGACGTCCAGAGCGCAGTAGTCGAGGGTCTCCTGGATGATGTCATACTTGAGCTGGCCCTTTTGT
TTCCACAGCTCGCGGTTGAGAAGGAACTCTTCGCGGTCCTTCCAGTACTCTTCGAGGGGGAACCC
GTCCTGATCTGCACGGTAAGAGCCTAGCATGTAGAACTGGTTGACGGCCTTGTAGGCGCAGCAGC
CCTTCTCCACGGGGAGGGCGTAGGCCTGGGCGGCCTTGCGCAGGGAGGTGTGCGTGAGGGCGAAG
GTGTCCCTGACCATGACCTTGAGGAACTGGTGCTTGAAATCGATATCGTCGCAGcCCCCCTGCTC
CCAGAGCTGGAAGTCCGTGCGCTTCTTGTAGGCGGGGTTGGGCAAAGCGAAAGTAACATCGTTGA
AAAGGATCTTGCCCGCGCGGGGCATAAAGTTGCGAGTGATGCGGAAAGGCTGGGGCACCTCGGCC
CGGTTGTTGATGACCTGGGCGGCGAGCACGATCTCGTCGAAACCGTTGATGTTGTGGCCCACGAT
GTAGAGTTCCACGAATCGCGGGCGGCCCTTGACGTGGGGCAGCTTCTTGAGCTCCTCGTAGGTGA
GCTCGTCGGGGTCGCTGAGACCGTGCTGCTCGAGCGCCCAGTCGGCGAGATGGGGGTTGGCGCGG
AGGAAGGAAGTCCAGAGATCCACGGCCAGGGCGGTTTGCAGACGGTCCCGGTACTGACGGAACTG
CTGCCCGACGGCCATTTTTTCGGGGGTGACGCAGTAGAAGGTGCGGGGGTCCCCGTGCCAGCGGT
CCCATTTGAGCTGGAGGGCGAGATCGAGGGCGAGCTCGACGAGGCGGTCGTCCCCTGAGAGTTTC
ATGACCAGCATGAAGGGGACGAGCTGCTTGCCGAAGGACCCCATCCAGGTGTAGGTTTCCACATC
GTAGGTGAGGAAGAGCCTTTCGGTGCGAGGATGCGAGCCGATGGGGAAGAACTGGATCTCCTGCC
ACCAATTGGAGGAATGGCTGTTGATGTGATGGAAGTAGAAATGCCGACGGCGCGCCGAACACTCG
TGCTTGTGTTTATACAAGCGGCCACAGTGCTCGCAACGCTGCACGGGATGCACGTGCTGCACGAG
CTGTACCTGAGTTCCTTTGACGAGGAATTTCAGTGGGAAGTGGAGTCGTGGCGCCTGCATCTCGT
GCTGTACTACGTCGTGGTGGTCGGCCTGGCCCTCTTCTGCCTCGATGGTGGTCATGCTGACGAGC
CCGCGCGGGAGGCAGGTCCAGACCTCGGCGCGAGCGGGTCGGAGAGCGAGGACGAGGGCGCGCAG
GCCGGAGCTGTCCAGGGTCCTGAGACGCTGCGGAGTCAGGTCAGTGGGCAGCGGCGGCGCGCGGT
TGACTTGCAGGAGTTTTTCCAGGGCGCGCGGGAGGTCCAGATGGTACTTGATCTCCACCGCGCCG
TTGGTGGCGACGTCGATGGCTTGCAGGGTCCCGTGCCCCTGGGGTGTGACCACCGTCCCCCGTTT
CTTCTTGGGCGGCTGGGGCGACGGGGGCGGTGCCTCTTCCATGGTTAGAAGCGGCGGCGAGGACG
CGCGCCGGGCGGCAGAGGCGGCTCGGGGCCCGGAGGCAGGGGCGGCAGGGGCACGTCGGCGCCGC
GCGCGGGTAGGTTCTGGTACTGCGCCCGGAGAAGACTGGCGTGAGCGACGACGCGACGGTTGACG
TCCTGGATCTGACGCCTCTGGGTGAAGGCCACGGGACCCGTGAGTTTGAACCTGAAAGAGAGTTC
GACAGAATCAATCTCGGTATCGTTGACGGCGGCCTGCCGCAGGATCTCTTGCACGTCGCCCGAGT
TGTCCTGGTAGGCGATCTCGGTCATGAACTGCTCGATCTCCTCCTCCTGAAGGTCTCCGCGACCG
GCGCGCTCCACGGTGGCCGCGAGGTCGTTGGAGATGCGGCCCATGAGCTGCGAGAAGGCGTTCAT
GCCCGCCTCGTTCCAGACGCGGCTGTAGACCACGACGCCCTCGGGATCGCGGGCGCGCATGACCA
CCTGGGCGAGGTTGAGCTCCACGTGGCGCGTGAAGACCGCGTAGTTGCAGAGGCGCTGGTAGAGG
TAGTTGAGCGTGGTGGCGATGTGCTCGGTGACGAAGAAATACATGATCCAGCGGCGGAGCGGCAT
CTCGCTGACGTCGCCCAGCGCCTCCAAGCGTTCCATGGCCTCGTAAAAGTCCACGGCGAAGTTGA
AAAACTGGGAGTTGCGCGCCGAGACGGTCAACTCCTCCTCCAGAAGACGGATGAGCTCGGCGATG
GTGGCGCGCACCTCGCGCTCGAAGGCCCCCGGGAGTTCCTCCACTTCCTCCTCTTCTTCCTCCTC
```

-continued

```
CACTAACATCTCTTCTACTTCCTCCTCAGGCGGTGGTGGTGGCGGGGGAGGGGCCTGCGTCGCC

GGCGGCGCACGGGCAGACGGTCGATGAAGCGCTCGATGGTCTCGCCGCGCCGGCGTCGCATGGTC

TCGGTGACGGCGCGCCCGTCCTCGCGGGGCCGCAGCGTGAAGACGCCGCCGCGCATCTCCAGGTG

GCCGGGGGGTCCCCGTTGGGCAGGGAGAGGGCGCTGACGATGCATCTTATCAATTGCCCCGTAG

GGACTCCGCGCAAGGACCTGAGCGTCTCGAGATCCACGGGATCTGAAAACCGTTGAACGAAGGCT

TCGAGCCAGTCGCAGTCGCAAGGTAGGCTGAGCACGGTTTCTTCTGCCGGGTCATGTTGGGGAGC

GGGGCGGGCGATGCTGCTGGTGATGAAGTTGAAATAGGCGGTTCTGAGACGGCGGATGGTGGCGA

GGAGCACCAGGTCTTTGGGCCCGGCTTGCTGGATGCGCAGACGGTCGGCCATGCCCCAGGCGTGG

TCCTGACACCTGGCCAGGTCCTTGTAGTAGTCCTGCATGAGCCGCTCCACGGGCACCTCCTCCTC

GCCCGCGCGGCCGTGCATGCGCGTGAGCCCGAAGCCGCGCTGGGGCTGGACGAGCGCCAGGTCGG

CGACGACGCGCTCGGCGAGGATGGCCTGCTGGATCTGGGTGAGGGTGGTCTGGAAGTCGTCAAAG

TCGACGAAGCGGTGGTAGGCTCCGGTGTTGATGGTGTAGGAGCAGTTGGCCATGACGGACCAGTT

GACGGTCTGGTGGCCCGGACGCACGAGCTCGTGGTACTTGAGGCGCGAGTAGGCGCGCGTGTCGA

AGATGTAGTCGTTGCAGGTGCGCACCAGGTACTGGTAGCCGATGAGGAAGTGCGGCGGCGGCTGG

CGGTAGAGCGGCCATCGCTCGGTGGCGGGGGCGCCGGGCGCGAGGTCCTCGAGCATGGTGCGGTG

GTAGCCGTAGATGTACCTGGACATCCAGGTGATGCCGGCGGCGGTGGTGGAGGCGCGCGGGAACT

CGCGGACGCGGTTCCAGATGTTGCGCAGCGGCAGGAAGTAGTTCATGGTGGGCACGGTCTGGCCC

GTGAGGCGCGCAGTCGTGGATGCTCTATACGGGCAAAAACGAAAGCGGTCAGCGGCTCGACTC

CGTGGCCTGGAGGCTAAGCGAACGGGTTGGGCTGCGCGTGTACCCCGGTTCGAATCTCGAATCAG

GCTGGAGCCGCAGCTAACGTGGTACTGGCACTCCCGTCTCGACCCAAGCCTGCACCAACCCTCCA

GGATACGGAGGCGGGTCGTTTTGCAACTTTTTTtGGAGGCCGGAAATGAAACTAGTAAGCGCGGA

AAGCGGCCGACCGCGATGGCTCGCTGCCGTAGTCTGGAGAAGAATCGCCAGGGTTGCGTTGCGGT

GTGCCCCGGTTCGAGGCCGGCCGGATTCCGCGGCTAACGAGGGCGTGGCTGCCCCGTCGTTTCCA

AGACCCCATAGCCAGCCGACTTCTCCAGTTACGGAGCGAGCCCCTCTTTTGTTTTGTTTGTTTTT

GCCAGATGCATCCCGTACTGCGGCAGATGCGCCCCCACCACCCTCCACCGCAACAACAGCCCCCT

CCTCCACAGCCGGCGCTTCTGCCCCCGCCCCAGCAGCAGCAGCAACTTCCAGCCACGACCGCCGC

GGCCGCCGTGAGCGGGGCTGGACAGACTTCTCAGTATGATCACCTGGCCTTGGAAGAGGGCGAGG

GGCTGGCGCGCCTGGGGGCGTCGTCGCCGGAGCGGCACCCGCGCGTGCAGATGAAAAGGGACGCT

CGCGAGGCCTACGTGCCCAAGCAGAACCTGTTCAGAGACAGGAGCGGCGAGGAGCCCGAGGAGAT

GCGCGCGGCCCGGTTCCACGCGGGGCGGGAGCTGCGGCGCGGCCTGGACCGAAAGAGGGTGCTGA

GGGACGAGGATTTCGAGGCGGACGAGCTGACGGGGATCAGCCCCGCGCGCGCACGTGGCCGCG

GCCAACCTGGTCACGGCGTACGAGCAGACCGTGAAGGAGGAGAGCAACTTCCAAAAATCCTTCAA

CAACCACGTGCGCACCCTGATCGCGCGCGAGGAGGTGACCCTGGGCCTGATGCACCTGTGGGACC

TGCTGGAGGCCATCGTGCAGAACCCCACCAGCAAGCCGCTGACGGCGCAGCTGTTCCTGGTGGTG

CAGCATAGTCGGGACAACGAGGCGTTCAGGGAGGCGCTGCTGAATATCACCGAGCCCGAGGGCCG

CTGGCTCCTGGACCTGGTGAACATTCTGCAGAGCATCGTGGTGCAGGAGCGCGGGCTGCCGCTGT

CCGAGAAGCTGGCGGCCATCAACTTCTCGGTGCTGAGTCTGGGCAAGTACTACGCTAGGAAGATC

TACAAGACCCCGTACGTGCCCATAGACAAGGAGGTGAAGATCGACGGGTTTTACATGCGCATGAC

CCTGAAAGTGCTGACCCTGAGCGACGATCTGGGGGTGTACCGCAACGACAGGATGCACCGCGCGG

TGAGCGCCAGCAGGCGGCGCGAGCTGAGCGACCAGGAGCTGATGCACAGCCTGCAGCGGGCCCTG
```

-continued

```
ACCGGGGCCGGGACCGAGGGGGAGAGCTACTTTGACATGGGCGCGGACCTGCACTGGCAGCCCAG
CCGCCGGGCCTTGGAGGCGGCAGGCGGTCCCCCCTACATAGAAGAGGTGGACGATGAGGTGGACG
AGGAGGGCGAGTACCTGGAAGACTGATGGCGCGACCGTATTTTTGCTAGATGCAACAACAGCCAC
CTCCTGATCCCGCGATGCGGGCGGCGCTGCAGAGCCAGCCGTCCGGCATTAACTCCTCGGACGAT
TGGACCCAGGCCATGCAACGCATCATGGCGCTGACGACCCGCAACCCCGAAGCCTTTAGACAGCA
GCCCCAGGCCAACCGGCTCTCGGCCATCCTGGAGGCCGTGGTGCCCTCGCGCTCCAACCCCACGC
ACGAGAAGGTCCTGGCCATCGTGAACGCGCTGGTGGAGAACAAGGCCATCCGCGGCGACGAGGCC
GGCCTGGTGTACAACGCGCTGCTGGAGCGCGTGGCCCGCTACAACAGCACCAACGTGCAGACCAA
CCTGGACCGCATGGTGACCGACGTGCGCGAGGCCGTGGCCCAGCGCGAGCGGTTCCACCGCGAGT
CCAACCTGGGATCCATGGTGGCGCTGAACGCCTTCCTCAGCACCCAGCCCGCCAACGTGCCCCGG
GGCCAGGAGGACTACACCAACTTCATCAGCGCCCTGCGCCTGATGGTGACCGAGGTGCCCCAGAG
CGAGGTGTACCAGTCCGGGCCGGACTACTTCTTCCAGACCAGTCGCCAGGGCTTGCAGACCGTGA
ACCTGAGCCAGGCGTTCAAGAACTTGCAGGGCCTGTGGGGCGTGCAGGCCCCGGTCGGGGACCGC
GCGACGGTGTCGAGCCTGCTGACGCCGAACTCGCGCCTGCTGCTGCTGCTGGTGGCCCCCTTCAC
GGACAGCGGCAGCATCAACCGCAACTCGTACCTGGGCTACCTGATTAACCTGTACCGCGAGGCCA
TCGGCCAGGCGCACGTGGACGAGCAGACCTACCAGGAGATCACCCACGTGAGCCGCGCCCTGGGC
CAGGACGACCCGGGCAATCTGGAAGCCACCCTGAACTTTTTGCTGACCAACCGGTCGCAGAAGAT
CCCGCCCCAGTACACGCTCAGCGCCGAGGAGGAGCGCATCCTGCGATACGTGCAGCAGAGCGTGG
GCCTGTTCCTGATGCAGGAGGGGCCACCCCCAGCGCCGCGCTCGACATGACCGCGCGCAACATG
GAGCCCAGCATGTACGCCAGCAACCGCCCGTTCATCAATAAACTGATGGACTACTTGCATCGGGC
GGCCGCCATGAACTCTGACTATTTCACCAACGCCATCCTGAATCCCCACTGGCTCCCGCCGCCGG
GGTTCTACACGGGCGAGTACGACATGCCCGACCCCAATGACGGGTTCCTGTGGGACGATGTGGAC
AGCAGCGTGTTCTCCCCCCGACCGGGTGCTAACGAGCGCCCCTTGTGGAAGAAGGAAGGCAGCGA
CCGACGCCCGTCCTCGGCGCTGTCCGGCCGCGAGGGTGCTGCCGCGGCGGTGCCCGAGGCCGCCA
GTCCTTTCCCGAGCTTGCCCTTCTCGCTGAACAGTATTCGCAGCAGCGAGCTGGGCAGGATCACG
CGCCCGCGCTTGCTGGGCGAGGAGGAGTACTTGAATGACTCGCTGTTGAGACCCGAGCGGGAGAA
GAACTTCCCCAATAACGGGATAGAGAGCCTGGTGGACAAGATGAGCCGCTGGAAGACGTATGCGC
AGGAGCACAGGGACGATCCGTCGCAGGGGGCCACGAGCCGGGGCAGCGCCGCCCGTAAACGCCGG
TGGCACGACAGGCAGCGGGGACTGATGTGGGACGATGAGGATTCCGCCGACGACAGCAGCGTGTT
GGACTTGGGTGGGAGTGGTAACCCGTTCGCTCACCTGCGCCCCCGCATCGGGCGCATGATGTAAG
AGAAACCGAAAATAAATGATACTCACCAAGGCCATGGCGACCAGCGTGCGTTCGTTTCTTCTCTG
TTGTTGTATCTAGTATGATGAGGCGTGCGTACCCGGAGGGTCCTCCTCCCTCGTACGAGAGCGTG
ATGCAGCAGGCGATGGCGGCGGCGGCGATGCAGCCCCCGCTGGAGGCTCCTTACGTGCCCCC
GCGGTACCTGGCGCCTACGGAGGGGCGGAACAGCATTCGTTACTCGGAGCTGGCACCCTTGTACG
ATACCACCCGGTTGTACCTGGTGGACAACAAGTCGGCGGACATCGCCTCGCTGAACTACCAGAAC
GACCACAGCAACTTCCTGACCACCGTGGTGCAGAACAATGACTTCACCCCCACGGAGGCCAGCAC
CCAGACCATCAACTTTGACGAGCGCTCGCGGTGGGGCGGTCAGCTGAAAACCATCATGCACACCA
ACATGCCCAACGTGAACGAGTTCATGTACAGCAACAAGTTCAAGGCGCGGGTGATGGTCTCCCGC
AAGACCCCCAACGGGGTGACAGTGACAGATGGTAGTCAGGATATCTTGGAGTATGAATGGGTGGA
GTTTGAGCTGCCCGAAGGCAACTTCTCGGTGACCATGACCATCGACCTGATGAACAACGCCATCA
TCGACAATTACTTGGCGGTGGGGCGGCAGAACGGGGTCCTGGAGAGCGATATCGGCGTGAAGTTC
```

-continued

```
GACACTAGGAACTTCAGGCTGGGCTGGGACCCCGTGACCGAGCTGGTCATGCCCGGGGTGTACAC
CAACGAGGCCTTCCACCCCGATATTGTCTTGCTGCCCGGCTGCGGGGTGGACTTCACCGAGAGCC
GCCTCAGCAACCTGCTGGGCATTCGCAAGAGGCAGCCCTTCCAGGAGGGCTTCCAGATCATGTAC
GAGGATCTGGAGGGGGCAACATCCCCGCGCTCCTGGATGTCGACGCCTATGAGAAAAGCAAGGA
GGAGAGCGCCGCCGCGGCGACTGCAGCTGTAGCCACCGCCTCTACCGAGGTCAGGGGCGATAATT
TTGCCAGCCCTGCAGCAGTGGCAGCGGCCGAGGCGGCTGAAACCGAAAGTAAGATAGTCATTCAG
CCGGTGGAGAAGGATAGCAAGGACAGGAGCTACAACGTGCTGCCGGACAAGATAAACACCGCCTA
CCGCAGCTGGTACCTGGCCTACAACTATGGCGACCCCGAGAAGGGCGTGCGCTCCTGGACGCTGC
TCACCACCTCGGACGTCACCTGCGGCGTGGAGCAAGTCTACTGGTCGCTGCCCGACATGATGCAA
GACCCGGTCACCTTCCGCTCCACGCGTCAAGTTAGCAACTACCCGGTGGTGGGCGCCGAGCTCCT
GCCCGTCTACTCCAAGAGCTTCTTCAACGAGCAGGCCGTCTACTCGCAGCAGCTGCGCGCCTTCA
CCTCGCTCACGCACGTCTTCAACCGCTTCCCCGAGAACCAGATCCTCGTCCGCCCGCCCGCCCC
ACCATTACCACCGTCAGTGAAAACGTTCCTGCTCTCACAGATCACGGGACCCTGCCGCTGCGCAG
CAGTATCCGGGGAGTCCAGCGCGTGACCGTTACTGACGCCAGACGCCGCACCTGCCCCTACGTCT
ACAAGGCCCTGGGCATAGTCGCGCCGCGCGTCCTCTCGAGCCGCACCTTCTAAAAAATGTCCATT
CTCATCTCGCCCAGTAATAACACCGGTTGGGGCCTGCGCGCGCCCAGCAAGATGTACGGAGGCGC
TCGCCAACGCTCCACGCAACACCCCGTGCGCGTGCGCGGGCACTTCCGCGCTCCCTGGGGCGCCC
TCAAGGGCCGCGTGCGGTCGCGCACCACCGTCGACGACGTGATCGACCAGGTGGTGGCCGACGCG
CGCAACTACACCCCCGCCGCCGCGCCCGTCTCCACCGTGGACGCCGTCATCGACAGCGTGGTGGC
CGACGCGCGCCGGTACGCCCGCGCCAAGAGCCGGCGGCGGCGCATCGCCCGGCGGCACCGGAGCA
CCCCCGCCATGCGCGCGGCGCGAGCCTTGCTGCGCAGGGCCAGGCGCACGGGACGCAGGGCCATG
CTCAGGGCGGCCAGACGCGCGGCTTCAGGCGCCAGCGCCGGCAGGACCCGGAGACGCGCGGCCAC
GGCGGCGGCAGCGGCCATCGCCAGCATGTCCCGCCCGCGGCGAGGGAACGTGTACTGGGTGCGCG
ACGCCGCCACCGGTGTGCGCGTGCCCGTGCGCACCCGcCCCCCTCGCACTTGAAGATGTTCACTT
CGCGATGTTGATGTGTCCCAGCGGCGAGGAGGATGTCCAAGCGCAAATTCAAGGAAGAGATGCTC
CAGGTCATCGCGCCTGAGATCTACGGCCCCGCGGTGGTGAAGGAGGAAAGAAAGCCCCGCAAAAT
CAAGCGGGTCAAAAAGGACAAAAAGGAAGAAGATGACGATCTGGTGGAGTTTGTGCGCGAGTTCG
CCCCCcGGCGGCGCGTGCAGTGGCGCGGGCGGAAAGTGCACCCGGTGCTGAGACCCGGCACCACC
GTGGTCTTCACGCCCGGCGAGCGCTCCGGCAGCGCTTCCAAGCGCTCCTACGACGAGGTGTACGG
GGACGAGGACATCCTCGAGCAGGCGGCCGAGCGCCTGGGCGAGTTTGCTTACGGCAAGCGCAGCC
GCCCCGCCCTGAAGGAAGAGGCGGTGTCCATCCCGCTGGACCACGGCAACCCCACGCCGAGCCTC
AAGCCCGTGACCCTGCAGCAGGTGCTGCCGAGCGCAGCGCCGCGCCGGGGGTTCAAGCGCGAGGG
CGAGGATCTGTACCCCACCATGCAGCTGATGGTGCCCAAGCGCCAGAAGCTGGAAGACGTGCTGG
AGACCATGAAGGTGGACCCGGACGTGCAGCCCGAGGTCAAGGTGCGGCCCATCAAGCAGGTGGCC
CCGGGCCTGGGCGTGCAGACCGTGGACATCAAGATCCCCACGGAGCCCATGGAAACGCAGACCGA
GCCCATGATCAAGCCCAGCACCAGCACCATGGAGGTGCAGACGGATCCCTGGATGCCATCGGCTC
CTAGCCGAAGACCCCGGCGCAAGTACGGCGCGGCCAGCCTGCTGATGCCCAACTACGCGCTGCAT
CCTTCCATCATCCCCACGCCGGGCTACCGCGGCACGCGCTTCTACCGCGGTCATACAACCAGCCG
CCGCCGCAAGACCACCACCCGCCGCCGCCGTCGCCGCACAGCCGCTGCATCTACCCCTGCCGCCC
TGGTGCGGAGAGTGTACCGCCGCGGCCGCGCGCCTCTGACCCTACCGCGCGCGCGCTACCACCCG
```

-continued

```
AGCATCGCCATTTAAACTTTCGCCTGCTTTGCAGATGGCCCTCACATGCCGCCTCCGCGTTCCCA
TTACGGGCTACCGAGGAAGAAAACCGCGCCGTAGAAGGCTGGCGGGGAACGGGATGCGTCGCCAC
CACCATCGGCGGCGGCGCGCCATCAGCAAGCGGTTGGGGGgAGGCTTCCTGCCCGCGCTGATCCC
CATCATCGCCGGCGATCGGGGCGATCCCCGGCATTGCTTCCGTGGCGGTGCAGGCCTCTCAGC
GCCACTGAGACACTTGGAAAACATCTTGTAATAAACCAATGGACTCTGACGCTCCTGGTCCTGTG
ATGTGTTTTCGTAGACAGATGGAAGACATCAATTTTTCGTCCCTGGCTCCGCGACACGGCACGCG
GCCGTTCATGGGCACCTGGAGCGACATCGGCACCAGCCAACTGAACGGGGGCGCCTTCAATTGGA
GCAGTCTCTGGAGCGGGCTTAAGAATTTCGGGTCCACGCTTAAAACCTATGGCAGCAAGGCGTGG
AACAGCACCACAGGGCAGGCGCTGAGGGATAAGCTGAAAGAGCAGAACTTCCAGCAGAAGGTGGT
CGATGGGCTCGCCTCGGGCATCAACGGGGTGGTGGACCTGGCCAACCAGGCCGTGCAGCGGCAGA
TCAACAGCCGCCTGGACCCGGTGCCGCCCGCCGGCTCCGTGGAGATGCCGCAGGTGGAGGAGGAG
CTGCCTCCCCTGGACAAGCGGGGCGAGAAGCGACCCCGCCCCGACGCGGAGGAGACGCTGCTGAC
GCACACGGACGAGCCGCCCCCGTACGAGGAGGCGGTGAAACTGGGTCTGCCCACCACGCGGCCCA
TCGCGCCCCTGGCCACCGGGGTGCTGAAACCCGAAAGTAATAAGCCCGCGACCCTGGACTTGCCT
CCTCCCGCTTCCCGCCCCTCTACAGTGGCTAAGCCCCTGCCGCCGGTGGCCGTGGCCCGCGCGCG
ACCCGGGGGCTCCGCCCGCCCTCATGCGAACTGGCAGAGCACTCTGAACAGCATCGTGGGTCTGG
GAGTGCAGAGTGTGAAGCGCCGCCGCTGCTATTAAACCTACCGTAGCGCTTAACTTGCTTGTCTG
TGTGTGTATGTATTATGTCGCCGCTGTCCGCCAGAAGGAGGAGTGAAGAGGCGCGTCGCCGAGTT
GCAAGATGGCCACCCCATCGATGCTGCCCCAGTGGGCGTACATGCACATCGCCGGACAGGACGCT
TCGGAGTACCTGAGTCCGGGTCTGGTGCAGTTCGCCCGCGCCACAGACACCTACTTCAGTCTGGG
GAACAAGTTTAGGAACCCCACGGTGGCGCCCACGCACGATGTGACCACCGACCGCAGCCAGCGGC
TGACGCTGCGCTTCGTGCCCGTGGACCGCGAGGACAACACCTACTCGTACAAAGTGCGCTACACG
CTGGCCGTGGGCGACAACCGCGTGCTGGACATGGCCAGCACCTACTTTGACATCCGCGGCGTGCT
GGATCGGGGCCCTAGCTTCAAACCCTACTCCGGCACCGCCTACAACAGCCTGGCTCCCAAGGGAG
CGCCCAATTCCAGCCAGTGGGAGCaAAAAAAAGGCAGGCAATGGTGACACTATGGAAACACACACA
TTTGGTGTGGCCCCAATGGGCGGTGAGAATATTACAATCGACGGATTACAAATTGGAACTGACGC
TACAGCTGATCAGGATAAACCAATTTATGCTGACAAAACATTCCAGCCTGAACCTCAAGTAGGAG
AAGAAAATTGGCAAGAAACTGAAAGCTTTTATGGCGGTAGGGCTCTTAAAAAAGACACAAGCATG
AAACCTTGCTATGGCTCCTATGCTAGACCCACCAATGTAAAGGGAGGTCAAGCTAAACTTAAAGT
TGGAGCTGATGGAGTTCCTACCAAAGAATTTGACATAGACCTGGCTTTCTTTGATACTCCCGGTG
GCACAGTGAATGGACAAGATGAGTATAAAGCAGACATTGTCATGTATACCGAAAACACGTATCTG
GAAACTCCAGACACGCATGTGGTATACAAACCAGGCAAGGATGATGCAAGTTCTGAAATTAACCT
GGTTCAGCAGTCCATGCCCAATAGACCCAACTATATTGGGTTCAGAGACAACTTTATTGGGCTCA
TGTATTACAACAGTACTGGCAATATGGGGGTGCTGGCTGGTCAGGCCTCACAGCTGAATGCTGTG
GTCGACTTGCAAGACAGAAACACCGAGCTGTCATACCAGCTCTTGCTTGACTCTTTGGGTGACAG
AACCCGGTATTTCAGTATGTGGAATCAGGCGGTGGACAGTTATGATCCTGATGTGCGCATTATTG
AAAACCATGGTGTGGAAGACGAACTTCCCAACTATTGCTTCCCCCTGGATGGGTCTGGCACTAAT
GCCGCTTACCAAGGTGTGAAAGTAAAAAATGGTAACGATGGTGATGTTGAGAGCGAATGGGAAAA
TGATGATACTGTCGCAGCTCGAAATCAATTATGCAAGGGCAACATTTTTGCCATGGAAATTAACC
TCCAAGCCAACCTGTGGAGAAGTTTCCTCTACTCGAACGTGGCCCTGTACCTGCCCGACTCTTAC
AAGTACACGCCAGCCAACATCACCCTGCCCACCAACACCAACACTTATGATTACATGAACGGGAG
```

-continued

```
AGTGGTGCCTCCCTCGCTGGTGGACGCCTACATCAACATCGGGGCGCGCTGGTCGCTGGACCCCA
TGGACAACGTCAATCCCTTCAACCACCACCGCAACGCGGGCCTGCGCTACCGCTCCATGCTCCTG
GGCAACGGGCGCTACGTGCCCTTCCACATCCAGGTGCCCCAGAAATTTTTCGCCATCAAGAGCCT
CCTGCTCCTGCCCGGGTCCTACACCTACGAGTGGAACTTCCGCAAGGACGTCAACATGATCCTGC
AGAGCTCCCTCGGCAACGACCTGCGCACGGACGGGGCCTCCATCTCCTTCACCAGCATCAACCTC
TACGCCACCTTCTTCCCCATGGCGCACAACACGGCCTCCACGCTCGAGGCCATGCTGCGCAACGA
CACCAACGACCAGTCCTTCAACGACTACCTCTCGGCGGCCAACATGCTCTACCCCATCCCGGCCA
ACGCCACCAACGTGCCCATCTCCATCCCCTCGCGCAACTGGGCCGCCTTCCGCGGCTGGTCCTTC
ACGCGCCTCAAGACCAAGGAGACGCCCTCGCTGGGCTCCGGGTTCGACCCCTACTTCGTCTACTC
GGGCTCCATCCCCTACCTCGACGGCACCTTCTACCTCAACCACACCTTCAAGAAGGTCTCCATCA
CCTTCGACTCCTCCGTCAGCTGGCCCGGCAACGACCGGCTCCTGACGCCCAACGAGTTCGAAATC
AAGCGCACCGTCGACGGCGAGGGATACAACGTGGCCCAGTGCAACATGACCAAGGACTGGTTCCT
GGTCCAGATGCTGGCCCACTACAACATCGGCTACCAGGGCTTCTACGTGCCCGAGGGCTACAAGG
ACCGCATGTACTCCTTCTTCCGCAACTTCCAGCCCATGAGCCGCCAGGTGGTGGACGAGGTCAAC
TACAAGGACTACCAGGCCGTCACCCTGGCCTACCAGCACAACAACTCGGGCTTCGTCGGCTACCT
CGCGCCCACCATGCGCCAGGGCCAGCCCTACCCCGCCAACTACCCGTACCCGCTCATCGGCAAGA
GCGCCGTCACCAGCGTCACCCAGAAAAAGTTCCTCTGCGACAGGGTCATGTGGCGCATCCCCTTC
TCCAGCAACTTCATGTCCATGGGCGCGCTCACCGACCTCGGCCAGAACATGCTCTATGCCAACTC
CGCCCACGCGCTAGACATGAATTTCGAAGTCGACCCCATGGATGAGTCCACCCTTCTCTATGTTG
TCTTCGAAGTCTTCGACGTCGTCCGAGTGCACCAGCCCCACCGCGGCGTCATCGAGGCCGTCTAC
CTGCGCACCCCCTTCTCGGCCGGTAACGCCACCACCTAAATTGCTACTTGCATGATGGCTGAGCC
CACAGGCTCCGGCGAGCAGGAGCTCAGGGCCATCATCCGCGACCTGGGCTGCGGGCCCTACTTCC
TGGGCACCTTCGATAAGCGCTTCCCGGGATTCATGGCCCCGCACAAGCTGGCCTGCGCCATCGTC
AACACGGCCGGCCGCGAGACCGGGGGCGAGCACTGGCTGGCCTTCGCCTGGAACCCGCGCTCGAA
CACCTGCTACCTCTTCGACCCCTTCGGGTTCTCGGACGAGCGCCTCAAGCAGATCTACCAGTTCG
AGTACGAGGGCCTGCTGCGCCGTAGCGCCCTGGCCACCGAGGACCGCTGCGTCACCCTGGAAAAG
TCCACCCAGACCGTGCAGGGTCCGCGCTCGGCCGCCTGCGGGCTCTTCTGCTGCATGTTCCTGCA
CGCCTTCGTGCACTGGCCCGACCGCCCCATGGACAAGAACCCCACCATGAACTTGCTGACGGGGG
TGCCCAACGGCATGCTCCAGTCGCCCCAGGTGGAACCCACCCTGCGCCGCAACCAGGAGGCGCTC
TACCGCTTCCTCAACTCCCACTCCGCCTACTTTCGCTCCCACCGCGCGCGCATCGAGAAGGCCAC
CGCCTTCGACCGCATGAACAATCAAGACATGTAAACCGTGTGTGTATGTTTAAAATATCTTTTAA
TAAACAGCACTTTAATGTTACACATGCATCTGAGATGATTTTATTTTAGAAATCGAAAGGGTTCT
GCCGGGTCTCGGCATGGCCCGCGGGCAGGGACACGTTGCGGAACTGGTACTTGGCCAGCCACTTG
AACTCGGGGATCAGCAGTTTGGGCAGCGGGGTGTCGGGGAAGGAGTCGGTCCACAGCTTCCGCGT
CAGCTGCAGGGCGCCCAGCAGGTCGGGCGCGGAGATCTTGAAATCGCAGTTGGGACCCGCGTTCT
GCGCGCGAGAGTTGCGGTACACGGGGTTGCAGCACTGGAACACCATCAGGGCCGGGTGCTTCACG
CTCGCCAGCACCGCCGCGTCGGTGATGCTCTCCACGTCGAGGTCCTCGGCGTTGGCCATCCCGAA
GGGGGTCATCTTGCAGGTCTGCCTTCCCATGGTGGGCACGCACCCGGGCTTGTGGTTGCAATCGC
AGTGCAGGGGGATCAGCATCATCTGGGCCTGGTCGGCGTTCATCCCCGGGTACATGGCCTTCATG
AAAGCCTCCAATTGCCTGAACGCCTGCTGGGCCTTGGCTCCCTCGGTGAAGAAGACCCCGCAGGA
```

-continued

```
CTTGCTAGAGAACTGGTTGGTGGCACAGCCGGCATCGTGCACGCAGCAGCGCGTCGTTGTTGG
CCAGCTGCACCACGCTGCGCCCCCAGCGGTTCTGGGTGATCTTGGCCCGGTCGGGGTTCTCCTTC
AGCGCGCGCTGCCCGTTCTCGCTCGCCACATCCATCTCGATCATGTGCTCCTTCTGGATCATGGT
GGTCCCGTGCAGGCACCGCAGTTTGCCCTCGGCCTCGGTGCACCCGTGCAGCCACAGCGCGCACC
CGGTGCACTCCCAGTTCTTGTGGGCGATCTGGGAATGCGCGTGCACGAACCCTTGCAGGAAGCGG
CCCATCATGGTCGTCAGGGTCTTGTTGCTAGTGAAGGTCAACGGGATGCCGCGGTGCTCCTCGTT
GATGTACAGGTGGCAGATGCGGCGGTACACCTCGCCCTGCTCGGGCATCAGTTGGAAGTTGGCTT
TCAGGTCGGTCTCCACGCGGTAGCGGTCCATCAGCATAGTCATGATTTCCATGCCCTTCTCCCAG
GCCGAGACGATGGGCAGGCTCATAGGGTTCTTCACCATCATCTTAGCACTAGCAGCCGCGGCCAG
GGGGTCGCTCTCATCCAGGGTCTCAAAGCTCCGCTTGCCGTCCTTCTCGGTGATCCGCACCGGGG
GGTAGCTGAAGCCCACGGCCGCCAGCTCCTCCTCGGCCTGTCTTTCGTCCTCGCTGTCCTGGCTG
ACGTCCTGCATGACCACATGCTTGGTCTTGCGGGGTTTCTTCTTGGGCGGCAGTGGCGGCGGAGA
TGCTTGTGGCGAGGGGGAGCGCGAGTTCTCGCTCACCACTACTATCTCTTCCTCTTCTTGGTCCG
AGGCCACGCGGCGGTAGGTATGTCTCTTCGGGGGCAGAGGCGGAGGCGACGGGCTCTCGCCGCCG
CGACTTGGCGGATGGCTGGCAGAGCCCCTTCCGCGTTCGGGGGTGCGCTCCCGGCGGCGCTCTGA
CTGACTTCCTCCGCGGCCGGCCATTGTGTTCTCCTAGGGAGGAACAACAAGCATGGAGACTCAGC
CATCGCCAACCTCGCCATCTGCCCCCACCGCCGGCGACGAGAAGCAGCAGCAGCAGAATGAAAGC
TTAACCGCCCCGCCGCCCAGCCCCGCCTCCGACGCAGCCGCGGTCCCAGACATGCAAGAGATGGA
GGAATCCATCGAGATTGACCTGGGCTATGTGACGCCCGCGGAGCATGAGGAGGAGCTGGCAGTGC
GCTTTCAATCGTCAAGCCAGGAAGATAAAGAACAGCCAGAGCAGGAAGCAGAGAACGAGCAGAGT
CAGGCTGGGCTCGAGCATGGCGACTACCTCCACCTGAGCGGGGAGGAGGACGCGCTCATCAAGCA
TCTGGCCCGGCAGGCCACCATCGTCAAGGACGCGCTGCTCGACCGCACCGAGGTGCCCCTCAGCG
TGGAGGAGCTCAGCCGCGCCTACGAGCTCAACCTCTTCTCGCCGCGCGTGcCCCCCAAGCGCCAG
CCCAACGGCACCTGCGAGCCCAACCCCCGCCTCAACTTCTACCCGGTCTTCGCGGTGCCCGAGGC
CCTGGCCACCTACCACATCTTTTtCAAGAACCAAAAGATCCCCGTCTCCTGCCGCGCCAACCGCA
CCCGCGCCGACGCCCTCTTCAACCTGGGTCCCGGCGCCCGCCTACCTGATATCGCCTCCTTGGAA
GAGGTTCCCAAGATCTTCGAGGGTCTGGGCAGCGACGAGACTCGGGCCGCGAACGCTCTGCAAGG
AGAAGGAGGAGGAGAGCATGAGCACCACAGCGCCCTGGTCGAGTTGGAAGGCGACAACGCGCGGC
TGGCGGTGCTCAAACGCACGGTCGAGCTGACCCATTTCGCCTACCCGGCTCTGAACCTGcCCCCG
AAAGTCATGAGCGCGGTCATGGACCAGGTGCTCATCAAGCGCGCGTCGCCCATCTCCGAGGACGA
GGGCATGCAAGACTCCGAGGAGGGCAAGCCCGTGGTCAGCGACGAGCAGCTGGCCCGGTGGCTGG
GTCCTAATGCTACCCCTCAAAGTTTGGAAGAGCGGCGCAAGCTCATGATGGCCGTGGTCCTGGTG
ACCGTGGAGCTGGAGTGCCTGCGCCGCTTCTTCGCCGACGCGGAGACCCTGCGCAAGGTCGAGGA
GAACCTGCACTACCTCTTCAGGCACGGGTTCGTGCGCCAGGCCTGCAAGATCTCCAACGTGGAGC
TGACCAACCTGGTCTCCTACATGGGCATCTTGCACGAGAACCGCCTGGGGCAGAACGTGCTGCAC
ACCACCCTGCGCGGGGAGGCCCGCCGCGACTACATCCGCGACTGCGTCTACCTCTACCTCTGCCA
CACCTGGCAGACGGGCATGGGCGTGTGGCAGCAGTGTCTGGAGGAGCAGAACCTGAAAGAGCTCT
GCAAGCTCCTGCAAAAGAACCTCAAGGGTCTGTGGACCGGGTTCGACGAGCGGACCACCGCCTCG
GACCTGGCCGACCTCATCTTCCCCGAGCGCCTCAGGCTGACGCTGCGCAACGGCCTGCCCGACTT
TATGAGCCAAAGCATGTTGCAAAACTTTCGCTCTTTCATCCTCGAACGCTCCGGAATCCTGCCCG
CCACCTGCTCCGCGCTGCCCTCGGACTTCGTGCCGCTGACCTTCCGCGAGTGCCCCCCGCCGCTG
```

-continued

```
TGGAGCCACTGCTACCTGCTGCGCCTGGCCAACTACCTGGCCTACCACTCGGACGTGATCGAGGA
CGTCAGCGGCGAGGGCCTGCTCGAGTGCCACTGCCGCTGCAACCTCTGCACGCCGCACCGCTCCC
TGGCCTGCAACCCCCAGCTGCTGAGCGAGACCCAGATCATCGGCACCTTCGAGTTGCAAGGGCCC
AGCGAGGGCGAGGGAGCCAAGGGGGGTCTGAAACTCACCCCGGGGCTGTGGACCTCGGCCTACTT
GCGCAAGTTCGTGCCCGAGGATTACCATCCCTTCGAGATCAGGTTCTACGAGGACCAATCCCAGC
CGCCCAAGGCCGAGCTGTCGGCCTGCGTCATCACCCAGGGGGCGATCCTGGCCCAATTGCAAGCC
ATCCAGAAATCCCGCCAAGAATTCTTGCTGAAAAAGGGCCGCGGGGTCTACCTCGACCCCCAGAC
CGGTGAGGAGCTCAACCCCGGCTTCCCCCAGGATGCCCCGAGGAAACAAGAAGCTGAAAGTGGAG
CTGCCGCCCGTGGAGGATTTGGAGGAAGACTGGGAGAACAGCAGTCAGGCAGAGGAGATGGAGGA
AGACTGGGACAGCACTCAGGCAGAGGAGGACAGCCTGCAAGACAGTCTGGAGGAAGACGAGGAGG
AGGCAGAGGAGGAGGTGGAAGAAGCAGCCGCCGCCAGACCGTCGTCCTCGGCGGGGAGAAAGCA
AGCAGCACGGATACCATCTCCGCTCCGGGTCGGGGTCCCGCTCGGCCCCACAGTAGATGGGACGA
GACCGGGCGATTCCCGAACCCCACCACCCAGACCGGTAAGAAGGAGCGGCAGGGATACAAGTCCT
GGCGGGGGCACAAAAACGCCATCGTCTCCTGCTTGCAGGCCTGCGGGGGCAACATCTCCTTCACC
CGGCGCTACCTGCTCTTCCACCGCGGGGTGAACTTCCCCCGCAACATCTTGCATTACTACCGTCA
CCTCCACAGCCCCTACTACTTCCAAGAAGAGGCAGCAGCAGCAGaAAAAGACCAGAAAACCAGCT
AGAAAATCCACAGCGGCGGCAGCGGCAGGTGGACTGAGGATCGCGGCGAACGAGCCGGCGCAGAC
CCGGGAGCTGAGGAACCGGATCTTTCCCACCCTCTATGCCATCTTCCAGCAGAGTCGGGGGCAGG
AGCAGGAACTGAAAGTCAAGAACCGTTCTCTGCGCTCGCTCACCCGCAGTTGTCTGTATCACAAG
AGCGAAGACCAACTTCAGCGCACTCTCGAGGACGCCGAGGCTCTCTTCAACAAGTACTGCGCGCT
CACTCTTAAAGAGTAGCCCGCGCCCGCCCAGTCGCAGAAAAAGGCGGGAATTACGTCACCTGTGC
CCTTCGCCCTAGCCGCCTCCACCCAGCACCGCCATGAGCAAAGAGATTCCCACGCCTTACATGTG
GAGCTACCAGCCCCAGATGGGCCTGGCCGCCGGCGCCGCCCAGGACTACTCCACCCGCATGAATT
GGCTCAGCGCCGGGCCCGCGATGATCTCACGGGTGAATGACATCCGCGCCCACCGAAACCAGATA
CTCCTAGAACAGTCAGCGCTCACCGCCACGCCCCGCAATCACCTCAATCCGCGTAATTGGCCCGC
CGCCCTGGTGTACCAGGAAATTCCCCAGCCCACGACCGTACTACTTCCGCGAGACGCCCAGGCCG
AAGTCCAGCTGACTAACTCAGGTGTCCAGCTGGCGGGCGGCGCCACCCTGTGTCGTCACCGCCCC
GCTCAGGGTATAAAGCGGCTGGTGATCCGGGGCAGAGGCACACAGCTCAACGACGAGGTGGTGAG
CTCTTCGCTGGGTCTGCGACCTGACGGAGTCTTCCAACTCGCCGGATCGGGGAGATCTTCCTTCA
CGCCTCGTCAGGCGGTCCTGACTTTGGAGAGTTCGTCCTCGCAGCCCCGCTCGGGCGGCATCGGC
ACTCTCCAGTTCGTGGAGGAGTTCACTCCCTCGGTCTACTTCAACCCCTTCTCCGGCTCCCCCGG
CCACTACCCGGACGAGTTCATCCCGAACTTTGACGCCATCAGCGAGTCGGTGGACGGCTACGATT
GATTAATTAATCAACTAACCCCTTACCCCTTTACCCTCCAGTAAAAATAAAGATTAAAAATGATT
GAATTGATCAATAAAGAATCACTTACTTGAAATCTGAAACCAGGTCTCTGTCCATGTTTTCTGTC
AGCAGCACTTCACTCCCCTCTTCCCAACTCTGGTACTGCAGGCCCCGGCGGGCTGCAAACTTCCT
CCACACTCTGAAGGGGATGTCAAATTCCTCCTGTCCCTCAATCTTCATTTTTATCTTCTATCAGA
TGTCCAAAAAGCGCGCGGGTGGATGATGGCTTCGACCCCGTGTACCCCTACGATGCAGACAAC
GCACCGACTGTGCCCTTCATCAACCCTCCCTTCGTCTCTTCAGATGGATTCCAAGAAAAGCCCCT
GGGGGTGTTGTCCCTGCGACTGGCCGACCCCGTCACCACCAAGAATGGGGCTGTCACCCTCAAGC
TGGGGGAGGGGGTGGACCTCGACGACTCGGGAAAACTCATCTCCAAAAATGCCACCAAGGCCACT
```

```
GCCCCTCTCAGTATTTCCAACGGCACCATTTCCCTTAACATGGCTGCCCCTTTTTACAACAACAA
TGGAACGTTAAGTCTCAATGTTTCTACACCATTAGCAGTATTTCCCACTTTTAACACTTTAGGTA
TCAGTCTTGGAAACGGTCTTCAAACTTCTAATAAGTTGCTGACTGTACAGTTAACTCATCCTCTT
ACATTCAGCTCAAATAGCATCACAGTAAAAACAGACAAAGGACTCTATATTAATTCTAGTGGAAA
CAGAGGGCTTGAGGCTAACATAAGCCTAAAAAGAGGACTGATTTTTGATGGTAATGCTATTGCAA
CATACCTTGGAAGTGGTTTAGACTATGGATCCTATGATAGCGATGGGAAAACAAGACCCATCATC
ACCAAAATTGGAGCAGGTTTGAATTTTGATGCTAATAATGCCATGGCTGTGAAGCTAGGCACAGG
TTTAAGTTTTGACTCTGCCGGTGCCTTAACAGCTGGAAACAAAGAGGATGACAAGCTAACACTTT
GGACTACACCTGACCCAAGCCCTAATTGTCAATTACTTTCAGACAGAGATGCCAAATTTACCCTA
TGTCTTACAAAATGCGGTAGTCAAATACTAGGCACTGTTGCAGTAGCTGCTGTTACTGTAGGTTC
AGCACTAAATCCAATTAATGACACAGTAAAAAGCGCCATAGTATTCCTTAGATTTGACTCTGACG
GTGTGCTCATGTCAAACTCATCAATGGTAGGTGATTACTGGAACTTTAGGGAAGGACAGACCACC
CAAAGTGTGGCCTATACAAATGCTGTGGGATTCATGCCCAATCTAGGTGCATATCCTAAAACCCA
AAGCAAAACACCAAAAAATAGTATAGTAAGTCAGGTATATTTAAATGGAGAAACTACTATGCCAA
TGACACTGACAATAACTTTCAATGGCACTGATGAAAAAGACACAACACCTGTGAGCACTTACTCC
ATGACTTTTACATGGCAGTGGACTGGAGACTATAAGGACAAGAATATTACCTTTGCTACCAACTC
CTTTACTTTCTCCTACATGGCCCAAGAATAAACCCTGCATGCCAACCCCATTGTTCCCACCACTA
TGGAAAACTCTGAAGCAGaAAAAAATAAAGTTCAAGTGTTTTATTGATTCAACAGTTTTCtcaca
gaaccctagtattcaacctgccacctccctcccaacacacagagtacacagtcctttctcccccgg
ctggccttaaaaagcatcatatcatgggtaacagacatattcttaggtgttatattccacacggt
ttcctgtcgagccaaacgctcatcagtgatattaataaactccccgggcagctcacttaagttca
tgtcgctgtccagctgctgagccacaggctgctgtccaacttgcggttgcttaacgggcggcgaa
ggagaagtccacgcctacatgggggtagagtcataatcgtgcatcaggatagggcggtggtgctg
cagcagcgcgcgaataaactgctgccgccgccgctccgtcctgcaggaatacaacatggcagtgg
tctcctcagcgatgattcgcaccgcccgcagcataaggcgccttgtcctccgggcacagcagcgc
accctgatctcacttaaatcagcacagtaactgcagcacagcaccacaatattgttcaaaatccc
acagtgcaaggcgctgtatccaaagctcatggcggggaccacagaacccacgtggccatcatacc
acaagcgcaggtagattaagtggcgacccctcataaacacgctggacataaacattacctcttt
ggcatgttgtaattcaccacctcccggtaccatataaacctctgattaaacatggcgccatccac
caccatcctaaaccagctggccaaaacctgcccgccggctatacactgcagggaaccgggactgg
aacaatgacagtggagagcccaggactcgtaaccatggatcatcatgctcgtcatgatatcaatg
ttggcacaacacaggcacacgtgcatacacttcctcaggattacaagctcctcccgcgttagaac
catatcccagggaacaacccattcctgaatcagcgtaaatcccacactgcagggaagacctcgca
cgtaactcacgttgtgcattgtcaaagtgttacattcgggcagcagcggatgatcctccagtatg
gtagcgcgggtttctgtctcaaaaggaggtagacgatccctactgtacggagtgcgccgagacaa
ccgagatcgtgttggtcgtagtgtcatgccaaatggaacgccggacgtagtcatatttcctgaag
caaaaccaggtgcgggcgtgacaaacagatctgcgtctccggtctcgccgcttagatcgctctgt
gtagtagttgtagtatatccactctctcaaagcatccaggcgccccctggcttcgggttctatgt
aaactccttcatgcgccgctgccctgataacatccaccaccgcagaataagccacacccagccaa
cctacacattcgttctgcgagtcacacacgggaggagcgggaagagctggaagaaccatGATTAA
CTTTATTCCAAACGGTCTCGGAGCACTTCAAAATGCAGGTCCCGGAGGTGGCACCTCTCGCCCCC
```

-continued

```
ACTGTGTTGGTGGAAAATAACAGCCAGGTCAAAGGTGACACGGTTCTCGAGATGTTCCACGGTGG

CTTCCAGCAAAGCCTCCACGCGCACATCCAGAAACAAGAGGACAGCGAAAGCGGGAGCGTTTTCT

AATTCCTCAATCATCATATTACACTCCTGCACCATCCCCAGATAATTTTCATTTTTCCAGCCTTG

AATGATTCGTATTAGTTCCTGAGGTAAATCCAAGCCAGCCATGATAAAAAGCTCGCGCAGAGCGC

CCTCCACCGGCATTCTTAAGCACACCCTCATAATTCCAAGAGATTCTGCTCCTGGTTCACCTGCA

GCAGATTAACAATGGGAATATCAAAATCTCTGCCGCGATCCCTAAGCTCCTCCCTCAACAATAAC

TGTATGTAATCTTTCATATCATCTCCGAAATTTTTAGCCATAGGGCCGCCAGGAATAAGAGCAGG

GCAAGCCACATTACAGATAAAGCGAAGTCCTCCCCAGTGWGCATTGCCAAATGTAAGATTGAAAT

AAGCATGCTGGCTAGACCCTGTGATATCTTCCAGATAACTGGACAGAAAATCAGGCAAGCAATTT

TTAAGAAAATCAACAAAAGAAAAGTCGTCCAGGTGCAGGTTTAGAGCCTCAGGAACAACGATGGA

ATAAGTGCAAGGAGTGCGTTCCAGCATGGTTAGTGtTTTTTTGGTGATCTGTAGAACAAAAAATA

AACATGCAATATTAAACCATGCTAGCCTGGCGAACAGGTGGGTAAATCACTCTTTCCAGCACCAG

GCAGGCTACGGGGTCTCCGGCGCGACCCTCGTAGAAGCTGTCGCCATGATTGAAAAGCATCACCG

AGAGACCTTCCCGGTGGCCGGCATGGATGATTCGAGAAGAAGCATACACTCCGGGAACATTGGCA

TCCGTGAGTGAAAAAAaGCGACCTATAAAGCCTCGGGGCACTACAATGCTCAATCTCAATTCCAG

CAAAGCCACCCCATGCGGATGGAGCACAAAATTGGCAGGTGCGTAAAAAATGTAATTACTCCCCT

CCTGCACAGGCAGCAAAGCCCCGCTCCCTCCAGAAACACATACAAAGCCTCAGCGTCCATAGCT

TACCGAGCACGGCAGGCGCAAGAGTCAGAGAAAAGGCTGAGCTCTAACCTGACTGCCCGCTCCTG

TGCTCAATATATAGCCCTAACCTACACTGACGTAAAGGCCAAAGTCTAAAAATACCCGCCAAAAT

GACACACACGCCCAGCACACGCCCAGAAACCGGTGACACACTCAAAAAAATACGTGCGCTTCCTC

AAACGCCCAAACCGGCGTCATTTCCGGGTTCCCACGCTACGTCACCGCTCAGCGACTTTCAAATT

CCGTCGACCGTTAAAAACGTCACTCGCCCCGCCCCTAACGGTCGCCCTTCTCTCGGCCAATCACC

TTCCTCCCTTCCCAAATTCAAACGCCTCATTTGCATATTAACGCGCACAAAAAGTTTGAGGTATA

TATTTGAATGATG
```

ChAdOx2 Sequence (SEQ ID NO: 67+68)

The ChAdOx2 sequence 5' to the immunogen cassette is provided as SEQ ID NO: 67 and the ChAdOx2 sequence 3' to the immunogen cassette is provided as SEQ ID NO: 68.

MVA Sequence (SEQ ID NO: 69+70)

The MVA sequence 5' to the immunogen cassette is provided as SEQ ID NO: 69 and the MVA sequence 3' to the immunogen cassette is provided as SEQ ID NO: 70.

MVA vaccines have been made using two different shuttle plasmids:

1. P7.5 shuttle plasmid. HPV insert with upstream and downstream flanks that are homologous to regions of the TK locus in parental MVA virus. Insert under control of p7.5 promoter.
2. F11 shuttle plasmid. HPV insert with upstream and downstream flanks that are homologous to regions of the F11 locus in parental MVA virus. Insert under control of F11 promoter.

Chicken embryo fibroblast cells are then infected with MVA parental virus and transfected with either p7.5 or F11 MVA shuttle plasmids to allow homologous recombination with the MVA genome. So you get parental MVA with the gene of interest inserted into the MVA genome at either the TK locus (p7.5 shuttle plasmid) or F11 locus (F11 shuttle plasmid). Resulting in two versions of the MVA vaccine.

P7.5 shuttle plasmid (insert underlined)

(SEQ ID NO: 158)

```
agcgcccaatacgcaaaccgcctctccccgcgcgttggccgattcattaatgcagctggcacgacaggtttcccgactgga aagcgggcagtgagcgcaacgcaattaatgtgagttagctcactcattaggcacccaggctttacactttatgcttccggct cgtatgttgtgtggaattgtgagcggataacaatttcacacaggaaacagctatgaccatgattacgccaagcttgcatgcA TCTGGAAACGGGCATCTCCATTTAAGACTAGAtGCCACGGGGTTTAAAATACT

AATCATGACATTTTGTAGAGCGTAATTACTTAGTAAATCCGCCGTACTAGGTT
```

```
CATTTCCTCCTCGTTTGGATCTCACATCAGAAATTAAAATAATCTTAGAAGGA

TGCAGTTGTTTTTTGATGGATCGTAGATATTCCTCATCAACGAACCGAGTCAC

TAGAGTCACATCACGCAATCCATTTAAAATAGGATCATGATGGCGGCCGTCA

ATTAGCATCCATTTGATGATCACTCCTAAATTATAGAAATGATCTCTCAAATA

ACGTATATGTGTACCGGGAGCAGATCCTATATACACTACGGTGGCACCATCTA

ATATACCGTGTCGCTGTAACTTACTAAGAAAAAATAATTCTCCTAGTAATAGT

TTTAACTGTCCTTGATACGGtAGTTTTTTTGCGACCTCATTTGCACTTTCTGGTT

CGTAATCTAACTCATTATCAATTTCCTCAAAATACATAAACGGTTTATCTAAC

GACACAACATCCATTTTTAAGTATTATATTAAAATTTAATCAATGTTTATTTTT

AGTTTTTTAGATAAAAAATATAATATTATGAGTCGATGTAACACTTTCTACAC

ACCGATTGATACATATCATTACCTCCTATTATcTCTATCTCGGTTTCCTCACCC

AATCGTTTAGAAAAGGAAGCCTCCTTAAAGCATTTCATACACACAGCAGTTAG

TTTTACCACCATTTCAGATAATGGAATAAGATTCAAAATATTATTAAACGGTT

TACGTTGAAATGTCCCATCGAGTGCGGCTACTATAACTATTTTTCCTTCGTTTG

CCaTACAGATCCTACGTACTCGAGCGGCCGCTTATCAGGTCCGGGTGGAGTCC

AGGCCCAGCAGTGGATTGGGGATAGGCTTGCCAGAGGCGCCAGGTCCAGAGC

CGGCGATTCTGGCCTCGCACTTGCAGCACATACACAGCATGGTGTGTCTCTGA

GGCTCGGCCCTTCTAGCGGGCAGATGCTGGTGGTTCACGCCGTCGATCTCGTC

GTTCTCTTCCACCAGAGATTCGCATCTGCAGCACTGTGTCTCGATCAGATAGC

AAGGGTGCTGTTCGTCCCGTCTAGCCTGCTGGGGCTGTTCCTGCAGATGGTCC

ACTTCGTCCTCATCCTCGTCCCCATCCAGGCCGCCAGTGTCCTCTTCATCGGAG

CTGTCTCCCAGCTGCTCATAACAGTGCAGATCAGTGGTTTCAGGCTGCTCGTA

GCAGTACAGGTCGGTTGTCTCGGGCTGCAGATCCAGCATGTACTCGTGCAGGG

TGTGGAACCGCTTGTTCAGGTCCACGTGTCTTTTCTTTTCCTGCGGACACAGTG

GCCGCTGGCAGTCGTACACCTCAGATCTCTGCAGGGTTTTCTTGCATTCCACG

CACAGTGTGGTGCCATACACGGAATATCTGTACCACCGGAACTCGGACACCTT

GGAGTCGCGATACACGATTGTCAGGTCTGTGAAGGCGAAATCCAGCACCTCT

GTCTCGGTCAGCTGTCCCTTGCAATACACCAGGCTGGCGCCATACACAGAGCA

GTTGTAGTACCTCAGCTTCCGCACTTTGCTGTCCCGATACACCACCCGCAGAT

CGGTGTAGGCGAAGTTGTACACCTCGCTGGCTGTCAGGGCCTTCTTGCAGAAC

ACCCGCAGGCATCTAATCAGCAGGTTGTACAGGCCAGTGTTGGTCAGCTTTTC

CAGGGTATCGCCGTACACGGAGTCGCTGTAGTGCCGCAGCTCTCTGATTCTGG

AGTAGAAGTCGATACACTTGTGGCAGGCGGCGTGGGGATGGAGTCTCTGTA

CACCACGTTGATGCACCGAATCAGCAGATCGCACAGGGGCTTGTTGTACTGCT

GTTCCAGGGTGGTGCCGTACAGGCTGTAGCAGTAGTGCCGGTACTCGCTGATC

TTGCTGTAGAACTTCAGGCACTTGTCGCACACGGCGTAAGGATTGCCATCCCG

GTACACGATGGCGGTGGCGGGGCTGGTAATCACGACGATGTACACGAACACC

AGCACCCAGGCATAGGCACACATGCACACGCTGGGCAGCAGGCTTCCGATGG

ACACCCACAGCAGCAGCACCAGCACCAGCACCTGAGCGTACACGCTGATAGA

CAGCAGCAGAGGCCTCAGGTAGGTGGACACACTCAGCAGCAGGGTCTGATC

AGCAGGCACACGCACAGCAGCACACAAAAGCACAGCAGGAAGCAAGGGGCC
```

-continued

```
CAAGGTCTTGGAGGAGGTGGAGGGGGCACCCATGGACAGTGTGGAGGTCTAG
GAGGTGCCCAGGGGCAAGGGGCAGGGATTCTAGGGGCCCATGGAGAAGGCTT
AGGGATGGGGGGCCTCTGAGGAGCCCAAGGACATGGAGCAGGGATCCGGTG
AGGGGGGGTGCTGTAGCTGTTCAGCAGTGACAGCAGTGGGTATCTGGTGGTC
AGGTGCAGCCTGATCACGACTGTGCTCTTGGGGGTGGTCACTCTCAGTTCCAC
CAGGGAGGTATTCTCGGGGGTGGTGGTCTGGGTGGTCAGCAGTTTCAGCAGA
GGATATGTTGGATCCAGAGGCACGGGCACAGGGTGGGCACGATGAACACCT
TGTTCTCCCAGATGCACTTGCCGTGGGCCTTCACGCCCATGTTGGGGGTCTG
GACAGCAGCTTCAGCAGGGGGTACTTGGTCACGAGCTGAGACTGATCCTGGT
CGCTGGACAGCCGCCGTCTGGCCTTGTAAAAAATGGCACATTCCAGGCGAAT
CAGCTTCCAATAGTCGATATGGTCCTTCACGAGCTCGGTGGCGGACACGTTGT
CGTCGAAGGTGCTGCACATGGAGTCGTTGCAGTCGATGCTGTTGCCGAAATGC
ACTTCCAGGTGCCCTTGCAGCCGTACTTCTCGGCCTCGGTCTTGCACCAGCC
ATCGTCGCCGCAGTAGTACACGCTGTCCCAGGCCACGTAGTCGAACCACACTT
CGATGTGCTGGCCGCCCTTCTTGAAGCAGTGCTTGGGCTCGGTGTTCCACTCG
ATGGCTTTACAGGCCTTGGCCTTGCAGATATTCAGGGCGGGCACCACCTGGTG
TCTGGCGGCGAAGAAGATGGCGTTTTCCTGCCTGATGGCTTTCCAATAATCAA
TGTGGTCGGCTTCCTCGGTGCTGATCTCATCGGAGGGGATGCTGGCGGGCAC
ACGATCACGTAGATTTCTTTCCAATTTGTGTAATCCATGGTATTGGCCTTGTCA
TTGTCGTACTGCACGGTGATGGTGATGCCGTGCTTCTTAAACTGGGGCTCGGC
CAGCCACATTTCCAGGCTGGTCTGCTGCAGGGTCCACTCATCGTAGGGGCTGG
CATTCAGGGCTTCCAGGGCCAGCTGCAGTTCGATGGCCTGGCAGGCTTTGGCT
TTAGAGGCGGCCAGTGGAGGCACCACCTGGTGGCAGATGCTGATGCCCAGCT
CTTTGGCCTTATAGAAGATTGCACATTCCATCCGGATCAGTTTCCAGTGCTCG
ATCTGGGCGTTCAGGTCGTTCTTGTCGGCCTCGTAGTAGGTCAGGGTCACAAT
GGCGTTCTTGTGTTTCCCATCGTGACATGTCCAATGCCACTTGTGCTTGCCGTC
GTGGCAGGTCCAGTGCCAGGTGCTGCTCAGCTTGCAGTGCTTCTTGAATCTGT
ACCGCAGGCACTTCAGGATCAGCAGCTTGTTGGGGTGGCAGTTCTCGCTTCTG
GGCCTCTTGATCCGCCGCTGGCCGCTCTCAGGACACAGGATCACTTGGCCGCC
AGCGTGCACCTCCCATTTCTTGTCCACCTGGCCTTCCACCACGGTGCACTGGG
CGTCCTCGCAGATATAGATCCAGTTGGTGTAGTGCATGGTGTTGCAGATGTCG
CCGTCGAACTGGTGGAAGCCCATCTCGCGAGCCTTATACATAATAGCACATTC
CAGTCTGATCCGGGCCTTGTACATGATGGCGCATTCCAGCCGGATGTGCTTCC
AGTAGTCGATGTGATCGCAGATGTGGTCGCACAGGTCCTTGGAATCATTCTCA
TAATGTTCCAGAATGTCCTTGCTGTCGTTCTCGTAGTGTTCCAGGATCTTGTCC
TGGCACACGTTGAAGGGGTTCAGAAACTGCAGCACGTGGATCCGGGAGTGCA
GGTATCTCAGAAAGGCATTGGGGAACTCGAACACGGTGATCCGGCTTTCCAG
GTAAGGCCAGAAGGGGTTGGGGAAGGTAAACACCACCAGTCTGCTGTGCAGG
TAGGGCCACAGAGACATGGCAAAGCAGGACTTGCCTGTGTTAGGTGGGCCGT
AGATCACGAGACAATTCAGGGACATGCCGAAGTAGGACTTTCCGGTATTGGC
```

-continued

TGGGCCGCACAGCACCAGGCAGTTCAGGCTCATGCCGAACAGGCTCTTGCCG

GTGTTGGCAGCGCCGTACAGCAGGATGCAGTTCTTCAGAAAAGCAGCGGCGT

TGCTGTTCACGTCTGCCAGCTGAGCCTTCAGGAAGGCGCAGGCATTGCTGTCG

CTGTCAGCCAGCTGGGCGGAGTTGTCGATAAAGCCGTCCAGGTCGCTCTCGGT

GCTCTCTTCGTCGGTTTCGTCGTTGTCGATGAAATCCACCATGTCCTCGCCGGT

GTCGGAGTCGTTCTCATTCTCGTCGCTGTCGTCGATGAAGTCGATCAGGTCGG

TGCCGCTGTCGTAGGCTGTCTCGTCCTCGTCGGCCAGCTTGCTGCCTCTTCTGA

ACCGGGCGTGGATTTCCTGGCTGGGGGACACAAACACGGCGCCACACAGCAG

CAGCACGCAGCACAGGCCCCTCTTCATAGCATCCATGGTGGCGGCGCGGCTA

GCGGTACCGgatctagatGGGGATCCGTCACtGTTCTTTATGATTCTACTTCCTTACC

GTGCAATAAATTAGAATATATTTTCTACTTTTACGAGAAATTAATTATTGTATT

TATTATTTATGGGTGAAAAACTTACTATAAAAAGCGGGTGGGTTTGGAATTAG

TGATCAGTTTATGTATATCGCAACTACCGGgCATATGGCTATCGACATCGAGA

ACATTACCCACATGATAAGAGATTGTATCAGTTTCGTAGTCTTGAGTATTGGT

ATTACTATATAGTATATagatGTCGACCTGcaggtcGACGAAGTTCCTATACTTTCT

AGAGAATAGGAACTTCGCAGCCAAGCTGGAATTcaTCCACTTTGGATAAGAAA

TCTGCATGATAAATATATTGATATCCTACCACCTATTAAAGTACCATTATCTA

ATAGCAATAAGATAGATAAACAAATGTTTTTTGATGAAGTTATTACGTGGATA

AATATATATCTTCAGGAAAAGGGTATTATGTTACCAGATGATATAAGAGAACT

CAGAGATGCTATTATTCCTTAACTAGTTACGTCTCTTTAGGTACTTATTTTGAT

ACGTTACAAGTAAAAAACTATCAAATATAAATGGAATCTGATTCTAATATAGC

GATTGAAGAggaTCCACCGGTCGCCACCATGGTGAGCAAGGGCGAGGAGCTGT

TCACCGGGGTGGTGCCCATCCTGGTCGAGCTGGACGGCGACGTAAACGGCCA

CAAGTTCAGCGTGTCCGGCGAGGGCGAGGGCGATGCCACCTACGGCAAGCTG

ACCCTGAAGTTCATCTGCACCACCGGCAAGCTGCCCGTGCCCTGGCCCACCCT

CGTGACCACCCTGACCTACGGCGTGCAGTGCTTCAGCCGCTACCCCGACCACA

TGAAGCAGCACGACTTCTTCAAGTCCGCCATGCCCGAAGGCTACGTCCAGGA

GCGCACCATCTTCTTCAAGGACGACGGCAACTACAAGACCCGCGCCGAGGTG

AAGTTCGAGGGCGACACCCTGGTGAACCGCATCGAGCTGAAGGGCATCGACT

TCAAGGAGGACGGCAACATCCTGGGGCACAAGCTGGAGTACAACTACAACAG

CCACAACGTCTATATCATGGCCGACAAGCAGAAGAACGGCATCAAGGTGAAC

TTCAAGATCCGCCACAACATCGAGGACGGCAGCGTGCAGCTCGCCGACCACT

ACCAGCAGAACACCCCCATCGGCGACGGCCCCGTGCTGCTGCCCGACAACCA

CTACCTGAGCACCCAGTCCGCCCTGAGCAAAGACCCCAACGAGAAGCGCGAT

CACATGGTCCTGCTGGAGTTCGTGACCGCCGCCGGGATCACTCTCGGCATGGA

CGAGCTGTACAAGTAAAGCGGccgcgaagttcctatactttctagagaataggaacTTCAACAAT

GTCTGGAAAGAACTGTCCTTCATCGATACCTATCACGGAGAAATCTGTAATTG

ATTCCAAGAcATCACATAGTTTAGTTGCTTCCAATGCTTCAAAATTATTCTTAT

CATGCGTCCATAGTCCCGTTCCGTATCTATTATCGTTAGAATATTTTATAGTCA

CGCATTTATATTGAGCTATTTGATAACGTCTAACTCGTCTAATTAATTCTGTAC

TTTTACCTGAAAACATGGGGCCGATTATCAACTGAATATGTCCGCCGTTCATG

-continued

ATGACAATAAAGAATTAATTATTGTTCACTTTATTCGACTTTAATATATCCATC
ACGTTAGAAAATGCGATATcGCGACGAGGATCTATGTATCTAACAGGATCTAT
TGCGGTGGTAGCTAGAGctGATTCTTTTTTGAATCGCATCAAACTAATCACAAA
GTCGAACAAATATCCTTTATTAAGTTTGACCCTTCCATCTGTAACAATAGGGA
CCTTGTTAAACAGTTTTTTAAAATCTTGAgAGTCTGTGAATTTTGTCAATTGTC
TGTATTCCTCTGAAAGAGATTCATAACAATGACCCACGGCTTCTAATTTATTTT
TTGATTGGATCAATAATAATAACAGAAAGTCTAGATATTGAGTGATTTGCAAT
ATATCAGATAATGAAGATTCATCATCTTGACTAGCCAAATACTTAAAAAATGA
ATCATCATCTGCGAAGAACATCGTTAAGAGATACTGGTTGTGATCCATTTATga
gctcgcgaaagcttggcactggccgtcgttttacaacgtcgtgactgggaaaaccctggcgttacccaacttaatcgccttgc
agcacatcccccttcgccagctggcgtaatagcgaagaggcccgcaccgatcgcccttcccaacagttgcgcagcctgaa
tggcgaatggcgcctgatgcggtatttttctccttacgcatctgtgcggtatttcacaccgcatatggtgcactctcagtacaatc
tgctctgatgccgcatagttaagccagccccgacacccgccaacacccgctgacgcgccctgacgggcttgtctgctcccg
gcatccgcttacagacaagctgtgaccgtctccgggagctgcatgtgtcagaggttttcaccgtcatcaccgaaacgcgcga
gacgaaagggcctcgtgatacgcctattttta taggttaatgtcatgataataatggtttcttagacgtcaggtggcacttttcgg
ggaaatgtgcgcggaacccctatttgtttatttttctaaatacattcaaatatgtatccgctcatgagacaataaccctgataaat
gcttcaataatattgaaaaaggaagagtatgagtattcaacatttccgtgtcgcccttattccctttttttgcggcattttgccttcct
gttttt gctcacccagaaacgctggtgaaagtaaaagatgctgaagatcagttgggtgcacgagtgggttacatcgaactgg
atctcaacagcggtaagatccttgagagttttcgccccgaagaacgttttccaatgatgagcacttttaaagttctgctatgtgg
cgcggtattatcccgtattgacgccgggcaagagcaactcggtcgccgcatacactattctcagaatgacttggttgagtact
caccagtcacagaaaagcatcttacggatggcatgacagtaagagaattatgcagtgctgccataaccatgagtgataacac
tgcggccaacttacttctgacaacgatcggaggaccgaaggagctaaccgcttttttgcacaacatgggggatcatgtaactc
gccttgatcgttgggaaccggagctgaatgaagccataccaaacgacgagcgtgacaccacgatgcctgtagcaatggca
acaacgttgcgcaaactattaactggcgaactacttactctagcttcccggcaacaattaatagactggatggaggcggataa
agttgcaggaccacttctgcgctcggcccttccggctggctggtttattgctgataaatctggagccggtgagcgtgggtctc
gcggtatcattgcagcactggggccagatggtaagccctcccgtatcgtagttatctacacgacggggagtcaggcaactat
ggatgaacgaaatagacagatcgctgagataggtgcctcactgattaagcattggtaactgtcagaccaagtttactcatatat
actttagattgatttaaaacttcatttttaatttaaaaggatctaggtgaagatccttttttgataatctcatgaccaaaatcccttaac
gtgagttttcgttccactgagcgtcagaccccgtagaaaagatcaaaggatcttcttgagatcctttttttctgcgcgtaatctgc
tgcttgcaaacaaaaaaaccaccgctaccagcggtggtttgtttgccggatcaagagctaccaactcttttccgaaggtaact
ggcttcagcagagcgcagataccaaatactgttcttctagtgtagccgtagttaggccaccacttcaagaactctgtagcacc
gcctacatacctcgctctgctaatcctgttaccagtggctgctgccagtggcgataagtcgtgtcttaccgggttggactcaag
acgatagttaccggataaggcgcagcggtcgggctgaacggggggttcgtgcacacagcccagcttggagcgaacgacc
tacaccgaactgagatacctacagcgtgagctatgagaaagcgccacgcttcccgaagggagaaaggcggacaggtatcc
ggtaagcggcagggtcggaacaggagagcgcacgagggagcttccaggggaaacgcctggtatctttatagtcctgtcg
ggtttcgccacctctgacttgagcgtcgatttttgtgatgctcgtcaggggggcggagcctatgaaaaacgccagcaacgc
ggcattttacggttcctggccttttgctggccttttgctcacatgttattcctgcgttatcccctgattctgtggataaccgtatta
ccgcctttgagtgagctgataccgctcgccgcagccgaacgaccgagcgcagcgagtcagtgagcgaggaagcggaag
a F11-HPV shuttle plasmid (vaccine construct insert is underlined) (SEQ ID NO: 159)

AGCGCCCAATACGCAAACCGCCTCTCCCCGCGCGTTGGCCGATTCATTAATGCAGCTGGCACGAC
AGGTTTCCCGACTGGAAAGCGGGCAGTGAGCGCAACGCAATTAATGTGAGTTAGCTCACTCATTA
GGCACCCCAGGCTTTACACTTTATGCTTCCGGCTCGTATGTTGTGTGGAATTGTGAGCGGATAAC
AATTTCACACAGGAAACAGCTATGACCATGATTACGCCAAGCTATTTAGGTGACACTATAGAATA
CTCAAGCTATGCATCAAGCTTGGTACCGAGCTCGGATCCACTAGTAACGGCCGCCAGTGTGCTGG
AATTCGCCCTTgtaatctattcgatataccgttgctaacagtatactggcccaataactgtggat
ggaaaatctataataatacattaatatcatccgatggtgctagggttatttggatggatgcgtat
aaatttcttgcggtttatctttacaagactattgttatcattggggtagcaaaccagagagccg
accattcgatttaataaaaaaatcagatgctaaacgcaattctaaatcgttggtcaaagaatcta
tggcatccttgaaatccttgtacgaggcattcgagacacaatcaggagcgttagaagttttaatg
agtccatgtaggatgttttcgttttctagaatagaagacatgttcttaactagtgtcattaatag
agtatccgagaatactggaatggggatgtattatcctaccaacgatataccttctctatttatcg
aatcatctatctgtctagattatattatagtaaataatcaggaatccaacaaatatcgtatcaaa
tctgttctcgatatcatttcttcaaaacaataccctgcaggacgtcccaactacgttaaaaatgg
tacaaaaggaaagttatatatcgcgttgtgtaaagttaccgtacctactaacgaccatattccag
tagtttatcacgatgatgacaatactaccacctttattacagtattgacgtccgtcgatattgaa
actgctatcagagcaggatattcgatagtcgaattaggggctttacaatgggataataatattcc
agaacttaaaaacggtttactggatagtatcaagatgatttatgacttgaacgcagttacaacaa
ataatttattggaacagctcatagaaaatattaactttaacaactctagtataatttcgttgttt
tatacatttgccattagttattgccgagcattcatttactcaattatggaaaccatagatccggt
gtatatatctcagttcagttataaagaattatacgttagtagctcttataaagatattaatgaat
ccatgagtcagatggtaaaattataaaaagtgaaaaacaatattattttatcgttggttgttac
act<u>ATGGATGCTATGAAGAGGGGCCTGTGCTGCGTGCTGCTGCTGTGTGGCGCCGTGTTTGTGTC
CCCCAGCCAGGAAATCCACGCCCGGTTCAGAAGAGGCAGCAAGCTGGCCGACGAGGACGAGACAG
CCTACGACAGCGGCACCGACCTGATCGACTTCATCGACGACAGCGACGAGAATGAGAACGACTCC
GACACCGGCGAGGACATGGTGGATTTCATCGACAACGACGAAACCGACGAAGAGAGCACCGAGAG
CGACCTGGACGGCTTTATCGACAACTCCGCCCAGCTGGCTGACAGCGACAGCAATGCCTGCGCCT
TCCTGAAGGCTCAGCTGGCAGACGTGAACAGCAACGCCGCTGCTTTTCTGAAGAACTGCATCCTG
CTGTACGGCGCTGCCAACACCGGCAAGAGCCTGTTCGGCATGAGCCTGAACTGCCTGGTGCTGTG
CGGCCCAGCCAATACCGGAAAGTCCTACTTCGGCATGTCCCTGAATTGTCTCGTGATCTACGGCC
CACCTAACACAGGCAAGTCCTGCTTTGCCATGTCTCTGTGGCCCTACCTGCACAGCAGACTGGTG
GTGTTTACCTTCCCCAACCCCTTCTGGCCTTACCTGGAAAGCCGGATCACCGTGTTCGAGTTCCC
CAATGCCTTTCTGAGATACCTGCACTCCCGGATCCACGTGCTGCAGTTTCTGAACCCCTTCAACG
TGTGCCAGGACAAGATCCTGGAACACTACGAGAACGACAGCAAGGACATTCTGGAACATTATGAG
AATGATTCCAAGGACCTGTGCGACCACATCTGCGATCACATCGACTACTGGAAGCACATCCGGCT
GGAATGCGCCATCATGTACAAGGCCCGGATCAGACTGGAATGTGCTATTATGTATAAGGCTCGCG
AGATGGGCTTCCACCAGTTCGACGGCGACATCTGCAACACCATGCACTACACCAACTGGATCTAT
ATCTGCGAGGACGCCCAGTGCACCGTGGTGGAAGGCCAGGTGGACAAGAAATGGGAGGTGCACGC
TGGCGGCCAAGTGATCCTGTGTCCTGAGAGCGGCCAGCGGCGGATCAAGAGGCCCAGAAGCGAGA
ACTGCCACCCCAACAAGCTGCTGATCCTGAAGTGCCTGCGGTACAGATTCAAGAAGCACTGCAAG</u>

-continued

```
CTGAGCAGCACCTGGCACTGGACCTGCCACGACGGCAAGCACAAGTGGCATTGGACATGTCACGA
TGGGAAACACAAGAACGCCATTGTGACCCTGACCTACTACGAGGCCGACAAGAACGACCTGAACG
CCCAGATCGAGCACTGGAAACTGATCCGGATGGAATGTGCAATCTTCTATAAGGCCAAAGAGCTG
GGCATCAGCATCTGCCACCAGGTGGTGCCTCCACTGGCCGCCTCTAAAGCCAAAGCCTGCCAGGC
CATCGAACTGCAGCTGGCCCTGGAAGCCCTGAATGCCAGCCCCTACGATGAGTGGACCCTGCAGC
AGACCAGCCTGGAAATGTGGCTGGCCGAGCCCCAGTTTAAGAAGCACGGCATCACCATCACCGTG
CAGTACGACAATGACAAGGCCAATACCATGGATTACACAAATTGGAAAGAAATCTACGTGATCGT
GTGCCCCGCCAGCATCCCCTCCGATGAGATCAGCACCGAGGAAGCCGACCACATTGATTATTGGA
AAGCCATCAGGCAGGAAAACGCCATCTTCTTCGCCGCCAGACACCAGGTGGTGCCCGCCCTGAAT
ATCTGCAAGGCCAAGGCCTGTAAAGCCATCGAGTGGAACACCGAGCCCAAGCACTGCTTCAAGAA
GGGCGGCCAGCACATCGAAGTGTGGTTCGACTACGTGGCCTGGGACAGCGTGTACTACTGCGGCG
ACGATGGCTGGTGCAAGACCGAGGCCGAGAAGTACGGCTGCAAGGGCACCTGGGAAGTGCATTTC
GGCAACAGCATCGACTGCAACGACTCCATGTGCAGCACCTTCGACGACAACGTGTCCGCCACCGA
GCTCGTGAAGGACCATATCGACTATTGGAAGCTGATTCGCCTGGAATGTGCCATTTTTTACAAGG
CCAGACGGCGGCTGTCCAGCGACCAGGATCAGTCTCAGCTCGTGACCAAGTACCCCCTGCTGAAG
CTGCTGTCCAGACCCCCAACATGGGCGTGAAGGCCCACGGCAAGTGCATCTGGGAGAACAAGGT
GTTCATCGTGCCCACCCTGTGCCCCGTGCCTCTGGATCCAACATATCCTCTGCTGAAACTGCTGA
CCACCCAGACCACCACCCCCGAGAATACCTCCCTGGTGGAACTGAGAGTGACCACCCCCAAGAGC
ACAGTCGTGATCAGGCTGCACCTGACCACCAGATACCCACTGCTGTCACTGCTGAACAGCTACAG
CACCCCCCCTCACCGGATCCCTGCTCCATGTCCTTGGGCTCCTCAGAGGCCCCCCATCCCTAAGC
CTTCTCCATGGGCCCCTAGAATCCCTGCCCCTTGCCCCTGGGCACCTCCTAGACCTCCACACTGT
CCATGGGTGCCCCCTCCACCTCCTCCAAGACCTTGGGCCCCTTGCTTCCTGCTGTGCTTTTGTGT
GCTGCTGTGCGTGTGCCTGCTGATCAGACCCCTGCTGCTGAGTGTGTCCACCTACCTGAGGCCTC
TGCTGCTGTCTATCAGCGTGTACGCTCAGGTGCTGGTGCTGGTGCTGCTGCTGTGGGTGTCCATC
GGAAGCCTGCTGCCCAGCGTGTGCATGTGTGCCTATGCCTGGGTGCTGGTGTTCGTGTACATCGT
CGTGATTACCAGCCCCGCCACCGCCATCGTGTACCGGGATGGCAATCCTTACGCCGTGTGCGACA
AGTGCCTGAAGTTCTACAGCAAGATCAGCGAGTACCGGCACTACTGCTACAGCCTGTACGGCACC
ACCCTGGAACAGCAGTACAACAAGCCCCTGTGCGATCTGCTGATTCGGTGCATCAACGTGGTGTA
CAGAGACTCCATCCCCCACGCCGCCTGCCACAAGTGTATCGACTTCTACTCCAGAATCAGAGAGC
TGCGGCACTACAGCGACTCCGTGTACGGCGATACCCTGGAAAAGCTGACCAACACTGGCCTGTAC
AACCTGCTGATTAGATGCCTGCGGGTGTTCTGCAAGAAGGCCCTGACAGCCAGCGAGGTGTACAA
CTTCGCCTACACCGATCTGCGGGTGGTGTATCGGGACAGCAAAGTGCGGAAGCTGAGGTACTACA
ACTGCTCTGTGTATGGCGCCAGCCTGGTGTATTGCAAGGGACAGCTGACCGAGACAGAGGTGCTG
GATTTCGCCTTCACAGACCTGACAATCGTGTATCGCGACTCCAAGGTGTCCGAGTTCCGGTGGTA
CAGATATTCCGTGTATGGCACCACACTGTGCGTGGAATGCAAGAAAACCCTGCAGAGATCTGAGG
TGTACGACTGCCAGCGGCCACTGTGTCCGCAGGAAAAGAAAAGACACGTGGACCTGAACAAGCGG
TTCCACACCCTGCACGAGTACATGCTGGATCTGCAGCCCGAGACAACCGACCTGTACTGCTACGA
GCAGCCTGAAACCACTGATCTGCACTGTTATGAGCAGCTGGGAGACAGCTCCGATGAAGAGGACA
CTGGCGGCCTGGATGGGGACGAGGATGAGGACGAAGTGGACCATCTGCAGGAACAGCCCCAGCAG
GCTAGACGGGACGAACAGCACCCTTGCTATCTGATCGAGACACAGTGCTGCAGATGCGAATCTCT
```

-continued

```
GGTGGAAGAGAACGACGAGATCGACGGCGTGAACCACCAGCATCTGCCCGCTAGAAGGGCCGAGC
CTCAGAGACACACCATGCTGTGTATGTGCTGCAAGTGCGAGGCCAGAATCGCCGGCtaatttta
taaccgagtttctgcattattgtaattcgtatgctggcaccatcaaagaatcacttctaaaagat
atcaatatcacacatacaaatattactaccctattgaatgagacagccaaggttatcaagttagt
aaaatctctggtagataaagaagatactgatattgtgaataatttcattaccaaagaaattaaaa
acagagacaaaatagttaatagtttgtctctatcaaacctggactttcgtttgtaaattggggct
Ttttgtacaataaatgggtgttgccaatgattcatcccctgaatatcaatggatgtctccccata
gattatcagatactgttatattaggagactgtttgtattttaacaatataatgtcccaattagat
ttacaccaaaattgggctccatcagttagattgttaaattattttaagaattttaataaggaaac
actactaaagatagaagagaatgattacattaattcatcctttttccaacaaaaggataaacgat
tttatcctataaacgacgattttatcacatatctacaggaggatatggtatagtctttaagata
gataactatgtagtaaaatttgtattcgaggccacaaaattatatagtcccatggaaactacggc
ggagttcacagtacccaaatttctatacaacaatctaaagggagatgaaaaaaaattaatcgtgt
gtgcgtgggccatgggattaaactataaattaacattttacatactctgtataaacgtgttctt
catatgttgctattattgatacaaactatggatggtcaggaactatcattgagatattcttctaa
agttttttaaaggcgtttaacgagagaaaggacagtatcaaattcgtgaaattactatcccact
tttatccggcagttattaacagtaatattaatgttataaactattttaaccgcatgtttcacttt
ttcgaacatgaaaagagaactaactacgaatacgaaagaggaaatattataattttttccctagc
actgtattcggcagataaagtagataccgagctagctatcaaattaggatttaaatctttggtac
aatacataaagtttatcttttttacagatggctctgttatacattaaaatttacgaactaccatgc
tgcgacaacttttttacacgcagatcttaaacccgataatatcttacttttttgattccaatgaacc
aataataattcatctaaaggataaaaagtttgttttaatgaacgtattaaatcggcattaaacg
actttgacttttcccaagAAGGGCGAATTCTGCAGATATCCATCACACTGGCggccgcTTACTTG
TACAGCTCGTCCATGCCGAGAGTGATCCCGGCGGCGGTCACGAACTCCAGCAGGACCATGTGATC
GCGCTTCTCGTTGGGGTCTTTGCTCAGGGCGGACTGGGTGCTCAGGTAGTGGTTGTCGGGCAGCA
GCACGGGGCCGTCGCCGATGGGGGTGTTCTGCTGGTAGTGGTCGGCGAGCTGCACGCTGCCGTCC
TCGATGTTGTGGCGGATCTTGAAGTTCACCTTGATGCCGTTCTTCTGCTTGTCGGCCATGATATA
GACGTTGTGGCTGTTGTAGTTGTACTCCAGCTTGTGCCCCAGGATGTTGCCGTCCTCCTTGAAGT
CGATGCCCTTCAGCTCGATGCGGTTCACCAGGGTaTCGCCCTCGAACTTCACCTCGGCGCGGGTC
TTGTAGTTGCCGTCGTCCTTGAAGAAGATGGTGCGCTCCTGGACGTAGCCTTCGGGCATGGCGGA
CTTGAAGAAGTCGTGCTGCTTCATGTGGTCGGGGTAGCGGCTGAAGCACTGCACGCCGTAGGTCA
GGGTGGTCACGAGGGTcGGCCAGGGCACGGGCAGCTTGCCGGTGGTGCAGATGAACTTCAGGGTC
AGCTTGCCGTAGGTGGCATCGCCCTCGCCCTCGCCGGACACGCTGAACTTGTGGCCGTTTACGTC
GCCGTCCAGCTCGACCAGGATGGGCACCACCCCGGTaAACAGCTCCTCGCCCTTGCTCACCATGt
ttaaacTTTATATTCCAAAAAAAAAAATAAAATTTCAATTTTTgtttaaacgttGTACGGCAGT
TTAAGGTTTACACCTATAAAAGAGAGAGCCGTTATCGTCTGTTTGTGGATGTACAGAGTGATATT
ATTGACACGCCGGGGCGACGGATGGTGATCCCCCTGGCCAGTGCACGTCTGCTGTCAGATAAAGT
CTCCCGTGAACTTTACCCGGTGGTGCATATCGGGGATGAAAGCTGGCGCATGATGACCACCGATA
TGGCCAGTGTGCCGGTCTCCGTTATCGGGGAAGAAGTGGCTGATCTCAGCCACCGCGAAAATGAC
ATCAAAAACGCCATTAACCTGATGTTCTGGGGAATATAAATGTCAGGCATGAGATTATCAAAAAG
GATCTTCACCTAGATCCTTTTCACGTAGAAAGCCAGTCCGCAGAAACGGTGCTGACCCCGGATGA
```

-continued

```
ATGTCAGCTACTGGGCTATCTGGACAAGGGAAAACGCAAGCGCAAAGAGAAAGCAGGTAGCTTGC
AGTGGGCTTACATGGCGATAGCTAGACTGGGCGGTTTTATGGACAGCAAGCGAACCGGAATTGCC
AGCTGGGGCGCCCTCTGGTAAGGTTGGGAAGCCCTGCAAAGTAAACTGGATGGCTTTCTCGCCGC
CAAGGATCTGATGGCGCAGGGGATCAAGCTCTGATCAAGAGACAGGATGAGGATCGTTTCGCATG
ATTGAACAAGATGGATTGCACGCAGGTTCTCCGGCCGCTTGGGTGGAGAGGCTATTCGGCTATGA
CTGGGCACAACAGACAATCGGCTGCTCTGATGCCGCCGTGTTCCGGCTGTCAGCGCAGGGGCGCC
CGGTTCTTTTTGTCAAGACCGACCTGTCCGGTGCCCTGAATGAACTGCAAGACGAGGCAGCGCGG
CTATCGTGGCTGGCCACGACGGGCGTTCCTTGCGCAGCTGTGCTCGACGTTGTCACTGAAGCGGG
AAGGGACTGGCTGCTATTGGGCGAAGTGCCGGGGCAGGATCTCCTGTCATCTCACCTTGCTCCTG
CCGAGAAAGTATCCATCATGGCTGATGCAATGCGGCGGCTGCATACGCTTGATCCGGCTACCTGC
CCATTCGACCACCAAGCGAAACATCGCATCGAGCGAGCACGTACTCGGATGGAAGCCGGTCTTGT
CGATCAGGATGATCTGGACGAAGAGCATCAGGGGCTCGCGCCAGCCGAACTGTTCGCCAGGCTCA
AGGCGAGCATGCCCGACGGCGAGGATCTCGTCGTGACCCATGGCGATGCCTGCTTGCCGAATATC
ATGGTGGAAAATGGCCGCTTTTCTGGATTCATCGACTGTGGCCGGCTGGGTGTGGCGGACCGCTA
TCAGGACATAGCGTTGGCTACCCGTGATATTGCTGAAGAGCTTGGCGGCGAATGGGCTGACCGCT
TCCTCGTGCTTTACGGTATCGCCGCTCCCGATTCGCAGCGCATCGCCTTCTATCGCCTTCTTGAC
GAGTTCTTCTGAATTATTAACGCTTACAATTTCCTGATGCGGTATTTTCTCCTTACGCATCTGTG
CGGTATTTCACACCGCATACAGGTGGCACTTTTCGGGGAAATGTGCGCGGAACCCCTATTTGTTT
ATTTTTCTAAATACATTCAAATATGTATCCGCTCATGAGACAATAACCCTGATAAATGCTTCAAT
AATAGCACGTGAGGAGGGCCACCATGGCCAAGTTGACCAGTGCCGTTCCGGTGCTCACCGCGCGC
GACGTCGCCGGAGCGGTCGAGTTCTGGACCGACCGGCTCGGGTTCTCCCGGGACTTCGTGGAGGA
CGACTTCGCCGGTGTGGTCCGGGACGACGTGACCCTGTTCATCAGCGCGGTCCAGGACCAGGTGG
TGCCGGACAACACCCTGGCCTGGGTGTGGGTGCGCGGCCTGGACGAGCTGTACGCCGAGTGGTCG
GAGGTCGTGTCCACGAACTTCCGGGACGCCTCCGGGCCGGCCATGACCGAGATCGGCGAGCAGCC
GTGGGGGCGGGAGTTCGCCCTGCGCGACCCGGCCGGCAACTGCGTGCACTTCGTGGCCGAGGAGC
AGGACTGACACGTGCTAAAACTTCATTTTTAATTTAAAAGGATCTAGGTGAAGATCCTTTTTGAT
AATCTCATGACCAAAATCCCTTAACGTGAGTTTTCGTTCCACTGAGCGTCAGACCCCGTAGAAAA
GATCAAAGGATCTTCTTGAGATCCTTTTTTTCTGCGCGTAATCTGCTGCTTGCAAACAAAAAAAC
CACCGCTACCAGCGGTGGTTTGTTTGCCGGATCAAGAGCTACCAACTCTTTTTCCGAAGGTAACT
GGCTTCAGCAGAGCGCAGATACCAAATACTGTCCTTCTAGTGTAGCCGTAGTTAGGCCACCACTT
CAAGAACTCTGTAGCACCGCCTACATACCTCGCTCTGCTAATCCTGTTACCAGTGGCTGCTGCCA
GTGGCGATAAGTCGTGTCTTACCGGGTTGGACTCAAGACGATAGTTACCGGATAAGGCGCAGCGG
TCGGGCTGAACGGGGGGTTCGTGCACACAGCCCAGCTTGGAGCGAACGACCTACACCGAACTGAG
ATACCTACAGCGTGAGCTATGAGAAAGCGCCACGCTTCCCGAAGGGAGAAAGGCGGACAGGTATC
CGGTAAGCGGCAGGGTCGGAACAGGAGAGCGCACGAGGGAGCTTCCAGGGGGAAACGCCTGGTAT
CTTTATAGTCCTGTCGGGTTTCGCCACCTCTGACTTGAGCGTCGATTTTTGTGATGCTCGTCAGG
GGGGCGGAGCCTATGGAAAAACGCCAGCAACGCGGCCTTTTTACGGTTCCTGGGCTTTTGCTGGC
CTTTTGCTCACATGTTCTTTCCTGCGTTATCCCCTGATTCTGTGGATAACCGTATTACCGCCTTT
GAGTGAGCTGATACCGCTCGCCGCAGCCGAACGACCGAGCGCAGCGAGTCAGTGAGCGAGGAAGC
GGAAG
```

HPV2-randomised nucleotide sequence (segments are in a randomisd order)
(includes tPA leading sequence and HindIII cloning linker, underlined)

(SEQ ID NO: 71)

ATGGATGCTATGAAGAGGGGCCTGTGCTGCGTGCTGCTGCTGTGTGGCGCCGTGTTTGTGTCCCC

CAGCCAGGAAATCCACGCCCGGTTCAGAAGAGGCAGCAAGCTGGCTGCTCAGCTGGCCGACAGCG

ACAGCAATGCCTGCGCCTTCCTGAAGCTGAGATACCTGCACAGCCGGATCCACGTGCTGCAGTTT

CTGAACCCCTTCACCCTGCACGAGTACATGCTGGACCTGCAGCCCGAGACAACCGACCTGTACTG

CTACGAGCAGGACGAGGATGAGGACGAGGTGGACCATCTGCAGGAACAGCCCCAGCAGGCCAGAA

GGGATGAGCAGCACCCCTGCTACCTGATCGAGACACAGTGCTGCAGATGCGAGAGCCTGGTGGCC

CAGCTGGCTGACGTGAACTCTAACGCCGCAGCCTTTCTGAAGAACAGCATCGACTGCAACGACAG

CATGTGCAGCACCTTCGACGACAACGTGTCCGCCACCGAGCTCGTGAAGAGAATCCCTGCCCCTT

GCCCCTGGGCCCCTGAGGAAAATGACGAGATCGACGGCGTGAACCACCAGCATCTGCCCGCTAGA

AGGGCCGAGCCTCAGAGACACACCATGCTGTGCATGTGCTGCAAGTGCGAGGCCCGGATCTGCTT

CCTGCTGTGCTTTTGTGTGCTGCTGTGCGTGTGCCTGCTGATCAGACCCCTGCTGCTGAGTGTGT

CCACCTACTGCCAGCGGCCGCTGTGTCCTCAGGAAAAGAAACGGCACGTGGACCTGAACAAGCGG

TTCCACATCTACATCTGCGAGGACGCCCAGTGCACCGTGGTGGAAGGCCAGGTGGACAGCAAGGT

GTCCGAGTTCCGGTGGTACAGATACAGCGTGTACGGCACCACCCTGGGCCAGCGGAGAATCAAGA

GGCCCAGATCCGAGGTGTACTGCAAGGGACAGCTGACCGAGACAGAGGTGCTGGACTTCGCCTTC

ACCGACCTGACCATCGTGTACCGGGACATCCGGCTGGAATGCGCCATCATGTACAAGGCCAGAGA

GATGGGCTTCCACGACCACATCGACTACTGGAAGCTGATTAGACTGGAATGTGCTATCTTCTACA

AAGCCCGGATCCTGAAGTGCCTGCGGTACAGATTCAAGAAGCACTGCAAGCTGTACGTGGCCTGG

GACTCCGTGTACTACTGCGGCGACGATGGCTGGTGCAAGACCAGCTCTACCTGGCACTGGACATG

CCACGACGGCAAGCACAAGAACGTGTGCCAGGACAAGATCCTGGAACACTACGAGAACGACTCCA

AGGACGACGAGGACGAGACAGCCTACGACAGCGGCACCGATCTGATCGACTTCATCGACGATAGC

AACTGCCACCCCAACAAGCTGCTGCGGAGACTGAGCAGCGACCAGGACCAGTCTCAGAGGCCCCC

CAACATGGGAGTGAAGGCCCACGGCAAGTGCATCTGGGAGAACAAGGTGTTCATCGTGCCCACCC

TGTGCCCCGTGCCTCTGGATCCAACATACCCCCTGCTGAAGCTGCTGACCCCCGAAACCACAGAT

CTGCACTGTTATGAGCAGCTGGGCGACTCCTCCGACGAAGAGGATACAGGCGGCCTGGATGGCTA

CGAGGCCGACAAGAACGACCTGAACGCCCAGATCGAGCACTGGAAACTGATCCGGATGGAATGTG

CAATTTTCTATAAGGCCAAAGAGCTGGGGATCAGCGACGAGAATGAGAACGACAGCGATACCGGC

GAGGACATGGTGGATTTCATCGACAATGAGGCCGAGAAGTACGGCTGCAAGGGCACCTGGGAGGT

GCACTTCGGCTTTAAGAAGCACGGCATCACCATCACCGTGCAGTACGACAACGACAAGGCCAACA

CCATGGACTACACCAACTGGAAAGAGATCTACCCCCCTCCCCCCCCACGGCCTTGGGCTCCTCCA

ATTCCTAAGCCCTCTCCATGGGCCCCTCAGTTCGACGGCGACATCTGCAATACCATGCACTATAC

CAATTGGGTGGTGTACAGAGACAGCATCCCCCACGCCGCCTGCCACAAGTGTATCGACTTCTACA

GCAGAATCAGAGAGCTGCGGCACTACAGCGACTCTGTGTACGGCGATACCCTGGAAAAGCTGACC

AACACCGGCCTGTACAATCTGCTGATCCGGTGCCTGAGGCTCGTGACCAAGTATCCTCTGCTGAA

ACTGCTGTCCAACTGCATCCTGTACGGCGCTGCCAATACCGGCAAGAGCCTGTTCGGCATGAGCC

TGAGCAAAGTGCGGAAGCTGAGGTACTACAACTGCTCCGTGTATGGGGCCAGCCTGTGCGTGGAA

TGCAAGAAAACCCTGCAGCGGAGCGAAGTGTACGACGACGAAACCGACGAGGAAAGCACCGAGAG

CGACCTGGACGGCTTCATCGATAACAGCGTGATCGTGTGCCCCGCCTCCATCCCCTCCGATGAGA

TCTCTACCGAGGAAGCCCCCAGACCCCCTCACTGTCCTTGGGTGCCAGTGTTCTGCAAGAAGGCC

-continued

```
CTGACCGCCTCTGAGGTGTACAATTTTGCCTATACCGACCTGCGCGTGGTGTATAGGGACATTCT

GGAACATTATGAGAATGATAGCAAGGACCTGTGCGATCACATCAACTGCCTCGTGATCTACGGCC

CTCCTAACACCGGCAAGTCCTGCTTCGCCATGTCCCTGTGGAACACCGAGCCCAAGCACTGCTTC

AAGAAGGGCGGCCAGCACATCGAAGTGTGGTTCGATATTGTGTACAGGGACGGCAACCCTTACGC

CGTGTGCGACAAGTGCCTGAAGTTCTACTCCAAGATCAGCGAGTACCGCCACTACTGCTACTCCC

TGTATGGCACAACACTGGAACAGCAGTACAACAAGCCCCTGTGCGACCTGCTGATTCGCTGCATC

AACACCACCAGATACCCTCTGCTGTCCCTGCTGAACAGCTACAGCACCCCCCCTCATCGGATTCC

CGCCCCATGTCCATGGGCTCCACAGAGGCCTACCCAGACCACCACCCCCGAGAATACCTCCCTGG

TGGAACTGAGAGTGACCACCCCCAAGAGCACAGTCGTGATCAGGCTGCACCTGTGGCCCTACCTG

CACTCCAGACTGGTGGTGTTCACCTTCCCCAACCCCTTTCACCAGGTGGTGCCCGCCCTGAATAT

CTGCAAGGCCAAGGCCTGCAAAGCCATCGAGAAGAAATGGGAAGTGCACGCTGGCGGCCAAGTGA

TCCTGTGTCCTGAGAGCCTGCGGCCTCTGCTGCTGTCCATTAGCGTGTACGCCCAGGTGCTGGTG

CTGGTGCTGCTGCTGTGGGTGTCCATCGGCAGCAACTGTCTGGTGCTGTGCGGCCCTGCCAACAC

AGGGAAGAGTTACTTCGGCATGTCTCTGATCTGCCATCAGGTGGTGCCTCCACTGGCCGCCTCTA

AGGCTAAAGCCTGTCAGGCCATCGAACTGCAGCTGGCCCTGGAAGCCCTGAATGCCAGCCCCTAT

GATCACATTGATTACTGGAAAGCCATCCGGCAGGAAAATGCCATCTTCTTCGCCGCCAGATGGCA

TTGGACCTGTCACGATGGAAAACACAAGAATGCCATTGTGACCCTGACCTACCTGCTGCCCAGCG

TGTGTATGTGCGCCTACGCTTGGGTGCTGGTGTTCGTGTACATCGTCGTGATTACCAGCCCCGCC

ACCGCCGATGAGTGGACACTGCAGCAGACAAGCCTGGAAATGTGGCTGGCCGAGCCCCAGTGTGA

CCATATCGATTATTGGAAACACATCCGCCTGGAATGTGCTATTATGTATAAGGCCCGGTGGCCTT

ACCTGGAAAGCAGAACCGTGTTCGAGTTCCCCAATGCCTTCGCCGGCTCTGGACCTGGCGCCTCT

GGAAAACCCATCCCCAATCCACTGCTGGGCCTGGACTCCACCCGGACC
```

HPV2-randomised sequence polypeptide (includes tPA leading sequence and HindIII cloning linker, underlined)

(SEQ ID NO: 72)

<u>MDAMKRGLCCVLLLCGAVFVSPSQEIHARFRRGSKLAAQLADSDSNACAFLKLRYLHSRIHVLQF</u>

LNPFTLHEYMLDLQPETTDLYCYEQDEDEDEVDHLQEQPQQARRDEQHPCYLIETQCCRCESLVA

QLADVNSNAAAFLKNSIDCNDSMCSTFDDNVSATELVKRIPAPCPWAPEENDEIDGVNHQHLPAR

RAEPQRHTMLCMCCKCEARICFLLCFCVLLCVCLLIRPLLLSVSTYCQRPLCPQEKKRHVDLNKR

FHIYICEDAQCTVVEGQVDSKVSEFRWYRYSVYGTTLGQRRIKRPRSEVYCKGQLTETEVLDFAF

TDLTIVYRDIRLECAIMYKAREMGFHDHIDYWKLIRLECAIFYKARILKCLRYRFKKHCKLYVAW

DSVYYCGDDGWCKTSSTWHWTCHDGKHKNVCQDKILEHYENDSKDDEDETAYDSGTDLIDFIDDS

NCHPNKLLRRLSSDQDQSQRPPNMGVKAHGKCIWENKVFIVPTLCPVPLDPTYPLLKLLTPETTD

LHCYEQLGDSSDEEDTGGLDGYEADKNDLNAQIEHWKLIRMECAIFYKAKELGISDENENDSDTG

EDMVDFIDNEAEKYGCKGTWEVHFGFKKHGITITVQYDNDKANTMDYTNWKEIYPPPPPRPWAPP

IPKPSPWAPQFDGDICNTMHYTNWVVYRDSIPHAACHKCIDFYSRIRELRHYSDSVYGDTLEKLT

NTGLYNLLIRCLRLVTKYPLLKLLSNCILYGAANTGKSLFGMSLSKVRKLRYYNCSVYGASLCVE

CKKTLQRSEVYDDETDEESTESDLDGFIDNSVIVCPASIPSDEISTEEAPRPPHCPWVPVFCKKA

LTASEVYNFAYTDLRVVYRDILEHYENDSKDLCDHINCLVIYGPPNTGKSCFAMSLWNTEPKHCF

KKGGQHIEVWFDIVYRDGNPYAVCDKCLKFYSKISEYRHYCYSLYGTTLEQQYNKPLCDLLIRCI

NTTRYPLLSLLNSYSTPPHRIPAPCPWAPQRPTQTTTPENTSLVELRVTTPKSTVVIRLHLWPYL

HSRLVVFTFPNPFHQVVPALNICKAKACKAIEKKWEVHAGGQVILCPESLRPLLLSISVYAQVLV

-continued

LVLLLWVSIGSNCLVLCGPANTGKSYFGMSLICHQVVPPLAASKAKACQAIELQLALEALNASPY

DHIDYWKAIRQENAIFFAARWHWTCHDGKHKNAIVTLTYLLPSVCMCAYAWVLVFVYIVVITSPA

TADEWTLQQTSLEMWLAEPQCDHIDYWKHIRLECAIMYKARWPYLESRTVFEFPNAFAGSGPGAS

GKPIPNPLLGLDSTRT**

HPV53del nucleotide sequence (segments from HPV53 have been removed) (includes tPA leading sequence and HindIII cloning linker, underlined)

(SEQ ID NO: 73)

<u>ATGGATGCTATGAAGCGAGGACTGTGCTGCGTGCTGCTGCTGTGTGGCGCTGTGTTTGTGTCCCCTAGCC</u>

<u>AAGAGATCCACGCCAGATTCAGACGGGGCAGCAAACTGGCC</u>GACGAGGATGAGACAGCCTACGACTCTGG

CACCGACCTGATCGACTTCATCGACGACAGCGACGAGAACGAGAATGACAGCGACACCGGCGAGGACATG

GTGGATTTCATCGACAATGCCCAGCTGGCCGACTCCGACTCTAATGCCTGTGCCTTTCTGAAGGCTCAGC

TGGCTGACGTGAACAGCAATGCCGCCGCTTTCCTGAAGAACTGCATCCTGCTGTACGGCGCTGCCAACAC

AGGCAAGAGCCTGTTTGGCATGAGCCTGAACTGCCTGGTGCTGTGCGGACCTGCCAATACCGGCAAAAGC

TACTTCGGCATGTCCCTGTGGCCTTACCTGCACAGCAGACTGGTGGTGTTTACATTCCCCAATCCTTTCT

GGCCCTACCTGGAAAGCCGGATCACCGTGTTCGAGTTCCCCAACGCCTTCAACGTGTGCCAGGACAAGAT

CCTGGAACACTATGAGAACGACAGCAAGGACATCCTTGAGCACTACGAAAACGACTCCAAGGACCTGTGC

GACCACATCTGCGATCACATCGACTACTGGAAGCACATCCGGCTGGAATGCGCCATCATGTACAAGGCCC

GGATCAGACTGGAATGTGCTATTATGTATAAGGCTCGCGAGATGGGCTTCCACCAGTTCGACGGCGACAT

CTGCAACACCATGCACTACACCAACTGGATCTATATCTGCGAGGACGCCCAGTGCACCGTGGTGGAAGGA

CAGGTGGACAAGAAATGGAAGTGCACGCTGGCGGCCAAGTGATTCTGTGTCCTGAGAGCGGCCAGCGGA

GAATCAAGAGGCCCAGATCCGAGAACTGTCACCCCAACAAGCTGCTGATCCTGAAGTGCCTGCGGTACAG

ATTCAAGAAGCACTGCAAGCTGAGCAGCACCTGGCACTGGACATGCCACGATGGCAAGCACAAGTGGCAT

TGGACCTGTCACGACGGGAAACACAAGAACGCCATCGTGACCCTGACCTACTACGAGGCCGACAAGAACG

ACCTGAACGCCCAGATTGAGCACTGGAAACTGATCCGGATGGAATGTGCAATCTTCTATAAGGCCAAAGA

GCTGGGGATCAGCATCTGCCACCAGGTGGTGCCTCCACTGGCTGCCTCTAAAGCCAAAGCCTGTCAGGCC

ATCGAACTGCAGCTGGCCCTGGAAGCCCTGAACGCTAGCCCTTACGATGAGTGGACCCTGCAGCAGACCA

GCCTGGAAATGTGGCTGGCCGAGCCTCAGTTTAAGAAGCACGGCATCACCATCACCGTGCAGTACGACAA

CGACAAGGCCAATACCATGGATTACACGAATTGGAAAGAAATCTACGTGATCGTGTGCCCCGCCAGCATT

CCCTCCGATGAGATCTCTACCGAGGAAGCCGACCACATTGATTATTGGAAGGCCATCCGGCAAGAGAATG

CCATCTTCTTCGCCGCCAGACATCAGGTGGTCCCCGCTCTGAATATCTGCAAGGCCAAGGCCTGCAAAGC

CATCGAGTGGAACACCGAGCCTAAGCACTGCTTCAAGAAAGGCGGCCAGCACATCGAAGTTTGGTTCGAC

TACGTGGCCTGGGACAGCGTGTACTACTGCGGAGATGATGGCTGGTGCAAGACCGAGGCCGAGAAGTACG

GCTGTAAAGGCACCTGGGAAGTCCACTTCGGCAACAGCATCGACTGCAACGATAGCATGTGCAGCACCTT

CGACGACAACGTGTCCGCCACAGAGCTGGTCAAGGACCATATAGACTATTGGAAGCTGATCAGGCTTGAG

TGCGCCATTTTCTACAAGGCCAGACGGCGGCTGTCCAGCGACCAGGATCAATCTCAGCTCGTGACCAAGT

ATCCCCTGCTGAAGCTGCTGTCTACCCAGACCACCACACCTGAGAACACAAGCCTGGTGGAACTGAGAGT

GACCACACCTAAGAGCACCGTCGTGATTCGGCTGCACCTGACCACAAGATACCCTCTGCTGAGCCTGCTG

AACAGCTACAGCACCCCTCCACACAGGATCCCCGCTCCATGTCCTTGGGCTCCTCAGAGGCCTCCTATTC

CTAAGCCTTCTCCATGGGCTCCTAGAATCCCCGCACCTTGTCCATGGGCACCACCAAGACCTCCACATTG

CCCTTGGGTGCCCTGTTTCCTGCTGTGCTTTTGCGTGCTCCTGTGCGTGTGCCTGCTGATCAGACCTCTG

CTGCTGAGCGTGTCCACCTACCTTAGACCACTGCTCCTGTCCATCTCCGTGTACGCACAGGTGCTGGTGC

TGGTCCTGCTTCTGTGGGTGTCCATCGGAAGCCTGCTGCCTAGCGTGTGCATGTGTGCCTATGCTTGGGT

```
GCTCGTGTTCGTGTACATCGTGGTCATCACAAGCCCCGCCACAGCCATCGTGTACAGAGATGGCAATCCC

TACGCCGTGTGCGACAAGTGCCTGAAGTTCTACAGCAAGATCAGCGAGTACCGGCACTACTGCTACAGCC

TGTACGGCACCACACTGGAACAGCAGTACAACAAGCCCCTGTGCGATCTGCTGATTCGGTGCATCAACGT

GGTGTACCGGGACAGCATTCCTCACGCCGCCTGCCACAAGTGCATCGACTTCTACTCCAGAATCAGAGAG

CTGCGGCACTACAGCGACTCTGTGTACGGCGACACCCTGGAAAAGCTGACCAACACCGGCCTGTACAACC

TGCTGATTAGATGCCTGCGGGTGTACTGCAAGGGACAGCTGACAGAGACAGAGGTGCTGGACTTCGCCTT

CACCGATCTGACAATCGTGTATCGGGATAGCAAGGTGTCCGAGTTCCGGTGGTACAGATATAGCGTGTAC

GGAACAACCCTGTGCGTCGAGTGCAAGAAAACCCTGCAGAGAAGCGAGGTGTACGACTGCCAGAGGCCAC

TGTGCCCTCAAGAGAAGAAACGGCACGTGGACCTGAACAAGCGGTTTCACACCCTGCACGAGTACATGCT

GGACCTGCAGCCTGAGACAACCGACCTGTACTGCTACGAGCAGCCCGAAACCACAGATCTGCACTGTTAT

GAGCAGCTGGGCGACAGCAGCGACGAAGAGGATACAGGCGGACTGGACGGCGAGGAAAACGACGAAATTG

ACGGCGTGAACCACCAGCATCTCCCCGCCAGAAGGGCTGAACCTCAGAGACACCATGCTGTGTATGTG

CTGCAAGTGCGAGGCCAGAATCGCCTGATGA
```

HPV53del polypeptide sequence (includes tPA leading sequence and HindIII cloning linker, underlined)

(SEQ ID NO: 74)

```
MDAMKRGLCCVLLLCGAVFVSPSQEIHARFRRGSKLADEDETAYDSGTDLIDFIDDSDENENDSDTGEDM

VDFIDNAQLADSDSNACAFLKAQLADVNSNAAAFLKNCILLYGAANTGKSLFGMSLNCLVLCGPANTGKS

YFGMSLWPYLHSRLVVFTFPNPFWPYLESRITVFEFPNAFNVCQDKILEHYENDSKDILEHYENDSKDLC

DHICDHIDYWKHIRLECAIMYKARIRLECAIMYKAREMGFHQFGDGICNTMHYTNWIYICEDAQCTVVEG

QVDKKWEVHAGGQVILCPESGQRRIKRPRSENCHPNKLLILKCLRYRFKKHCKLSSTWHWTCHDGKHKWH

WTCHDGKHKNAIVTLTYYEADKNDLNAQIEHWKLIRMECAIFYKAKELGISICHQVVPPLAASKAKACQA

IELQLALEALNASPYDEWTLQQTSLEMWLAEPQFKKHGITITVQYDNDKANTMDYTNWKEIYVIVCPASI

PSDEISTEEADHIDYWKAIRQENAIFFAARHQVVPALNICKAKACKAIEWNTEPKHCFKKGGQHIEVWFD

YVAWDSVYYCGDDGWCKTEAEKYGCKGTWEVHFGNSIDCNDSMCSTFDDNVSATELVKDHIDYWKLIRLE

CAIFYKARRLSSDQDQSQLVTKYPLLKLLSTQTTTPENTSLVELRVTTPKSTVVIRLHLTTRYPLLSLL

NSYSTPPHRIPAPCPWAPQRPPIPKPSPWAPRIPAPCPWAPPRPPHCPWVPCFLLCFCVLLCVCLLIRPL

LLSVSTYLRPLLLSISVYAQVLVLVLLLWVSIGSLLPSVCMCAYAWVLVFVYIVVITSPATAIVYRDGNP

YAVCDKCLKFYSKISEYRHYCYSLYGTTLEQQYNKPLCDLLIRCINVVYRDSIPHAACHKCIDFYSRIRE

LRHYSDSVYGDTLEKLTNTGLYNLLIRCLRVYCKGQLTETEVLDFAFTDLTIVYRDSKVSEFRWYRYSVY

GTTLCVECKKTLQRSEVYDCQRPLCPQEKKRHVDLNKRFHTLHEYMLDLQPETTDLYCYEQPETTDLHCY

EQLGDSSDEEDTGGLDGEENDEIDGVNHQHLPARRAEPQRHTMLCMCCKCEARIA**
```

HPV3-linkers nucleotide sequence (includes tPA leading sequence and HindIII cloning linker, underlined)

(SEQ ID NO: 75)

```
ATGGATGCTATGAAGAGGGGCCTGTGCTGCGTGCTGCTGCTGTGTGGCGCCGTGTTTGTGTCCCCCAGCC

AGGAAATCCACGCCCGGTTCAGAAGAGGCAGCAAGCTGGCCGACGAGGACGAGACAGCCTACGACAGCGG

CACCGACCTGATCGACTTCATCGACGATAGCGCCGCTGCCGACGAGAATGAGAACGACAGCGATACCGGC

GAGGACATGGTGGATTTCATCGACAACGCTGCCGCCGACGAAACCGACGAAGAGAGCACCGAGAGCGACC

TGGACGGCTTTATCGACAACAGCGCAGCCGCCCAGCTGGCTGACAGCGACTCTAATGCCTGCGCCTTCCT

GAAGGCCGCTGCTCAGCTGGCAGACGTGAACAGCAATGCCGCCGCTTTTCTGAAGGCTGCCGCCAACTGC

ATCCTGCTGTACGGCGCTGCCAACACCGGCAAGAGCCTGTTCGGCATGTCTCTGGCCGCAGCCAACTGCC

TGGTGCTGTGCGGACCTGCCAATACTGGCAAAAGCTACTTCGGCATGAGCCTGGCAGCCGCCAATTGTCT

CGTGATCTACGGCCCTCCTAATACCGGCAAGTCCTGCTTTGCCATGAGTCTGGCCGCTGCCTGGCCCTAC
```

-continued

```
CTGCACTCTAGACTGGTGGTGTTCACCTTCCCCAACCCCTTCGCTGCCGCTTGGCCTTACCTGGAAAGCC

GGATCACCGTGTTCGAGTTCCCCAATGCCTTCGCCGCAGCCCTGAGATACCTGCACAGCAGAATCCACGT

GCTGCAGTTTCTGAACCCCTTTGCCGCCGCAAACGTGTGCCAGGACAAGATCCTGGAACACTACGAGAAC

GACTCCAAGGATGCCGCTGCCATTCTGGAACATTATGAGAATGATAGCAAGGACCTGTGCGACCACATTG

CTGCCGCCTGCGATCACATCGACTACTGGAAGCACATCCGGCTGGAATGCGCCATCATGTACAAGGCCAG

AGCCGCCGCTATCAGACTGGAATGTGCTATTATGTATAAGGCTCGCGAGATGGGCTTCCACGCTGCTGCC

CAGTTCGACGGCGACATCTGCAACACCATGCACTACACCAACTGGGCTGCCGCTATCTACATCTGCGAGG

ACGCCCAGTGCACCGTGGTGGAAGGACAGGTGGACGCCGCTGCTAAGAAATGGGAGGTGCACGCTGGCGG

CCAAGTGATCCTGTGTCCAGAGTCTGCTGCCGCAGGCCAGCGGAGAATCAAGAGGCCTAGAAGCGAGGCA

GCCGCTAACTGCCACCCCAACAAACTGCTGGCTGCTGCCATCCTGAAGTGCCTGCGGTACAGATTCAAGA

AGCACTGCAAACTGGCTGCAGCTAGCAGCACCTGGCACTGGACCTGTCACGACGGCAAGCACAAAGCCGC

CGCATGGCATTGGACATGCCACGATGGAAAACACAAGAACGCCATCGTGACCCTGACCTATGCAGCCGCC

TACGAGGCCGACAAGAACGACCTGAACGCCCAGATCGAGCACTGGAAGCTGATCAGGATGGAATGTGCAA

TCTTCTATAAGGCCAAAGAGCTGGGCATCAGCGCTGCCGCAATCTGCCACCAGGTGGTGCCTCCACTGGC

CGCCTCTAAAGCCAAAGCCTGCCAGGCCATCGAACTGCAGCTGGCCCTGGAAGCCCTGAATGCCAGCCCT

TATGCCGCAGCCGATGAGTGGACCCTGCAGCAGACCAGCCTGGAAATGTGGCTGGCCGAACCTCAGGCCG

CAGCTTTTAAGAAGCACGGCATCACCATCACCGTGCAGTACGACAACGACAAGGCCAATACCATGGATTA

CACCAATTGGAAAGAGATCTACGCCGCAGCTGTGATCGTGTGCCCCGCCAGCATCCCTAGCGACGAGATC

AGCACAGAGGAAGCAGCCGCCGACCACATCGATTATTGGAAAGCCATCAGACAGGAAAACGCCATCTTCT

TCGCCGCTAGAGCCGCTGCCCACCAGGTGGTGCCAGCCCTGAATATCTGCAAGGCCAAGGCCTGTAAAGC

CATCGAAGCCGCTGCTTGGAACACCGAGCCCAAGCACTGCTTCAAGAAGGGCGGCCAGCACATCGAAGTG

TGGTTCGACGCTGCAGCCTACGTGGCCTGGGACAGCGTGTACTACTGTGGCGACGACGGCTGGTGCAAGA

CCGCCGCTGCAGAGGCCGAGAAGTATGGCTGCAAGGGCACCTGGGAAGTGCATTTCGGCGCAGCTGCCAA

CTCCATCGACTGCAACGACAGCATGTGCAGCACCTTCGACGACAACGTGTCCGCCACCGAGCTCGTGAAA

GCTGCCGCTGACCATATTGATTACTGGAAACTGATTCGCCTGGAATGCGCTATTTTCTACAAAGCCAGGG

CCGCAGCACGGCGGCTGTCCTCAGATCAGGATCAGAGCCAGGCTGCTGCACTCGTGACCAAGTACCCCCT

GCTGAAGCTGCTGAGCGCCGCAGCAAGACCCCCCAACATGGGAGTGAAGGCCCACGGCAAGTGCATCTGG

GAGAACAAGGTGTTCATCGTGCCCACCCTGTGCCCCGTGCCTCTGGATCCAACATATCCTCTGCTGAAAC

TGCTGACCGCTGCCGCCACCCAGACCACCACACCTGAGAATACCTCCCTGGTGGAACTGAGAGTGACCAC

CCCCAAGAGCACAGTCGTGATCAGGCTGCACCTGGCTGCCGCAACCACCAGATACCCTCTGCTGTCCCTG

CTGAACAGCTACAGCACCCCCCCTCATCGGATCCCTGCCCCTTGTCCTTGGGCTCCTCAGAGGCCTGCCG

CTGCACCTATCCCTAAGCCTTCTCCATGGGCCCCTGCCGCAGCTAGAATCCCAGCTCCATGTCCATGGGC

ACCAGCTGCTGCTCCCAGACCTCCTCATTGCCCTTGGGTGCCAGCAGCCGCTCCTCCACCTCCTCCTAGA

CCTTGGGCCCCAGCCGCCGCTTGTTTCCTGCTGTGCTTCTGTGTGCTGCTGTGCGTGTGCCTGCTGATCA

GACCCCTGCTGCTGAGTGTGTCCACCTACGCAGCTGCTCTGCGGCCACTGCTGCTGTCCATCTCTGTGTA

CGCACAGGTGCTGGTGCTGGTGCTGCTGCTGTGGGTGTCCATCGGATCTGCCGCAGCACTGCTGCCCTCC

GTGTGCATGTGTGCCTATGCCTGGGTGCTGGTGTTCGTGTACATCGTCGTGATTACCAGCCCCGCCACCG

CAGCCGCAATCGTGTACAGGGACGGCAACCCTTACGCCGTGTGCGACAAGTGCCTGAAGTTCTACAGCAA

GATCAGCGAGTACCGCCACTACTGCTACAGCCTGTACGGCACCACCCTGGAACAGCAGTACAACAAGCCC

CTGTGCGATCTGCTGATCCGGTGCATCAACGCAGCCGCTGTGGTGTACAGAGACAGCATCCCACACGCCG
```

-continued

```
CCTGCCACAAGTGTATCGACTTCTACTCCCGGATCAGAGAGCTGAGACACTACTCCGACTCCGTGTACGG

CGATACCCTGGAAAAGCTGACCAATACCGGCCTGTACAACCTGCTGATTAGATGCCTGCGGGCAGCCGCA

GTGTTCTGCAAGAAAGCCCTGACCGCCAGCGAGGTGTACAACTTCGCCTACACCGATCTGCGGGTGGTGT

ACCGGGATGCTGCTGCCTCCAAAGTGCGGAAGCTGCGGTACTACAACTGCTCTGTGTATGGCGCCTCCCT

GGCAGCTGCCGTGTATTGCAAGGGACAGCTGACCGAGACAGAGGTGCTGGATTTCGCCTTCACAGACCTG

ACCATCGTGTATAGAGATGCAGCTGCTAGCAAGGTGTCCGAGTTCCGGTGGTACAGATATAGCGTGTACG

GAACAACACTGGCAGCAGCTTGCGTGGAATGCAAGAAAACACTGCAGCGGAGCGAAGTGTACGATGCTGC

AGCTTGCCAGAGGCCGCTGTGTCCTCAGGAAAAGAAAAGACACGTGGACCTGAACAAGCGGTTCCACGCA

GCAGCTACCCTGCACGAGTACATGCTGGACCTGCAGCCCGAGACAACCGACCTGTACTGCTACGAGCAGG

CAGCTGCACCCGAAACCACAGATCTGCACTGTTATGAGCAGCTGGGAGACAGCTCCGATGAAGAGGACAC

CGGCGGACTGGATGCTGCCGCTGGGGATGAGGACGAGGATGAGGTGGACCATCTGCAGGAACAGCCCCAG

CAGGCCAGAAGGGATGAGCAGCACCCCTGCTATCTGATCGAGACACAGTGCTGCAGATGCGAGAGCCTGG

TGGCCGCTGCTGAGGAAAACGACGAGATCGACGGCGTGAACCACCAGCATCTGCCCGCTAGAAGGGCCGA

GCCTCAGAGACACACCATGCTGTGTATGTGTTGCAAGTGCGAGGCCCGGATCGCCGGATCTGGACCTGGC

GCTAGCGGAAAGCCCATCCCCAATCCACTGCTGGGCCTGGACTCCACCCGGACCTGATAA
```

HPV3-linkers polypeptide sequence (includes tPA leading sequence and HindIII cloning linker, underlined)

(SEQ ID NO: 76)

<u>MDAMKRGLCCVLLLCGAVFVSPSQEIHARFRRGSKLA</u>DEDETAYDSGTDLIDFIDDSAAADENENDSDTG

EDMVDFIDNAAADETDEESTESDLDGFIDNSAAAQLADSDSNACAFLKAAAQLADVNSNAAAFLKAAANC

ILLYGAANTGKSLFGMSLAAANCLVLCGPANTGKSYFGMSLAAANCLVIYGPPNTGKSCFAMSLAAAWPY

LHSRLVVFTFPNPFAAAWPYLESRITVFEFPNAFAAALRYLHSRIHVLQFLNPFAAANVCQDKILEHYEN

DSKDAAAILEHYENDSKDLCDHIAAACDHIDYWKHIRLECAIMYKARAAAIRLECAIMYKAREMGFHAAA

QFDGDICNTMHYTNWAAAIYICEDAQCTVVEGQVDAAAKKWEVHAGGQVILCPESAAAGQRRIKRPRSEA

AANCHPNKLLAAAILKCLRYRFKKHCKLAAASSTWHWTCHDGKHKAAAWHWTCHDGKHKNAIVTLTYAAA

YEADKNDLNAQIEHWKLIRMECAIFYKAKELGISAAAICHQVVPPLAASKAKACQAIELQLALEALNASP

YAAADEWTLQQTSLEMWLAEPQAAAFKKHGITITVQYDNDKANTMDYTNWKEIYAAAVIVCPASIPSDEI

STEEAAADHIDYWKAIRQENAIFFAARAAAHQVVPALNICKAKACKAIEAAAWNTEPKHCFKKGGQHIEV

WFDAAAYVAWDSVYYCGDDGWCKTAAAEAEKYGCKGTWEVHFGAAANSIDCNDSMCSTFDDNVSATELVK

AAADHIDYWKLIRLECAIFYKARAAARRLSSDQDQSQAAALVTKYPLLKLLSAAARPPNMGVKAHGKCIW

ENKVFIVPTLCPVPLDPTYPLLKLLTAAATQTTTPENTSLVELRVTTPKSTVVIRLHLAAATTRYPLLSL

LNSYSTPPHRIPAPCPWAPQRPAAAPIPKPSPWAPAAARIPAPCPWAPAAAPRPPHCPWVPAAAPPPPPR

PWAPAAAACFLLCFCVLLCVCLLIRPLLLSVSTYAAALRPLLLSISVYAQVLVLVLLLWVSIGSAAALLPS

VCMCAYAWVLVFVYIVVITSPATAAAIVYRDGNPYAVCDKCLKFYSKISEYRHYCYSLYGTTLEQQYNKP

LCDLLIRCINAAAVVYRDSIPHAACHKCIDFYSRIRELRHYSDSVYGDTLEKLTNTGLYNLLIRCLRAAA

VFCKKALTASEVYNFAYTDLRVVYRDAAASKVRKLRYYNCSVYGASLAAAVYCKGQLTETEVLDFAFTDL

TIVYRDAAASKVSEFRWYRYSVYGTTLAAACVECKKTLQRSEVYDAAACQRPLCPQEKKRHVDLNKRFHA

AATLHEYMLDLQPETTDLYCYEQAAAPETTDLHCYEQLGDSSDEEDTGGLDAAAGDEDEDEVDHLQEQPQ

QARRDEQHPCYLIETQCCRCESLVAAAEENDEIDGVNHQHLPARRAEPQRHTMLCMCCKCEARIAGSPG

ASGKPIPNPLLGLDSTRT**

TABLE 9

Summary of Fragment Variants with SEQ ID NOs. (FIGS. 2-4)

| SEQ ID NO: | Protein | Fragment |
|---|---|---|
| 160 | conserved region 1 | DEDENASDTGXDLVDFIDNS |
| 161 | conserved region 1 | DENENDSDTGEDLVDFIVND |
| 162 | conserved region 1 | DEDENATDTGSDMVDFIDTQ |
| 163 | conserved region 1 | DENEDSSDTGEDMVDFIDNC |
| 164 | conserved region 1 | DEDENAYDSGTDLIDFIDDS |
| 3 | conserved region 1 | DETDEESTESDLDGFIDNS |
| 165 | conserved region 1 | DEDETADDSGTDLIEFIDDS |
| 166 | conserved region 1 | DEDEXAXDSGTDLIXFIDDS |
| 167 | conserved region 1 | DEDENAYDSGTDLIDFIDDS |
| 168 | conserved region 1 | DEDETADDSGTDLIEFIDDS |
| 169 | conserved region 1 | DENENXSDTGEDMVDFIDN |
| 170 | conserved region 1 | DENEDSSDTGEDMVDFIDN |
| 171 | conserved region 1 | DENENDSDTGEDLVDFIVN |
| 172 | conserved region 1 | DEDENATDTGSDMVDFIDT |
| 3 | conserved region 1 | DETDEESTESDLDGFIDNS |
| 5 | conserved region 2 | AQLADVNSNAAAFLK |
| 173 | conserved region 2 | AQLADTNSNASAFLK |
| 174 | conserved region 2 | ALLADSNSNAAAFLK |
| 175 | conserved region 2 | AQLADSDSNACAFLK |
| 5 | conserved region 2 | AQLADVNSNAAAFLK |
| 176 | conserved region 2 | AQLADVDSNAQAFLK |
| 177 | conserved region 2 | AQLADVNSNAAAFLR |
| 4 | conserved region 2 | AQLADSDSNACAFLK |
| 4 | conserved region 2 | AQLADSDSNACAFLK |
| 178 | conserved region 2 | AQLADVDSNAQAFLK |
| 5 | conserved region 2 | AQLADVNSNAAAFLK |
| 5 | conserved region 2 | AQLADVNSNAAAFLK |
| 179 | conserved region 2 | AQLADVNSNAAAFLR |
| 180 | conserved region 2 | ALLADSNSNAAAFLK |
| 181 | conserved region 2 | AQLADTNSNASAFLK |
| 182 | conserved region 3 | NCLXLYGPANTGKSYFGMSL |
| 6 | conserved region 3 | NCILLYGAANTGKSLFGMSL |
| 183 | conserved region 3 | NCLVFCGPANTGKSYFGMSF |
| 184 | conserved region 3 | NCILIHGAPNTGKSYFGMSL |
| 185 | conserved region 3 | NCLVLYGPANTGKSYFGMSL |
| 8 | conserved region 3 | NCLVIYGPPNTGKSCFAMSL |
| 186 | conserved region 3 | SCMLLCGPANTGKSYFGMSL |
| 187 | conserved region 3 | NCILJYGAANTGKSLFGMSL |
| 6 | conserved region 3 | NCILLYGAANTGKSLFGMSL |
| 188 | conserved region 3 | NCILIHGAPNTGKSYFGMSL |
| 7 | conserved region 3 | NCLVLCGPANTGKSYFGMSL |
| 189 | conserved region 3 | NCLVFCGPANTGKSYFGMSF |
| 190 | conserved region 3 | NCLVLYGPANTGKSYFGMSL |
| 191 | conserved region 3 | SCMLLCGPANTGKSYFGMSL |
| 8 | conserved region 3 | NCLVIYGPPNTGKSCFAMSL |
| 192 | conserved region 4 | DEDENASDTGXDLVDFIDNS |
| 193 | conserved region 4 | DENENDSDTGEDLVDFIVND |
| 194 | conserved region 4 | DEDENATDTGSDMVDFIDTQ |
| 195 | conserved region 4 | DENEDSSDTGEDMVDFIDNC |
| 196 | conserved region 4 | DEDENAYDSGTDLIDFIDDS |
| 3 | conserved region 4 | DETDEESTESDLDGFIDNS |
| 197 | conserved region 4 | DEDETADDSGTDLIEFIDDS |
| 9 | conserved region 4 | WPYLHSRLVVFTFPNPF |
| 198 | conserved region 4 | WPYLHNRLVVFTFPNEF |
| 9 | conserved region 4 | WPYLHSRLVVFTFPNPF |
| 199 | conserved region 4 | WPYLHSRLVVFHFKNPF |
| 200 | conserved region 4 | WPYLESRJTVFEFPNAF |
| 10 | conserved region 4 | WPYLESRITVFEFPNAF |
| 201 | conserved region 4 | WPYLHSRLTVFEFNNPF |
| 11 | conserved region 4 | LRYLHSRIHVLQFLNPF |
| 202 | conserved region 1 | DHIDYWKHMRLECAIYYKAR |
| 202 | conserved region 1 | DHIDYWKHMRLECAIYYKAR |
| 203 | conserved region 1 | SQIQYWQLIRWENAIFFAAR |
| 204 | conserved region 1 | DHIDYWKHIRLECVLMYKAR |
| 205 | conserved region 1 | AQIEHWKLTRMECVLFYKAK |
| 206 | conserved region 1 | DHIDYWKAVRQENVIYYKAR |
| 207 | conserved region 1 | SQIEHWKLIRMECAIMYTAR |
| 35 | conserved region 1 | DHIDYWKLIRLECAIFYKAR |
| 208 | conserved region 1 | PIPPPCPWAPKK |
| 209 | conserved region 1 | TPPHRPIPKPSPWAPKKE |
| 210 | conserved region 1 | TPPHRIPAPCPWAPQRP |
| 211 | conserved region 1 | TPPHRIPKPAPWAPVKV |
| 212 | conserved region 1 | PRPPHCPWVPKTE |
| 213 | conserved region 1 | PPPPPRPWAPTKP |

TABLE 9-continued

Summary of Fragment Variants with SEQ ID NOs.
(FIGS. 2-4)

| SEQ ID NO: | Protein | Fragment |
|---|---|---|
| 41 | conserved region 1 | PIPKPSPWAP |
| 41 | conserved region 1 | PIPKPSPWAP |
| 214 | conserved region 1 | RIPKPAPWAP |
| 42 | conserved region 1 | RIPAPCPWAP |
| 43 | conserved region 1 | PRPPHCPWVP |
| 44 | conserved region 1 | PPPPPRPWAP |

SEQUENCE LISTING

<160> NUMBER OF SEQ ID NOS: 214

<210> SEQ ID NO 1
<211> LENGTH: 20
<212> TYPE: PRT
<213> ORGANISM: Artificial Sequence
<220> FEATURE:
<223> OTHER INFORMATION: Consensus sequence

<400> SEQUENCE: 1

Asp Glu Asp Glu Thr Ala Tyr Asp Ser Gly Thr Asp Leu Ile Asp Phe
1               5                   10                  15

Ile Asp Asp Ser
            20

<210> SEQ ID NO 2
<211> LENGTH: 19
<212> TYPE: PRT
<213> ORGANISM: Artificial Sequence
<220> FEATURE:
<223> OTHER INFORMATION: Consensus sequence

<400> SEQUENCE: 2

Asp Glu Asn Glu Asn Asp Ser Asp Thr Gly Glu Asp Met Val Asp Phe
1               5                   10                  15

Ile Asp Asn

<210> SEQ ID NO 3
<211> LENGTH: 19
<212> TYPE: PRT
<213> ORGANISM: Artificial Sequence
<220> FEATURE:
<223> OTHER INFORMATION: Consensus sequence

<400> SEQUENCE: 3

Asp Glu Thr Asp Glu Glu Ser Thr Glu Ser Asp Leu Asp Gly Phe Ile
1               5                   10                  15

Asp Asn Ser

<210> SEQ ID NO 4
<211> LENGTH: 15
<212> TYPE: PRT
<213> ORGANISM: Artificial Sequence
<220> FEATURE:
<223> OTHER INFORMATION: Consensus sequence

<400> SEQUENCE: 4

Ala Gln Leu Ala Asp Ser Asp Ser Asn Ala Cys Ala Phe Leu Lys
1               5                   10                  15

```
<210> SEQ ID NO 5
<211> LENGTH: 15
<212> TYPE: PRT
<213> ORGANISM: Artificial Sequence
<220> FEATURE:
<223> OTHER INFORMATION: Consensus sequence

<400> SEQUENCE: 5

Ala Gln Leu Ala Asp Val Asn Ser Asn Ala Ala Ala Phe Leu Lys
1               5                   10                  15

<210> SEQ ID NO 6
<211> LENGTH: 20
<212> TYPE: PRT
<213> ORGANISM: Artificial Sequence
<220> FEATURE:
<223> OTHER INFORMATION: Consensus sequence

<400> SEQUENCE: 6

Asn Cys Ile Leu Leu Tyr Gly Ala Ala Asn Thr Gly Lys Ser Leu Phe
1               5                   10                  15

Gly Met Ser Leu
            20

<210> SEQ ID NO 7
<211> LENGTH: 20
<212> TYPE: PRT
<213> ORGANISM: Artificial Sequence
<220> FEATURE:
<223> OTHER INFORMATION: Consensus sequence

<400> SEQUENCE: 7

Asn Cys Leu Val Leu Cys Gly Pro Ala Asn Thr Gly Lys Ser Tyr Phe
1               5                   10                  15

Gly Met Ser Leu
            20

<210> SEQ ID NO 8
<211> LENGTH: 20
<212> TYPE: PRT
<213> ORGANISM: Artificial Sequence
<220> FEATURE:
<223> OTHER INFORMATION: Consensus sequence

<400> SEQUENCE: 8

Asn Cys Leu Val Ile Tyr Gly Pro Pro Asn Thr Gly Lys Ser Cys Phe
1               5                   10                  15

Ala Met Ser Leu
            20

<210> SEQ ID NO 9
<211> LENGTH: 17
<212> TYPE: PRT
<213> ORGANISM: Artificial Sequence
<220> FEATURE:
<223> OTHER INFORMATION: Consensus sequence

<400> SEQUENCE: 9

Trp Pro Tyr Leu His Ser Arg Leu Val Val Phe Thr Phe Pro Asn Pro
1               5                   10                  15

Phe

<210> SEQ ID NO 10
<211> LENGTH: 17
<212> TYPE: PRT
```

```
<213> ORGANISM: Artificial Sequence
<220> FEATURE:
<223> OTHER INFORMATION: Consensus sequence

<400> SEQUENCE: 10

Trp Pro Tyr Leu Glu Ser Arg Ile Thr Val Phe Glu Phe Pro Asn Ala
1               5                   10                  15

Phe

<210> SEQ ID NO 11
<211> LENGTH: 17
<212> TYPE: PRT
<213> ORGANISM: Artificial Sequence
<220> FEATURE:
<223> OTHER INFORMATION: Consensus sequence

<400> SEQUENCE: 11

Leu Arg Tyr Leu His Ser Arg Ile His Val Leu Gln Phe Leu Asn Pro
1               5                   10                  15

Phe

<210> SEQ ID NO 12
<211> LENGTH: 17
<212> TYPE: PRT
<213> ORGANISM: Artificial Sequence
<220> FEATURE:
<223> OTHER INFORMATION: Consensus sequence

<400> SEQUENCE: 12

Asn Val Cys Gln Asp Lys Ile Leu Glu His Tyr Glu Asn Asp Ser Lys
1               5                   10                  15

Asp

<210> SEQ ID NO 13
<211> LENGTH: 16
<212> TYPE: PRT
<213> ORGANISM: Artificial Sequence
<220> FEATURE:
<223> OTHER INFORMATION: Consensus sequence

<400> SEQUENCE: 13

Ile Leu Glu His Tyr Glu Asn Asp Ser Lys Asp Leu Cys Asp His Ile
1               5                   10                  15

<210> SEQ ID NO 14
<211> LENGTH: 21
<212> TYPE: PRT
<213> ORGANISM: Artificial Sequence
<220> FEATURE:
<223> OTHER INFORMATION: Consensus sequence

<400> SEQUENCE: 14

Cys Asp His Ile Asp Tyr Trp Lys His Ile Arg Leu Glu Cys Ala Ile
1               5                   10                  15

Met Tyr Lys Ala Arg
            20

<210> SEQ ID NO 15
<211> LENGTH: 17
<212> TYPE: PRT
<213> ORGANISM: Artificial Sequence
<220> FEATURE:
<223> OTHER INFORMATION: Consensus sequence

<400> SEQUENCE: 15
```

```
Ile Arg Leu Glu Cys Ala Ile Met Tyr Lys Ala Arg Glu Met Gly Phe
1               5                   10                  15

His

<210> SEQ ID NO 16
<211> LENGTH: 17
<212> TYPE: PRT
<213> ORGANISM: Artificial Sequence
<220> FEATURE:
<223> OTHER INFORMATION: Consensus sequence

<400> SEQUENCE: 16

Ile Arg Leu Glu Cys Ala Ile Met Tyr Lys Ala Arg Glu Met Gly Phe
1               5                   10                  15

His

<210> SEQ ID NO 17
<211> LENGTH: 17
<212> TYPE: PRT
<213> ORGANISM: Artificial Sequence
<220> FEATURE:
<223> OTHER INFORMATION: Consensus sequence

<400> SEQUENCE: 17

Ile Tyr Ile Cys Glu Asp Ala Gln Cys Thr Val Val Glu Gly Gln Val
1               5                   10                  15

Asp

<210> SEQ ID NO 18
<211> LENGTH: 17
<212> TYPE: PRT
<213> ORGANISM: Artificial Sequence
<220> FEATURE:
<223> OTHER INFORMATION: Consensus sequence

<400> SEQUENCE: 18

Lys Lys Trp Glu Val His Ala Gly Gly Gln Val Ile Leu Cys Pro Glu
1               5                   10                  15

Ser

<210> SEQ ID NO 19
<211> LENGTH: 11
<212> TYPE: PRT
<213> ORGANISM: Artificial Sequence
<220> FEATURE:
<223> OTHER INFORMATION: Consensus sequence

<400> SEQUENCE: 19

Gly Gln Arg Arg Ile Lys Arg Pro Arg Ser Glu
1               5                   10

<210> SEQ ID NO 20
<211> LENGTH: 8
<212> TYPE: PRT
<213> ORGANISM: Artificial Sequence
<220> FEATURE:
<223> OTHER INFORMATION: Consensus sequence

<400> SEQUENCE: 20

Asn Cys His Pro Asn Lys Leu Leu
1               5

<210> SEQ ID NO 21
```

```
<211> LENGTH: 15
<212> TYPE: PRT
<213> ORGANISM: Artificial Sequence
<220> FEATURE:
<223> OTHER INFORMATION: Consensus sequence

<400> SEQUENCE: 21

Ile Leu Lys Cys Leu Arg Tyr Arg Phe Lys Lys His Cys Lys Leu
1               5                   10                  15

<210> SEQ ID NO 22
<211> LENGTH: 14
<212> TYPE: PRT
<213> ORGANISM: Artificial Sequence
<220> FEATURE:
<223> OTHER INFORMATION: Consensus sequence

<400> SEQUENCE: 22

Ser Ser Thr Trp His Trp Thr Cys His Asp Gly Lys His Lys
1               5                   10

<210> SEQ ID NO 23
<211> LENGTH: 19
<212> TYPE: PRT
<213> ORGANISM: Artificial Sequence
<220> FEATURE:
<223> OTHER INFORMATION: Consensus sequence

<400> SEQUENCE: 23

Trp His Trp Thr Cys His Asp Gly Lys His Lys Asn Ala Ile Val Thr
1               5                   10                  15

Leu Thr Tyr

<210> SEQ ID NO 24
<211> LENGTH: 34
<212> TYPE: PRT
<213> ORGANISM: Artificial Sequence
<220> FEATURE:
<223> OTHER INFORMATION: Consensus sequence

<400> SEQUENCE: 24

Tyr Glu Ala Asp Lys Asn Asp Leu Asn Ala Gln Ile Glu His Trp Lys
1               5                   10                  15

Leu Ile Arg Met Glu Cys Ala Ile Phe Tyr Lys Ala Lys Glu Leu Gly
                20                  25                  30

Ile Ser

<210> SEQ ID NO 25
<211> LENGTH: 34
<212> TYPE: PRT
<213> ORGANISM: Artificial Sequence
<220> FEATURE:
<223> OTHER INFORMATION: Consensus sequence

<400> SEQUENCE: 25

Ile Cys His Gln Val Val Pro Pro Leu Ala Ala Ser Lys Ala Lys Ala
1               5                   10                  15

Cys Gln Ala Ile Glu Leu Gln Leu Ala Leu Glu Ala Leu Asn Ala Ser
                20                  25                  30

Pro Tyr

<210> SEQ ID NO 26
<211> LENGTH: 18
<212> TYPE: PRT
```

```
<213> ORGANISM: Artificial Sequence
<220> FEATURE:
<223> OTHER INFORMATION: Consensus sequence

<400> SEQUENCE: 26

Asp Glu Trp Thr Leu Gln Gln Thr Ser Leu Glu Met Trp Leu Ala Glu
1               5                   10                  15

Pro Gln

<210> SEQ ID NO 27
<211> LENGTH: 29
<212> TYPE: PRT
<213> ORGANISM: Artificial Sequence
<220> FEATURE:
<223> OTHER INFORMATION: Consensus sequence

<400> SEQUENCE: 27

Phe Lys Lys His Gly Ile Thr Ile Thr Val Gln Tyr Asp Asn Asp Lys
1               5                   10                  15

Ala Asn Thr Met Asp Tyr Thr Asn Trp Lys Glu Ile Tyr
            20                  25

<210> SEQ ID NO 28
<211> LENGTH: 18
<212> TYPE: PRT
<213> ORGANISM: Artificial Sequence
<220> FEATURE:
<223> OTHER INFORMATION: Consensus sequence

<400> SEQUENCE: 28

Val Ile Val Cys Pro Ala Ser Ile Pro Ser Asp Glu Ile Ser Thr Glu
1               5                   10                  15

Glu Ala

<210> SEQ ID NO 29
<211> LENGTH: 20
<212> TYPE: PRT
<213> ORGANISM: Artificial Sequence
<220> FEATURE:
<223> OTHER INFORMATION: Consensus sequence

<400> SEQUENCE: 29

Asp His Ile Asp Tyr Trp Lys Ala Ile Arg Gln Glu Asn Ala Ile Phe
1               5                   10                  15

Phe Ala Ala Arg
            20

<210> SEQ ID NO 30
<211> LENGTH: 19
<212> TYPE: PRT
<213> ORGANISM: Artificial Sequence
<220> FEATURE:
<223> OTHER INFORMATION: Consensus sequence

<400> SEQUENCE: 30

His Gln Val Val Pro Ala Leu Asn Ile Cys Lys Ala Lys Ala Cys Lys
1               5                   10                  15

Ala Ile Glu

<210> SEQ ID NO 31
<211> LENGTH: 21
<212> TYPE: PRT
<213> ORGANISM: Artificial Sequence
<220> FEATURE:
```

```
<223> OTHER INFORMATION: Consensus sequence

<400> SEQUENCE: 31

Trp Asn Thr Glu Pro Lys His Cys Phe Lys Lys Gly Gly Gln His Ile
1               5                   10                  15
Glu Val Trp Phe Asp
            20

<210> SEQ ID NO 32
<211> LENGTH: 18
<212> TYPE: PRT
<213> ORGANISM: Artificial Sequence
<220> FEATURE:
<223> OTHER INFORMATION: Consensus sequence

<400> SEQUENCE: 32

Tyr Val Ala Trp Asp Ser Val Tyr Tyr Cys Gly Asp Asp Gly Trp Cys
1               5                   10                  15
Lys Thr

<210> SEQ ID NO 33
<211> LENGTH: 16
<212> TYPE: PRT
<213> ORGANISM: Artificial Sequence
<220> FEATURE:
<223> OTHER INFORMATION: Consensus sequence

<400> SEQUENCE: 33

Glu Ala Glu Lys Tyr Gly Cys Lys Gly Thr Trp Glu Val His Phe Gly
1               5                   10                  15

<210> SEQ ID NO 34
<211> LENGTH: 24
<212> TYPE: PRT
<213> ORGANISM: Artificial Sequence
<220> FEATURE:
<223> OTHER INFORMATION: Consensus sequence

<400> SEQUENCE: 34

Asn Ser Ile Asp Cys Asn Asp Ser Met Cys Ser Thr Phe Asp Asp Asn
1               5                   10                  15
Val Ser Ala Thr Glu Leu Val Lys
            20

<210> SEQ ID NO 35
<211> LENGTH: 20
<212> TYPE: PRT
<213> ORGANISM: Artificial Sequence
<220> FEATURE:
<223> OTHER INFORMATION: Consensus sequence

<400> SEQUENCE: 35

Asp His Ile Asp Tyr Trp Lys Leu Ile Arg Leu Glu Cys Ala Ile Phe
1               5                   10                  15
Tyr Lys Ala Arg
            20

<210> SEQ ID NO 36
<211> LENGTH: 11
<212> TYPE: PRT
<213> ORGANISM: Artificial Sequence
<220> FEATURE:
<223> OTHER INFORMATION: Consensus sequence

<400> SEQUENCE: 36
```

Arg Arg Leu Ser Ser Asp Gln Asp Gln Ser Gln
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Consensus sequence

<400> SEQUENCE: 37

Leu Val Thr Lys Tyr Pro Leu Leu Lys Leu Leu Ser
1               5                   10

<210> SEQ ID NO 38
<211> LENGTH: 41
<212> TYPE: PRT
<213> ORGANISM: Artificial Sequence
<220> FEATURE:
<223> OTHER INFORMATION: Consensus sequence

<400> SEQUENCE: 38

Arg Pro Pro Asn Met Gly Val Lys Ala His Gly Lys Cys Ile Trp Glu
1               5                   10                  15

Asn Lys Val Phe Ile Val Pro Thr Leu Cys Pro Val Pro Leu Asp Pro
                20                  25                  30

Thr Tyr Pro Leu Leu Lys Leu Leu Thr
            35                  40

<210> SEQ ID NO 39
<211> LENGTH: 29
<212> TYPE: PRT
<213> ORGANISM: Artificial Sequence
<220> FEATURE:
<223> OTHER INFORMATION: Consensus sequence

<400> SEQUENCE: 39

Thr Gln Thr Thr Thr Pro Glu Asn Thr Ser Leu Val Glu Leu Arg Val
1               5                   10                  15

Thr Thr Pro Lys Ser Thr Val Val Ile Arg Leu His Leu
                20                  25

<210> SEQ ID NO 40
<211> LENGTH: 31
<212> TYPE: PRT
<213> ORGANISM: Artificial Sequence
<220> FEATURE:
<223> OTHER INFORMATION: Consensus sequence

<400> SEQUENCE: 40

Thr Thr Arg Tyr Pro Leu Leu Ser Leu Leu Asn Ser Tyr Ser Thr Pro
1               5                   10                  15

Pro His Arg Ile Pro Ala Pro Cys Pro Trp Ala Pro Gln Arg Pro
                20                  25                  30

<210> SEQ ID NO 41
<211> LENGTH: 10
<212> TYPE: PRT
<213> ORGANISM: Artificial Sequence
<220> FEATURE:
<223> OTHER INFORMATION: Consensus sequence

<400> SEQUENCE: 41

Pro Ile Pro Lys Pro Ser Pro Trp Ala Pro

-continued

```
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Consensus sequence

<400> SEQUENCE: 42

Pro Ile Pro Lys Pro Ser Pro Trp Ala Pro
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Consensus sequence

<400> SEQUENCE: 43

Pro Arg Pro Pro His Cys Pro Trp Val Pro
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Consensus sequence

<400> SEQUENCE: 44

Pro Pro Pro Pro Pro Arg Pro Trp Ala Pro
1               5                   10

<210> SEQ ID NO 45
<211> LENGTH: 26
<212> TYPE: PRT
<213> ORGANISM: Artificial Sequence
<220> FEATURE:
<223> OTHER INFORMATION: Consensus sequence

<400> SEQUENCE: 45

Cys Phe Leu Leu Cys Phe Cys Val Leu Leu Cys Val Cys Leu Leu Ile
1               5                   10                  15

Arg Pro Leu Leu Leu Ser Val Ser Thr Tyr
            20                  25

<210> SEQ ID NO 46
<211> LENGTH: 27
<212> TYPE: PRT
<213> ORGANISM: Artificial Sequence
<220> FEATURE:
<223> OTHER INFORMATION: Consensus sequence

<400> SEQUENCE: 46

Leu Arg Pro Leu Leu Leu Ser Ile Ser Val Tyr Ala Gln Val Leu Val
1               5                   10                  15

Leu Val Leu Leu Leu Trp Val Ser Ile Gly Ser
            20                  25

<210> SEQ ID NO 47
<211> LENGTH: 28
<212> TYPE: PRT
<213> ORGANISM: Artificial Sequence
<220> FEATURE:
```

```
<223> OTHER INFORMATION: Consensus sequence

<400> SEQUENCE: 47

Leu Leu Pro Ser Val Cys Met Cys Ala Tyr Ala Trp Val Leu Val Phe
1               5                   10                  15

Val Tyr Ile Val Val Ile Thr Ser Pro Ala Thr Ala
            20                  25

<210> SEQ ID NO 48
<211> LENGTH: 54
<212> TYPE: PRT
<213> ORGANISM: Artificial Sequence
<220> FEATURE:
<223> OTHER INFORMATION: Consensus sequence

<400> SEQUENCE: 48

Ile Val Tyr Arg Asp Gly Asn Pro Tyr Ala Val Cys Asp Lys Cys Leu
1               5                   10                  15

Lys Phe Tyr Ser Lys Ile Ser Glu Tyr Arg His Tyr Cys Tyr Ser Leu
            20                  25                  30

Tyr Gly Thr Thr Leu Glu Gln Gln Tyr Asn Lys Pro Leu Cys Asp Leu
        35                  40                  45

Leu Ile Arg Cys Ile Asn
    50

<210> SEQ ID NO 49
<211> LENGTH: 54
<212> TYPE: PRT
<213> ORGANISM: Artificial Sequence
<220> FEATURE:
<223> OTHER INFORMATION: Consensus sequence

<400> SEQUENCE: 49

Val Val Tyr Arg Asp Ser Ile Pro His Ala Ala Cys His Lys Cys Ile
1               5                   10                  15

Asp Phe Tyr Ser Arg Ile Arg Glu Leu Arg His Tyr Ser Asp Ser Val
            20                  25                  30

Tyr Gly Asp Thr Leu Glu Lys Leu Thr Asn Thr Gly Leu Tyr Asn Leu
        35                  40                  45

Leu Ile Arg Cys Leu Arg
    50

<210> SEQ ID NO 50
<211> LENGTH: 26
<212> TYPE: PRT
<213> ORGANISM: Artificial Sequence
<220> FEATURE:
<223> OTHER INFORMATION: Consensus sequence

<400> SEQUENCE: 50

Val Phe Cys Lys Lys Ala Leu Thr Ala Ser Glu Val Tyr Asn Phe Ala
1               5                   10                  15

Tyr Thr Asp Leu Arg Val Val Tyr Arg Asp
            20                  25

<210> SEQ ID NO 51
<211> LENGTH: 18
<212> TYPE: PRT
<213> ORGANISM: Artificial Sequence
<220> FEATURE:
<223> OTHER INFORMATION: Consensus sequence

<400> SEQUENCE: 51
```

```
Ser Lys Val Arg Lys Leu Arg Tyr Tyr Asn Cys Ser Val Tyr Gly Ala
1               5                   10                  15

Ser Leu

<210> SEQ ID NO 52
<211> LENGTH: 26
<212> TYPE: PRT
<213> ORGANISM: Artificial Sequence
<220> FEATURE:
<223> OTHER INFORMATION: Consensus sequence

<400> SEQUENCE: 52

Val Tyr Cys Lys Gly Gln Leu Thr Glu Thr Glu Val Leu Asp Phe Ala
1               5                   10                  15

Phe Thr Asp Leu Thr Ile Val Tyr Arg Asp
            20                  25

<210> SEQ ID NO 53
<211> LENGTH: 18
<212> TYPE: PRT
<213> ORGANISM: Artificial Sequence
<220> FEATURE:
<223> OTHER INFORMATION: Consensus sequence

<400> SEQUENCE: 53

Ser Lys Val Ser Glu Phe Arg Trp Tyr Arg Tyr Ser Val Tyr Gly Thr
1               5                   10                  15

Thr Leu

<210> SEQ ID NO 54
<211> LENGTH: 15
<212> TYPE: PRT
<213> ORGANISM: Artificial Sequence
<220> FEATURE:
<223> OTHER INFORMATION: Consensus sequence

<400> SEQUENCE: 54

Cys Val Glu Cys Lys Lys Thr Leu Gln Arg Ser Glu Val Tyr Asp
1               5                   10                  15

<210> SEQ ID NO 55
<211> LENGTH: 21
<212> TYPE: PRT
<213> ORGANISM: Artificial Sequence
<220> FEATURE:
<223> OTHER INFORMATION: CQRPLCPQEKKRHVDLNKRFH

<400> SEQUENCE: 55

Cys Gln Arg Pro Leu Cys Pro Gln Glu Lys Lys Arg His Val Asp Leu
1               5                   10                  15

Asn Lys Arg Phe His
            20

<210> SEQ ID NO 56
<211> LENGTH: 21
<212> TYPE: PRT
<213> ORGANISM: Artificial Sequence
<220> FEATURE:
<223> OTHER INFORMATION: Consensus sequence

<400> SEQUENCE: 56

Thr Leu His Glu Tyr Met Leu Asp Leu Gln Pro Glu Thr Thr Asp Leu
1               5                   10                  15
```

Tyr Cys Tyr Glu Gln
            20

<210> SEQ ID NO 57
<211> LENGTH: 26
<212> TYPE: PRT
<213> ORGANISM: Artificial Sequence
<220> FEATURE:
<223> OTHER INFORMATION: Consensus sequence

<400> SEQUENCE: 57

Pro Glu Thr Thr Asp Leu His Cys Tyr Glu Gln Leu Gly Asp Ser Ser
1               5                   10                  15

Asp Glu Glu Asp Thr Gly Gly Leu Asp Gly
            20                  25

<210> SEQ ID NO 58
<211> LENGTH: 39
<212> TYPE: PRT
<213> ORGANISM: Artificial Sequence
<220> FEATURE:
<223> OTHER INFORMATION: Consensus sequence

<400> SEQUENCE: 58

Asp Glu Asp Glu Asp Glu Val Asp His Leu Gln Glu Gln Pro Gln Gln
1               5                   10                  15

Ala Arg Arg Asp Glu Gln His Pro Cys Tyr Leu Ile Glu Thr Gln Cys
            20                  25                  30

Cys Arg Cys Glu Ser Leu Val
        35

<210> SEQ ID NO 59
<211> LENGTH: 37
<212> TYPE: PRT
<213> ORGANISM: Artificial Sequence
<220> FEATURE:
<223> OTHER INFORMATION: Consensus sequence

<400> SEQUENCE: 59

Glu Glu Asn Asp Glu Ile Asp Gly Val Asn His Gln His Leu Pro Ala
1               5                   10                  15

Arg Arg Ala Glu Pro Gln Arg His Thr Met Leu Cys Met Cys Cys Lys
            20                  25                  30

Cys Glu Ala Arg Ile
        35

<210> SEQ ID NO 60
<211> LENGTH: 3960
<212> TYPE: DNA
<213> ORGANISM: Artificial Sequence
<220> FEATURE:
<223> OTHER INFORMATION: vaccine construct

<400> SEQUENCE: 60
atggatgcta tgaagagggg cctgtgctgc gtgctgctgc tgtgtggcgc cgtgtttgtg      60
tcccccagcc aggaaatcca cgcccggttc agaagaggca gcaagctggc cgacgaggac     120
gagacagcct acgacagcgg caccgacctg atcgacttca tcgacgacag cgacgagaat     180
gagaacgact ccgacaccgg cgaggacatg gtggatttca tcgacaacga cgaaaccgac     240
gaagagagca ccgagagcga cctggacggc tttatcgaca actccgccca gctggctgac     300
agcgacagca atgcctgcgc cttcctgaag gctcagctgg cagacgtgaa cagcaacgcc     360

-continued

```
gctgcttttc tgaagaactg catcctgctg tacggcgctg ccaacaccgg caagagcctg      420
ttcggcatga gcctgaactg cctggtgctg tgcggcccag ccataccgg aaagtcctac       480 ttcggcatgt ccctgaattg tctcgtgatc tacgcccac ctaacacagg caagtcctgc       540
tttgccatgt ctctgtggcc ctacctgcac agcagactgg tggtgtttac cttccccaac     600
cccttctggc cttacctgga aagccggatc accgtgttcg agttccccaa tgcctttctg     660
agatacctgc actcccggat ccacgtgctg cagtttctga ccccttcaa cgtgtgccag      720 gacaagatcc tggaacacta cgagaacgac agcaaggaca ttctggaaca ttatgagaat     780
gattccaagg acctgtgcga ccacatctgc gatcacatcg actactggaa gcacatccgg     840
ctggaatgcg ccatcatgta caaggcccgg atcagactgg aatgtgctat tatgtataag     900
gctcgcgaga tgggcttcca ccagttcgac ggcgacatct gcaacaccat gcactacacc     960
aactggatct atatctgcga ggacgcccag tgcaccgtgg tggaaggcca ggtggacaag    1020
aaatgggagg tgcacgctgg cggccaagtg atcctgtgtc ctgagagcgg ccagcggcgg    1080
atcaagaggc cagaagcga gaactgccac cccaacaagc tgctgatcct gaagtgcctg     1140
cggtacagat tcaagaagca ctgcaagctg agcagcacct ggcactggac ctgccacgac    1200
ggcaagcaca agtggcattg gacatgtcac gatgggaaac acaagaacgc cattgtgacc    1260
ctgacctact acgaggccga caagaacgac ctgaacgccc agatcgagca ctggaaactg    1320
atccggatgg aatgtgcaat cttctataag gccaagagc tgggcatcag catctgccac     1380
caggtggtgc ctccactggc cgcctctaaa gccaaagcct gccaggccat cgaactgcag    1440
ctggccctgg aagccctgaa tgccagcccc tacgatgagt ggaccctgca gcagaccagc    1500
ctggaaatgt ggctggccga gccccagttt aagaagcacg gcatcaccat caccgtgcag    1560
tacgacaatg acaaggccaa taccatggat tacacaaatt ggaaagaaat ctacgtgatc    1620
gtgtgccccg ccagcatccc ctccgatgag atcagcaccg aggaagccga ccacattgat    1680
tattggaaag ccatcaggca ggaaaacgcc atcttcttcg ccgccagaca ccaggtggtg    1740
cccgccctga atatctgcaa ggccaaggcc tgtaaagcca tcgagtggaa caccgagccc    1800
aagcactgct tcaagaaggg cggccagcac atcgaagtgt ggttcgacta cgtggcctgg    1860
gacagcgtgt actactgcgg cgacgatggc tggtgcaaga ccgaggccga aagtacggc     1920 tgcaagggca cctgggaagt gcatttcggc aacagcatcg actgcaacga ctccatgtgc    1980
agcaccttcg acgacaacgt gtccgccacc gagctcgtga aggaccatat cgactattgg    2040
aagctgattc gcctggaatg tgccattttt tacaaggcca gacggcggct gtccagcgac    2100
caggatcagt ctcagctcgt gaccaagtac cccctgctga gctgctgtc cagacccccc     2160 aacatgggcg tgaaggccca cggcaagtgc atctgggaga acaaggtgtt catcgtgccc    2220
accctgtgcc ccgtgcctct ggatccaaca tatcctctgc tgaaactgct gaccacccag    2280
accaccaccc ccgagaatac ctccctggtg gaactgagag tgaccacccc caagagcaca    2340
gtcgtgatca ggctgcacct gaccaccaga tacccactgc tgtcactgct gaacagctac    2400 agcaccccc ctcaccggat ccctgctcca tgtccttggg ctcctcagag gccccccatc     2460
cctaagcctt ctccatgggc ccctagaatc cctgcccctt gccctgggc accctcctaga   2520 cctccacact gtccatgggt gccccctcca cctcctccaa gaccttgggc cccttgcttc    2580
ctgctgtgct tttgtgtgct gctgtgcgtg tgcctgctga tcagacccct gctgctgagt    2640
gtgtccacct acctgaggcc tctgctgctg tctatcagcg tgtacgctca ggtgctggtg    2700
ctggtgctgc tgctgtgggt gtccatcgga agcctgctgc ccagcgtgtg catgtgtgcc    2760
```

-continued

```
tatgcctggg tgctggtgtt cgtgtacatc gtcgtgatta ccagcccgc accgccatc    2820
gtgtaccggg atggcaatcc ttacgccgtg tgcgacaagt gcctgaagtt ctacagcaag   2880
atcagcgagt accggcacta ctgctacagc ctgtacggca ccaccctgga acagcagtac   2940
aacaagcccc tgtgcgatct gctgattcgg tgcatcaacg tggtgtacag agactccatc   3000
ccccacgccg cctgccacaa gtgtatcgac ttctactcca gaatcagaga gctgcggcac   3060
tacagcgact ccgtgtacgg cgataccctg gaaaagctga ccaacactgg cctgtacaac   3120
ctgctgatta gatgcctgcg ggtgttctgc aagaaggccc tgacagccag cgaggtgtac   3180
aacttcgcct acaccgatct gcgggtggtg tatcgggaca gcaaagtgcg gaagctgagg   3240
tactacaact gctctgtgta tggcgccagc ctggtgtatt gcaagggaca gctgaccgag   3300
acagaggtgc tggatttcgc cttcacagac ctgacaatcg tgtatcgcga ctccaaggtg   3360
tccgagttcc ggtggtacag atattccgtg tatggcacca cactgtgcgt ggaatgcaag   3420
aaaaccctgc agagatctga ggtgtacgac tgccagcggc cactgtgtcc gcaggaaaag   3480
aaaagacacg tggacctgaa caagcggttc cacaccctgc acgagtacat gctggatctg   3540
cagcccgaga caaccgacct gtactgctac gagcagcctg aaaccactga tctgcactgt   3600
tatgagcagc tgggagacag ctccgatgaa gaggacactg gcggcctgga tggggacgag   3660
gatgaggacg aagtggacca tctgcaggaa cagccccagc aggctagacg ggacgaacag   3720
caccttgct atctgatcga cacagtgc tgcagatgcg aatctctggt ggaagagaac   3780
gacgagatcg acggcgtgaa ccaccagcat ctgcccgcta aagggccga gcctcagaga   3840
cacaccatgc tgtgtatgtg ctgcaagtgc gaggccagaa tcgccggctc tggacctggc   3900
gcctctggca agcctatccc caatccactg ctgggcctgg actccacccg gacctgataa   3960
```

<210> SEQ ID NO 61
<211> LENGTH: 1318
<212> TYPE: PRT
<213> ORGANISM: Artificial Sequence
<220> FEATURE:
<223> OTHER INFORMATION: Vaccine construct

<400> SEQUENCE: 61

```
Met Asp Ala Met Lys Arg Gly Leu Cys Cys Val Leu Leu Cys Gly
1               5                   10                  15

Ala Val Phe Val Ser Pro Ser Gln Glu Ile His Ala Arg Phe Arg Arg
                20                  25                  30

Gly Ser Lys Leu Ala Asp Glu Asp Glu Thr Ala Tyr Asp Ser Gly Thr
            35                  40                  45

Asp Leu Ile Asp Phe Ile Asp Asp Ser Asp Glu Asn Glu Asn Asp Ser
        50                  55                  60

Asp Thr Gly Glu Asp Met Val Asp Phe Ile Asp Asn Asp Glu Thr Asp
65                  70                  75                  80

Glu Glu Ser Thr Glu Ser Asp Leu Asp Gly Phe Ile Asp Asn Ser Ala
                85                  90                  95

Gln Leu Ala Asp Ser Asp Ser Asn Ala Cys Ala Phe Leu Lys Ala Gln
            100                 105                 110

Leu Ala Asp Val Asn Ser Asn Ala Ala Phe Leu Lys Asn Cys Ile
        115                 120                 125

Leu Leu Tyr Gly Ala Ala Asn Thr Gly Lys Ser Leu Phe Gly Met Ser
    130                 135                 140

Leu Asn Cys Leu Val Leu Cys Gly Pro Ala Asn Thr Gly Lys Ser Tyr
```

```
                145                 150                 155                 160
            Phe Gly Met Ser Leu Asn Cys Leu Val Ile Tyr Gly Pro Pro Asn Thr
                            165                 170                 175
            Gly Lys Ser Cys Phe Ala Met Ser Leu Trp Pro Tyr Leu His Ser Arg
                            180                 185                 190
            Leu Val Val Phe Thr Phe Pro Asn Pro Phe Trp Pro Tyr Leu Glu Ser
                            195                 200                 205
            Arg Ile Thr Val Phe Glu Phe Pro Asn Ala Phe Leu Arg Tyr Leu His
                            210                 215                 220
            Ser Arg Ile His Val Leu Gln Phe Leu Asn Pro Phe Asn Val Cys Gln
            225                 230                 235                 240
            Asp Lys Ile Leu Glu His Tyr Glu Asn Asp Ser Lys Asp Ile Leu Glu
                            245                 250                 255
            His Tyr Glu Asn Asp Ser Lys Asp Leu Cys Asp His Ile Cys Asp His
                            260                 265                 270
            Ile Asp Tyr Trp Lys His Ile Arg Leu Glu Cys Ala Ile Met Tyr Lys
                            275                 280                 285
            Ala Arg Ile Arg Leu Glu Cys Ala Ile Met Tyr Lys Ala Arg Glu Met
                            290                 295                 300
            Gly Phe His Gln Phe Asp Gly Asp Ile Cys Asn Thr Met His Tyr Thr
            305                 310                 315                 320
            Asn Trp Ile Tyr Ile Cys Glu Asp Ala Gln Cys Thr Val Val Glu Gly
                            325                 330                 335
            Gln Val Asp Lys Lys Trp Glu Val His Ala Gly Gly Gln Val Ile Leu
                            340                 345                 350
            Cys Pro Glu Ser Gly Gln Arg Arg Ile Lys Arg Pro Arg Ser Glu Asn
                            355                 360                 365
            Cys His Pro Asn Lys Leu Leu Ile Leu Lys Cys Leu Arg Tyr Arg Phe
                            370                 375                 380
            Lys Lys His Cys Lys Leu Ser Ser Thr Trp His Trp Thr Cys His Asp
            385                 390                 395                 400
            Gly Lys His Lys Trp His Trp Thr Cys His Asp Gly Lys His Lys Asn
                            405                 410                 415
            Ala Ile Val Thr Leu Thr Tyr Tyr Glu Ala Asp Lys Asn Asp Leu Asn
                            420                 425                 430
            Ala Gln Ile Glu His Trp Lys Leu Ile Arg Met Glu Cys Ala Ile Phe
                            435                 440                 445
            Tyr Lys Ala Lys Glu Leu Gly Ile Ser Ile Cys His Gln Val Val Pro
                            450                 455                 460
            Pro Leu Ala Ala Ser Lys Ala Lys Ala Cys Gln Ala Ile Glu Leu Gln
            465                 470                 475                 480
            Leu Ala Leu Glu Ala Leu Asn Ala Ser Pro Tyr Asp Glu Trp Thr Leu
                            485                 490                 495
            Gln Gln Thr Ser Leu Glu Met Trp Leu Ala Glu Pro Gln Phe Lys Lys
                            500                 505                 510
            His Gly Ile Thr Ile Thr Val Gln Tyr Asp Asn Asp Lys Ala Asn Thr
                            515                 520                 525
            Met Asp Tyr Thr Asn Trp Lys Glu Ile Tyr Val Ile Val Cys Pro Ala
                            530                 535                 540
            Ser Ile Pro Ser Asp Glu Ile Ser Thr Glu Glu Ala Asp His Ile Asp
            545                 550                 555                 560
            Tyr Trp Lys Ala Ile Arg Gln Glu Asn Ala Ile Phe Phe Ala Ala Arg
                            565                 570                 575
```

```
His Gln Val Val Pro Ala Leu Asn Ile Cys Lys Ala Lys Ala Cys Lys
            580                 585                 590

Ala Ile Glu Trp Asn Thr Glu Pro Lys His Cys Phe Lys Lys Gly Gly
        595                 600                 605

Gln His Ile Glu Val Trp Phe Asp Tyr Val Ala Trp Asp Ser Val Tyr
    610                 615                 620

Tyr Cys Gly Asp Asp Gly Trp Cys Lys Thr Glu Ala Glu Lys Tyr Gly
625                 630                 635                 640

Cys Lys Gly Thr Trp Glu Val His Phe Gly Asn Ser Ile Asp Cys Asn
                645                 650                 655

Asp Ser Met Cys Ser Thr Phe Asp Asn Val Ser Ala Thr Glu Leu
            660                 665                 670

Val Lys Asp His Ile Asp Tyr Trp Lys Leu Ile Arg Leu Glu Cys Ala
            675                 680                 685

Ile Phe Tyr Lys Ala Arg Arg Arg Leu Ser Ser Asp Gln Asp Gln Ser
        690                 695                 700

Gln Leu Val Thr Lys Tyr Pro Leu Leu Lys Leu Leu Ser Arg Pro Pro
705                 710                 715                 720

Asn Met Gly Val Lys Ala His Gly Lys Cys Ile Trp Glu Asn Lys Val
                725                 730                 735

Phe Ile Val Pro Thr Leu Cys Pro Val Pro Leu Asp Pro Thr Tyr Pro
            740                 745                 750

Leu Leu Lys Leu Leu Thr Thr Gln Thr Thr Pro Glu Asn Thr Ser
        755                 760                 765

Leu Val Glu Leu Arg Val Thr Thr Pro Lys Ser Thr Val Val Ile Arg
    770                 775                 780

Leu His Leu Thr Thr Arg Tyr Pro Leu Leu Ser Leu Leu Asn Ser Tyr
785                 790                 795                 800

Ser Thr Pro Pro His Arg Ile Pro Ala Pro Cys Pro Trp Ala Pro Gln
                805                 810                 815

Arg Pro Pro Ile Pro Lys Pro Ser Pro Trp Ala Pro Arg Ile Pro Ala
            820                 825                 830

Pro Cys Pro Trp Ala Pro Arg Pro Pro His Cys Pro Trp Val Pro
        835                 840                 845

Pro Pro Pro Pro Arg Pro Trp Ala Pro Cys Phe Leu Leu Cys Phe
    850                 855                 860

Cys Val Leu Leu Cys Val Cys Leu Leu Ile Arg Pro Leu Leu Leu Ser
865                 870                 875                 880

Val Ser Thr Tyr Leu Arg Pro Leu Leu Leu Ser Ile Ser Val Tyr Ala
                885                 890                 895

Gln Val Leu Val Leu Val Leu Leu Trp Val Ser Ile Gly Ser Leu
            900                 905                 910

Leu Pro Ser Val Cys Met Cys Ala Tyr Ala Trp Val Leu Val Phe Val
            915                 920                 925

Tyr Ile Val Val Ile Thr Ser Pro Ala Thr Ala Ile Val Tyr Arg Asp
        930                 935                 940

Gly Asn Pro Tyr Ala Val Cys Asp Lys Cys Leu Lys Phe Tyr Ser Lys
945                 950                 955                 960

Ile Ser Glu Tyr Arg His Tyr Cys Tyr Ser Leu Tyr Gly Thr Thr Leu
                965                 970                 975

Glu Gln Gln Tyr Asn Lys Pro Leu Cys Asp Leu Leu Ile Arg Cys Ile
            980                 985                 990
```

Asn Val Val Tyr Arg Asp Ser Ile Pro His Ala Ala Cys His Lys Cys
            995                 1000                1005

Ile Asp Phe Tyr Ser Arg Ile Arg Glu Leu Arg His Tyr Ser Asp
    1010                1015                1020

Ser Val Tyr Gly Asp Thr Leu Glu Lys Leu Thr Asn Thr Gly Leu
    1025                1030                1035

Tyr Asn Leu Leu Ile Arg Cys Leu Arg Val Phe Cys Lys Lys Ala
    1040                1045                1050

Leu Thr Ala Ser Glu Val Tyr Asn Phe Ala Tyr Thr Asp Leu Arg
    1055                1060                1065

Val Val Tyr Arg Asp Ser Lys Val Arg Lys Leu Arg Tyr Tyr Asn
    1070                1075                1080

Cys Ser Val Tyr Gly Ala Ser Leu Val Tyr Cys Lys Gly Gln Leu
    1085                1090                1095

Thr Glu Thr Glu Val Leu Asp Phe Ala Phe Thr Asp Leu Thr Ile
    1100                1105                1110

Val Tyr Arg Asp Ser Lys Val Ser Glu Phe Arg Trp Tyr Arg Tyr
    1115                1120                1125

Ser Val Tyr Gly Thr Thr Leu Cys Val Glu Cys Lys Lys Thr Leu
    1130                1135                1140

Gln Arg Ser Glu Val Tyr Asp Cys Gln Arg Pro Leu Cys Pro Gln
    1145                1150                1155

Glu Lys Lys Arg His Val Asp Leu Asn Lys Arg Phe His Thr Leu
    1160                1165                1170

His Glu Tyr Met Leu Asp Leu Gln Pro Glu Thr Thr Asp Leu Tyr
    1175                1180                1185

Cys Tyr Glu Gln Pro Glu Thr Thr Asp Leu His Cys Tyr Glu Gln
    1190                1195                1200

Leu Gly Asp Ser Ser Asp Glu Glu Asp Thr Gly Gly Leu Asp Gly
    1205                1210                1215

Asp Glu Asp Glu Asp Glu Val Asp His Leu Gln Glu Gln Pro Gln
    1220                1225                1230

Gln Ala Arg Arg Asp Glu Gln His Pro Cys Tyr Leu Ile Glu Thr
    1235                1240                1245

Gln Cys Cys Arg Cys Glu Ser Leu Val Glu Glu Asn Asp Glu Ile
    1250                1255                1260

Asp Gly Val Asn His Gln His Leu Pro Ala Arg Arg Ala Glu Pro
    1265                1270                1275

Gln Arg His Thr Met Leu Cys Met Cys Cys Lys Cys Glu Ala Arg
    1280                1285                1290

Ile Ala Gly Ser Gly Pro Gly Ala Ser Gly Lys Pro Ile Pro Asn
    1295                1300                1305

Pro Leu Leu Gly Leu Asp Ser Thr Arg Thr
    1310                1315

<210> SEQ ID NO 62
<211> LENGTH: 42783
<212> TYPE: DNA
<213> ORGANISM: Artificial Sequence
<220> FEATURE:
<223> OTHER INFORMATION: Viral vector construct

<400> SEQUENCE: 62
gtttaaacgc ggccgccagg cctacccact agtcaattcg ggaggatcga acggcagat    60 cgcaaaaaac agtacataca gaaggagaca tgaacatgaa catcaaaaaa attgtaaaac   120

```
aagccacagt tctgactttt acgactgcac ttctggcagg aggagcgact caagccttcg    180
cgaaagaaaa taaccaaaaa gcatacaaag aaacgtacgg cgtctctcat attacacgcc    240
atgatatgct gcagatccct aaacagcagc aaaacgaaaa ataccaagtg cctcaattcg    300
atcaatcaac gattaaaaat attgagtctg caaaaggact tgatgtgtgg acagctggc     360 cgctgcaaaa cgctgacgga acagtagctg aatacaacgg ctatcacgtt gtgtttgctc    420
ttgcgggaag cccgaaagac gctgatgaca catcaatcta catgttttat caaaaggtcg    480
gcgacaactc aatcgacagc tggaaaaacg cgggccgtgt ctttaaagac agcgataagt    540
tcgacgccaa cgatccgatc ctgaaagatc agacgcaaga atggtccggt tctgcaacct    600
ttacatctga cggaaaaatc cgtttattct cactgactac ttccggtaaa cattacggca    660
aacaaagcct gacaacagcg caggtaaatg tgtcaaaatc tgatgacaca ctcaaaatca    720
acggagtgga agatcacaaa acgattttt acggagacgg aaaaacatat cagaacgttc     780
agcagtttat cgatgaaggc aattatacat ccggcgacaa ccatacgctg agagaccctc    840
actacgttga agacaaaggc cataaatacc ttgtattcga agccaacacg ggaacagaaa    900
acggatacca aggcgaagaa tctttatttta acaaagcgta ctacggcggc ggcacgaact    960
tcttccgtaa agaaagccag aagcttcagc agagcgctaa aaaacgcgat gctgagttag   1020
cgaacggcgc cctcggtatc atagagttaa ataatgatta cacattgaaa aaagtaatga   1080
agccgctgat cacttcaaac acggtaactg atgaaatcga gcgcgcgaat gttttcaaaa   1140
tgaacggcaa atggtacttg ttcactgatt cacgcggttc aaaaatgacg atcgatggta   1200
ttaactcaaa cgatatttac atgcttggtt atgtatcaaa ctctttaacc ggcccttaca   1260
agccgctgaa caaaacaggg cttgtgctgc aaatgggtct tgatccaaac gatgtgacat   1320
tcacttactc tcacttcgca gtgccgcaag ccaaaggcaa caatgtggtt atcacaagct   1380
acatgacaaa cagaggcttc ttcgaggata aaaaggcaac atttgcgcca agcttcttaa   1440
tgaacatcaa aggcaataaa acatccgttg tcaaaaacag catcctggag caaggacagc   1500
tgacagtcaa ctaataacag caaaaagaaa atgccgatac ttcattggca ttttctttta   1560
tttctcaaca agatggtgaa ttgactagtg ggtagatcca caggacgggt gtggtcgcca   1620
tgatcgcgta gtcgatagtg gctccaagta gcgaagcgag caggactggg cggcggccaa   1680
agcggtcgga cagtgctccg agaacgggtg cgcatagaaa ttgcatcaac gcatatagcg   1740
ctagcagcac gccatagtga ctggcgatgc tgtcggaatg gacgatatcc cgcaagaggc   1800
ccggcagtac cggcataacc aagcctatgc ctacagcatc cagggtgacg gtgccgagga   1860
tgacgatgag cgcattgtta gatttcatac acggtgcctg actgcgttag caatttaact   1920
gtgataaact accgcattaa agcttatcga tgataagctg tcaaacatga gaattgatcc   1980 ggaacccttta atataacttc gtataatgta tgctatacga agttattagg tccctcgact   2040
atagggtcac cgtcgacagc gacacacttg catcggatgc agcccggtta acgtgccggc   2100
acggcctggg taaccaggta ttttgtccac ataaccgtgc gcaaaatgtt gtggataagc   2160
aggacacagc agcaatccac agcaggcata caaccgcaca ccgaggttac tccgttctac   2220
aggttacgac gacatgtcaa tacttgccct tgacaggcat tgatggaatc gtagtctcac   2280
gctgatagtc tgatcgacaa tacaagtggg accgtggtcc cagaccgata atcagaccga   2340
crayacgagt gggaycgtgg tcccagacta ataatcagac cgacgatacg agtgggaccg   2400
tggtcccaga ctaataatca gaccgacgat acgagtggga ccgtggtycc agwctratwa   2460
```

```
tcagaccgac gatacragtg gracmgtggk cccagasaka atawtcagrc cgagwtaygc    2520
wktckggcct gtaacaaagg acattaagta aagacagata mrmgtgrgac taaaacgtgg    2580
tcccagtctg attatcagac cgacgatacg agtgggaccg tggtcccaga ctaataatca    2640
gaccgacgat acgagtggga ccgtggtccc agactaataa tcagaccgac gatacgagtg    2700
ggaccgtggt cccagtctga ttatcagacc gacgatacaa gtggaacagt gggcccagag    2760
agaatattca ggccagttat gctttctggc ctgtaacaaa ggacattaag taaagacaga    2820
taaacgtaga ctaaaacgtg gtcgcatcag ggtgctggct tttcaagttc cttaagaatg    2880
gcctcaattt tctctataca ctcagttgga acacgagacc tgtccaggtt aagcaccatt    2940
ttatcgccct tatacaatac tgtcgctcca ggagcaaact gatgtcgtga gcttaaacta    3000
gttcttgatg cagatgacgt tttaagcaca aagttaaaa gagtgataac ttcttcagct    3060
tcaaatatca ccccagcttt tttctgctca tgaaggttag atgcctgctg cttaagtaat    3120
tcctctttat ctgtaaaggc ttttttgaagt gcatcacctg accgggcaga tagttcaccg    3180
gggtgagaaa aaagagcaac aactgattta ggcaatttgg cggtgttgat acagcgggta    3240
ataatcttac gtgaaatatt ttccgcatca gccagcgcag aaatatttcc agcaaattca    3300
ttctgcaatc ggcttgcata acgctgacca cgttcataag cacttgttgg gcgataatcg    3360
ttacccaatc tggataatgc agccatctgc tcatcatcca gctcgccaac cagaacacga    3420
taatcacttt cggtaagtgc agcagcttta cgacggcgac tcccatcggc aatttctatg    3480
acaccagata ctcttcgacc gaacgccggt gtctgttgac cagtcagtag aaaagaaggg    3540
atgagatcat ccagtgcgtc ctcagtaagc agctcctggt cacgttcatt acctgaccat    3600
acccgagagg tcttctcaac actatcaccc cggagcactt caagagtaaa cttcacatcc    3660
cgaccacata caggcaaagt aatggcatta ccgcgagcca ttactcctac gcgcgcaatt    3720
aacgaatcca ccatcggggc agctggtgtc gataacgaag tatcttcaac cggttgagta    3780
ttgagcgtat gttttggaat aacaggcgca cgcttcatta tctaatctcc cagcgtggtt    3840
taatcagacg atcgaaaatt tcattgcaga caggttccca aatagaaaga gcatttctcc    3900
aggcaccagt tgaagagcgt tgatcaatgg cctgttcaaa aacagttctc atccggatct    3960 gaccttttacc aacttcatcc gtttcacgta caacattttt tagaaccatg cttccccagg    4020
catcccgaat ttgctcctcc atccacgggg actgagagcc attactattg ctgtatttgg    4080
taagcaaaat acgtacatca ggctcgaacc ctttaagatc aacgttcttg agcagatcac    4140
gaagcatatc gaaaaactgc agtgcggagg tgtagtcaaa caactcagca ggcgtgggaa    4200
caatcagcac atcagcagca catacgacat taatcgtgcc gatacccagg ttaggcgcgc    4260
tgtcaataac tatgacatca tagtcatgag caacagtttc aatggccagt cggagcatca    4320
ggtgtggatc ggtgggcagt ttaccttcat caaatttgcc cattaactca gtttcaatac    4380
ggtgcagagc cagacaggaa ggaataatgt caagccccgg ccagcaagtg ggctttattg    4440
cataagtgac atcgtccttt tccccaagat agaaaggcag gagagtgtct tctgcatgaa    4500
tatgaagatc tggtacccat ccgtgataca ttgaggctgt tccctggggg tcgttacctt    4560
ccacgagcaa aacacgtagc cccttcagag ccagatcctg agcaagatga acagaaactg    4620
aggttttgta acgccacct ttatgggcag caaccccgat caccggtgga aatacgtctt    4680
cagcacgtcg caatcgcgta ccaaacacat cacgcatatg attaatttgt tcaattgtat    4740
aaccaacacg ttgctcaacc cgtcctcgaa tttccatatc cgggtgcggt agtcgccctg    4800 cttttctcggc atctctgata gcctgagaag aaaccccaac taaatccgct gcttcaccta    4860
```

```
ttctccagcg ccgggttatt ttcctcgctt ccgggctgtc atcattaaac tgtgcaatgg    4920
cgatagcctt cgtcatttca tgaccagcgt ttatgcactg gttaagtgtt tccatgagtt    4980
tcattctgaa catcctttaa tcattgcttt gcgtttttt attaaatctt gcaatttact     5040
gcaaagcaac aacaaaatcg caaagtcatc aaaaaaccgc aaagttgttt aaaataagag    5100
caacactaca aaaggagata agaagagcac atacctcagt cacttattat cactagcgct    5160
cgccgcagcc gtgtaaccga gcatagcgag cgaactggcg aggaagcaaa gaagaactgt    5220
tctgtcagat agctcttacg ctcagcgcaa gaagaaatat ccaccgtggg aaaaactcca    5280
ggtagaggta cacacgcgga tagccaattc agagtaataa actgtgataa tcaaccctca    5340
tcaatgatga cgaactaacc cccgatatca ggtcacatga cgaagggaaa gagaaggaaa    5400
tcaactgtga caaactgccc tcaaatttgg cttccttaaa aattacagtt caaaagtat     5460 gagaaaatcc atgcaggctg aaggaaacag caaaactgtg acaaattacc ctcagtaggt    5520
cagaacaaat gtgacgaacc accctcaaat ctgtgacaga taaccctcag actatcctgt    5580
cgtcatggaa gtgatatcgc ggaaggaaaa tacgatatga gtcgtctggc ggcctttctt    5640
tttctcaatg tatgagaggc gcattggagt tctgctgttg atctcattaa cacagacctg    5700
caggaagcgg cggcggaagt caggcatacg ctggtaactt tgaggcagct ggtaacgctc    5760
tatgatccag tcgattttca gagagacgat gcctgagcca tccggcttac gatactgaca    5820
cagggattcg tataaacgca tggcatacgg attggtgatt tcttttgttt cactaagccg    5880
aaactgcgta aaccggttct gtaacccgat aagaaggga  atgagatatg ggttgatatg    5940
tacactgtaa agccctctgg atggactgtg cgcacgtttg ataaaccaag gaaaagattc    6000
atagcctttt tcatcgccgg catcctcttc agggcgataa aaaaccactt ccttccccgc    6060
gaaactcttc aatgcctgcc gtatatcctt actggcttcc gcagaggtca atccgaatat    6120
ttcagcatat ttagcaacat ggatctcgca gataccgtca tgttcctgta gggtgccatc    6180
agattttctg atctggtcaa cgaacagata cagcatacgt ttttgatccc gggagagact    6240
atatgccgcc tcagtgaggt cgtttgactg gacgattcgc gggctatttt tacgtttctt    6300
gtgattgata accgctgttt ccgccatgac agatccatgt gaagtgtgac aagttttag    6360 attgtcacac taaataaaaa agagtcaata agcagggata actttgtgaa aaaacagctt    6420
cttctgaggg caatttgtca cagggttaag ggcaatttgt cacagacagg actgtcattt    6480
gagggtgatt tgtcacactg aaagggcaat tgtcacaac accttctcta gaaccagcat    6540
ggataaaggc ctacaaggcg ctctaaaaaa gaagatctaa aaactataaa aaaataatt     6600 ataaaaatat ccccgtggat aagtggataa ccccaaggga agttttttca ggcatcgtgt    6660
gtaagcagaa tatataagtg ctgttccctg gtgcttcctc gctcactcga ggcttcgcc    6720 ctgtcgctca actgcggcga gcactactgg ctgtaaaagg acagaccaca tcatggttct    6780
gtgttcatta ggttgttctg tccattgctg acataatccg ctccacttca acgtaacacc    6840
gcacgaagat ttctattgtt cctgaaggca tattcaaatc gttttcgtta ccgcttgcag    6900
gcatcatgac agaacactac ttcctataaa cgctacacag gctcctgaga ttaataatgc    6960
ggatctctac gataatggga gattttcccg actgtttcgt tcgcttctca gtggataaca    7020
gccagcttct ctgtttaaca gacaaaaaca gcatatccac tcagttccac atttccatat    7080
aaaggccaag gcattattc tcaggataat gtttcagca tcgcaaccgc atcagactcc      7140
ggcatcgcaa actgcacccg gtgccgggca gccacatcca gcgcaaaaac cttcgtgtag    7200
```

```
acttccgttg aactgatgga cttatgtccc atcaggcttt gcagaacttt cagcggtata    7260
ccggcataca gcatgtgcat cgcataggaa tggcggaacg tatgtggtgt gaccggaaca    7320
gagaacgtca caccgtcagc agcagcggcg gcaaccgcct ccccaatcca ggtcctgacc    7380
gttctgtccg tcacttccca gatccgcgct ttctctgtcc ttcctgtgcg acggttacgc    7440
cgctccatga gcttatcgcg aataaatacc tgtgacggaa gatcacttcg cagaataaat    7500
aaatcctggt gtccctgttg ataccgggaa gccctgggcc aacttttggc gaaaatgaga    7560
cgttgatcgg cacgtaagag gttccaactt tcaccataat gaaataagat cactaccggg    7620
cgtatttttt gagttatcga gattttcagg agctaaggaa gctaaaatgg agaaaaaaat    7680
cactggatat accaccgttg atatatccca atggcatcgt aaagaacatt ttgaggcatt    7740
tcagtcagtt gctcaatgta cctataacca gaccgttcag ctggatatta cggcctttt    7800
aaagaccgta agaaaaata agcacaagtt ttatccggcc tttattcaca ttcttgcccg    7860
cctgatgaat gctcatccgg agttccgtat ggcaatgaaa gacggtgagc tggtgatatg    7920
ggatagtgtt caccctgtt acaccgtttt ccatgagcaa actgaaacgt tttcatcgct    7980
ctggagtgaa taccacgacg atttccggca gtttctacac atatattcgc aagatgtggc    8040
gtgttacggt gaaaacctgg cctatttccc taaagggttt attgagaata tgttttcgt    8100
ctcagccaat ccctgggtga gtttcaccag ttttgattta acgtggcca atatggacaa    8160
cttcttcgcc cccgttttca ccatgggcaa atattatacg caaggcgaca aggtgctgat    8220
gccgctggcg attcaggttc atcatgccgt ttgtgatggc ttccatgtcg cagaatgct    8280
taatgaatta caacagtact gcgatgagtg gcagggcggg gcgtaattt tttaaggcag    8340
ttattggtgc ccttaaacgc ctggttgcta cgcctgaata agtgataata agcggatgaa    8400
tggcagaaat tcgatgataa gctgtcaaac atgagaattg gtcgacggcg cgccaaagct    8460
tgcatgcctg cagccgcgta acctggcaaa atcggttacg gttgagtaat aaatggatgc    8520
cctgcgtaag cggggcacat ttcattacct ctttctccgc acccgacata gataataact    8580
tcgtatagta tacattatac gaagttatct agtagactta atcgcgttta aacccatcat    8640
caataatata cctcaaactt tttgtgcgcg ttaatatgca aatgaggcgt ttgaatttgg    8700
gaagggagga aggtgattgg ccgagagaag ggcgaccgtt aggggcgggg cgagtgacgt    8760
tttgatgacg tgaccgcgag gaggagccag tttgcaagtt ctcgtgggaa aagtgacgtc    8820
aaacgaggtg tggtttgaac acggaaatac tcaattttcc cgcgctctct gacaggaaat    8880
gaggtgtttc taggcggatg caagtgaaaa cgggccattt tcgcgcgaaa actgaatgag    8940
gaagtgaaaa tctgagtaat ttcgcgttta tgacagggag gagtatttgc cgagggccga    9000
gtagactttg accgattacg tggggttttc gattaccgtg ttttcacct aaatttccgc    9060
gtacggtgtc aaagtccggt gttttacgt aggtgtcagc tgatcgccag ggtatttaaa    9120
cctgcgctct ccagtcaaga ggccactctt gagtgccagc gagaagagtt ttctcctccg    9180
cgcgcgagtc agatctacac tttgaaaggc gatcgctagc gacatcgatc acaagtttgt    9240
acaaaaaagc aggctccacc atgggaacca attcagtcga gcctttcact cattagatgc    9300
atgtcgttac ataacttacg gtaaatggcc cgcctggctg accgcccaac gacccccgcc    9360
cattgacgtc aataatgacg tatgttccca tagtaacgcc aatagggact tccattgac    9420
gtcaatgggt ggagtattta cggtaaactg cccacttggc agtacatcaa gtgtatcata    9480
tgccaagtac gccccctatt gacgtcaatg acggtaaatg gcccgcctgg cattatgccc    9540
agtacatgac cttatgggac tttcctactt ggcagtacat ctacgtatta gtcatcgcta    9600
```

```
ttaccatggt gatgcggttt tggcagtaca tcaatgggcg tggatagcgg tttgactcac    9660
ggggatttcc aagtctccac cccattgacg tcaatgggag tttgttttgg caccaaaatc    9720
aacgggactt tccaaaatgt cgtaacaact ccgccccatt gacgcaaatg ggcggtaggc    9780
gtgtacggtg ggaggtctat ataagcagag ctctccctat cagtgataga gatctcccta    9840
tcagtgatag agatcgtcga cgagctcgtt tagtgaaccg tcagatcgcc tggagacgcc    9900
atccacgctg ttttgacctc catagaagac accgggaccg atccagcctc cggttaagct    9960
cggtaccgct agccgcgccg ccaccatgga tgctatgaag aggggcctgt gctgcgtgct   10020
gctgctgtgt ggcgccgtgt tgtgtcccc cagccaggaa atccacgccc ggttcagaag   10080
aggcagcaag ctggccgacg aggacgagac agcctacgac agcggcaccg acctgatcga   10140
cttcatcgac gacagcgacg agaatgagaa cgactccgac accggcgagg acatggtgga   10200
tttcatcgac aacgacgaaa ccgacgaaga gagcaccgag agcgacctgg acggctttat   10260
cgacaactcc gcccagctgg ctgacagcga cagcaatgcc tgcgccttcc tgaaggctca   10320
gctggcagac gtgaacagca cgccgctgc ttttctgaag aactgcatcc tgctgtacgg   10380
cgctgccaac accggcaaga gcctgttcgg catgagcctg aactgcctgg tgctgtgcgg   10440
cccagccaat accggaaagt cctacttcgg catgtccctg aattgtctcg tgatctacgg   10500
cccacctaac acaggcaagt cctgctttgc catgtctctg tggccctacc tgcacagcag   10560
actggtggtg tttaccttcc ccaaccccTT ctggccttac ctggaaagcc ggatcaccgt   10620
gttcgagttc cccaatgcct ttctgagata cctgcactcc cggatccacg tgctgcagtt   10680
tctgaacccc ttcaacgtgt gccaggacaa gatcctggaa cactacgaga acgacagcaa   10740
ggacattctg gaacattatg agaatgattc caaggacctg tgcgaccaca tctgcgatca   10800
catcgactac tggaagcaca tccggctgga atgcgccatc atgtacaagg cccggatcag   10860 actgaatgt gctattatgt ataaggctcg cgagatgggc ttccaccagt tcgacggcga   10920
catctgcaac accatgcact acaccaactg gatctatatc tgcgaggacg cccagtgcac   10980
cgtggtggaa ggccaggtgg acaagaaatg ggaggtgcac gctggcggcc aagtgatcct   11040
gtgtcctgag agcggccagc ggcggatcaa gaggcccaga agcgagaact gccacccaa   11100 caagctgctg atcctgaagt gcctgcggta cagattcaag aagcactgca agctgagcag   11160
cacctggcac tggaccctgcc acgacggcaa gcacaagtgg cattggacat gtcacgatgg   11220
gaaacacaag aacgccattg tgaccctgac ctactacgag gccgacaaga acgacctgaa   11280
cgcccagatc gagcactgga aactgatccg gatggaatgt gcaatcttct ataaggccaa   11340
agagctgggc atcagcatct gccaccaggt ggtgcctcca ctggccgcct ctaaagccaa   11400
agcctgccag gccatcgaac tgcagctggc cctggaagcc ctgaatgcca gccctacga   11460 tgagtggacc ctgcagcaga ccagcctgga atgtggctg gccgagcccc agtttaagaa   11520
gcacggcatc accatcaccg tgcagtacga caatgacaag gccaatacca tggattacac   11580
aaattggaaa gaaatctacg tgatcgtgtg ccccgccagc atccctccg atgagatcag   11640 caccgaggaa gccgaccaca ttgattattg gaaagccatc aggcaggaaa cgccatctt   11700 cttcgccgcc agacaccagg tggtgcccgc cctgaatatc tgcaaggca aggcctgtaa   11760 agccatcgag tggaacaccg agcccaagca ctgcttcaag aagggcggcc agcacatcga   11820
agtgtggttc gactacgtgg cctgggacag cgtgtactac tgcggcgacg atggctggtg   11880
caagaccgag gccgagaagt acggctgcaa gggcacctgg gaagtgcatt tcggcaacag   11940
```

-continued

| | |
|---|---|
| catcgactgc aacgactcca tgtgcagcac cttcgacgac aacgtgtccg ccaccgagct | 12000 |
| cgtgaaggac catatcgact attggaagct gattcgcctg gaatgtgcca tttttttacaa | 12060 |
| ggccagacgg cggctgtcca gcgaccagga tcagtctcag ctcgtgacca agtaccccct | 12120 |
| gctgaagctg ctgtccagac cccccaacat gggcgtgaag gcccacggca agtgcatctg | 12180 |
| ggagaacaag gtgttcatcg tgcccaccct gtgccccgtg cctctggatc aacatatcc | 12240 |
| tctgctgaaa ctgctgacca cccagaccac caccccgag aatacctccc tggtggaact | 12300 |
| gagagtgacc accccaaga gcacagtcgt gatcaggctg cacctgacca ccagataccc | 12360 |
| actgctgtca ctgctgaaca gctacagcac ccccctcac cggatccctg ctccatgtcc | 12420 |
| ttgggctcct cagaggcccc ccatccctaa gccttctcca tgggcccta gaatccctgc | 12480 |
| cccttgcccc tgggcacctc ctagacctcc acactgtcca tgggtgcccc ctccacctcc | 12540 |
| tccaagacct tgggccccct gcttcctgct gtgcttttgt gtgctgctgt gcgtgtgcct | 12600 |
| gctgatcaga cccctgctgc tgagtgtgtc cacctacctg aggcctctgc tgctgtctat | 12660 |
| cagcgtgtac gctcaggtgc tggtgctggt gctgctgctg tgggtgtcca tcggaagcct | 12720 |
| gctgcccagc gtgtgcatgt gtgcctatgc ctgggtgctg gtgttcgtgt acatcgtcgt | 12780 |
| gattaccagc cccgccaccg ccatcgtgta ccgggatggc aatccttacg ccgtgtgcga | 12840 |
| caagtgcctg aagttctaca gcaagatcag cgagtaccgg cactactgct acagcctgta | 12900 |
| cggcaccacc ctggaacagc agtacaacaa gcccctgtgc gatctgctga ttcggtgcat | 12960 |
| caacgtggtg tacagagact ccatccccca cgccgcctgc cacaagtgta tcgacttcta | 13020 |
| ctccagaatc agagagctgc ggcactacag cgactccgtg tacggcgata ccctggaaaa | 13080 |
| gctgaccaac actggcctgt acaacctgct gattagatgc ctgcgggtgt ctgcaagaa | 13140 |
| ggccctgaca gccagcgagg tgtacaactt cgcctacacc gatctgcggg tggtgtatcg | 13200 |
| ggacagcaaa gtgcggaagc tgaggtacta caactgctct gtgtatggcg ccagcctggt | 13260 |
| gtattgcaag gacagctga ccgagacaga ggtgctggat ttcgccttca cagacctgac | 13320 |
| aatcgtgtat cgcgactcca aggtgtccga gttccggtgg tacagatatt ccgtgtatgg | 13380 |
| caccacactg tgcgtggaat gcaagaaaac cctgcagaga tctgaggtgt acgactgcca | 13440 |
| gcggccactg tgtccgcagg aaaagaaaag acacgtggac ctgaacaagc ggttccacac | 13500 |
| cctgcacgag tacatgctgg atctgcagcc cgagacaacc gacctgtact gctacgagca | 13560 |
| gcctgaaacc actgatctgc actgttatga gcagctggga gacagctccg atgaagagga | 13620 |
| cactggcggc ctggatgggg acgaggatga ggacgaagtg gaccatctgc aggaacagcc | 13680 |
| ccagcaggct agacgggacg aacagcaccc ttgctatctg atcgagacac agtgctgcag | 13740 |
| atgcgaatct ctggtggaag agaacgacga gatcgacggc gtgaaccacc agcatctgcc | 13800 |
| cgctagaagg gccgagcctc agagacacac catgctgtgt atgtgctgca gtgcgaggc | 13860 |
| cagaatcgcc ggctctggac ctggcgcctc tggcaagcct atccccaatc cactgctggg | 13920 |
| cctggactcc acccggacct gataagcggc cgctcgagca tgcatctaga gggccctatt | 13980 |
| ctatagtgtc acctaaatgc tagagctcgc tgatcagcct cgactgtgcc ttctagttgc | 14040 |
| cagccatctg ttgtttgccc ctcccccgtg ccttccttga ccctggaagg tgccactccc | 14100 |
| actgtccttt cctaataaaa tgaggaaatt gcatcgcatt gtctgagtag gtgtcattct | 14160 |
| attctggggg gtggggtggg gcaggacagc aaggggagg attggaagaca caatagcagg | 14220 |
| catgctgggg atgcggtggg ctctatggct tctgaggcgg aaagaaccag ctggggctcg | 14280 |
| aggggggatc gatcccgtcg agatatctag acccagcttt cttgtacaaa gtggtgatcg | 14340 |

```
attcgacaga tcgcgatcgc agtgagtagt gttctggggc gggggaggac ctgcatgagg    14400
gccagaatga ctgaaatctg tgcttttctg tgtgttgcag catcatgagc ggaagcggct    14460
cctttgaggg aggggtattc agcccttatc tgacggggcg tctcccctcc tgggcgggag    14520
tgcgtcagaa tgtgatggga tccacggtgg acggccggcc cgtgcagccc gcgaactctt    14580
caaccctgac ctatgcaacc ctgagctctt cgtcggtgga cgcagctgcc gccgcagctg    14640
ctgcatccgc cgccagcgcc gtgcgcggaa tggccatggg cgccggctac tacggcactc    14700
tggtggccaa ctcgagttcc accaataatc ccgccagcct gaacgaggag aagctgctgc    14760
tgctgatggc ccagcttgag gccttgaccc agcgcctggg cgagctgacc cagcaggtgg    14820
ctcagctgca ggagcagacg cgggccgcgg ttgccacggt gaaatccaaa taaaaaatga    14880
atcaataaat aaacggagac ggttgttgat tttaacacag agtctgaatc tttatttgat    14940
ttttcgcgcg cggtaggccc tggaccaccg gtctcgatca ttgagcaccc ggtggatctt    15000
ttccaggacc cggtagaggt gggcttggat gttgaggtac atgggcatga gcccgtcccg    15060
ggggtggagg tagctccatt gcagggcctc gtgctcgggg gtggtgttgt aaatcaccca    15120
gtcatagcag gggcgcaggg cgtggtgttg cacaatatct ttgaggagga gactgatggc    15180
cacgggcagc cctttggtgt aggtgtttac aaatctgttg agctgggagg gatgcatgcg    15240 ggggagatg aggtgcatct tggcctggat cttgagattg gcgatgttac cgcccagatc    15300
ccgcctgggg ttcatgttgt gcaggaccac cagcacggtg tatccggtgc acttggggaa    15360
tttatcatgc aacttggaag ggaaggcgtg aaagaatttg gcgacgccct tgtgtccgcc    15420
caggttttcc atgcactcat ccatgatgat ggcaatgggc ccgtgggcgg cggcctgggc    15480
aaagacgttt cggggtcgg acacatcata gttgtggtcc tgggtgaggt catcataggc    15540
cattttaatg aatttggggc ggagggtgcc ggactggggg acaaaggtac cctcgatccc    15600
gggggcgtag ttcccctcac agatctgcat ctcccaggct ttgagctcag aggggggat    15660 catgtccacc tgcggggcga taaagaacac ggtttccggg gcggggagaa tgagctgggc    15720
cgaaagcaag ttccggagca gctgggactt gccgcagccg gtgggccgt aaatgacccc    15780 gatgaccggc tgcaggtggt agttgaggga gagacagctg ccgtcctccc ggaggagggg    15840
ggccacctcg ttcatcatct cgcgcacgtg catgttctcg cgcaccagtt ccgccaggag    15900
gcgctctccc cccagagata ggagctcctg gagcgaggca agttttttca gcggcttgag    15960
tccgtcggcc atgggcattt tggagagggt ctgttgcaag agttccaagc ggtcccagag    16020
ctcggtgatg tgctctacgg catctcgatc cagcagacct cctcgtttcg cgggttggga    16080
cgactgcggg agtagggcac cagacgatgg gcgtccagcg cagccagggt ccggtccttc    16140
cagggccgca gcgtccgcgt cagggtggtc tccgtcacgg tgaagggtg cgcgccggc    16200 tgggcgcttg cgagggtgcg cttcaggctc atccggctgg tcgaaaaccg ctcccgatcg    16260
gcgccctgcg cgtcggccag gtagcaattg accatgagtt cgtagttgag cgcctcggcc    16320
gcgtggcctt tggcgcggag cttacctttg gaagtctgcc cgcaggcggg acagaggagg    16380
gacttgaggg cgtagagctt gggggcgagg aagacggaat cgggggcgta ggcgtccgcg    16440
ccgcagtggg cgcagacggt ctcgcactcc acgagccagg tgaggtcggg ctggtcgggg    16500
tcaaaaacca gtttcccgcc gttcttttg atgcgtttct tacctttggt ctccatgagc    16560
tcgtgtcccc gctgggtgac aaagaggctg tccgtgtccc cgtagaccga ctttatgggc    16620
cggtcctcga gcggtgtgcc gcggtcctcc tcgtagagga accccgccca ctccgagacg    16680
```

```
aaagcccggg tccaggccag cacgaaggag gccacgtggg acgggtagcg gtcgttgtcc    16740
accagcgggt ccacttttc  cagggtatgc aaacacatgt cccctcgtc  cacatccagg    16800 aaggtgattg gcttgtaagt gtaggccacg tgaccggggg tcccggccgg ggggtataa     16860 aaggggggcgg gcccctgctc gtcctcactg tcttccggat cgctgtccag gagcgccagc   16920
tgttggggta ggtattccct ctcgaaggcg ggcatgacct cggcactcag gttgtcagtt   16980
tctagaaacg aggaggattt gatattgacg gtgccagcgg agatgccttt caagagcccc   17040
tcgtccatct ggtcagaaaa gacgattttt ttgttgtcga gcttggtggc gaaggagccg   17100
tagagggcgt tggaaaggag cttggcgatg gagcgcatgg tctggttttt ttccttgtcg   17160
gcgcgctcct tggccgcgat gttgagctgc acgtactcgc gcgccacgca cttccattcg   17220
gggaagacgg tggtcatctc gtcgggcacg attctgacct gccaacctcg attatgcagg   17280
gtgatgaggt ccacactggt ggccacctcg ccgcgcaggg gctcgttggt ccagcagagg   17340
cggccgccct tgcgcgagca aaggggggc  agagggtcca gcatgacctc gtcgggggg    17400 tcggcatcga tggtgaagat gccgggcagg agatcgggt  cgaagtagct gatggaagtg   17460
gccagatcgt ccagggaagc ttgccattcg cgcacggcca gcgcgcgctc gtagggactg   17520
aggggcgtgc cccagggcat ggggtgggtg agcgcggagg cgtacatgcc gcagatgtcg   17580
tagacgtaga ggggctcctc gaggatgccg atgtaggtgg ggtagcagcg ccccccgcgg   17640
atgctggcgc gcacgtagtc atacagctcg tgcgagggcg cgaggagccc cgggcccagg   17700
ttggtgcgac tgggcttttc ggcgcggtag acgatctggc gaaagatggc atgcgagttg   17760
gaggagatgg tgggccttg  gaagatgttg aagtgggcgt ggggggaggcc gaccgagtcg   17820 cggatgaagt gggcgtagga gtcttgcagt ttggcgacga gctcggcggt gacgaggacg   17880
tccagagcgc agtagtcgag ggtctcctgg atgatgtcat acttgagctg gcccttttgt   17940
ttccacagct cgcggttgag aaggaactct tcgcggtcct tccagtactc ttcgaggggg   18000
aacccgtcct gatctgcacg gtaagagcct agcatgtaga actggttgac ggccttgtag   18060
gcgcagcagc ccttctccac ggggagggcg taggcctggg cggccttgcg cagggaggtg   18120
tgcgtgaggg cgaaggtgtc cctgaccatg accttgagga actggtgctt gaaatcgata   18180
tcgtcgcagc ccccctgctc ccagagctgg aagtccgtgc gcttcttgta ggcggggttg   18240
ggcaaagcga aagtaacatc gttgaaaagg atcttgcccg cgcggggcat aaagttgcga   18300
gtgatgcgga aaggctgggg cacctcggcc cggttgttga tgacctgggc ggcgagcacg   18360
atctcgtcga aaccgttgat gttgtggccc acgatgtaga gttccacgaa tcgcgggcgg   18420
cccttgacgt ggggcagctt cttgagctcc tcgtaggtga gctcgtcggg gtcgctgaga   18480
ccgtgctgct cgagcgccca gtcggcgaga tgggggttgg cgcggaggaa ggaagtccag   18540
agatccacgg ccagggcggt ttgcagacgg tcccggtact gacggaactg ctgcccgacg   18600 gccattttt  cggggtgac  gcagtagaag gtgcggggt  cccgtgcca  gcggtcccat    18660 ttgagctgga gggcgagatc gagggcgagc tcgacgaggc ggtcgtcccc tgagagtttc   18720
atgaccagca tgaaggggac gagctgcttg ccgaaggacc ccatccaggt gtaggtttcc   18780
acatcgtagg tgaggaagag cctttcggtg cgaggatgcg agccgatggg gaagaactgg   18840
atctcctgcc accaattgga ggaatggctg ttgatgtgat ggaagtagaa atgccgacgg   18900
cgcgccgaac actcgtgctt gtgtttatac aagcggccac agtgctcgca acgctgcacg   18960
ggatgcacgt gctgcacgag ctgtacctga gttccttga  cgaggaattt cagtgggaag   19020
tggagtcgtg gcgcctgcat ctcgtgctgt actacgtcgt ggtggtcggc ctggccctct   19080
```

```
tctgcctcga tggtggtcat gctgacgagc ccgcgcggga ggcaggtcca gacctcggcg   19140
cgagcgggtc ggagagcgag gacgagggcg cgcaggccgg agctgtccag ggtcctgaga   19200
cgctgcggag tcaggtcagt gggcagcggc ggcgcgcggt tgacttgcag gagttttcc    19260 agggcgcgcg ggaggtccag atggtacttg atctccaccg cgccgttggt ggcgacgtcg   19320
atggcttgca gggtcccgtg cccctggggt gtgaccaccg tccccgtttt cttcttgggc   19380
ggctggggcg acggggcgg tgcctcttcc atggttagaa gcgcggcga ggacgcgcgc    19440 cgggcggcag aggcggctcg gggcccggag gcaggggcgg caggggcacg tcggcgccgc   19500
gcgcgggtag gttctggtac tgcgcccgga gaagactggc gtgagcgacg acgcgacggt   19560
tgacgtcctg gatctgacgc ctctgggtga aggccacggg acccgtgagt ttgaacctga   19620
aagagagttc gacagaatca atctcggtat cgttgacggc ggcctgccgc aggatctctt   19680
gcacgtcgcc cgagttgtcc tggtaggcga tctcggtcat gaactgctcg atctcctcct   19740
cctgaaggtc tccgcgaccg gcgcgctcca cggtggccgc gaggtcgttg gagatgcggc   19800
ccatgagctg cgagaaggcg ttcatgcccg cctcgttcca gacgcggctg tagaccacga   19860
cgccctcggg atcgcgggcg cgcatgacca cctgggcgag gttgagctcc acgtggcgcg   19920
tgaagaccgc gtagttgcag aggcgctggt agaggtagtt gagcgtggtg gcgatgtgct   19980
cggtgacgaa gaaatacatg atccagcggc ggagcggcat ctcgctgacg tcgcccagcg   20040
cctccaagcg ttccatggcc tcgtaaaagt ccacggcgaa gttgaaaaac tgggagttgc   20100
gcgccgagac ggtcaactcc tcctccagaa gacggatgag ctcggcgatg gtggcgcgca   20160
cctcgcgctc gaaggccccc gggagttcct ccacttcctc ctcttcttcc tcctccacta   20220
acatctcttc tacttcctcc tcaggcggtg gtggtggcgg gggagggggc ctgcgtcgcc   20280
ggcggcgcac gggcagacgg tcgatgaagc gctcgatggt ctcgccgcgc cggcgtcgca   20340
tggtctcggt gacggcgcgc ccgtcctcgc ggggccgcag cgtgaagacg ccgccgcgca   20400
tctccaggtg gccgggggg tccccgttgg gcagggagag ggcgctgacg atgcatctta   20460
tcaattgccc cgtagggact ccgcgcaagg acctgagcgt ctcgagatcc acgggatctg   20520
aaaaccgttg aacgaaggct tcgagccagt cgcagtcgca aggtaggctg agcacggttt   20580
cttctgccgg gtcatgttgg ggagcggggc gggcgatgct gctggtgatg aagttgaaat   20640
aggcggttct gagacggcgg atggtggcga ggagcaccag gtcttttggc ccggcttgct   20700
ggatgcgcag acggtcggcc atgcccagg cgtggtcctg acacctggcc aggtccttgt    20760
agtagtcctg catgagccgc tccacgggca cctcctcctc gcccgcgcgg ccgtgcatgc   20820
gcgtgagccc gaagccgcgc tggggctgga cgagcgccag gtcggcgacg acgcgctcgg   20880
cgaggatggc ctgctggatc tgggtgaggg tggtctggaa gtcgtcaaag tcgacgaagc   20940
ggtggtaggc tccggtgttg atggtgtagg agcagttggc catgacggac cagttgacgg   21000
tctggtggcc cggacgcacg agctcgtggt acttgaggcg cgagtaggcg cgcgtgtcga   21060
agatgtagtc gttgcaggtg cgcaccaggt actggtagcc gatgaggaag tgcggcggcg   21120
gctggcggta gagcggccat cgctcggtgg cgggggcgcc gggcgcgagg tcctcgagca   21180
tggtgcggtg gtagccgtag atgtacctgg acatccaggt gatgccggcg gcggtggtgg   21240
aggcgcgcgg gaactcgcgg acgcggttcc agatgttgcg cagcggcagg aagtagttca   21300
tggtgggcac ggtctggccc gtgaggcgcg cgcagtcgtg gatgctctat acgggcaaaa   21360
acgaaagcgg tcagcggctc gactccgtgg cctggaggct aagcgaacgg gttgggctgc   21420
```

```
gcgtgtaccc cggttcgaat ctcgaatcag gctggagccg cagctaacgt ggtactggca    21480
ctcccgtctc gacccaagcc tgcaccaacc ctccaggata cggaggcggg tcgttttgca    21540 acttttttg  gaggccggaa atgaaactag taagcgcgga aagcggccga ccgcgatggc    21600
tcgctgccgt agtctggaga agaatcgcca gggttgcgtt gcggtgtgcc ccggttcgag    21660
gccggccgga ttccgcggct aacgagggcg tggctgcccc gtcgtttcca agaccccata    21720
gccagccgac ttctccagtt acggagcgag cccctctttt gttttgtttg ttttgccag     21780 atgcatcccg tactgcggca gatgcgcccc caccaccctc caccgcaaca acagccccct    21840
cctccacagc cggcgcttct gccccgcccc agcagcagc  agcaacttcc agccacgacc    21900
gccgcggccg ccgtgagcgg ggctggacag acttctcagt atgatcacct ggccttggaa    21960
gagggcgagg ggctggcgcg cctggggcg  tcgtcgccgg agcggcaccc gcgcgtgcag    22020
atgaaaaggg acgctcgcga ggcctacgtg cccaagcaga acctgttcag agacaggagc    22080
ggcgaggagc ccgaggagat gcgcgcggcc cggttccacg cggggcggga gctgcggcgc    22140
ggcctggacc gaaagagggt gctgagggac gaggatttcg aggcggacga gctgacgggg    22200
atcagccccg cgcgcgcgca cgtggccgcg gccaacctgg tcacggcgta cgagcagacc    22260
gtgaaggagg agagcaactt ccaaaaatcc ttcaacaacc acgtgcgcac cctgatcgcg    22320
cgcgaggagg tgaccctggg cctgatgcac ctgtgggacc tgctggaggc catcgtgcag    22380
aaccccacca gcaagccgct gacgcgcag  ctgttcctgg tggtgcagca tagtcggac    22440 aacgaggcgt tcagggaggc gctgctgaat atcaccgagc ccgagggccg ctggctcctg    22500
gacctggtga acattctgca gagcatcgtg gtgcaggagc gcgggctgcc gctgtccgag    22560
aagctggcgg ccatcaactt ctcggtgctg agtctgggca agtactacgc taggaagatc    22620
tacaagaccc cgtacgtgcc catagacaag gaggtgaaga tcgacgggtt ttacatgcgc    22680
atgaccctga aagtgctgac cctgagcgac gatctggggg tgtaccgcaa cgacaggatg    22740
caccgcgcgc tgagcgccag caggcggcgc gagctgagcg accaggagct gatgcacagc    22800
ctgcagcggg ccctgaccgg ggccgggacc gaggggggaga gctactttga catgggcgcg    22860
gacctgcact ggcagcccag ccgccggccc ttggaggcgg caggcggtcc cccctacata    22920
gaagaggtgg acgatgaggt ggacgaggag ggcgagtacc tggaagactg atggcgcgac    22980 cgtattttg  ctagatgcaa caacagccac ctcctgatcc cgcgatgcgg gcggcgctgc    23040
agagccagcc gtccggcatt aactcctcgg acgattggac ccaggccatg caacgcatca    23100
tggcgctgac gacccgcaac cccgaagcct ttagacagca gccccaggcc aaccggctct    23160
cggccatcct ggaggccgtg gtgccctcgc gctccaaccc cacgcacgag aaggtcctgg    23220
ccatcgtgaa cgcgctggtg gagaacaagg ccatccgcgg cgacgaggcc ggcctggtgt    23280
acaacgcgct gctggagcgc gtggcccgct acaacagcac caacgtgcag accaacctgg    23340
accgcatggt gaccgacgtg cgcgaggccg tgcccagcg  cgagcggttc caccgcgagt    23400
ccaacctggg atccatggtg gcgctgaacg ccttcctcag cacccagccc gccaacgtgc    23460
cccggggcca ggaggactac accaacttca tcagcgccct gcgcctgatg gtgaccgagg    23520
tgccccagag cgaggtgtac cagtccggcc cggactactt cttccagacc agtcgccagg    23580
gcttgcagac cgtgaacctg agccaggcgt tcaagaactt gcagggcctg tggggcgtgc    23640 aggcccggt  cggggaccgc gcgacggtgt cgagcctgct gacgccgaac tcgcgcctgc    23700
tgctgctgct ggtggccccc ttcacggaca gcggcagcat caaccgcaac tcgtacctgg    23760
gctacctgat taacctgtac cgcgaggcca tcggccaggc gcacgtggac gagcagacct    23820
```

```
accaggagat cacccacgtg agccgcgccc tgggccagga cgacccgggc aatctggaag   23880
ccaccctgaa cttttttgctg accaaccggt cgcagaagat cccgccccag tacacgctca   23940
gcgccgagga ggagcgcatc ctgcgatacg tgcagcagag cgtgggcctg ttcctgatgc   24000
aggagggggc caccccagc gccgcgctcg acatgaccgc gcgcaacatg gagcccagca   24060
tgtacgccag caaccgcccg ttcatcaata aactgatgga ctacttgcat cgggcggccg   24120
ccatgaactc tgactatttc accaacgcca tcctgaatcc ccactggctc ccgccgccgg   24180
ggttctacac gggcgagtac gacatgcccg accccaatga cgggttcctg tgggacgatg   24240
tggacagcag cgtgttctcc ccccgaccgg gtgctaacga gcgcccttg tggaagaagg   24300
aaggcagcga ccgacgcccg tcctcggcgc tgtccggccg cgagggtgct gccgcggcgg   24360
tgcccgagcc cgccagtcct ttcccgagct tgcccttctc gctgaacagt attcgcagca   24420
gcgagctggg caggatcacg cgcccgcgct tgctgggcga ggaggagtac ttgaatgact   24480
cgctgttgag acccgagcgg gagaagaact cccccaataa cgggatagag agcctggtgg   24540
acaagatgag ccgctggaag acgtatgcgc aggagcacag ggacgatccg tcgcagggg   24600
ccacgagccg gggcagcgcc gcccgtaaac gccggtggca cgacaggcag cggggactga   24660
tgtgggacga tgaggattcc gccgacgaca gcagcgtgtt ggacttgggt gggagtggta   24720
accccgttcgc tcacctgcgc ccccgcatcg ggcgcatgat gtaagagaaa ccgaaaataa   24780
atgatactca ccaaggccat ggcgaccagc gtgcgttcgt ttcttctctg ttgttgtatc   24840
tagtatgatg aggcgtgcgt acccggaggg tcctcctccc tcgtacgaga gcgtgatgca   24900
gcaggcgatg gcggcggcgg cggcgatgca gcccccgctg gaggctcctt acgtgccccc   24960
gcggtacctg gcgcctacgg aggggcggaa cagcattcgt tactcggagc tggcaccctt   25020
gtacgatacc acccggttgt acctggtgga caacaagtcg gcggacatcg cctcgctgaa   25080
ctaccagaac gaccacagca acttcctgac caccgtggtg cagaacaatg acttcaccc   25140
cacggaggcc agcacccaga ccatcaactt tgacgagcgc tcgcggtggg gcggtcagct   25200
gaaaaccatc atgcacacca acatgcccaa cgtgaacgag ttcatgtaca gcaacaagtt   25260
caaggcgcgg gtgatggtct cccgcaagac ccccaacggg gtgacagtga cagatggtag   25320
tcaggatatc ttggagtatg aatgggtgga gtttgagctg cccgaaggca acttctcggt   25380
gaccatgacc atcgacctga tgaacaacgc catcatcgac aattacttgg cggtggggcg   25440
gcagaacggg gtcctggaga gcgatatcgg cgtgaagttc gacactagga acttcaggct   25500
gggctgggac cccgtgaccg agctggtcat gcccgggggtg tacaccaacg aggccttcca   25560
ccccgatatt gtcttgctgc ccggctgcgg ggtggacttc accgagagcc gcctcagcaa   25620
cctgctgggc attcgcaaga ggcagccctt ccaggagggc ttccagatca tgtacgagga   25680
tctggagggg gcaacatcc ccgcgctcct ggatgtcgac gcctatgaga aaagcaagga   25740
ggagagcgcc gccgcggcga ctgcagctgt agccaccgcc tctaccgagg tcaggggcga   25800
taattttgcc agccctgcag cagtggcagc ggccgaggcg gctgaaaccg aaagtaagat   25860
agtcattcag ccggtggaga aggatagcaa ggacaggagc tacaacgtgc tgccggacaa   25920
gataaacacc gcctaccgca gctggtacct ggcctacaac tatggcgacc ccgagaaggg   25980
cgtgcgctcc tggacgctgc tcaccacctc ggacgtcacc tgcggcgtgg agcaagtcta   26040
ctggtcgctg cccgacatga tgcaagaccc ggtcaccttc cgctccacgc gtcaagttag   26100
caactacccg gtggtgggcg ccgagctcct gcccgtctac tccaagagct tcttcaacga   26160
```

```
gcaggccgtc tactcgcagc agctgcgcgc cttcacctcg ctcacgcacg tcttcaaccg    26220
cttccccgag aaccagatcc tcgtccgccc gcccgcgccc accattacca ccgtcagtga    26280
aaacgttcct gctctcacag atcacgggac cctgccgctg cgcagcagta tccggggagt    26340
ccagcgcgtg accgttactg acgccagacg ccgcacctgc ccctacgtct acaaggccct    26400
gggcatagtc gcgccgcgcg tcctctcgag ccgcaccttc taaaaaatgt ccattctcat    26460
ctcgcccagt aataacaccg gttggggcct gcgcgcgccc agcaagatgt acggaggcgc    26520
tcgccaacgc tccacgcaac accccgtgcg cgtgcgcggg cacttccgcg ctccctgggg    26580
cgccctcaag ggccgcgtgc ggtcgcgcac caccgtcgac gacgtgatcg accaggtggt    26640
ggccgacgcg cgcaactaca cccccgccgc cgcgcccgtc tccaccgtgg acgccgtcat    26700
cgacagcgtg gtggccgacg cgcgccggta cgcccgcgcc aagagccggc ggcggcgcat    26760
cgcccggcgg caccggagca cccccgccat gcgcgcggcg cgagccttgc tgcgcagggc    26820
caggcgcacg ggacgcaggg ccatgctcag ggcggccaga cgcgcggctt caggcgccag    26880
cgccggcagg acccggagac gcgcggccac ggcggcggca gcgccatcg ccagcatgtc    26940 ccgcccgcgg cgagggaacg tgtactgggt gcgcgacgcc gccaccggtg tgcgcgtgcc    27000
cgtgcgcacc cgcccccctc gcacttgaag atgttcactt cgcgatgttg atgtgtccca    27060
gcggcgagga ggatgtccaa gcgcaaattc aaggaagaga tgctccaggt catcgcgcct    27120
gagatctacg gccccgcggt ggtgaaggag gaaagaaagc cccgcaaaat caagcgggtc    27180
aaaaaggaca aaaaggaaga agatgacgat ctggtggagt tgtgcgcga gttcgccccc    27240 cggcggcgcg tgcagtggcg cgggcggaaa gtgcacccgg tgctgagacc cggcaccacc    27300
gtggtcttca cgcccggcga gcgctccggc agcgcttcca agcgctccta cgacgaggtg    27360
tacggggacg aggacatcct cgagcaggcg gccgagcgcc tgggcgagtt tgcttacggc    27420
aagcgcagcc gccccgccct gaaggaagag gcggtgtcca tcccgctgga ccacggcaac    27480
cccacgccga gcctcaagcc cgtgaccctg cagcaggtgc tgccgagcgc agcgccgcgc    27540 cggggggttca agcgcgaggg cgaggatctg taccccacca tgcagctgat ggtgcccaag    27600
cgccagaagc tggaagacgt gctggagacc atgaaggtgg acccgacgt gcagcccgag    27660 gtcaaggtgc ggcccatcaa gcaggtggcc ccgggcctgg gcgtgcagac cgtggacatc    27720
aagatcccca cggagcccat ggaaacgcag accgagccca tgatcaagcc cagcaccagc    27780
accatggagg tgcagacgga tccctggatg ccatcggctc ctagccgaag accccggcgc    27840
aagtacggcg cggccagcct gctgatgccc aactacgcgc tgcatccttc catcatcccc    27900
acgccgggct accgcggcac gcgcttctac cgcggtcata caaccagccg ccgccgcaag    27960
accaccaccc gccgccgccg tcgccgcaca gccgctgcat ctacccctgc cgccctggtg    28020
cggagagtgt accgccgcgg ccgcgcgcct ctgacctac cgcgcgcgcg ctaccacccg    28080
agcatcgcca tttaaacttt cgcctgcttt gcagatggcc ctcacatgcc gcctccgcgt    28140
tcccattacg ggctaccgag gaagaaaacc gcgccgtaga aggctggcgg ggaacgggat    28200
gcgtcgccac caccatcggc ggcggcgcgc catcagcaag cggttggggg gaggcttcct    28260
gcccgcgctg atccccatca tcgcgcggcg gatcggggcg atcccggca ttgcttccgt    28320 ggcggtgcag gcctctcagc gccactgaga cacttggaaa acatcttgta ataaaccaat    28380
ggactctgac gctcctggtc ctgtgatgtg ttttcgtaga cagatggaag acatcaattt    28440
ttcgtccctg gctccgcgac acggcacgcg gccgttcatg ggcacctgga gcgacatcgg    28500
caccagccaa ctgaacgggg gcgccttcaa ttggagcagt ctctggagcg ggcttaagaa    28560
```

```
tttcgggtcc acgcttaaaa cctatggcag caaggcgtgg aacagcacca cagggcaggc  28620
gctgagggat aagctgaaag agcagaactt ccagcagaag gtggtcgatg ggctcgcctc  28680
gggcatcaac ggggtggtgg acctggccaa ccaggccgtg cagcggcaga tcaacagccg  28740
cctggacccg gtgccgcccg ccggctccgt ggagatgccg caggtggagg aggagctgcc  28800
tcccctggac aagcggggcg agaagcgacc ccgccccgac gcggaggaga cgctgctgac  28860
gcacacggac gagccgcccc cgtacgagga ggcggtgaaa ctgggtctgc ccaccacgcg  28920
gcccatcgcg cccctggcca ccggggtgct gaaacccgaa agtaataagc ccgcgaccct  28980
ggacttgcct cctcccgctt cccgcccctc tacagtggct aagcccctgc cgccggtggc  29040
cgtggcccgc gcgcgacccg ggggctccgc ccgccctcat gcgaactggc agagcactct  29100
gaacagcatc gtgggtctgg gagtgcagag tgtgaagcgc cgccgctgct attaaaccta  29160
ccgtagcgct taacttgctt gtctgtgtgt gtatgtatta tgtcgccgct gtccgccaga  29220
aggaggagtg aagaggcgcg tcgccgagtt gcaagatggc cacccccatcg atgctgcccc  29280 agtgggcgta catgcacatc gccggacagg acgcttcgga gtacctgagt ccgggtctgg  29340
tgcagttcgc ccgcgccaca gacacctact tcagtctggg gaacaagttt aggaaccccca  29400 cggtggcgcc cacgcacgat gtgaccaccg accgcagcca gcggctgacg ctgcgcttcg  29460
tgcccgtgga ccgcgaggac aacacctact cgtacaaagt gcgctacacg ctggccgtgg  29520
gcgacaaccg cgtgctggac atggccagca cctactttga catccgcggc gtgctggatc  29580
ggggccctag cttcaaaccc tactccggca ccgcctacaa cagcctggct cccaagggag  29640
cgcccaattc cagccagtgg gagcaaaaaa aggcaggcaa tggtgacact atggaaacac  29700
acacatttgg tgtggcccca atgggcggtg agaatattac aatcgacgga ttacaaattg  29760
gaactgacgc tacagctgat caggataaac caatttatgc tgacaaaaca ttccagcctg  29820
aacctcaagt aggagaagaa aattggcaag aaactgaaag cttttatggc ggtagggctc  29880
ttaaaaaaga cacaagcatg aaaccttgct atggctccta tgctagaccc accaatgtaa  29940
agggaggtca agctaaactt aaagttggag ctgatggagt tcctaccaaa gaatttgaca  30000
tagacctggc tttctttgat actcccggtg gcacagtgaa tggacaagat gagtataaag  30060
cagacattgt catgtatacc gaaaacacgt atctggaaac tccagacacg catgtggtat  30120
acaaaccagg caaggatgat gcaagttctg aaattaacct ggttcagcag tccatgccca  30180
atagacccaa ctatattggg ttcagagaca ctttattgg gctcatgtat tacaacagta  30240
ctggcaatat gggggtgctg gctggtcagg cctcacagct gaatgctgtg gtcgacttgc  30300
aagacagaaa caccgagctg tcataccagc tcttgcttga ctctttgggt gacagaaccc  30360
ggtatttcag tatgtggaat caggcggtgg acagttatga tcctgatgtg cgcattattg  30420
aaaaccatgg tgtggaagac gaacttccca actattgctt cccctggat gggtctggca  30480 ctaatgccgc ttaccaaggt gtgaaagtaa aaaatggtaa cgatggtgat gttgagagcc  30540
aatgggaaaa tgatgatact gtcgcagctc gaaatcaatt atgcaagggc aacatttttg  30600
ccatggaaat taacctccaa gccaacctgt ggagaagttt cctctactcg aacgtggccc  30660
tgtacctgcc cgactcttac aagtacacgc cagccaacat cacccctgcc accaacacca  30720
acacttatga ttcatgaac gggagagtgg tgcctccctc gctggtggac gcctacatca  30780
acatcggggc gcgctggtcg ctggacccca tggacaacgt caatccctc aaccaccacc  30840 gcaacgcggg cctgcgctac cgctccatgc tcctgggcaa cgggcgctac gtgcccttcc  30900
```

```
acatccaggt gccccagaaa tttttcgcca tcaagagcct cctgctcctg cccgggtcct   30960
acacctacga gtggaacttc cgcaaggacg tcaacatgat cctgcagagc tccctcggca   31020
acgacctgcg cacggacggg gcctccatct ccttcaccag catcaacctc tacgccacct   31080
tcttccccat ggcgcacaac acggcctcca cgctcgaggc catgctgcgc aacgacacca   31140
acgaccagtc cttcaacgac tacctctcgg cggccaacat gctctacccc atcccggcca   31200
acgccaccaa cgtgcccatc tccatcccct cgcgcaactg gccgccttc cgcggctggt    31260
ccttcacgcg cctcaagacc aaggagacgc cctcgctggg ctccgggttc gaccccact    31320
tcgtctactc gggctccatc ccctacctcg acggcacctt ctacctcaac cacaccttca   31380
agaaggtctc catcacccttc gactcctccg tcagctggcc cggcaacgac cggctcctga   31440
cgcccaacga gttcgaaatc aagcgcaccg tcgacggcga gggatacaac gtggcccagt   31500
gcaacatgac caaggactgg ttcctggtcc agatgctggc ccactacaac atcggctacc   31560
agggcttcta cgtgcccgag ggctacaagg accgcatgta ctccttcttc cgcaacttcc   31620
agcccatgag ccgccaggtg gtggacgagg tcaactacaa ggactaccag gccgtcaccc   31680
tggcctacca gcacaacaac tcgggcttcg tcggctacct cgcgcccacc atgcgccagg   31740
gccagcccta ccccgccaac tacccgtacc cgctcatcgg caagagcgcc gtcaccagcg   31800
tcacccagaa aaagttcctc tgcgacaggg tcatgtggcg catccccttc tccagcaact   31860
tcatgtccat gggcgcgctc accgacctcg gccagaacat gctctatgcc aactccgccc   31920
acgcgctaga catgaatttc gaagtcgacc ccatggatga gtccacccctt ctctatgttg   31980
tcttcgaagt cttcgacgtc gtccgagtgc accagcccca ccgcggcgtc atcgaggccg   32040
tctacctgcg cacccccttc tcggccggta acgccaccac ctaaattgct acttgcatga   32100
tggctgagcc cacaggctcc ggcgagcagg agctcagggc catcatccgc gacctgggct   32160
gcgggcccta cttcctgggc accttcgata agcgcttccc gggattcatg gccccgcaca   32220
agctggcctg cgccatcgtc aacacggccg gccgcgagac cggggggcgag cactggctgg   32280
ccttcgcctg gaacccgcgc tcgaacacct gctacctctt cgaccccttc gggttctcgg   32340
acgagcgcct caagcagatc taccagttcg agtacgaggg cctgctgcgc cgtagcgccc   32400
tggccaccga ggaccgctgc gtcaccctgg aaaagtccac ccagaccgtg cagggtccgc   32460
gctcggccgc ctgcgggctc ttctgctgca tgttcctgca cgccttcgtg cactggcccg   32520
accgcccat ggacaagaac cccaccatga acttgctgac ggggtgccc aacggcatgc     32580
tccagtcgcc ccaggtggaa cccacccctgc gccgcaacca ggaggcgctc taccgcttcc   32640
tcaactccca ctccgcctac tttcgctccc accgcgcgcg catcgagaag gccaccgcct   32700
tcgaccgcat gaacaatcaa gacatgtaaa ccgtgtgtgt atgtttaaaa tatcttttaa   32760
taaacagcac tttaatgtta cacatgcatc tgagatgatt ttatttttaga aatcgaaagg   32820
gttctgccgg gtctcggcat ggcccgcggg cagggacacg ttgcggaact ggtacttggc   32880
cagccacttg aactcgggga tcagcagttt gggcagcggg gtgtcgggga aggagtcggt   32940
ccacagcttc cgcgtcagct gcagggcgcc cagcaggtcg ggcgcggaga tcttgaaatc   33000
gcagttggga cccgcgttct gcgcgcgaga gttgcggtac acggggttgc agcactggaa   33060
caccatcagg gccgggtgct tcacgctcgc cagcaccgcc gcgtcggtga tgctctccac   33120
gtcgaggtcc tcggcgttgg ccatcccgaa gggggtcatc ttgcaggtct gccttcccat   33180
ggtgggcacg cacccgggct tgtggttgca atcgcagtgc aggggggatca gcatcatctg   33240
ggcctggtcg gcgttcatcc ccgggtacat ggccttcatg aaagcctcca attgcctgaa   33300
```

```
cgcctgctgg gccttggctc cctcggtgaa gaagaccccg caggacttgc tagagaactg   33360
gttggtggca cagccggcat cgtgcacgca gcagcgcgcg tcgttgttgg ccagctgcac   33420
cacgctgcgc ccccagcggt tctgggtgat cttggcccgg tcggggttct ccttcagcgc   33480
gcgctgcccg ttctcgctcg ccacatccat ctcgatcatg tgctccttct ggatcatggt   33540
ggtcccgtgc aggcaccgca gtttgccctc ggcctcggtg cacccgtgca gccacagcgc   33600
gcacccggtg cactcccagt tcttgtgggc gatctgggaa tgcgcgtgca cgaacccttg   33660
caggaagcgg cccatcatgg tcgtcagggt cttgttgcta gtgaaggtca acgggatgcc   33720
gcggtgctcc tcgttgatgt acaggtggca gatgcgcgcg tacacctcgc cctgctcggg   33780
catcagttgg aagttggctt tcaggtcggt ctccacgcgg tagcggtcca tcagcatagt   33840
catgatttcc atgcccttct cccaggccga gacgatgggc aggctcatag ggttcttcac   33900
catcatctta gcactagcag ccgcggccag ggggtcgctc tcatccaggg tctcaaagct   33960
ccgcttgccg tccttctcgg tgatccgcac cgggggtag ctgaagccca cggccgccag   34020
ctcctcctcg gcctgtcttt cgtcctcgct gtcctggctg acgtcctgca tgaccacatg   34080
cttggtcttg cggggtttct tcttgggcgg cagtggcggc ggagatgctt gtggcgaggg   34140
ggagcgcgag ttctcgctca ccactactat ctcttcctct tcttggtccg aggccacgcg   34200
gcggtaggta tgtctcttcg ggggcagagg cggaggcgac gggctctcgc cgccgcgact   34260
tggcggatgg ctggcagagc cccttccgcg ttcgggggtg cgctcccggc ggcgctctga   34320
ctgacttcct ccgcggccgg ccattgtgtt ctcctaggga ggaacaacaa gcatggagac   34380
tcagccatcg ccaacctcgc catctgcccc caccgccggc gacgagaagc agcagcagca   34440
gaatgaaagc ttaaccgccc cgccgccag cccgcctcc gacgcagccg cggtcccaga   34500
catgcaagag atggaggaat ccatcgagat tgacctgggc tatgtgacgc ccgcggagca   34560
tgaggaggag ctggcagtgc gctttcaatc gtcaagccag gaagataaag aacagccaga   34620
gcaggaagca gagaacgagc agagtcaggc tgggctcgag catggcgact acctccacct   34680
gagcggggag gaggacgcgc tcatcaagca tctggcccgg caggccacca tcgtcaagga   34740 ccgcgctgctc gaccgcaccg aggtgcccct cagcgtggag gagctcagcc gcgcctacga   34800
gctcaacctc ttctcgccgc gcgtgccccc caagcgccag cccaacggca cctgcgagcc   34860 caaccccgc ctcaacttct acccggtctt cgcggtgccc gaggccctgg ccacctacca   34920 catcttttc aagaaccaaa agatccccgt ctcctgccgc gccaaccgca cccgcgccga   34980
cgccctcttc aacctgggtc ccggcgcccg cctacctgat atcgcctcct tggaagaggt   35040
tcccaagatc ttcgagggtc tgggcagcga cgagactcgg gccgcgaacg ctctgcaagg   35100
agaaggagga ggagagcatg agcaccacag cgccctggtc gagttggaag gcgacaacgc   35160
gcggctggcg gtgctcaaac gcacggtcga gctgacccat ttcgcctacc cggctctgaa   35220 cctgccccg aaagtcatga gcgcggtcat ggaccaggtg ctcatcaagc gcgcgtcgcc   35280
catctccgag gacgagggca tgcaagactc cgaggagggc aagcccgtgg tcagcgacga   35340
gcagctggcc cggtggctgg gtcctaatgc taccccctcaa agtttggaag agcggcgcaa   35400
gctcatgatg gccgtggtcc tggtgaccgt ggagctggag tgcctgcgcc gcttcttcgc   35460
cgacgcggag accctgcgca aggtcgagga gaacctgcac tacctcttca ggcacgggtt   35520
cgtgcgccag gcctgcaaga tctccaacgt ggagctgacc aacctggtct cctacatggg   35580
catcttgcac gagaaccgcc tggggcagaa cgtgctgcac accaccctgc gcggggaggc   35640
```

```
ccgccgcgac tacatccgcg actgcgtcta cctctacctc tgccacacct ggcagacggg   35700
catgggcgtg tggcagcagt gtctggagga gcagaacctg aaagagctct gcaagctcct   35760
gcaaaagaac ctcaagggtc tgtggaccgg gttcgacgag cggaccaccg cctcggacct   35820
ggccgacctc atcttccccg agcgcctcag gctgacgctg cgcaacggcc tgcccgactt   35880
tatgagccaa agcatgttgc aaaactttcg ctctttcatc ctcgaacgct ccggaatcct   35940
gcccgccacc tgctccgcgc tgccctcgga cttcgtgccg ctgaccttcc gcagtgccc    36000
ccgccgctg tggagccact gctacctgct gcgcctggcc aactacctgg cctaccactc    36060
ggacgtgatc gaggacgtca gcggcgaggg cctgctcgag tgccactgcc gctgcaacct   36120
ctgcacgccg caccgctccc tggcctgcaa ccccagctg ctgagcgaga cccagatcat    36180
cggcaccttc gagttgcaag ggccagcga gggcgaggga gccaaggggg gtctgaaact    36240
caccccgggg ctgtggacct cggcctactt gcgcaagttc gtgcccgagg attaccatcc   36300
cttcgagatc aggttctacg aggaccaatc ccagccgccc aaggccgagc tgtcggcctg   36360
cgtcatcacc cagggggcga tcctggccca attgcaagcc atccagaaat cccgccaaga   36420
attcttgctg aaaaagggcc gcggggtcta cctcgacccc cagaccggtg aggagctcaa   36480
ccccggcttc ccccaggatg ccccgaggaa acaagaagct gaaagtggag ctgccgcccg   36540
tggaggattt ggaggaagac tgggagaaca gcagtcaggc agaggagatg gaggaagact   36600
gggacagcac tcaggcagag gaggacagcc tgcaagacag tctggaggaa gacgaggagg   36660
aggcagagga ggaggtggaa gaagcagccg ccgccagacc gtcgtcctcg gcgggggaga   36720
aagcaagcag cacggatacc atctccgctc cgggtcgggg tcccgctcgg ccccacagta   36780
gatgggacga gaccgggcga ttcccgaacc ccaccaccca gaccggtaag aaggagcggc   36840
agggatacaa gtcctggcgg gggcacaaaa acgccatcgt ctcctgcttg caggcctgcg   36900
ggggcaacat ctccttcacc cggcgctacc tgctcttcca ccgcggggtg aacttccccc   36960
gcaacatctt gcattactac cgtcacctcc acagcccta ctacttccaa gaagaggcag    37020
cagcagcaga aaagaccag aaaccagct agaaaatcca cagcggcggc agcggcaggt     37080
ggactgagga tcgcggcgaa cgagccggcg cagacccggg agctgaggaa ccggatcttt   37140
cccacccctct atgccatctt ccagcagagt cgggggcagg agcaggaact gaaagtcaag   37200
aaccgttctc tgcgctcgct caccgcagt tgtctgtatc acaagagcga agaccaactt     37260
cagcgcactc tcgaggacgc cgaggctctc ttcaacaagt actgcgcgct cactcttaaa   37320
gagtagcccg cgcccgccca gtcgcagaaa aaggcgggaa ttacgtcacc tgtgcccttc   37380
gccctagccg cctccaccca gcaccgccat gagcaaagag attcccacgc cttacatgtg   37440
gagctaccag ccccagatgg gcctggccgc cggcgccgcc caggactact ccacccgcat   37500
gaattggctc agcgccgggc ccgcgatgat ctcacgggtg aatgacatcc gcgcccaccg   37560
aaaccagata ctcctagaac agtcagcgct caccgccacg ccccgcaatc acctcaatcc   37620
gcgtaattgg ccgccgccc tggtgtacca ggaaattccc cagcccacga ccgtactact   37680
tccgcgagac gcccaggccg aagtccagct gactaactca ggtgtccagc tggcgggcgg   37740
cgccaccctg tgtcgtcacc gccccgctca gggtataaag cggctggtga tccggggcag   37800
aggcacacag ctcaacgacg aggtggtgag ctcttcgctg gtctgcgac ctgacggagt     37860
cttccaactc gccggatcgg ggagatcttc cttcacgcct cgtcaggcgg tcctgacttt   37920
ggagagttcg tcctcgcagc cccgctcggg cggcatcggg actctccagt tcgtggagga   37980
gttcactccc tcggtctact tcaaccccctt ctccggctcc cccggccact acccggacga   38040
```

```
gttcatcccg aactttgacg ccatcagcga gtcggtggac ggctacgatt gattaattaa  38100
tcaactaacc ccttacccct ttaccctcca gtaaaaataa agattaaaaa tgattgaatt  38160
gatcaataaa gaatcactta cttgaaatct gaaaccaggt ctctgtccat gttttctgtc  38220
agcagcactt cactcccctc ttcccaactc tggtactgca ggccccggcg ggctgcaaac  38280
ttcctccaca ctctgaaggg gatgtcaaat tcctcctgtc cctcaatctt cattttatc   38340
ttctatcaga tgtccaaaaa gcgcgcgcgg gtggatgatg gcttcgaccc cgtgtacccc  38400
tacgatgcag acaacgcacc gactgtgccc ttcatcaacc ctcccttcgt ctcttcagat  38460
ggattccaag aaaagcccct gggggtgttg tccctgcgac tggccgaccc cgtcaccacc  38520
aagaatgggg ctgtcaccct caagctgggg gaggggtgg acctcgacga ctcgggaaaa   38580
ctcatctcca aaaatgccac caaggccact gcccctctca gtatttccaa cggcaccatt  38640
tcccttaaca tggctgcccc ttttacaac aacaatggaa cgttaagtct caatgtttct   38700
acaccattag cagtatttcc cacttttaac actttaggta tcagtcttgg aaacggtctt  38760
caaacttcta ataagttgct gactgtacag ttaactcatc ctcttacatt cagctcaaat  38820
agcatcacag taaaaacaga caaaggactc tatattaatt ctagtggaaa cagagggctt  38880
gaggctaaca taagcctaaa aagaggactg attttttgatg gtaatgctat tgcaacatac  38940
cttggaagtg gtttagacta tggatcctat gatagcgatg ggaaaacaag acccatcatc  39000
accaaaattg gagcaggttt gaattttgat gctaataatg ccatggctgt gaagctaggc  39060
acaggtttaa gttttgactc tgccggtgcc ttaacagctg gaaacaaaga ggatgacaag  39120
ctaacacttt ggactacacc tgacccaagc cctaattgtc aattactttc agacagagat  39180
gccaaattta ccctatgtct tacaaaatgc ggtagtcaaa tactaggcac tgttgcagta  39240
gctgctgtta ctgtaggttc agcactaaat ccaattaatg acacagtaaa aagcgccata  39300
gtattcctta gatttgactc tgacggtgtg ctcatgtcaa actcatcaat ggtaggtgat  39360
tactggaact ttagggaagg acagaccacc caaagtgtgg cctatacaaa tgctgtggga  39420
ttcatgccca atctaggtgc atatcctaaa acccaaagca aaacaccaaa aaatagtata  39480
gtaagtcagg tatatttaaa tggagaaact actatgccaa tgacactgac aataactttc  39540
aatggcactg atgaaaaaga cacaacacct gtgagcactt actccatgac ttttacatgg  39600
cagtggactg gagactataa ggacaagaat attacctttg ctaccaactc ctttactttc  39660
tcctacatgg cccaagaata aaccctgcat gccaaccca ttgttccac cactatggaa   39720
aactctgaag cagaaaaaaa taagttcaa gtgttttatt gattcaacag ttttctcaca   39780
gaaccctagt attcaacctg ccacctccct cccaacacac agagtacaca gtcctttctc  39840
cccggctggc cttaaaaagc atcatatcat gggtaacaga catattctta ggtgttatat  39900
tccacacggt ttcctgtcga gccaaacgct catcagtgat attaataaac tccccgggca  39960
gctcacttaa gttcatgtcg ctgtccagct gctgagccac aggctgctgt ccaacttgcg  40020
gttgcttaac gggcggcgaa ggagaagtcc acgcctacat gggggtagag tcataatcgt  40080
gcatcaggat agggcggtgg tgctgcagca gcgcgcgaat aaactgctgc cgccgccgct  40140
ccgtcctgca ggaatacaac atggcagtgg tctcctcagc gatgattcgc accgccgca   40200
gcataaggcg ccttgtcctc cgggcacagc agcgcaccct gatctcactt aaatcagcac  40260
agtaactgca gcacagcacc acaatattgt tcaaaatccc acagtgcaag gcgctgtatc  40320
caaagctcat ggcggggacc acagaaccca cgtggccatc ataccacaag cgcaggtaga  40380
```

```
ttaagtggcg accccctcata aacacgctgg acataaacat tacctctttt ggcatgttgt    40440
aattcaccac ctcccggtac catataaacc tctgattaaa catggcgcca tccaccacca    40500
tcctaaacca gctggccaaa acctgcccgc cggctataca ctgcagggaa ccgggactgg    40560
aacaatgaca gtggagagcc caggactcgt aaccatggat catcatgctc gtcatgatat    40620
caatgttggc acaacacagg cacacgtgca tacacttcct caggattaca agctcctccc    40680
gcgttagaac catatcccag ggaacaaccc attcctgaat cagcgtaaat cccacactgc    40740
agggaagacc tcgcacgtaa ctcacgttgt gcattgtcaa agtgttacat tcgggcagca    40800
gcggatgatc ctccagtatg gtagcgcggg tttctgtctc aaaaggaggt agacgatccc    40860
tactgtacgg agtgcgccga gacaaccgag atcgtgttgg tcgtagtgtc atgccaaatg    40920
gaacgccgga cgtagtcata tttcctgaag caaaaccagg tgcgggcgtg acaaacagat    40980
ctgcgtctcc ggtctcgccg cttagatcgc tctgtgtagt agttgtagta tatccactct    41040
ctcaaagcat ccaggcgccc cctggcttcg ggttctatgt aaactccttc atgcgccgct    41100
gccctgataa catccaccac cgcagaataa gccacaccca gccaacctac acattcgttc    41160
tgcgagtcac acacgggagg agcgggaaga gctggaagaa ccatgattaa ctttattcca    41220
aacggtctcg gagcacttca aaatgcaggt cccggaggtg gcacctctcg cccccactgt    41280
gttggtggaa aataacagcc aggtcaaagg tgacacggtt ctcgagatgt tccacggtgg    41340
cttccagcaa agcctccacg cgcacatcca gaaacaagag gacagcgaaa gcgggagcgt    41400
tttctaattc ctcaatcatc atattacact cctgcaccat ccccagataa ttttcatttt    41460
tccagccttg aatgattcgt attagttcct gaggtaaatc caagccagcc atgataaaaa    41520
gctcgcgcag agcgccctcc accggcattc ttaagcacac cctcataatt ccaagagatt    41580
ctgctcctgg ttcacctgca gcagattaac aatgggaata tcaaaatctc tgccgcgatc    41640
cctaagctcc tccctcaaca ataactgtat gtaatctttc atatcatctc cgaaattttt    41700
agccataggg ccgccaggaa taagagcagg gcaagccaca ttacagataa agcgaagtcc    41760
tccccagtgw gcattgccaa atgtaagatt gaaataagca tgctggctag accctgtgat    41820
atcttccaga taactggaca gaaaatcagg caagcaattt ttaagaaaat caacaaaaga    41880
aaagtcgtcc aggtgcaggt ttagagcctc aggaacaacg atggaataag tgcaaggagt    41940
gcgttccagc atggttagtg ttttttttggt gatctgtaga acaaaaaata aacatgcaat    42000
attaaaccat gctagcctgg cgaacaggtg ggtaaatcac tctttccagc accaggcagg    42060
ctacggggtc tccggcgcga ccctcgtaga agctgtcgcc atgattgaaa agcatcaccg    42120
agagaccttc ccggtggccg gcatggatga ttcgagaaga agcatacact ccgggaacat    42180
tggcatccgt gagtgaaaaa aagcgaccta taaagcctcg gggcactaca atgctcaatc    42240
tcaattccag caaagccacc ccatgcggat ggagcacaaa attggcaggt gcgtaaaaaa    42300
tgtaattact cccctcctgc acaggcagca agcccccgc tccctccaga aacacataca    42360
aagcctcagc gtccatagct taccgagcac ggcaggcgca agagtcagag aaaaggctga    42420
gctctaacct gactgcccgc tcctgtgctc aatatatagc cctaacctac actgacgtaa    42480
aggccaaagt ctaaaaatac ccgccaaaat gacacacacg cccagcacac gcccagaaac    42540
cggtgacaca ctcaaaaaaa tacgtgcgct tcctcaaacg cccaaaccgg cgtcatttcc    42600
gggttcccac gctacgtcac cgctcagcga ctttcaaatt ccgtcgaccg ttaaaaacgt    42660
cactcgcccc gcccctaacg gtcgcccttc tctcggccaa tcaccttcct cccttcccaa    42720
attcaaacgc ctcatttgca tattaacgcg cacaaaaagt ttgaggtata tatttgaatg    42780
```

```
atg                                                    42783

<210> SEQ ID NO 63
<211> LENGTH: 32
<212> TYPE: PRT
<213> ORGANISM: Artificial Sequence
<220> FEATURE:
<223> OTHER INFORMATION: peptide adjuvant

<400> SEQUENCE: 63

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

<210> SEQ ID NO 64
<211> LENGTH: 27
<212> TYPE: PRT
<213> ORGANISM: Artificial Sequence
<220> FEATURE:
<223> OTHER INFORMATION: peptide adjuvant

<400> SEQUENCE: 64

Ser Leu Leu Trp Gly Gly Val Thr Val Leu Ala Ala Met Leu Ile Ala
1               5                   10                  15

Gly Gln Val Ala Ser Ser Val Val Phe Leu Val
            20                  25

<210> SEQ ID NO 65
<211> LENGTH: 3849
<212> TYPE: DNA
<213> ORGANISM: Artificial Sequence
<220> FEATURE:
<223> OTHER INFORMATION: vaccine construct

<400> SEQUENCE: 65
gacgaggacg agacagccta cgacagcggc accgacctga tcgacttcat cgacgacagc      60
gacgagaatg agaacgactc cgacaccggc gaggacatgg tggatttcat cgacaacgac     120
gaaaccgacg aagagagcac cgagagcgac ctggacggct ttatcgacaa ctccgcccag     180
ctggctgaca gcgacagcaa tgcctgcgcc ttcctgaagg ctcagctggc agacgtgaac     240
agcaacgccg ctgcttttct gaagaactgc atcctgctgt acggcgctgc caacaccggc     300
aagagcctgt tcggcatgag cctgaactgc ctggtgctgt gcggcccagc caataccgga     360
aagtcctact tcggcatgtc cctgaattgt ctcgtgatct acggcccacc taacacaggc     420
aagtcctgct ttgccatgtc tctgtggccc tacctgcaca gcagactggt ggtgtttacc     480
ttccccaacc ccttctggcc ttacctggaa agccggatca ccgtgttcga gttccccaat     540
gcctttctga gatacctgca ctcccggatc cacgtgctgc agtttctgaa ccccttcaac     600
gtgtgccagg acaagatcct ggaacactac gagaacgaca gcaaggacat tctggaacat     660
tatgagaatg attccaagga cctgtgcgac cacatctgcg atcacatcga ctactggaag     720
cacatccggc tggaatgcgc catcatgtac aaggcccgga tcagactgga atgtgctatt     780
atgtataagg ctcgcgagat gggcttccac cagttcgacg cgacatctg caacaccatg     840 cactacacca actggatcta tatctgcgag gacgcccagt gcaccgtggt ggaaggccag     900
gtggacaaga atgggaggt gcacgctggc ggccaagtga tcctgtgtcc tgagagcggc     960
cagcggcgga tcaagaggcc cagaagcgag aactgccacc ccaacaagct gctgatcctg    1020
```

| | |
|---|---|
| aagtgcctgc ggtacagatt caagaagcac tgcaagctga gcagcacctg gcactggacc | 1080 |
| tgccacgacg gcaagcacaa gtggcattgg acatgtcacg atgggaaaca caagaacgcc | 1140 |
| attgtgaccc tgacctacta cgaggccgac aagaacgacc tgaacgccca gatcgagcac | 1200 |
| tggaaactga tccggatgga atgtgcaatc ttctataagg ccaaagagct gggcatcagc | 1260 |
| atctgccacc aggtggtgcc tccactggcc gcctctaaag ccaaagcctg ccaggccatc | 1320 |
| gaactgcagc tggccctgga agccctgaat gccagcccct acgatgagtg gaccctgcag | 1380 |
| cagaccagcc tggaaatgtg gctggccgag ccccagttta gaagcacgg catcaccatc | 1440 |
| accgtgcagt acgacaatga caaggccaat accatggatt acacaaattg gaaagaaatc | 1500 |
| tacgtgatcg tgtgccccgc cagcatcccc tccgatgaga tcagcaccga ggaagccgac | 1560 |
| cacattgatt attggaaagc catcaggcag gaaaacgcca tcttcttcgc cgccagacac | 1620 |
| caggtggtgc ccgccctgaa tatctgcaag gccaaggcct gtaaagccat cgagtggaac | 1680 |
| accgagccca gcactgctt caagaagggc ggccagcaca tcgaagtgtg gttcgactac | 1740 |
| gtggcctggg acagcgtgta ctactgcggc gacgatggc ggtgcaagac cgaggccgag | 1800 |
| aagtacggct gcaagggcac ctgggaagtg catttcggca acagcatcga ctgcaacgac | 1860 |
| tccatgtgca gcaccttcga cgacaacgtg tccgccaccg agctcgtgaa ggaccatatc | 1920 |
| gactattgga agctgattcg cctggaatgt gccatttttt acaaggccag acggcggctg | 1980 |
| tccagcgacc aggatcagtc tcagctcgtg accaagtacc cctgctgaa gctgctgtcc | 2040 |
| agacccccca catgggcgt gaaggcccac ggcaagtgca tctgggagaa caaggtgttc | 2100 |
| atcgtgccca ccctgtgccc cgtgcctctg gatccaacat atcctctgct gaaactgctg | 2160 |
| accacccaga ccaccacccc cgagaatacc tccctggtgg aactgagagt gaccaccccc | 2220 |
| aagagcacag tcgtgatcag gctgcacctg accaccagat acccactgct gtcactgctg | 2280 |
| aacagctaca gcacccccc tcaccggatc cctgctccat gtccttgggc tcctcagagg | 2340 |
| ccccccatcc ctaagccttc tccatggggc cctagaatcc ctgccccttg ccctggca | 2400 |
| cctcctagac ctccacactg tccatgggtg cccctccac ctcctccaag accttgggcc | 2460 |
| ccttgcttcc tgctgtgctt ttgtgtgctg ctgtgcgtgt gcctgctgat cagacccctg | 2520 |
| ctgctgagtg tgtccaccta cctgaggcct ctgctgctgt ctatcagcgt gtacgctcag | 2580 |
| gtgctggtgc tggtgctgct gctgtgggtg tccatcggaa gcctgctgcc cagcgtgtgc | 2640 |
| atgtgtgcct atgcctgggt gctggtgttc gtgtacatcg tcgtgattac cagccccgcc | 2700 |
| accgccatcg tgtaccggga tgcaatcct tacgccgtgt gcgacaagtg cctgaagttc | 2760 |
| tacagcaaga tcagcgagta ccggcactac tgctacagcc tgtacggcac caccctggaa | 2820 |
| cagcagtaca acaagcccct gtgcgatctg ctgattcggt gcatcaacgt ggtgtacaga | 2880 |
| gactccatcc cccacgccgc ctgccacaag tgtatcgact tctactccag aatcagagag | 2940 |
| ctgcggcact acagcgactc cgtgtacggc gatacccctgg aaaagctgac caacactggc | 3000 |
| ctgtacaacc tgctgattag atgcctgcgg gtgttctgca agaaggccct gacagccagc | 3060 |
| gaggtgtaca acttcgccta caccgatctg cgggtggtgt atcgggacag caaagtgcgg | 3120 |
| aagctgaggt actacaactg ctctgtgtat ggcgccagcc tggtgtattg caagggacag | 3180 |
| ctgaccgaga cagaggtgct ggatttcgcc ttcacagacc tgacaatcgt gtatcgcgac | 3240 |
| tccaaggtgt ccgagttccg gtggtacaga tattccgtgt atggcaccac actgtgcgtg | 3300 |
| gaatgcaaga aaccctgca gagatctgag gtgtacgact gccagcggcc actgtgtccg | 3360 |
| caggaaaaga aaagacacgt ggacctgaac aagcggttcc acaccctgca cgagtacatg | 3420 |

-continued

```
ctggatctgc agcccgagac aaccgacctg tactgctacg agcagcctga aaccactgat    3480
ctgcactgtt atgagcagct gggagacagc tccgatgaag aggacactgg cggcctggat    3540
ggggacgagg atgaggacga agtggaccat ctgcaggaac agccccagca ggctagacgg    3600
gacgaacagc accctttgcta tctgatcgag acacagtgct gcagatgcga atctctggtg    3660
gaagagaacg acgagatcga cggcgtgaac caccagcatc tgcccgctag aagggccgag    3720
cctcagagac acaccatgct gtgtatgtgc tgcaagtgcg aggccagaat cgccggctct    3780
ggacctggcg cctctggcaa gcctatcccc aatccactgc tgggcctgga ctccacccgg    3840
acctgataa                                                            3849
```

<210> SEQ ID NO 66
<211> LENGTH: 1281
<212> TYPE: PRT
<213> ORGANISM: Artificial Sequence
<220> FEATURE:
<223> OTHER INFORMATION: vaccine construct

<400> SEQUENCE: 66

```
Asp Glu Asp Glu Thr Ala Tyr Asp Ser Gly Thr Asp Leu Ile Asp Phe
1               5                   10                  15

Ile Asp Asp Ser Asp Glu Asn Glu Asn Asp Ser Asp Thr Gly Glu Asp
            20                  25                  30

Met Val Asp Phe Ile Asp Asn Asp Glu Thr Asp Glu Glu Ser Thr Glu
        35                  40                  45

Ser Asp Leu Asp Gly Phe Ile Asp Asn Ser Ala Gln Leu Ala Asp Ser
    50                  55                  60

Asp Ser Asn Ala Cys Ala Phe Leu Lys Ala Gln Leu Ala Asp Val Asn
65                  70                  75                  80

Ser Asn Ala Ala Ala Phe Leu Lys Asn Cys Ile Leu Leu Tyr Gly Ala
                85                  90                  95

Ala Asn Thr Gly Lys Ser Leu Phe Gly Met Ser Leu Asn Cys Leu Val
            100                 105                 110

Leu Cys Gly Pro Ala Asn Thr Gly Lys Ser Tyr Phe Gly Met Ser Leu
        115                 120                 125

Asn Cys Leu Val Ile Tyr Gly Pro Asn Thr Gly Lys Ser Cys Phe
    130                 135                 140

Ala Met Ser Leu Trp Pro Tyr Leu His Ser Arg Leu Val Val Phe Thr
145                 150                 155                 160

Phe Pro Asn Pro Phe Trp Pro Tyr Leu Glu Ser Arg Ile Thr Val Phe
                165                 170                 175

Glu Phe Pro Asn Ala Phe Leu Arg Tyr Leu His Ser Arg Ile His Val
            180                 185                 190

Leu Gln Phe Leu Asn Pro Phe Asn Val Cys Gln Asp Lys Ile Leu Glu
        195                 200                 205

His Tyr Glu Asn Asp Ser Lys Asp Ile Leu Glu His Tyr Glu Asn Asp
    210                 215                 220

Ser Lys Asp Leu Cys Asp His Ile Cys Asp His Ile Asp Tyr Trp Lys
225                 230                 235                 240

His Ile Arg Leu Glu Cys Ala Ile Met Tyr Lys Ala Arg Ile Arg Leu
                245                 250                 255

Glu Cys Ala Ile Met Tyr Lys Ala Arg Glu Met Gly Phe His Gln Phe
            260                 265                 270

Asp Gly Asp Ile Cys Asn Thr Met His Tyr Thr Asn Trp Ile Tyr Ile
```

```
            275                 280                 285
Cys Glu Asp Ala Gln Cys Thr Val Val Glu Gly Gln Val Asp Lys Lys
    290                 295                 300

Trp Glu Val His Ala Gly Gly Gln Val Ile Leu Cys Pro Glu Ser Gly
305                 310                 315                 320

Gln Arg Arg Ile Lys Arg Pro Arg Ser Glu Asn Cys His Pro Asn Lys
                325                 330                 335

Leu Leu Ile Leu Lys Cys Leu Arg Tyr Arg Phe Lys Lys His Cys Lys
            340                 345                 350

Leu Ser Ser Thr Trp His Trp Thr Cys His Asp Gly Lys His Lys Trp
        355                 360                 365

His Trp Thr Cys His Asp Gly Lys His Lys Asn Ala Ile Val Thr Leu
    370                 375                 380

Thr Tyr Tyr Glu Ala Asp Lys Asn Asp Leu Asn Ala Gln Ile Glu His
385                 390                 395                 400

Trp Lys Leu Ile Arg Met Glu Cys Ala Ile Phe Tyr Lys Ala Lys Glu
                405                 410                 415

Leu Gly Ile Ser Ile Cys His Gln Val Val Pro Leu Ala Ala Ser
            420                 425                 430

Lys Ala Lys Ala Cys Gln Ala Ile Glu Leu Gln Leu Ala Leu Glu Ala
        435                 440                 445

Leu Asn Ala Ser Pro Tyr Asp Glu Trp Thr Leu Gln Gln Thr Ser Leu
    450                 455                 460

Glu Met Trp Leu Ala Glu Pro Gln Phe Lys Lys His Gly Ile Thr Ile
465                 470                 475                 480

Thr Val Gln Tyr Asp Asn Asp Lys Ala Asn Thr Met Asp Tyr Thr Asn
                485                 490                 495

Trp Lys Glu Ile Tyr Val Ile Val Cys Pro Ala Ser Ile Pro Ser Asp
            500                 505                 510

Glu Ile Ser Thr Glu Glu Ala Asp His Ile Asp Tyr Trp Lys Ala Ile
        515                 520                 525

Arg Gln Glu Asn Ala Ile Phe Phe Ala Ala Arg His Gln Val Val Pro
    530                 535                 540

Ala Leu Asn Ile Cys Lys Ala Lys Ala Cys Lys Ala Ile Glu Trp Asn
545                 550                 555                 560

Thr Glu Pro Lys His Cys Phe Lys Lys Gly Gly Gln His Ile Glu Val
                565                 570                 575

Trp Phe Asp Tyr Val Ala Trp Asp Ser Val Tyr Tyr Cys Gly Asp Asp
            580                 585                 590

Gly Trp Cys Lys Thr Glu Ala Glu Lys Tyr Gly Cys Lys Gly Thr Trp
        595                 600                 605

Glu Val His Phe Gly Asn Ser Ile Asp Cys Asn Asp Ser Met Cys Ser
    610                 615                 620

Thr Phe Asp Asp Asn Val Ser Ala Thr Glu Leu Val Lys Asp His Ile
625                 630                 635                 640

Asp Tyr Trp Lys Leu Ile Arg Leu Glu Cys Ala Ile Phe Tyr Lys Ala
                645                 650                 655

Arg Arg Arg Leu Ser Ser Asp Gln Asp Gln Ser Gln Leu Val Thr Lys
            660                 665                 670

Tyr Pro Leu Leu Lys Leu Leu Ser Arg Pro Pro Asn Met Gly Val Lys
        675                 680                 685

Ala His Gly Lys Cys Ile Trp Glu Asn Lys Val Phe Ile Val Pro Thr
    690                 695                 700
```

-continued

```
Leu Cys Pro Val Pro Leu Asp Pro Thr Tyr Pro Leu Lys Leu Leu
705                 710                 715                 720

Thr Thr Gln Thr Thr Thr Pro Glu Asn Thr Ser Leu Val Glu Leu Arg
                725                 730                 735

Val Thr Thr Pro Lys Ser Thr Val Val Ile Arg Leu His Leu Thr Thr
                740                 745                 750

Arg Tyr Pro Leu Leu Ser Leu Leu Asn Ser Tyr Ser Thr Pro Pro His
            755                 760                 765

Arg Ile Pro Ala Pro Cys Pro Trp Ala Pro Gln Arg Pro Pro Ile Pro
            770                 775                 780

Lys Pro Ser Pro Trp Ala Pro Arg Ile Pro Ala Pro Cys Pro Trp Ala
785                 790                 795                 800

Pro Pro Arg Pro Pro His Cys Pro Trp Val Pro Pro Pro Pro Pro Pro
                805                 810                 815

Arg Pro Trp Ala Pro Cys Phe Leu Leu Cys Phe Cys Val Leu Leu Cys
            820                 825                 830

Val Cys Leu Leu Ile Arg Pro Leu Leu Leu Ser Val Ser Thr Tyr Leu
            835                 840                 845

Arg Pro Leu Leu Leu Ser Ile Ser Val Tyr Ala Gln Val Leu Val Leu
850                 855                 860

Val Leu Leu Leu Trp Val Ser Ile Gly Ser Leu Leu Pro Ser Val Cys
865                 870                 875                 880

Met Cys Ala Tyr Ala Trp Val Leu Val Phe Val Tyr Ile Val Val Ile
                885                 890                 895

Thr Ser Pro Ala Thr Ala Ile Val Tyr Arg Asp Gly Asn Pro Tyr Ala
                900                 905                 910

Val Cys Asp Lys Cys Leu Lys Phe Tyr Ser Lys Ile Ser Glu Tyr Arg
            915                 920                 925

His Tyr Cys Tyr Ser Leu Tyr Gly Thr Thr Leu Glu Gln Gln Tyr Asn
            930                 935                 940

Lys Pro Leu Cys Asp Leu Leu Ile Arg Cys Ile Asn Val Val Tyr Arg
945                 950                 955                 960

Asp Ser Ile Pro His Ala Ala Cys His Lys Cys Ile Asp Phe Tyr Ser
                965                 970                 975

Arg Ile Arg Glu Leu Arg His Tyr Ser Asp Ser Val Tyr Gly Asp Thr
            980                 985                 990

Leu Glu Lys Leu Thr Asn Thr Gly  Leu Tyr Asn Leu Leu  Ile Arg Cys
            995                 1000                1005

Leu Arg  Val Phe Cys Lys Lys  Ala Leu Thr Ala Ser  Glu Val Tyr
         1010                1015                 1020

Asn Phe  Ala Tyr Thr Asp Leu  Arg Val Val Tyr Arg  Asp Ser Lys
         1025                1030                 1035

Val Arg  Lys Leu Arg Tyr Tyr  Asn Cys Ser Val Tyr  Gly Ala Ser
         1040                1045                 1050

Leu Val  Tyr Cys Lys Gly Gln  Leu Thr Glu Thr Glu  Val Leu Asp
         1055                1060                 1065

Phe Ala  Phe Thr Asp Leu Thr  Ile Val Tyr Arg Asp  Ser Lys Val
         1070                1075                 1080

Ser Glu  Phe Arg Trp Tyr Arg  Tyr Ser Val Tyr Gly  Thr Thr Leu
         1085                1090                 1095

Cys Val  Glu Cys Lys Lys Thr  Leu Gln Arg Ser Glu  Val Tyr Asp
         1100                1105                 1110
```

Cys Gln Arg Pro Leu Cys Pro Gln Glu Lys Lys Arg His Val Asp
     1115                1120                1125

Leu Asn Lys Arg Phe His Thr Leu His Glu Tyr Met Leu Asp Leu
    1130                1135                1140

Gln Pro Glu Thr Thr Asp Leu Tyr Cys Tyr Gln Pro Glu Thr
    1145                1150                1155

Thr Asp Leu His Cys Tyr Glu Gln Leu Gly Asp Ser Ser Asp Glu
    1160                1165                1170

Glu Asp Thr Gly Gly Leu Asp Gly Asp Glu Asp Glu Asp Glu Val
    1175                1180                1185

Asp His Leu Gln Glu Gln Pro Gln Gln Ala Arg Arg Asp Glu Gln
    1190                1195                1200

His Pro Cys Tyr Leu Ile Glu Thr Gln Cys Cys Arg Cys Glu Ser
    1205                1210                1215

Leu Val Glu Glu Asn Asp Glu Ile Asp Gly Val Asn His Gln His
    1220                1225                1230

Leu Pro Ala Arg Arg Ala Glu Pro Gln Arg His Thr Met Leu Cys
    1235                1240                1245

Met Cys Cys Lys Cys Glu Ala Arg Ile Ala Gly Ser Gly Pro Gly
    1250                1255                1260

Ala Ser Gly Lys Pro Ile Pro Asn Pro Leu Leu Gly Leu Asp Ser
    1265                1270                1275

Thr Arg Thr
    1280

<210> SEQ ID NO 67
<211> LENGTH: 2661
<212> TYPE: DNA
<213> ORGANISM: Artificial Sequence
<220> FEATURE:
<223> OTHER INFORMATION: viral construct

<400> SEQUENCE: 67
ttaattaacc atcttcaata atatacctca aacttttgt gcgcgttaat atgcaaatga      60
ggcgtttgaa tttggggagg aagggcggtg attggtcgag ggatgagcga ccgttagggg    120
cggggcgagt gacgttttga tgacgtggtt gcgaggagga gccagtttgc aagttctcgt    180
gggaaaagtg acgtcaaacg aggtgtggtt tgaacacgga aatactcaat tttcccgcgc    240
tctctgacag gaaatgaggt gtttctgggc ggatgcaagt gaaaacgggc cattttcgcg    300
cgaaaactga atgaggaagt gaaaatctga gtaatttcgc gtttatggca gggaggagta    360
tttgccgagg gccgagtaga cttttgaccga ttacgtgggg gtttcgatta ccgtgttttt    420
cacctaaatt tccgcgtacg gtgtcaaagt ccggtgtttt tacgcgatcg ctagcgacat    480
cgatcacaag tttgtacaaa aaagcaggct ccaccatggg aacccgcgtt ttgagatttc    540
tgtcgccgac taaattcatg tcgcgcgata tggtgtttta tcgccgatag agatggcgat    600
attggaaaaa tcgatatttg aaaatatggc atattgaaaa tgtcgccgat gtgagtttct    660
gtgtaactga tatcgccatt tttccaaaag tgattttgg gcatacgcga tatctggcga    720
tagcgcttat atcgtttacg ggggatggcg atagacgact ttggtgactt gggcgattct    780
gtgtgtcgca aatatcgcag tttcgatata ggtgacagac gatatgaggc tatatcgccg    840
atagaggcga catcaagctg gcacatggcc aatgcatatc gatctataca ttgaatcaat    900
attggccatt agccatatta ttcattggtt atatagcata aatcaatatt ggctattggc    960
cattgcatac gttgtatcca tatcataata tgtacattta tattggctca gtccaacat    1020

```
taccgccatg ttgacattga ttattgacta gttattaata gtaatcaatt acggggtcat    1080
tagttcatag cccatatatg gagttccgcg ttacataact tacggtaaat ggcccgcctg    1140
gctgaccgcc caacgacccc cgcccattga cgtcaataat gacgtatgtt cccatagtaa    1200
cgccaatagg gactttccat tgacgtcaat gggtggagta tttacggtaa actgcccact    1260
tggcagtaca tcaagtgtat catatgccaa gtacgccccc tattgacgtc aatgacggta    1320
aatggcccgc ctggcattat gcccagtaca tgaccttatg ggactttcct acttggcagt    1380
acatctacgt attagtcatc gctattacca tggtgatgcg gttttggcag tacatcaatg    1440
ggcgtggata gcggtttgac tcacggggat ttccaagtct ccaccccatt gacgtcaatg    1500
ggagtttgtt ttggcaccaa aatcaacggg actttccaaa atgtcgtaac aactccgccc    1560
cattgacgca aatgggcggt aggcgtgtac ggtgggaggt ctatataagc agagctctcc    1620
ctatcagtga tagagatctc cctatcagtg atagagatcg tcgacgagct cgtttagtga    1680
accgtcagat cgcctggaga cgccatccac gctgttttga cctccataga agacaccggg    1740
accgatccag cctccgcggc cgggaacggt gcattggaac gcggattccc cgtgccaaga    1800
gtgacgtaag taccgcctat agagtctata ggcccacccc cttggcttct tatgcatgct    1860
atactgtttt tggcttgggg tctatacacc cccgcttcct catgttatag gtgatggtat    1920
agcttagcct ataggtgtgg gttattgacc attattgacc actcccctat tggtgacgat    1980
actttccatt actaatccat aacatggctc tttgccacaa ctctctttat tggctatatg    2040
ccaatacact gtccttcaga gactgacacg gactctgtat ttttacagga tggggtctca    2100
tttattattt acaaattcac atatacaaca ccaccgtccc cagtgcccgc agttttatt    2160 aaacataacg tgggatctcc acgcgaatct cgggtacgtg ttccggacat gggctcttct    2220
ccggtagcgg cggagcttct acatccgagc cctgctccca tgcctccagc gactcatggt    2280
cgctcggcag ctccttgctc ctaacagtgg aggccagact taggcacagc acgatgccca    2340
ccaccaccag tgtgccgcac aaggccgtgg cggtagggta tgtgtctgaa aatgagctcg    2400
gggagcgggc ttgcaccgct gacgcatttg gaagacttaa ggcagcggca gaagaagatg    2460
caggcagctg agttgttgtg ttctgataag agtcagaggt aactcccgtt gcggtgctgt    2520
taacggtgga gggcagtgta gtctgagcag tactcgttgc tgccgcgcgc gccaccagac    2580
ataatagctc acagactaac agactgttcc tttccatggg tcttttctgc agtcaccgtc    2640
cttgacacga agcttggtac c                                             2661

<210> SEQ ID NO 68
<211> LENGTH: 37490
<212> TYPE: DNA
<213> ORGANISM: Artificial Sequence
<220> FEATURE:
<223> OTHER INFORMATION: viral construct

<400> SEQUENCE: 68
gcggccgctc gagcatgcat ctagagggcc ctattctata gtgtcaccta aatgctagag      60
ctcgctgatc agcctcgact gtgccttcta gttgccagcc atctgttgtt tgcccctccc     120
ccgtgccttc cttgaccctg gaaggtgcca ctcccactgt cctttcctaa taaaatgagg     180
aaattgcatc gcattgtctg agtaggtgtc attctattct ggggggtggg gtggggcagg     240
acagcaaggg ggaggattgg gaagacaata gcaggcatgc tggggatgcg gtgggctcta     300
tggcttctga ggcggaaaga accagctggg gctcgagggg ggatcgatcc cgtcgagata     360
```

```
tctagaccca gctttcttgt acaaagtggt gatcgattcg acagatcgcg atcgcaagtg    420
agtagtgttc tggggcgggg gaggacctgc atgagggcca gaataactga aatctgtgct    480
tttctgtgtg ttgcagcagc atgagcggaa gcggctcctt tgagggaggg gtattcagcc    540
cttatctgac ggggcgtctc ccctcctggg cgggagtgcg tcagaatgtg atgggatcca    600
cggtggacgg ccggcccgtg cagcccgcga actcttcaac cctgacctat gcaaccctga    660
gctcttcgtc gttggacgca gctgccgccg cagctgctgc atctgccgcc agcgccgtgc    720
gcggaatggc catgggcgcc ggctactacg gcactctggt ggccaactcg agttccacca    780
ataatcccgc cagcctgaac gaggagaagc tgttgctgct gatggcccag ctcgaggcct    840
tgacccagcg cctgggcgag ctgacccagc aggtggctca gctgcaggag cagacgcggg    900
ccgcggttgc cacggtgaaa tccaaataaa aatgaatca ataaataaac ggagacggtt    960
gttgatttta acacagagtc tgaatcttta tttgattttt cgcgcgcggt aggccctgga   1020
ccaccggtct cgatcattga gcacccggtg gatcttttcc aggacccggt agaggtgggc   1080
ttggatgttg aggtacatgg gcatgagccc gtcccggggg tggaggtagc tccattgcag   1140
ggcctcgtgc tcggggggtgg tgttgtaaat cacccagtca tagcaggggc gcagggcatg   1200
gtgttgcaca atatctttga ggaggagact gatggccacg gcagcccctt tggtgtaggt   1260
gtttacaaat ctgttgagct gggagggatg catgcggggg gagatgaggt gcatcttggc   1320
ctggatcttg agattggcga tgttaccgcc cagatcccgc ctggggttca tgttgtgcag   1380
gaccaccagc acggtgtatc cggtgcactt ggggaattta tcatgcaact tggaagggaa   1440
ggcgtgaaag aatttggcga cgcctttgtg cccgcccagg ttttccatgc actcatccat   1500
gatgatggcg atgggcccgt gggcggcggc ctgggcaaag acgtttcggg ggtcggacac   1560
atcatagttg tggtcctggg tgaggtcatc ataggccatt ttaatgaatt tggggcggag   1620
ggtgccggac tgggggacaa aggtaccctc gatcccgggg gcgtagttcc cctcacagat   1680
ctgcatctcc caggctttga gctcggaggg ggggatcatg tccacctgcg gggcgataaa   1740
gaacacggtt tccggggcgg gggagatgag ctgggccgaa agcaagttcc ggagcagctg   1800
ggacttgccg cagccggtgg ggccgtagat gaccccgatg accggctgca ggtggtagtt   1860
gagggagaga cagctgccgt cctcccggag gagggggggcc acctcgttca tcatctcgcg   1920
cacgtgcatg ttctcgcgca ccagttccgc caggaggcgc tctcccccca gggataggag   1980
ctcctggagc gaggcgaagt ttttcagcgg cttgagtccg tcggccatgg gcattttgga   2040
gagggtttgt tgcaagagtt ccaggcggtc ccagagctcg gtgatgtgct ctacggcatc   2100
tcgatccagc agacctcctc gtttcgcggg ttgggacggc tgcgggagta gggcaccaga   2160
cgatgggcgt ccagcgcagc cagggtccgg tccttccagg gtcgcagcgt ccgcgtcagg   2220
gtggtctccg tcacggtgaa ggggtgcgcg ccgggctggg cgcttgcgag ggtgcgcttc   2280
aggctcatcc ggctggtcga aaaccgctcc cgatcggcgc cctgcgcgtc ggccaggtag   2340
caattgacca tgagttcgta gttgagcgcc tcggccgcgt ggcctttggc gcggagctta   2400
cctttggaag tctgcccgca ggcgggacag aggagggact tgagggcgta gagcttgggg   2460
gcgaggaaga cggactcggg ggcgtaggcg tccgcgccgc agtgggcgca gacggtctcg   2520
cactccacga gccaggtgag gtcgggctgg tcggggtcaa aaaccagttt ccgccgttc    2580 ttttttgatgc gtttcttacc tttggtctcc atgagctcgt gtcccgctg ggtgacaaag    2640 aggctgtccg tgtccccgta gaccgacttt atggccggt cctcgagcgg tgtgccgcg     2700 tcctcctcgt agaggaaccc cgcccactcc gagacgaaag cccgggtcca ggccagcacg   2760
```

```
aaggaggcca cgtgggacgg gtagcggtcg ttgtccacca gcgggtccac cttttccagg   2820
gtatgcaaac acatgtcccc ctcgtccaca tccaggaagg tgattggctt gtaagtgtag   2880
gccacgtgac cggggggtccc ggccgggggg gtataaaagg gtgcgggtcc ctgctcgtcc   2940
tcactgtctt ccggatcgct gtccaggagc gccagctgtt ggggtaggta ttccctctcg   3000
aaggcgggca tgacctcggc actcaggttg tcagtttcta gaaacgagga ggatttgata   3060
ttgacggtgc cggcggagat gccttttcaag agcccctcgt ccatctggtc agaaaagacg   3120
atcttttttgt tgtcgagctt ggtggcgaag gagccgtaga gggcgttgga gaggagcttg   3180
gcgatggagc gcatggtctg gtttttttcc ttgtcggcgc gctccttggc ggcgatgttg   3240
agctgcacgt actcgcgcgc cacgcacttc cattcgggga agacggtggt cagctcgtcg   3300
ggcacgattc tgacctgcca gccccgatta tgcaggggtga tgaggtccac actggtggcc   3360
acctcgccgc gcagggcgctc attagtccag cagaggcgtc cgcccttgcg cgagcagaag   3420
gggggcaggg ggtccagcat gacctcgtcg gggggtcgg catcgatggt gaagatgccg   3480
ggcaggaggt cggggtcaaa gtagctgatg gaagtggcca gatcgtccag ggcagcttgc   3540
cattcgcgca cggccagcgc gcgctcgtag ggactgaggg gcgtgcccca gggcatggga   3600
tgggtaagcg cggaggcgta catgccgcag atgtcgtaga cgtagagggg ctcctcgagg   3660
atgccgatgt aggtggggta gcagcgcccc ccgcggatgc tggcgcgcac gtagtcatac   3720
agctcgtgcg aggggggcgag gagccccggg cccaggttgg tgcgactggg cttttcggcg   3780
cggtagacga tctggcggaa aatggcatgc gagttggagg agatggtggg cctttggaag   3840
atgttgaagt gggcgtgggg cagtccgacc gagtcgcgga tgaagtgggc gtaggagtct   3900
tgcagcttgg cgacgagctc ggcggtgact aggacgtcca gagcgcagta gtcgagggtc   3960
tcctggatga tgtcatactt gagctgtccc ttttgtttcc acagctcgcg gttgagaagg   4020
aactcttcgc ggtccttcca gtactcttcg aggggggaacc cgtcctgatc tgcacggtaa   4080
gagcctagca tgtagaactg gttgacggcc ttgtaggcgc agcagccctt ctccacgggg   4140
agggcgtagg cctgggcggc cttgcgcagg gaggtgtgcg tgaggcgaa agtgtccctg   4200
accatgacct tgaggaactg gtgcttgaag tcgatatcgt cgcagccccc ctgctcccag   4260
agctggaagt ccgtgcgctt cttgtaggcg gggttgggca aagcgaaagt aacatcgttg   4320
aagaggatct tgcccgcgcg gggcataaag ttgcgagtga tgcggaaagg ttggggcacc   4380
tcggcccggt tgttgatgac ctgggcggcg agcacgatct cgtcgaagcc gttgatgttg   4440
tggcccacga tgtagagttc cacgaatcgc ggacggccct tgacgtgggg cagtttcttg   4500
agctcctcgt aggtgagctc gtcggggtcg ctgagcccgt gctgctcgag cgcccagtcg   4560
gcgagatggg ggttggcgcg gaggaaggaa gtccagagat ccacggccag ggcggtttgc   4620
agacggtccc ggtactgacg gaactgctgc ccgacggcca ttttttcggg ggtgacgcag   4680
tagaaggtgc gggggtcccc gtgccagcga tcccatttga gctggagggc gagatcgagg   4740
gcgagctcga cgagccggtc gtccccggag agtttcatga ccagcatgaa ggggacgagc   4800
tgcttgccga aggaccccat ccaggtgtag gtttccacat cgtaggtgag gaagagcctt   4860
tcggtgcgag gatgcgagcc gatggggaag aactggatct cctgccacca attggaggaa   4920
tggctgttga tgtgatggaa gtagaaatgc cgacggcgcg ccgaacactc gtgcttgtgt   4980
ttatacaagc ggccacagtg ctcgcaacgc tgcacgggat gcacgtgctg cacgagctgt   5040
acctgagttc ctttgacgag gaatttcagt gggaagtgga gtcgtggcgc ctgcatctcg   5100
```

```
tgctgtacta cgtcgtggtg gtcggcctgg ccctcttctg cctcgatggt ggtcatgctg   5160
acgagcccgc gcgggaggca ggtccagacc tcggcgcgag cgggtcggag agcgaggacg   5220
agggcgcgca ggccggagct gtccagggtc ctgagacgct gcggagtcag gtcagtgggc   5280
agcggcggcg cgcggttgac ttgcaggagt ttttccaggg cgcgcgggag gtccagatgg   5340
tacttgatct ccaccgcgcc attggtggcg acgtcgatgg cttgcagggt cccgtgcccc   5400
tggggtgtga ccaccgtccc ccgtttcttc ttgggcggct ggggcgacgg gggcggtgcc   5460
tcttccatgg ttagaagcgg cggcgaggac gcgcgccggg cggcaggggc ggctcggggc   5520
ccggaggcag gggcggcagg ggcacgtcgg cgccgcgcgc gggtaggttc tggtactgcg   5580
cccggagaag actggcgtga gcgacgacgc gacggttgac gtcctggatc tgacgcctct   5640
gggtgaaggc cacgggaccc gtgagtttga acctgaaaga gagttcgaca gaatcaatct   5700
cggtatcgtt gacggcggcc tgccgcagga tctcttgcac gtcgcccgag ttgtcctggt   5760
aggcgatctc ggtcatgaac tgctcgatct cctcctcttg aaggtctccg cggccggcgc   5820
gctccacggt ggccgcgagg tcgttggaga tgcggcccat gagctgcgag aaggcgttca   5880
tgcccgcctc gttccagacg cggctgtaga ccacgacgcc ctcgggatcg ccggcgcgca   5940
tgaccacctg ggcgaggttg agctccacgt ggcgcgtgaa gaccgcgtag ttgcagaggc   6000
gctggtagag gtagttgagc gtggtggcga tgtgctcggt gacgaagaaa tacatgatcc   6060
agcggcggag cggcatctcg ctgacgtcgc ccagcgcctc caaacgttcc atggcctcgt   6120
aaaagtccac ggcgaagttg aaaaactggg agttgcgcgc cgagacggtc aactcctcct   6180
ccagaagacg gatgagctcg gcgatggtgg cgcgcacctc gcgctcgaag gcccccggga   6240
gttcctccac ttcctcttct tcctcctcca ctaacatctc ttctacttcc tcctcaggcg   6300
gcagtggtgg cggggagggg ggcctgcgtc gccggcggcg cacgggcaga cggtcgatga   6360
agcgctcgat ggtctcgccg cgccggcgtc gcatggtctc ggtgacggcg cgcccgtcct   6420
cgcggggccg cagcgtgaag acgccgccgc gcatctccag gtggccgggg gggtccccgt   6480
tgggcaggga gagggcgctg acgatgcatc ttatcaattg ccccgtaggg actccgcgca   6540
aggacctgag cgtctcgaga tccacgggat ctgaaaaccg ctgaacgaag gcttcgagcc   6600
agtcgcagtc gcaaggtagg ctgagcacgg tttcttctgg cgggtcatgt tggttgggag   6660
cggggcgggc gatgctgctg gtgatgaagt tgaaataggc ggttctgaga cggcggatgg   6720
tggcgaggag caccaggtct ttgggcccgg cttgctggat gcgcagacgg tcggccatgc   6780
cccaggcgtg gtcctgacac ctggccaggt ccttgtagta gtcctgcatg agccgctcca   6840
cgggcacctc ctcctcgccc gcgcggccgt gcatgcgcgt gagcccgaag ccgcgctggg   6900
gctggacgag cgccaggtcg gcgacgacgc gctcggcgag gatggcttgc tggatctggg   6960
tgagggtggt ctggaagtca tcaaagtcga cgaagcggtg gtaggctccg gtgttgatgg   7020
tgtaggagca gttggccatg acggaccagt tgacggtctg gtggcccgga cgcacgagct   7080
cgtggtactt gaggcgcgag taggcgcgcg tgtcgaagat gtagtcgttg caggtgcgca   7140
ccaggtactg gtagccgatg aggaagtgcg gcggcggctg gcggtagagc ggccatcgct   7200
cggtggcggg ggcgccgggc gcgaggtcct cgagcatggt gcggtggtag ccgtagatgt   7260
acctggacat ccaggtgatg ccggcggcgg tggtggaggc gcgcgggaac tcgcggacgc   7320
ggttccagat gttgcgcagc ggcaggaagt agttcatggt gggcacggtc tggcccgtga   7380
ggcgcgcgca gtcgtggatg ctctatacgg gcaaaaacga aagcggtcag cggctcgact   7440
ccgtggcctg gaggctaagc gaacgggttg ggctgcgcgt gtaccccggt tcgaatctcg   7500
```

```
aatcaggctg gagccgcagc taacgtggta ttggcactcc cgtctcgacc caagcctgca   7560
ccaaccctcc aggatacgga ggcgggtcgt tttgcaactt ttttttggag gccggatgag   7620
actagtaagc gcggaaagcg gccgaccgcg atggctcgct gccgtagtct ggagaagaat   7680
cgccagggtt gcgttgcggt gtgccccggt tcgaggccgg ccggattccg cggctaacga   7740
gggcgtggct gccccgtcgt ttccaagacc ccatagccag ccgacttctc cagttacgga   7800
gcgagcccct cttttgtttt gtttgttttt gccagatgca tcccgtactg cggcagatgc   7860 gccccacca ccctccaccg caacaacagc cccctccaca gccggcgctt ctgccccgc    7920 cccagcagca acttccagcc acgaccgccg cggccgccgt gagcggggct ggacagagtt   7980
atgatcacca gctggccttg aagagggcg aggggctggc gcgcctgggg gcgtcgtcgc   8040
cggagcggca cccgcgcgtg cagatgaaaa gggacgctcg cgaggcctac gtgcccaagc   8100
agaacctgtt cagagacagg agcggcgagg agcccgagga gatgcgcgcg gcccggttcc   8160
acgcggggcg ggagctgcgg cgcggcctgg accgaaagag ggtgctgagg gacgaggatt   8220
tcgaggcgga cgagctgacg gggatcagcc ccgcgcgcgc gcacgtggcc gcggccaacc   8280
tggtcacggc gtacgagcag accgtgaagg aggagagcaa cttccaaaaa tccttcaaca   8340
accacgtgcg caccctgatc gcgcgcgagg aggtgaccct gggcctgatg cacctgtggg   8400
acctgctgga ggccatcgtg cagaacccca ccagcaagcc gctgacggcg cagctgttcc   8460
tggtggtgca gcatagtcgg gacaacgaag cgttcaggga ggcgctgctg aatatcaccg   8520
agcccgaggg ccgctggctc ctggacctgg tgaacattct gcagagcatc gtggtgcagg   8580
agcgcgggct gccgctgtcc gagaagctgg cggccatcaa cttctcggtg ctgagtttgg   8640
gcaagtacta cgctaggaag atctacaaga ccccgtacgt gcccatagac aaggaggtga   8700
agatcgacgg gttttacatg cgcatgaccc tgaaagtgct gaccctgagc gacgatctgg   8760
gggtgtaccg caacgacagg atgcaccgtg cggtgagcgc cagcaggcgg cgcgagctga   8820
gcgaccagga gctgatgcat agtctgcagc gggccctgac cggggccggg accgaggggg   8880
agagctactt tgacatgggc gcggacctgc actggcagcc cagccgccgg gccttggagg   8940
cggcggcagg accctacgta aagaggtgg acgatgaggt ggacgaggag ggcgagtacc   9000
tggaagactg atggcgcgac cgtatttttg ctagatgcaa caacaacagc cacctcctga   9060
tcccgcgatg cgggcggcgc tgcagagcca gccgtccggc attaactcct cggacgattg   9120
gacccaggcc atgcaacgca tcatggcgct gacgacccgc aaccccgaag cctttagaca   9180
gcagccccag gccaaccggc tctcggccat cctggaggcc gtggtgccct cgcgctccaa   9240
ccccacgcac gagaaggtcc tggccatcgt gaacgcgctg gtggagaaca aggccatccg   9300
cggcgacgag gccggcctgg tgtacaacgc gctgctggag cgcgtggccc gctacaacag   9360
caccaacgtg cagaccaacc tggaccgcat ggtgaccgac gtgcgcgagg ccgtggccca   9420
gcgcgagcgg ttccaccgcg agtccaacct gggatccatg gtggcgctga acgccttcct   9480
cagcacccag cccgccaacg tgccccgggg ccaggaggac tacaccaact tcatcagcgc   9540
cctgcgcctg atggtgaccg aggtgccccg agcgaggtg taccagtccg ggccggacta   9600
cttcttccag accagtcgcc agggcttgca gaccgtgaac ctgagccagg cttttcaagaa   9660 cttgcagggc ctgtggggcg tgcaggcccc ggtcggggac cgcgcgacgg tgtcgagcct   9720
gctgacgccg aactcgcgcc tgctgctgct gctggtggcc cccttcacgg acagcggcag   9780
catcaaccgc aactcgtacc tgggctacct gattaacctg taccgcgagg ccatcggcca   9840
```

```
ggcgcacgtg gacgagcaga cctaccagga gatcacccac gtgagccgcg ccctgggcca   9900
ggacgacccg ggcaacctgg aagccaccct gaacttttg ctgaccaacc ggtcgcagaa    9960
gatcccgccc cagtacgcgc tcagcaccga ggaggagcgc atcctgcgtt acgtgcagca  10020
gagcgtgggc ctgttcctga tgcaggaggg ggccaccccc agcgccgcgc tcgacatgac  10080
cgcgcgcaac atggagccca gcatgtacgc cagcaaccgc ccgttcatca taaactgat   10140
ggactacttg catcgggcgg ccgccatgaa ctctgactat ttcaccaacg ccatcctgaa  10200
tccccactgg ctcccgccgc cggggttcta cacgggcgag tacgacatgc ccgacccaa   10260
tgacgggttc ctgtgggacg atgtggacag cagcgtgttc tcccccgac cgggtgctaa   10320
cgagcgcccc ttgtggaaga aggaaggcag cgaccgacgc ccgtcctcgg cgctgtccgg  10380
ccgcgagggt gctgccgcgg cggtgccga ggccgccagt cctttcccga gcttgccctt   10440
ctcgctgaac agtatccgca gcagcgagct gggcaggatc acgcgccgc gcttgctggg  10500
cgaagaggag tacttgaatg actcgctgtt gagacccgag cgggagaaga acttcccaa   10560
taacgggata gaaagcctgg tggacaagat gagccgctgg aagacgtatg cgcaggagca  10620
cagggacgat ccccgggcgt cgcagggggc cacgagccgg ggcagcgccg cccgtaaacg  10680
ccggtggcac gacaggcagc ggggacagat gtgggacgat gaggactccg ccgacgcag   10740
cagcgtgttg gacttgggtg ggagtggtaa cccgttcgct cacctgcgcc cccgtatcgg  10800
gcgcatgatg taagagaaac cgaaaataaa tgatactcac caaggccatg cgaccagcg   10860
tgcgttcgtt tcttctctgt tgttgttgta tctagtatga tgaggcgtgc gtacccggag  10920
ggtcctcctc cctcgtacga gagcgtgatg cagcaggcga tggcggcggc ggcgatgcag  10980
ccccgctgg aggctcctta cgtgccccg cggtacctgg cgcctacgga ggggcggaac   11040
agcattcgtt actcggagct ggcacccttg tacgatacca cccggttgta cctggtggac  11100
aacaagtcgg cggacatcgc ctcgctgaac taccagaacg accacagcaa cttcctgacc  11160
accgtggtgc agaacaatga cttcacccc acggaggcca gcacccagac catcaacttt  11220
gacgagcgct cgcggtgggg cggccagctg aaaaccatca tgcacaccaa catgcccaac  11280
gtgaacgagt tcatgtacag caacaagttc aaggcgcggg tgatggtctc ccgcaagacc  11340
cccaatgggg tgacagtgac agaggattat gatggtagtc aggatgagct gaagtatgaa  11400
tgggtggaat ttgagctgcc cgaaggcaac ttctcggtga ccatgaccat cgacctgatg  11460
aacaacgcca tcatcgacaa ttacttggcg gtggggcggc agaacggggt gctggagagc  11520
gacatcggcg tgaagttcga cactaggaac ttcaggctgg gctgggaccc cgtgaccgag  11580
ctggtcatgc ccggggtgta caccaacgag gctttccatc ccgatattgt cttgctgccc  11640
ggctgcgggg tggacttcac cgagagccgc tcagcaacc tgctgggcat tcgcaagagg  11700
cagcccttcc aggaaggctt ccagatcatg tacgaggatc tggaggggg caacatcccc  11760
gcgctcctgg atgtcgacgc ctatgagaaa agcaaggagg atgcagcagc tgaagcaact  11820
gcagccgtag ctaccgcctc taccgaggtc aggggcgata ttttgcaag cgccgcagca  11880
gtggcagcgg ccgaggcggc tgaaaccgaa agtaagatag tcattcagcc ggtggagaag  11940
gatagcaaga acaggagcta caacgtacta ccggacaaga taaacaccgc ctaccgcagc  12000
tggtacctag cctacaacta tggcgacccc gagaagggcg tgcgctcctg gacgctgctc  12060
accacctcgg acgtcacctg cggcgtggag caagtctact ggtcgctgcc cgacatgatg  12120
caagacccgg tcaccttccg ctccacgcgt caagttagca actacccggt ggtgggcgcc  12180
gagctcctgc ccgtctactc caagagcttc ttcaacgagc aggccgtcta ctcgcagcag  12240
```

```
ctgcgcgcct tcacctcgct tacgcacgtc ttcaaccgct tccccgagaa ccagatcctc   12300
gtccgcccgc ccgcgcccac cattaccacc gtcagtgaaa acgttcctgc tctcacagat   12360
cacgggaccc tgccgctgcg cagcagtatc cggggagtcc agcgcgtgac cgttactgac   12420
gccagacgcc gcacctgccc ctacgtctac aaggccctgg gcatagtcgc gccgcgcgtc   12480
ctctcgagcc gcaccttcta aatgtccatt ctcatctcgc ccagtaataa caccggttgg   12540
ggcctgcgcg cgcccagcaa gatgtacgga ggcgctcgcc aacgtccac gcaacacccc    12600 gtgcgcgtgc gcgggcactt ccgcgctccc tggggcgccc tcaagggccg cgtgcggtcg   12660
cgcaccaccg tcgacgacgt gatcgaccag gtggtggccg acgcgcgcaa ctacacccccc  12720 gccgccgcgc ccgtctccac cgtggacgcc gtcatcgaca gcgtggtggc ggacgcgcgc   12780
cggtacgccc gcgccaagag ccggcggcgg cgcatcgccc ggcggcaccg gagcaccccc   12840
gccatgcgcg cggcgcgagc cttgctgcgc agggccaggc gcacgggacg cagggccatg   12900
ctcagggcgg ccagacgcgc ggcttcaggc gccagcgccg gcaggacccg gagacgcgcg   12960
gccacggcgg cggcagcggc catcgccagc atgtcccgcc cgcggcgagg gaacgtgtac   13020
tgggtgcgcg acgccgccac cggtgtgcgc gtgcccgtgc gcacccgccc ccctcgcact   13080
tgaagatgtt cacttcgcga tgttgatgtg tcccagcggc gaggaggatg tccaagcgca   13140
aattcaagga agagatgctc caggtcatcg cgcctgagat ctacgccct gcggtggtga    13200 aggaggaaag aaagccccgc aaaatcaagc gggtcaaaaa ggacaaaaag gaagaagaaa   13260
gtgatgtgga cggattggtg gagtttgtgc gcgagttcgc ccccggcgg cgcgtgcagt    13320 ggcgcgggcg gaaggtgcaa ccggtgctga gacccggcac caccgtggtc ttcacgcccg   13380
gcgagcgctc cggcaccgct tccaagcgct cctacgacga ggtgtacggg gatgatgata   13440
ttctggagca ggcggccgag cgcctgggcg agtttgctta cggcaagcgc agccgttccg   13500
caccgaagga agaggcggtg tccatcccgc tggaccacgg caaccccacg ccgagcctca   13560
agcccgtgac cttgcagcag gtgctgccga ccgcggcgcc gcgccggggg ttcaagcgcg   13620
agggcgagga tctgtacccc accatgcagc tgatggtgcc caagcgccag aagctggaag   13680
acgtgctgga gaccatgaag gtggaccccgg acgtgcagcc cgaggtcaag gtgcggccca   13740
tcaagcaggt ggccccgggc ctgggcgtgc agaccgtgga catcaagatt cccacggagc   13800
ccatggaaac gcagaccgag cccatgatca agcccagcac cagcaccatg gaggtgcaga   13860
cggatccctg gatgccatcg gctcctagtc gaagacccccg gcgcaagtac ggcgcggcca   13920
gcctgctgat gcccaactac gcgctgcatc cttccatcat cccacgccg ggctaccgcg    13980 gcacgcgctt ctaccgcggt cataccagca gccgccgccg caagaccacc actcgccgcc   14040
gccgtcgccg caccgccgct gcaaccaccc ctgccgccct ggtgcggaga gtgtaccgcc   14100
gcggccgcgc acctctgacc ctgccgcgcg cgcgctacca cccgagcatc gccatttaaa   14160
ctttcgccag ctttgcagat caatggccct cacatgccgc cttcgcgttc ccattacggg   14220
ctaccgagga agaaaaccgc gccgtagaag gctggcgggg aacgggatgc gtcgccacca   14280
ccaccggcgg cggcgcgcca tcagcaagcg gttgggggga ggcttcctgc ccgcgctgat   14340
ccccatcatc gccgcggcga tcgggggcgat ccccggcatt gcttccgtgg cggtgcaggc   14400
ctctcagcgc cactgagaca cacttggaaa catcttgtaa taaacccatg gactctgacg   14460
ctcctggtcc tgtgatgtgt tttcgtagac agatggaaga catcaatttt tcgtccctgg   14520
ctccgcgaca cggcacgcgg ccgttcatgg gcacctggag cgacatcggc accagccaac   14580
```

```
tgaacggggg cgccttcaat tggagcagtc tctggagcgg gcttaagaat ttcgggtcca   14640
cgcttaaaac ctatggcagc aaggcgtgga acagcaccac agggcaggcg ctgagggata   14700
agctgaaaga gcagaacttc cagcagaagg tggtcgatgg gctcgcctcg ggcatcaacg   14760
gggtggtgga cctggccaac caggccgtgc agcggcagat caacagccgc ctggacccgg   14820
tgccgcccgc cggctccgtg gagatgccgc aggtggagga ggagctgcct cccctggaca   14880
agcggggcga gaagcgaccc cgccccgatg cggaggagac gctgctgacg cacacggacg   14940
agccgccccc gtacgaggag gcggtgaaac tgggtctgcc caccacgcgg cccatcgcgc   15000
ccctggccac cggggtgctg aaacccgaaa agcccgcgac cctggacttg cctcctcccc   15060
agccttcccg cccctctaca gtggctaagc ccctgccgcc ggtggccgtg gcccgcgcgc   15120
gacccggggg caccgcccgc cctcatgcga actggcagag cactctgaac agcatcgtgg   15180
gtctgggagt gcagagtgtg aagcgccgcc gctgctatta aacctaccgt agcgcttaac   15240
ttgcttgtct gtgtgtgtat gtattatgtc gccgccgccg ctgtccacca gaaggaggag   15300
tgaagaggcg cgtcgccgag ttgcaagatg ccaccccat cgatgctgcc ccagtgggcg    15360
tacatgcaca tcgccggaca ggacgcttcg gagtacctga gtccgggtct ggtgcagttt   15420
gcccgcgcca cagacaccta cttcagtctg gggaacaagt ttaggaaccc cacggtggcg   15480
cccacgcacg atgtgaccac cgaccgcagc cagcggctga cgctgcgctt cgtgcccgtg   15540
gaccgcgagg acaacaccta ctcgtacaaa gtgcgctaca cgctggccgt gggcgacaac   15600
cgcgtgctgg acatggccag cacctacttt gacatccgcg gcgtgctgga tcggggccct   15660
agcttcaaac cctactccgg caccgcctac aacagtctgg cccccaaggg agcacccaac   15720
acttgtcagt ggacatataa agccgatggt gaaactgcca cagaaaaaac ctatacatat   15780
ggaaatgcac ccgtgcaggg cattaacatc acaaaagatg gtattcaact tggaactgac   15840
accgatgatc agccaatcta cgcagataaa acctatcagc ctgaacctca agtgggtgat   15900
gctgaatggc atgacatcac tggtactgat gaaaagtatg gaggcagagc tcttaagcct   15960
gataccaaaa tgaagccttg ttatggttct tttgccaagc ctactaataa agaaggaggt   16020
caggcaaatg tgaaaacagg aacaggcact actaaagaat atgacataga catggctttc   16080
tttgacaaca gaagtgcggc tgctgctggc ctagctccag aaattgtttt gtatactgaa   16140
aatgtggatt tggaaactcc agatacccat attgtataca agcaggcac agatgacagc    16200 agctcttcta ttaatttggg tcagcaagcc atgcccaaca gacctaacta cattggtttc   16260
agagacaact ttatcgggct catgtactac aacagcactg gcaatatggg ggtgctggcc   16320
ggtcaggctt ctcagctgaa tgctgtggtt gacttgcaag acagaaacac cgagctgtcc   16380
taccagctct tgcttgactc tctgggtgac agaacccggt atttcagtat gtggaatcag   16440
gcggtggaca gctatgatcc tgatgtgcgc attattgaaa atcatggtgt ggaggatgaa   16500
cttcccaact attgtttccc tctggatgct gttggcagaa cagatactta tcagggaatt   16560
aaggctaatg gaactgatca aaccacatgg accaaagatg acagtgtcaa tgatgctaat   16620
gagataggca agggtaatcc attcgccatg gaaatcaaca tccaagccaa cctgtggagg   16680
aacttcctct acgccaacgt ggccctgtac ctgcccgact cttacaagta cacgccggcc   16740
aatgttaccc tgcccaccaa caccaacacc tacgattaca tgaacggccg ggtggtggcg   16800
ccctcgctgg tggactccta catcaacatc ggggcgcgct ggtcgctgga tccatggac    16860 aacgtgaacc ccttcaacca ccaccgcaat gcggggctgc gctaccgctc catgctcctg   16920
ggcaacgggc gctacgtgcc cttccacatc caggtgcccc agaaattttt cgccatcaag   16980
```

```
agcctcctgc tcctgcccgg gtcctacacc tacgagtgga acttccgcaa ggacgtcaac   17040
atgatcctgc agagctccct cggcaacgac ctgcgcacgg acggggcctc catctccttc   17100
accagcatca acctctacgc caccttcttc cccatggcgc acaacacggc ctccacgctc   17160
gaggccatgc tgcgcaacga caccaacgac cagtccttca cgactacct ctcggcggc    17220
aacatgctct accccatccc ggccaacgcc accaacgtgc ccatctccat cccctcgcgc   17280
aactgggccg ccttccgcgg ctggtccttc acgcgtctca agaccaagga gacgccctcg   17340
ctgggctccg ggttcgaccc ctacttcgtc tactcgggct ccatcccca cctcgacggc   17400
accttctacc tcaaccacac cttcaagaag gtctccatca ccttcgactc ctccgtcagc   17460
tggcccggca acgaccggct cctgacgccc aacgagttcg aaatcaagcg caccgtcgac   17520
ggcgagggct acaacgtggc ccagtgcaac atgaccaagg actggttcct ggtccagatg   17580
ctggcccact acaacatcgg ctaccagggc ttctacgtgc ccgagggcta caaggaccgc   17640
atgtactcct tcttccgcaa cttccagccc atgagccgcc aggtggtgga cgaggtcaac   17700
tacaaggact accaggccgt caccctggcc taccagcaca caactcggg cttcgtcggc    17760
tacctcgcgc ccaccatgcg ccagggccag ccctaccccg ccaactaccc ctacccgctc   17820
atcggcaaga gcgccgtcac cagcgtcacc cagaaaaagt tcctctgcga cagggtcatg   17880
tggcgcatcc ccttctccag caacttcatg tccatgggcg cgctcaccga cctcggccag   17940
aacatgctct atgccaactc cgcccacgcg ctagacatga atttcgaagt cgaccccatg   18000
gatgagtcca cccttctcta tgttgtcttc gaagtcttcg acgtcgtccg agtgcaccag   18060
ccccaccgcg gcgtcatcga ggccgtctac ctgcgcaccc ccttctcggc cggtaacgcc   18120
accacctaag ctcttgcttc ttgcaagcca tggccgcggg ctccggcgag caggagctca   18180
gggccatcat ccgcgacctg gctgcgggc cctacttcct gggcaccttc gataagcgct    18240
tcccgggatt catggccccg cacaagctgg cctgcgccat cgtcaacacg gccggccgcg   18300
agaccggggg cgagcactgg ctggccttcg cctggaaccc gcgctcgaac acctgctacc   18360
tcttcgaccc cttcggggttc tcggacgagc gcctcaagca gatctaccag ttcgagtacg   18420
agggcctgct gcgccgcagc gccctggcca ccgaggaccg ctgcgtcacc ctggaaaagt   18480
ccacccagac cgtgcagggt ccgcgctcgg ccgcctgcgg gctcttctgc tgcatgttcc   18540
tgcacgcctt cgtgcactgg cccgaccgcc ccatggacaa gaaccccacc atgaacttgc   18600
tgacggggt gcccaacggc atgctccagt cgccccaggt ggaacccacc ctgcgccgca   18660
accaggagcc gctctaccgc ttcctcaact cccactccgc ctactttcgc tcccaccgcg   18720
cgcgcatcga gaaggccacc gccttcgacc gcatgaatca agacatgtaa accgtgtgtg   18780
tatgttaaat gtctttaata acagcactt tcatgttaca catgcatctg agatgattta    18840
tttagaaatc gaaagggttc tgccgggtct cggcatggcc cgcgggcagg gacacgttgc   18900
ggaactggta cttggccagc cacttgaact cggggatcag cagtttgggc agcggggtgt   18960
cggggaagga gtcggtccac agcttccgcg tcagttgcag ggcgcccagc aggtcgggcg   19020
cggagatctt gaaatcgcag ttgggacccg cgttctgcgc gcgggagttg cggtacacgg   19080
ggttgcagca ctggaacacc atcagggccg ggtgcttcac gctcgccagc accgtcgcgt   19140
cggtgatgct ctccacgtcg aggtcctcgg cgttggccat cccgaagggg gtcatcttgc   19200
aggtctgcct tccatggtg ggcacgcacc cgggcttgtg gttgcaatcg cagtgcaggg    19260
ggatcagcat catctgggcc tggtcggcgt tcatccccgg gtacatggcc ttcatgaaag   19320
```

```
cctccaattg cctgaacgcc tgctgggcct tggctccctc ggtgaagaag accccgcagg    19380
acttgctaga gaactggttg gtggcgcacc cggcgtcgtg cacgcagcag cgcgcgtcgt    19440
tgttggccag ctgcaccacg ctgcgccccc agcggttctg ggtgatcttg gcccggtcgg    19500
ggttctcctt cagcgcgcgc tgcccgttct cgctcgccac atccatctcg atcatgtgct    19560
ccttctggat catggtggtc ccgtgcaggc accgcagctt gccctcggcc tcggtgcacc    19620
cgtgcagcca cagcgcgcac ccggtgcact cccagttctt gtgggcgatc tgggaatgcg    19680
cgtgcacgaa gccctgcagg aagcggccca tcatggtggt cagggtcttg ttgctagtga    19740
aggtcagcgg aatgccgcgg tgctcctcgt tgatgtacag gtggcagatg cggcggtaca    19800
cctcgccctg ctcgggcatc agctggaagt tggctttcag gtcggtctcc acgcggtagc    19860
ggtccatcag catagtcatg atttccatac ccttctccca ggccgagacg atgggcaggc    19920
tcatagggtt cttcaccatc atcttagcgc tagcagccgc ggccaggggg tcgctctcgt    19980
ccagggtctc aaagctccgc ttgccgtcct tctcggtgat ccgcaccggg ggtagctga    20040 agcccacggc cgccagctcc tcctcggcct gtctttcgtc ctcgctgtcc tggctgacgt    20100
cctgcaggac cacatgcttg gtcttgcggg gtttcttctt gggcggcagc ggcggcggag    20160
atgttggaga tggcgagggg gagcgcgagt tctcgctcac cactactatc tcttcctctt    20220
cttggtccga ggccacgcgg cggtaggtat gtctcttcgg gggcagaggc ggaggcgacg    20280
ggctctcgcc gccgcgactt ggcggatggc tggcagagcc ccttccgcgt tcgggggtgc    20340
gctcccggcg gcgctctgac tgacttcctc cgcggccggc cattgtgttc tcctagggag    20400
gaacaacaag catggagact cagccatcgc caacctcgcc atctgccccc accgccgacg    20460
agaagcagca gcagcagaat gaaagcttaa ccgccccgcc gcccagcccc gccacctccg    20520
acgcggccgt cccagacatg caagagatgg aggaatccat cgagattgac ctgggctatg    20580
tgacgcccgc ggagcacgag gaggagctgg cagtgcgctt ttcacaagaa gagatacacc    20640
aagaacagcc agagcaggaa gcagagaatg agcagagtca ggctgggctc gagcatgacg    20700
gcgactacct ccacctgagc gggggggagg acgcgctcat caagcatctg gcccggcagg    20760
ccaccatcgt caaggatgcg ctgctcgacc gcaccgaggt gccctcagc gtggaggagc    20820 tcagccgcgc ctacgagttg aacctcttct cgccgcgcgt gccccccaag cgccagccca    20880
atggcacctg cgagcccaac ccgcgcctca acttctaccc ggtcttcgcg gtgcccgagg    20940
ccctggccac ctaccacatc tttttcaaga accaaaagat cccgtctcc tgccgcgcca    21000 accgcacccg cgccgacgcc cttttcaacc tgggtcccgg cgcccgccta cctgatatcg    21060
cctccttgga agaggttccc aagatcttcg agggtctggg cagcgacgag actcgggccg    21120
cgaacgctct gcaaggagaa ggaggagagc atgagcacca cagcgccctg gtcgagttgg    21180
aaggcgacaa cgcgcggctg gcggtgctca aacgcacggt cgagctgacc catttcgcct    21240
acccggctct gaacctgccc cccaaagtca tgagcgcggt catggaccag gtgctcatca    21300
agcgcgcgtc gcccatctcc gaggacgagg gcatgcaaga ctccgaggag ggcaagcccg    21360
tggtcagcga cgagcagctg gcccggtggc tgggtcctaa tgctagtccc cagagtttgg    21420
aagagcggcg caaactcatg atggccgtgg tcctggtgac cgtggagctg gagtgcctgc    21480
gccgcttctt cgccgacgcg gagaccctgc gcaaggtcga ggagaacctg cactacctct    21540
tcaggcacgg gttcgtgcgc caggcctgca agatctccaa cgtggagctg accaacctgg    21600
tctcctacat gggcatcttg cacgagaacc gcctggggca gaacgtgctg cacaccaccg    21660
tgcgcgggga ggcccggcgc gactacatcc gcgactgcgt ctacctctac ctctgccaca    21720
```

```
cctggcagac gggcatgggc gtgtggcagc agtgtctgga ggagcagaac ctgaaagagc    21780
tctgcaagct cctgcagaag aacctcaagg gtctgtggac cgggttcgac gagcgcacca    21840
ccgcctcgga cctggccgac ctcatttttcc ccgagcgcct caggctgacg ctgcgcaacg    21900
gcctgcccga ctttatgagc caaagcatgt tgcaaaactt tcgctctttc atcctcgaac    21960
gctccggaat cctgcccgcc acctgctccg cgctgccctc ggacttcgtg ccgctgacct    22020
tccgcgagtg cccccccgccg ctgtggagcc actgctacct gctgcgcctg gccaactacc    22080
tggcctacca ctcggacgtg atcgaggacg tcagcggcga gggcctgctc gagtgccact    22140
gccgctgcaa cctctgcacg ccgcaccgct ccctggcctg caacccccag ctgctgagcg    22200
agacccagat catcggcacc ttcgagttgc aagggcccag cgaaggcgag ggttcagccg    22260
ccaagggggg tctgaaactc accccggggc tgtggacctc ggcctacttg cgcaagttcg    22320
tgcccgagga ctaccatccc ttcgagatca ggttctacga ggaccaatcc catccgccca    22380
aggccgagct gtcggcctgc gtcatcaccc aggggggcgat cctggcccaa ttgcaagcca    22440
tccagaaatc ccgccaagaa ttcttgctga aaaagggccg cggggtctac ctcgaccccc    22500
agaccggtga ggagctcaac cccggcttcc cccaggatgc cccgaggaaa caagaagctg    22560
aaagtggagc tgccgcccgt ggaggatttg gaggaagact gggagaacag cagtcaggca    22620
gaggaggagg agatggagga agactgggac agcactcagg cagaggagga cagcctgcaa    22680
gacagtctgg aggaagacga ggaggaggca gaggaggagg tggaagaagc agccgccgcc    22740
agaccgtcgt cctcggcggg ggagaaagca agcagcacgg ataccatctc cgctccgggt    22800
cggggtcccg ctcgaccaca cagtagatgg gacgagaccg gacgattccc gaaccccacc    22860
acccagaccg gtaagaagga gcggcaggga tacaagtcct ggcggggggca caaaaacgcc    22920 atcgtctcct gcttgcaggc ctgcgggggc aacatctcct tcacccggcg ctacctgctc    22980
ttccaccgcg gggtgaactt tcccccgcaac atcttgcatt actaccgtca cctccacagc    23040
ccctactact tccaagaaga ggcagcagca gcagaaaaag accagcagaa aaccagcagc    23100
tagaaaatcc acagcggcgg cagcaggtgg actgaggatc gcggcgaacg agccggcgca    23160
aacccgggag ctgaggaacc ggatctttcc caccctctat gccatcttcc agcagagtcg    23220
ggggcaggag caggaactga aagtcaagaa ccgttctctg cgctcgctca cccgcagttg    23280
tctgtatcac aagagcgaag accaacttca gcgcactctc gaggacgccg aggctctctt    23340
caacaagtac tgcgcgctca ctcttaaaga gtagcccgcg cccgcccagt cgcagaaaaa    23400
ggcgggaatt acgtcacctg tgcccttcgc cctagccgcc tccacccatc atcatgagca    23460
aagagattcc cacgccttac atgtggagct accagcccca gatgggcctg ccgccggtg    23520 ccgcccagga ctactccacc cgcatgaatt ggctcagcgc cgggcccgcg atgatctcac    23580
gggtgaatga catccgcgcc caccgaaacc agatactcct agaacagtca gcgctcaccg    23640
ccacgccccg caatcacctc aatccgcgta attggcccgc cgcccggtg taccaggaaa    23700 ttccccagcc cacgaccgta ctacttccgc gagacgccca ggccgaagtc cagctgacta    23760
actcaggtgt ccagctggcg ggcggcgcca cctgtgtcg tcaccgcccc gctcagggta    23820
taaagcggct ggtgatccgg ggcagaggca cacagctcaa cgacgaggtg gtgagctctt    23880
cgctgggtct gcgacctgac ggagtcttcc aactcgccgg atcggggaga tcttccttca    23940
cgcctcgtca ggccgtcctg actttggaga gttcgtcctc gcagcccgc tcgggtggca    24000 tcggcactct ccagttcgtg gaggagttca ctcccctcgg ctacttcaac cccttctccg    24060
```

```
gctcccccgg ccactacccg gacgagttca tcccgaactt cgacgccatc agcgagtcgg    24120
tggacggcta cgattgagtt taaactcacc cccttatcca gtgaaataaa gatcatattg    24180
atgatgattt tacagaaata aaaaataatc atttgatttg aaataaagat acaatcatat    24240
tgatgatttg agtttaacaa aaaaataaag aatcacttac ttgaaatctg ataccaggtc    24300
tctgtccatg ttttctgcca acaccacttc actccctct tcccagctct ggtactgcag     24360
gccccggcgg gctgcaaact tcctccacac gctgaagggg atgtcaaatt cctcctgtcc    24420
ctcaatcttc attttatctt ctatcagatg tccaaaaagc gcgtccgggt ggatgatgac    24480
ttcgaccccg tctaccccta cgatgcagac aacgcaccga ccgtgccctt catcaacccc    24540
cccttcgtct cttcagatgg attccaagag aagcccctgg gggtgttgtc cctgcgactg    24600
gccgaccccg tcaccaccaa gaacggggaa atcaccctca gctgggagag ggggtggac     24660 ctcgattcct cgggaaaact catctccaac acggccacca aggccgccgc ccctctcagt    24720
ttttccaaca acaccatttc ccttaacatg gatcacccct tttacactaa agatggaaaa    24780
ttatccttac aagtttctcc accattaaat atactgagaa caagcattct aaacacacta    24840
gctttaggtt ttggatcagg tttaggactc cgtggctctg ccttggcagt acagttagtc    24900
tctccactta catttgatac tgatggaaac ataaagctta ccttagacag aggtttgcat    24960
gttacaacag gagatgcaat tgaaagcaac ataagctggg ctaaaggttt aaaatttgaa    25020
gatggagcca tagcaaccaa cattggaaat gggttagagt ttggaagcag tagtacagaa    25080
acaggtgttg atgatgctta cccaatccaa gttaaacttg gatctggcct tagctttgac    25140
agtacaggag ccataatggc tggtaacaaa gaagacgata aactcacttt gtggacaaca    25200
cctgatccat caccaaactg tcaaatactc gcagaaaatg atgcaaaact aacactttgc    25260
ttgactaaat gtggtagtca aatactggcc actgtgtcag tcttagttgt aggaagtgga    25320
aacctaaacc ccattactgg caccgtaagc agtgctcagg tgtttctacg ttttgatgca    25380
aacggtgttc ttttaacaga acattctaca ctaaaaaaat actgggggta taggcaggga    25440
gatagcatag atggcactcc atataccaat gctgtaggat tcatgcccaa tttaaaagct    25500
tatccaaagt cacaaagttc tactactaaa aataatatag tagggcaagt atacatgaat    25560
ggagatgttt caaaacctat gcttctcact ataaccctca atggtactga tgacagcaac    25620
agtacatatt caatgtcatt ttcatacacc tggactaatg gaagctatgt tggagcaaca    25680 tttgggggcta actcttatac cttctcatac atcgcccaag aatgaacact gtatcccacc    25740
ctgcatgcca acccttccca ccccactctg tggaacaaac tctgaaacac aaaataaaat    25800
aaagttcaag tgttttattg attcaacagt ttcacagaac cctagtattc aacctgccac    25860
ctccctccca acacacagag tacacagtcc tttctccccg gctggcctta aaaagcatca    25920
tatcatgggt aacagacata ttcttaggtg ttatattcca cacggtttcc tgtcgagcca    25980
aacgctcatc agtgatatta ataaactccc cgggcagctc acttaagttc atgtcgctgt    26040
ccagctgctg agccacaggc tgctgtccaa cttgcgttg cttaacgggc ggcgaaggag      26100
aagtccacgc ctacatgggg gtagagtcat aatcgtgcat caggataggg cggtggtgct    26160
gcagcagcgc gcgaataaac tgctgccgcc gccgctccgt cctgcaggaa tacaacatgg    26220
cagtggtctc ctcagcgatg attcgcaccg cccgcagcat aaggcgcctt gtcctccggg    26280
cacagcagcg caccctgatc tcacttaaat cagcacagta actgcagcac agcaccacaa    26340
tattgttcaa aatcccacag tgcaaggcgc tgtatccaaa gctcatggcg gggaccacag    26400
aacccacgtg gccatcatac cacaagcgca ggtagattaa gtggcgaccc ctcataaaca    26460
```

```
cgctggacat aaacattacc tcttttggca tgttgtaatt caccacctcc cggtaccata   26520
taaacctctg attaaacatg gcgccatcca ccaccatcct aaaccagctg gccaaaacct   26580
gcccgccggc tatacactgc agggaaccgg gactggaaca atgacagtgg agagcccagg   26640
actcgtaacc atggatcatc atgctcgtca tgatatcaat gttggcacaa cacaggcaca   26700
cgtgcataca cttcctcagg attacaagct cctcccgcgt tagaaccata tcccagggaa   26760
caacccattc ctgaatcagc gtaaatccca cactgcaggg aagacctcgc acgtaactca   26820
cgttgtgcat tgtcaaagtg ttacattcgg gcagcagcgg atgatcctcc agtatggtag   26880
cgcgggtttc tgtctcaaaa ggaggtagac gatccctact gtacgagtg cgccgagaca   26940 accgagatcg tgttggtcgt agtgtcatgc caaatggaac gccggacgta gtcatatttc   27000
ctgaagcaaa accaggtgcg ggcgtgacaa acagatctgc gtctccggtc tcgccgctta   27060
gatcgctctg tgtagtagtt gtagtatatc cactctctca aagcatccag gcgcccctg    27120 gcttcgggtt ctatgtaaac tccttcatgc gccgctgccc tgataacatc caccaccgca   27180
gaataagcca cacccagcca acctacacat tcgttctgcg agtcacacac gggaggagcg   27240
ggaagagctg gaagaaccat gattaacttt attccaaacg gtctcggagc acttcaaaat   27300
gcaggtcccg gaggtggcac ctctcgcccc cactgtgttg gtggaaaata acagccaggt   27360
caaaggtgac acggttctcg agatgttcca cggtggcttc cagcaaagcc tccacgcgca   27420
catccagaaa caagaggaca gcgaaagcgg gagcgttttc taattcctca atcatcatat   27480
tacactcctg caccatcccc agataatttt cattttttcca gccttgaatg attcgtatta   27540
gttcctgagg taaatccaag ccagccatga taaaaagctc gcgcagagcg ccctccaccg   27600
gcattcttaa gcacaccctc ataattccaa gagattctgc tcctggttca cctgcagcag   27660
attaacaatg ggaatatcaa aatctctgcc gcgatcccta agctcctccc tcaacaataa   27720
ctgtatgtaa tctttcatat catctccgaa attttttagcc atagggccgc caggaataag   27780
agcagggcaa gccacattac agataaagcg aagtcctccc cagtgwgcat tgccaaatgt   27840
aagattgaaa taagcatgct ggctagaccc tgtgatatct tccagataac tggacagaaa   27900
atcaggcaag caatttttaa gaaaatcaac aaaagaaaag tcgtccaggt gcaggtttag   27960
agcctcagga acaacgatgg aataagtgca aggagtgcgt tccagcatgg ttagtgtttt   28020
tttggtgatc tgtagaacaa aaaataaaca tgcaatatta aaccatgcta gcctggcgaa   28080
caggtgggta aatcactctt tccagcacca ggcaggctac ggggtctccg gcgcgaccct   28140
cgtagaagct gtcgccatga ttgaaaagca tcaccgagag accttcccgg tggccggcat   28200
ggatgattcg agaagaagca tacactccgg gaacattggc atccgtgagt gaaaaaaagc   28260
gacctataaa gcctcgggc actacaatgc tcaatctcaa ttccagcaaa gccacccat    28320 gcggatggag cacaaaattg gcaggtgcgt aaaaaatgta attactcccc tcctgcacag   28380
gcagcaaagc ccccgctccc tccagaaaca catacaaagc ctcagcgtcc atagcttacc   28440
gagcacggca ggcgcaagag tcagagaaaa ggctgagctc taacctgact gcccgctcct   28500
gtgctcaata tatagcccta acctacactg acgtaaaggc caaagtctaa aaatacccgc   28560
caaataatca cacacgccca gcacacgccc agaaaccggt gacacactca aaaaaatacg   28620
cgcacttcct caaacgccca aaactgccgt catttccggg ttcccacgct acgtcatcaa   28680
aacacgactt tcaaattccg tcgaccgtta aaaacgtcac ccgccccgcc cctaacggtc   28740
gcccgtctct cagccaatca gcgccccgca tccccaaatt caaacacctc atttgcatat   28800
```

```
taacgcgcac aaaaagtttg aggtatatta ttgatgatgg ttaattaagg atccttctat    28860
agtgtcacct aaatgtcgac ggccaggcgg ccgccaggcc tacccactag tcaattcggg    28920
aggatcgaaa cggcagatcg caaaaaacag tacatacaga aggagacatg aacatgaaca    28980
tcaaaaaaat tgtaaaacaa gccacagttc tgacttttac gactgcactt ctggcaggag    29040
gagcgactca agccttcgcg aaagaaaata accaaaaagc atacaaagaa acgtacggcg    29100
tctctcatat tacacgccat gatatgctgc agatccctaa acagcagcaa aacgaaaaat    29160
accaagtgcc tcaattcgat caatcaacga ttaaaaatat tgagtctgca aaaggacttg    29220
atgtgtggga cagctggccg ctgcaaaacg ctgacggaac agtagctgaa tacaacggct    29280
atcacgttgt gtttgctctt gcgggaagcc cgaaagacgc tgatgacaca tcaatctaca    29340
tgttttatca aaaggtcggc gacaactcaa tcgacagctg gaaaaacgcg ggccgtgtct    29400
ttaaagacag cgataagttc gacgccaacg atccgatcct gaaagatcag acgcaagaat    29460
ggtccggttc tgcaaccttt acatctgacg gaaaaatccg tttattctac actgactatt    29520
ccggtaaaca ttacggcaaa caaagcctga caacagcgca ggtaaatgtg tcaaaatctg    29580
atgacacact caaaatcaac ggagtggaag atcacaaaac gatttttgac ggagacggaa    29640
aaacatatca gaacgttcag cagtttatcg atgaaggcaa ttatacatcc ggcgacaacc    29700
atacgctgag agaccctcac tacgttgaag acaaaggcca taaatacctt gtattcgaag    29760
ccaacacggg aacagaaaac ggataccaag gcgaagaatc tttatttaac aaagcgtact    29820
acggcggcgg cacgaacttc ttccgtaaag aaagccagaa gcttcagcag agcgctaaaa    29880
aacgcgatgc tgagttagcg aacggcgccc tcggtatcat agagttaaat aatgattaca    29940
cattgaaaaa agtaatgaag ccgctgatca cttcaaacac ggtaactgat gaaatcgagc    30000
gcgcgaatgt tttcaaaatg aacggcaaat ggtacttgtt cactgattca cgcggttcaa    30060
aaatgacgat cgatggtatt aactcaaacg atatttacat gcttggttat gtatcaaact    30120
ctttaaccgg cccttacaag ccgctgaaca aaacaggggc tgtgctgcaa atgggtcttg    30180
atccaaacga tgtgacattc acttactctc acttcgcagt gccgcaagcc aaaggcaaca    30240
atgtggttat cacaagctac atgacaaaca gaggcttctt cgaggataaa aaggcaacat    30300
ttgcgccaag cttcttaatg aacatcaaag gcaataaaac atccgttgtc aaaaacagca    30360
tcctggagca aggacagctg acagtcaact aataacagca aaaagaaaat gccgatactt    30420
cattggcatt ttcttttatt tctcaacaag atggtgaatt gactagtggg tagatccaca    30480
ggacgggtgt ggtcgccatg atcgcgtagt cgatagtggc tccaagtagc gaagcgagca    30540
ggactgggcg gcggccaaag cggtcggaca gtgctccgag aacgggtgcg catagaaatt    30600
gcatcaacgc atatagcgct agcagcacgc catagtgact ggcgatgctg tcggaatgga    30660
cgatatcccg caagaggccc ggcagtaccg gcataaccaa gcctatgcct acagcatcca    30720
gggtgacggt gccgaggatg acgatgagcg cattgttaga tttcatacac ggtgcctgac    30780
tgcgttagca atttaactgt gataaactac cgcattaaag cttatcgatg ataagctgtc    30840
aaacatgaga attgatccgg aacccttaat ataacttcgt ataatgtatg ctatacgaag    30900
ttattaggtc cctcgactat agggtcaccg tcgacagcga cacacttgca tcggatgcag    30960
cccggttaac gtgccggcac ggcctgggta accaggtatt ttgtccacat aaccgtgcgc    31020
aaaatgttgt ggataagcag gacacagcag caatccacag caggcataca accgcacacc    31080
gaggttactc cgttctacag gttacgacga catgtcaata cttgcccttg acaggcattg    31140
atggaatcgt agtctcacgc tgatagtctg atcgacaata caagtgggac cgtggtccca    31200
```

```
gaccgataat cagaccgaca acacgagtgg gatcgtggtc ccagactaat aatcagaccg   31260
acgatacgag tgggaccgtg gtcccagact aataatcaga ccgacgatac gagtgggacc   31320
gtggttccag actaataatc agaccgacga tacgagtggg accgtggtcc cagactaata   31380
atcagaccga cgatacgagt gggaccatgg tcccagacta ataatcagac cgacgatacg   31440
agtgggaccg tggtcccagt ctgattatca gaccgacgat acgagtggga ccgtggtccc   31500
agactaataa tcagaccgac gatacgagtg gaccgtggt cccagactaa taatcagacc   31560
gacgatacga gtgggaccgt ggtcccagtc tgattatcag accgacgata caagtggaac   31620
agtgggccca gagagaatat tcaggccagt tatgctttct ggcctgtaac aaaggacatt   31680
aagtaaagac agataaacgt agactaaaac gtggtcgcat cagggtgctg gcttttcaag   31740
ttccttaaga atggcctcaa ttttctctat acactcagtt ggaacacgag acctgtccag   31800
gttaagcacc attttatcgc ccttatacaa tactgtcgct ccaggagcaa actgatgtcg   31860
tgagcttaaa ctagttcttg atgcagatga cgttttaagc acagaagtta aaagagtgat   31920
aacttcttca gcttcaaata tcaccccagc ttttttctgc tcatgaaggt tagatgcctg   31980
ctgcttaagt aattcctctt tatctgtaaa ggcttttga agtgcatcac ctgaccgggc   32040
agatagttca ccggggtgag aaaaaagagc aacaactgat ttaggcaatt tggcggtgtt   32100
gatacagcgg gtaataatct tacgtgaaat attttccgca tcagccagcg cagaaaatatt   32160 tccagcaaat tcattctgca atcggcttgc ataacgctga ccacgttcat aagcacttgt   32220
tgggcgataa tcgttaccca atctggataa tgcagccatc tgctcatcat ccagctcgcc   32280
aaccagaaca cgataatcac tttcggtaag tgcagcagct ttacgacggc gactcccatc   32340 ggcaattct atgacaccag atactcttcg accgaacgcc ggtgtctgtt gaccagtcag   32400
tagaaaagaa gggatgagat catccagtgc gtcctcagta agcagctcct ggtcacgttc   32460
attacctgac catacccgag aggtcttctc aacactatca ccccggagca cttcaagagt   32520
aaacttcaca tcccgaccac atacaggcaa agtaatggca ttaccgcgag ccattactcc   32580
tacgcgcgca attaacgaat ccaccatcgg ggcagctggt gtcgataacg aagtatcttc   32640
aaccggttga gtattgagcg tatgttttgg aataacaggc gcacgcttca ttatctaatc   32700
tcccagcgtg gtttaatcag acgatcgaaa atttcattgc agacaggttc ccaaatagaa   32760
agagcatttc tccaggcacc agttgaagag cgttgatcaa tggcctgttc aaaaacagtt   32820
ctcatccgga tctgaccttt accaacttca tccgtttcac gtacaacatt ttttagaacc   32880
atgcttcccc aggcatcccg aatttgctcc tccatccacg gggactgaga gccattacta   32940
ttgctgtatt tggtaagcaa aatacgtaca tcaggctcga acccttttaag atcaacgttc   33000 ttgagcagat cacgaagcat atcgaaaaac tgcagtgcgg aggtgtagtc aaacaactca   33060
gcaggcgtgg gaacaatcag cacatcagca gcacatacga cattaatcgt gccgataccc   33120
aggttaggcg cgctgtcaat aactatgaca tcatagtcat gagcaacagt ttcaatggcc   33180
agtcggagca tcaggtgtgg atcggtgggc agtttacctt catcaaattt gcccattaac   33240
tcagtttcaa tacggtgcag agccagacag gaaggaataa tgtcaagccc cggccagcaa   33300 gtgggctta ttgcataagt gacatcgtcc ttttccccaa gatagaaagg caggagagtg   33360
tcttctgcat gaatatgaag atctggtacc catccgtgat acattgaggc tgttccctgg   33420
gggtcgttac cttccacgag caaaacacgt agcccttca gagccagatc ctgagcaaga   33480
tgaacagaaa ctgaggtttt gtaaacgcca cctttatggg cagcaacccc gatcaccggt   33540
```

```
ggaaatacgt cttcagcacg tcgcaatcgc gtaccaaaca catcacgcat atgattaatt    33600
tgttcaattg tataaccaac acgttgctca acccgtcctc gaatttccat atccgggtgc    33660
ggtagtcgcc ctgctttctc ggcatctctg atagcctgag aagaaacccc aactaaatcc    33720
gctgcttcac ctattctcca gcgccgggtt attttcctcg cttccgggct gtcatcatta    33780
aactgtgcaa tggcgatagc cttcgtcatt tcatgaccag cgtttatgca ctggttaagt    33840
gtttccatga gtttcattct gaacatcctt taatcattgc tttgcgtttt tttattaaat    33900
cttgcaattt actgcaaagc aacaacaaaa tcgcaaagtc atcaaaaaac cgcaaagttg    33960
tttaaaataa gagcaacact acaaaaggag ataagaagag cacatacctc agtcacttat    34020
tatcactagc gctcgccgca gccgtgtaac cgagcatagc gagcgaactg gcgaggaagc    34080
aaagaagaac tgttctgtca gatagctctt acgctcagcg caagaagaaa tatccaccgt    34140
gggaaaaact ccaggtagag gtacacacgc ggatagccaa ttcagagtaa taaactgtga    34200
taatcaaccc tcatcaatga tgacgaacta accccgata tcaggtcaca tgacgaaggg    34260
aaagagaagg aaatcaactg tgacaaactg ccctcaaatt tggcttcctt aaaaattaca    34320
gttcaaaaag tatgagaaaa tccatgcagg ctgaaggaaa cagcaaaact gtgacaaatt    34380
accctcagta ggtcagaaca aatgtgacga accaccctca aatctgtgac agataaccct    34440
cagactatcc tgtcgtcatg gaagtgatat cgcggaagga aaatacgata tgagtcgtct    34500
ggcggccttt cttttctca atgtatgaga ggcgcattgg agttctgctg ttgatctcat    34560
taacacagac ctgcaggaag cggcggcgga agtcaggcat acgctggtaa ctttgaggca    34620
gctggtaacg ctctatgatc cagtcgattt cagagagac gatgcctgag ccatccggct    34680
tacgatactg acacagggat tcgtataaac gcatggcata cggattggtg atttcttttg    34740
tttcactaag ccgaaactgc gtaaaccggt tctgtaaccc gataaagaag ggaatgagat    34800
atgggttgat atgtacactg taaagccctc tggatggact gtgcgcacgt ttgataaacc    34860
aaggaaaaga ttcatagcct ttttcatcgc cggcatcctc ttcagggcga taaaaaacca    34920
cttccttccc cgcgaaactc ttcaatgcct gccgtatatc cttactggct tccgcagagg    34980
tcaatccgaa tatttcagca tatttagcaa catggatctc gcagataccg tcatgttcct    35040
gtagggtgcc atcagatttt ctgatctggt caacgaacag atacagcata cgttttgat    35100 cccgggagag actatatgcc gcctcagtga ggtcgtttga ctggacgatt cgcgggctat    35160
ttttacgttt cttgtgattg ataaccgctg tttccgccat gacagatcca tgtgaagtgt    35220
gacaagtttt tagattgtca cactaaataa aaaagagtca ataagcaggg ataactttgt    35280
gaaaaaacag cttcttctga gggcaatttg tcacagggtt aagggcaatt tgtcacagac    35340
aggactgtca tttgagggtg atttgtcaca ctgaaagggc aatttgtcac aacaccttct    35400
ctagaaccag catggataaa ggcctacaag cgcgctctaaa aagaagatc taaaaactat    35460 aaaaaaaata attataaaaa tatccccgtg gataagtgga taaccccaag ggaagttttt    35520
tcaggcatcg tgtgtaagca gaatatataa gtgctgttcc ctggtgcttc ctcgctcact    35580
cgagggcttc gccctgtcgc tcaactgcgg cgagcactac tggctgtaaa aggacagacc    35640
acatcatggt tctgtgttca ttaggttgtt ctgtccattg ctgacataat ccgctccact    35700
tcaacgtaac accgcacgaa gatttctatt gttcctgaag gcatattcaa atcgttttcg    35760
ttaccgcttg caggcatcat gacagaacac tacttcctat aaacgctaca caggctcctg    35820
agattaataa tgcggatctc tacgatatg ggagattttc ccgactgttt cgttcgcttc    35880
tcagtggata acagccagct tctctgttta acagacaaaa acagcatatc cactcagttc    35940
```

```
cacatttcca tataaaggcc aaggcattta ttctcaggat aattgtttca gcatcgcaac    36000
cgcatcagac tccggcatcg caaactgcac ccggtgccgg gcagccacat ccagcgcaaa    36060
aaccttcgtg tagacttccg ttgaactgat ggacttatgt cccatcaggc tttgcagaac    36120
tttcagcggt ataccggcat acagcatgtg catcgcatag gaatggcgga acgtatgtgg    36180
tgtgaccgga acagagaacg tcacaccgtc agcagcagcg gcggcaaccg cctccccaat    36240
ccaggtcctg accgttctgt ccgtcacttc ccagatccgc gctttctctg tccttcctgt    36300
gcgacggtta cgccgctcca tgagcttatc gcgaataaat acctgtgacg gaagatcact    36360
tcgcagaata aataaatcct ggtgtccctg ttgataccgg gaagccctgg gccaactttt    36420
ggcgaaaatg agacgttgat cggcacgtaa gaggttccaa ctttcaccat aatgaaataa    36480
gatcactacc gggcgtattt tttgagttat cgagattttc aggagctaag gaagctaaaa    36540
tggagaaaaa aatcactgga tataccaccg ttgatatatc ccaatggcat cgtaaagaac    36600
attttgaggc atttcagtca gttgctcaat gtacctataa ccagaccgtt cagctggata    36660
ttacggcctt tttaaagacc gtaaagaaaa ataagcacaa gttttatccg gcctttattc    36720
acattcttgc ccgcctgatg aatgctcatc cggagttccg tatggcaatg aaagacggtg    36780
agctggtgat atgggatagt gttcacccct gttacaccgt tttccatgag caaactgaaa    36840
cgttttcatc gctctggagt gaataccacg acgatttccg gcagtttcta cacatatatt    36900
cgcaagatgt ggcgtgttac ggtgaaaacc tggcctattt ccctaaaggg tttattgaga    36960
atatgttttt cgtctcagcc aatccctggg tgagtttcac cagttttgat ttaaacgtgg    37020
ccaatatgga caacttcttc gcccccgttt tcaccatggg caaatattat acgcaaggcg    37080
acaaggtgct gatgccgctg gcgattcagg ttcatcatgc cgtttgtgat ggcttccatg    37140
tcggcagaat gcttaatgaa ttacaacagt actgcgatga gtggcagggc ggggcgtaat    37200
ttttttaagg cagttattgg tgcccttaaa cgcctggttg ctacgcctga taagtgata    37260
ataagcggat gaatggcaga aattcgatga taagctgtca acatgagaa ttggtcgacg    37320
gcgcgccaaa gcttgcatgc ctgcagccgc gtaacctggc aaaatcggtt acggttgagt    37380
aataaatgga tgccctgcgt aagcggggca catttcatta cctctttctc cgcacccgac    37440
atagataata acttcgtata gtatacatta tacgaagtta tctagtagac                37490
```

<210> SEQ ID NO 69  
<211> LENGTH: 143055  
<212> TYPE: DNA  
<213> ORGANISM: Artificial Sequence  
<220> FEATURE:  
<223> OTHER INFORMATION: viral construct

<400> SEQUENCE: 69

```
tatttattta gtgtctagaa aaaatgtgt gaccaacgac cgtaggaaac tctagagggt        60
aagaaaaatc aatcgcttta tagagaccat cagaaagagg tttaatatttt ttgtgagacc     120
atcgaaggag aaagagataa aacttttta cgactccatc agaaagaggt ttaatatttt       180
tgtgagacca tcgaagagag aaagagataa aacttttta cgactccatc                  240
agaaagaggt ttaatatttt tgtgagacca tcgaagagag aaagagataa aacttttta      300
cgactccatc agaaagaggt ttaatatttt tgtgagacca tcgaaggaga aagagataaa     360
acttttttac gactccatca gaaagaggtt taatatttt gtgagaccat cgaaggagaa     420
agagataaaa cttttttacg actccatcag aaagaggttt aatatttttg tgagaccatc     480
```

```
gagataaaac ttttttacga ctccatcaga aagaggttta atattttttgt gagaccatcg      540 aagagagaaa gagataaaac ttttttacga ctccatcaga aagaggttta atattttttgt      600 gagaccatcg aaggagaaag agataaaact ttttacgac tccatcagaa agaggtttaa       660 tattttttgtg agaccatcga agagagaaag agaataaaaa tattttagtg acaccatcag      720
aaagaggttt aatattttttg tgagaccatc gaagagagaa agagataaaa ctttttttacg    780 actccatcag aaagaggttt aatattttttg tgagaccatc gaaggagaaa gagataaaac     840
ttttttacga ctccatcaga aagaggttta atattttttgt gagaccatcg aagagagaaa    900
gagataaaac ttttttacga ctccatcaga aagaggttta atattttttgt gagaccatcg     960 aagagagaaa gagataaaac ttttttacga ctccatcaga aagaccatcg aagagagaaa    1020
gagaaagaga tagttagtct agatattttt cttagtacaa aagtcaatgt tttaaaatat    1080
atggacaaga atttgtctgt ataaaaactt gtgtgaaatt ttgtaccaaa gaaaaaatgt    1140
gagcagtatc ccctacatgg attttactag atcattatata taccaaaaaa tattatacga   1200
tctacgtttt attatatgat tttaacgtgt aaattataaa cattatttta tgatatacaa    1260
ttgtctggta acctagatgg gcataggggaa tgagtatatg ttgttggacg ttattgttta   1320
agaaatagtt gatgcatcag aaagaggttt aatattttttg tgagaccatc gaagagagaa    1380
agagataaaa cttttttacg actccatcag aaagaggttt aatattttttg tgagaccatc    1440 gaagagagaa agagataaaa cttttttatg actccattga agagagaatg agaataaaaa     1500
tattttagtg acaccatcag aaagaggttt aatattttttt atgagaccat caaagagaga   1560
aagagaataa aaatattttta tgactccatt gaagagagaa agagaaaatg agaataaaaa    1620
tattttagtg acaccatcag aaagaggttt aatattttttt atgagaccat caaagagaga   1680
aagagaataa aaatattttt gtaaaacttt ttttatgaga ccatcaaaga gagaaagaga     1740
ataaaaatat ttttgtaaaa ctttttttat gagaccatca agagagaaa gagaataaaa     1800 atattttttgt aaaacttttt ttatgagacc atcaaagaga gaaagagaat aaaaatattt    1860
ttgtaaaact ttttttatga ccatcaaaa gagagaaaga gaataaaaat attttttgtaa     1920 aactttttttt atgagaccat caaagagaga aagagaataa aaatattttt gtaaaacttt    1980
ttttatgaga ccatcaaaga gaaagagaga ataaaaatat ttttgtaaaa ctttttttat    2040
gagaccatca aagagagaaa gagaataaaa atattttatg actccattga agagagaaag    2100
agataaaaaa tattttagtg acaccatcag aaagaggttt aatattttttg tgagaccatc    2160 gaagagagaa agagaataaa aatattttat gactccattg aagagagaaa gagaataaaa    2220
atattttagt gacaccatca gaaagaggtt taatatttttt tatgagacca tcaaagagag   2280
aaagagaata aaaatatttt tgtaaaactt ttttttatgag accatcaaag agagaaagag    2340
aataaaaata tttttgtaaa actttttttta tgagaccatc aaagagagaa agagaataaa    2400 aatattttttg taaaacttttt ttatgagac catcaaagag agaaagagaa taaaaatatt    2460
tttgtaaaac ttttttttatg agaccatcaa agagagaaag agaataaaaa tattttttgta   2520 aacttttttt tatgagacca tcaaagagag aaagagaata aaaatatttt atgactccat    2580
tgaagagaga atgagaataa aaatattttta gtgacaccat cagaaagagg tttaatatttt   2640 ttgtgagacc atcgaagaga gaaagagaat aaaaatatttt tatgactcca ttgaagagag   2700
aaagagaata aaaatatttt agtgacacca tcagaaagag gtttaatatt ttttatgaga    2760
ccatcaaaga gagaaagaga ataaaaatat ttttgtaaaa ctttttttat gagaccatca    2820
aagagagaaa gagaataaaa atattttttgt aaaacttttt ttatgagacc atcaaagaga    2880
```

-continued

```
gaaagagaat aaaaatattt ttgtaaaact ttttttatga gaccatcaaa gagagaaaga      2940
gaataaaaat attttgtaa aacttttttt atgagaccat caaagagaga aagagaataa      3000 aaatatttt gtaaaacttt ttttatgaga ccatcaaaga gagaaagaga ataaaaatat      3060
ttttgtaaaa ctttttttat gagaccatca aagagagaaa gagaataaaa atattttgt      3120 aaaactttt ttatgagacc atcaaagaga gaaagagaat aaaaatattt tatgactcca      3180
ttgaagagag aatgagaata aaaatatttt agtgacacca tcagaaagag gtttaatatt      3240
tttgtgagac catcgaagag agaaagagaa taaaaatatt ttatgactcc attgaagaga      3300
gaatgagaat aaaaatattt tagtgacacc atcagaaaga ggtttaatat ttttatgag      3360 accatcaaag agagaaagag aataaaaata tttttgtaaa acttttttta tgagaccatc      3420
aaagagagaa agagaataaa aatattttg taaaaattat aaacattatt ttatgatata      3480
caattgtctg gtaacctaga tgggcatagg ggatgttgat aagctcgacg agtatatgtt      3540
gttggacgtt attgtttaag aaatagttga tgcatcagaa agagaataaa aaatatttta      3600
gtgagaccat cgaagagaga aagagataaa acttttttac gactccatca gaaagaggtt      3660 taatatttt gtgagaccat cgaagagaga aagagataaa acttttttac gactccatca      3720
gaaagaggtt taatatttt gtgagaccat cgaaggagaa agagataaaa cttttttacg      3780
actccatcag aaagaggttt aatatttttg tgagaccatc aaagagagaa agagaataaa      3840 aatattttg taaaacttt tttatgagac catcaaagag agaaagagaa taaaaatatt      3900
tttgtaaaac ttttttatg agaccatcaa agagagaaag agaataaaaa tattttgta      3960 aaactttttt tatgagacca tcaaagagag aagagaata aaaatattt tgtaaaactt      4020 tttttatgag accatcaaag agagaaagag aataaaaata ttttatgact ccattgaaga      4080
gagaatgaga ataaaaatat tttagtgaca ccatcagaaa gaggtttaat attttgtga      4140 gaccatcgaa gagagaaaga gaataaaaat attttatgac tccattgaag agagaatgag      4200
aataaaaata ttttagtgac accatcagaa agaggtttaa tattttat gagaccatca      4260 aagagagaaa gagaataaaa atattttgt aaaactttt ttatgagacc atcaaagaga      4320
gaaagagaat aaaaatattt ttgtaaaact ttttttatga gaccatcaaa gagagaaaga      4380
gaataaaaat attttgtaa aacttttttt atgagaccat caaagagaga aagagaataa      4440 aaatatttt gtaaaacttt ttttatgaga ccatcaaaga gagaaagaga ataaaaatat      4500
tttatgactc cattgaagag agaatgagaa taaaaatatt ttagtgacac catcagaaag      4560
aggtttaata tttttgtgag accatcgaag agagaaagag aataaaaata ttttatgact      4620
ccattgaaga gagaaagaga ataaaaatat tttagtgaca ccatcagaaa gaggtttaat      4680 atttttatg agaccatcaa agagagaaag agaataaaaa tattttgta aaactttttt      4740 tatgagacca tcaaagagag aaagagaata aaaatatttt atgactccat tgaagagaga      4800
atgagaataa aaatattta gtgacaccat cagaaagagg tttaatattt ttgtgagacc      4860
atcgaagaga gaaagagaat aaaaatattt tatgactcca ttgaagagag aatgagaata      4920
aaaatatttt agtgacacca tcagaaagag gtttaatatt tttgtgagac catcgaagag      4980
agaaagagaa taaaaatatt ttatgactcc attgaagaga gaatgagaat aaaaatattt      5040
tagtgacacc atcagaaaga ggtttaatat ttttatgag accatcaaag agagaaagag      5100
aataaaaata ttttgtaaa acttttttta tgagaccatc aaagagagaa agagaataaa      5160 aatattttg taaaacttt tttatgagac catcaaagag agaaagagaa taaaaatatt      5220
```

```
tttgtaaaac ttttttttatg agaccatcaa agagagaaag agaataaaaa tattttttgtg      5280
agaccatcaa agagagaaag agaataaaaa tattttttgtg agaccatcaa agagagaaag      5340
agaataaaaa tattttttgtg agaccatcaa agagagaaag agaataaaaa tatttttatga     5400
ctccattgaa gagagaaaga gaataaaaat attttagtga caccatcaga aagaggttta       5460
atattttttgt gagaccatcg aagagagaaa gagaataaaa atattttatg actccattga      5520
agagagaaag agaataaaaa tattttagtg acaccatcag aaagaggttt aatattttt        5580
atgagaccat caaagagaga aagagaataa aaatatttt tatgagacca tcaaagagag        5640
aaagagaata aaaatatttt atgagaccat caaagagaga aagagaataa aaatatttt        5700
tatgagacca tcaaagagag aaagagaata aaaatatttt atgagaccat caaagagaga       5760
aagagaataa aaatatttt tatgagacca tcaaagagag aaagagaata aaaatatttt        5820
tgtatgagac catcagaaag aggtttaata ttttgtgat accctgaaag gaataggaa         5880
tagtgtcata atcgtatcac actattgaga cagaaaaga agaagtcgcg agaggtaact        5940
ttttgttttg caaaccggaa tatagtgtcc ggtacacttt tttaattcgt ggtgtgcctg       6000
aatcgttcga ttaaccctac tcatccaatt tcagatgaat agagttatcg attcagacac       6060
acgctttgag ttttgttgaa tcgatgagtg aagtatcatc ggttgcacct tcagatgccg       6120
atccgtcgac atacttgacc tcaagttcag atgattcctt gcacatgtct ccgatacgaa       6180
cgctaaactc tagattcttg acacattttg tatcgacgat cgttgaaccg atgatatctt       6240
cgtaactcac tttcttatga gagatgttag acccgagtac tggatgggtc ttgatgtcgc       6300
tgtctttctc ttcttcgcta catctgatgt cgatagacac ctcacagtct ttccatcagc       6360
ggattctgag atggatttaa tctgaggaca tttggtgaat ccaaagttca ttctcagacc       6420
tccaccgatg atgagtaat aagtggtagg aggatctaca tcctcgactg attccacctc        6480
gggatctgga tctgactcgg actctgtaat ttccgttacg gattggcaaa tcttatcatc       6540
ggtcggtgtt tggtcttgct ttgtgacttt gataataaca tcgattccca tatgatgttt       6600
gttttcttct tccgtacacg atgaggatga ttgctgaaga ctggcaggca catgcatgcc       6660
agtacgatat attgtttcat gattgctatt gattgagtac tgttctttat gattctactt       6720
ccttaccgtg caataaatta gaatatattt tctacttta cgagaaatta attattgtat        6780
ttatgggtga aaaacttact ataaaaagcg ggtgggtttg gaattagtga tcagtttatg       6840
tatatcgcaa ctaccgggca tatggctaca ttacccacat gataagagat tgtatcagtt       6900
tcgtagtctt gagtattggt attactatat agtatataga tgtcgacgct agagttactg      6960
tctccgaatg cggcatgata gtatcattct ttgctttcgt taactgtttg gaggaagaat       7020
ctttgttatt gcatttaatc tcgaaattca gagtgcacac ctttctcctg taaagaaacc       7080
tgaagtcgct accttattaa gaagacggga tcgcagtctt tatgattcat agtaatagtt       7140
agttccgacg ttgagatgga ttcgctgaga ccggtagtgg tcgtccgagt acacgatgtg       7200
tcgttaactg gatacaggtt aatttccaca tcgatatagt taaaggtatt tctgggtacg       7260
ggttcgcatt tatctgcgga agagacggtg tgagaatatg ttccgagacc acacggagaa       7320
cagatgacgt ctccggatac tccgtatcct attccacatt ttgtttggga aacacatgcc       7380
ttgcatccat gatcgggaga gcattcacag attctattgt gagtcgtgtt acacgatcgc       7440
gtcgacattg ttgacagaaa cgtgaccttc attcttaccg tcgtccataa atacgttagg      7500
tatgtaccac atactgtcgc gaacgatgcg tccatctcat aatgatttac ttttttcataa     7560
ttaaagatgt gaaagaaaac cgaacaatat attttttttag taatgtttat gcgagacata     7620
```

```
taaaataaac tccgtgttta tgatgccggt aaatgttttt atcatcttgg acggaatcga   7680
ttttgtaata tgccatggaa acaggacatt atcactccat gataaattat ttaatggagt   7740
cgatcctctc attgttcttt gcgtatctca atctgtggcg tttgcttcgt ttaaataata   7800
tatcaaacat ggagacgcct gatatgtagg cattcttcat tctattaatg tctgctctat   7860
agcgctttag ttccttatga cgaccggcga tatcatactt actttagaag gaaaatcatc   7920
atctaggatt aaggcgtatc tgatacaggc gaataatggt tcaggatata gatagcgtat   7980
atctctatta aatgcgtcaa tcatagtctc tagagtggga tggtaactca gtaataaatc   8040
aactagcttc tctttggtaa ctgcttttct ggatggccgt attgattatc gagcgtgaca   8100
ctcgctccat attccaataa ccgctttgca aattgtatat tattgacatc gaccgcgtaa   8160
tatagtagag ttatcgatca tatctatatc atccatgtac ttgcttagta tatcaaatac   8220
atcttcataa cagtgatacc cgcaattatt aaatctcgat aatatcagac cgtacataca   8280
tagacggcca ttgttagata tgtgatttac agccgcgtgt ccatattttc cacgataaac   8340
cttacgacgt ttacatcgac gagattatta ttaacaaagt tgttgtccgt cgtcttatcc   8400
aacatgcatt gaatgatagg tatacttacc atatcgccgt aatgtaagta gtttatcagt   8460
atggcttgta cgatggattc atcctgttgt ctaaatctct ttagaatgtt atcgatgatg   8520
tagtggttat attctctgga atcgtacgaa gtaatactac gcattacgtc gacaagagta   8580
tgacgtctct caataagaag attaacgatt ccatgtctca cattatatgg ggttactcta   8640
aatcgcttgt ttagataata cgcctctaat atagggctga cgtcgtatac tctacacgtg   8700
tccacatcct ttattaataa tctctatatc tatggttgag caagaccagt agtattggat   8760
ggaaacattg ttatcgatca aacatttaat tacatccttg gatagagatt ctctatgaga   8820
cgatatatag taatgaagag agttcttaca catatcactg ttgtacatac aggtacgaaa   8880
tacgtaaccg gtgctgtaac attctgattt aagaagccat agcaatactt ctggtctcgg   8940
attaggcgtc gttacgtata tatccaccaa tccgagacca ttgattgcat aattcgtatt   9000
cttggacgga cgtatccgtt tatccacaat taggtatttt agcagacgta agtcgaaatc   9060
atttatattc gacttgagtt cgttagagga attcgaatag ctggatatca gtagatgcac   9120
aatctgagat tttacgtatc tatgcttact gtatgctcct agcggagtta atccttcgtt   9180
gtttctacaa agtctctcga ctccgcgaga gagtaacagt cgaacaatct taatgtctgt   9240
atcgcattta ttggagacgt aacaatgtag cgcattgttt cctcgtctat ctatatgttt   9300
tgataagttg tgcacgtttt caatttctag ttttattttt ttgtacgtca catcttcatc   9360
cagtagacga catagaatac atgtgcaatc catagctatt ctggtgctaa ttattcctca   9420
taagatgata aaaagtgtag tgagagagca tgaaggagat ttagtattta gcagtgcgga   9480
tatgatccaa gagggtgaga tagtcgttct cgttcagaat ctttcgcagc ataagtagta   9540
tgtcgatata cttatcgttg aagactcttc cagagacgat agctgattga gtacaaagtc   9600
caatgattgc acgaagttct tcggcggttt tcatggagtc atttaatgat ctccacggaa   9660
gtgaatcctt caactcacca ccaaagagct ccgttgcatc agttctgaaa gagatgagaa   9720
gcctgtagag agaccctgcg ctttctctat gggtccatct atgagaaacc cacaggatgt   9780
attcagtcag acaatgtctg acgtcggcca cggtattcag ggagtcctta gtagcgtggc   9840
aatgacaggg tctgaactgg gcacaaggaa aggccattgt aaaggtagac ctgtagccgt   9900
ttatgctaat agagggcttt aatttccatt ttttaatggg ttgtggatga ggaatgagag   9960
```

```
tgatatcata ttgagatacg tagttatgta gaggtgtatt tcctatatta tttactttcg   10020
gtttcatatt ttaccaactc tttaataaat ttcttttcac gatgcatctt attaaatgac   10080
gttttctcat aagtggacat atagatgcag aagtattacc tctatcatct acataattag   10140
ggtctgctcc taacttatac agtacgtagt agtagtttat cggttttaaa tcaagtctag   10200
aatatatagt ggattaatat attttatat tagctaaagc atatcattct caacttcatc    10260
atgagttaaa tatttgtgtc tactagtttg tttatatcac agcattctac aaacagtcta   10320
aacaatagag aagacggaca gactttaacg tataaatgac acatgttatc gatattcgtt   10380
gataaatgat tctaacgaca tctctcgcta gagataaaat ctagtatcgt atcatactcg   10440
catagcatag ttttttcataa ttaatacaat atttaaaaga cttattcgga aagtatttta  10500
atacatgtat catcgatgga gatccatatg aggagtcact tgtagttctt cagtagtgct   10560
atcatcgata gtataattat atgttgttgt aattggagta actgttggta gttcttccgt   10620
ggaatcaata attatactaa cagcaatagt ataattatat aaatatgttc cgttgatatc   10680
acatatttta atgaactcat ttctaaagcc gtacatccac atctattagg atctgatatt   10740
ttacacaact gtttaataga gtctacattt atatgttctc tatcggtgag atacaaatac   10800
ctagatagtc gcgttatagc acaaatacga tataaataat aataataatt attcagtaat   10860
gtatataaaa atgcattgtg tatttactcc aatactactg tagttgtaag ggttttttca   10920
aaataatagt tgtgtccacg acatttatat gtattaccta tatattcttc agtaacattt   10980
tcaaagtaca aggtcgcctc ggtgataccg cctctactag ttaaaacaga gtatacatca   11040
aaatcgaatc ctataagcca tccggatgga ttttcccatt caatcagtac atcgtcaatc   11100
aataatgacg ttgacacagc agtgcatgtt atattggcag gttctcctat cgttacgttg   11160
attttttggat ctagtattag tttaaacctg tggtcttgcg acggtataac cgtaagtatt  11220
ttacatcttg attctaacgt cgtcgtaatg aacgtaacag ttgtatcttc cactatcttc   11280
taactctgga ttatgaataa ttaatttctt tcccgtttgt gaatacttaa tatcgtcgat   11340
attaatttcc ttattatctt tataccaagt tatattatta taatgttttg cgtaaagaat   11400
tccacagtat aagtctatgc catacttatc atgagtacct agttcatatg ttttttggaat  11460
gcatgaagga ggttttttaa tatgagatct aactataccc tgaacacagt caccattctt   11520
tgtagttacg gtacacaaat acctacggtt actgaattta gatgtatagt tggctatcca   11580
taaatcacca tgtttaacac gtttattaga aacctgtcgc cgtctatttt tttctagcct   11640
ctcccattta accacatagt ctttatatct gtgcgataaa agactgtctt caataggagg   11700
acactttgcg ctgaatggct ctcctagagc ggctatatca ttcattgtgc ctccgaacat   11760
acatgctgga ttcaaccatt tagagtcttt agctggtaga gtatctctca ttttattgaa   11820
gaattctgtg atttcatttt cgatgtctat ggcgtaactg tggaatagca ataacaataa   11880
tgatacgaaa tatatatgta ccatcatttt catcgtcatc ttcattatac ggcactaaaa   11940
tatttatata atatcagttt ttttacacac atcgcatgag aaaaatacaa ctatactttg   12000
gtaggtggat acgatatatt ataaagatcg ttaattgtca gcatgtataa tatttcgtat   12060
ataatttctg aaggtagtaa tgttagtaga caattttttat ctgtgaaaac aggaaatagt  12120
ttatcatata cctttgacac gtacatatct ttataatata cattaaggta tctctcattc   12180
ataatattag aatatatttt aaaggactta tcgttattat attttttaa ctcgttgagg    12240
tatcttctta acttttcga attatggcat cttaaaactg catatagtgt agtgtctaga   12300
acagtggata gtttgagcaa tattgtttct ttatgacatt tagttattat accatcgtat  12360
```

```
ttatcaaacg acatgtattt tgaaaatgcg tatcgatacg ttttagaatt gcgattccta    12420
acgtgtctat tgtaaaatgt gtcatctaaa agtatacagt aggatatgaa tttctcaaat    12480
gattttatat cgaagatagg tagagatgga agttgatcca ccaacgatct tatcacattc    12540
ttatctacaa tatatctaag tatatacagt aaacaattaa tggtatatgg ggaattttct    12600
ttgttatcta taatgagttg tgtagcgtgt ttgttattgt cggttaacgc atttatatct    12660
ccgttgatac gtataagata atctattacg tgtgtattat tatattcaca tgctacgtgt    12720
aataatgtct ttccttcata gcgggtataa atatctatat ttttaaacct attcatcaaa    12780
taagttatcg aatctgccgg acgtgtagaa tatgttttga taaactcgaa tacgattata    12840
cgacgctcat ctatcggcat ttctccaaca tttgtttcat agtgatgtat taacataaca    12900
agaatatcgt gttgtatgta gtcggaagtt atataacata gtataggcgt taatccatga    12960
ttattacata ttttgaaatt cggattaaaa gtcaacagca ttttagtcat atgaatatta    13020
ttacacattt caatactaag atacaaatgg aatggtgtat taccacaatt atctaacgcg    13080
tttagattag ctccatgttg tataaacaaa gaaataattc gcttggcctt ttttatcgtt    13140
atcggttttc tacactcacc tggtttataa acgtgtgcga gacacaaata ataataatgt    13200
aacgctgtat atccgtcttg tttaaagtta ggatcgattc ccttatctaa taaagtggat    13260
actatgttct catcgatatc ctcttccttc aataacatgt aacgagattt tatatactct    13320
agtagtaggt tggaatagtc tctatgcgat aagtggtttt tatctttgtc tatcatatct    13380
atcactacat catgtgaaat attacaacat ctagtaagca atatataaac aggcatacgt    13440
ccgctactgg ttttcatcgt tacatccact ccatgattta ataatatctt cagtacatcg    13500
tttgtaaagt aattattata caaatagcag tgtagtgcag tatacccagt tacaggttgt    13560
cgtctgttta gatcatagtt tttaactaca aaatcaagtt ctgtagaagt atggtctata    13620
ttgcaatgac taaaatatgt atatatttca ttctcttgta ttttatgagt tgattcgcgg    13680
ttgatattta aaacataaat cagacgacga ctcatttttta tgatgctttg tggtaaaagt    13740
cctcatataa ttgtttaata ttcattatta tagacgattc ccattaacta atctaacatc    13800
tttgatatac ccgtaaatat gtaaatatga tcctaaaata acacggattg taagatgtct    13860
agaaagttta tgcaggtgta tgaatatgac agagagcaat atctcgatga gttcattgaa    13920
gacagatata acgatagttt tatcactagt ccagaatact atagtgcgga aaaatacatg    13980
tgtagatata ctacactaaa tcacaattgt ataaacgtac gacgatgcgc gttagactcc    14040
aagttattac atgatatcat aaccaattgt aaaatatata acaatataga attagttagg    14100
gcgacaaaat ttgtttatta tctggatctg ataaaatgta attgggtatc taaggtaggt    14160
gattcagttc tatatcccgt tatatttata acacatacaa gcactagaaa tttagataaa    14220
gtctctgtaa aaacatacaa gggcgttaaa gtaaaaaaac ttaatagatg cgcggatcat    14280
gctattgtaa ttaatccatt cgtcaagttt aaactaacgt tgccgaacaa acaagtcat    14340 gcaaaggtat tggttacatt ttgtaagtta agaacggata taacgcagat agaggcaccg    14400
ctttcgggca atgttttagt ttatacattt cctgacatta ataaaagaat tcctggatat    14460
atacatgtca acatagaagg atgtatcgat ggaatgattt atataaattc ttcaaagttc    14520
gcgtgtgttt taaaactaca tagatcaatg tatcgcattc caccctttcc tatagatatc    14580
tgctcttgtt gttcacaata tattaacgat gacatagaaa ttcccattca tgatttaata    14640
aaggatgtgg caatttttaa aaataaggag acggtatatt atctaaaatt aaataataaa    14700
```

```
actatagcta gatttacgta ctttaataat atagataccg caattacaca agaacatgag   14760
tatgtcaaaa tagcactagg tatagtctgc aagttaatga ttaataatat gcatagtatc   14820
gtgggagtta atcatagcaa tacgttcgtc aattgtttgt tggaagataa tgtataaaaa   14880
ttcttataaa ctcaattgac atggaaatgt aacaacatac attcacgtta tactaacagt   14940
aactgttttg ctgatgctag gaatagtaaa cgccatacac gtaaacgttg tagcatcttc   15000
ttccttgaca ggattaatgt ttaaccggga tgtaataaca cgtctcttat cggtcatata   15060
gattttattt gctacactta ttctaccgtc tccgtcccca tcatcttctt cgtaatacat   15120
accattactt atccaaaaga cgtctgcatc cgttgtggga ggtctcaacg atactctaca   15180
cgcaatagtc aaattactac ctattgaagt tacaacacct tctggtaatt gcatagtaga   15240
aggtattatt ttatcccgta cctctaattt tacaattctg gttacgttat atgttttgcc   15300
accgtatata tattctaaaa cacatgtata ataaccagca tcatttttc taacatcttc    15360 tatggtaata attccaggtg tccgttgttt aagtctctta tttctaaggc gtcgatgccc   15420
gctccatata atatctgcgt ttacgttact agcaataaat gcattaatat tgggacatac   15480
catttcgcca gtagatctct catttactat ttgtggatac gagataagat ctatatttga   15540
ttctgagaca gacacgattg tcaaatttaa cgacatcatg tcacagtagg tttcgttcgt   15600
ggtaatgcat ataaaatac cagagtctga ttgtgtcggg ttcagaatta gcatattgct    15660
accattatct atcggtataa ttctatcatt atccgctcct cgttttccc ataaaatatc    15720 taatatatta tatccggatg atagcgtatt tatttgagga catggtaaga ttactggctc   15780
gttttctaac tccatgaatg atgcaaaata ttgccctttg tcgatacatt caggcgcgtt   15840
aaaagtctga acgaatgaag aataaaaaaa tatagaaaga aatataacag gtagtatact   15900 catttttattt tatagtgggt aaaaaaagtt tgtttctggg aaagggagaa gagaagaaag   15960
aagaaaatgt caagatgtac aactcatcaa ttcatacgcc ggaatatgat gttataatcc   16020
acgtaattta gcatctcaag catcacaaac aatgcgttca gactgttact agtgggatgg   16080
tcttcacctc cccagtaagt agcagcatat gcacaaagtc cgatgatggt ttttgctca    16140 tccggtatat aacaacggat gatttctaca caatctttga catcatccca cggcatattt   16200
tttaccagct cgcgaatgtc gatgaacact aattccgcat catctctaaa agagaggagt   16260
gtggaataca attgtccagc gcattgcctg ttgcggtatg cataggacga ccaataaata   16320
tattcagtca aacattgttt gacgtcatca atactggtca gtctgtcaca tccacagtgc   16380
tgtggtgaaa agacgtgggt actaaagttg gccgtcatct taccaattgc aattggaaga   16440
ataacgacct gcactaatac cacatgtttt ttctattttt ttaaaaaaaa tggttaacaa   16500
ttagttgtcg gagagcaata tctaccaacg aaaaaaattt ttccatcaac atgcctaatc   16560
acatagatga acggatgatc tacacagaac tcatttgtaa ttgttgatgc acagtctgac   16620
accagtgcac aagttgctgc agctgcttct gtatactctt cattgacatc tatatacgtt   16680
ttgtggatca tagcgtcgac actcacatct aaattacaca tattgctata atctccagtt   16740
gaaccgaaca cctctgtcag tcctgacttt actagagtat ccaccagatt atacgagcct   16800
gttaccttaa acttgggaat gtgaacatcg ataaacgtag cttccagaga gttacaccat   16860
ttcttaaaat ttgtatctgt tagattttgt tctatggatt ctaatccatc aatcttgtct   16920
ggaagaatga ccatcatact agtatctcca acatatggca gttctatgat tgaaaagtta   16980
ccgaatgatt cttttacaga tgcgtgatta aatagctcgc cgtacataga catcatactt   17040
acgtctacca tttccgttgg tgatacgtaa aagggataat cactggtaaa ttcctttcg    17100
```

```
aatggcgtca accattttgc tttaaagtat acggcactaa ttgctaggag acaattgttc    17160
atccaatagt ggattgattt tccccctcagt aaagatatct acacacttgt tgattgcatc    17220
tatagtgcga caatcagtga agtcaacagt ttgaaactta tcgccaattt ttctcaaaaa    17280
ggaatcttta aacacggcag aatatcgccc atatacttta ttcatggatt tgaatgagat    17340
attctgagcg ctaaccttat ccgtgttctc ctccttttct acatattttg atagctgttc    17400
agcagtggat ccattagctc cataatacag tattgtcaat actgacgaga ttgacgctgg    17460
agaaatgaat acattctctc ctttcataga agatatccat agtaatcgat attggtcgtg    17520
tagcgcgata gagatagtct aatattaata ttagatatcc gtaacactac cacactctat    17580
aaaaaaagaa tatttcaatc ttgtataaac agtctacgta gtctgtcata attaggagtt    17640
tgagaataat ctaacgtgta tactaattct atatatctaa ctaattccag aggttcattt    17700
ccttcaggaa aacagtcctc aaagaaagta gctataaatt ttttatattc ttttttttgt    17760
tttattactt ttatactact ttcgttttc catggaagtt tgccaccgaa ccattctatc    17820
atgcaatatc ccaacatttc taaatctcct cgttttgaaa ctgttgctcc aagatgattg    17880
tctacacaca tataattgat atttcctgaa gttatcatgt cctcgttgta atctatatgt    17940
gagtttccac tcttgtatag tttgttagtt ctagaatagt caattagtga aagacgttta    18000
tttctaatca gtatattcct cggttctatt tttccatggg taaatcctcg agagtgtata    18060
aactctaacg tgtttatcat agtgacgcat gcttcgaaga ctgattcagt atcctttggg    18120
gcgaatactc ttcccaaatt ctttataacg aagaacatat aatcatcggt ttctccaatt    18180
ccatacagat ctggaatagc caaatacttt ataccacgtt cccgtgtcca gttgtcgata    18240
gtcaaaggat ccaatacaga tatatagaat cgtatttcag acaacaatgg cttgtgtgat    18300
ttgtgatcta tcttcattac gtaattgtag aacgaactag tgaaattttt tctgacctta    18360
tagagtattg aattaccaga atataaagta tttccgataa tccatttctt gccatcgtta    18420
tcaaaacaat acttgaagga ttccatgcct gctatgtaat aacgagttgt tttttatgtt    18480
ttgtattgat tataaaaatt agtagatatg atctatattc ctacatcgtg actgatacat    18540
tctataactt ctttatcaat ggaatcacta ttactacttg tattaataac gagtgcttct    18600
ctaatatatt cattgggatg attcttgtta atgttttat tattttcaat ttctacatt    18660 tttagtattt cttctttctc tctatctatt tcattcatga tatcttctac atttgtaaca    18720
tctgtatctg tatccatgtt agtagtaagc aataaaacta tagggtaata ctgctataca    18780
taaaaactat ttatattttc atttcaatc aataaggaga agttgataat gcctttatag    18840
cggggagacc atcatacttt tccacatatc caatgtcctt actaaataca tagaagacgt    18900
tatttagttt acacaatgat gatatggata tcttataaat agtatatgaa atatcaaacc    18960
acttattcgt tctaggattg taacaagata tctcgttgtt tttctctaaa ttaccatatt    19020
gttcggtaac ggatagacct ccggcaaaat ataacattcc aaatgtcgag tcgatgccgt    19080
gatataccct agccataggc atttctataa tcgaccattg tttgtcttta taaatgtcaa    19140
gtttttccat attgttaacc acgatcgtgc tattagagtt attatgaat aatccgccag    19200 ttacgaaaat agtattatta acggaaacag cggacacatt gcttttttta taatttatcg    19260
gtgtttcgta tatccctgaa tccattgcct tcacttgcag ttgggagatg aacactgcaa    19320
tcagttcttt cgggatagaa atctttggca attatacaca accctatttt caatccccat    19380
gtttcctctt cagtcttctc acatcgtcta atagacatgg agtagatgat agaggggaac    19440
```

```
agaaggacta taatcaggga cctcatcttg aaaatggtta gagcctataa gggcgttaac   19500
cagtgtataa tatgcagttt tatttcgttt ttgtatcatt aataaaaatt agttatgaat   19560
atttagtcaa gttaagcatg ctaagaaaag tggtaacatc atttgatgtg ctaccgagaa   19620
atttagttaa attttctctt gataactctg gccattttgt ccttgaaatt gggaacatct   19680
tctttggatc taattgcgca tgtatataca ctcttttag gtgtcagaca tactttcgaa    19740
ctccatggag taattttttc gagaaaccct tctgtggctc cctgtgctgt cacgcacact   19800
ttttctgttg tgacaaagtc tatgctgcaa cctgtagacg tgcaatcgta gtcatcgata   19860
tcatatggta ctggttcttt agaatctccg aatgtgaagt tagccgtata caacaagtag   19920
atatcacaca tgtcaccgcg tttgtaaata ggaatctttt tgctacctct agtagcatac   19980
ggatggtcgt cgtattcagt taatgttaca gtcggtggtc ccgtacaata ctcttccact   20040
ttataatcgc cttgttcaaa tttaacccag aaagatacga aatcattctt tggaaatgcg   20100
gatatgtcgt atgttccttc tggtacattt gtatacattg tttgccacgt cttgatgcca   20160 taattttaa gggatatatt gtatagacca tccccagtcc attcaatttt ggaatcaaaa    20220
ttgacggatt caaacttata actagttatt ttagcgtgta tactattaat gaacaaaact   20280
gcgagaatta taatatatct catggtgttg tttgttattt gactactgtc actgaagtga   20340
taatatattt taaatttta aaaatcatat tttgaataat atgtattact atgtccatga    20400
cgatcaaata tataagtaga tccaatttta agagtatgtt ttctcaatag agtatcatcg   20460
ttgatcatac ttatttcata ttttattcct ttatagcatt ttccctctgc agtaatagaa   20520
tattgtcgct catcaccatc atatttgtga atataagggt acttatcata atggcatgat   20580
aatttggtag atattctaca cgtgtgacct ctgcgttgaa tagtagacat atcaataatt   20640
ttatagtcgt ttataacatc tatatctatg gaatcaaatc cgacgtcgca tgactctgta   20700
ataatagaaa ttgtgtactc tttaaaattt aacaccaatt cattattatc atcagtatat   20760
gaattttcta tattatctac tccatctata tagagtttta cactcagttt attaaacgga   20820
gtgtactcat tattcgaata ggatgctaat gcacctatta caaataaaaa cgttattagt   20880
tttttataca tttaaaatct taaaattta actagtatat tgaaataatt atttatacaa    20940
actaactaga tgcatcaaca gataataaca aacacctcca gcgatcgtgc caatagtagt   21000
tagagatgcg tatccgtaca acttgttaat catatttcta cggatgtata taccatcgtc   21060
gttaaaagcg cttctatatc tctcattagc tagaattata gatacgctat taattatatc   21120
atacattagt tgattgttga tactattttt attgtaatcg aaaacatttt ccatgaatag   21180
tattccggtg ccaacgctta cagaaacatc gcgttcattc atcattatac cattaagtgt   21240
atccatcacc cattgtttaa cacgtgattc atttggcata gtacgtacta tatcatcgaa   21300
cggtataacg gcgcatcttg taaatagcct gtatatatta tgtaatatgg cgttacttct   21360
tccatacaca ataaatctct tgttataata gtgcctgagt aaaaatgctc taacggcatc   21420
gtagatatca acatccactg aagaagacat ctcaattgat tctagctata agtctttaat   21480
cttttgatac ttgtttgtta ttaaattatt aattattaat tattcattat tttaacggat   21540
ttatattcac ggtagcaatt tatggaactt atattggtca ttattttgt cacaggaaca    21600 aactaatact ataacggaga ttaaaaatat gacgcccata attgttaacg ccactatgat   21660
tatatgataa gttgcttcta acgattctat ttcttgttca tattgtacaa cgtctttcga   21720
gagtttgctc aaatctgtct catcgtcggg accatcatcc actggatcaa attttcgtt    21780 agatcgtaca catgttggga gtatgggatt ccatttaccg tcgatacatg tggatgatgg   21840
```

```
agatcccgtt agtataaaac cacttttaca actaagatgt ataacgccac cgatagaaaa   21900
tgtagatccg gaaattaatc cattagatag agacggtata tcacattttt gttgacatga   21960
tggaataaca ttccaagaat tagctgtaca acttatgtac gaagcaccaa taacctcata   22020
tccaacatca cagttgatag ttatatattc cccaaatgag tatttttctt taactggttg   22080
acacgatccg tgttctaatt gaagaggttg acattccgca ttaggacacg taacagtatc   22140
attccaagaa gtatttccat ttttttcttc gcaacgaaaa tattttgttt cgccgttgca   22200
acttagtgtc atggtggaat tcacttcgta tagcggttta ttatatagtt cagagatgta   22260
atcagaaact gtgcacattt ttttgcatgg atttcgtat ttccatttat ctgtttcgca   22320
gacagcattt ggatccgaag aatgatatcc ctgatcacat gtaaacgtaa ctttctggtt   22380
attattaaac gatgtttcgg tagacgttaa tttagcgtta ttcatagtgg gtacagtaca   22440
tgttgaataa acaacagcag gtagtacgca taacaacgta acaacggaaa tcgttttcat   22500
ttttatttat gagcgttaaa aatagtatac actgtcgagc actaaaagga aacaatgatg   22560
tagtgtgatt ttatatttta atagtgttta taagattttt agatatgtgg acagttcgtt   22620
atcgttatat tttatttcgt taggaaaaca cgaccattta tctccaggat ccagcttctt   22680
ggataataga ctaattaatc tctgacgata tctaatagat gctatgatat tacgtacacg   22740
acttccgtat acgtcgagac tagtgcactt cacgaaagaa ggatgtttac cgtatctcat   22800
taaagtatta atgtctttga tacaaaaaac taattggaat acagttttat tttttatata   22860
acatctcttc atgatatcta tttcatcgaa acatcttaaa ataccatt tatattgctg    22920 tagtgattgt acatctataa gagtatcata atcggtcata cacgcagtat attttataca   22980
cattttcaat aaatctgcat tatgctgttt atgtttagta attgctatca tagactgtat   23040
cataattttc aaagatggtc gtttagacaa tagtacttcc attattattt tgttgttgtt   23100
tgcgactgct tccgaaatac atgtacatcc actagtagta atcgtctcaa atcaccatt   23160 tctgtttaat agatagacca acgtattata cgcattataa ctgacagcgt cgtaaatagt   23220
acgatagtta atatcaataa ctcctctgga taatagataa tctaaagatt caacagcatc   23280
aaaaattatt aaatgacgaa ctatatgttc attatctatt tctaactctg tgtctgattc   23340
caaatatagt tttataagcg agataccgtg tataattcca caataaaatg gagtagttcc   23400
gaatttatta cgcgcattaa catttgctcc tttagaaatt aataacttta caaaatcata   23460
tttattacga catgagacat aatgaagagg tgtatatcta ttaaagtcta cagagtctat   23520
attagcattc tctaaacata tctcaaacaa ttccacgttg ttgatatcgt gtttacataa   23580
taggataaaa ggtgtgtttc cgtacgtatc ttttttatct acatctgatc cattatttaa   23640
caatatctta attaattcat tgtatgattc tgattctgat tctgatttct tatagtgata   23700
tatacatcta tgtaataatg tacaaccgta actgtcttcg gcatctatat aaaatacata   23760
tatagatatt aactgtatct gatatatagg acaaaaaatg tcttgttcta cgtccatttt   23820
caagcattag tcttatccta ttatctggat gatcattatt aactaattga tatacatatt   23880
cttttatatt aatggatgat gataacctga gattgtgtat aaatgacccg ttcttattaa   23940
tatttaatac tctatctaga aaaaaaatta taatattcgt attagcatca tccatagaat   24000
aaatatgtag aatatttttcc ccatattcta aaatatggaa taaatttggc aacctagata   24060
aaaaatcaac tattgtttta tccactttct cgtatgttcg aacgagatta taatcctgta   24120
ttatatggga tgtggaaaaa ttggaaaaca cgcgtgctat ataatgaaga gataaatata   24180
```

-continued

```
cactccagtc aagtatttcc tttttaaaaa aaatccatat ataatttata ttctgtaaca  24240
tgttatccct tttcaattaa caatgttggt ttataaaaaa ttaaagaagc gaatcaatga  24300
ttaatagatg ttaagaacta taattacgat gtattaatag gtatagttag ttagttaaaa  24360
agagataaca gttactaatt aattgttagt tattgtctat atgatattac aacctattat  24420
ttgttctcta tagttacatt aattaaaatt ttatatgtga cacctattca tctggagaat  24480
acttcttgat accatgattc tggccaatct gcaaacacag cacaacagca tctttccact  24540
ttgatagcgc acacgtatgt cgaggtagcc tcatcccag gtttatatac cttgatgaat  24600
cgacacgtgt acttgatgtc ctctttcttc tcacagaaat acacaacaca aagtcttttg  24660
atatgctttt ctatatcatt ctctatcagt ctgaggtagt cgtaacccac cgtgaatcca  24720
aatactttgt gtgtattatt atcaactcca atgaacaaat atccaccctc tgtgttggca  24780
aaagatgaga gtatacgtgt tcttagttgc ttagctgaaa cagatgtatg tttaacatta  24840
atagatttac cagcctgaag ttctgatcta ttgaagaact cctctaccaa tctctcaatt  24900
gattcagtgt cttccactcc atctggatat tcaaattcct gcatttctgg tctgggactc  24960
catccacctg attccttcag ttcgctaaga tactcatttg aatgcatgat cccatagtct  25020
tcatgtacaa atttgttttt acagtactcg gtataagatt ttgattagac aaatgcgtat  25080
gcacataaca gcattcttta ccattcacaa tatcaaaatg atcatataca acagaccaca  25140
tatggcgtat agattccaaa cgtttcatga gtacatgatt cacactgtct tccagagagg  25200
tggttacctc gatggtgccg ccgatatagt agaagaaaga ttttctgtat cattctcccc  25260
aagtttaact tttaccagat ttgggatcgg aagcaccgca ccctttttga atctcattct  25320
cataatttcc tttccatgta cgtccacagc agtaacttga cagatacaat ctcctatcca  25380
gacgtggtaa tcgatgatag gtcctgaact gagtgcattc atttctttgg ccttctcttt  25440
gatagtagaa taatcatgtt gaacttttcc atatacagcg ttttctgttt caagtacgtg  25500
atgatgaatc cctactcctt ccaaacacaa gtctagactc tcgtacccga ttccgcttag  25560
agcatagtag tttttgtggc gatatgtgat ttccttcttg atcatggatc ggatctccaa  25620
tttgtagata ttcattgcac tcaaacatag gcagcagtgc tccaatatat ctcttgttca  25680
cctgactgta acaccacata tatttgtctt ttacaatgtc atacttgtta ttataaactg  25740
acatcattgg caacagtcga tgatattcca ggaaaggcat gaagattctc gtcgtaccca  25800
ccgagagcgt gtgcgtaaaa catcgccatg atttcggttg tacacacgag atcaataata  25860
aattaagtta tttttttaatt tttatcgaca aaaattttac atcaaccaaa caccacactt  25920
aataatatac accctgcatt aatatgtgcc gaaacttgtc gtaattgggt tcctcaaaat  25980
atgtcaaaga gttaccatg gtaatatatt gcagcaattc tctaggtgca tattgcaaac  26040
tggtcattaa caaagtcgca gtattgttaa catatttctg ttttgtggca cttactaatg  26100
cacaattctt tgtttcagat atcttagtcc atggcaagat acctcccaac catctaatca  26160
tacaatatcc aagtgtttct agatctccac gtctagatac aacgtatcct ttatgcgaat  26220
ctataggtgt aaattctaga gtaccgttat ccatttttatt tggatttctt ataaatggaa  26280
catgttcgcc attagacatg aatttagaaa ccaatccgta atccactaga tataatttat  26340
tcttatctat ttgatccaag actatattac tcgctttaat atctccgtga gaatatcctt  26400
gctcgtgcat aaattgtatg gtatttaaga tttcgattcc gatcaacatc accgaccttt  26460
ttggtaatct attattattg gctctgatca ccgcatctag atctgcacct aatctattaa  26520
ttaccaagaa tcgatattcc acattaatgg atttgtatag accaaatgcc ttgcacgtga  26580
```

```
taagacctac gtgctttata ttgtgagatt ttttccattc ttcgataacg gatggtttaa  26640
gtactctagt ataaaatgcc tgttcggtaa ataatgatcc gttagctttg ggctctattt  26700
ttactacata attattgtca ttagtagtat aaatactacc aaatccacct tttcctatta  26760
atggtccaac gacccattga tttttgcaat tgtcagttaa cacaagtcct tgaaagttca  26820
taatgtgtga tctatctgtc aatgaaatat cattttaaat tttaagtttt acgtggtaag  26880
ttttaatatt taactaatac attagacgtt gaaatagcca catataaaaa cgagttatat  26940
tattaattat caagttttaa gtcttaagtc tctaattagt gttaaaatac attctaatac  27000
ggtcctgtag tatctgaatt aacttactat atgctaaatt cacatcatct tcaatgataa  27060
tagtgtcgaa tagaccggct tcacctgcct catccatgtc agttttgcc aacatcacac  27120 gacgatgaat ctcatcatcc gcttcagtgt ttctacaacg aagcttggtc tcaaccattt  27180
taagagaggt aggtcttata tacaccgagt aaggcattag gtaagtattt ttaaaacttc  27240
taacaccgtc gatgtttaga tccatcacac aaatacgatt attaatagcc gctgtattca  27300
cagcagtttt agaagttccg taaatatttc ctaaaaactc agtatgttcc ggcggctatt  27360
cccttccaga tggcctctct gttaacgtaa tggtaatcga caccttctcg ttccatagga  27420
cgaggaaatc tagtggtatg ggacaccaca aatccaaata tattcccata gtcttttggc  27480
tatggctgtc tttcctaaac cagatggccc gctcaatatg atagatttta ctatcccaga  27540
catttatgta agtcaaaaat ctagactttg ttctctgttt tgtatttacg tgaacgttta  27600
ttatatatat aatatgtaat acagaatatt gccacggccg acaatataat taatgcggta  27660
ataccaaata tttctacaaa gtccttggtt ttataattgc taatagaggt tgtactaccg  27720
cctacagtag ttgatggtac tgtatcatta tcattgtacg tatcataaag atccgcatca  27780
tcggtggttg atttagtagt gacaattcca gatgatgtac ttactgtagt gtatgagaca  27840
gtgtctgtaa ctgtatgatc ttcttcttta tcagtaattg gttccggagt ctcgtctgtt  27900
gtggattctc cagatgatgc acttactgta ttaatgctat cactagtgta tgtgacggtg  27960
tctgtatgat cttctacatt atcagtaatt ggttccggag tcgcgatttc gaataccgac  28020
gagcaattag aattatctat ataatcaggt ttctcagaac tagtttccgg tgaatgtgta  28080
gatccagata gtattatgtc tatagtcgat tcactatctg tatttacaat caactctgtg  28140
gagtattctt cataatctac tttatcagtg tcatttgtag gcgatgtcat aaagaatgca  28200
catacataag taccggcatc tctagcagtc aatgatttaa ttgtgatagt tgtaactaga  28260
tcatcgtatg gagagtcgta agatatttta tccttggtat aattatcaaa atacaagacg  28320
tcgcttttag cagctaaaag aataatggaa ttgggctcct tataccaagc actcataaca  28380
acgtagtcat ttgtattatt tcgattacat gataaagttg catcatcacc tatttttta  28440 gatgtctgag gaaaaggtgt agcgtatact aatgatatta gtaacaaaag tattggtaat  28500
cgtgtcatat tagtataaaa agtgatttat ttttacaaaa ttatgtattt tgttctatca  28560
actacctata aaactttcca aataccagcc accgaaagag caatcttaat catgtcaggt  28620
tcatatttcc ccaacatact agatccaaat tcgcctacat caggtaaatt catcataata  28680
caatgtctgt tcatatcaca cgatgatcca ttgagcatct catctctatc aagaatccta  28740
atctgtggtt caaaataaca gcatctacac tcatcgttaa ttgtagtatt gtctaatata  28800 ttttttgctaa tatttgcgta agttctatta tcagctattg catgcatcac agatccatca  28860
acaaccatat ataatataga acaatagtcg gactttatac ttatgtaaaa cttgaaccaa  28920
```

```
ttggaactcg gaagctcgtc atgtagacgc tggtgtctag atataataac attattatcg   28980
gttacacttc ttaagagagg tgccgcatcg atagagaaat caaacaggag aataatcaat   29040
gatgcatttc ctttggtaaa aaggaaaca tccatgggaa gaatggctac tttatatgaa    29100
tttaactcta tacacgcaca cgctttatca gatgagatta atagttcaca aacatctcta   29160
tcctttccta tggatataat aacaggaatg gcatctttag gtttaaaata attatataca   29220
ccagtaggag tcttgtcatc gtcatctatc tttatcaaat tagcaaatct ggatattctt   29280
gatacattct ttttatacag tgaattgcat acatcggata ccgcattatc catatatggc   29340
aaatctgcaa tcactgtatt gttttttagat tgtccgccaa tgtgaacgtt cttgactttt   29400
tcacaacatg gtttaatcat gaaatcattt tttatatgat ttatttcctc gccatgtttt   29460
actaacgcgt ttagacagta tacaataaca ccatccatgg cgaccaccaa ctaaatagtg   29520 ttatttttaat ttgtatgtaa ctattaagat ttagtcaagt ttactaaatc gtttagatga   29580
gtagattctt tccacgtttt atcctctctt atcctagtaa atctaggaaa tctaatggat   29640
attccatttg cggtatggga cttggaagat gtaaactctg ctcctgaaat ttcccatatc   29700
tgagattgtt ttggatcctc tactacaaaa tcgggaatat agatttttatt aactactaac   29760 cactctggaa ttttttttggg atccttgtta attttaatca tctttaattg gtcttgcaac   29820
tcccttaacg tattatcatc gtgtcctgaa cacttggtaa ccgtcttcca tttaccggat   29880
tcatcgtcgt aacaacccat tagaaagact gccatgatac caccctttgc tcctttacca   29940
tagtaagcac ctagtactac taaatcggca gaatctgcca tggaaccctc gttcaaatag   30000
tctcgcttta ttttttaacca tcttctcttt cccggttcgt atactccatt aatatctttt   30060
aagaccaatc cttctaattt tctcgttagt gcatcatcca atacgtcagt taactgagac   30120
tcgttactaa tattcgtcaa ctctgagaat actattctat tgggtatttc aaccataaca   30180
tctttgagaa aagatcttcg ttcgtacaat ggaatgtccg tcatatcgaa tccatcaaag   30240
tacaaacagt caaacacgaa caaacacatg ttagagtttt tatattcttt cttttttgtgt   30300 atacctaaac ttccaaacgg gagcggtaca ttatgttcgt ctacaagaac aatttcagaa   30360
tccaatacga tagacgtagc ttttttaaat gctttcggta tgtattcttt gagataatcc   30420
actttatgag agagtactgg tttcatgttt ctactaaaga aggcaaactc gttattattt   30480
ttatgaactt gtactctttc accatcgtat ttgacttccg caaacattcc tgatggaaat   30540
tttttaaacg ccttattgac agaatcacac gattccgcta acatgggatt aattggagtc   30600
ataacagaaa tagatataga gtctagattt tgtttagatg catttctat tatctctttc    30660 aagttattag attttctaaa cacatcatag gcatgaggac taatagcgtt aagtacgtac   30720
cgagggcccg ctttaatttt tagatctta tcaataagca tgactacaca ttttaaatca    30780
ttacatgtac aaacggatgc gatatcagtc aataatttta tttgatgcga ttctttagtt   30840
acggatgata acgtagttaa aaaactatcc acttcttcta aagttaaaat gcttttatct   30900
cgtggacgga tttctgtgtt ctctttgaag aaagtcctaa tagtgtctcc tatatatccg   30960
tatcctaaat cttgtagcat atcttcctga gattgtttaa atattatact atataatttt   31020
ataatttgtt tatcgttcat gttataaatt ctatcgtcta atccgggaag caatagctta   31080
atgatcaaat atttatcatc cctatctgtt ataaagtctc taattaattt agatttttct   31140
ttatatcctg atgcgtgata tatatcacag cataattttc taaattcgcg aagcgacgtc   31200
atttaataaa aaaagtattt ttttttaata tttttcacaaa tatcgttcgc ggatattatt   31260
agacaattgt agtatattct cacgtatcac ttgtttaata tctatatccg ctattctgga   31320
```

```
accgagtact tcggcatacg tagttttaaa atctggatta ttcattatat attttagagt   31380
aatgatagca tctactatat tttctaggtt atccttataa aagctcataa acttgttaac   31440
tatacaatcg ataatttcat tgtcgtctaa tgaattaatc aattcggtct gatagatctc   31500
ttgatctata atagtatata cagtatctag gaaagagata aatggattat ccaagtttga   31560
tctacacatg ataaaattta caatgtcctt gtttaatata tcattatcta tagtttctat   31620
cttggcaata actaattgag atattgatgc gagttcggta tgcatatcgg acacgtatcc   31680
gagtactgat tccaagttgc cagagtaata tgcttcatcc atttataaaa aatgtaattt   31740
cactattaca tccacagttg ccccactggt ccagtaaccg tgtgtatagc ctctataact   31800
atattcttaa tcaactcctt ctttacatct tcctcgaatt cagaagaaat aatttgccaa   31860
tgaatatctc cttcttcaat catttttta tattcttgta ataccttttg ttggaatgta   31920
acatcttcat aaatttcctc gccgacgttt ctattaattt ctttgctacc agattccaag   31980
aatataacta gtcgggttt aggcaatcca gattcataac tcttactgag agtcattgac   32040
gcgcctttag cggcggcata cgctactcca gagaatgcgt atctatcaac tattaaagta   32100
attccctgtt ctagttgttc ttgtataaaa gatgcaaact cccatctatt tgcacaaaat   32160
aatagattaa ctatatgatc attataggtt tttttacgag ttagatagtc atctatcatc   32220
tttccagtga cagtggatct ctgaggaaag ttaagatatt ttatcgtgtt tgccggtata   32280
gattccatga tgttcataca ttgtgttgtt tttccagatt tgtccaatcc ttcaaaaacg   32340
attaatgccc cacgagacat ttttgtaaac ctaacatatt ttttacaatt tatgcgtata   32400
ataaaactga aaataaatat atggtcatcc gagacgatta ggtctacctt tatagatcat   32460
gggtaacaaa aatattaaac catctaagga aaatagactg tccatcttgt ccaaggataa   32520
gatggattca tttaagagag gatcctttag agaaaagtcg cgtgcaacca tccaaagatt   32580
ttcatctctt agacgagaac atattaaagt agaccatcct gacaagttcc tggagttaaa   32640
gagagggata tatgaaataa ttcagaaatc gtcgtctata gatgtggaca aacggactaa   32700
gctcatgtcc aacataaaaa cgatgatgat aaatccattc atgatcgagg gtttaatgac   32760
atctttagaa aacttggatc ccgataacaa gatgagctac tcatcggtga tgatattggg   32820
agaattcgac atcatcaata taagcgacaa tgaggcggca ttcgagttca taaacagtct   32880
gttgaaatct cttctcttgg aatactccat tagtaatgac ttgttgtatg cccacataaa   32940
tgcgttggag tatatcataa aaaatacatt taatgttcca gaacggcaac tgattctgag   33000
aggtcaatac ctaactccaa ttttcagtga tttgttaaag tatgcgggtc taaccataaa   33060
gtcaaacata cttatgtgga ataaacagtt tatcaaacca gtatctgacc tctatacatc   33120
tataagactc cttcattgtg ttacagaatc atataaggtg attggaatgg gataaataca   33180
acaattatat tttttatcat atccttcacg ctataaaaaa aattatacat ccgtttccct   33240
gtcggttacg gcagaacatg tagacgaatc atcgtcttca aaataatcaa attcatcctc   33300
tatgctctca gtgtgcccgc gtagatactt acatagattg tatcgtagtc tagatagctc   33360
agatattgga atactatcag atatatgttc ggctaatgcc atacacctat attttttatt   33420
tgtcaattcc caatgtttag atactagact agatagagct actactattc tagaatcaca   33480
acatatcata tcctttacaa agttgacaaa gtcaaatagt cccgaatcgg agtctacttt   33540
aagtttctca ttaaataata gatcaatgtc tccatactgt ttaatagcca aatcatctag   33600
tgtcatcaat gccgaataaa tattgccgga tatagtattt ctgtgtctta tatattctgc   33660
```

```
taaaatcagt ttaaaactat acttattata caagtaagtc atactaaccg gcgtattaac    33720
cgcgcaacca atattagttt cctctggaag caccCctctt atctctatgg agtcattatg    33780
tctattatat gaaataaacg tgtcaactac tttgtcccta tcaaattcga cagtgtagtg    33840
tgtatcatta acttcattac gtatgactaa tttattttgc tgagtagaaa agtaaactaa    33900
tgcatttatt gttttagacg cattaactga tatatcaaac gccattctcg ttaattgtaa    33960
gaaaatgtat tatcttttca tttatgtaag aaataccaat aactccacac gctaatctct    34020
gatcattttt tgaaatagat aacgcctttc caataattgt agatatattt acatctgtat    34080
ctaaataaac atatgctaca ccatatctgt ttacaaagat gttaccgata aatatttctg    34140
gactgcctat ggaatcacat ccttgactaa tatctccgta acgatgaatt atcaaactat    34200
acgttccgga ttttaatcca ataactttat cttttccatg gactggttca agtaaataa    34260 ctcctctgat attatcgtgg tctattatac aaacagccat tatttagtaa aatagaataa    34320
gtagtctgat attatgagtg gcagcaatgg ccgtgtacgc ggttactggt ggtgccggat    34380
ttctaggcag gtatatagta aaactgttaa ttagtgcaga tgatgttcaa gaaatcagag    34440
tcatagatat tgtagaagat ccacaaccaa taacctcgaa agttaaggtt ataaactata    34500
tacaatgtga tataaacgac tttgataagg taagagaagc gctagatggg gtaaatctga    34560
ttattcatac agctgctcta gtggatgtat ttggaaaata caccgataat gaaatcatga    34620 aagtaaaacta ttatggaaca cagactatat tggcagcttg tgtggaccta ggaatcaagt    34680
atttgatcta tactagtagc atggaagcaa taggacccaa taaacacggt gatccattca    34740
tcggccatga gcatacccctt tatgatatat caccaggaca tgtatacgca aaagtaaac    34800 gtatggccga gcaactggtt atgaaagcca ataattccgt aatcatgaat ggagcaaaat    34860
tgtatacttg ttgcctaaga cccactggaa tttacggaga aggagacaaa ttgatgaaag    34920
tcttttacga gcaatgtaag caacacggta acattatgta tcgtacagtc gatgataacg    34980
cggtacatag ccgggtatat gtaggaaatg ctgcatggat gcacgtgttg gctgcaaaat    35040
atatccagta tccgggatct gagattaaag gaaatgctta cttttgctac gattactctc    35100
catcgtgttc gtacgatatg tttaatcttc tattgatgaa accattggga atagaacaag    35160
gatctaggat tccaagatgg atgctaaaaa tgtacgcgtg caagaatgat atgaagagaa    35220
ttctatttag aaaaccatca ctactcaaca actatacgtt gaagatatcc aacactacat    35280
ttgaggtgcg taccaacaat gcagaactag atttcaacta ctcccctatc tttaacgtcg    35340
atgtggcatt cgaacgaaca cggaaatggc tagaagaatc agaataagta tttttttta    35400 aaaaaataat cgagtagggt atcaccacta cacagtaaga gtacagtaaa taaaaagtat    35460
ttatatactt atttttatag atcgtattat gcgctttcta catccatatc atcgtcatct    35520
tcaatatcga taatatttt tcttctacc ttgacatctt ttgcctcttc gacagcaact    35580
gattgcgcta ataatacatc ctttttcttt tctttttag gtgtgacatc aatagttatc    35640
ttttccaagt tatacgatat ggtaacaaca ttaccaattt tgaatcaac cgtaattttg    35700 attttatcca tttctaatag catagcataa ttaagagttc atttttattt ttttaaacac    35760
gtatatggtc actatcaatg tagacgctat tagcatacat attgcagtaa aatcatagat    35820
gtcatttata tctttatacc atataataga atcgtatcct attatagtaa tacacgtgga    35880
ccgatgtaga gaataagtct tatgtttaga tgttaatata gtagatgtac tcgttgccaa    35940
atttttaatg agacacgata catttactga gcattgtata tcattatatt ttaagtttcc    36000
tgataatgag acaatcaaac taggattaag tgaaccatat ttgtgttta aaaaataacc    36060
```

```
atgtgtaaaa aagacattat cgtctagttc atctacggtt aacgtgcgat taataaaatt   36120
atatctatat ggaatatgcg gattatattt tatatttact acattataga tcctatcaaa   36180
atacaaatgc ccataacata attccacatc ctctgaatga aatctaaaaa tcgatgaact   36240
gtatgccaat accggcatta ttgacatcgt caatatggat attatccatt tcatcatcat   36300
catttaaaat tgacactaca tatgaatatt acttttatt ttaattacca gttgcacgta   36360
cacgggtagc gtgatctcta cacgttctat acacgtcacg tctggatgtt gttggcttac   36420
ccatcaaaaa tataagtgcg gtatgagttc tcgctataac gatcggagat acaggggcgt   36480
acccagtaag caactccata gcatacgtgt tctcatccat tagagagtta gtatatacaa   36540
tacaatattt ctgaccaata agaggtttta gaatattacg attagtgatg agaggattaa   36600
tcttggcaaa tgttctgtta ggaatagcag ctagaacatt ctttgtagtc ttgtaatcaa   36660
cgatggcggc atcctcgaac ttattatttt ttgagatatc ctcgataatt ttatgccatt   36720
cagccattgt tatttattat atatgttttt taataagaca tctattggaa taaacttgac   36780
attagcattc tattcttact acaaaatata aaatataaaa taaaatatac aatccaatac   36840
tcacataatc caactcactc gaacactatt tttccaatta cgataacaat attgcagaat   36900
gtactcgtta ttatttatta ttttgatgtg tataccattt agttttcaaa cagtgtatga   36960
tgataaatcg gtatgcgatt ctgacaataa agaatatatg ggaatcgaag tttacgtaga   37020
agcaacacta gacgaacacc tcagacaaac aacgtgtgaa tccgaaatcc ataaatatgg   37080
cgcatctgta tcaaacggag gattaaatat ttctgttgat ttattaaact gttttcttaa   37140
ttttcataca gttggtgtat acactaatcg cgataccgta tacgcgaagt tgctagtttt   37200
ggatccatgg actacggaac ctataaattc tatgacccat gacgatctag taaaattaac   37260
agaagaatgt atagtggaca tttatttaaa atgtgaagtg gataaaacaa aggatttcat   37320
gaaaactaat ggcaatagat taaaccaag agactttaaa actgttcctc cttctgatgt   37380
aggaagcatg atagaactac agtctgacta ttgcgtaaac gatgtgactg catacgtcaa   37440
aatatacgat gagtgcggaa acattaaaca gcattccatt ccaacactaa gagattattt   37500
taccaccaag aatggtcaac cacgtaaaat attaaagaaa aaatttgata attgttaatt   37560
gttattttta taaaaacaag aacggtacgg cgatatttat ttttttctaa aacatctaac   37620
cgaagtagtg gtatgataaa aatgtagttt gggagtattc gttgtactac aaatatattt   37680 ccgttttta gttccattct tcgtggcatt tttagctata aaattatatg gggttgtctg   37740
gtttaatatt tcggattctc ctacccaata tccgcgtcta atgcttctta aaaaacttaa   37800
ctcgtttgga gtctctatct taattagatc cgaatttgga tttagagctt tgcatgcatt   37860
acgtccttcc tcccaggttt ttcgatcagt agataaatgg atacatttat tattatagct   37920
tatccagtca gtaggacaat cttctctaat atatgcatct tttatcgttt tatctattga   37980
tggtgtatga actaatttac gttctacaac ttttaatagt gtcgctgtaa aataattcc   38040 aacaattaga ccgcatatta cgcagcaagc ataaccagca taatctgtct tatgtttgtt   38100
cattgtcgtg cggtgtactc gattaagatt acattttaag tattttttc atttgtggca   38160 ttcctactcc tatccctata tctgctataa ataacggttt cgaagttacc attactgaaa   38220
atagtcgcgc atcgacttgc gagctacgag tttgtttaga ttttgtatcg aacgaatata   38280
tagaattttc ttttatgaag tatattctat attcccgatg ttcatttcc ttctccttta   38340 tatcgaacca tttaacacca gacggtcctt cgaagatagg ttggttagat aaaggcttta   38400
```

```
taatatcatc tagtacatta tattttccta tgacttcaaa cgtggtatgt ggaacaactt    38460
ttccagctgg taaacatata ccaggagctg gagacggcaa ttgctttgta tatccttcca    38520
attttgacgt agaaaaagat tgtttaatgg tattcataga ataggtacat aatgcggact    38580
tggaataagg actatcgaag aatacatata gtatcgtatc attatctgtt tttatagttc    38640
tagaatgaat aatttgtcta taacttcttc cgtcgatatc acattctaat tcgactttga    38700
gaaacgtcga ccatctatga ctagacaatg atgatggacc accttcgtcg tttaggcaca    38760
tttgtgctat atacggaatt ttgacaattc tctttgagcc gatagtatca gtgaaaagaa    38820
tgtaaacttt gtcataagta ccatctttat cgacgaatgc tcctcgtaaa ccatcttttg    38880
gaattacgtt atccgccgtg tataaatcat aaccacatgg tccgtcaaat cttctccatc    38940
gtttaattcc ttcttttgat atgtttatgt cagatagtac acatccgttg tgactgatta    39000
tcgttacttt gctattttga taaggagcgt atcctctacc tctatgtttt gggtcgtctg    39060
aaccgtctat tttccaacat ttgggatttc cgttattggt tccgcatcct ctactttat    39120 agatgttgtt atataattat tattagttaa accagttttg tttagtttat tatttgaaaa    39180
tgtgtatacc gccccattaa cacccgtgta taatacgtcg tctaataagt aagtagaaat    39240
tatttcttca ctcgtttcaa acttatgcca ttcaataccg ttagcaaaat agaataaaat    39300
aaataacaaa ggtatcattt taaataaata aaaaatgtca agagttagaa tatcgttgat    39360 ataccctctat acgttggttg ttataacaac tacaaagacc atagagtata cagcatgtaa    39420
tgataccatc attattccgt gtactataga taatccgaca aagtatatta gatggaaatt    39480
ggataaccat gatatttta cttataataa aacttccaag acgacaatat taagtaaatg    39540
gcatactagt gctagacttc attcgttatc agatagtgat gtctcattga ttatggaata    39600
taaagatatc ttaccaggta cttatacatg cggggataat actggaataa aatctactgt    39660
gaaattagtt caacttcata ctaattggtt taatgattac caaacaatgt tgatgtttat    39720
ctttacgggc attactttat tcttattatt tctcgagatc acttatacat cgatatccgt    39780
tgtatttcct actaatttag gaatcttaca agtatttggt tgtgttattg ccatgataga    39840
gttatgcgga gcattttgt tttatccgtc aatgtttact ctccggcata ttattggatt    39900
gttgatgatg acgttaccat ctatatttct tataattact aaagtatttt cattttggtt    39960
actgtgtaaa tcatcatgcg ctgtacacct cattatctac tatcaattgg ccggatacat    40020
tttaacggtt ttgggtttgg gattgagttt aaaggaatgt gttgatggta ctctgttatt    40080
atctgggttg ggaactatta tggtgtctga acattttagc ctgttatttc tagtctgctt    40140
tccgtcaacg caaagagact attactaggc atgtgtataa taccacgagc tagtagacgt    40200
ggaagaggaa ccaggaacta ttgttatttt ataataatcc ttgatcttat tcttattctt    40260
tttatcagat tttttgcttc cagttttatc agtagatata caacagagtt tcataaaaag    40320
agaagagaat gaatccattc cgtacagtat ttgataatag cttttttttc gtttatgag    40380 gtatttagag attagagatg attaatgatc cccatactag aaatctatta atccacagaa    40440
atactaatgc tcatatttat attatcaatt ctaccgtaca atatttgttc cttgataggt    40500
acagaattgt acgactgcat ttttttgtat actaagtcga atggatgctc gaggttacaa    40560
acatgtatta aagtatcttg ctcgatgcta gaatttatgt acttggcaga ggacatacct    40620
atacagtttg atggaatagg aaactgctta ttgtcgatgg ttataatgga ataccactta    40680
ttattcgcaa atatctgatc gcatatgtgt ctatccaaat agtcggtaac tcgtctaata    40740
atgaatacag acaacggcga ataattaatc agtgatagat tgtttacata cagtatgtcg    40800
```

```
tttgtaaacg atgttaccaa tcgtttgcta ggtatatccg ctttaacaac caatatggtt   40860
gtaggaccct tgctaactac gacacattta ctcagtgggg atatgattac agcatgatca   40920
atgggaaagg ttagaatatt tttgccattg acgtcattat ctatagagat aacacatcct   40980
ccgacagaac taatacagag tataatcgtc gataatctat gaggaataag atggtacatc   41040
tcattgtcat ttacaacttc tacgcttaag atgttggtaa aagtaccgt ttcatccatc    41100 tgtctattga tctcatcaga tataattttt tgatgttctg tatctatata atatctacag   41160
tcattattag caataaaatt gctaatttta gaaatgccga atacagggaa tatctccatt   41220
tgtacaacgt gacggcagca ataatactaa atattacttc aattttataa aaaggaaact   41280
aatcacacca atgattctat atcatcgtgt tcatgatctt gttcttgctt attaagataa   41340
tcatcgctat gtgctcgtct aaacggatta ttctcactaa atttattgtt gagttctgta   41400
atgaacggat ttgacttgct acaaatactg gttttattat aatttacgaa aggattggat   41460
gaatagttag gattctgttt ggtatcttca ttaagtacta ctgtagtgtt ctgataaata   41520
gtctgttcat tacgatcatt atttattagc agcgtgcttc cagcaacact atcgtaaatg   41580
tgttctgtgc taggcgccat aacattggat tcgttatccc atattaaact accagcgaag   41640
ctatcatcgt ccaatatctc attcctagaa atattatcta cgtcattgtt ttgttccata   41700
gcactacagt gatcctccca gtctgattcg ctatcagttg atttactaga tttgctggaa   41760
ttagaactct ttatctttt taattttgtc atgataattt tattgtcatt atagacagta    41820
cgtatctttt tcctacaaat atataatata taacatacta atattgttcc cgcaactacg   41880
gtcaccgtga taagaggtac cagcatcatt tctgattgct caatatacgt actactagtt   41940
caatatttat tgttttatta tttactttac aactttatg ataaaaaatt actattgcat    42000
ttcccatcaa ttatgatcca tccattgccg tctgatatgc agaatgaaga attaaacgac   42060
aatttcattt tcagattatc tgaaggattg atgattagat gataatctcc agctgtatac   42120
aggttatacg cttctatgat tgtagcgtta aaaacatcaa tagatgggaa tagataaaat   42180
ggctgatgtt tatcttctat atctaacatg atatcatagt cgcatgctat gatgatggta   42240 tttttgatc tgtatgcggc acaaatgcta taaatgttga atctagccaa atcattagaa    42300
tcctgaggaa ctatttacc cttatagcta aagtagcatt tttgcatgtc ggaatatttt    42360
atatcccgta catctatttg gacagttttt atgttaccta taatgtatgg tcctataaag   42420
tccatgattg agatatcgag atcatcatac aatgtatctg ttatagtcaa cacacccatt   42480
ggagtaataa caaacgcggc gtccatggcg gcgtacgtta acgacttatt attaattcat   42540
tttttgttgt cacttgtaga attttttaac acatagtaca gattgagtac ttttacatac   42600
tgttttaacc agttttccag acttgtatat ataacacgct tcagcatccg tcgtactgtt   42660
tagttgttta aaatttgtta atttactaat atctatatct ttatcattat aatatctaa    42720 ccatttatca ttggtctttt ttaaacttac ccaataatct ttataaaaaa tactaaacaa   42780
tactctcaga tgtctagtat ccggtctagg caatctggct cgtaatttac gacactgata   42840
aaccgcatta tctgtagaca ttttaatgtt agtatctaaa taacaatgtt tatcgtattg   42900
tatccatcca ttggcgcaag cactaggcat cagttcttct ttgtaatgca gaaatgttcc   42960
tatgccacta ataatggttg agagtatcat cattatagcg accggcaccg acaacttctt   43020
aaacctactt acagtttgtc tattaagcga tttcatttat taatgtacaa aaataaatat   43080
tagttcattg tttaacaca aaaatacttt ctaacttctt gtgatacatc agaatcttga    43140
```

```
taatcggatg tagttttgt  aattggatta  ccatcagatc  cccatgtatc  cttaacataa  43200
tcaatgagcc aggtagtcaa gacatcggat  ttattgggta  gtgttgatga  ttccgcagtg  43260
caatttgctt tagcatccga gaataactgg  tagtctgaat  gtaatatata  acaagaaccc  43320
tggtaatata aaccattaca gctttctttg  tgatcatatt  gcgtagtgct  agacgcaacc  43380
tttctatgag tagatgatgc agcagcaacg  gcaacagcgg  cgtcagtaat  agcagcctcg  43440
ttagcagaca tgcattgatt taggcgcact  atgagaaacg  cggacatggt  aatcatagat  43500
agtagtgaaa taaccataga tattctaata  catagaccaa  tcacgcgttt  gcgtttattc  43560
tttccctgaa ttttgtctct gtaaacagta  gcggagaaca  cagatgtctg  ctcttcgtcg  43620
ttttctggtg tcatcatgat aataaatgtt  atttatgtca  cgatgtgcct  tctttgttct  43680
cctccctact aacgacctta gttttccata  ttttgattta  ttatcaaatt  aatttagtaa  43740
ctgtaaatat aattatgaat tgtttccaag  aaaaacaatt  ttcaagagaa  aatttattaa  43800
aaatgccgtt tagaatggtt ttaacgggag  gatctggatc  tggaaaaact  atctatttac  43860
tatctctgtt ttctacacta gttaaaaaat  ataaacatgt  attcttgttt  acacccgttt  43920
ataatccaga ttatgatgga tacatttggc  caaatcatat  taatttcgtt  agtagtcagg  43980
aatctctaga atataatctg atacgaacta  aaagtaacat  agaaaaatgt  attgctgtcg  44040
cacaaaatca taaaaaatca gcacactttt  tacttatttt  tgatgatgta  ggcgataaac  44100
tatcaaaatg caatactcta atagaattct  taaactttgg  aaggcattta  aacacgtcta  44160
ttattctact atgccaaact tatagacacg  taccaatatt  aggacgggct  aacattacgc  44220
atttttgtag ttttaacatt tccatctcag  acgcggaaaa  tatgctacga  tcgatgcctg  44280
taaagggaa  acgaaaggat atattaaaca  tgttgaatat  gatacagaca  gctagatcca  44340
ataatcgatt ggctattatt atcgaagact  ccgtattttg  tgaaggtgaa  ttacgtatat  44400
gtaccgatac cgccgataag gacgttatag  aacaaaagtt  aaacatagat  attttagtaa  44460
atcaatattc gcacatgaaa aagaatctaa  acgctatatt  agaaagtaaa  aaaacaaaat  44520
tgtgcaatag cgatcaatca tcatcgtcaa  aaaatgtatc  ataattataa  ttattaactt  44580
ttgtaacaat agtcctattt agagaaagtc  tatcgataga  cgatcccaat  ttgtaaattg  44640
ttccactact tgtcactcca tgatatgata  aatccatgta  aaatagcatc  atctttagat  44700
cattaattgt taccttcccc aatacaacca  aatcatcatg  atatatacct  cctccagaca  44760
agtatttaac aacggtagaa tgctttggct  tataaaatac  aaatgacatt  cccttatgtt  44820
taatcttaat cttttcttta gttattgaat  cgttacaatt  ataaaatgat  gttttttcca  44880
aaaacctaag tgtatttaaa atagatgcca  tgttaaaaat  gtccgccgtc  gacttttgg   44940
aacgattgat aaaagctggt gtttatattt  atgttttacg  gacaaagtgt  gtaattgcag  45000
ctttactagt aaaaaactat tccataaaag  acgaataaga  tacaaacaca  aatgtttata  45060
taatatttaa atggaagacc ttaacgaggc  aaacttctca  catttattga  taaatttatc  45120
taataataaa gatatcgatg cgcaatacgc  gtctacatta  tccgtggtac  atgaattgct  45180
atccgctata aattttaaaa tatttaatat  aaacaaaag   tcgaaaaaga  attccaaatc  45240
aatcgaacaa catcccgtcg ttcatcatgc  agcatccgcg  ggaagagaat  tcaatcgtcg  45300
ttgaactcga accctcattg gctacattta  tcaaacaagg  atttaataat  ctcgtaaaat  45360
ggcccttgtt aaacattgga atagttttgt  ctaatacatc  taccgctgtc  aatgaggaat  45420
ggctaactgc ggtagagcat attcccacca  tgaagatatt  ttacaaacat  atacataaga  45480
tacttactag agaaatgggg ttttagtct   atttgaaaag  atcccaatct  gaacgcgata  45540
```

```
attatataac tttatacgat tttgattatt atattataga taaggataca aattctgtaa   45600
ctatggtaga taaaccgacc gagttaaagg aaactttgtt acatgtattt caagaatatc   45660
gtttaaagag ttctcaaaca atagagctta tagcgtttag ttcaggtacg gtaataaacg   45720 aagcatagt ttcaaaatta acatttttag atgtggaggt atttaataga gaatataata    45780
atgttaaaac tatcatagat ccggattttg tatttagatc tccatttata gttatttctc   45840
ctatgggtaa actaactttc ttcgtagaag tatattcgtg gtttgatttt aaatcgtgtt   45900
tcaaagatat tatagatttc ttagaaggtg ctctaatagc caatattcat aatcacatga   45960
ttaaggtagg taattgtgac gaaacagtat cgtcttataa tccagagtct ggaatgttgt   46020
ttgttaatga cttaatgact atgaacatag tcaacttttt cggatgtaat tctaggttag   46080
aatcatacca tcggttcgat atgacaaaag tagatgttga actatttatt aaagcattgt   46140
ctgatgcgtg taaaaaaatt ttgtcagctt ctaatagatt ataaatgaac tctctatcaa   46200 tttttttat tgtggtagct acggctgcgg tgtgtttact ttttatccag ggttactcaa    46260
tatatgaaaa ttatggcaat attaaggaat ttaatgctac tcatgcagca ttcgaatatt   46320
caaaatctat aggtggaaca ccggcattag ataggagagt tcaagatgtc aacgacacaa   46380
tttctgatgt aaagcaaaag tggagatgtg tggtttatcc aggaaacggt tttgtatccg   46440
cttccatatt tggatttcag gcagaagttg gacccaataa tactagatcc attagaaaat   46500
ttaacacgat gcaacaatgt atagacttta cattttctga tgttattaac atcaatattt   46560
ataatccatg tgttgtacca aatataaata acgcagagtg tcagtttcta aaatctgtac   46620
tttaaatgga cggaactctt ttccccggag atgacgatct tgcaattcca gcaactgaat   46680
ttttttctac aacggctgct aaaaagccag aggctaaacg cgaagcaatt gttaaagccg   46740
atgaagacga caatgaggaa actctcaaac aacggctaac taatttggaa aaaaagatta   46800
ctaatgtaac aacaaagttt gaacaaatag aaaagtgttg taaacgcaac gatgaagttc   46860
tatttaggtt ggaaaatcac gctgaaactc taagagcggc tatgatatct ctggctaaaa   46920
agattgatgt tcagactgga cggcgtccat atgagtaact taactctttt gttaattaaa   46980
agtatattca aaaaatgagt tatataaatg gcgaacatta taaatttatg gaacggaatt   47040
gtaccaacgg ttcaagatgt taatgttgcg agcattactg cgtttaaatc tatgatagat   47100
gaaacatggg ataaaaaaat cgaagcaaat acatgcatca gtagaaaaca tagaaacatt   47160
attcacgaag ttattaggga ctttatgaaa gcctatccta aaatggatga gaataaaaaa   47220
tctccattag gagccccaat gcaatggcta acacaatatt atattttaaa gaatgaatat   47280
cataagacca tgctagcgta tgataatgga tcattgaata caaaatttaa aacgttaaac   47340
atttacatga ttactaacgt gggtcaatat attttatata tagtattttg tataatatct   47400
ggtaagaatc acgatggtac tccttatata tacgattctg aaataacgag caatgataaa   47460
aatcttatta atgatcgtat caagtatgca tgtaagcaaa tattacacgg tcaattaact   47520
atagctctga gaattagaaa taaattcatg tttataggat cacccatgta tttatggttt   47580
aacgtaaacg gatcacaggt atatcacgac atatatgatc gtaatgccgg ttttcataat   47640
aaagagatag gtagactact atacgcattt atgtactatc tatctatcta taagtggtag   47700 attttttgaat gatttcgcac tattaaagtt tacgtattta ggagaatcct ggacatttag   47760
tttgagtgtt cctgaatata tattatatgg tttaggatat tctgtttttcg atactattga   47820 aaaatttagc aatgatgcta tactcgttta tattagaaca aacaatagaa atggatatga   47880
```

| | |
|---|---|
| ttatgtagag tttaataaaa aaggaattgc taaggtgaca gaagctaaac ccgataacga | 47940 |
| taagcgaatt catgctataa gacgcatgaa ggctgaacgt gaaatcgctc gtaaaaactg | 48000 |
| cggaggtaac ccatgcgaac gtgaagaggt tggaatatca actagatgcg gagaaagaaa | 48060 |
| aagttaagtt ctacaaaaga gaactagaac gtgatcggta tctttctagt agatatctta | 48120 |
| cctcttcttc agatccacat gagaaaccat taccaaatta tacatttcct cgcattgaag | 48180 |
| tagctccgtt gatgactgag gataaagaac cagaacctgt agaagtggtg cctccatcgt | 48240 |
| ccacagacgt taccgaaccg attagtgatg tgacaccatc ggtggatgtc gaaccagaac | 48300 |
| atcccccagc tttctgaata tcagacttca gtatcccaag tagcagttac acctccacca | 48360 |
| aaacctaaaa ctccacagat tttcgaatat cagacgtccg attctatagt taacaatcca | 48420 |
| cgcccatttt ataattcgga tctcgaattt gatgatattg atatgtatct actaccaaac | 48480 |
| tagaatatta caccagaaaa gacggtttga gatcaacttt atctaatggt ttataaaacg | 48540 |
| aaggaggcct tcgttcgaaa tctaatttaa cttttacgcc tctggcgttc atttgagtaa | 48600 |
| gaaatacttt agatacgtgc gtggtatcaa ttttgttaa gagaggagag agattaagtt | 48660 |
| ttgaacatct aagacatgta ttaatacct tgatttgtgc tgctatgtct ccacaatttt | 48720 |
| cacaaacata cacatcttga taatcttctt ccgaatcttt caaaacttct gtaatagtat | 48780 |
| tggctgcacc atgcgctatt aaacagtctc tctccatttc tccgaacttg atacctcctc | 48840 |
| cacgttttcg tccctcattc gcctgtctaa tgagcttcgt cttttacct ctacatctaa | 48900 |
| cggttgcctt gtcctgagtt aaatgcctca gacgcaagta ataaattggt ccaaaaata | 48960 |
| ctttggatgc ataaggctta tccgtttcag gatcatagag aatcttttca caaagatttt | 49020 |
| tatccgataa ttcttcatca gacaatttcg gatttgaatg ctcataacat tgtttagcga | 49080 |
| attgcatata tgtatcgatg gatgtttcgt tactactagg aaaacagaca ggtcggtttt | 49140 |
| ctcccttatt gttgtacggc ttagcagaat atgcggctgt taaaataacc tctatcaaca | 49200 |
| tagatatagt ttttctagag aagatggatg tagaattaat aatgacatct ggtgtgatac | 49260 |
| catttcatc gtatggaagt tccgtttcat ccgcgatata cgcgactgtt cccttttgac | 49320 |
| tcgttctagt ggtaaatttg tctcctagaa tgggtcttct ttctttcatg gttaatactc | 49380 |
| gtaccttaac tttgtcagta agttctactt gtactcgttc aacgcgagat tgtacatat | 49440 |
| cggtatattt ttcggaaaca tcaaagctaa tctgattatc tctagcaaaa tcatcttcaa | 49500 |
| gagttcttga tgagatattt cgtgctatag cgtctccgga ttccaagaaa gcattcagtc | 49560 |
| taactaatcc attactttct aattttgaat aggcgttaga cctatctctt tctttgttat | 49620 |
| taaagttttc caacggaatt tctacttgat gtttcttggc tgtaacaata tcgagaccgc | 49680 |
| ctctctgaat aaattgtttt ttgatgataa ttccatcctc ttgattgata cctttgtacg | 49740 |
| acattaatgc tatagtaaca tgttggccga agcaattagc cgcaatcttt gaagtttcta | 49800 |
| aagccttact aatcacgatt ggcctctctg gatacatcaa atgaattcca ttgtctatt | 49860 |
| tatttcgtat atccgagctc agacaagaga tagcttgttt agcttgagca catccaagaa | 49920 |
| tagctctggg tccagaattg tgattgattc ccactagtga agatgctaca tatccatctc | 49980 |
| taaattcggc aggaaagtca cataaatcgt attgctttct ttcatccttt gacatcattc | 50040 |
| taaattttg aaccgattca catacgttac taaaagtaaa ttgttctata tctaccattt | 50100 |
| cgatgacatg cggaaactct ttctgaatgt cagagaatgt catgtcgtct aatctgcttt | 50160 |
| ctaactccgg acacacatcc atcatgagct ctccgttatc cacaaccaag aatggtctga | 50220 |
| ctaatcttcc cgctccaata ttaatgcgaa tttcattcat gtgatcccta actaaagtaa | 50280 |

```
tacctacctc caagttaccg aagaatccca tccgttttct acgtctaaag tcagttacaa   50340
aatcacatat catatttgga ttaagagatg cgactagagc attttctata gtgattggaa   50400
atcctgtttc aaagtaactt atatcatctt tataatatga tctgatatac tcacaaattt   50460
tcttttccaa atccaaatac tcagacgtta gtatatttgt aatggaactc aagacagaca   50520
attgagatac taaacctacc tgaggacctc tttccggaac gtccgatgaa caaaagtaaa   50580
gatattgact tggatggtat tttctgacag aaaacatctt tgaaatcttt acttgatccg   50640
gataaaatcc aacactccta ggaatagaaa tattctgcat ccatgaatag tgaggatgtg   50700
ttcgataact accgtctgac tttttgaact ttccactcaa tagactagaa aatgcatgat   50760
taagtccagg agttgttagt acatgaatgt ttaccgcgta agtgcctctg ttcttgtgat   50820
tgttcatgat atcgtttcgg atgttgccta tgtaattctc taattcatca tgtgccaacg   50880
tctcaaaata tttgccgtac gttaggatgc gatgacaaac catcgaatct ctatctggat   50940
atctagaagt gtggtagata cagtagagaa actttcttag taaagatatc atataaaatc   51000
cctttagttg atcgggtgta tagttcatat gaggtaaaaa gttatgcagc atttcatatt   51060
tgaactcgtt gatcgttaac tgagattttt gtttaatgtg ttcagcttcc accaggtcat   51120
taatgtatgt atcaatatta aagtcagtaa tagattcagt aattcgttta gcactatcta   51180
ttatcgcgtt tactagatag acaacttctg gaggcatatc gtatgataaa ctacgtctaa   51240
tgaattctag actcactcta gataaatatt gagacagcaa aacaatattg accgttataa   51300
atgtctttgt cgatgatata ttcaacgctt ccaattgtga tatatccaga gatatcttgt   51360
aatggcgata tcttgtcggt aatacattag gaggggatac ggaggaaaac gagaaagtga   51420
atgagtttgg cttaacaacc ctaaattttg gccatgttgt aatcttttct actagattaa   51480
ttcctacttt ttcgacagat tgtttattga taaagactcc acctatgaca ttaggaacaa   51540
gatacttggc tgtatcaagt ggatttttat tcccgtatcc tattagtagc ggaattttta   51600
tcaaatgaga atcttttccc tcataactac ttattttagt gatggatata ccctctttgg   51660
tcattacctc tttaaagata tttacagtga acgtggctaa tgcgtcataa ctcttacctt   51720
taatactcgc gattataggt gagtaatctg gaggagtcac tttaacattg ctaatttcta   51780
tcataattcg ttctgtatta ttcttaaacg ataagagtgg ccgcttgacg gtcaagattt   51840
catgcaatcg atgcaatata aaattagaat acgatacata ttggaaatgt aacggtctat   51900
aaaaaactcc ggctttagga tcaggcacca aaaacttata tccgagtcgt tgatccattt   51960
ctgaattagt gttttttttt catttagaa gcaattcttt tagacgatct accgattccg   52020
tttctatatc tatgctattt aaaatagtcg atctttcctt catcatttct atcatattct   52080
cggatttagt cacgtaattt atacaatcct ccagagatcg taatgctaca atattgagct   52140
ttttccccctt aaaaaacttt attttgctat cctcatctaa cagagagggg aaaacggtat   52200
gatccaacga cttaataaat gtcaggttaa acatccctat tttgaaattg ctaactccat   52260
aaacatcgtg ttcagccatt ttcttaatta ggaataattt ctcatctaat gccgtagccg   52320
tgagtacgtg gttacaaca ttagctactt ctttaaagta ctcgttttgg atgatatcct   52380
cgaacaacag aaataaatta taatagacat agaataattg gtcaatcatg tgtatacacc   52440
ccttttcatc cttgtccttg gatagaataa tgtgcatagt agaatccttg aatattttca   52500
cacatgttct attagtaaaa ataatttcta tagtttgtaa tatagagctt tttccacgcg   52560
ttactataga gtgattaatg atatctactc tcattctctt agaaatggtt ttgatccaag   52620
```

```
gttgattaat gttggacctg actgtagtgc tcagatactc atcagacttt ttaccggaaa    52680
agtaatttgc attagtgcct ccatgtacag ttttctttat ttccccataa ttgaccttc     52740 tcttcttatt ggtagtttta atatatgata caagagatga cttttccctc tcaaatatct    52800
ctactgtacg agagctaata ttgctattat ctgagtttat atcgaaataa tgacaacatt    52860
tcacttgtga agaatcgtta aataccggat acgtattctg attaataatg tgtttagtaa    52920
gttggatgtc gcaatacact agtttcttaa tggcatgatg tatatcttta ttatacacta    52980
tattatcaaa catatcctct gaggaaatgc gttctttcat aagaccatat atatctccta    53040
tttcatcgca acttattaga tgaaagttaa aaatagttct ggcatatcta tcttctattt    53100
catgtagaaa ggtaaataga ttatccataa tggcgttact aacgttatta cattttttt     53160 atgtaatttc tagatttaca cctattataa ggtgtataat tagtattcca tttatctaat    53220
acgtatctca tagccaaatt gaaactatcc gctacatcgt ctaatttgcg tctatccgga    53280
acggagtctc gcaatccgaa tgtgtccatc caatcaagaa atgcttcgac cgatctcttt    53340
tttcgatctc tatatgaatt accagacatg acaggcgaga cgcaaataac tttggcagcc    53400
gatgtatgat ataaaaagcc tttaataaaa tagataaatt tgacgtacgg cgaccttcta    53460
ggctgacgtt ctagaagaac tgtagtgtat tcatattgtg acaaatcttt agctatgtgc    53520
ctttcccaat cagaactcca gtctaatttt gatatatcca atacctaac  ggagttatcc     53580 ttgacttcta aaacagttct ggcaggattt tttgcaccta tcaaaggc gcatattatt       53640 tcactcgaat aatcttttt tgacatcggt gacgatatta aagattgaga cgaactggtt      53700
aaagtttcca tatatagtct caatactcgg gttatttaaa caattagtat tttcaatatt    53760
gaaatttaca accttacaat tttctatttt gaaccgcatg ttattaacta acgttataaa    53820
atccgcttct ggatatccca acattctct gcttaaatca aatgctgatt ggttttttat     53880
ttttcgtttt acagttccgg atttattaat ctcatcaact aactcatcga cagttgcgca    53940
ctcattaata tctaatttat tagtcaattg ctttaagcct gcactaccaa ccttagaaga    54000
atactttccg ttaacataat agtctcgtcc tatagtgtct ataattcgtt ttattacttc    54060
tcctctagtt tctgttccgt ttccatcata gtcgtataaa atggaaaatg tgttttttct    54120
ttttactttt acaaatgtat gttctctaac cttggatcgt attaaatggt ctacatcttt    54180
tactaatatc ttttttcctg atttttgttat aacgctagga ataaaaatat tatctcctat    54240
acgatctacc ttgatggact caatatacat gaatgagaat ttgaaaaagt ctacaacttg    54300
ccgcctaagt tctcccaact taatatacga tatggatatt tttggaaatt tatcatcgaa    54360
agagcgttct ataatagagt ataactcgtc gtcaaataat gtgtcttcct ctatttcaat    54420
ttctaaatat ttgggtatgt ttaatccgta ctcactagct agtttaaata tattaactgg    54480
agactgatat tttgatatag catcttccat tatccatcta ttgtttaaca aaacaaatct    54540
cagaaagtct attccgttat cgctgtctaa tactttgtta cacgcacttc gcatatcatc    54600
tggtatttga aaagagtttc cagatccaag ttctaccata ttttaccct  tcgaataaat     54660 aaagacgctc ccaaaatata ccggtaagaa aatgtaatag cccggatcaa tattaaacgg    54720 tttattttt acctcatcat aataatcaga tattgacgtc tcgacattag ctaccttttg     54780
cacgcctatt ttccagtaag tagatgttcc ccattctacc aaagaattat acttttctat    54840
agccgcagaa tctgaaaatt tcaaactttt gtacagacta agtaattctt ttaagttagt    54900
taaatcagcg ctagaagtca tgataacttt attttttaatc ctatgttatt tcattcttat    54960
ttttaatatt atagtacctg caatatctga aaaaatgaga cgcgaacgag ccgcatacgt    55020
```

```
aaactacaaa cgtctaaaca agaatttcat ttgtgtcgat gatagactgt ttagttataa   55080
ttttacaaca tctggaatta aggcaaaggt ggccgttgat aacaaaaatg ttcccattcc   55140
atgttccaag ataaacgagg tcaataataa taaagatgtc gatacactat attgtgataa   55200
agatagagac gatataccag gttttgcacg atcgtgctat agggcatatt ctgacttatt   55260
ttttactacc taaatggata gcaccaatgt gcgttccgga atgaagagcc gcaaaagaa    55320
gcccaagact acagttatcg atgacgatga tgattgcatg acgtgttctg cctgtcagtc   55380
taaattggtt aagatttccg acatcacaaa agtatcattg gattatatta atactatgag   55440
gggtaataca ctggcctgcg cagcatgcgg atcgtcgctt aaacttctta acgattttgc   55500
gagttaaata ttctatttaa tacacgttct tctctggagg atgttgtaca tacagaagtg   55560
ggatcggatt cttgatgttt ccgataactt ttttgtttaa atcctagttt atctacagac   55620
agactaataa ttcgttgaac gaaatttcct atcatgtact ttatttcttt gatggatgtg   55680
ctaggaaata catataccgt cctatctaat agttctgttt ctcgacatac cctcccctagt  55740
aattgctcta tttgcatatt gttgattact gccgagcaaa tgaacaaaga atccaaacta   55800
ggaatatcta aaccagtacc ggaataaaat aaggtggata cgaatataaa tctatttagt   55860
tccttgattg atttgaccat atctggagta cgtctatttt gggcgtctcc tataaataca   55920
acctctgatc cgaaaaaatc taataatcgt ttgtagaaga ataccatatg ttcacgtagt   55980
ttagtaataa ctaaaatgcg attaatagtt cctgacttga attcttctac cagggtatta   56040
agaataagtt gatttctagg ctcgtctaca gataataact tctcggtata tatatgatat  56100
ttattagatg gtccatctaa tcgttttatc atatgtctaa tattatctgt ggaatatggc   56160
tcaaaaaaac tatctactgc atagatagtt tttttttagat cggataactt ggcaatatta   56220
ataatactgt tacaataaat tctgttagat ggtctaggtg tagcagttaa aaaataacac   56280
atcatcggag gataatacgc taaaaatctt gtaactgctg tattgttcat cagattatac   56340
gtatgtgatt catccaagat gaacaaatca taatgcttat tgatatattt acaaaaggca   56400
tcgtttgtca gatgtctact gactactatt aatacatccg gactttgagt ctttagttcc   56460
tttaatagac tacttactcc atctatggat atcttatgtt ccaatccgac tgcctctacc   56520
tgtgtcttcc attgatgtat taacatttta ttgggtacgc aaatgacggt ttttctaccg   56580
tgtgtagcca taagataaca cgtggtaata gtcttaccaa atccacacgc caagtgaaga   56640
gtgatgtata gaggacgttt tgattcgatc attttcctca tattagaaac tacttcagat   56700
acgactttgc gttgaagagg ataactttt ggcgcatttg ttggattgat actagtaatt    56760
ttattatcgg tcgttgttaa tgtttcaaat actagactcg tctttacgga aggagaggcg   56820
taaaatccct taggtatcag aaacttaaag gatgatcccg gttcaacttc tacgaaatcc   56880
ccgtcttcgt taaaaagact tagggggttga ccacaagtca ttttttttag ttcggcataa  56940
agattatact ccatctttaa tagtgacatt ttttaatata taaatgagtt atttaagata   57000
ttacaatatg cttgacgact tctctgcggg tgctggagtg cttgataaag atttatttac   57060
agaggaacag cagcaatcgt ttatgcctaa agatggaggt atgatgcaaa acgattatgg   57120
aggaatgaat gattatttgg gaatcttcaa aaataatgat gttagaacgt tactcggttt   57180
gattttgttc gtcttggctc tatatagccc tcctctaatc tctatattga tgatatttat   57240
ctcatctttt ctattgcctc ttactagctt agtattacc tattgcttag taactcaaat    57300
gtatcgtgga ggtaatggca acactgtggg aatgtctatt gtatgtattg tagctgctgt   57360
```

```
aattattatg gcaatcaatg tatttacgaa ttcacagata tttaatatta tttcttacat    57420
tattttgttt attctgttct ttgcatatgt gatgaacatc gaaagacagg actatagaaa    57480
aagtataaat gtaaccattc ctgaacagta tacctgcaac aaaccttata ctgcgggaaa    57540
taaggtaaat gttgatatac caacatttaa cagtttaaat actgacgatt attaaaaatg    57600
ggggcagccg ttactcttaa tagaatcaaa atagcaccag gaatagcaga tatacgagac    57660
aaatatatgg aattaggttt taattatcct gaatataata gagctgttaa gtttgcagaa    57720
gaaagttata cgtactatta tgaaacatct ccgggagaaa ttaaacccaa gttttgtttg    57780
atagatggta tgtcgataga tcattgtagt agttttatag ttcctgaatt tgctaaacaa    57840
tatgtattaa ttcatggaga accatgtagt tctttcaaat ttcgtcctgg atcattaatc    57900
tattatcaga acgaggtaac tcctgaatat attaaggatt taaacacgc tactgattat    57960 atagcatccg ggcaacgatg tcattttata aaaaggatt atctcctggg cgatagtgat    58020
agcgtggcaa aatgttgttc taagacaaat accaaacact gtccaaaaat atttaataat    58080
aattacaaga cagaacattg tgatgatttc atgactggat tttgtagaaa cgatcctgga    58140
aaccccaatt gtttagaatg gttacgtgca aaacggaaac cggctatgtc tacttattcc    58200
gatatttgct ccaaacatat ggatgcgaga tattgttctg agtttattag aattattcgt    58260
cctgattatt ttactttttgg ggatacggca ttatacgtct tttgtaacga tcataaagga    58320
aatagaaatt gttggtgcgc gaattatcca aaatctaatt ccggagataa atatttagga    58380
cctagggtat gttggttaca tgagtgcacc gacgaatcta gagatagaaa atggttatat    58440
tataatcaag atgttcaaag aactagatgt aaatacgttg ggtgcacgat taacgttaac    58500
tctttagcgt taaaaaattc ccaagcggaa cttacgtcta attgtactag aactacgtcc    58560
gccgttggtg acgtacatcc aggagaacct gtagtaaaag ataaaataaa actgcctacc    58620
tggttgggcg cggccataac attggttgta atatctgtta ttttctattt tatatctatt    58680
tattcgcgta ctaaaattaa aacaaatgat ataaatgttc gtagacgata attcgttgat    58740
aatttattct acatggccca gtacattgtc cgattcatcg ggtagagtca tcgttatgcc    58800
agataataga tcattcacgt ttaaggaagg gtttaaatta tgatgaatcga taaaatctat    58860 attgttggta aacccgtcgt ctatagatct attaaagatt agagtatata aacatcgcat    58920
aaaatggatg ggtgatatat tcgtattatt tgagcaagaa aatatcccac caccttttcg    58980
tctagtaaat gataagtaat tacgagccgt tgctgctgtt agttataaca tgctgtgtac    59040
tactatttaa ttttaccata tcttcgaaaa caaaaataga tattattttt gcagtacaaa    59100
ctattgtttt tatatggttt atattccact ttgttcattc ggcgatttaa aattttattt    59160
agttaaatgg atatgatgct tatgattgga aattattttt ccggcgtgct aatcgctgga    59220
atcattcttt tgattctttc gtgtatcttc gcctttattg actttagtaa gtctaccagt    59280
cccactcgta catggaaagt attgagtatt atggcgttta cttggtat tattatcaca    59340 gtcggaatgc taatttattc tatgtgggga aagcactgcg cgccccacag agttagcgga    59400
gtcattcata ccaatcatag cgatatttcc atgaactaaa ttattatcgt ccatatatct    59460
cgacattgtt gaatcattat tactacttat ttagtgaaaa gatgatatat tgcatacttg    59520
atcaatagtg aagttattgt caataaatga ttggtattct tttgttgatc ggtatttgcg    59580
tagcagttac cgtcgccatc ctatatgcgc tgtataataa gatcaagaac ccacaaaatc    59640
caaatccaag tccgaattta aattcgcctc ctccagaacc aaaaaatacc aagttttgtaa    59700 ataatctgga aaaggatcat attagttcat tgtataatct agttaaatct tctgcataaa    59760
```

```
taaaaatatt tttagcttct aaatggcgga taaaaaaaat ttagccgtta gaagcagtta    59820
cgatgattat atcgaaacag ttaataagat tacaccacag cttaaaaatc tactagcgca    59880
aatcggtgga gatgcagccg tcaaaggagg caacaataat cttaattctc aaacagatgt    59940
gactgccggc gcatgtgata caaaatgtat tacatgtaaa ccaaaatcaa aatcctcgtc    60000
ttcttctaca tcaacatcca agggctccaa aaatacttct ggtgctccta gacgtagaac    60060
aacagttact actacatcgt acaatgcgat ggatggtcag attgtccaag ctgttactaa    60120
tgctggtaaa atagtttatg gtaccgtcag agacggccaa ttagaagttc gtggaatggt    60180
cggagagatc aatcacgatc ttctaggtat cgactcagtt aatgctggga aaagaaacc     60240 atctaaaaag atgcctacta ataaaaagat taatatgtcg tccggtatga gacgacagga    60300
acagattaat ccagacgatt gttgtctgga tatgggaatg tattaaatta aataatttta    60360
attcgtttaa cgaatatctt gagtataaac aatacaatat taagaaccgg actgttaccg    60420
attcctagtt ttgatgctac agcatcgcag tcatctccga tctccacatc gataatttct    60480
gaagtgatat cggtactcag tcctttgatt tcttcaaatc cgagttttag caatgcttgc    60540
tcgataatat ttatgacaat aataatcacg ttagtgacga taattttcg ttttctactt    60600 tcgtgatatt gtttaatcgt tttatagatt ctatctattt catcctctga acaaacatcc    60660
aagtcctcga ctgataaggg agaccgttc aaatttgcat aattaacgat ggctatacgc    60720
ttattaactt ctgttgattt atacggagtc ttaccaaata gtattctggt aaaattatct    60780
aaattatcag atgattttgt attagatcgt tgatttctaa gattaaccac ttcatcctcc    60840
aacatctgaa ttcttttatc tttatcataa actactccca aggatggtgt tgtgttggc     60900 atagaagata tcatagatct agattccatt attgcttcag cattttcga tactgtaata    60960 ttaaatcttt tttctcgttg ttgacgttgt tccgatatca ataactctct acgaaacgta    61020
ggaggtggag tatcgtcaat aatagtagta tgaggttgta ctcgttcgat aatagtggcc    61080
ggagaatcat catctggaaa tagatcttca ttaagttgtg aggatatttc ctctggagat    61140
gacactacgg cggcattatg ttctctatct accacgttgt taacgtgagt tagaatagac    61200
atttgacgaa gagttatttc ataattttg ttagatggat aattatcttc tgaaaactct     61260
gtaattaaat cgttttgtat atccgtcact ggtacggtcg tcatttaata ctaaataaat    61320
gatgcctatt aagtcaatag ttactcttga tcaattagag gactctgaat atttatttcg    61380
tatagtttct accgttcttc cgcatctatg tctagattac aaagtatgtg accaacttaa    61440
aacaaccttc gttcatccgt tcgatatatt gcttaataac tcattaggat ccgtaactaa    61500
acaagatgag cttcaggctg ctatatccaa attgggcatt aattatttaa ttgataccac    61560
gtcacgtgaa ttaaaactgt ttaatgttac acttaacgct ggaaatatag atattattaa    61620
taccccaatt aacattagtt cggaaactaa tcctatcatt aatactcaca gcttttacga    61680
tcttccacct ttcactcaac accttcttaa tattagattg acggatacag aatacagagc    61740
tagatttatc ggtggttata ttaaaccaga tggctccgac tcaatggatg ttctagcaga    61800
aaagaaatat ccagatctta actttgataa cacttatttg tttaacatcc tctataagga    61860
tgttattaat gcaccaataa aagaattcaa ggcaaaaatt gttaacggtg tattaagcag    61920
acaagatttt gataatctta taggtgttag acaatatata acagcacaag atcgaccccg    61980
ctttgacaac gcttataaca tcgcagatgc tgctagacat tatggagtta atcttaatac    62040
attgccatta ccaaacgtag atctcactac tatgccaaca tataaacatc tcatcatgtt    62100
```

```
tgaacagtac ttcatttata catatgacag agtggatatt tattacaatg gtaacaaaat   62160
gctcttagat gatgagatta tgaactttg tatttctatg cgatatcaat ctcttattcc    62220
tagactggta gaattctttc cagatatacc agtaaacaat aacatcgtac ttcatactcg   62280
cgatcctcaa aatgctgcag tgaatgtaac cgtggcgctt ccaaacgtgc aatttgtaga   62340
cataggtaga aaccacaaat tctttattaa tttctttaac ctgttggcga aggaacaaag   62400
atctacggct atcaaagtta ccaaatccat gttttgggac ggtatggatt acgaggaata   62460
caagtctaaa aaccttcagg acatgatgtt tataaattct acctgttatg tattcggtct   62520
ttataatcac aataatacta cttattgctc tatcctttct gatattatct ccgcagagaa   62580
aacacctatt agagtttgtt tgttacctag agtagtcgga ggtaagactg ttactaatct   62640
tatttcagaa actttgaaga gtatttcatc tatgactata cgagagtttc ccaggaaaga   62700
taaatctatc atgcatatag acttctga dacaggattc atgagattct tccaactact    62760
caggctcatg gctgataaac ctcatgaaac ggctattaaa gaggttgtta tggcttatgt   62820
gggtataaag ttgggtgaca aaggtagtcc gtactatatt agaaaggagt cataccaaga   62880
ctttatctat ctgctatttg catcaatggg ctttaaggtg actactagaa gatccattat   62940
gggaagtaat aatatctcta tcatcagtat tagaccaaga gtaactaaac aatacatcgt   63000
cactacattg atgaaaacta gttgtagtaa aaacgaggca gaaaaattaa ttacttcagc   63060
gtttgatctt ctcaatttca tggtatcagt tagtgacttt agagattatc agagttacag   63120
acagtataga aactattgtc ctagatattt ctatgcagga tctcccgaag gagaggaaac   63180
cattatctgt gactcggaac cgataagtat cttggataga attgatactc gtggtatctt   63240
ttctgcgtat actattaatg aaatgatgga cactgatatc ttttctccag agaataaggc   63300
atttaagaat aatctgagta gatttatcga gagtggaaat attacaggag aagatatttt   63360
ctgcgcaatg ccatacaaca tcttagatag gattattaca aatgctggta cgtgtaccgt   63420
atccataggt gatatgttgg ataacattac aacccagtca gactgtaata tgactaacga   63480
aatcacagat atgataaacg cctcattgaa gaatacaatt tctaaagata ataatatgct   63540
agtcagccaa gcattggact ctgtagctaa tcgttctaaa caaacgattg gagacttgag   63600
gcaatcatcg tgtaaaatgg cattgttgtt taaaaatctt gctacatcca tctacacaat   63660
agaacgtatt tcaatgcta aagtaggcga tgatgttaag gcatcgatgt tggagaagta    63720 taagtattc acagatattt ccatgtcatt gtataaagac ttgatagcta tggagaatct    63780
caaagcgatg ctatacatta ttcgacgaag cggatgcaga atagacgatg cacaaattac   63840
tactgacgat ctagtcaagt cttactcatt gatccgtcct aaaattctaa gtatgataaa   63900
ctattataat gaaatgagta gaggatactt tgaacacatg aaaaaaaatc taaatatgac   63960
agatggtgac tctgtctctt ttgatgatga ataaatgtca tgttatacag ctatattaaa   64020
atctgtagga ggactggcgc tatttcaagt agccaatggc gccatagatt tatgtagaca   64080
tttctttatg tatttttgtg aacaaaagct acgaccaaat tcattttggt tcgtcgttgt   64140
tagagccatt gcaagcatga taatgtattt agtattaggc atagcattgc tgtatatttc   64200
tgaacaagat aacaagaaga atactaataa tgataaacga aatgagtcgt ctataaattc   64260
taactccagt cctaagtaaa atattttagt agcgtatcct tatcgcgttt gcttatcttg   64320
aatgaactgg tctttttaa ctcgttgatg aattttgtaa ataattcatt tctatcttta    64380 agtaattta ttggaagttt tgattccaca gccaatgaac atgtaaattg tgaatcattt    64440
tctatgacca gttgtaactt ttcatacact gtaatcaata cagtatttac catttgatta   64500
```

```
attacagcgc ccgtactagc actccattga acaagatcag attttagatt aattagataa    64560
aatctatatg ttatttcaga taatgaactt accagataac tctcttgacg gatattaaaa    64620
atgccagatg aatgttcatc tcgaatagcc agagctactg tagagtaata cggttcaaaa    64680
tcataaacgt gatagtttcc aaactggtat ccgagttttt cttggatgat ggatacttga    64740
gagttgaatt taaatttctt actatgttca ttatatagtt ctggaaagaa tgcttcaatc    64800
attgtttctg taagtttgca tccttttgat gcgatagtta aaagtgctat ataaggcgcc    64860
acgataatgt tattttttt ggtaatagtg acgtctttta cagcgtcaac gcatctgaac     64920
aaataatgaa tctctctatg atctaaaaaa taaagtctt gtaaaaagaa tcgtagtgct     64980
agttttctct catcatcctt agatctatgg gcgaatagac gtctactacg ggatataaaa    65040
ccgctatttt cctttatcat aggtgttgtt tgatctatat ttacctcccc tagttctacg    65100
gaggcctcca aattaagatc tggtactggt tcgaacattg taagacttac atcatcggta    65160
gtagattttc actttacccc acgatataaa tatgcgatat atagtaagtc cgcaattggt    65220
attacaggtg ggtaaggggc aggaggtaga acgagcccta tatctcactc catatgatta    65280
catagatgag aagtcgccca tatattattt tttacgaagt catttaaata tacaacagcc    65340
ggaaatagtt aagagacata ttctattgac gcttcgaatg actcaattaa agggatattt    65400
aggaaatttg ttagatatta aggacgatat tattatctat tctcataaga ataatttgga    65460
atatagttac gttgataata ctattttaa tcccttcgta tatactcaga aaaaacact     65520
actaaaaaac gatagctttt tatacaatgt atatcctgga gcgtgtgact ttttggttat    65580
ctgggtggcc agagcgtgcg atacatctat tccggaattt ggatcgtatg aagatgtaga    65640
taataatatt atcaagtttg aaacaatgtt gatggaagta tttccacaac tagatttgga    65700
cattactgta gaatcaaagt ttaacaatat atttcgtacc aatctaaaac taactgggtt    65760
aaaaagatc attcagcgag ttcaagactt ggacattaat tataagtcgt tgttatctag     65820
atacgatgaa cactttatta atatgaccgg taatcatttt attctaaacg atgaacagtt    65880
aaatctctcc atttgggact tggatggtac attagcgtta tctagcgacg gcgataccgt    65940
gatgattaat aacgtaaaac tatttacaga tcttgtgtcc gatatagata cacaaatgga    66000
acgcatcaag ggagatataa cgtataaggt acatttggcg actcctatca attctagaat    66060
aaaattggat atcgagacta gcttcatttt tatagagacg gcgactaata atattttact    66120
atcctcggat aaaaaaatat ctatcatttt ggccaaaaac catatatcta ttaaagtgaa    66180
aaaccatatt cctaacatag aaaaatattt tacatttta gttattgcca ttaatgccat     66240
gtttaatagc gttcaaaagt ctgctgattt taccaaagtg gaaactgttt actggtctag    66300
gatatgccaa aatacaaaga ataagaatag aaaacccatc attattaatt atctagatcc    66360
tggaatgaaa aaaatcagta acaactttta cagatccgat gagaaagaag tctttattaa    66420
tgataacggc ataatgttta catgcatgga tcctttgggg aaatataata aggtgggatt    66480
tcttaatata tttcatgata tgtggaaata ttgtatccct tgttgttttc tacatgatca    66540
atctcatcga agtacatttt catcgtgtgt tcatcaaatc gacgttgaga aaagagatagt   66600
aagtccgtat atccttaatt ttggtaaagt tgtaacagaa tccaaaatgt catttctccc    66660
tattatcttt gacgccttct taaatgatgg aatgactgct aatatggaac aagataataa    66720
acgactaaag gaaactagtg gatatcatat agttagatgt tgtgctggtg atgatatagt    66780
tcgtttacga actacatctg atattattca gtttgtaaac gaggataaaa atattcttat    66840
```

```
agttaacgac atggtatatt ttccaatgaa cgcgtccgat ataggaaaga aaatacatat   66900
actcattcaa gaaatagttc atgaggtaat gatagtaaaa aagaaagagt ctagtgataa   66960
aatcgatttt ttcccaccca actataagtt attgaaggat ctatttccaa aacaaactat   67020
tcaaactcct attcaatctg acgcgggaat ggtgttaaca accgatggat tctacataga   67080
tggaaaactt tttaacgaag atctgtcgtc taaatacgtt acatttacaa aaaatgttat   67140
tgcgtctgat gccgtagcta aatattttc tcctttgttt aaatacgtta tttcagaagc   67200
taaagataga tttatcaaaa cgtggatgat taatattatg atacatatga acgtagatcc   67260
taataatata ataccgacgt tagaaaaata ctatcccaac tctggaagag cacaaataaa   67320
ttaaacaact aaatctgtaa ataaataatg gacaaactta gagttctata cgatgagttc   67380
gtcaccatta gtaaagataa tcttgaacgc gagactggtc ttagcgcatc agatgttgat   67440
atggattttg atttaaacat ttttatgacg ttggttccag tcttggagaa aaaggtatgc   67500
gctattacac caactataga agatgataaa atcgtaacta tgatgaaata ttgtagttat   67560
cagagttttt cattctggtt ccttaaatct ggtgccgttg tgaaatcggt atataataaa   67620
ctagatgatg tggaaaagga aaagtttgca gccacattta gagacatgtt gcttaatgta   67680
caaactctaa tttctcttaa ctctatgtat actagattgc gtcaagatac cgaagatatt   67740
gtatccgatt ccaaaaaaat aatggagatt gtttcccatt tgagagcgtc gactacagag   67800
aacgcggcgt atcaagttct ccaacaaaac aatagtttta tcatatctac actaaataaa   67860
atcttatctg atgaaaacta tctcttgaaa attattgcag tattcgactc taaactaatt   67920
tctgaaaaag agacattgaa tgaatacaaa caattgtaca ccatttcttc tgaaagtttg   67980
gtatatggaa tcagatgcgt tagtaatctg gatatatcat ctgttcaact gagtaacaat   68040
aaatacgttc tctttgttaa gaaaatgcta cctaaaatca tactgtttca gaataacgac   68100
atcaatgcac aacaattcgc taatgttatt tctaaaattt atacgttgat ttatagacaa   68160
ttgacgtcga atgtcgatgt tggatgtcta ttgacagata cgatagaatc tgccaaaact   68220
aaaatatctg tagaaaaaat taaacagacg ggtatcaata atgttcaaag tcttatcaaa   68280
ttcatatctg ataacaagaa agaatataag acaataatct ctgaagaata tctatcgaag   68340
gaagatagaa tcattactat tttgcaagat atcgttaatg aacacgatat aaagtacgac   68400
aataaattgc tgaacatgcg agacttgatt gtgacattta gagaacgata ttcgtataaa   68460
ttctaatatc gttttgaag tttccaaatt ttgataatat agtctagatg gaattttaga   68520
ccatctttgt caaaatcgtt taccgacaac aattctccgt tcttttcgat gactatagga   68580
caagaaccct cctctatctc ttgtataatt acatgtagca tattttgctt catcgtttcg   68640
tcagaaaatt ctgaaactag aggtaatctt cctcgttgaa gcaagttata gctttctgct   68700
attatacccg ctatttcaaa tagacttata cgtctagtat agcgtcgttt aagagcagat   68760
atatgattcc ctatatgttt aagattggaa tgcgcatctt ctatatgagt ggatgctgat   68820
tctacaatct tataagaaga tttgggatct atatcactag tttctagtga ctctccatct   68880
tcttcctctt cttcatcatc ctcgtattcg gtgagatcat cggattcata gtcgataata   68940
tcgtctgtgt ctgccatttta atcttataat cgcaattcaa ttttaaagcc ttaaatggac   69000
ttctttaaca agttctcaca ggggctggca gaatcctcta caccaaagtc gtcaatctat   69060
tattctgaag aaaaggatcc ggatacgaaa aaggatgaag cgattgaaat aggactaaag   69120
tctcaagagt cgtattatca aagacagttg cgagaacaac tagctagaga taatatgatg   69180
gccgccagca gacagcctat ccaaccgcta caaccaacta ttcatataac tccacagccg   69240
```

```
gttccaacag ctacaccggc tcctacacca aaaccacgac aacaaactaa tacatcatct   69300
gatatgtcta atcttttga ttggctgtct gcagatactg atgcgccggc gagttcactc    69360
cttccagcgt tgacgccgag caatgctgtt caggatatta tctctaaatt taataaagat   69420
caaaagacga cgacgccgcc atctacccaa ccttctcaga cgttaccaac aactacatgt   69480
acacaacaat cggatggaag tatttcttgt actactccaa cggttacacc tcctcaacct   69540
cctattgtgg ccactgtatg tactcctaca cctactggtg gtacagtatg tacaacagca   69600
caacaaaatc caaatccagg agcagcatct caacaaaatc tagacgatat ggcccttaag   69660
gatctcatgt cgaatgttga aagagatatg caccaacttc aggccgaaac aaacgatctg   69720
gtgacgaacg tatatgatgc aagggagtat acgcgtaggg caatagatca aattctacaa   69780
ttagtcaaag gttttgaacg attccaaaag taataagatt gaatattaaa atcacgcttt   69840
cgagtaaaaa ctacgaatat aaataatgga agccgtggtc aatagcgatg ttttttttaac  69900 atctaacgca ggactaaaat ctagttatac taatcaaact ctttctttgg tagatgaaga   69960
tcatattcac acttctgata aatctttgtc ttgtagtgta tgcaattcat tatccaaaat   70020
tgtagacgat gactttatat ccgcaggggc tagaaatcaa cgtaccaaac ctaaacgtgc   70080
aggaaataat caatctcaac agcctatcaa aaaggattgt atggtttcca tcgacgaagt   70140
agcatccacg catgattgga gtacgagatt gagaaatgat gggaatgcaa ttgctaaata   70200
tctaactact aacaagtatg acacatctaa ctttactatt caggatatgc ttaacattat   70260
gaataaacta atattgtca gaacaaatag aaacgagcta tttcaactcc ttacccatgt    70320
aaagagcaca ttgaacaatg ctagtgtttc tgtgaaatgt actcatcctt tagtacttat   70380
tcattctcga gctagtccta aatcggtga ccaactcaaa gagttagata aaatatactc     70440
tccatctaat catcatattc ttctgtcgac tacacgattc caatccatgc attttaccga   70500 tatgtcagt tcacaagatt tgtctttat ttatagaaaa ccagaaacta attactatat      70560
tcatcctatt ctgatggcac tattcggtat taaacttcct gcgctcgaga acgcgtatgt   70620
acatggagac acctatagcc taatccagca actttatgaa tttagaaaag taaagtctta   70680
taattatatg ttgttggtta atcgtcttac ggaggataat ccgatagtga ttacaggtgt   70740
atcagatcta atttccacag agattcagag agcaaacatg cataccatga ttagaaaagc   70800
aattatgaac attagaatgg gaattttta ttgtaacgat gatgatgcgg tagatccccca   70860 tctaatgaag attattcata ctggatgctc tcaagttatg acagatgaag aacagatatt   70920
ggcttctatt ttgtctatag ttggatttag acctacgttg gtttctgtgg ctagacctat   70980
aaacggcatc agttacgata tgaaacttca ggcggcacca tacatagttg ttaatcctat   71040
gaagatgatc acaacatccg acagtccgat ttctatcaat tccaaggata tttattctat   71100
ggcattcgat ggcaatagtg aagagtggt gttcgctcct cctaacatag gatatggaag   71160
atgttctgga gttacacaca ttgatccatt gggaactaat gtgatgggta gtgctgttca   71220
ttcccctgtt atcgttaatg gagcaatgat gttttatgta gaacgacgtc agaataagaa   71280
tatgtttggt ggagaatgtt acaccggctt tagatctcta atagatgata ctccgattga   71340
cgtatcacca gaaatcatgc taaacggtat catgtatagg ttaaagtccg cagttttgtta  71400 caaactcgga gaccaattct ttgattgtgg atcgtctgat atcttcttga agggacatta   71460
tacgattcta tttacagaaa atggaccctg gatgtacgat cctctttctg ttttcaatcc   71520
gggagctaga aatgctagat tgatgcgagc tctcaaaaac cagtacaaga aattatcaat   71580
```

```
ggattcagac gatggttttt atgaatggtt gaatggcgac ggttcagtat ttgctgcctc    71640
aaaacagcaa atgttgatga atcacgttgc taactttgac gacgatcttc taactatgga    71700
agaagccatg tcgatgattt cgagacattg ttgtatctta atttatgcac aggattatga    71760
tcaatatatt agcgctagac atattacaga actatttag attatgatat ttaaatgagt     71820
tggtacgaaa aatataacat tgtactgaat ccgcctaagc ggtgttcttc tgcatgtgcg    71880
gataatttaa ctactatatt ggcggaggac ggtaaccata ttagggcgat actttattca    71940
cagcccaaaa aactaaaaat attacaggat tttctggcaa cgtctagaaa taaaatgttt    72000
ttatataaaa tattggacga cgagatacgt agagtgttaa catgaatcta cgattatgta    72060
gcggttgtag acacaacggt atagtatctg aacaaggata tgaatattgt attttttgcg    72120
agtctgtatt tcaaaaatgt acaaaggtac aaaaaaagtc aaacttccat gtgtctaata    72180
aacttattca tttgagaaat gtattgcgga gattattgtc tcatcaatgt tctggagaaa    72240
ttatctcgga actcttggat atcatggaaa aaaatcaaat atccacggat gatgtagatg    72300
caaattttgt atctagtttt cttaaggcta acgagagaat aaataaaaag gattataagt    72360
tagtctttga aataatcaat caagtaaaag atgagaaact gaatctgagt acagaaaaga    72420
ttaatgaagt agtagaaata tttaagcact tggtattctt ttgccaagaa aacactcctt    72480
ctaagacaat taattattca ttcttttttgg ataaaatatt cgatatcact tctgtaacta    72540
aaaatctaaa acctcaaact gttaaaaatt atacgaaaaa taatagtaac caattagtat    72600
gggaaaactt tttagcacat atgagatcta aaaaacgtgt aactatggta gaggattatg    72660
gacacgagta tgttttgta gatgagaggt tttctacttg ctcattagaa gtataaaaaa     72720
atagttccgt aattaaatgg ctaagcgagt aagccttcca gatgtggtta tttcagcacc    72780
taaagcagtc tttaagcccg ctaaagaaga agcactcgct tgtatactac caaagtatta    72840
taaatctatg gcagatgtgt ctattaagac aaatagtgta attgataagt gttggttttg    72900
taatcaagat ttggttttta gacctattag tattgagaca ttcaagggtg gtgaagttgg    72960
gtatttctgt tctaaaatat gtagggattc gttggcttct atggttaagt ctcacgtagc    73020
tcttagagaa gaaccaaaaa tttctttgtt gcctttagta ttctatgaag ataaggaaaa    73080
ggtcataaat acaataaacc tactaagaga taaagacggc gtttacggaa gctgttactt    73140
taaggaaaac tcacaaatta tagatatttc tctacggagt ttattgtaag ctttttccat    73200
tttaaataga aaatgaataa tactatcatt aattctttga tcggtgggga tgactctatt    73260
aaacggtcta atgtcttcgc agtcgatagt caaattccaa cttttgtatat gccgcaatat    73320 atttctctat ccggagttat gacaaacgat ggtccagaca atcaggctat cgctagcttc    73380
gaaattaggg atcagtatat tactgcgctt aatcatttgg ttctgagttt ggaacttcca    73440
gaagttaaag gtatgggaag attcggttac gtaccatatg ttggatataa atgtattaat    73500
cacgtatcta tctcttcgtg taacggtgtt atttgggaaa ttgagggcga agaattatat    73560
aataattgta tcaataatac aattgctttg aaacactctg gatattctag tgaacttaat    73620
gatatttcta ttggcctaac tcctaatgac actattaaag aaccatctac agtatacgtt    73680
tatattaaaa ctccgtttga tgtggaagat acattcagca gtcttaaact atccgattca    73740
aaaattaccg taacggtaac cttcaatcca gtatccgata tcgttattcg tgactcttcg    73800
ttcgactttg aaacgttcaa caaagaattt gtttatgttc ctgaattgag ctttattgga    73860
tatatggtta agaatgtaca aattaaacca tcgtttatag agaaacctag gagagtaata    73920
ggtcaaataa accaaccaac ggcgactgta actgaagttc atgcggcaac atcgctctct    73980
```

-continued

```
gtttatacta aaccttatta tggaaatacg gataataaat ttatttcgta tccagggtac   74040
tcacaagatg aaaaagatta tatagatgca tatgtgagta gattgttgga tgatctagtt   74100
attgttagtg atggcccacc gactggttat ccggagtctg ccgagattgt tgaggttcca   74160
gaagatggta tcgtttctat tcaagatgct gatgtgtatg taaaaattga taatgttcct   74220
gataatatga gtgtttatct tcatactaat ctgctaatgt ttggaacacg aaaaaattct   74280
tttatatata acatttctaa aaagttttcc gccattactg gaacatatag tgatgccact   74340
aagagaacaa tctttgctca catatcacat agtatcaaca tcatcgatac atctattcct   74400
gtaagtcttt ggactagtca acgtaacgtc tataacggag ataatagatc agccgaatca   74460
aaggccaagg atttgttcat taacgatccc ttcatcaagg gaatagattt taagaataag   74520
accgatatta tttctagact agaagttaga tttggaaatg atgttctata ttcagagaac   74580
ggacccatct cgagaattta taatgaacta ctgacaaaaa gcaataatgg aacaagaacc   74640
ctaactttta actttacacc aaagatattc tttaggccga caactattac ggccaatgta   74700
tctaggggga aagataaact atctgttcga gtagtttatt ccaccatgga tgtcaaccat   74760
ccaatctatt atgtacaaaa acaattggta gttgtatgta atgacctgta taaggtatct   74820
tacgatcaag gggtaagtat taccaagatt atgggagata ataactaata ataatgaaaa   74880
caaactatag agttgtaaat ggatgaaatt gtaaaaaata tccgggaggg aacgcatgtc   74940
cttcttccat tttatgaaac attgccagaa cttaacttgt ctttaggtaa aagcccatta   75000
cctagtctgg aatacggagc taattacttt cttcagattt ctagagttaa tgatctaaat   75060
agaatgccga ccgacatgtt aaaactttt acacatgata tcatgttacc agaaagcgat   75120
ctagataaag tctatgaaat tttaaagatt aatagcgtaa agtattatgg gaggagtact   75180
aaagcggacg ccgtagttgc cgacctcagc gcacacaata aactgttcaa acgtgaacga   75240
gatgctatta aatctaataa tcatctcact gaaaacaatc tatacattag cgattataag   75300
atgttaacct tcgacgtgtt tcgaccatta tttgattttg taaacgaaaa atattgtatt   75360
attaaacttc caactttatt cggtagaggt gtaatcgata ctatgagaat atattgtagt   75420
ctctttaaaa atgttagact gctaaaatgc gtaagcgata gctggttgaa agatagcgcc   75480
attatggtgg ctagtgatgt ttgtaaaaaa aatttggatt tatttatgtc tcatgttaag   75540
tccgtcacta agtcttcttc ttggaaggat gtgaacagtg ttcaatttag tatttttaaac   75600 aatccagtgg atacggaatt cattaataag ttcttagagt tttcgaatag agtatacgaa   75660
gctctctatt acgttcactc gttgctttat tctagtatga cttctgattc aaaaagtatc   75720
gaaaacaaac atcagagaag actagttaaa ctactgctgt gattttttaaa acatagttat   75780 tacttatcac tcataaatga gtaaatcaca cgcggcctat atcgattatg cattgcgcag   75840
aactactaat atgcctgttg aaatgatggg aacagacgta gtacgcctca aggattatca   75900
acattttgta gcaagagttt tcttaggatt agacagtatg cattctcttt tattgttcca   75960
tgaaacgggt gttggtaaaa caatgactac tgtatatatt ctcaaacatc ttaaggatat   76020
ttatacgaat tgggctatta tcttattggt gaaaaaggct ttgatagaag atccttggat   76080
gaacactata ctcagatacg ctccagagat aacgaaggat tgtattttta ttaattacga   76140
tgatcaaaat tttagaaata aattttttac taatatcaaa actattaatt ccaagagtag   76200
aatatgcgtc attattgatg aatgtcataa cttcatttct aaatcattaa tcaaagaaga   76260
tggtaagatc cgtcctactc gttcagtata taatttttta tctaagacca tcgcattaaa   76320
```

```
aaaccataag atgatttgtt tatcggctac acctatcgtt aatagtgtgc aagaattcac    76380
catgttggtt aacttactac gaccaggatc cttacaacac caatcgctat ttgagaataa    76440
acgtctagtt gatgagaaag aattagtctc caaactagga ggcctatgtt cgtacatagt    76500
taataacgag ttttctattt ttgatgacgt agaagggtct gcatcattcg ctaagaaaac    76560
agtattaatg cgatacgtta atatgtcgaa aaagcaagaa gaaatttatc aaaaggctaa    76620
actcgctgaa ataaaaacag gtatatcatc atttagaatt ctgagacgta tggctactac    76680
gtttacgttc gatagctttc ctgaaagaca aaatcgtgat ccgggcgaat acgcgcaaga    76740
gatagcaaca ctatataatg attttaaaaa ttcattaaga gatagagagt tttctaaatc    76800
cgcattagat acctttaaaa agggagaact attgaaaggg gatgctagtg cggctgatat    76860
ctctctattt actgaattaa aagagaaaag cgtcaaattt atagatgtat gtttgggaat    76920
attagcatcc catggtaaat gtctagtctt tgaaccattt gttaatcagt caggaataga    76980
aatcttatta ctatatttca aagtctttgg tatctctaat atagagttct catctagaac    77040
aaaagatact agaatcaagg cggtggctga gtttaaccaa gaatcaaaca ctaacggaga    77100
atgcattaaa acatgcgtat tctcttctag tggaggcgag ggtattagtt ttttctcaat    77160
taatgatatc ttcattttag atatgacatg gaacgaggcg tctcttcgtc agatagtagg    77220
aagagccatt cgtctcaata gtcacgttct tactcctcca gaacgtagat atgtaaacgt    77280
gcactttata atggctagat tatctaatgg tatgcctact gtagacgaag acctatttga    77340
aatcattcaa agcaaatcaa aagaatttgt ccaattgttt agagtgttta aacatacatc    77400
attagaatgg attcatgcta atgaaaaaga cttctcaccg atcgacaatg agtccggttg    77460
gaaaaccttg gtttcaagag ccatcgatct atcgtctaaa aaaaatatta ccaataaact    77520
aattgagggt actaatattt ggtattccaa ttctaataga ttaatgtcaa taaatagagg    77580
atttaaaggc gtagatggtc gagtatacga tgtagacggt aactatctac atgatatgcc    77640
ggacaatccc gttataaaaa tacacgatgg taaattaatt tatattttct aatcaatcat    77700
cctcagttaa ttttttttaat gattcgtaat aacatcctct atggccataa catttgagtt    77760
ttgcagtatc tagagcatat tttgcaattt cgtattggag tccattacct gaattcggat    77820
ctaaaaatat tagatccttg atttcatgat tacttttaaa tgtatcaatg atttgatcac    77880
tcgttaaaga tattcttccg acaaagaaga ttacctcaaa aaatttatta ataatgtat     77940
cttctatgat gccatgaata aaaaaccgag tgtctatgaa tacaaaagaa ttgtctatat    78000
taacttcttc tttaatttcc ctggataaac actctggaac attctcaccc cttttgggta    78060
tgccacccgg ataaatagca tctattctat cattatcagt agtagctgga tctagagaaa    78120
aaaatgacga tagtatactt cttttcctgtt tggacaaata attggaataa ttcagaaata    78180
atcgtttctt tctagacatg tttctagttc taattatttc agaatagaga aaactatctc    78240
gtctgttaca tactaatatt ttgttatcag tagttaataa aatagcggac acggatactc    78300
gtttatgaca ccataggcat tggttaacga atgccgtgag tgtaataatt tgagagtcat    78360
cctcgcaaat aatagactta gctagtcgtc tattatactt aataatctga ctaattatac    78420
tagatctgta aaagttcatt tactattaac tagcatatta taaatataag acagatattc    78480
gtatttatcg tcgttaatac aatcatttaa tgatttaatc tttctaattt ctacattgta    78540
aatactagta tgcgataaat cctccaacga ttgattaata aaacacgcca tgcaataact    78600
tatatatact ttattaaata atttatcccg tgttgtaagt tttagaatta catttccaaa    78660
ttcttttact gttatacgtt catcactttc ctcttttaat tctcttctta aacaatcttt    78720
```

```
aatagattcc ttttatcta gtttaccacc caataatatt aactcttcaa agtgaggatc  78780
gatatcgttg atagaacctt ttctcaaccg tctaaagatt tctcttagtt cattgtagta  78840
cataaaccgt aatagtttag tggatactct aaagatagaa tctgaatttt gttgagataa  78900
tatcgcttgg aatgcgaatg aagttcttct agctcctatt aacggatatc cgtcacttgt  78960
tatacacgca gcaaacacat gcgtgtcttt tgatcttgga atatctttta ttcgtttaat  79020
agatattaat tctctaggag tttcaaatat cacttcctca tccattgtaa ttcccatact  79080
aagagctatt tttaaacagt tatcatttca tttttactat gccgcaacaa ctatctccta  79140
ttaatataga aactaaaaaa gcaatttcta acgcgcgatt gaagccgtta gacatacatt  79200
ataatgagtc gaaaccaacc actatccaga acactggaaa actagtaagg attaattta  79260 aaggaggata tataagtgga gggtttctcc ccaatgaata tgtgttatca tcactacgta  79320
tatattgggg aaaggaagac gattatggat ccaatcactt gatagatgtg tacaaatact  79380
ctggagagat taatcttgtt cattggaata agaaaaaata tagttcttat gaagaggcaa  79440
aaaaacacga tgatggactt atcattattt ctatattctt acaagtatcg gatcataaaa  79500
atgtatattt tcaaaagata gttaatcaat tggattccat tagatccacc aatacgtctg  79560
caccgtttga ttcagtattt tatctagaca atttgctgcc tagtaagttg gattatttta  79620
catatctagg aacaactatc aaccactctg cagacgctgt atggataatt tttccaacgc  79680
caataaacat tcattctgat caactatcta aatttagaac actattgtcg tcgtctaatc  79740
atgatggaaa accgcattat ataacagaga actatagaaa tccgtataaa ttgaacgacg  79800
acacgcaagt atattattct ggggagatta tacgagcagc aactacctct ccagcgcgcg  79860
agaactattt tatgagatgg ttgtccgatt tgagagagac atgttttca tattatcaaa  79920 aatatatcga agggaataaa acattcgcaa ttattgccat agtattcgtg tttatactta  79980
ccgctattct cttttttatg agtcaacgat attcgcgaga aaaacaaaac tagattcgat  80040
accttgttga gcctccatta gaacggcagt gacttcgctg ccattgtcat acgcattacc  80100
atttcgaaaa aagcagtact ttgaatcgct aaatgataca gtacccgaat ctctacttag  80160
tttacagatt aaatctccac attgaatagt tacatttgat tcatcttcga tgtttaatgt  80220
tcctctgact atatccccaa cgtgataata cgcgtaggtt attacacacg gaacgtttat  80280
aactacagaa ttattaacta tttcgccgag aggtaattcc acgtcttcac gaatttctat  80340
tttcttggcc attttaccac taatttctct atggagatac gtcttatata cggcattcct  80400
aatattagtt tttatgtcta acgtcagctc gtgtggctcc aatgtaactg gaaggtatcc  80460
attggtaaca aagctcgaca tttatttctt tatatatctc atcagtttta tggagaagat  80520
accacgttat attctttacg aaagttaact ccccaaacaa atggttcgta ggaaagtcta  80580
aacggtactg taataatatc gttttcgtat ttgtataaaa gagatttatc aaatacttta  80640
ttcgatacaa agaagtgacc gtttacaata tcatctatgt aattcctagc gtcttcttta  80700
ttttttataa ctgatgtaac cattttaagt aacttggtat cgttatactt aatacgagaa  80760
ttattataaa aaaattgtct gaccaattct cccaataaaa cttttacaat tgatggatgt  80820
ggtggaagag aatacgtttc agacatctct tgaagaatag agtatattct attcgtttct  80880
ttagtcttaa attttagata caacagcttt ttgatgtcaa atggtaaaac attaattaat  80940
tcatcctgtg tgtaatcgtt taatgacgtc acttcgtcat tgaaatcgga atatacggcg  81000
gctaaaagat atacattaac tggttcagaa atatcggcgt aagagaattt tctaatagat  81060
```

```
cgtccaagaa tttggttgta ttgagaaaaa gtatctggga tagtcataaa ccaaatatgc    81120
cttacctctt tcagagtata ggattcggac ataatgtttg acgaaaacaa aaacatcaat    81180
tgactgccat catcgttttc aggagaatta tacacatcta atagatcctc taaagacgat    81240
ttcattttac tagtaacgat agcaaatgtt tttggtttgc cgtttatcat atgtggatta    81300
gttccctgag aaccattata ttcagaatat ccattactga gcatgatata tttaattacc    81360
aatccgccat atgtagaatt agaaaagtat ataaaatgtt ttccgttgag tgtctgtatc    81420
cgattaataa agtatttaaa tttggaacta atgtttaacg ttaccaattc ttctccgtat    81480
aacacgccat tatttatttt cagatttggg tacaattcct tatcctgttc ctgaaataaa    81540
gtatctaaat tattcatcag attaagttgt cccaatactg ccattgacac gttatacata    81600
tttttatcaa acatttcatg ataacatagc tgtcgtctag taatcatata atctctctct    81660
tgaagtttag acatgtgaca atatactact ctagtatcta gaaacttacg tccgtgatat    81720
cttatcgttg gtagatcttt atcaggcatt tcgtaatatg atattcttcc tttaagcaaa    81780
tccttaagta cattcacacc tcgttcgtta agaagtgtct gaattacttt cttaccacga    81840
ctaataattt caccaaaatc tatcgtctct tcggacatta aatctataat atgacccaga    81900
gtattaggtg tgttagtaat gggagatcca gacaatagta aaaaggaat cttgttttta    81960 tttttttatca cggtcataag ttctccagta ttattcccaa agatattatg tgcctcatca    82020
acgataaaaa tagagttatt gtagcgagat aatccgttat aattaatgac gttatcgtta    82080
taattaagag aataaaaact tgttgtggaa tgaataaaga tattctcagc tatgaattcg    82140
tcattaaaca agttcatagc tacacccata ttataattaa aaattttcaa aatgttaata    82200
ttaggcacta gaatgtaaac cttttttaaat ctggaagcta ccaaggcgaa caacaaagcg    82260
attattgttt tacctgatcc cataaatatgg aacaataaca cgcttctgtt ctcatctatg    82320
atagttctaa ctagataatc tagagtagct aactgatgag gtaatatagt tggtatacta    82380
tcaacatgat tatcaaataa atctatgatt ccggtattca tttagatatg tgatatcttc    82440
tataaatata tgagcatata tttacggaga tgaaatatcc tctatgaata tatattgcag    82500
atattcatca ctaacattgg caaatttctt atgtctattg atgaagctct ctatatcgtg    82560
tccaaatagt ctagaattaa aatacttgga tattttctgt tggaaagtag tcaacggaag    82620
agtaaccaca ttatcgtaca atatatatcc ctttttggag aggtccgtca ttaatggaat    82680
atgctttaca gagctagata ctaacagagt acctattttg agatagaatg caaagtccgg    82740
aatctcttcc ggtgtaggat atagtttcat aataggaaca tgatattttt tgtaccattt    82800
caccaacaag tatagaaatg cgaatctata tctattattt tgtatttac catctaaccc    82860 ctcgtctaat agtttgactt tatcgtacgc gtcattattt tcagcagcct ctctaccaga    82920
aggttgagaa aagtgtgttc tgaatcgcac gacggcaatt cttctcatta atgcgttatc    82980
tatcctatca aagacaggtt tgtaattagt atcgataatg attgtcgcat ggtttctatt    83040
attaatttta ttggagaaac acggtcttcc aatgacacaa ggttctgtca actttttaat    83100
attgtcagat ctaattttct ttgatccact acaggcaaaa tcaggtagtt cgctacagaa    83160
tacagatctt ttcaaatgca tgttagcgat aaatggatta ggtcctttat ccaatacatc    83220
tgttaaaatt gtttgacccg tctcaacaaa caggtcaccg atagcagact taacaaacg    83280 tttggttgtc gactttccag ttgcagtttc tccaaaaaag aatgttaaac atcctttggt    83340
agcaccgcat aaacaactag ataaagtttt ttcgtacaac tctctatttt tcttattttc    83400
atccgttaat ggttggatat cgttaatgat attcattaac tcttccattt ctggactgtc    83460
```

```
ttcgacgaac tttgtatcgt caaatttaaa tccggttgat acagtacacg tatattttt    83520
agcatcatct ccagagtaaa acattccgtc taccaggtcc aatacaccat ttttaaacgg    83580
aagtttatcc ggataggtat cggtctccac tgaatctatt aacatgtctc gtatgttagc    83640
ttctacagtc tttcgtttcc tcggacagag taattcgctt gaatattcct taggtagttg    83700
atgtcttatt gacagaatta gttttgttat caagggttct tcgctgttaa atttccatga    83760
attattaatc caaactatat ggtctcctcg ttcggttaat aaaacagagt tagtgtctaa    83820
aattctttgt gcaatattaa acagtttatt accatccaac ggaacaattt taactttaca    83880
actatgtgga ttaccagttt tgtaaattct aatagcacca ttttccaacg atagttgatg    83940
cggatgttta tgcgatcgtt ttttacataa tgcacaaggt gttacgtaat ctatgaccag    84000
tggtaccgtt gtaaaattat tttcatcgag atcattaaag tttattatag aattaatgaa    84060
tatttttgaa actcttttta tagcgtcttc gaatgaaata aaccctggtt cccataactt    84120
atcaggaact aaatcctcca atcgtcgttg tagagaaaag taataactat tgttgttcat    84180
atccacgtaa gtgaataggt aatcttctat attatcatgc ggtggttgca ttacatgaat    84240
agtgtcgcaa tttggatttt tcctagtacc tacaacccga agagttgttt ttctcctata    84300
tacggcagtg tctatcgatc tggttagtgg attttcagat gatctactta attctaatag    84360
tgttcgtttc atagctatca atgtatccat agtggtatac gtgtctaaaa agataaatatg   84420
aaaacttgtt ttatctctat ttgtagactt agtcaatgaa aaattagatc tcatggattt    84480
tattacattt tcatgaatgg caccgcattc tgtaaacgcg aatctagcta cacagtttga    84540
cacctcgata ataaaatctt gaatagccgt taaataatct atttcgtcta gacacgcgtc    84600
taaatctaca tccatgaaaa ttctgactat agagtatgct tcctcatccc taagactttc    84660
gaatagtgta cattctggat tattctcaat atatctttct aactcgtcgc atttaaatgc    84720
ttctacaaat cttggatctt cattttgtct gcacgctgac gggacaccta tagtcttaag    84780
aacaaagata acatcattac ctctaatagt tgcatccatt tagaacacaa gttaaaattt    84840
cactaaagca ttaataaata aacccttgag cccaatttat aggtgccttg ttgtctaatt    84900
ccagtaaaac gttgataatt tcaaatgatc tatcttctc gaattggcgg tctctagccg      84960
ctggatgata tccgactatg gtagttaccg gggattctaa ctttgcccgt atattcgaga    85020
aatctgtttt acccaaacaa taagaacac taacgtgttt agttatatgc tgcagcagta     85080
acttggaaat cttatcccag tagatcgcgt gacttttgt ttctcctaat ttacaactta     85140
agtaataatt ccagggtata accccgtcta ttatattaag gttataacct ttataatcaa    85200
ttactccggt taatctagat atagatgaag ctatctcctt aattgatttt tttgtaaaat    85260
ttggtgattc gaacggtaca ccagttccat ctttcggata cggatctata ccacacacac    85320
atactcgttt atttctaagc ggttgtttca actgtataaa gaacttatca ggataggcg     85380
acgtctcgtc tcgtagcagc caactggcta cttcgttata aaactctacc aattgactca    85440
ttactggttc ccaatcatcg tgataagtaa tagtatatgg cgcgtgtgat acagtcactg    85500
aattcattat atcaaattag ataccttttt atacgtatct agtaccttt catttttccga    85560
aacgccgtta aaccaagcga atacaaacgc cttaaactta tctctattat aacatattct    85620
cgttagattt aattcttcgg tatccttgta tctaactatt gttatatgtt tagaaactct    85680
atagtggctt ctaatcagat gttctaataa atatttaaa aatgaatctt gattaaaaat     85740
catatcattg accatttgtc tggctactga attacgataa tacggagaca ataacggatt    85800
```

-continued

```
agtcaaatag ctatcatctc ctaatgatgg aggcacctgt acaaatacca atcgtttatt    85860
cttgaacgaa tcaaacgtat aaatatcata aatgacaaat ttatcagtgt gcatatcttc    85920
agatatatga ttggatgtag aacaccatct aacttgtctt ccagcatcta taaattcctc    85980
cacctctata tatctaccac cgtgctgaaa actagaccca tttaattcga cgcataaaga    86040
tccatatgta tctggagtca caatatattc agaaaaaaat acatgctcct ttaattttgt    86100
taattttgat ctgataaagt cattgtgatt tcctaaaagt ataaatactt cgttatcgtc    86160
gttatcgact ttgggatact tattatcctt aactataaaa atgtccatca atatcgatat    86220
aaaaaaaata actgatttac tcaacagtag tattttattc ccagatgatg tgcaagaact    86280
tcttcgagag aaatatatag tattagaaag aaaatcaaat ggtacaccta cagtagctca    86340
catctataag acaatggcta gatttgataa taagagtata tatagaatcg ccaagttttt    86400
atttatgaac aggccagatg ttatcaaact tttattttta gaagacgtag aacctctgtt    86460
acccgacaaa agtattaata tatctattaa caatacagag tatccacagt tggaaggtcc    86520
tataggaaca aaaatcgctc tattggaatt atttaatgca tttagaacgg ggatatcaga    86580
acccatacca tattattatt taccgcttag aaaagacata aacaacatag taactaagta    86640
agtcttcgac atctaaacct tcacatttaa tggctcctct atttagttcg aaaaagtttt    86700
ttgtagacgg tctatcttcc attgtagatg cgccattaat aaactttta cttcgttcta    86760 taattgtagc gaaatcaacg ttatctacaa gaacaaatcc gtattcgtta aacactctga    86820
ctatatcgtt cttttgata atgtattcag tcattggagt agacattgtt gatggattat    86880
ataccactat tctatcatca gctatttttt ctacagacat atagtttcg ctactaggta    86940 aattcttatg aattataaaa gtcttttat ctgttaattt tgataatttg tctccgtcca    87000
tggtagtgat taataccttg cctccagaag cagttagttc ggataagtta ttcatgacgg    87060
tagcataatg tctcggatga aaagaataat ggatagcaaa ctgccagtcg atgatattaa    87120
actttccaaa atagaatact tctctgacac tagagacaaa tgtatcggat cgaatagttt    87180
cctgaatgta gtcaaatttg tagtacttgg ttttaattcc agagtttaat ttgttgtatc    87240
tttcatttcc tctagctata gcatcagcat ccggatccgt cgctaccaat aacgcaatct    87300
ctccataaaa gtattttttcc aggtccgcac cgtttccaaa atcaatcgcc aataccttc    87360 gtttgttgga atcgtctaaa aatgttttgg aacaatacat agaaataaga agagtcttga    87420
cgtagtttga taaaattccc aacggtcctc tagttcgttt attcgtaaaa taactaactt    87480
ctggatttaa tctaaattta tcattattgg cgtattgatg tcccacatcc gatagttat    87540 cctcgttaaa gatatctcct atttttgatgc tttgatctct taaatgttcg actatgatat    87600
tatgttgatt tccataataa tcttctgagt taatatattt catggtttta tcaattctag    87660
gtttaagtat ttctccatta actaagaatt ctgctataaa cttaataggt acaaccacgg    87720
acttaatacc cacttcatta tgtgtattaa tatattccaa acaatagata ttatttagat    87780
aattaacgcc gttatataac acaatcttac cagaaccata ttctttagga aagcctttat    87840
cgttgctaaa tttcttatac tctacaaaga tagacgattc tccaaagata attggttcac    87900
tggacatgta cctaaatact acatttgcag tttggtctat agtattttcc ttttaattt    87960 taaaatcaat gttagattta ggtcccttg aatagaacag aataacacct tctggttgct    88020
ttggtaaata tgtagataac atatcgacga cttcactagt tgtagtaaac ggaccttcgt    88080
atttctttga cttgaatact atccgatcac aaatatccac tagtttagat tcaacatact    88140
tactttcttc tagtctatca ttgattgcat tcacaggctc tattagctta atgagatata    88200
```

```
cggtccagtt cttatcctta actgcctcac caaagactac tacttcggaa tctattattc   88260
tcttaacagg atatctaata atataaccaa gatgtgtaaa ataacaatac aacccttttg   88320
atgtaactct gatagttata ggaattccgt cagtcttagt tacggcatat agattttcca   88380
gatccaaacc tactatatct tgtttaggca acataaaggt ttttataggc gcgttaatag   88440
gcggagaaag aattcattc tctggagaag ccataaatat atgacgtgat agagtcgtca    88500
attcctttat tagttcatca tatggaactt tttcattgtc tctaggtgtg aattctattt   88560
ccagagatgt attaggcctt gactttggat gattaatagc gtgtaataaa gaacttttag   88620
actgggcacc ggatcctaga aaatatttta gcttaaagtc tatcgtaaag ttttttgttt   88680
ttgcttgaat aagattgact aattctagtc ggatagagga tccatatttc ttgtaatcca   88740
aaaatatatg acgttcctct gtcgatagtc tcaacaagca ttctttgtga agacgatttt   88800
ccgtcactaa tgatttcttt tcccaaacta tgttatctat agcatctact aactgtacat   88860
tttttacatc tagaccatgt acctagata atggaatctt agttctaatt ttaacacctt    88920
ccttattagt aacggtaaat cgaataaacg attcctgaat cgtagagata ttcactacat   88980
ttgtcaaagt aattaatggc ggcttaataa atactagttc caattcatta tttatttcgt   89040
atgcggtaga cctctgttct aattctgaag cattcttcgc taaagcgtct atatacgttg   89100
caatagtaga agatgatact atgttggcat ccatattgtg ttttattata aacgactagt   89160 ttttttcat ttacttatta acaagcgtct tttatatatt cgtaatctat gcctttagct     89220
agagctattt taagcttttc tgtatctcga ctgatacgag tatctgatct attgcggtat   89280
ttttttataa atcgtttaag acggggagta gttttgatat attcgctaat atcctcttta   89340
ataatatcca cacacgccaa ttgttcggct atactcgatg cgtgagtctt gcattcatct   89400
ccagatatcg gagtgagggt cagatccaaa tattgagaag ccttataatt atcgtattcg   89460
aaatcaatca taaactgacc atccttatcc actgaaaaaa tggtattgtt tggatggcgt   89520
ttaaatatag acattatcaa tgccataata tctaatgtgt ttagctctcc gaagaaagct   89580
gtcattgcga gagatttcat acgcttatcc atttccattt atcggtcttg taattatttg   89640
tgtaaagatc tatatcatcc atccgtagat gatttaacgt gatctacgac tatagatagg   89700
aattcatcga acgtagtttt agatactaca tctaaaaaat ttttatcctt taccatttct   89760
aaaatagtcg ttgccatata agctctttt gaaattgatg gagtatgacc taccacttca    89820
gcagtttgtt tgatagttaa cgctattaac ttttttggtg acggaagagg agatatggac   89880
tttacatttg tccaaaaatt atataaaaac gtataattga ctccatacgt tcggagatcc   89940
ttgattctaa taccaaactg tttgatacat tcgtatacct ttcgttcact tagtttgttg   90000
aacagaaatt cttcgggact agaatcatcc gtcagtttca atagcggttt atatagtcta   90060
ttagacttat gaacaacaaa ttcatgtgaa actttgtcct ttcctacaaa cttgataact   90120
atttcatcgg gacttatttc tatgtgttta ttttttagtg ttaataaccc tactgtttca   90180
ttctccttaa gatatttcat tttaccaaat ctaataaaaa acatagtttc cattaacata   90240
aaaaccgcca actgataatt ggaatctgtg gacgatttct ttatattttt gtttataaaa   90300
caattaattc gtttcataac gttatatact ctaacaaaaa tacgatctct tttagcgttg   90360
cgattctgta catgcatttt tccgtaaaag tattgtctac gtccttttga atcacttccc   90420
acaaaaatta atctagttaa cgcctcctcc cacgtttgtt catatactac tacatctgtt   90480
aaatgagtag gaattttaac atgttgcaaa acctcatacg ctggattatc gtctgataca   90540
```

```
ggatttaaaa aattattatc ggtaaagagt ttaccatctt tataaaaaag tgcacgcatt    90600
tacttcttac aagttttaac ttttttacga acaactttag attttccctc ggtgactaga    90660
tcagatagtg ttgtaatagc tttagtcata gaagtaaatt gtctagagat accagctgct    90720
tgaacatcct ctagaaccgt cgatactgca gagattctag taataatttt cttaagatct    90780
ttaacgatat tgtcggtagc cacctttagg tcagaaagat cgcttctagc actatgattt    90840
actttaccag cttcaacttg taccataggt tcatcatccc cgtcgctatc atcgagctct    90900
acagcagcca cgctttctac aatgtcgctg actccaggag atggagaatt tttttcagtt    90960
gtttgatgat attcctctat aactacttct tcttccactt cctccttttt ggttgatctt    91020
ttagtagccg ctggtttacg aggagtagtg gctcgtttgg ttttgggctt agtagatgga    91080
attattacat cttccgggaa aatatcctcg ttttatctt tattttcagc gctatttttt    91140
agatgagctc tgatttcagc catctttgtg aagctactag tatccgcttt atttgtaatt    91200
gaccacgcca ttacgataca aacttaacgg atatcgcgat aatgaaataa tttatgatta    91260
tttctcgctt tcaatttaac acaaccctca agaacctttg tatttatttt catttttaa    91320 gtatagaata aagaatctat aaaaactaaa aaaattatac atcataaacc aatttcctag    91380
ttgtttgtaa ctttaaatgg actctaaaga gactattcta attgagatca ttccaaaaat    91440
aaaagcatat ctactagacg cgaatataag tccaaaatcc tacgatgact ttatctcacg    91500
aaataaaaat attttcgtta tcaacccttta taacgtatcg actatcacag aagaagatat    91560
acgattgtta tacactacga tagaacagaa tattgacgcg gatgatcaaa cactggttgc    91620 tatttttcg tatataggat ataaatttga acaggctgtt aaagaagaga ttagtacgag    91680
tttatccttc aatgacaaga ataccacaga tgaaatgacg tataacttgt atgatctttt    91740
ttttaacaca ttagacatgt atttacgaca aagaagatc agtattctgg taaatgatga    91800
tgttagaggt gatgtaatcg ttagttataa aaatagtgac ttagtttcat catttaatgc    91860
ggaactagaa ccagagatta agaagatacc gttcaatatg aaaaatctat taccgtactt    91920 ggaaagaat ttggaccaac taagattctc taaaaaatat ttagactttg catatttatg    91980
tagacacatc ggtattccca tttccaaaaa aaagtataat gtgcgatatg tatttcttta    92040
taaaatagac ggattatcca ttcctattat cattaaggat ttttagatg ttaagtacgt    92100 atatttggaa aatactggaa aaatttataa aaattctttt tccgaagacc ataacaacag    92160
tctatctgat tggggtaaag tcatcatacc tctcttaaag gatcgtcatc tatatagcta    92220 catcttttcta tctagttatc atttacatag ttactataca gatctcatcg cgagagacga    92280
gcctgtgttt gtgaaacgca aaaaactaga tattatagag atcgatgaac ctgaggcatg    92340
gaaaagggat gttagagtgg aattcgcacc gtgtgagcat caaattagat tgaaggaagc    92400
tatgaaagtt gacgctaact atttcactaa aattaataat tttgctaacg aatttattta    92460
ttatgaagat ggtgtggcat attgtagagt gtgtggaata aatataccta tatttaattt    92520
agatgccgct gacgtgatta aaaatacagt tatcgtttcc acgtttaaca agactatatt    92580
cttgagcgaa ccatatagct atttcgttca tagtcagcgc tttatcttta atattatcat    92640
gtcttttgat aatattatga atctcaaac ttgggtaatg aaatacaaca ttaaccgact    92700
aattcttaac tttcttattg atataaactc tagacgtcag gaatacgaaa aaaagttttc    92760
ttctgaaatt aagagaggtc tgttcttct tcgtttgtct gcaaacttat tcgaaagtca    92820
agtatcgtct acagagttat tttatgtttc caagatgctt aatttaaact atatagttgc    92880
gttagtaatc attcttaaca gtagtgcgga ctttatagtt tcttatatga aatccaagaa    92940
```

```
caaaacggta gaagaatcca ctcttaaata cgccatctcc gtggttatat acgattttt   93000 ggttaagact agaatttgcg agaagggatc gttggatact atagttttat ttaccgatgt   93060
atacacatct ataatgccgg aggaattgga tttacatttt cagagaatca cattagaact   93120
tagaaaacta gtatccattc agagatcggc gttagaaccc aattacgatg tagaaagtcg   93180
cggcgaagag cttccattat ctgcattaaa gtttttcgat acaagcacca ttatagttaa   93240
gacaatggct ccagtacata catacatcga acaaaaaatt gttgcaccta ctccatcggt   93300
cgaaccaact gatgcatctc ttaaaaactt caaagaacta acgtgtgacg aagatattaa   93360
gatctcgatt agagttcatg atactaatgc tacaaaatta gtcattttc catcacatct   93420 aaaaatagaa atcgagagaa aaaaactaat tataccgcta aagagtttat atattaccaa   93480
tactctcaaa tattattatt ctaactccta tttatacgtt ttcagattcg gagatcctat   93540
gccattcgaa gaagaactca tagatcacga acatgtgcaa tacaaaataa attgttacaa   93600
tattctaaga tatcatttat tgccagacag tgacgtgttt gtatatttta gtaattcatt   93660
aaacagagaa gcattggaat acgcatttta tatctttttg tcgaaatatg taaatgtgaa   93720
acaatggata gacgaaaata taactcgtat taaagagttg tatatgatta atttcaataa   93780
ctaaatggcg gcggtgaaaa ctcctgttat tgttgtgcca gttattgata gacctccatc   93840
agaaacattt cctaatgttc atgagcatat taatgatcag aagttcgatg atgtaaagga   93900
caatgaagtt atgccagaaa aagaaatgt tgtggtagtc aaggatgatc cagatcatta   93960
caaggattat gcgtttatac agtggactgg aggaaacatt agaatgatg acaagtatac   94020 tcacttcttt tcagggtttt gtaacactat gtgtacagag gaaacgaaaa gaaatatcgc   94080 tagacatttta gccctatggg attctaattt ttttaccgag ttagaaaata aaaaggtaga   94140
atatgtagtt attgtagaaa acgataacgt tattgaggat attacgtttc ttcgtcccgt   94200
cttgaaggca atgcatgaca aaaaaataga tatcctacag atgagagaaa ttattacagg   94260
caataaagtt aaaaccgagc ttgtaatgga caaaaatcat gccatattca catatacagg   94320
agggtatgat gttagcttat cagcctatat tattagagtt actacggcgc tgaacatcgt   94380
agatgaaatt ataaagtctg gaggtctatc atcgggattt tattttgaaa tagccagaat   94440
cgaaaacgaa atgaagatca ataggcagat actggataac gccgccaaat atgtagaaca   94500
cgatcctcga cttgttgcag aataccgttt cgaaaacatg aaaccgaatt tttggtctag   94560
aataggaacg gcagctgcta acgttatcc aggagttatg tacgcgttta ctactccact   94620
gatttcattt tttggattgt tgatattaa tgttataggt ttgattgtaa ttttgtttat   94680
tatgtttatg ctcatctttta acgttaaatc taagctgtta tggttcctta caggaacatt   94740
cgttaccgca tttatctaac actattccat attactaaaa tcggaacacc aatgcggtga   94800
cataaaataa ccgctataac ctaattcatt taacatctca ttaccacaag taataacatt   94860
attagacttg tgttttatca aatactgaca aaattgttga gcagatggat cgacctttgc   94920
cgccttttta accatccacg cgtctccagt acctcgccta atagcttgcg gcagatatgt   94980
tttcttatcc aatcgcatag ctataaaata ggcgccgaaa tccacacatt tgaattcgaa   95040
tatatcatcc ttaccagcgg ctagaagtct acctctatca ctttctaatt ttgttttgct   95100
atccgttaat gatttccaat cgttaaccgt atttttaatt cgcatatatc tcgttaattc   95160
attaaagact ggattatcag acgtctgaaa ccagagtaat agcgcactaa ttgccaatat   95220
aataacaaag aatataagtg ttgatgtttt ggctgcttgt acgcctacta tagccttttc   95280
```

```
tctaacgtat tctaaattac acgcgtttac cgataaagta gttttatcca tttgtacgtt    95340
ataaatggat aagaaaagtt tgtataaata cttactacta cgttcaactg gagatatgca    95400
caaagccaaa tctcccacta taatgacaag agtaaccaat aatgtgtatt tgggaaatta    95460
taaaaatgct atggatgcac catcatctga agttaagttc aaatatgttt taaatttgac    95520
gatggataaa tatacattac ctaactctaa tattaatatt attcatatac cgttggtaga    95580
tgatacaact accgatatta gtaaatattt tgacgacgta accgcctttt tatctaaatg    95640
tgatcaacga aacgagcccg tgttggttca ttgtgctgcg ggagtaaata gaagcggggc    95700
tatgattttg gcatatctaa tgtctaaaaa taaggagtca ttgcctatgc tatattttt     95760 atacgtgtat cattctatga gggacttgag aggcgcattt gtggaaaatc catcgtttaa    95820
aagacagatc atagaaaaat atgttattga taagaattaa aagtcttctg tttcttccat    95880
ttccttgatc ttttgagaag atatcttatc agatagtttc ctttccattc tcatgagaag    95940
acccaagtcg ataaagtatt tgtaatatcc agttcctata ttagggacct tgctaaaaaa    96000
gtggcagcta ctattatcgt taataggttc tgactttta tgaagagccg cgtttaacaa     96060
tgctttattg tctccgaacg tagctctctt aagagtacta gctgcgccga acttgaattt    96120
attcactgat tctggttcgt aactagcaca tagtaaacta gcgagaagat cacaaggctg    96180
atacagataa tcgaacccct ctccataggt gtttaacatg gcttcgcaca agtattcacg    96240
agcggcctcg ataccgaaga tatcgtatgt attccatact ccaggataca cgttgacgtt    96300
ttccaaatcg aaagaaccca attctttag attcatgagt ctacagtca tcttattgag       96360 ctttttgtt tgattgaagt cgtcatatcc cgtataatca gagataggaa tcttgaattt       96420
actaatcttg cccttgttgg cggcacccgg aagaaccatc ataaacttac taagattcaa    96480
ttcttccggt tcaacgaaat ttaggtagac agtaaatcta atattatcct catcctcaat     96540
gaatgtttcc atacccccatt cctttacaat gacgctaaag gagatgaatc gttcaatcat   96600
atattcgacg actaattcgg taatttctgc tctcttgatg tataatctat tgactattat    96660
atctactaca tacctatctg tttcttttcg aagagtgatg tttggattta attctcccaa    96720
acatacaaat tcgaaattaa tcttaacaga ttgaagttta gagatatcat cggataccag    96780
agtgataatt tcggtcttat tcttactcaa attagtcaag ttattaaact cgttgaaacc    96840 aagttttgt ttgacggcac cacttttttc agtagtgtga aaactggaca gggcttgttg      96900
tgtaaacttc tcagacaata cctgtgcaga ataattcca ataggagttc caccacctag      96960
agtataattg agttttttcat agaacttttc aaagatagtg atagccgttt cttttgtaat   97020
tctaattcta gaaggattaa gatgcgtcaa gaatatatac tccataaaat ctatattaga    97080
taccgtaaag aagtatttct ctctcacatc atcaatgacg ttatgaatca tatcgtacag    97140
atccttaacc ttaatagcat tatcctcagt ggtgggtttg acgaatacta ggaaattaaa    97200
cggcgccaat gtcttttttg caagtttctg tttctgagag taaacgaatc cctgttttat    97260
tttattccac agagcactaa tttccaaata ccaagtcatg gactcatctg gatagataag    97320
atctacaggt ttacatactg agcctagaat tttggtataa ttggcggcgt acttgatgag    97380
cgtattacct ataactactt gtccgtatcc gtcgaccacc atatcctcca tcttttaat     97440 gatttttcta gccagtgttc cggtacgtga tgtttcacag acgatatcag tagattgaga    97500
tcttgcaacc agcatcgaaa agtaatattg agaaccgtt aatccttttg ttaaagaatt     97560
aagaatgtaa cctcttcctt ctggatcctt agagtctgga agatagtaag gtaagactct    97620
acccaatact cgagtctctg ctggttcacc atcaatcctc tgttgtccat aagtacctag    97680
```

```
aatatacatt agttctgtgg gatttacttt ataacccgct ttggccattt tcaggaggtt    97740
attatctgga tcatctatca gcgtttgtct catatgttct tctatctctc ggatattaag    97800
atttgtcaag ttggataaca tggattccac atagtccgcc tctaaagctt tagataatgg    97860
aactattttc ccgtctctta catcgttgag atatttggcg tatgcttctt tgataagttc    97920
tattttttct acgttgatgg cctccaattt attagtgaac gtcgaatttg gtctcagatc    97980
tttgaatgtc accccaaaac cgtaaataga tagatatctc ttaaaaacat aagatgactt    98040
gataataaag ttgataccct ccacgttcga cttatgatcg gataagagtc cagccaatga    98100
cagatgcctc atagccacaa caaaattact atctacgtcg tttgcaataa tttcaccatc    98160
ctttaagaga cccggataat taatcttttc acctatcaag taagtataga tatctttacc    98220
gctgaattta catttacctt taggatcgaa ctctcttcca tatttcccca agatgttcaa    98280
tacttcatct aaacaaagat cttgtatcct aaacaatgaa tacgctgcta cgatttcatc    98340
ttgaatagat ccataaacgg gggctccatg aatatcgtgt ttgagtaacg tcgtcggata    98400
cataagaata ctttgttcaa ttacggcttt aggattttgc tccaatatca tccattcttc    98460
atctccgtcg aaatcagcat tttgagagtt gacaattccg ggagatattt tgatagtatc    98520
tccttcggta gctctgatag atgaagcgat gacgttgtat ctatgtagag acggctgtct    98580
tccaaaaata atacttgtat attcttgaac agctacttct acccaatcac caggcaataa    98640 atgtattta ttttgataa actttccttg gcgtattctt gttaattggt ttaatcgttt    98700
attaaagtaa aatttaactt ggtttgacgc taatagttgt ttaactttat ccactgtaaa    98760
ggcattaaca aatatctttt ctgtaagtgt atttctaata tatgcgggca ttcctacctc    98820
attaacggtg atagatgtac tgggaccaat tacagatcta gcggtctgat cttttcgccg    98880
ggcgacgata taacttctaa tcatattatt tttgccggat gtgatatatg ataaattgat    98940
actggaagtg ttattagaaa taattttaat atcatcgtat tctattaccg ccttctggat    99000
aacctgttca tcagcattca agttacaatt cttaacgatc atacctaata agtaagttaa    99060
ttcattggtt tctttgggta tactatctat ccaaaaacta atagccggtc taataatcaa    99120
cggagggatg ggaaagtagt ctgtataaaa taagttagct ggatattgat gaattctaa    99180 taatggccaa aacttttcat gaatagaaat taacttttga tagatgagag aattaggaac    99240
gttaatatca tccaacttgt tgacgaaaca aacctttttc tttgaaaaag taatttttttg    99300 atacggttgc atacattcac tgttccaaca tgacttttc ttggataata tttatccctt    99360
taatctccta agagcgtgtc ccgataactc ttttaggtta atatcgtcgg aatacggttc    99420
tcgtgaacgc aataatccgc agtgaataca tatataattc agtaaacgaa taatttctga    99480
aataaattca ggcttaacta tatgagtttt ataaatactt actttacccc agtgaccgaa    99540
acattccaat tccgttttcc cacaagtttt acataatgcc ccatccatag cacctagtct    99600
accatcttta acggtaccga tatcgtcgtc atttttaaca tgactaatga taatatctgt    99660
agcattaatc tctttttgat catatagact atacgtaacc ttagagatta cagccatttt    99720
tatcaagtca gtttcttta aagaaccgaa agtatacaat caaatttccc tttttattac    99780
aactataaaa taatagttat atttacactt taaattttta tcatgacgga cgaacaaatt    99840
tatgcattct gtgatgctaa caaagacgat atacgatgta aatgtattta tcctgataaa    99900
agcatagtac ggataggaat agatacaaga ttaccctatt attgttggta cgagccatgt    99960
aaacgaagcg atgcgttgtt accagcctct ttaaaaaaaa atataacaaa atgcaatgta   100020
```

```
tcggattgta ccatttcatt gggaaacgtt tccattacag atagtaaatt agatgtaaat   100080
aatgtttgtg attccaaacg agtagctacc gagaatatag ctgtccgcta tctgaatcag   100140
gaaattagat accctattat agatatcaaa tggcttccga ttggattact agcgttagct   100200
attttaatat tagcattttt ctaaacaaga tataagatat aaaatatatt attgattatt   100260
ataatgttct tatctcatct ctactaattg attaatcagc gactgaaata acagatctat   100320
cggctatctc tactccagtt accatgttat tgcggaaaaa tctaacaatt tttaatggta   100380
tattaggacg gtagagaatc ttgacaacta tttccgtctc taacattttg ggaagacgaa   100440
gagtcttttt accatcgcct gtttgtagta cactattaac tatattagtt tctgtagtat   100500
ctagtctaac aaagctagga ataagtcag atattaccac atctatgtat agaaaattta   100560
caggaaactt gttatgacct ttttgaagat acgatgttat aatgattggt tctccataat   100620
catcatcaac cggagtataa tttatggatg attcgttaaa tacctgaaac acagttttca   100680
tagaatcaat tttatgtcta acggttatta agtaactaa atcattatac tctatatcgg   100740
tagtatatct cagtagtacg tttctatta ttactgcgta cggatctctt gctatttctg   100800
tttttagaca tagaattttt gctagatatt ttacgttgta ttggttcatg actaactttt   100860
tcagttgatg ttgttggaat atttaagaaa cgaaatatag attgttgtag aaatagtacc   100920
tttgctttag tagtaggaaa tgttttattg cagtacacgg tcctcagcat aaagtacatg   100980
tgaaaatagt catattcctg attaggataa tcaaagttaa caactacttt gttacggacg   101040
atcttattaa ggtagtacat cttttttca taatttacag cgtctgattt ggtaactcga   101100
gtcagtctca tgttctcacc ggtataaata cttaataatc tcatttcagc tgaatatgaa   101160
ggagcaaaag gttgtaacat tttattaccg tgtgggatat aaaagtcctt gatccattga   101220
tctgaaaacg gcatctcca tttaagacta dacgccacgg ggtttaaaat actaatcatg   101280
acattttgta gagcgtaatt acttagtaaa tccgccgtac taggttcatt tcctcctcgt   101340
ttggatctca catcagaaat taaaataatc ttagaaggat gcagttgttt tttgatggat   101400
cgtagatatt cctcatcaac gaaccgagtc actagagtca catcacgcaa tccatttaaa   101460
ataggatcat gatggcggcc gtcaattagc atccatttga tgatcactcc taaattatag   101520
aaatgatctc tcaaataacg tatatgtgta ccgggagcag atcctatata cactacggtg   101580
gcaccatcta atataccgtg tcgctgtaac ttactaagaa aaaataattc tcctagtaat   101640
agttttaact gtccttgata cggcagtttt tttgcgacct catttgcact ttctggttcg   101700
taatctaact cattatcaat ttcctcaaaa tacataaacg gtttatctaa cgacacaaca   101760
tccatttta agtattatat taaaatttaa tcaatgttta tttttagttt tttagataaa   101820
aaatataata ttatgagccg acgtaacact ttctacacac cgattgatac atatcattac   101880
ctcctattat ctctatctcg gtttcctcac ccaatcgttt agaaaggaa gcctccttaa   101940
agcatttcat acacacagca gttagtttta ccaccatttc agataatgga ataagattca   102000
aaatattatt aaacggttta cgttgaaatg tcccatcgag tgcggctact ataactatt   102060
ttccttcgtt tgccatacgc tcacagaatt caacaatgtc tggaaagaac tgtccttcat   102120
cgatacctat cacggagaaa tctgtaattg attccaagac atcacatagt ttagttgctt   102180
ccaatgcttc aaaattattc ttatcatgcg tccatagtcc cgttccgtat ctattatcgt   102240
tagaatattt tatagtcacg catttatatt gagctatttg ataacgtcta actcgtctaa   102300
ttaattctgt acttttacct gaaaacatgg ggccgattat caactgaata tgtccgccgt   102360
tcatgatgac aataaagaat taattattgt tcactttatt cgactttaat atatccatca   102420
```

```
cgttagaaaa tgcgatatcg cgacgaggat ctatgtatct aataggatct attgcggtgg 102480
tagctagaga ggattctttt ttgaatcgca tcaaactaat cacaaagtcg aacaaatatc 102540
ctttattaag tttgacccct ccatctgtaa caatagggac cttgttaaac agttttttaa 102600
aatcttgaaa gtctgtgaat tttgtcaatt gtctgtattc ctctgaaaga gattcataac 102660
aatgacccac ggcttctaat ttatttttg attggatcaa taataataac agaaagtcta 102720
gatattgagt gatttgcaat atatcagata atgaagattc atcatcttga ctagccaaat 102780
acttaaaaaa tgaatcatca tctgcgaaga acatcgttaa gagatactgg ttgtgatcca 102840
tttattgatc gcaaaagctt tgcacaatct ttatacacta tcggtttact atttattgat 102900
aacgcagatg tttgagttgt catccatggt aatccataga tcattaattt atcgtcttca 102960
cacgctagat tagcacgtcg taatctatca ataggatcgg gtattttcg tttaggcatg 103020 aagaacatat ttaattcaga tctaaaaaat acatatatta gaatgaatac aatgaatact 103080
tcaaataaaa ctattaatct gtgtttataa acacttaata aagaatgttt aaacgtgggc 103140
tctataaaca caggattaaa gtatacatta ggaacattct ccatttatag taatcaatcc 103200
tttgtcggaa tatctgttag aggaatattc ttttaacac attccaatag tcccagaaaa 103260
tcatttaacc taatgggttc ttgaagaggg ctagaactat acgattctag ttccttatta 103320
gtactaagtt tctctagttt attttttattg gtgaatccgt aaatggcatt caatctcatg 103380
gatgtggaag gagaatacac attcaggaca ttaattcccg catatttaga tatcaaagcc 103440
ttgttgtctc cgataggtgt atactcagtc gacgcggatt ccatattttc tttataaata 103500
ttaatctttt tacgagtttc gaaaatacac aagataggtg atgatccttg acggaaaata 103560
accatgttct tattctttct cctaccactt tttttaggaa tgacggcagt catatccgta 103620
ttattaatga taagaggcat aacctcattg ttaggatcca agaaatagtt ttcaatggct 103680
tcaatagtta gtttatcatc tcctagaccc aaattgtttc ttatattata cattgtggta 103740
aacattgccc ctgtgatatt ctcgttatga atcaactcca actcatattt tgacatcgtt 103800
ctaggtacta tattaaaaat agaaagcata gatcttggaa atttggattt tgcgccggca 103860
ataaccattt gtaaatcatc atactcagat atacttcctg caaaaaatat ggtatcttct 103920
tcgatgaggt tttctagcag tagactcatt tagagaagtt ttttttgtga taaatgaata 103980
cccgtaccga tgttacaaac gataaatatag acaaaaatcc aaccaaacga ggtgatagaa 104040
atataccagg aagaaatgaa agatttaatg accaaaatag attcaacaac gatataccaa 104100
agcctaaacc aagactacag cctaatcagc caccgaaaca agataataaa tgcagagaag 104160
agaatggaga ttttatcaat attagattgt gtgcctacga aaaggaatat tgcaatgacg 104220
gatatctatc tcctgcctat tatatgttaa acaggtgga tgatgaagaa ataagttgct 104280
ggtcagaact atcgtcgttg gtgagatcca gaaaggcggt gggatttcct ctattaaagg 104340
cggctaaacg tatttctcat ggatcgatgc tatattttga acagtttaaa aacagtaaag 104400
ttgtgaaatt aaccccgcaa gttaaatgtt taaatgatac tgttattttt caaactgtag 104460 ttatttata ttccatgtat aaacgtggca tatattctaa cgaattttgt tttgatctgg 104520
tttctattcc cagaacgaac attgtttttt ctgttaatca attaatgttt aacatttgta 104580
cagacatatt ggtagttcta tctatttgcg gcaaccggct ctatagaaca aatctaccac 104640
agtcgtgtta cttaaatttc atacacggcc atgagacaat agcccgtaga ggatatgaac 104700
actccaatta ctttttgag tggttgataa aaaatcacat atcgctattg accaagcaaa 104760
```

-continued

```
cgatggatat tctcaaggta agaaaaagt atgctacagg agcaccagta aataggttgt  104820
tagaacctgg tacactggta tatgtgccca aagaagatta ttactttata ggcatatcac  104880
tcaccgatgt gtcaattagc gataatgtca gagtattatt ttccacagat ggaatagtgt  104940
tagaaataga agactttaat atcaagcatt tatttatggc aggtgagatg tttgttagaa  105000
gtcagtctag tactattata gtataaagta ataaaaaata gttaatgtga tgactagcgc  105060
caccaacgcc aacaacattt gataatttct acttactaga cgtaccgtaa aaatataaat  105120
tactataaca aataatagta tatcaataaa caacctaatt aatggtcgaa gtatagcagg  105180
acattgatgc tctagaccgt gtataacaaa atctacaaat ttttcatccg ctatattttg  105240
tttcactata tcgtctagac gatcagcgat aacttccatg ttaatctatt aaaatattat  105300
caatatattt tcagttttgc atatccgtgg tagcaataac catcggagaa gttctaaaga  105360
atgtgtccat gtaagtagtc caatggacgt tttccttatt ggctaaaata agtttgattt  105420
tatcattggt ggatgtgaac aacatacgct tggcatagta cataaacaac gctgccaata  105480
ttataacacc gataacaatc atataaaact gaactcctgt accagcaact tgtctaggtg  105540
ctatttgagt agtggcctta gtcgtcaatt gcatcaacgc tttaatggca caatttcctt  105600
tgctagatcc tgtattaata aattccaaat tgttggaga tcctgggget ccgtaacatt  105660 catctatgat tacgttttgt atctttaatt tgttatcgac gaccgcgcta gaattacaag  105720
tctgtttcac ataattttca aaatctctaa caacagtgtt tacactcgtc tgaatgttta  105780
acgcagcagt aaacatagct ggtacgtatg cttttgttc cggtgttaat ccactatatg  105840
tttctgtagc ggctgataac acagcatcca actgagcatc cgcgtccgca gagcacatat  105900
ttttaacagt gaggttacat ccatggtttt gtcggatata aaaatttccg atttctatat  105960
cacattttgt ttgagcacta gcgttcgctt cttgttctaa tttagacgag atacgttcgc  106020
tgagtgtatt caccgtcgtc tgtatgcttg ccgcggcacc catttaaata gctacaatta  106080
gtatccatat taccaagaga gataataaac tgatcaaatg caattttagg tcgaacgaat  106140
gtttaatatt atgttgaact acttttgctc tattgacggg aacagtagaa aatctatcac  106200
tattgcttaa tccacatgac aatcttaatg aggaagtttt atccatctgt aagttgttca  106260
cgctagtatt acatcgtaca atattgcaaa gtcctaaatt attataatta cgtgttagta  106320
agaaattaac attggcattc gaacactctg gatcccaaca ttctcgaggt tccgcatatt  106380
ttaatgactc ttctaactta tctctagtgg gataactaca tctcatatat ttctgtttaa  106440
agtccgcaga ctgttgtctt agaatataat cgatcatctc tttgctatct tctgtattgt  106500
gtgcgcgtaa atgatgcaaa aatgattcac atattggtac actagcatct ttactacata  106560
atgtttgcat cttattatac agatttatta acgattgttg accctctaca gttctatcac  106620
tcctattaaa ggctgaaccg atccactgat ggcatatgtt tctatcgaac gtatccccct  106680
gacaccagtc gaataaatca acatcgcatt ttccagtgtc gtgaacgtct ggccaacacg  106740
attctaatac tgcaccctct tcatacttat ctgatatctt tccatccttt ttccaataat  106800
gagtacgatt aaaagtgcga cagcaattgg gtgcggttcc attatacgat tgtcttaaca  106860
atgccgaaag accaccgggt cctgtgttga ctaatctaaa ctctggatat cttttctta  106920 ctttatcctc tttatctttt gctagtggtc ctatatgcac atattctaaa agcttagcgg  106980
gagctatcac gtcatgcatt ttatccacgt ttaataacat ctcatcagtg ggtactcccg  107040
gaggcggatc ccgtttaggg agctcaacac ttactctgcc acccatattt atctcattga  107100
aagtattaat ctaaaaacgt cataaagatg ttgatcttaa aggattgaac tctatccgaa  107160
```

```
aacaacattc ctagaatgtt atcgtcatta tccattacga ttctagtttc aaaaacattg  107220
actctctttt tgaatcctcg tagtttgttg agagacgaga tagctatttt gaaagaaaac  107280
ttttgtagtt cttgagaaca ttcagtcata gaatattccc tggaaaacgc atcagtatta  107340
ccaggagtct tcataataat attgtcatct ttaaacataa tagccaaatg ctgatgctga  107400
ctaatacact tgataaagcc caacaaccat tctaaatgaa tgacggttct accacaacat  107460
ttttcttcat acttgtgaaa attaaacacg taagatttct tttgatctat acttagacaa  107520
atagtagtat ctgtcctaat aggcatcagt tccttgttac aatcgacact tactacatga  107580
taactagaaa gttttactag attattttcc agatcaggtt ctatatctat gatggcatca  107640
ttgtgaaaac tacacaaaca cgattttacc ttggacacag gaagattaaa cacaatgttt  107700
tcggctccgc ggtagaacac tgatgcactg agaggtataa tggcccaaat gtttacagat  107760
ccgcccaagg cggcaaaaat atacattaac tcatccgtcg agtctacatt tatagatact  107820
tcttcactga actctgaaaa atatgccaca atttggcgca gtttatcgat ttttatacgg  107880
atgctcattt taaattttg taaattattt aaagttaaat ggctgcagaa cagcgtcgtt  107940
ctacaatttt tgacatagtt tcaaaatgta tagtgcaatc tgtattgaga gatatatcta  108000
ttaattctga atacatagag tccaaagcta acaattgtg ctattgtccg gcatcgaaaa  108060
aggaatcagt gattaatggt atctacaatt gttgcgagtc aaatatagaa ataatggaca  108120
aagagcagct attaaaaata ttggacaatc ttcgatgtca ttcggctcat gtatgtaacg  108180
ccacagattt ctggagacta tataattcgt taaaacggtt tactcatact accgcattct  108240
ttaatacatg caagcccact attctagcca cgctaaacac tttgataacc ctgattttat  108300
ctaacaagtt attgtatgcg gcagaaatgg tagagtatct agagaaccaa ctagattcat  108360
caaataaatc aatgtctcaa gaactagcag aattattgga aatgaaatat gctctcatta  108420
atctggtaca atataggatt ttgccaatga tcatcggtga gcctattata gtagctggat  108480
tttctggtaa agaaccaatt tctgattatt ctgcagaagt ggaaaggcta atggaactac  108540
cagttaaaac tgatatagtg aataccacat atgacttctt agccagaaaa ggtattgata  108600
ctagcaacaa tatagcagaa tatatagccg gcttgaaaat agaagagatt gaaaaggtag  108660
aaaaatattt accagaagtt atatctacaa ttgccaatag taatataata aaaaataaaa  108720
aatctatctt tccggccaat atcaacgata aacagatcat ggaatgctct agaatgttag  108780
acacgagtga gaaatactct aaaggatata aaactgatgg agctgtgact agtccattga  108840
cgggaaataa tacaattaca acatttatac caatttctgc gtccgatatg caaaagttta  108900
ccattttaga atatctttac attatgagag tgatggcaaa caacgttaag aaaaagaacg  108960
agggaaaaaa caacggagga gtagttatgc atattaactc accctttaag gtaatcaatt  109020
tgccaaaatg ttaaattatt agaatcatat atctttatcc atctattatc atctgtgaag  109080
ttttggctca gaaaaatatc tttacctaat attcgtttag acgatgtatc aataccggca  109140
tttttataac attcagctac caatttaaaa caatacattc tattatgacc aaatccatac  109200 ggaatacccca ataaagttaa tgacgtatca gctgctattt tcataacttg aatattctct  109260
aacatgtata cttttgcact aagatatcct tcaaaaaaac tatccaatgg gactattcga  109320
actccttttc tataggtaga ttcaactacc aagtgttccg ataataacgt accataataa  109380
atacccacat gtttttctat cgatggattc aaatgacttg ttaatgacat ggtataatta  109440
ataaaaataa tagaacctct aggcgcatat gtcttgataa aattaaccgg atccatatta  109500
```

```
gtttatatcc aatagaggtt gcactgttaa gttacgttga ggttctattt gtgtagataa    109560
ttttaaccta caacattcgt tctttacact gacgagtaca tcctttaatg attttttcg    109620 tataatcaat ttatatcgtt cgtgagaaat atctttgccg cacgtagagc acacgagttg    109680
gaacaccatt tttaatctag taacctatat ttattatatt atcactttta gtattggtta    109740
ttaacagact atcgttaaag taaaatgaac tatttatact cagtagtaaa ttatccttat    109800
agatgccgaa cactatagtg ttacagtttt cgttagaata tccgaagatc gaagatatag    109860
attttataac atcgatatct gatttagtat tttcgaaatc tatataagat gataaagttt    109920
taacttctga aacatcaatc tccttgcgtg gttctaatgc atacattaat tggcagggta    109980
acggaacggt ctctaaataa gatgatttaa aattgttcca ttttttcatct aatgcggaaa    110040 atataaattc ttgaacagtg cattgacaag gaggaacata cgagtagaca tcgtctaaat    110100
tagcgtaatc gtttataaac gtaacaatat tacgcacgtc tacggtagag ttagtctttc    110160
tataataatt tttaattgcc aaactagtga ctatattatc gattgtaaaa tcactaaaca    110220
attgtatttt gtttaagttg gtgggtgtta tagatgcccc atagagtcca ggaaagaaat    110280
cacatccatt cactaacgcc gttaattttg ctaaatagtt atcctctgcc gagggaacaa    110340
atttaaacag ttgagttaag ttttttatca tcttaggatg attatcagta gatgcaaata    110400
gcatagtatc ctgatcggta cttattatca acggccattc tcctgtggta gagaaatgtg    110460
ttttagcctc gagacacata acgaattctg cgtctcgttc atcacaataa aataatgtaa    110520
cattctcatt attgttgaaa tgtgttagta tctcattcaa tgatattttt atgttatcag    110580
aatcagataa atatatttga aatgtgagtt tatcgatttt taattgcatt tctgccttta    110640
tttcttcttc cataaatccg gtaacatttt gtatttcgga tgtacacttt tctaattcta    110700 gcattttctct gtccttggtt aatttagaat atttacgtct cttgtctcta acgtcttgtt    110760
taatttttat acttcctcta tcgataaaaa gggttacatg ccctcccttt tttacccatc    110820
cgtttacgta ttttatgaat accgtagtta actcttctaa gttctgaca caattggcga    110880 cggctatata aatactcatt gtatccacaa atattccatt gtatactttg tataaattat    110940
catctaatat cgtcagtgat ttattttcca gcagtaacga ttttaagttt ttgataccca    111000
taaatgaaga acgtactgat tatttttcggt aaaccgtatt gtagtatttg tgaaaatgtc    111060
agtgatgcag tagaagaatt aaaatccgag tatgatatac tccatgttga tatcttatca    111120 tttttttaa aggatggtga ttcaagtatg ctgggtgacg taaagcgcgg aaccctaata    111180
ggaaactttg cagcgcatct atctaactac atcgtttcca ttttcaaata caatccacag    111240
acaaaacaaa tggcatttgt ggacattaat aaatccttgg atttcaccaa aaccgataaa    111300
tcgctggtga atttggaaat tctaaaatcc gaaatagaaa aagcaaatta tggagtttgg    111360
ccaccggtta ccgaataaaa tatcttcctg agtattttgt ttattgttcc gcttcccttta    111420 tcaaataaat tttgaagtat ttgataattt attggatcga ctagttcatc tatacatttt    111480
ttggaaacga gaacatctac cttttttattt gttgttatat gcgacgttgt atacgccata    111540
aatgtaactt gagaaaatcc acaagaatt aattttgaac cagttatggg gacgcgctca    111600
ttagaatatg tataaatctg aggagtgtat tccttgagga gatattctat caagtcatca    111660
tttgcttctc taatataaat attcctgtcc tttataacaa ctatgccttt tagattatct    111720
cctaatttat aacacggccg tatacacttg gaatacttgt acaatctaag atagactaaa    111780
tctctcagag ttgtatcatg gaattccata cttaattcct ccgataaatc tacatgttca    111840
aatactttag aaatatattt atggtatttc ctatctggaa agtaagttat caagtcatca    111900
```

```
taagatattt caaatcctct acataaggaa gacactatct ccaacgattc ctcatcttct  111960
gtaagtagga atttggacaa gttaaacaaa attagatctc taaatggcat ctttattata  112020
tcttatttta tttttgttat tcgtatgtat ttcttattat tttacatatt atccgaccaa  112080
taaacttcag gcagctgtaa tggaaacaga tagagaaaac gctattatta gacagcgaaa  112140
tgatgaaata ccgactagaa cattagatac agctatattt accgatgcat caaccgtcgc  112200
gagtgcgcaa atacacctat attataattc caatattggt aaaattataa tgtcacttaa  112260
tggtaaaaaa cacaccttta atttatacga tgataacgac atacgaacat tacttcctat  112320
tttactcctt agtaaatgat tgtcttaccg aataaagttc gtattttcat caacgatcgg  112380
atgaaaaagg atatctactt gggaatttct aatttcggat tcgagaatga tatagatgaa  112440
atcttgggaa ttgctcactt gttggaacat ctacttatat cctttgattc tactaatttt  112500
ttagcgaatg cttctacatc tagaagttat atgagttttt ggtgtaaatc cattaattca  112560
gcaacggaat cggacgcaat cagaacatta gtttcgtggt tcttttctaa cggaaaactc  112620
aaagataatt tttcccttc tagtatacga tttcacatta aagaattaga aaacgaatac  112680
tattttagaa atgaagtatt ccattgtatg gatatactaa cgtttcttag cggaggcgat  112740
ttatataacg gtgggagaat agacatgata gataatctta atatagttcg tgatatgctg  112800
gtaaatagaa tgcaaaggat atcgggatcg aaatatcgtaa tttttgttaa gagattagga  112860
cctggaacat tggatttctt caaacagaca tttgggtctt taccagcatg tccggagatt  112920
attccttcgt ctattccagt aagtacaaac ggtaaaatag ttatgactcc gtctccattt  112980
tatacagtta tggtaaagat taatccaaca ttagataata ttttagggat tctgtatttg  113040
tacgaaactt accacttaat agactatgag actatcggca accagttata tttaacggta  113100
tcctttatcg atgaaactga atacgagagc tttcttcgtg gcgaggctat attacaaatt  113160
agtcaatgtc aacgtattaa tatgaattat agcgacgatt atatgatgaa catctattta  113220 aatttttcctt ggctatcgca tgatttatat gattacatta cacgtattaa tgacgatagc  113280
aagtcgatac taatatcctt gacaaatgaa atatatgcat ctataattaa tagagatatc  113340
atagttattt acccaaactt tagtaaggcc atgtgtaaca ctagagatac ccaacaacat  113400
ccgatagtag ttcttgacgc aaccaatgat ggactgatta agaaacctta tagaagtata  113460
cccctaatga agcgtctaac atctaatgaa atatttatac gatacggaga cgcgtctctc  113520
atggacatga taactttatc attgtctaaa caagatatat cattaaaaag aaatgccgaa  113580
ggaatacgtg taaaacatag ttttttcagct gatgatatac aggcaattat ggaatctgat  113640 tcgttttttaa agtatagtag atcaaaacca gctgcgatgt atcaatatat atttctatca  113700
ttttttgcta gtggtaattc catagatgac atattggcaa atagagattc taccttagaa  113760
ttttctaaaa gaactaaaag taaaattttg tttggtagga ataccagata cgacgtcact  113820
gcaaaatcta gttttgtatg tggtatagta cgaggtaaat cattggataa aacgtctctg  113880
gttgaaatga tgtgggatct caagaagaaa ggattaatat attctatgga atttaccaat  113940
ctattgagca agaataccctt ttatctgttc acatttacta tctacactga tgaagtatac  114000
gattatctaa acactaataa acttttttct gcaaaatgtt tagtcgtgtc tacaaaagga  114060
gatgtggaaa atttttcatc tctaaaaaaa gatgtggtca ttagagtttg attttttagtt  114120 attatctaca ggaacaaata tagtatctga aatcatattc atatatcccg ttagaggtct  114180
atgataatat atagtagcgt ttgttccgtt atagacaccg aataatattt tacaaaagtg  114240
```

```
tatatacgta tcatcatctt tatgtttaaa atttaaaatc ttaattcgta aatttagaga    114300
taaaatggct tcttgtacaa tactagttaa ttctcccgtc ctctcaaaat tatccaactc    114360
ctcagcgaga ataggactta gtacataaag tttagcatac tctatcatct tcatataata    114420
attggataat aatttattcc atgtttctgt actaatatcg aacgagtcta tatattcctt    114480
tgtacgccat agaatatcca aatttgtagg gattataaac aaatcttcgg ggagtgttag    114540
attaaactta ttagcgtaca atatataatt atgtagaaat tctgaatcta ttcgctgtat    114600
agacttcata taagacagat catagaaata tacgtatgtc ccaggattaa ctcttcctac    114660
tcttcctttt cgttgatctc tcatagattt agaaataaat tcttgcgatc tccaaaagg    114720 agcggggaca aaaactctac ccatatcata aatgtgtgta acattgcgta tagtaacgct    114780
ggattccaaa taaggagtag aaataattat cgatacatta ggtgatgaat acactttttc    114840
taatatttcg tctatatcta agaccttacc atgaataata tacatatcat acggtaatct    114900
tttttctaaa tatgatttat attcgtgaca ctgtgcaacg gatgccacaa agactatacc    114960
ggatgatcca tcaggaggag tatacatctg tatagcagta actaaatttc tcttttcttc    115020
ttctatgtat gccattctgg aagatggatt tatcttatta tgaataaata cctcgctaat    115080
tttaaacagt gtatctccag gaatatgtat aaatgcggga ttaggtaaaa atacttttag    115140
ccgttccctg tcatcctcta acgtggcagt cattaaaaac atagaatcta ttttcgtatg    115200
atgctttctc gctactgcta taataatatc tcctatttga tcatgctcat gaacttcgtc    115260
tataataaga gtgccataac taaatagttt tgttagagat aacttatggg tagaaaatac    115320
aattccatat ttttttggtt gtttgtttat taattcttcc ggtatagatc cgtaccgtaa    115380
agaaatagga gatccatcta gtaccttaaa tcccaatgat tttaaaatgg tattgctatg    115440
caatctaact aaagctatcc taggaagaga tagaatgact ggtctttcgt gaaagtcagt    115500
gattttatct agagtagaga atccaccaaa taaataatta aaccaaagca ataacttggg    115560
tacctgtgac gtcttaccca ctccagttcc tccagttaaa actacaggtc tatgagaaat    115620
ccacgctgaa aatatctctc gttgtgcttt aggagttaat gaggccaatg gaattttgct    115680
aaatggatac ttattcccta gtacacctat agtatctgtt cgtttaccta cggaattgga    115740
aaatatctgt aaactattac cagcttctaa tagtcctctt aatatatact catcgaacga    115800
attgatttct gtatttgtta tacattttag aaaactataa cattcaaagc ttattgtgtg    115860
ttcactgtat atatattgct tcgcggttag gtttatgtgt gcgggttttc ctagtgatgg    115920
aggagatact ttttttccac gtgcttctgt actaactttg tatattcctt tatgttttac    115980
aacgtgtgcg ttatgccatc tatgttttat aactggaaac accgccaatg agaaactatc    116040
acgttccgtt ttactcatat tactgaattc atcttgtgaa tatttgtaag agaatacatt    116100
aacgcagttt ggaaaaaaga agatatctgg taaattcttt tccatgataa atggaaagat    116160
atacagattt agtaattagt aaaataccag aactaggatt taccaattta ttatgtcata    116220
tatattcact agctggatta tgtagcaata tagatgtatc taaatttttta acaaattgta    116280 acggatatgt agtggagaaa tatgataaat ctacaaccgc cggcaaagtg tcttgtattc    116340
ctatcggtat gatgttggaa ctagtagagt cggggcacct gagcagaccc aatagtagcg    116400
acgaactcga tcaaaagaaa gagttaaccg acgagttaaa gacgcgttac cattctatat    116460
atgatgtctt tgagttacct actagtatac cgttagcgta tttctttaaa cctcgactac    116520
gggaaaaagt atctaaggcg atagacttct cacaaatgga tttgaaaatc gatgatttat    116580
cacgtaaagg aatacatact ggtgaaaatc caaaggtcgt caagatgaaa atagagcctg    116640
```

-continued

```
agagaggagc ctggatgagc aatcgaagta ttaagaactt agtctctcag tttgcttatg    116700
gatccgaagt ggattatata ggacaatttg acatgagatt cttaaactcc ttagcgattc    116760
atgaaaaatt tgacgcgttt atgaataaac atatcttatc gtatatactt aaagacaaaa    116820
ttaaaagttc tacctctaga tttgtaatgt ttggattttg ttatttgtct cattggaaat    116880
gtgtaattta tgataaaaaa caatgtttag tatccttta tgactccgga ggcaatattc    116940
caactgaatt ccaccactat aataattttt attttattc cttctccgat ggttttaaca    117000
cgaatcacaa acattctgta ttggataata caaattgtga catcgatgtt ttattcagat    117060
ttttcgaatg tacatttgga gcgaaaatag gctgtattaa tgtagaagtt aatcagctgt    117120
tggaatctga atgtggaatg tttattagtt tgtttatgat attgtgtact aggacaccac    117180
ctaagagttt caaatctctg aaaaaggttt atacattctt taaattttta gcggataaga    117240
aaatgacatt atttaagagc attctattta acttgcaaga tctatccctg gatataacgg    117300
aaacggataa cgcaggatta aaagaatata acgtatgga aaaatggacc aaaaagtcaa    117360
ttaatgtgat atgtgataaa ttaactacaa aattaaatag aatagtaaac gacgatgaat    117420
aactttgtta aacaagtagc ttcaaagtct ctaaaaccta ccaaaaaatt gtctccgtca    117480
gatgaggtga tatctttaaa cgaatgcata atatccttta acttggataa cttttattat    117540
tgcaacgatg gactgtttac taagcccatt aatactccgg aggatgttct taaatcactc    117600
ttgatcatgg aatcattcgc ctacgagaag atgataatca aaggattgat aaaaatacta    117660
atatctagag catatattaa tgatatttat tttactccat tcggttggtt gacgggcgtc    117720
gacgatgatc ctgaaacaca cgtggtgata aaaataattt tcaattcatc actaatatct    117780
atcaagtctc aagttataga atatttaaaa ccatacaatg tcataaccct atcggtactt    117840
accacagaaa aagaattaag tattaatacg ttcaatgttc cagattctat acctatgtcg    117900
ataatttcgt ttttcccatt cgatacagat tttatactag ttatttttgtt ttttggagta    117960
tataatgact cgtattgtgg aataagctat ataagtccga aagagagact accgtatatc    118020
atcgaaatat taaaaccgtt ggtgtcggaa attaacatgt tatcggatga aataggtaga    118080
acatcatcca ttagaatctt caattccact agcgtcaaaa aatttcctac taatacatta    118140
acatccattt gtgaaattgt ttattcgttt gatgaatcat cctttccgac gcctaagacg    118200
ttcactcctc taaacgcgag tccatacatt cctaaaaaga tagtttcact attggattta    118260
ccatctaatg tggaaataaa agcgatatct agaggcggtg tggatttcat cactccatatt    118320
aataataagc gtctaaacac aatcttggta atagcaaaag ataactttt aaaaaattct    118380
acattttctg gaactttat caaagagaat attatttgga agggtatcta tacttataga    118440
ataatcaagt ctagtttcc agttcctact attaagtcgg ttactaataa aaaaaaaata    118500
tgtaagaaac attgtttcgt caattctcag tatacaacta ggactttgtc acatattctt    118560
tgatctaatt tttagatata aatggtggat gctataaccg ttctaactgc gatcggcata    118620
actgtattaa tgcttttgat ggtaatttct ggcgccgcca tgatagtcaa ggagttaaat    118680
cctaatgata tattcactat gcaatcatta aagtttaatc gagccgtaac gattttcaaa    118740
tatataggac tctttatcta tataccagga acgataattt tgtacgctac atacgtcaaa    118800
tccctattaa tgaaaagtta ataattttt tttattacac caacaaaaat gtttgtcatt    118860
aaacgaaatg gatacaagga aaatgtcatg tttgataaaa tcacgtctcg tattagaaaa    118920
ttatgttatg gcttaaacac ggatcatata gatcctatta aaatagctat gaaggttatt    118980
```

```
caaggaatat ataatggagt aacaacggta gaattggaca ctctggcagc cgaaatagca  119040
gccacttgta ctacacaaca tccggattat gccattctag ccgccagaat agccgtatca  119100
aatctacaca aggaaacaaa aaaactattt agtgaagtga tggaggattt attcaactat  119160
gttaatccta aaaatgggaa acattctccg attatttcaa gtatcaccat ggatatagtt  119220
aacaaatata aggataaact caactcggtt attatttacg aacgagactt ttcatacaac  119280
tattttggtt ttaaaacttt ggaaaaatcc tacttgttga aaataaacaa caagatcgtt  119340
gaaagacctc agcacatgtt aatgcgtgtc gcagtaggaa ttcatcaatg ggatatagac  119400
tcagctattg agacgtacaa tctactttct gaaaaatggt ttacgcacgc ttctcctacc  119460
ttatttaatg cgggaactag tcgtcaccaa atgtctagct gttttctact taacatgatc  119520
gatgatagca tagagggtat ctatgacacg ttaaaacgat gcgcattaat ctctaaaatg  119580 gcaggggaa taggtctatc aattagtaat attcgtgcca gtggaagcta tatctccggt  119640
accaatggta tatcaaacgg tattattcca atgttgagag tttataataa caccgctaga  119700
tacatagatc agggaggaaa caaacggcct ggagttatgg ccatatactt ggaaccgtgg  119760
cattctgata ttatggcgtt cctcgatctt aaaaagaata caggaaacga ggaacataga  119820
accagagatc tatttatagc tctttggatt cctgatctct ttatgaaacg agtgaaggat  119880
gacggagagt ggtcgttgat gtgtccggat gaatgtcctg gattggacaa tgtttgggga  119940
gacgagttcg aacgattgta tacactatac gaaagagaaa ggagatacaa atctataata  120000
aaggctcgag tcgtctggaa agcgattata gaatctcaga ttgaaactgg tactccattc  120060
attctttata aggatgcgtg taacaaaaag agtaatcaac aaaatttagg aactatcaag  120120
tgtagtaatc tttgcactga gataatacaa tatgcggatg ctaatgaggt agccgtttgt  120180
aatctggcat ctgttgcctt gaacatgttt gtaatagatg ggcgatttga ttttctcaaa  120240
ctgaaggatg tggtcaaagt aattgtcaga atctcaata aaattataga tattaattat  120300
tatcctattc cagaagctga aatctctaat aagagacata gacctatcgg tattggtgtt  120360
caaggattag cggacgcgtt tattctctta aattatccat ttgatagcct ggaagcacaa  120420
gatctaaata agaagatctt cgaaaccatt tattacggtg cattagaggc gagttgtgaa  120480
ctagctgaga aggaaggacc atacgataca tatgtaggat cgtacgccag taacggtatt  120540
ctacaatatg atcttttggaa tgttgtaccg tcggatcttt ggaattggga acctctaaaa  120600
gataaaatca gaacatacgg tcttagaaat agtttattgg tggcacctat gccgactgca  120660
tcaactgctc aaattttggg aaataatgag tcggtggaac cgtataccag taatatttac  120720
actcggagag tattgtctgg agaatttcaa gtagttaatc cgcatctcct tagagtttta  120780
accgagagaa aattatggaa tgatgagatc aagaatagga ttatggcaga tggtggatcc  120840
attcagaata caaaccttcc agaagatatt aagcgagttt ataaaactat ttgggaaatt  120900
ccacaaaaga cgatcataaa aatggctgca gacaggggag ccttcatcga tcaaagtcaa  120960
tctatgaata tccatatagc agatccgagt tattccaaac taacgagtat gcatttttac  121020
ggatggagtc tcggtctaaa aacgggaatg tactatctac gtacgaaacc cgcatccgct  121080
cccattcaat tcacattgga caaggataaa ataaaccac tggtggtttg cgattccgaa  121140
atctgtacat catgcagtgg ttaaacaaaa acattttttat tctcaaatga gataaagtga  121200
aaatatatat cattatatta caaagtacaa ttatttaggt ttaatcatga gtaaggtaat  121260
caagaagaga gttgaaactt caccaagacc tactgcatct agcgattctc tacagacttg  121320
tgcgggtgtt atagagtatg caaaatcgat tagtaaatct aatgcaaaat gtatcgaata  121380
```

```
cgttacacta aatgcttctc aatacgctaa ttgttcgtct atctctataa aacttactga   121440
tagtttatct agtcaaatga cttccacttt tattatgttg aaggagaga ctaaacttta    121500 taaaaataaa tctaaacaag atagaagcga tggatacttt ctaaaaataa aagttaccgc   121560
ggctagtcct atgttgtatc aacttctaga agccgtctat ggaaacatta agcacaagga   121620
acgcattcca aattctttgc atagtctttc ggtggaaact attacagaga aacatttaa    121680 ggatgaatcc atcttcatca acaaattaaa cggatccatg gtagaatatg tttcgactgg   121740
agaatcatcc attctcagat ctatagaagg tgaactagaa tcactcagta aagagaaag    121800 acaattggcc aaggcaatta tcacacctat cgtcttctat agatccggaa cggaaacaaa   121860
aattacattc gcactcaaga aactaatcat tgatagagaa gtggtggcta acgttatcgg   121920
actctctgga gatagtgaac gtgtatcaat gactgaaaat gtagaagaag atctggctcg   121980
taatctggga cttgttgata ttgatgatga atatgatgaa gatagcgata aagaaaagcc   122040
aatattcaat gtataaatgg ataagttgta cgccgctata tttggtgtat ttatggggtc   122100
tccggaagat gatttgacag actttataga aattgttaaa tctgttctaa gtgatgagaa   122160
aacagtcaca tcaactaata ataccggttg ttggggttgg tattggttaa ttattatttt   122220
ttttatagtt cttattctac tactattgat atatttgtat ttaaaagttg tttggtgaac   122280
ttaaatggcg gaatttgaag atcaactcgt tttcaatagt atcagtgccc gtgcattgaa   122340
agcttatttc actgctaaaa tcaatgaaat ggtagatgag ttggtcacaa gaaaatgtcc   122400
acaaaagaaa aaatcacaag ctaagaaacc tgaattacgc attcctgtag atcttgtaaa   122460
gtctagtttt gttaaaaagt ttggattgtg caattatgga ggaatcctta tcagtcttat   122520
taatagtcta gtagaaaata atttctttac aaaggatgga aaactggatg atacaggcaa   122580
aaaggaattg gttttgacag atgtcgaaaa acgaattctt aataccatag ataaatcatc   122640
tcctttgtat atcgatatta gtgatgttaa agtattggct gctagactaa aaagaagcgc   122700
tacacaattt aactttaatg gacatacata tcatctggaa aatgataaaa tagaagatct   122760
cattaatcag ttggttaagg acgaatccat tcaactggat gaaaagagtt ctattaaaga   122820
tagtatgtat gtcattcccg atgaacttat cgatgttctc aaaactagat tgtttagatc   122880
tcctcaagtc aaggataata ttatttcgcg tactagattg tatgattatt ttactagagt   122940
tactaagaga gacgaatcgt caatctatgt gattctaaag gatcctagga tcgctagcat   123000
tttgtcacta gaaactgtta aaatgggcgc ctttatgtat acaaaacata gtatgttgac   123060
gaacgctatt tcatctagag tcgatagata ttctaaaaag tttcaagaat cttttacga    123120 agatattgta gaatttgtta aagaaaatga gagagttaat gtatcgagag tggttgaatg   123180
tttgactgtg cctaatatta ctatatcaag taatgctgaa taaaaatatt tataaatatg   123240
ctcgtcgtaa ttatgttttt tatgcgtttt gccttctgta gttggctatc atatagctat   123300
ctgcgtccat atatctcgac taaagagtta aataagtcga gatagtttta tatcacttaa   123360
atattaaaat ggccgaggaa tttgtacaac aaaggttggc caataacaaa gtgacaattt   123420
ttgtcaagta tacatgtcct ttttgtagaa atgcactgga tattctaaat aagtttagtt   123480 tcaaagagg agcgtatgaa attgtcgata ttaaagaatt taaacccgaa aatgaattgc    123540
gtgactattt tgaacaaatt actggtggta gaactgttcc tagaatcttt tttggaaaaa   123600
cttctattgg tggatatagc gacctgttgg aaatagacaa catggacgca ttgggtgata   123660
ttctatcatc tattggggta ttgagaactt gttgagaaaa taatgaaaaa acaatactta   123720
```

-continued

```
atcatgtcgc cgacatgttc atgtatccgg aatttgcgag gaaggcttta tcaaagctta   123780
tttcaaaaaa attaaacatt gaaaaggtgt ctagcaagca ccagctcgtg ttactggatt   123840
atggattaca cggactattg ccaaaatcac tgtatctgga agctattaat tccgatattc   123900
tcaatgttag attctttcct cctgaaataa taaacgtcac tgatatcgtt aaggctctcc   123960
aaaattcttg tagagtagat gagtacctaa atctgtttc cttatatcat aagaattctt    124020
taatggtatc gggaccaaat gtagtcaagc ttatgataga atataatctt cttacacaca   124080
gtgacttgga atggttaatt aatgagaatg tagtcaaggc tacatacctt ttaaaaatca   124140
atgcctatat gattaacttt aaaatagatc taacggttga tgaaatcatt gacttagtta   124200
aagatattcc tgtaggagct acgctacatc tatataatat attaaacaat atagatttgg   124260
acattgttct tcgtatatct gatgaatata atataccacc tgttcacgat attctgtcta   124320
aacttaccga tgaagagatg tgtataaaac tagttacaaa gtatcctatg acaatgttta   124380
taaattttat taatcaagat gttagatata gtcccacctt catcaagaca attaaagatt   124440
ttgtcaacaa gcatcttcca accatgtacg atggattaaa tgattatcta cattctgtta   124500
ttatcgacga ggacttaata gaggaatata aaattaaatc cgttgccatg tttaatttgg   124560
aatacaaaac tgatgtagat actctaacat tggacgaaca gatatttgta gaggtaaaca   124620
tctcatatta tgattttaga tatagacaat ttgccgatga atttagagat tacattatga   124680
taaaagaaag aagacaaatc accatgcaat ctggtgatag aataagaagg tttagacgtc   124740
ccatgtcatt gagatccact atcatcaaaa aggatactga ttctctagag gatattctcg   124800
cacatataga taatgccaga aaaaatagca aggtatccat tgaagatgtt gagagaatca   124860
tttcatcttt ccgtcttaat ccttgtgttg tcagacgcac catgctgtct gatatagata   124920
tcaaaacaaa gattggaaat cttgtgctct gacactatca gccatcaaag gaattatggt   124980
aacagatacc atcaataccg tgttatccaa aattctgcat catcatagga atgtcttcaa   125040
gtatcttaca tctgtagaga ataaagaaat tgctgtctgt cgctcttcta tagaaattaa   125100
aaaagtgtac gatgtgatct acgcacagat gatggattat tggataggct atacgatctg   125160
actagatacg ccttacacgg aaaaatcaat caaaacttaa tcggtcaacg atgttggggt   125220
ccgttgacag aaatgctgtt taacgagaat aaaaagaaaa aactaaataa tttaatggaa   125280
tacatcaaaa tatcagacat gttggtatac ggacactcta tcgagaagac gcttattcca   125340
attactgatt ctcttccatt caagctatct gttgatacca tgtctgtgtt aaatgatcaa   125400
tatgccaaga ttgtcatctt cttcaatacc atcatagaat atattatagc tactatctat   125460
tatagattga cagtcttgga caattatact aatgtcaaac attttgtatc caaagtgtta   125520
cacactgtca tggaagcatg tggcgtactg ttttcataca ttaaagttaa tgacaaaata   125580
gagcatgaat tggaggagat ggtggacaaa ggtaccgtac cttcttattt gtatcatctg   125640
tccatcaacg tcatttcaat aatattggat gatataaatg gaactcgtta atatttttt    125700 agaaacggat gctggaagag taaagtttgc cataaaaaat accgacgatg tatgtgcctc   125760
ggagttaata aataaatttg tggaactgtt aagtgaatac attcacattg accaatcaga   125820
attttatttg gtggtaaagg ataaggtat ttttttattt aagtgtgata gggggtctat     125880
ttcgattgta aacaatgagt tttatgtctt tgacgaaccc ttgctgtttg ttaaagattt   125940
cactaatgta acgggggttg aattcatagt tacagaaacc atgccgtgta gaattatacc   126000
aaaaaataat cacgcggtta tttcagtcgt gactaatcat aagttttata atgggttaag   126060
tttataaagg gttaaccttt gtcacatcga tcgcgtattt gggatcagat gccaaattgt   126120
```

```
taaataatct gatgaaaaaa taataaatat aattcagatc atcgctagac atgacattat  126180
tgtcctctat agcgatagtc gcgtgccgtc tacatgcagg acatggaaga gtgctgacta  126240
tagtatatag ttttcgttta cacgcttcta tgttgccgtc taaacccgct tgcgaaagta  126300
ctataaaaat aatggtccat acggctcttc cccaatgttt gggattcatt taaatgaaaa  126360
tatatttcta aattctataa atggatgttc ggtgcattaa ttggtttgaa agtcacggtg  126420
aaaacagatt tttatatctg aaatccagat gtcgaaatgg cgagaccgta tttatacgat  126480
ttcctcatta cttttattac gtagttacgg acgaaatata tcagtcattg tctcctcctc  126540
catttaatgc gaggccgttg ggaaagatga gaactataga cattgacgag acaataagtt  126600
ataatctaga tattaaagat agaaaatgct ccgtcgcaga tatgtggttg atagaagagc  126660
caaagaaacg cagcatacaa aatgccacca tggatgaatt tctcaatatt agttggtttt  126720
atatttctaa cgggatatct ccagacggat gttactcgtt ggacgagcaa tatttgacaa  126780
agattaacaa tggatgttat cattgtgacg atccacgtaa ctgtttcgct aaaaaaatac  126840
ctagattcga tatcccaaga tcgtacttat ttctagatat agagtgtcac ttcgataaga  126900
agtttccttc tgtatttatt aacccaatct cgcatacaag ttactgttat atcgatttaa  126960
gtggtaaacg attattgttt acgctcatta atgaagagat gttaacggaa caggaaatac  127020
aagaagccgt cgatagagga tgtttgagga tacagtcact aatggaaatg gattacgaac  127080
gagaactagt tctatgttct gaaatagttt tgttacgaat agctaaacaa ttgttggaac  127140
taacgttcga ctacgtcgtt acctttaacg gacataactt tgatctgaga tatattacta  127200
atcgtctaga gttattaaca ggagagaaga ttatctttag atctccggac aaaaaggaag  127260
ctgtacatct ctgtatttat gagagaaatc agtctagtca taagggagta ggcggcatgg  127320
ccaatactac gtttcacgtt aataacaata atggaactat attttcgat ctatattcat  127380
tcattcaaaa atctgaaaaa ttggattcgt acaaattgga ttctatatcc aagaacgcgt  127440
tcagttgcat gggtaaagta ttaaatagag gagttagaga aatgacgttc atcggtgacg  127500
atactacgga cgcgaaaggc aaagccgctg catttgcaaa ggtttaacc acaggtaatt  127560
atgtgactgt tgatgaggat attatatgta aagtaattcg taaagatatt tgggaaaatg  127620
gatttaaagt cgtactatca tgtcctactt tacctaatga tacatataaa ttatcttcg  127680
gaaaggatga cgttgattta gctcagatgt ataaggatta taatctaaac atagcttag  127740
atatggctag atactgtatt catgatgctt gtttgtgtca gtatttgtgg gagtattatg  127800
gagtagaaac aaaaacagac gcgggtgcgt caacatatgt gcttcctcaa tccatggtat  127860
tcgaatatag agcgagtaca gtcatcaagg gtccactgtt aaagctattg ttggaaacta  127920
aaactatctt agttagatca gaaacaaaac aaaagtttcc ttatgaaggc ggtaaggtat  127980
ttgctccaaa acaaaaaatg tttagtaata atgtattaat ctttgattat aacagtctgt  128040
atcctaatgt gtgtatcttt ggaaatctat ctccggaaac attagtcggt gtcgttgtta  128100
gtaccaatag attggaagaa gaaataaata tcagctctt gcttcagaaa tatccacctc  128160
ctagatatat tacggttcat tgtgaaccta gactaccgaa cctcatctct gaaatagcaa  128220
ttttcgatag atcgatagaa ggaaccattc ctagactatt aagaacattt ttggcagaga  128280
gagccagata taaaaagatg ctaaaacagg ctaccagttc aactgaaaag gccatctatg  128340
attccatgca atatacgtac aagatagtag ccaactcagt atatggtctg atgggatta  128400
gaaatagtgc tctatactca tacgcttcgg ctaagagttg cacatccata ggacgtagaa  128460
```

```
tgatcttgta tctagaatcg gtactaaatg gagcagagtt atctaacggt atgttacggt    128520
ttgccaatcc attaagtaat ccattttata tggacgatag agatattaat ccgattgtga    128580
aaacatcgtt gcctatagat tacagatttc gttttcgtag cgtgtatgga gataccgact    128640
ccgtgtttac agagatagac agtcaagatg tcgataagtc tatagaaata gcgaaagagt    128700
tagaacgact gattaataat agagtattgt ttaataattt taaaatagag tttgaggcgg    128760
tatataagaa tctgattatg caatcgaaga agaaatatac aacgatgaaa tactcagcat    128820
cgtcgaattc aaaatctgta cctgagagaa ttaataaagg tactagtgaa actagaagag    128880
atgtttccaa gttcataag aatatgatta agacatacaa gaccagactg tctgagatgt    128940
tgtctgaagg acggatgaat tctaatcagg tatgtataga tattctccgt tctttagaaa    129000
cagatttacg atccgaattt gatagtagat cgtctcctct agaattattt atgttgagtc    129060
gaatgcatca ctcaaattat aaatccgcag ataaccctaa tatgtatttg gttactgaat    129120
ataataaaaa taatccagaa actatagaac ttggagaacg atattatttt gcatatattt    129180
gtccggctaa tgtaccatgg accaaaaaac ttgtaaatat taaaacatat gaaacaatta    129240
tcgatagaag ttttaaactc ggcagtgatc aaagaatatt ttacgaagtt tactttaaac    129300
gattgacgtc cgaaatagtc aatctattgg ataataaagt tttatgcatc tcattctttg    129360
aaagaatgtt tggttcaaaa cctacatttt acgaagcata aataattta caacagttgt    129420 acgtcgctct ttgttagatt cagtttatcc attagatatt ctacggctgg agtaattttt    129480
gtagtaattg aatacccagg tacgtaaaac aataaaaaca ttaataccgg atcatacttg    129540
gtaaagtaca atatagtact aatattagct aatgtctcat aatcggatgg acttcttgct    129600
ctactaagat tagggtgatc tatatctttg atacttattg gaacgggacc ggtaaatata    129660
taattctctt tgagacgact aaacaaaggc ttatagtctc ctgtttgatg catataccta    129720
gccaacgcca ggtgtttggc attatctgta tagacgtatc tgaataatgt gtgtttagta    129780
atatcaaact gagtattttt aaaccagaac aagatattat agattggaat ggaagtcagt    129840
aacaaaaaac taataaactc gtttgttgga agggcagaaa actttcgaag atatgatacg    129900
tatctaccag agaacgatcc attagcaatg aattcagtat ttacttttc ttcatatacg    129960 ggaataggac ctttatatag agacatgaga aactcgaact ttttaagtaa tcccaacgaa    130020
atgggataat agtcacttgc atcaagtttt gcgtatctac tactccaaat tgcagtttct    130080
ggtatccatc catacgcgta attatcaaat agatatgtgt ttttcattaa cggtctactt    130140
agacctctac taaaaatgt ttcttgatct agaattcttc tttgtgcatt tttgtacacg    130200
tcgtcaaaac gcggaacggt ggcagccata atatttatat cctaccgctt tttatcaact    130260
atgttatgtc ttttagttag gttaatattc taataagatg caggtaatac atcaggttaa    130320
agtattagaa tgggattata cttatatatt tagtttatct ttcatcagat aactaaaaaa    130380
tgtataaaac agacgcgtta cattgcctat gctacatgag ttccatgtgc ggagattgtt    130440
aaagtttagg gtagagagtt gttctagcat ccattcattg tctttacatc cgttatatgt    130500
aattatgtca cccatggaca ttataggttt taatagtact tcagatactg gaataagata    130560
ttgttcgtat atgtgtttga taatcatttg ttgcgtttct ggagaacttt tctctgcatg    130620
atttttacat agctttacaa actcgtgatc acttttata atgagagatc tatagtcttc    130680
gtatctgtta cgaaaatcaa tatattcagg attattttct gaatcacttg attcgtcact    130740
aatatacata actatatgat caacaatttt ttccaaaatc atttctgcat tttctttatt    130800
cattaatttg gtgggagtct gaattgttgc agcagttccc atttatcaaa aatgtgtgat    130860
```

```
aattatatct atgtatatac aaattattaa taatatattt ggtctgttct atgatctacc   130920
gtgtcttatc aattgaagta tatatttctt atccgtcttg gttagatgga tgcttttatc   130980
caagaattct tctacatgat atagattatc tctcaaaaac ctttgaaata agacgatgat   131040
ggaaatatta taactagcta aaatagtttt gattagcgat ggaagaatac tagggttttt   131100
atctgtagaa aatcgaacga atgcggatac atcctccaca gacttaagat ggtttatcat   131160
tttaactaac aagtctcctt tataatcatc taacacaaga cctagacgag ccaattgtcc   131220
gtctaaataa tattttaaaa tgttttttgct aaacaagttc agccgtctac tcttggattt   131280
tatagatgac agtttcttta gtattccgtt ctctatgacc atgggatccg actcgtgcaa   131340
aaacaggtat gtattgtatt ccttaacata atacgacgta tcctcgttaa agatttgaca   131400
cttcttcata tcatccattg tatctaatgt gatatcgttc acctcataaa ttatattaga   131460
tatataactg ttattaatat ctaactcatc aaatcgttta atgtccgcag cactcgtaga   131520
gaataaagac ataattcgtt cattatcgaa atattcggga tctatttgaa caacaactct   131580
gaataagtcc tcgttaaacg ttctatcact aataaatgta ttaccgttaa taaaattagc   131640
tttataaaaa ctaataaaat attttttcca atcgtcgttt tttgcatcaa taatagatag   131700
gatatctcca ggaatatcat atatgatttc tagcagaagt tctctgatat cttttttcagg   131760 ctcaaagata taaactaact taagcatgtt tttattaacg cgtccttgtt ttatctcaga   131820
gtatatataa ctaagaattt tatcatacat ggtaatggcg tgtctattaa gaacaatatc   131880
cgcatcatta gctatacttt cgtttaacca cacccaatag ctagtcttat ctccgggaaa   131940
gatataatct ctaaacgttt ctgttagatt gctatggact attctaccag tttgttgaaa   132000
tagagtgtat atatcttgtc tatcattatc cgcaaactct atgcctgtat ctttcttgct   132060
taggtaagcc caaataagta atcttataac acttaattt ttaacaactt tgaagtctgt   132120
tttcttaaac agttttaaaa aaatgatttc catatctttg atgggttccc ctccgtgaaa   132180
taatggatta agaactaagt cataaatttac gcctataagt tctcctaatt cgtccatgta   132240
ttcggcaacc tctaaaaatt tttcatcttg tgttagttta tgcacggttt ccttgtacga   132300
ttgtattgcg ttactaaacg ataaataatt cttagtcaat gctttaacgt acaacgtggg   132360
tgcatcaaat gcgtgtcgta aaaccgcttc gtacactta caacatcgta ccatatgtat   132420
gaaaacaaaa aaattggtat tagctaatac atccttagta ataacgtgtt gaggaaaatt   132480
gctaactaga tacttgagag ctagtacatg attgagggta aaattgttta ctttacttaa   132540
tgtatcatcc tttaaaaaat ctatattatt ttctactgtg tatataagat actttctacg   132600
aataaaatcc atttttatag aagagagtta tctatgatac tacactctta ttctaataat   132660 tattttact attttatcac taataactat ttatactatc cattattaat ttaacaattt   132720
gaattagtat tggagaaaga tgaaatgcct attcactaac aaagtcaatg cactcttgaa   132780 gattttacc aataatatgt agcggattct caaagtattt attaccatt tctttacaca   132840 gtatcttagc cactggccta cgaacaggca tacatggttc aactatatca tgaacaatgt   132900
ttaattttag tgtatccaat ccaataaatc cattttctac atcatcatcg tatctgtacg   132960
ctttgtattc tccactcttg aacaaatctc taaacagtat cttcaacact ttttccacca   133020
attcctggga tgtcacacat tgttctacca tctgtttgat aaagagggta tcttcttcag   133080
attttccctt gattctatac atgggttta ggttatacct tgcatctatt gtatatttat   133140
cagattcagc tatcaacatt ttatcaactt gtgttccaat tattctccat ttattagatc   133200
```

```
tgcattcatt attatagaat ctttcttcca ctaatattct aataagatta agtttgaaag  133260
gagagaagat cttgtgtttg attttactca ttggatgcat tctataacga atgaatctat  133320
gatcatctcc aaacaaattg ggaaacatgt aaagcagcag agcatatacc atcttactcg  133380
gattctgtga tgctttgccg atggctgaaa tgtccgagaa tagtttataa gttttctgat  133440
tatttggaat agatggtgct atatcttcta gagtagtagt cctaatcatt ctcttaaatt  133500
ttatgtatcc tagtttcaat gtctcgtaat gagtttgtgc tgctcttatt gtctgattta  133560
tttcttttac cattttggct ctattctgaa actttatcct cttcttatcc atttttattg  133620
ttgactccgc actatcgatt tgatactttc ttttcagagt aaagctatcg tcattgatca  133680
tcggacactg acttccactc attatgaaat tgtagccgta taaccacaat acaattatta  133740
acatatatat tcacttttgt taatatcaac ataataatga aaaatataaa atgaacaaag  133800
ttaatacata agtgttataa atggaaaatg tatacattag tagttactca tccaatgaac  133860
aaacatcaat ggcggtagcc gctactgata tccgagaatt actatcacaa tatgtggatg  133920
atgccaactt ggaagactta atagaatggg ccatggaaaa atcatcaaag tactacatca  133980
agaatatagg taatacaaaa tctaatatcg aagaaactaa attcgaatca agaataata  134040 ttggtataga atactcaaag gattccagaa acaaactatc gtatagaaat aaaccgtcta  134100
ttgccacaaa tttggaatat aaaacactat gtgatatgat taagggtact agcggcaccg  134160
aaaaagaatt ccttcgctat ctcttattcg gtataaaatg cattaagaaa ggagtagaat  134220
acaatataga taaaataaag gatgtgagtt acaacgatta ttttaacgtt ctcgacgaga  134280
aatacaatac accgtgtcct aactgtaaaa gtaggaatac tacgccgatg atgattcaaa  134340
ctagagccgc tgacgaacct ccactagtta gacatgcgtg tagagattgc aaacaacact  134400
ttaagcctcc caaatttaga gcatttcgca atcttaatgt tacaacgcaa tcgtacatg  134460 aaaacaagga ataacagag attcttccag ataataatcc atctcctcca gaatctccag  134520
aaccagcatc acctatagat gacggggttaa tcagatccac attcgataga acgacgaac  134580 caccagagga tgatgaataa aaaaatgata aaataaatta gttttattgc tggttgtgtt  134640
agttctctct aaaaatgtct aagatctata ttgacgagcg ttctgacgca gagattgtgt  134700
gtgcggctat taaaaacatt ggaatcgaag gagctactgc tgcacaacta actagacaac  134760
ttaatatgga gaagcgagaa gttaataaag ctctgtacga tcttcaacgt agtgctatgg  134820
tgtacagctc cgacgatatt cctcctcgtt ggtttatgac aacggaggcg gataagccgg  134880
atgctgatgt tatggctgac gccataatag atgatgtatc ccgcgaaaaa tcaatgagag  134940
aggatcataa gtcttttgat gatgttattc cggctaaaaa aattattgat tggaaagatg  135000
ctaaccctgt caccattatt aatgagtact gccaaataac taagagagat tggtcttttc  135060
gtattgaatc agtgggcct agtaactctc ctacatttta tgcctgtgta gatatcgacg  135120
gaagagtatt cgataaggca gatggaaaat ctaaacgaga tgctaaaaat aatgcagcta  135180
aattggcagt agataaactt cttggttacg tcatcattag attctgattc tagttatcaa  135240
taacagttag tagtttagtt atacattgaa tcatacatat taattttttt attgagatag  135300
attaaaaaat acaaattgta gtactattaa cgcgactagt atattctcta aagatgtat  135360 ctgtcacaga tattcgtaga gcgtttctag acaatgaatg ccatactatc acaaaagcgt  135420
ttggatatct gcacgaggac aaggctatcg cattaattaa aataggattt catcccactt  135480
atctacccaa agtcctttat aataatgttg tagaattcgt tccagaaaaa ctatatctgt  135540
ttaagccaag aactgtagct ccattggatt tgatatctac tataacaaaa ttaaagaacg  135600
```

```
tggacaaatt tgcctcacac ataaattatc acaagaatag tatattgata acaggagaca  135660
agtctctaat tgttaaatgt atgccttaca tgattatttc agatgatgat atacgattca  135720
taagagaaca gtttgttggt acaaattcta ttgagtatat tctatccttc atcaacaagg  135780
aaagcatata tagaatgagt taccaatttt cagagaatga aatagtcact atcatcaata  135840
gagatcattt catgtatgaa ccaatatatg aacatcaggt cttagattct gactttctta  135900
aaactatgtt agatagatac ggaatagttc ccattaattc tggtataata gatgaattat  135960
gtccagaagc tataatagag atattaatgg cagtagttcg tcctagggac gctatccgtt  136020
tcttagatat agtgaataag aatcaattga cagaagatag tgtcaaaaac tatatcatta  136080
atgatatcag aagaggtaaa atagattatt atattccata cgttgaagat tttttagaag  136140
atagaactga agacttggga atatatgcga atatattttt tgaggatgct atagatatta  136200
cgaaactaga catcacaaag acagagttgg aacatatatc gaaatacatg aattattaca  136260
ctacttatat agatcacata gttaacatca tcttacaaaa taattatata gatatcttgg  136320
catctataat agattacgtg caagacgtat taacagaaga attatgtatt agaatagttt  136380
gcgaatcaac aaaccctgtt cccgttacat ctcttcctat acattctacg ttagtaatgg  136440
ttatgtgtat acaaatgaaa tatgtcgata tagttgaatt cttagacgag atcgacatcg  136500
atactttaat agaaaaagga gcagatccga taaccgaata cacatttaca acaagatggt  136560
acaataaaca caatgatttg atcactcttt acattaagaa atatggattc tgtccaatga  136620
tgatgaaacg gttaatgttc gaatatccat tgactaaaga agccagtgat catttactta  136680
aaaccatgga tgaaaacagg ggagctatta tgttttttcc gcgtactatt tgcacacttc  136740
cttatctatt atgttgtaat tataaactaa ttcaaaaacc tattccattc aaagaagaaa  136800
atcgtaacat cgtatataag aaaaccaaca gagtattatg ctttgactcg ttggagaact  136860
ctgcgtttaa aagcctcatt aaaatagatt ctattccagg attaaaaact tataacatga  136920
aagacattac atacgaaaag tctaataata taatttgtgt taggtttata cctcaagaat  136980
caattcataa tgaagagcga agaataaaat tacagttatt cgacattgct agattggcat  137040
cctatggact atattatatt ccctctagat atttatcatc gtggacacca gtagtgaaca  137100
tgatagaggg aagagagtac actaatccac aaaaaataga atgtctagtt attttggatt  137160
tattttcaga ggaattcata gaatatcaaa atctgggcaa tgcggtatct aataaatatg  137220
aactggaata tactatatct aattatcaag ctgccataaa ctgcctaatg agcacgttat  137280
taatatatct agttctagga tcaatcagat cgatatcaaa aactgaagat tttgtattat  137340
ctatattaaa tatcttctat aaaggactga aaattaatga attactttct gaaccagtat  137400
caggagtttg tatcgaatta aataaaataa agatagagc gagctctgga gacagtagtt  137460
ttatatttct taagaaaaac gagttatcaa aaactctatc gctctgtgaa aaagtttgtg  137520
ttgagaccat attagacaat aatcagagtt ttaaatcctc aaaatgaata ggaatcctga  137580
tcagaatact tttcctaata ttacattaaa gattatagaa acctatttag gcagagtacc  137640
tagtgtgaac gaatatcata tgttaaaatt acaagctaga atattcaga aaataactgt  137700 ttttaacaaa gacatatttg tatctttagt aaaaaagaat aaaaaaagat tttttccga  137760 tgttgataca tctgcatcag aaataaaaga tcgtatactt agctactttt ctaaacagac  137820
tcaaacatat aatataggta aattatttac gattatagaa ctacaatctg tattagtgac  137880
cacatacacg gacatattag gagttcttac tattaaagct ccaaatgtaa tttcatctaa  137940
```

```
aatttcttat aatgtaacat caatggaaga attggcaaga gatatgctaa attctatgaa   138000
cgtcgcagta atagacaagg caaaagtaat gggacgtcat aatgtatctt ccctagtcaa   138060
aaatgttaat aagttgatgg aagaatatct tagacgccat aataaaagtt gtatatgtta   138120
cggatcatat tctctatatc taattaatcc aaatatacgg tacggcgata tagatattct   138180
tcaaactaat tcgaggactt ttcttataga tttggcattt ctaataaaat ttattacggg   138240
aaataatatt atattaagta aaatcccata tcttagaaac tatatggtga taaaagatga   138300
aaacgataat catatcattg atagttttaa tattcgccag gataccatga acgtagttcc   138360
taaaatcttt atagataata tctatatagt ggatccgacg tttcaactat tgaacatgat   138420
aaaaatgttt tctcaaatag atagattgga agatctatcc aaagatcctg aaaagtttaa   138480
tgcgcgtatg gcaaccatgc tagaatacgt tagatataca catggtatag tctttgatgg   138540
taagcgtaat aatatgccga tgaaatgtat catcgatgaa aataatcgca tagttactgt   138600
tactactaaa gactatttta gctttaaaaa atgtctagtg tatctagatg aaaatgtgtt   138660
atcgagtgat atattagatc ttaacgccga cacatcgtgt gatttcgaga gtgttacaaa   138720
ttctgtatat ctaattcatg ataatatcat gtatacatat ttctcaaata ctattctcct   138780
tagtgataag gggaaggtac atgaaataag tgccagaggt ttatgtgcac atatattgtt   138840
gtatcagatg ctgacatctg gagaatacaa acaatgttta tcggatctct taaattcgat   138900
gatgaataga gataaaatac ctatctattc acatactgaa agagataaaa aacctggacg   138960
acacggattt attaatatcg aaaaggatat aattgtattt taggacaaaa gtctagaagc   139020
tacattatcg cgattagccg cgaacatatt ttgtagcatg tccgtcctca taaacggaac   139080
ttgttttcct gggttattca ttctctcgca tctggaaggg gacgaaggtc ttctctcaca   139140
cgcgggtgat gagggtttat ctactttgag tacgcaggaa gctttacttc cttcgcattc   139200
tacagttcta acatcgcata ctttaacggc ttttagaacc agatatcttc cttctttggt   139260
attgatataa aacggagtat gagcagatgc aaaatgagaa ttcatttata gcatagaaaa   139320
aaaacaaaat gaaattctac tatattttta catatatata ttctaaatat gaaagtggtg   139380
attgtgacta gcgtagcatc gcttctagac gcatctattc agtttcaaaa aacggcatgt   139440
aggcatcact gtaattacct atctatgcaa gtagttaaag agatagaaga atttggtact   139500
atcaatgaaa aaaatttgga atttgacact tggaaagacg ttatacaaaa cgatgaaata   139560
gatgcattag tattttatag agtaaaacaa attagtattt ctacgggtgt tctatataaa   139620
tctatgatgc gcaatagaac aaaacctatt tccatgtact ttgtacgtga ttgtctggca   139680
tttgatggag atcctccgtc ttttagaatg acgtcttgca atatcaacgc atacaatcgt   139740
agtaagatta aagatttaat aatcctaatg aaatatgaaaa catgtaataa aaaaattatc   139800
ggtgagttta taatagacaa ttttggaagc gtcgatgcat tactatcgat agttaattcc   139860
aatgttacgt ggattacatc agttataaat aatagtaacg gcaggggtat taatatcagg   139920
gtatcaaata ataaaatgtt aactataact agttttcgac gattcgtcaa taaacttaaa   139980
atgtacaaaa ctactaaatg cgcttctcaa ttggataatc tatgtaccga gatgaacaaa   140040
atggatatta tagacaaaaa atgaaacgta atgaggagta ttgcggggct acataaatta   140100
aaaatggaaa ttttttaatgt agaagaattg ataaatatga aaccttttaa gaatatgaat   140160
aaaataacaa ttaatcaaaa tgataattgt atattagcaa atcgatgctt tgttaaaata   140220
gatactccta gatacatacc atcgacatcc attagcagtt ctaatatcat cagaatacgg   140280
aatcatgatt ttacattatc tgaattattg tattcaccgt ttcattttca acagcctcag   140340
```

```
tttcaatatc tccttcctgg gtttgtatta acgtgtattg ataaagtttc gaaacagcaa  140400
aaaaaatgta aatattgtat ctctaatcgt ggagatgatg atagtttaag cattaatcta  140460
tttattccga ctattaacaa gtctatatat attattatcg gtttacggat gaaaaatttt  140520
tggaagccta aattcgaaat agaataatgt ttttatatta tacatgttct aaaagaataa  140580
tcgatacagt ttaagtgaaa gctagagagg ggttttaaa tggtcatcgg tttagtcata  140640
ttcgtgtctg tggcggccgc catcgtcggt gtgttgtcta acgtattgga catgtttatg  140700
tacgtagaag aaaataatga agaggatgct agaatcaagg aggagcaaga actactgttg  140760
ctatattgat acataattga aaatctacca acttaaatac accgcctata aatttacaat  140820
gaaacacaga ttgtattctg aaggattgag tattagtaat gatttaaact cgataatcgg  140880
tcaacaatct acaatggata cggatataga aatagacgaa gatgacatca tggaacttct  140940
taatatattg actgagttag gttgtgatgt cgactttgat gaaaatttta gcgatatagc  141000
cgatgatatt ctagaatcgt tgatagaaca ggatgtataa gttttatgt taactaaatg  141060
tggccatttg caccggtacc tgcgggagca aaatgtaggc tggtagaaac actaccagaa  141120
aatatggatt ttagatccga tcatttaaca acatttgaat gttttaacga aattatcact  141180
ctagctaaga aatatatata catagcatct ttttgttgta atcctctgag tacgactagg  141240
ggagcgctta ttttgataa actaaaagag gcatctgaaa aagggattaa aataatagtt  141300
ttgctagatg aacgagggaa aagaaatctg ggagagctac aaagtcactg cccggatata  141360
aattttataa ccgttaatat agataaaaaa aataatgtgg gactactact cggttgtttt  141420
tgggtgtcag ataatgaaag atgttatgta ggaaacgcgt catttactgg aggatctata  141480
catacgatta aaacgttagg tgtatattct gattatcccc cgctggccac agatcttcgt  141540
agaagatttg atacttttaa agcctttaat agcgcaaaaa attcatggtt gaatttatgc  141600
tctgcggctt gttgtctgcc agttagcact gcgtatcata ttaagaatcc tataggtgga  141660
gtgttctta ctgattctcc ggaacaccta ttgggatatt ctagagatct agacactgat  141720
gtagttattg ataaactcaa gtcggctaag actagtatag atattgaaca tttggccata  141780
gttcccacta cacgtgtcga cggtaatagc tactattggc ccgacattta caactccatt  141840
atagaagcag ccattaatag aggagttaag atcagacttc tagttggtaa ttgggataag  141900
aacgacgtat attctatggc aaccgccaga agtctagacg cgttgtgtgt tcaaaatgat  141960
ctatctgtga aggttttcac tattcagaat aatacaaaat tgttgatagt cgacgacgaa  142020
tatgttcata tcacttcggc aaatttcgac ggaacccatt accaaaatca cggattcgtc  142080
agttttaata gtatagataa acagcttgta agcgaggcta aaaaaatatt tgagagagat  142140
tgggtatcta gccacagtaa atcgttaaaa atttaaaaaa tagaaacgta tagaacgcca  142200
tcatgttaaa caggatacaa accttgatga aaacagctaa caattatgaa actattgaga  142260
tattgcgtaa ctatttaaga ctgtatatca ttttggcacg aaatgaagaa ggtcatggta  142320
tactaatata cgatgataac atagatagtg ttatgtcgat gatgaatatt acaatattag  142380
aagttatagg attgacgact cattgcacaa aattaagatc atcgcctcca attcctatgt  142440
ctagattgtt tatggacgaa atagatcatg agtcatatta ttctccaaaa acttcagatt  142500
atccgttgat cgatattata cgaaagcgtt ctcacgaaca gggagatata gcactggctt  142560
tagaacgata cggtattgag aatacagatt ccatatcaga aattaatgaa tggttgtcgt  142620
caaaaggttt agcatgttat agatttgtaa aatttaacga ttataggaaa cagatgtatc  142680
```

-continued

```
gtaagttctc taggtgtact atagttgaca gtatgataat agggcatata ggtcatcatt    142740
atatttggat taaaaattta gaaacatata cgcgtcccga aattgatgtg ttaccgtttg    142800
atattaaata catatctaga gatgaattgt gggcgcgaat tcttcctcg ttagatcaaa     142860 cacatataaa aaccatcgcc gtatcagttt atggagctat tactgataat ggaccaatac   142920
catatatgat atccacgtat ccgggtaata cctttgttaa ctttaacagt gtaaaaaatc   142980
taattttaaa tttcttagat tggattaaag atattatgac tagtacacga actatcattc   143040
tagtaggtta catga                                                    143055
```

<210> SEQ ID NO 70
<211> LENGTH: 31690
<212> TYPE: DNA
<213> ORGANISM: Artificial Sequence
<220> FEATURE:
<223> OTHER INFORMATION: viral construct

<400> SEQUENCE: 70

```
tggctggaat cattaacaag aaataaaaaa acaatttcaa agttaaacat aactggtatt       60
acgatttcca tttctttgtt catactttat taaaaacata tccagaaatc gaaaaagata     120
tcgaatttag tacggcattg gaagaattca tcatgtgtac caaaacagac tgtgataaat     180
atagattaaa ggtttccatt cttcacccaa ttagtttctt ggaaaaattt attatgagag     240
acattttctc agactggata aatggcggaa actaaagagt ttaaaacttt gtataatctt     300
tttatagata gttatttaca aaaattagct caacattcta tccctactaa tgtcacttgt     360
gctattcata taggagaggt tataggacag tttaaaaatt gcgcgctccg aataactaac     420
aaatgcatga gtaattctcg acttagtttc acactcatgg ttgaatcatt tattgaagtg     480
atttcattgc ttccggaaaa ggatagaaga gctatcgctg aggaaatagg aatagatcta     540
gacgatgtac ctagtgcggt atccaagcta gaaaagaact gtaatgcgta tgcggaggtt     600
aataatatta tagatataca gaaattggat atcggagaat gttcggctcc gcccggtcaa     660
catatgcttt tacagatagt taatacagga tccgcggaag caaattgtgg tttacagaca     720
attgttaagt cccttaaataa aatatacgtt ccacctatta tcgaaaaccg attgccgtat     780
tacgatccgt ggtttctagt gggtgtagca attattctag ttattttac tgtagctatt     840 tgttctatta gacgaaatct ggctcttaaa tacagatacg gaacgttttt atacgtttaa     900
ttaataaaaa aatttaatta caaggtataa aatagtactc catctacgca atcgcgataa     960 tgagggatc taaacgcaga cacgacagtc ggcgactaca acaagaacag gagcagcctc    1020
gtccacgtac accgccatca tatgaagaaa ttgcaaaata tggacactca tttaacgtga    1080
aaagatttac gaatgaagaa atgtgtctta agaatgatta tccacgaatt atatcatata    1140
atcctccacc aaaatagagt atatatatat catcatttca tgatgtatac tactgacata    1200
gtttcaatgt gaacttttca ctttcttgcc ggttatgaag aatatttta ttttaatggt    1260 cattactaat cgtatattat aattgaaaat ggattagttt aatatgacgc tcgtcatggg    1320
atcctgctgt ggtagattct gtgacgctaa gaataagaat aagaaggaag atgtagaaga    1380
gggaagagaa ggatgttaca attataagaa ccttaatgat ctggatgaat ccgaagcacg    1440
tgtagaattt ggaccattat atatgataaa tgaagaaaaa tcagacataa atacattgga    1500
tataaaaaga agatatagac acacgataga gtctgtatat ttctaaaagt ttttataaaa    1560
aatgagtaaa atactcacgt ttgttaaaaa taagataatt gacttgatta ataatgacca    1620
aattaaatat tctagagtta taatgataga agagtccgat agtctttac cggttgatga    1680
```

```
ggtgcatgct aaccacggat ttgactgtgt ggagatgata gatgaaaata taagcaatga      1740
gaatatcgaa cagtataaaa ccgaatcttt ttttacaata aattgaaatc aaaacattta      1800
ttaaaccgca tcaagatggg tacgaacggc gttagagtat ttgtcatttt atatttgttg      1860
gctgtatgcg gatgtatcga atacgacgta gacgataatg tacatatttg tacccacact      1920
aacgtgtcac atattaatca cactagttgg tattataatg ataaggttat agcgctagcc      1980
accgaggata aaacttctgg ttatatatca tcattcataa aacgcgttaa tatctcatta      2040
acttgtttaa atatatcgag tttgaggtac gaagattctg gtacatacaa aggagtatcg      2100
catctaaaag atggagtcat cgttacgact actatgaata tatctgtaaa ggctaatatc      2160
attgacttga ctggtagagt gcgttatcta accagaaatt attgcgaagt taaaatacga      2220
tgcgaaataa catcttttcg cgcttaatggt tctactacac caccacatat gatattagga      2280
acagtagata aatggaaata tcttccattt cctacagatg attatagata cgtaggggaa      2340
ctgaaaagat atatatctgg aaacccatat ccaacagagt cgctagcgtt agaaattagc      2400
tcgacgttta atcggtttac tatcgttaaa aatttgaacg atgacgagtt ttcttgttat      2460
ctgtttccat aaaatgttga acgcgcgcca tatttgtgaa tccgaatggg aggctttaaa      2520
taataataac gataattcat cctccatgcc cgcttcccac aacaatctcg caaacgattt      2580
atctagtatg atgtcacaat tacaaaatga taataacgat aatttaatta tgatagtact      2640
aataacaatg ctatcaataa tacttgtaat tattgtagtg attgcggcga tatcgatgta      2700
caaaagatcc aagtacaggc atatagataa ctgaaaaaaa atttattgtt attgttaatt      2760
tagttatgga acccatcctt gcaccaaatc caaatagatt tgttatttc ccaatccaat        2820 atcatgacat ctggaacatg tataaaaagg cagaggcatc attttggaca gtggaagaag      2880
tagatatatc taaagatatc aatgattgga ataaactaac accagacgaa aaatattta       2940 taaaacatgt attggcgttt tttgcagcca gtgacggaat agtgaatgaa atttggcgg       3000 aacgattttg tacagaagta cagattaccg aggctagatg tttctacgga tttcagatgg      3060
ccattgaaaa cattcattcg gaatgtata gtcttttgat cgatacttat gttaaagata       3120
gtaatgaaaa aaactatctc tttaatgcca tagaaacgat gccttgtgta aaaagaagg       3180 ccgattgggc tcaaaagtgg atacatgaca gcgccggtta tggagagaga cttattgcct      3240
ttgctgcagt agaaggaatc ttcttttccg gatcattcgc ttccatattt tggcttaaaa      3300
agcgtggcct aatgcccgga ctcacgtttt ccaacgaatt gattagtaga gacgagggtc      3360
tacactgcga cttcgcatgt ttgatgttta aacatttatt gcatccaccg agtgaagaaa      3420
ccgttagatc tattataaca gatgcggtat ccattgaaca agaattctt actgcggctc       3480 ttccagttaa acttatagga atgaattgtg aaatgatgaa aacatatata gaattcgtcg      3540
cggatagatt gatttctgaa ttgggattta aaaaaattta taatgttacc aatccgtttg      3600
atttcatgga aaatatatca ttagaaggta aaactaattt tttcgaaaaa cgtgtgggtg      3660
aataccaaaa aatgggagtt atgtctcaag aagataatca tttttcttta gatgttgact      3720
tttaaagaaa cataaatgcc gatatttgtc aatactgtgt actgtaagaa tatattagca      3780
ttgtctatga ctaagaaatt caaaacaatt attgatgcca taggaggcaa tataaagtc        3840 aattctacga tattgaaaaa gttatctcct tactttcgca cacatttacg tcaaaaatac      3900
acgaaaaata aagatccagt tacgagggtt tgtctagacc ttgacattca cagtctaact      3960
tctatagtta tttactcata tactggaaag gtatatatag atagtcataa cgtcgtcaat      4020
```

-continued

```
ttattacgtg cttctatatt aacctctgta gaatttatca tctacacttg tataaacttt     4080
atcctacgag attttagaaa ggaatattgt gtcgagtgtt acatgatggg tatagaatac     4140
ggactatcca atctcttatg tcatactaaa aactttattg ccaaacactt tttggaactg     4200
gaagatgaca tcatagacaa ttttgattat ctatctatga aacttattct agaaagcgat     4260
gaactaaatg ttccagatga ggattttgtc attaagtggt atataaagcg aagaaataaa     4320
ttaggaaatc tgctactcct tatcaaaaat gtaatcaggt caaattatct ttctcccaga     4380
ggtataaata atgtaaaatg gatactagac tgtaccaaaa tatttcattg tgataaacaa     4440
ccacgcaaat catacaagta tccattcata gagtatccta tgaacatgga tcaaattata     4500
gatatattcc atatgtgtac aagtactcat gttggagaag tagtatatct catcggtgga     4560
tggatgaaca atgaaataca taacaatgct atagctgtaa attatatatc aaacaattgg     4620
attccaattc ctccgatgaa tagccccaga ctgtatgcta gcgggatacc cgctaacaat     4680
aaattatacg tagtaggagg tctaccaaat cccacatctg ttgagcgttg gttccacggg     4740
gatgctgctt gggttaatat gccgagtctt ctgaaaccta gatgtaatcc agcagtggca     4800
tccataaaca atgttatata cgtaatggga ggacattctg aaactgatac aactacagaa     4860
tatttgctac ccaatcatga tcagtggcag tttggaccat ccacttatta tcctcattat     4920
aaatcatgcg cgttagtgtt cggtagaagg ttattcttgg ttggtagaaa tgcggaattt     4980
tattgtgaat ccagcaatac atggactctg atagatgatc ctatttatcc gagggataat     5040
ccagaattga tcatagtgga taataaactg ctattgatag gaggatttta tcgtgaatcg     5100
tatatagata ctatagaagt gtacaatcat cacacttatt catggaatat atgggatggt     5160
aaataatttt gaaataaaat attagtttta tgttcaacat gaatattaac tcaccagtta     5220
gatttgttaa ggaaactaac agagctaaat ctcctactag gcaatcgccg ggtgctgccg     5280
gatatgattt gtatagcgct tacgattata ctatccctcc aggagaaaga cagttaatta     5340
agacagatat tagtatgtcc atgcctaaga tttgctatgg tagaatagct cctaggtctg     5400
gtctgtcact aaaaggcatt gatataggag gtggtgtaat agacgaagat tataggggaa     5460
acataggagt cattcttatt aataatggaa aatgtacgtt taatgtaaat actggagata     5520
gaatagctca gctaatctat caacgtatat attatccaga actggaagaa gtacaatctc     5580
tagatagtac aaatagagga gatcaagggt ttggatcaac aggacttaga taataaacaa     5640
tagtatgttg tcgatgttta tgtgtaataa tatcgtagat tatgtagatg gtatagtaca     5700
ggatatagaa gatgaggcta gcaataatgt tgatcacgac tatgtatatc cacttccaga     5760
aaatatggta tatagatttg acaagtccac taacatactc gattatctat caacggaacg     5820
ggaccatgta atgatggctg ttcgatacta tatgagtaaa caacgtttag acgacttgta     5880
tagacagttg cccacaaaga ctagatcata tatagatatt atcaacatat attgtgataa     5940
agttagtaat gattataata gggacatgaa tatcatgtat gatatggcat ctacaaaatc     6000
atttacagtt tatgacataa ataacgaagt taatactata ctaatggata caagggggtt     6060
gggtgtaaga ttggcgacaa tttcattcat aaccgaattg ggtagacgat gtatgaatcc     6120
agtaaaaact ataaaaatgt ttactctact atcgcatact atatgcgatg attgttttgt     6180
agattatata acggacattt caccaccaga taataccatc cctaacacta gcacgcgtga     6240
atatctaaag cttattggca tcacagctat catgttgct acatataaaa ctctcaaata     6300
catgatagga taattttttt taacacggat atagaatgct aacgtaataa ttatgcgtta     6360
tgaagacccc tatatcatca attcaatttt ttttctagaa aaagtatcaa gatgtttata     6420
```

```
ttatcgtcgg tcatcagatc tgtaatgttt cccaatgatt ggaatctaga ttctgaaatc   6480 ttttttgtatc cccaatgttc agtgatttta gcacatattc ctatggtagc gaataaactt   6540
tcctgatcat ggactttttgt aaaattgatg tagtggtctc cttcgctcat agcttcgaca   6600
atctcattaa ttttatcaat accatagtac cgtatagcga catcatcgaa cttcatcaat   6660
tccttgtaca gtcttccaca actggtaata tctttgttaa acactataac atgatttctc   6720
cacgtaatat attcatctat tagatcgatg atggagtcgc gactacatat tttatcatca   6780
tccacaaagt aaaaaacagc atcctcataa tctaatttag tcgccatgac tatctcacaa   6840
aagacagtag ccgtctcctt cctctatatt gatttaattg tatgttttta caattatcaa   6900
taaaacataa aaataatatg atcatcaaac gaactgttaa tattgatagt tatataacgt   6960
gaatcatgag tgcaaactgt atgttcaatc tggacaatga ttacatatcc taaggcatta   7020
gtattcataa gtcatggagc tggtaaacat tctggacgtt atgacgaact agctgaaaac   7080
atatcatcgt taggaatttt agtattctca catgatcata ttggacatgg aagaagtaat   7140
ggtgaaaaaa tgatgattga tgactttggt acagcacgtg gtaactatta aatctactta   7200
ttgggtcatt ccatgggagc aacaatttct atactagcct cttacgataa tccaaacttg   7260
tttacagcaa tgattctaat gtctcctcta gttaatgcag atgctgtttc aagactgaat   7320
ctgctagctg ccaaacttat gggaaccatc acaccaaatg cgccagtcgg aaagctatgt   7380
ccagaatcag tatctagaga tatggataaa gtttataaat accaatacga cccattaatc   7440
aatcatgaaa aaattaaggc tggatttgct agtcaggtct tgaaggctac caacaaggtt   7500
agaaaaataa tttccaagat taacaccccg actctcatac tccagggaac aaacaatgag   7560
attagcgatg ttttaggtgc atattatttc atgcaacatg caaattgtaa tagagaaata   7620
aaaatttatg aaggtgccaa acatcatctt cataaggaaa cggatgaagt taaaaaatca   7680
gtcatgaaag aaatagaaac ttggattttt aatagagtga agtgatatag gattattctt   7740
ttaacaaata aaatgaatcc ggataataca atcgcagtga ttacagagac tattcctata   7800
ggtatgcaat ttgataaagt atatttgtct acatttaaca tgtggaggga aattctatcc   7860
aataccacaa aaacactaga tatatcatct ttttattgga gtttatcgga tgaagtgggt   7920
acgaatttcg gcacgataat attaaacgag attgtacaat tacccaaaag aggagtacga   7980
gttagagtag ccgtcaataa atctaacaaa ccattaaagg atgttgaaag actacaaatg   8040
gccggagttg aagtacgata catagatatt acaaatatcc taggaggagt tcttcataca   8100
aaattttgga tatctgataa tacacatatt tatttaggaa gcgctaacat ggattggaga   8160
tcactaactc aggtcaaaga attgggtatt gcgatcttca ataataggaa cttggcagcg   8220
gatctcactc aaattttttga ggtatactgg tatcttggag ttaacaatct accatataat   8280
tggaaaaact tttatccgtc gtattataat acagatcatc ctcttagtat taacgtaagt   8340
ggtgttccac actctgtatt tattgcttct gcaccgcaac aactatgtac tatggaaaga   8400
accaatgatt taaccgcttt attgtcatgt attagaaatg cgagtaaatt cgtttatgta   8460
tctgttatga actttatccc tattatttat tcgaaggcgg gtaaaatttt gttttggcct   8520
tatatagaag atgaattaag aagatccgct atagacagac aagtatccgt taagctattg   8580
attagttgct ggcaacgatc ttcgtttatc atgagaaact ttttaagatc tatcgctatg   8640
ctaaaatcta aaaacataaa tatagaagta aagctatttta ttgtaccaga tgctgatcct   8700
cccattccgt attctagggt aaaccatgcc aaatatatgg taaccgataa aacggcctat   8760
```

-continued

```
ataggtacct caaattggac aggaaattac tttacggata catgtggagc atctattaat    8820
attacaccgg atgatggatt aggtcttcgt caacaattag aagatatttt tatgcgtgat    8880
tggaattcaa aatacagcta tgaattgtac gatactagtc ctactaaaag gtgtaaacta    8940
ttaaaaaata tgaaacaatg tacaaatgat atatactgcg atgagataca accggaaaaa    9000
gaaattcctg aatattctct tgaataaaat agatataaaa acataatttt tatcccaatt    9060
tacgagcccg ttaacaagat gcttgcattt tgttattcgt tgcccaatgc gggcgatgta    9120
ataaagggca gagtatacga gaatgattat gctctatata tttatctttt tgactatcct    9180
cactctgaag ctatcttggc agagagtgtt aagatgcata tggatagata tgttgaatat    9240
agggataaac tggtagggaa aactgtaaaa gttaaagtga ttagagttga ttatacaaaa    9300
ggatatatag atgtcaatta caaaaggatg tgtagacatc aataattttt ataccgaaca    9360
taaaaataag gttaattatt aataccataa aatcatgatt gcgttattga tactatcgtt    9420
aacgtgttca gcgtctacct atcgtctaca aggatttacc aatgccggta tagtagcgta    9480
taaaaatatt caagatgata atattgtctt ctcaccgttt ggttattcgt tttctatgtt    9540
tatgtcgcta ttgcctgcat caggtaatac tagaatagaa ttattgaaga ctatggattt    9600
gagaaaaaga gatctgggtc cagcatttac agaattaata tcaggattag ctaagctgaa    9660
aacatctaaa tatacgtaca ctgatctaac ttatcaaagt ttcgtagata atactgtgtg    9720
tattaaaccg tcgtattatc aacaatatca tagattcggc ctatatagat aaactttag    9780
acgagatgcg gttaataaaa ttaattctat agtagaacgt agatccggta tgtctaatgt    9840
agtagattct aatatgctcg acaataatac tctatgggca atcattaata ctatatattt    9900
taaaggtata tggcaatatc cgtttgatat cactaaaaca cgcaatgcta gttttactaa    9960
taagtacggt acgaaaacgg ttcccatgat gaacgtagtt actaaattgc aaggaaatac   10020
aatcacaatc gatgacaaag aatatgacat ggtacgcctt ccgtataagg atgctaatat   10080
tagtatgtac ctggcaatag gtgataatat gacccatttc acagattcta ttacggctgc   10140
aaaattagac tattggtcgt ttcaattagg gaataaagtg tacaatctta aactccctaa   10200
atttctatc gaaaataaga gggatattaa gtcgatagcc gaaatgatgg ctcctagtat   10260
gtttaatcca gataatgcgt cgtttaaaca tatgactagg gacccattat atatttataa   10320
aatgtttcag aatgcaaaga tagatgtcga cgaacaagga actgtagcag aggcatctac   10380
tattatggta gctacggcga gatcatctcc tgaaaaactg gaatttaata caccatttgt   10440
gttcatcatc agacatgata ttactggatt tatattgttt atgggtaagg tagaatctcc   10500
ttaatatggg tacggtgtaa ggaatcatta ttttatttat attgatgggt acgtgaaatc   10560
tgaattttct taataaatat tatttttatt aaatgtgtat atgttgtttt gcgatagcca   10620
tgtatctact aatcagatct attagagata ttattaattc tggtgcaata tgacaaaaat   10680
tatacactaa ttagcgtctc gtttcagaca tggatctgtc acgaattaat acttggaagt   10740
ctaagcagct gaaaagcttt ctctctagca aagatgcatt taaggcggat gtccatggac   10800
atagtgcctt gtattatgca atagctgata ataacgtgcg tctagtatgt acgttgttga   10860
acgctggagc attgaaaaat cttctagaga atgaatttcc attacatcag gcagccacat   10920
tggaagatac caaaatagta aagatttgc tattcagtgg actggatgat tcgtattcga   10980
tgattatttt taacaaaata acataaaaat aatatatttt tttaggatgc gatcatgacg   11040
tcctctgcaa tggataacaa tgaacctaaa gtactagaaa tggtatatga tgctacaatt   11100
ttacccgaag gtagtagcat ggattgtata aacagacaca tcaatatgtg tatacaacgc   11160
```

```
acctatagtt ctagtataat tgccatattg gatagattcc taatgatgaa caaggatgaa    11220
ctaaataata cacagtgtca tataattaaa gaatttatga catacgaaca aatggcgatt    11280
gaccattatg gagaatatgt aaacgctatt ctatatcaaa ttcgtaaaag acctaatcaa    11340
catcacacca ttaatctgtt taaaaaaata aaaagaaccc ggtatgacac ttttaaagtg    11400
gatcccgtag aattcgtaaa aaaagttatc ggatttgtat ctatcttgaa caaatataaa    11460
ccggtttata gttacgtcct gtacgagaac gtcctgtacg atgagttcaa atgtttcatt    11520
gactacgtgg aaactaagta tttctaaaat taatgatgca ttaattttg tattgattct     11580 caatcctaaa aactaaaata tgaataagta ttaaacatag cggtgtacta attgatttaa    11640
cataaaaaat agttgttaac taatcatgag gactctactt attagatata ttctttggag    11700
aaatgacaac gatcaaacct attataatga tgattttaaa aagcttatgt tgttggatga    11760
attggtagat gacggcgatg tatgtacatt gattaagaac atgagaatga cgctgtccga    11820
cggtccattg ctagatagat tgaatcaacc agttaataat atagaagacg ctaagcgaat    11880
gatcgctatt agtgccaaag tggctagaga cattggtgaa cgttcagaaa ttagatatag    11940
agaaaatagc tccagaatac agacaatgct tacaggatct ataccatatg aaaattacgc    12000
gtcctagaca ctttgataac tagttatgtc attctcgttt ttatagagtg tactcgttac    12060
taaatattaa ttaatgaaat aataacaatt attaagacat actattcatc caacttaaac    12120
aacgaaaaac attttcatt aagtttatca tgaatgcgta taataaagcc gattcgtttt     12180
ctttagagtc tgattctatc aaagatgtta tacacgatta tatttgttgg ctcagtatga    12240
ctgatgaaat gagaccatct atcggaaacg tctttaaagc gatggaaacg tttaagatag    12300
acgcggttag atattacgat ggtaacatat acgatttagc taaagatata aatgcgatgt    12360
cattcgacag ttttataaga tctctacaaa atatctcttc aaagaaagat aaactcactg    12420
tttatggaac catgggactg ctgtctattg tcgtagatat taacaaaggt tgtgatatat    12480
ccaatatcaa gttcgctgcc ggaataatca ttttaatgga gtatatttt gatgacacgg     12540 atatgtctca tcttaaagta gcactctatc gtagaataca gagacgtgat gatgtagata    12600
gatatttttt tttcctaaac tgatttctct gtttaaattc gtagcgatat ataaaacaac    12660
atgtaattaa ttaataaact ttaagacatg tgtgttatac taagatggtt ggcttattcc    12720
atagtagctt gtggaattta taaacttatg atagtaaaac tagtacccaa tatgtaaaga    12780
tgaaaaagta aattactatt aacgccgtcg gtattcgttc atccattcag tatgggtata    12840
cagcacgaat tcgacatcat tattaatgga gatatcgcgt tgagaaattt acagttacat    12900
aaaggggata actacggatg caaactaaaa attatttcga atgattacaa gaaattaaag    12960
tttagattca ttatacgccc agattggtcg gaaatcgacg aggtcaaagg attaaccgta    13020
tttgcaaaca actatgcggt gaaagttaat aaggtagatg acacgttcta ttacgtaata    13080
tatgaggctg taatacatct gtataacaaa aaaacagaga tattgattta ttctgatgat    13140
gagaacgaac tctttaaaca ctattaccca tacatcagtc taaatatgat tagtaaaaag    13200
tataaagtta aagaagaaaa ctactcatcc ccgtatatag aacatccgtt aatcccgtat    13260
agagattatg agtccatgga ttaatatgag tatagtgtta aatgacactt actaaatagc    13320
caaggtgatt attcgtattt ttttaaggag taaccatgtc cgcaattaga tttattgcat    13380
gtctatatct catttccatc ttcggaaatt gtcatgagga tccatattat caaccatttg    13440
ataaattaaa cattactcta gatatataca cttatgagga tctagtacca tacaccgtag    13500
```

```
acaatgacac aacttctttc gttaagatat actttaaaaa ttttttggatt acggttatga    13560
ctaaatggtg tgctccgttt attgataccg ttagcgtata cacatctcat gataatctga    13620
atatacaatt ttatagtagg gacgaatatg atacacaaag cgaggataaa atttgtacca    13680
ttgatgttaa agcacgatgc aaacatctaa caaaacgaga agttacagta caacaagaag    13740
cctacagata ttcattatct tctgacctat cgtgttttga ttctatagat ctagagattg    13800
atcttattga aactaatagt actgacacta cagtactgaa atcatatgag ctcatgcttc    13860
ccaaacgtgc taaatccata cataactgaa atgaaagaaa ccaaaaaatg cgatagcatc    13920
aacaaccaat catggttaac gataagatac tctatgatag ttgtaaaaca tttaacatcg    13980
atgccagcag tgcacaatca ttgatagaaa gtggtgcaaa tccattatat gagtatgatg    14040
gtgaaactcc attaaaggca tacgttacca agaaaaataa taatatcaaa aacgatgttg    14100
tgattttgtt attgtcgtca gtcgactata aaaatatcaa tgattttgat atactcgaat    14160
atctatgttc tgataacatc gatatagact tattgaaatt actaatttcg aaaggtatag    14220
aaataaatag tatcaaaaat ggtattaata ttgtagaaaa atacgctaca acatcaaatc    14280
ccaatgtaga tgtgtttaaa ctattattgg ataaggaat acctacatgt agcaacatac    14340
agtatggata caagatcaaa atagaacaga ttagacgtgc tggtgaatat tataattggg    14400
atgatgaatt agacaattac gattacgact acaccactga ttatgatgat agaatgggta    14460
aaacagttct ctattattat attattacta ggtcacaaga tggttatgct acatctttgg    14520
acgtaataaa ctatttaatt tcacacgaaa aagagatgcg ttattatact tatcgtgaac    14580
ataccacact ctattattat cttgacaaat gcgatattaa acgggaaata tttgacgcgt    14640
tattcgatag taactatagt ggtcatgaac taatgaatat tctatctaac tatttacgta    14700
aacagtttag gaagaaaaat cacaaaatcg ataattatat agttgatcaa ctattattcg    14760
accgtgatac gttttatatt ttagaattgt gtaatagttt acgtaataat atccacaatt    14820
cttaaaagat atacagattc tataagagat ctattgttag aatatgtatc ttatcataca    14880
gtatacatca atgttattaa atgtatgatt gatgaaggag ctacattata tagatttaag    14940
catataaata aatatttca aaaatttggc aatagagatc ctaaagttgt cgagtatatt    15000
ttaaaaaatg gaaacttagt tgtagataat gacaatgatg ataacctaat aaatattatg    15060
ccattattcc ctaccttctc tatgcgtgag ttggatgtgt tatcgatact aaaactttgt    15120
aagccgtata ttgatgatat aaacatggat gtagtatact ttatcattgt attaagtcgc    15180
atagtgtcag cctagtagaa tggttaatag ataatggcgc agacattaat ataataacaa    15240
aatatgggtt tacatgtatt actatttgtg ttatactggc agataaatat atcccagaaa    15300
tagcagaatt atatattaag atattggaaa ttattctgag taaattacca accatcgaat    15360
gtattaagaa aacagttgat tacctagacg atcacaggta cttattcata ggtggtaata    15420
ataaatcgtt actgaaaata tgtatcaagt acttcatatt agtcgattat aagtacacat    15480
gtagcatgta tccatcatat atagaattta taaccgactg cgaaaaagaa attgcggata    15540
tgcgtcaaat taaaataaat ggtacggaca tgcttacagt gatgtacatg ttaaataaac    15600
ctacaaagaa acgatatgtt aataatccga tatttacaga ttgggctaat aagcaatata    15660
agttttataa tcaaataata tataatgcta ataagttaat agaacaaagt aagaaaatag    15720
acgacatgat agaggaggta tccattgacg ataatcgttt atcaacacta ccgttagaaa    15780
ttagacattt gatttctcg tacgcgttcc tataaaaata gaaactataa tcatataata    15840
gtgtaggttg gtagtattgc tcttgtgact agagactta gttaaggtac tgtaaaaata    15900
```

```
gaaactataa tcatataata gtgtaggttg gtagtagggt actcgtgatt aattttattg    15960
ttaaacttgt ccttaagtct tattaatatg tcttctaaag ggggtagtgg cggcatgtgg    16020
agtgtcttta tccatggaca tgatggtagt aataaaggat ctaaaactta tacatctggt    16080
ggcggtggaa tgtggggagg aggatcgtcc agtggtgtaa aaagtggggt taacggaggt    16140
gtaaaatctg gaactggtaa aatttaaaca ctaaattatt tttattaata attgtacaag    16200
tttttgacat gatatttaat gacattagtt gtgtgggtgt atagagttca cagtagctca    16260
ttcagtcaaa atgtttgact atttggaaaa tgaggaggtg gctctcgatg aacttaaaca    16320
gatgttgaga gacagagatc ctaatgatac caggaaccaa ttcaagaata atgctttaca    16380
cgcataccct tttaatgagc attgtaataa tgtcgaggtc gtcaaactac tactagacag    16440
tggcactaat ccattacgca aaaattggag acagctaccc cattagaaga atacacaaat    16500
agtagacatg ttaaagttaa aggatatagc gatggctcta ctagaagcca ctggatttag    16560
caacataaat gactttaata tattcagcta tatgaaatcc aaaaatgtag acgttgactt    16620
gataaaggtg ttggtagaac atggatttga cttgagtgtt aaatgtgaaa accatcgttc    16680
agttatagaa aattatgtaa tgacagatga tcctgttcct gaaattattg atttgttcat    16740
agaaaatggc tgcagtgttc tttatgagga cgagtactga tacgcgtatg atgattatca    16800
actacgaaat tgcggtaccg tattgcatct gtatatcatc tctcatctgt attcagagtc    16860
ggatacgaga gcatatgtgc gtccggaagt tgttaaatgt ctaattaatc acggaatcaa    16920
gccgtctttt atagataaaa actattgtac agctcttcaa tattatatta agtcatctca    16980
tatagatata gacatcgtta aattgttaat gaaaggaata gataacacgg cttattcata    17040
tatagacgat ctaacatgtt gcactcgagt aattatggct gattatctaa atagtgatta    17100
tagatacaat aaagatgtag atttggtcaa attgttttg gaaaatggaa agccgcacgg    17160
aataatgtgt agtattgtac cactatggag aaatgataag gaaaccatct ttttgatatt    17220
gaaaacaatg aactcggatg tcctccaaca tatactaatt gagtatatga cattcggcga    17280
tatccctcta gtggaatatg gaactgtggt aaataaagag gctatacacg gatactttag    17340
aaatattaat attgattctt acacgatgaa atatctacta aaaaaggaag ggagatgcca    17400
tcaattatct cgatgatgga gagatcccga ttggacacct atgtaaatcc aactatgaat    17460
gttataattt ttacacttat acatacaaaa agggtctttg tgacatgtct tatgcttgcc    17520
caattcttag tactataaac atttgcctac cttatcttaa agacattaac atgattgaca    17580
aacgaggaga aacacttctt cacaaggctg ttagatataa taaacaatct ctagtatctt    17640
tactgctaga atccggttca gatgtcaaca ttagatcaaa taacggatat acatgtatag    17700
ccattgccat caacgaatct aaaaacattg aactgctgaa aatgctatta tgtcataaac    17760
ctacattaga ttgtgtgatt gattcattga gagaaatatc taacatcgta gataacgact    17820
atgctataaa acaatgtatt aaatatgcca tgattataga tgactgtaca tcgtctaaga    17880
ttccagagtc cataagtcaa cgctataatg attatataga tctttgcaat taagaattga    17940
atgagatgaa aaaaataatg gtaggtggta atactatgtt ctcattaata tttactgatc    18000
atggagctaa aattattcat agatatgtca ataatccaga attacgtgag tattatgagt    18060
taaaacaaaa taaaatatat gtggaagcat atgatattat ttccaacgca atagtgaaac    18120
atgatagaat acataaaacc atagaatcag ttgatgataa tacctacatt tctaatcttc    18180
cgtataccat caaatacaaa atattcgagc aacaataagt attttttata cctttaaaat    18240
```

```
tgataaataa attttttcta gtgatatttt ggcaagatga aaatcctatt tctcatcgct    18300
ttcatgtatg ggtgtgttca ctcatatgtt aacgcggttg aaaccaaatg tccaaatcta    18360
gacattgtaa catcttctgg agaatttcat tgttcaggat gtgtggaaca tatgcctgag    18420
tttagctata tgtattggtt ggcaaaggat accaagttta tagaacatct gggtgatggc    18480
atcaaagaag atgaaaccgt tcgtaccaca gatagtggaa tcaccactct acgtaaagtc    18540
cttcatgtaa ccgatactaa taaatttgct cattataggt tcacttgtgt cctcactacg    18600
atagatggcg tttcaaaaaa gaatatttgg ctgaagtagt gcgtgctact attttttattt    18660 atgatataat ctaatggaat taatttgaat tgatatttat ccaatactaa agattatatt    18720
agaatcaaat taatctttta tacgagaaaa aataacgaca tacgtcgtca acaaattaaa    18780
ctttttattt attagttaac ttgctcattg ttatgtttct aaaacgggta cgacatatag    18840
gacaattatc cgacgcaccg gtttctcttc gtgttctatg ccatatattg atgcatgtta    18900
tgcaaaatat atgattacac gaatccaata aaccaaagta tctatcgttt tgagtaaaca    18960
acttcatagc aaatttcaca ttcttttttct ttacttactc tatacacgtc ctcgtattta    19020
tccagtattt tgatgatatc caactcagaa atggttgttg tattattggg tgtataggta    19080
ttattagcta tgtaccaatt taccaacctt cttaatattg attgataatc acatcggtta    19140
tccaattaat aactaaattg tagtgtatat atagaccata tatgtttcta ttttttttgac    19200 agtttcagta agttttgatt gttgtattcc tgtatctcta gataagttag tcatatagtc    19260
ccttccggcg atacgttttt tccaagcccg aaattgatta gccaaatgtg gatttatttt    19320
tgtgataatg catactgtta gtcttatatc atttggttca tctatgtatt gtaatattgt    19380
tacatgatct atagatgatg tattgatttt ggcaggatcg aattccatat ccgcgactaa    19440
acagtgaaaa aaatgtaaat aattttaaat tagtaaaact ttttttttatt ttttatgatt    19500 ccaaaaaaac tgaatacaaa gtcctaaatt ataaatatgg agatcatact accacaactt    19560
attattatgt atacaaggcc ggtgtaatag atagatatat ataattctat tacaccggca    19620
gacaattacc gatcggtatt tgtcgttacc aacataccgt ataatatgta atatacaatt    19680
ccataaccca ttgacagttg ttatacatca aaattgcaat tcttttgatt acgatgttat    19740
aagaatgtag ttaattgatg tatgatgtta atgtgtcctc tttcctctta taacatcgta    19800
atcaaaaact ttttttataat atatacctaa taatgtgtct taatagttct cgtgattcgt    19860
caaacaatca ttcttataaa atataataaa gcaacgtaaa aacacataaa aataagcgta    19920
actaataaga caatggatat ttacgacgat aaaggtctac agactattaa actgtttaat    19980
aatgaatttg attgtataag gaatgacatc agagaattat ttaaacatgt aactgattcc    20040
gatagtatac aacttccgat ggaagacaat tctgatatta tagaaaatat cagaaaaata    20100
ctatatagac gattaaaaaa tgtagaatgt gttgacatcg atagtacaat aacttttatg    20160
aaatacgatc caaatgatga taataagcgt acgtgttcta attgggtacc cttaactaat    20220
aactatatgg aatattgtct agtaatatat ttggaaacac cgatatgtgg aggcaaaata    20280
aaattatacc accctacagg aaatataaag tcggataagg atattatgtt tgcaaagact    20340
ctagacttta aatcaacgaa agtgttaact ggacgtaaaa caattgccgt tctagacata    20400
tccgtttcat ataatagatc aatgactact attcactaca acgacgacgt tgatatagat    20460
atacatactg ataaaaacgg aaaagagtta tgttattgtt atataacaat agatgatcat    20520
tacttggttg atgtggaaac tataggagtt atagtcaata gatctggaaa atgtctgtta    20580
gtaaataacc atctaggtat aggtatcgtt aaagataaac gtataagcga tagttttgga    20640
```

```
gatgtatgta tggatacaat atttgacttt tctgaagcac gagagttatt ttcattaact   20700
aatgatgata acaggaatat agcatgggac gatgatacag atatatggac tcccgtcaca   20760
gaagatgatt acaaatttct ttctagacta gtattgtatg caaaatctca atcggatact   20820
gtattcgact attatgttct tactggtgat acggaaccac ccactgtatt cattttcaag   20880
gtaactagat tttactttaa tatgccgaaa taaaaatttt ttgtataata tctagaggta   20940
gaggtattgt ttagataaat acaaataaca tagatacatc gcatatttag cattttata   21000
aatatacata agacatacac tttatacatt tttgtaaaaa tactcataaa aaaaatttat   21060
aaaaattatg gcacaaccat atcttgtata ggtagtttag ttcgtcgagt gaacctataa   21120
acagataata gacaacacgt aataataata atgcctacta atacaagcat aataccggga   21180
gatgggatat atgacgttgt agtgtttggt ttttctgaac gttgatagtc tactaatact   21240
acatgctgac atctaatgcc tgtataacca tgagagcatc tacaatacat accgtcgata   21300
tctctagcgt ggatacagtc accgtgtaaa caatatccat ctccctctgg accgcataat   21360
ctgatagctg gaatatctgt tgtagcgttt gtaatttctg gcgatgtcgt ttcgatagcg   21420
ttaccactat cggcgaatga tctgattatc atagcagcga acaacaacat cagataattt   21480
atcaacattt ttgatggatt ttgtgtttat gctgtttctc agtgtgtgtt tatgacaaga   21540
ttgggaattt tatattatta attcagtaat ataaactaat aatatattgt taattgtgta   21600
aataatataa aaataacaat acaatattga atgtgttgct gttaaaaatg tatgtgttaa   21660
tataatagaa taaataaat gagtatgatc atttagata acgattgatt ttatcattac   21720
cgcttcattc ttatattctt tgcttacgga acctatattt agaaacatct actaacgatt   21780
ttttatgctt gcattattaa tggtatgtaa taccaatttg ttaagtatga atacggggta   21840
caaacataaa ctgaaattta gatcattaaa tgtttcatca gaaatgactc catgaaaacc   21900
gccgaagaac ttcgtgcaat cattggactt tgtactcaat cagctatcgt ctctggaaga   21960
gtcttcaacg ataagtatat cgacatacta cttatgctgc gaaagattct gaacgagaac   22020
gactatctca ccctcttgga tcatatccgc actgctaaat actaaatctc cttcatgctc   22080
tctcactaca cttttatca tcttatgagg aataattagc accagaatag ctatggattg   22140
cacatgtatt ctatgtcgtc tactggatga agatgtgacg tacaaaaaaa taaaactaga   22200
aattgaaacg tgtcacaact tatcaaaaca tatagataga cgaggaaaca atgcgctaca   22260
ttgttacgtc tccaataaat gcgatacaga cattaagatt gttcgactgt tactctctcg   22320
cggagtcgag agactttgta gaaacaacga aggattaact ccgctaggag catacagtaa   22380
gcatagatac gtaaaatctc agattgtgca tctactgata tccagctatt cgaattcctc   22440
taacgaactc aagtcgaata taatgatttt cgacttacgt ctgctaaaat acctaattgt   22500
ggataaacgg atacgtccgt ccaagaatac gaattatgca atcaatggtc tcggattggt   22560
ggatatatac gtaacgacgc ctaatccgag accagaagta ttgctatggc ttcttaaatc   22620
agaatgttac agcaccggtt acgtatttcg tacctgtatg tacaacagtg atatgtgtaa   22680
gaactctctt cattactata tatcgtctca tagagaatct ctatccaagg atgtaattaa   22740
atgtttgatc gataacaatg tttccatcca atactactgg tcttgctcaa ccatagatat   22800
agagattatt aataaggat gtggacacgt gtagagtata cgacgtcagc cctatattag   22860
aggcgtatta tctaaacaag cgatttagag taacccccata taatgtagac atggaaatcg   22920
ttaatcttct tattgagaga cgtcatactc ttgtcgacgt aatgcgtagt attacttcgt   22980
```

```
acgattccag agaatataac cactacatca tcgataacat tctaaagaga tttagacaac    23040
aggatgaatc catcgtacaa gccatactga taaactactt acattacggc gatatggtaa    23100
gtatacctat cattcaatgc atgttggata agacgacgga caacaacttt gttaataata    23160
atctcgtcga tgtaaacgtc gtaaggttta tcgtggaaaa tatggacacg cggctgtaaa    23220
tcacatatct aacaatggcc gtctatgtat gtacggtctg atattatcga gatttaataa    23280
ttgcgggtat cactgttatg aagatgtatt tgatatacta agcaagtaca tggatgatat    23340
agatatgatc gataactcta ctatattacg cggtcgatgt caataatata caatttgcaa    23400
agcggttatt ggaatatgga gcgagtgtca cgctcgataa tcaatacggc catccagaaa    23460
agcagttacc aaagagaagc tagttgattt attactgagt taccatccca ctctagagac    23520
tatgattgac gcatttaata gagatatacg ctatctatat cctgaaccat tattcgcctg    23580
tatcagatac gccttaatcc tagatgatga ttttccttct aaagtaagta tgatatcgcc    23640
ggtcgtcata aggaactaaa gcgctataga gcagacatta atagaatgaa gaatgcctac    23700
atatcaggcg tctccatgtt tgatatatta tttaaacgaa gcaaacgcca cagattgaga    23760
tacgcaaaga acaatgagag gatcgactcc attaaataat ttatcatgga gtgataatgt    23820 cctgttttcca tggcatatta caaaatcgat tccgtccaag atgataaaaa catttaccgg    23880
catcataaac acggagttta ttttatatgt ctcgcataaa cattactaaa aaatatatt    23940 gttcggtttt ctttcacatc tttaattatg aaaaagtaaa tcattatgag atggacgcat    24000
cgttcgcgac agtatgtggt acatacctaa cgtatttatg gacgacggta agaatgaagg    24060
tcacgtttct gtcaacaatg tcgacgcgat cgtgtaacac gactcacaat agaatctgtg    24120
aatgctctcc cgatcatgga tgcaaggcat gtgtttccca aacaaaatgt ggaataggat    24180
acggagtatc cggagacgtc atctgttctc cgtgtggtct cggaacatat tctcacaccg    24240
tctcttccgc agataaatgc gaacccgtac ccagaaatac ctttaactat atcgatgtgg    24300
aaattaacct gtatccagtt aacgacacat cgtgtactcg gacgaccact accggtctca    24360
gcgaatccat ctcaacgtcg gaactaacta ttactatgaa tcataaagac tgcgatcccg    24420
tcttcttaat aaggtagcga cttcaggttt ctttacagga gaaaggtgtg cactctgaat    24480
ttcgagatta aatgcaataa caaagattct tcctccaaac agttaacgaa agcaaagaat    24540
gatactatca tgccgcattc ggagacagta actctagcgt cgacatctat atactatata    24600
gtaataccaa tactcaagac tacgaaactg atacaatctc ttatcatgtg ggtaatgtag    24660
ccatatgccc ggtagttgcg atatacataa actgatcact aattccaaac ccacccgctt    24720
tttatagtaa gttttttcacc cataaataca ataattaatt tctcgtaaaa gtagaaaata    24780
tattctaatt tattgcacgg taaggaagta gaatcataaa gaacagtact caatcaatag    24840
caatcatgaa acaatatatc gtactggcat gcatgtgcct gccagtcttc agcaatcatc    24900
ctcatcgtgt acgaagaag aaaacaaaca tcatatggga atcgatgtta ttatcaaagt    24960
cacaaagcaa gaccaaacac cgaccgatga taagatttgc caatccgtaa cggaaattac    25020
agagtccgag tcagatccag atcccgaggt ggaatcagtc gaggatgtag atcctcctac    25080
cacttattac tccatcatcg gtggaggtct gagaatgaac tttggattca ccaaatgtcc    25140
tcagattaaa tccatctcag aatccgctga tggaaagact gtgaggtgtc tatcgacatc    25200
agatgtagcg aagaagagaa agacagcgac atcaagaccc atccagtact cgggtctaac    25260
atctctcata agaaagtgag ttacgaagat atcatcggtt caacgatcgt cgatacaaaa    25320
tgtgtcaaga atctagagtt tagcgttcgt atcggagaca tgtgcaagga atcatctgaa    25380
```

```
cttgaggtca agtatgtcga cggatcggca tctgaaggtg caaccgatga tacttcactc   25440
atcgattcaa caaaactcaa agcgtgtgtc tgaatcgata actctattca tctgaaattg   25500
gatgagtagg gttaatcgaa cgattcaggc acaccacgaa ttaaaaaagt gtaccggaca   25560
ctatattccg gtttgcaaaa caaaaagtta cctctcgcga cttcttcttt ttctgtctca   25620
atagtgtgat acgattatga cactattcct atttcctttc agggtatcac aaaaatatta   25680
aacctctttc tgatggtctc atacaaaaat attttttattc tctttctctc tttgatggtc   25740
tcataaaaaa tattttatt ctctttctct ctttgatggt ctcataaaat attttattc   25800 tctttctctc tttgatggtc tcataaaaaa tattttatt ctctttctct ctttgatggt   25860
ctcataaaat attttattc tctttctctc tttgatggtc tcataaaaaa tattttatt   25920 ctctttctct cttgatggt ctcataaaaa atattaaacc tctttctgat ggtgtcacta   25980 aaatatttt attctctttc tctcttcaat ggagtcataa aatattttta ttctctttct   26040
ctcttcgatg gtctcacaaa aatattaaac ctctttctga tggtgtcact aaaatatttt   26100
tattctcttt ctctcttcaa tggagtcata aaatattttt attctctttc tctctttgat   26160
ggtctcacaa aaatattttt attctctttc tctctttgat ggtctcacaa aaatattttt   26220
attctctttc tctctttgat ggtctcacaa aaatattttt attctctttc tctctttgat   26280
ggtctcataa aaaagtttt acaaaaatat ttttattctc tttctctctt tgatggtctc   26340
ataaaaaaag ttttacaaaa atattttat tctctttctc tctttgatgg tctcataaaa   26400
aaagttttac aaaaatattt ttattctctt tctctctttg atggtctcat aaaaaatatt   26460
aaacctcttt ctgatggtgt cactaaaata ttttattct cattctctct tcaatggagt   26520
cataaaatat ttttattctc tttctctctt cgatggtctc acaaaaatat taaacctctt   26580
tctgatggtg tcactaaaat attttattc tcattctctc ttcaatggag tcataaaata   26640 ttttattct ctttctctct tcgatggtct cacaaaaata ttaaacctct ttctgatggt   26700
gtcactaaaa tattttatt ctcattctct cttcaatgga gtcataaaat atttttattc   26760
tctttctctc tttgatggtc tcataaaaaa agttttacaa aaatattttt attctctttc   26820
tctctttgat ggtctcataa aaaatattaa acctctttct gatggtgtca ctaaaatatt   26880
tttattctct ttctctcttc aatggagtca taaaatattt ttattctctt tctctcttcg   26940
atggtctcac aaaaatatta aacctctttc tgatggtgtc actaaaatat ttttattctc   27000
attctctctt caatggagtc ataaaatatt tttattctct ttctctcttt gatggtctca   27060
taaaaaaagt tttacaaaaa tattttatt ctctttctct ctttgatggt ctcataaaaa   27120 agttttaca aaaatatttt tattctcttt ctctctttga tggtctcata aaaaagtttt   27180
tacaaaaata ttttattct ctttctctct tgatggtctc ataaaaaaa gttttacaaa   27240 aatattttta ttctctttct ctctttgatg gtctcataaa aaatattaaa cctctttctg   27300
atggtgtcac taaaatattt ttattctcat tctctcttca atggagtcat aaaatatttt   27360
tattctcttt ctctcttcga tggtctcaca aaaatattaa acctctttct gatggtgtca   27420
ctaaaatatt tttattctca ttctctcttc aatggagtca taaaatattt ttattctctt   27480
tctctctttg atggtctcat aaaaaagtt ttacaaaaat attttatt ctttctctc   27540 tttgatggtc tcataaaaaa agttttacaa aaatattttt attctctttc tctctttgat   27600
ggtctcataa aaaagttttt acaaaaatat ttttattctc tttctctctt tgatggtctc   27660
ataaaaaaag ttttacaaaa atattttat tctctttctc tctttgatgg tctcacaaaa   27720
```

```
atattaaacc tctttctgat ggagtcgtaa aaaagttttta tctctttctc cttcgatggt    27780
ctcacaaaaa tattaaacct ctttctgatg gagtcgtaaa aaagttttat ctctttctct    27840
cttcgatggt ctcacaaaaa tattaaacct ctttctgatg gagtcgtaaa aaagttttat    27900
ctctttctct cttcgatggt ctcactaaaa tatttttttat tctctttctg atgcatcaac   27960
tatttcttaa acaataacgt ccaacaacat atactcgtcg agcttatcaa catccctat     28020 gcccatctag gttaccagac aattgtatat cataaaataa tgtttataat ttttacaaaa    28080
atatttttat tctctttctc tctttgatgg tctcataaaa aaagttttac aaaaatattt    28140
ttattctctt tctctctttg atggtctcat aaaaaatatt aaacctcttt ctgatggtgt    28200
cactaaaata tttttattct cattctctct tcaatggagt cataaaatat ttttattctc    28260
tttctctctt cgatggtctc acaaaaatat taaacctctt tctgatggtg tcactaaaat    28320 attttttattc tcattctctc ttcaatggag tcataaaata ttttttattct ctttctctct  28380 ttgatggtct cataaaaaaa gttttacaaa aatatttttta ttctctttct ctctttgatg   28440
gtctcataaa aaagttttta caaaatatt tttattctct ttctctcttt gatggtctca     28500 taaaaaagt tttacaaaaa tattttttatt ctctttctct ctttgatggt ctcataaaaa    28560
aagttttaca aaaatatttt tattctcttt ctctctttga tggtctcata aaaaagttt     28620 tacaaaaata ttttattct ctttctctct tgatggtct cataaaaaaa gttttacaaa      28680
aatattttta ttctctttct ctctttgatg gtctcataaa aaagttttta caaaatatt     28740 tttattctct ttctctcttt gatggtctca taaaaaatat taaacctctt tctgatggtg    28800
tcactaaaat attttattc tctttctctc ttcaatggag tcataaaata ttttattct      28860 ctttctctct tcgatggtct cacaaaaata ttaaacctct ttctgatggt gtcactaaaa    28920
tattttattt ctcattctct cttcaatgga gtcataaaat attttattc tctttctctc     28980 tttgatggtc tcataaaaaa agttttacaa aatatttttt attctctttc tctctttgat    29040
ggtctcataa aaaagttttt acaaaatat ttttattctc tttctctctt tgatggtctc     29100
ataaaaaaag ttttacaaaa atattttat tctctttctc tctttgatgg tctcataaaa     29160
aaagttttac aaaaatattt ttattctctt tctctctttg atggtctcat aaaaaaagtt    29220
ttacaaaaat attttattc tctttctctc tttgatggtc tcataaaaaa tattaaacct    29280
ctttctgatg gtgtcactaa aatattttta ttctctttct ctcttcaatg gagtcataaa    29340
atatttttat tctctttctc tcttcgatgg tctcacaaaa atattaaacc tctttctgat    29400
ggtgtcacta aaatatttt attctctttc tctcttcaat ggagtcataa atatttttta    29460
ttctctttct ctctttgatg gtctcataaa aaagttttta caaaaatatt tttattctct    29520
ttctctcttt gatggtctca taaaaaagt tttacaaaaa tattttattt ctctttctct    29580
ctttgatggt ctcataaaaa aagttttaca aaaatatttt tattctcttt ctctctttga    29640
tggtctcata aaaaagttt tacaaaaata ttttattct ctttctctct tgatggtct      29700 cataaaaaaa gttttacaaa aatattttta ttctctttct ctctttgatg gtctcataaa    29760
aaagttttta caaaatatt tttattctct ttctctcttt gatggtctca taaaaaagt      29820 tttacaaaaa tattttattt ctctttctct ctttgatggt ctcataaaaa atattaaacc    29880
tctttctgat ggtgtcacta aaatatttt attctcattt tctctttctc tcttcaatgg     29940
agtcataaaa tatttttatt ctctttctct ctttgatggt ctcataaaaa atattaaacc    30000
tctttctgat ggtgtcacta aaatatttt attctcattc tctcttcaat ggagtcataa     30060
aaagttttta tctctttctc tcttcgatgg tctcacaaaa atattaaacc tctttctgat    30120
```

```
ggagtcgtaa aaaagtttta tctctttctc tcttcgatgg tctcacaaaa atattaaacc    30180
tctttctgat gcatcaacta tttcttaaac aataacgtcc aacaacatat actcatcccc    30240
tatgcccatc taggttacca gacaattgta tatcataaaa taatgtttat aatttacacg    30300
ttaaaatcat ataataaaac gtagatcgta taatattttt tggtatataa atgatctagt    30360
aaaatccatg tagggatac tgctcacatt ttttctttgg tacaaaattt cacacaagtt    30420
tttatacaga caaattcttg tccatatatt ttaaaacatt gacttttgta ctaagaaaaa    30480
tatctagact aactatctct ttctctttct ctcttcgatg gtctttctga tggagtcgta    30540
aaaaagtttt atctctttct ctcttcgatg gtctcacaaa atattaaaac ctctttctga    30600
tggagtcgta aaaagttttt atctctttct ctcttcgatg gtctcacaaa atattaaac    30660 ctctttctga tggagtcgta aaaagtttt atctctttct ccttcgatgg tctcacaaaa    30720
atattaaacc tctttctgat ggagtcgtaa aaagttttta tctctttctc tcttcgatgg    30780
tctcacaaaa atattaaacc tctttctgat ggtgtcacta aaatatttt attctctttc    30840 tctcttcgat ggtctcacaa aaatattaaa cctctttctg atggagtcgt aaaaaagttt    30900
tatctctttc tccttcgatg gtctcacaaa aatattaaac ctctttctga tggagtcgta    30960
aaaagttttt atctctttct ctcttcgatg gtctcacaaa aatattaaac ctctttctga    31020
tggagtcgta aaaagttttt atctctttct ccttcgatgg tctcacaaaa atattaaacc    31080
tctttctgat ggagtcgtaa aaagttttta tctctttctc cttcgatggt ctcacaaaaa    31140
tattaaacct ctttctgatg gagtcgtaaa aagttttat ctctttctcc ttcgatggtc    31200
tcacaaaaat attaaacctc tttctgatgg agtcgtaaaa aagttttatc tctttctctc    31260
ttcgatggtc tcacaaaaat attaaacctc tttctgatgg agtcgtaaaa aagttttatc    31320
tctttctctc ttcgatggtc tcacaaaaat attaaacctc tttctgatgg agtcgtaaaa    31380
aagttttatc tctttctcct tcgatggtct cacaaaaata ttaaacctct ttctgatggt    31440
ctctataaag cgattgattt ttcttaccct ctagagtttc ctacggtcgt tggtcacaca    31500 ttttttctcta gacactaaat aaatatttaa aatataatat taatatacta aaatttatgt    31560
attattaatt tataatatta atatactaaa atttatgtat tattaattta tctaactaaa    31620
gttagtaaat catatacata atttt ataat taatattata tacataattt tataattaat    31680
ttaatcttac                                                           31690
```

<210> SEQ ID NO 71
<211> LENGTH: 3948
<212> TYPE: DNA
<213> ORGANISM: Artificial Sequence
<220> FEATURE:
<223> OTHER INFORMATION: vaccine construct

<400> SEQUENCE: 71

```
atggatgcta tgaagagggg cctgctgctg gtgctgctgc tgtgtggcgc cgtgtttgtg      60
tcccccagcc aggaaatcca cgcccggttc agaagaggca gcaagctggc tgctcagctg     120
gccgacagcg acagcaatgc ctgcgccttc ctgaagctga gatacctgca cagccggatc     180
cacgtgctgc agtttctgaa ccccttcacc ctgcacgagt acatgctgga cctgcagccc     240
gagacaaccg acctgtactg ctacgagcag gacgaggatg aggacgaggt ggaccatctg     300
caggaacagc cccagcaggc cagaagggat gagcagcacc cctgctacct gatcgagaca     360
cagtgctgca gatgcgagag cctggtggcc cagctggctg acgtgaactc taacgccgca     420
```

```
gcctttctga agaacagcat cgactgcaac gacagcatgt gcagcacctt cgacgacaac    480
gtgtccgcca ccgagctcgt gaagagaatc cctgcccctt gcccctgggc ccctgaggaa    540
aatgacgaga tcgacggcgt gaaccaccag catctgcccg ctagaagggc cgagcctcag    600
agacacacca tgctgtgcat gtgctgcaag tgcgaggccc ggatctgctt cctgctgtgc    660
ttttgtgtgc tgctgtgcgt gtgcctgctg atcagacccc tgctgctgag tgtgtccacc    720
tactgccagc ggccgctgtg tcctcaggaa aagaaacggc acgtggacct gaacaagcgg    780
ttccacatct acatctgcga ggacgcccag tgcaccgtgg tggaaggcca ggtggacagc    840
aaggtgtccg agttccggtg gtacagatac agcgtgtacg gcaccaccct gggccagcgg    900
agaatcaaga ggcccagatc cgaggtgtac tgcaagggac agctgaccga gacagaggtg    960
ctggacttcg ccttcaccga cctgaccatc gtgtaccggg acatccggct ggaatgcgcc   1020
atcatgtaca aggccagaga gatgggcttc cacgaccaca tcgactactg gaagctgatt   1080
agactggaat gtgctatctt ctacaaagcc cggatcctga agtgcctgcg gtacagattc   1140
aagaagcact gcaagctgta cgtggcctgg gactccgtgt actactgcgg cgacgatggc   1200
tggtgcaaga ccagctctac ctggcactgg acatgccacg acggcaagca caagaacgtg   1260
tgccaggaca agatcctgga acactacgag aacgactcca aggacgacga ggacgagaca   1320
gcctacgaca gcggcaccga tctgatcgac ttcatcgacg atagcaactg ccaccccaac   1380
aagctgctgc ggagactgag cagcgaccag gaccagtctc agaggccccc caacatggga   1440
gtgaaggccc acggcaagtg catctgggag aacaaggtgt tcatcgtgcc caccctgtgc   1500
cccgtgcctc tggatccaac ataccccctg ctgaagctgc tgaccccga aaccacagat   1560
ctgcactgtt atgagcagct gggcgactcc tccgacgaag aggatacagg cggcctggat   1620
ggctacgagg ccgacaagaa cgacctgaac gcccagatcg agcactggaa actgatccgg   1680
atggaatgtg caattttcta taaggccaaa gagctgggga tcagcgacga gaatgagaac   1740
gacagcgata ccggcgagga catggtggat ttcatcgaca atgaggccga agtacggc    1800
tgcaagggca cctgggaggt gcacttcggc tttaagaagc acggcatcac catcaccgtg   1860
cagtacgaca acgacaaggc caacaccatg gactacacca actggaaaga gatctacccc   1920
cctcccccc cacggccttg ggctcctcca attcctaagc cctctccatg ggcccctcag   1980
ttcgacggcg acatctgcaa taccatgcac tataccaatt gggtggtgta cagagacagc   2040
atcccccacg ccgcctgcca caagtgtatc gacttctaca gcagaatcag agagctgcgg   2100
cactacagcg actctgtgta cggcgatacc ctggaaaagc tgaccaacac cggcctgtac   2160
aatctgctga tccggtgcct gaggctcgtg accaagtatc ctctgctgaa actgctgtcc   2220
aactgcatcc tgtacggcgc tgccaatacc ggcaagagcc tgttcggcat gagcctgagc   2280
aaagtgcgga agctgaggta ctacaactgc tccgtgtatg gggccagcct gtgcgtggaa   2340
tgcaagaaaa ccctgcagcg gagcgaagtg tacgacgacg aaaccgacga ggaaagcacc   2400
gagagcgacc tggacggctt catcgataac agcgtgatcg tgtgccccgc ctccatcccc   2460
tccgatgaga tctctaccga ggaagccccc agaccccctc actgtccttg ggtgccagtg   2520
ttctgcaaga aggccctgac cgcctctgag gtgtacaatt ttgcctatac cgacctgcgc   2580
gtggtgtata gggacattct ggaacattat gagaatgata gcaaggacct gtgcgatcac   2640
atcaactgcc tcgtgatcta cggccctcct aacaccggca gtcctgcttc gccatgtcc    2700
ctgtggaaca ccgagcccaa gcactgcttc aagaagggcg ccagcacat cgaagtgtgg    2760
ttcgatattg tgtacaggga cggcaaccct tacgccgtgt gcgacaagtg cctgaagttc   2820
```

-continued

```
tactccaaga tcagcgagta ccgccactac tgctactccc tgtatggcac aacactggaa  2880
cagcagtaca acaagcccct gtgcgacctg ctgattcgct gcatcaacac caccagatac  2940
cctctgctgt ccctgctgaa cagctacagc accccccctc atcggattcc cgccccatgt  3000
ccatgggctc cacagaggcc tacccagacc accacccccg agaatacctc cctggtggaa  3060
ctgagagtga ccaccccaa gagcacagtc gtgatcaggc tgcacctgtg ccctacctg  3120
cactccagac tggtggtgtt caccttcccc aacccctttc accaggtggt gcccgccctg  3180
aatatctgca aggccaaggc ctgcaaagcc atcgagaaga atgggaagt gcacgctggc  3240
ggccaagtga tcctgtgtcc tgagagcctg cggcctctgc tgctgtccat tagcgtgtac  3300
gcccaggtgc tggtgctggt gctgctgctg tgggtgtcca tcggcagcaa ctgtctggtg  3360
ctgtgcggcc ctgccaacac agggaagagt tacttcggca tgtctctgat ctgccatcag  3420
gtggtgcctc cactggccgc ctctaaggct aaagcctgtc aggccatcga actgcagctg  3480
gccctggaag ccctgaatgc cagcccctat gatcacattg attactgaa agccatccgg  3540
caggaaaatg ccatcttctt cgccgccaga tggcattgga cctgtcacga tggaaaacac  3600
aagaatgcca ttgtgaccct gacctacctg ctgcccagcg tgtgtatgtg cgcctacgct  3660
tgggtgctgg tgttcgtgta catcgtcgtg attaccagcc ccgccaccgc cgatgagtgg  3720
acactgcagc agacaagcct ggaaatgtgg ctggccgagc cccagtgtga ccatatcgat  3780
tattggaaac acatccgcct ggaatgtgct attatgtata aggcccggtg gccttacctg  3840
gaaagcagaa ccgtgttcga gttccccaat gccttcgccg ctctggacc tggcgcctct  3900
ggaaaaccca tccccaatcc actgctgggc ctggactcca cccggacc         3948
```

<210> SEQ ID NO 72
<211> LENGTH: 1316
<212> TYPE: PRT
<213> ORGANISM: Artificial Sequence
<220> FEATURE:
<223> OTHER INFORMATION: vaccine construct

<400> SEQUENCE: 72

```
Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ser Lys Leu Ala Ala Gln Leu Ala Asp Ser Asp Ser Asn Ala Cys
        35                  40                  45

Ala Phe Leu Lys Leu Arg Tyr Leu His Ser Arg Ile His Val Leu Gln
    50                  55                  60

Phe Leu Asn Pro Phe Thr Leu His Glu Tyr Met Leu Asp Leu Gln Pro
65                  70                  75                  80

Glu Thr Thr Asp Leu Tyr Cys Tyr Glu Gln Asp Glu Asp Glu Asp Glu
                85                  90                  95

Val Asp His Leu Gln Glu Gln Pro Gln Gln Ala Arg Arg Asp Glu Gln
            100                 105                 110

His Pro Cys Tyr Leu Ile Glu Thr Gln Cys Cys Arg Cys Glu Ser Leu
        115                 120                 125

Val Ala Gln Leu Ala Asp Val Asn Ser Asn Ala Ala Phe Leu Lys
    130                 135                 140

Asn Ser Ile Asp Cys Asn Asp Ser Met Cys Ser Thr Phe Asp Asp Asn
145                 150                 155                 160
```

```
Val Ser Ala Thr Glu Leu Val Lys Arg Ile Pro Ala Pro Cys Pro Trp
            165                 170                 175
Ala Pro Glu Glu Asn Asp Glu Ile Asp Gly Val Asn His Gln His Leu
        180                 185                 190
Pro Ala Arg Arg Ala Glu Pro Gln Arg His Thr Met Leu Cys Met Cys
        195                 200                 205
Cys Lys Cys Glu Ala Arg Ile Cys Phe Leu Leu Cys Phe Cys Val Leu
        210                 215                 220
Leu Cys Val Cys Leu Leu Ile Arg Pro Leu Leu Ser Val Ser Thr
225                 230                 235                 240
Tyr Cys Gln Arg Pro Leu Cys Pro Gln Glu Lys Lys Arg His Val Asp
                245                 250                 255
Leu Asn Lys Arg Phe His Ile Tyr Ile Cys Glu Asp Ala Gln Cys Thr
            260                 265                 270
Val Val Glu Gly Gln Val Asp Ser Lys Val Ser Glu Phe Arg Trp Tyr
        275                 280                 285
Arg Tyr Ser Val Tyr Gly Thr Thr Leu Gly Gln Arg Ile Lys Arg
    290                 295                 300
Pro Arg Ser Glu Val Tyr Cys Lys Gly Gln Leu Thr Glu Thr Glu Val
305                 310                 315                 320
Leu Asp Phe Ala Phe Thr Asp Leu Thr Ile Val Tyr Arg Asp Ile Arg
                325                 330                 335
Leu Glu Cys Ala Ile Met Tyr Lys Ala Arg Glu Met Gly Phe His Asp
            340                 345                 350
His Ile Asp Tyr Trp Lys Leu Ile Arg Leu Glu Cys Ala Ile Phe Tyr
        355                 360                 365
Lys Ala Arg Ile Leu Lys Cys Leu Arg Tyr Arg Phe Lys Lys His Cys
    370                 375                 380
Lys Leu Tyr Val Ala Trp Asp Ser Val Tyr Tyr Cys Gly Asp Asp Gly
385                 390                 395                 400
Trp Cys Lys Thr Ser Ser Thr Trp His Trp Thr Cys His Asp Gly Lys
                405                 410                 415
His Lys Asn Val Cys Gln Asp Lys Ile Leu Glu His Tyr Glu Asn Asp
            420                 425                 430
Ser Lys Asp Asp Glu Asp Glu Thr Ala Tyr Asp Ser Gly Thr Asp Leu
        435                 440                 445
Ile Asp Phe Ile Asp Asp Ser Asn Cys His Pro Asn Lys Leu Leu Arg
    450                 455                 460
Arg Leu Ser Ser Asp Gln Asp Gln Ser Gln Arg Pro Pro Asn Met Gly
465                 470                 475                 480
Val Lys Ala His Gly Lys Cys Ile Trp Glu Asn Lys Val Phe Ile Val
                485                 490                 495
Pro Thr Leu Cys Pro Val Pro Leu Asp Pro Thr Tyr Pro Leu Leu Lys
            500                 505                 510
Leu Leu Thr Pro Glu Thr Thr Asp Leu His Cys Tyr Glu Gln Leu Gly
        515                 520                 525
Asp Ser Ser Asp Glu Glu Asp Thr Gly Gly Leu Asp Gly Tyr Glu Ala
    530                 535                 540
Asp Lys Asn Asp Leu Asn Ala Gln Ile Glu His Trp Lys Leu Ile Arg
545                 550                 555                 560
Met Glu Cys Ala Ile Phe Tyr Lys Ala Lys Glu Leu Gly Ile Ser Asp
                565                 570                 575
Glu Asn Glu Asn Asp Ser Asp Thr Gly Glu Asp Met Val Asp Phe Ile
```

-continued

```
            580                 585                 590
Asp Asn Glu Ala Glu Lys Tyr Gly Cys Lys Gly Thr Trp Glu Val His
                595                 600                 605

Phe Gly Phe Lys Lys His Gly Ile Thr Ile Thr Val Gln Tyr Asp Asn
            610                 615                 620

Asp Lys Ala Asn Thr Met Asp Tyr Thr Asn Trp Lys Glu Ile Tyr Pro
625                 630                 635                 640

Pro Pro Pro Pro Arg Pro Trp Ala Pro Pro Ile Pro Lys Pro Ser Pro
                645                 650                 655

Trp Ala Pro Gln Phe Asp Gly Asp Ile Cys Asn Thr Met His Tyr Thr
            660                 665                 670

Asn Trp Val Val Tyr Arg Asp Ser Ile Pro His Ala Ala Cys His Lys
            675                 680                 685

Cys Ile Asp Phe Tyr Ser Arg Ile Arg Glu Leu Arg His Tyr Ser Asp
            690                 695                 700

Ser Val Tyr Gly Asp Thr Leu Glu Lys Leu Thr Asn Thr Gly Leu Tyr
705                 710                 715                 720

Asn Leu Leu Ile Arg Cys Leu Arg Leu Val Thr Lys Tyr Pro Leu Leu
                725                 730                 735

Lys Leu Leu Ser Asn Cys Ile Leu Tyr Gly Ala Ala Asn Thr Gly Lys
                740                 745                 750

Ser Leu Phe Gly Met Ser Leu Ser Lys Val Arg Lys Leu Arg Tyr Tyr
            755                 760                 765

Asn Cys Ser Val Tyr Gly Ala Ser Leu Cys Val Glu Cys Lys Lys Thr
770                 775                 780

Leu Gln Arg Ser Glu Val Tyr Asp Asp Glu Thr Asp Glu Glu Ser Thr
785                 790                 795                 800

Glu Ser Asp Leu Asp Gly Phe Ile Asp Asn Ser Val Ile Val Cys Pro
                805                 810                 815

Ala Ser Ile Pro Ser Asp Glu Ile Ser Thr Glu Glu Ala Pro Arg Pro
            820                 825                 830

Pro His Cys Pro Trp Val Pro Val Phe Cys Lys Lys Ala Leu Thr Ala
            835                 840                 845

Ser Glu Val Tyr Asn Phe Ala Tyr Thr Asp Leu Arg Val Val Tyr Arg
            850                 855                 860

Asp Ile Leu Glu His Tyr Glu Asn Asp Ser Lys Asp Leu Cys Asp His
865                 870                 875                 880

Ile Asn Cys Leu Val Ile Tyr Gly Pro Pro Asn Thr Gly Lys Ser Cys
                885                 890                 895

Phe Ala Met Ser Leu Trp Asn Thr Glu Pro Lys His Cys Phe Lys Lys
            900                 905                 910

Gly Gly Gln His Ile Glu Val Trp Phe Asp Ile Val Tyr Arg Asp Gly
            915                 920                 925

Asn Pro Tyr Ala Val Cys Asp Lys Cys Leu Lys Phe Tyr Ser Lys Ile
            930                 935                 940

Ser Glu Tyr Arg His Tyr Cys Tyr Ser Leu Tyr Gly Thr Thr Leu Glu
945                 950                 955                 960

Gln Gln Tyr Asn Lys Pro Leu Cys Asp Leu Leu Ile Arg Cys Ile Asn
                965                 970                 975

Thr Thr Arg Tyr Pro Leu Leu Ser Leu Leu Asn Ser Tyr Ser Thr Pro
            980                 985                 990

Pro His Arg Ile Pro Ala Pro Cys  Pro Trp Ala Pro Gln  Arg Pro Thr
            995                 1000                1005
```

```
Gln Thr Thr Thr Pro Glu Asn Thr Ser Leu Val Glu Leu Arg Val
        1010                1015                1020

Thr Thr Pro Lys Ser Thr Val Val Ile Arg Leu His Leu Trp Pro
    1025                1030                1035

Tyr Leu His Ser Arg Leu Val Val Phe Thr Phe Pro Asn Pro Phe
    1040                1045                1050

His Gln Val Val Pro Ala Leu Asn Ile Cys Lys Ala Lys Ala Cys
    1055                1060                1065

Lys Ala Ile Glu Lys Lys Trp Glu Val His Ala Gly Gly Gln Val
    1070                1075                1080

Ile Leu Cys Pro Glu Ser Leu Arg Pro Leu Leu Leu Ser Ile Ser
    1085                1090                1095

Val Tyr Ala Gln Val Leu Val Leu Val Leu Leu Leu Trp Val Ser
    1100                1105                1110

Ile Gly Ser Asn Cys Leu Val Leu Cys Gly Pro Ala Asn Thr Gly
    1115                1120                1125

Lys Ser Tyr Phe Gly Met Ser Leu Ile Cys His Gln Val Val Pro
    1130                1135                1140

Pro Leu Ala Ala Ser Lys Ala Lys Ala Cys Gln Ala Ile Glu Leu
    1145                1150                1155

Gln Leu Ala Leu Glu Ala Leu Asn Ala Ser Pro Tyr Asp His Ile
    1160                1165                1170

Asp Tyr Trp Lys Ala Ile Arg Gln Glu Asn Ala Ile Phe Phe Ala
    1175                1180                1185

Ala Arg Trp His Trp Thr Cys His Asp Gly Lys His Lys Asn Ala
    1190                1195                1200

Ile Val Thr Leu Thr Tyr Leu Leu Pro Ser Val Cys Met Cys Ala
    1205                1210                1215

Tyr Ala Trp Val Leu Val Phe Val Tyr Ile Val Ile Thr Ser
    1220                1225                1230

Pro Ala Thr Ala Asp Glu Trp Thr Leu Gln Gln Thr Ser Leu Glu
    1235                1240                1245

Met Trp Leu Ala Glu Pro Gln Cys Asp His Ile Asp Tyr Trp Lys
    1250                1255                1260

His Ile Arg Leu Glu Cys Ala Ile Met Tyr Lys Ala Arg Trp Pro
    1265                1270                1275

Tyr Leu Glu Ser Arg Thr Val Phe Glu Phe Pro Asn Ala Phe Ala
    1280                1285                1290

Gly Ser Gly Pro Gly Ala Ser Gly Lys Pro Ile Pro Asn Pro Leu
    1295                1300                1305

Leu Gly Leu Asp Ser Thr Arg Thr
    1310                1315

<210> SEQ ID NO 73
<211> LENGTH: 3321
<212> TYPE: DNA
<213> ORGANISM: Artificial Sequence
<220> FEATURE:
<223> OTHER INFORMATION: vaccine construct

<400> SEQUENCE: 73
atggatgcta tgaagcgagg actgtgctgc gtgctgctgc tgtgtggcgc tgtgtttgtg      60
tcccctagcc aagagatcca cgccagattc agacggggca gcaaactggc cgacgaggat     120
gagacagcct acgactctgg caccgacctg atcgacttca tcgacgacag cgacgagaac     180
```

-continued

```
gagaatgaca gcgacaccgg cgaggacatg gtggatttca tcgacaatgc ccagctggcc      240
gactccgact ctaatgcctg tgcctttctg aaggctcagc tggctgacgt gaacagcaat      300
gccgccgctt tcctgaagaa ctgcatcctg ctgtacggcg ctgccaacac aggcaagagc      360
ctgtttggca tgagcctgaa ctgcctggtg ctgtgcggac tgccaatac cggcaaaagc       420 tacttcggca tgtccctgtg gccttacctg cacagcagac tggtggtgtt tacattcccc     480
aatcctttct ggccctacct ggaaagccgg atcaccgtgt tcgagttccc caacgccttc     540
aacgtgtgcc aggacaagat cctggaacac tatgagaacg acagcaagga catccttgag     600
cactacgaaa acgactccaa ggacctgtgc gaccacatct cgatcacat cgactactgg      660 aagcacatcc ggctggaatg cgccatcatg tacaaggccc ggatcagact ggaatgtgct     720
attatgtata aggctcgcga gatgggcttc caccagttcg acggcgacat ctgcaacacc     780
atgcactaca ccaactggat ctatatctgc gaggacgccc agtgcaccgt ggtggaagga     840
caggtggaca agaaatggga agtgcacgct ggcggccaag tgattctgtg tcctgagagc     900
ggccagcgga gaatcaagag gcccagatcc gagaactgtc accccaacaa gctgctgatc     960
ctgaagtgcc tgcggtacag attcaagaag cactgcaagc tgagcagcac ctggcactgg    1020
acatgccacg atggcaagca caagtggcat ggacctgtc acgacgggaa acacaagaac     1080
gccatcgtga ccctgaccta ctacgaggcc gacaagaacg acctgaacgc ccagattgag    1140
cactggaaac tgatccggat ggaatgtgca atcttctata aggccaaaga gctggggatc    1200
agcatctgcc accaggtggt gcctccactg gctgcctcta agccaaagc ctgtcaggcc     1260 atcgaactgc agctggccct ggaagccctg aacgctagcc cttacgatga gtggaccctg    1320
cagcagacca gcctggaaat gtggctggcc gagcctcagt ttaagaagca cggcatcacc    1380
atcaccgtgc agtacgacaa cgacaaggcc aataccatgg attacacgaa ttggaaagaa    1440
atctacgtga tcgtgtgccc cgccagcatt ccctccgatg agatctctac cgaggaagcc    1500
gaccacattg attattggaa ggccatccgg caagagaatg ccatcttctt cgccgccaga    1560
catcaggtgg tcccccgctct gaatatctgc aaggccaagg cctgcaaagc catcgagtgg    1620
aacaccgagc ctaagcactg cttcaagaaa ggcggccagc acatcgaagt ttggttcgac    1680
tacgtggcct gggacagcgt gtactactgc ggagatgatg gctggtgcaa gaccgaggcc    1740
gagaagtacg gctgtaaagg cacctgggaa gtccacttcg caacagcat cgactgcaac    1800 gatagcatgt gcagcacctt cgacgacaac gtgtccgcca cagagctggt caaggaccat    1860
atagactatt ggaagctgat caggcttgag tgcgccattt tctacaaggc cagacggcgg    1920
ctgtccagcg accaggatca atctcagctc gtgaccaagt atccctgct gaagctgctg    1980 tctacccaga ccaccacacc tgagaacaca agcctggtgg aactgagagt gaccacacct    2040
aagagcaccg tcgtgattcg gctgcacctg accacaagat ccctctgct gagcctgctg    2100 aacagctaca gcacccctcc acacaggatc cccgctccat gtccttgggc tcctcagagg    2160
cctcctattc ctaagccttc tccatgggct cctagaatcc ccgcaccttg tccatgggca    2220
ccaccaagac ctccacattg cccttgggtg ccctgtttcc tgctgtgctt ttgcgtgctc    2280
ctgtgcgtgt gcctgctgat cagacctctg ctgctgagcg tgtccaccta ccttagacca    2340
ctgctcctgt ccatctccgt gtacgcacag gtgctggtgc tggtcctgct tctgtgggtg    2400
tccatcggaa gcctgctgcc tagcgtgtgc atgtgtgcct atgcttgggt gctcgtgttc    2460
gtgtacatcg tggtcatcac aagccccgcc acagccatcg tgtacagaga tggcaatccc    2520
```

```
tacgccgtgt gcgacaagtg cctgaagttc tacagcaaga tcagcgagta ccggcactac    2580
tgctacagcc tgtacggcac cacactggaa cagcagtaca acaagcccct gtgcgatctg    2640
ctgattcggt gcatcaacgt ggtgtaccgg gacagcattc ctcacgccgc ctgccacaag    2700
tgcatcgact ctactccag aatcagagag ctgcggcact acagcgactc tgtgtacggc    2760
gacaccctgg aaaagctgac caacaccggc ctgtacaacc tgctgattag atgcctgcgg    2820
gtgtactgca agggacagct gacagagaca gaggtgctgg acttcgcctt caccgatctg    2880
acaatcgtgt atcgggatag caaggtgtcc gagttccggt ggtacagata tagcgtgtac    2940
ggaacaaccc tgtgcgtcga gtgcaagaaa accctgcaga gaagcgaggt gtacgactgc    3000
cagaggccac tgtgccctca agagaagaaa cggcacgtgg acctgaacaa gcggtttcac    3060
accctgcacg agtacatgct ggacctgcag cctgagacaa ccgacctgta ctgctacgag    3120
cagcccgaaa ccacagatct gcactgttat gagcagctgg cgacagcag cgacgaagag    3180 gatacaggcg gactggacgg cgaggaaaac gacgaaattg acggcgtgaa ccaccagcat    3240
ctccccgcca gaagggctga acctcagaga cacaccatgc tgtgtatgtg ctgcaagtgc    3300
gaggccagaa tcgcctgatg a                                              3321
```

<210> SEQ ID NO 74
<211> LENGTH: 1105
<212> TYPE: PRT
<213> ORGANISM: Artificial Sequence
<220> FEATURE:
<223> OTHER INFORMATION: vaccine construct

<400> SEQUENCE: 74

```
Met Asp Ala Met Lys Arg Gly Leu Cys Cys Val Leu Leu Cys Gly
1               5                   10                  15

Ala Val Phe Val Ser Pro Ser Gln Glu Ile His Ala Arg Phe Arg Arg
            20                  25                  30

Gly Ser Lys Leu Ala Asp Glu Asp Glu Thr Ala Tyr Asp Ser Gly Thr
        35                  40                  45

Asp Leu Ile Asp Phe Ile Asp Asp Ser Asp Glu Asn Glu Asn Asp Ser
    50                  55                  60

Asp Thr Gly Glu Asp Met Val Asp Phe Ile Asp Asn Ala Gln Leu Ala
65                  70                  75                  80

Asp Ser Asp Ser Asn Ala Cys Ala Phe Leu Lys Ala Gln Leu Ala Asp
                85                  90                  95

Val Asn Ser Asn Ala Ala Ala Phe Leu Lys Asn Cys Ile Leu Leu Tyr
            100                 105                 110

Gly Ala Ala Asn Thr Gly Lys Ser Leu Phe Gly Met Ser Leu Asn Cys
        115                 120                 125

Leu Val Leu Cys Gly Pro Ala Asn Thr Gly Lys Ser Tyr Phe Gly Met
    130                 135                 140

Ser Leu Trp Pro Tyr Leu His Ser Arg Leu Val Val Phe Thr Phe Pro
145                 150                 155                 160

Asn Pro Phe Trp Pro Tyr Leu Glu Ser Arg Ile Thr Val Phe Glu Phe
                165                 170                 175

Pro Asn Ala Phe Asn Val Cys Gln Asp Lys Ile Leu Glu His Tyr Glu
            180                 185                 190

Asn Asp Ser Lys Asp Ile Leu Glu His Tyr Glu Asn Asp Ser Lys Asp
        195                 200                 205

Leu Cys Asp His Ile Cys Asp His Ile Asp Tyr Trp Lys His Ile Arg
    210                 215                 220
```

```
Leu Glu Cys Ala Ile Met Tyr Lys Ala Arg Ile Arg Leu Glu Cys Ala
225                 230                 235                 240

Ile Met Tyr Lys Ala Arg Glu Met Gly Phe His Gln Phe Asp Gly Asp
                245                 250                 255

Ile Cys Asn Thr Met His Tyr Thr Asn Trp Ile Tyr Ile Cys Glu Asp
            260                 265                 270

Ala Gln Cys Thr Val Val Glu Gly Gln Val Asp Lys Lys Trp Glu Val
        275                 280                 285

His Ala Gly Gly Gln Val Ile Leu Cys Pro Glu Ser Gly Gln Arg Arg
    290                 295                 300

Ile Lys Arg Pro Arg Ser Glu Asn Cys His Pro Asn Lys Leu Leu Ile
305                 310                 315                 320

Leu Lys Cys Leu Arg Tyr Arg Phe Lys Lys His Cys Lys Leu Ser Ser
                325                 330                 335

Thr Trp His Trp Thr Cys His Asp Gly Lys His Lys Trp His Trp Thr
            340                 345                 350

Cys His Asp Gly Lys His Lys Asn Ala Ile Val Thr Leu Thr Tyr Tyr
        355                 360                 365

Glu Ala Asp Lys Asn Asp Leu Asn Ala Gln Ile Glu His Trp Lys Leu
    370                 375                 380

Ile Arg Met Glu Cys Ala Ile Phe Tyr Lys Ala Lys Glu Leu Gly Ile
385                 390                 395                 400

Ser Ile Cys His Gln Val Pro Pro Leu Ala Ala Ser Lys Ala Lys
                405                 410                 415

Ala Cys Gln Ala Ile Glu Leu Gln Leu Ala Leu Glu Ala Leu Asn Ala
            420                 425                 430

Ser Pro Tyr Asp Glu Trp Thr Leu Gln Gln Thr Ser Leu Glu Met Trp
        435                 440                 445

Leu Ala Glu Pro Gln Phe Lys Lys His Gly Ile Thr Ile Thr Val Gln
    450                 455                 460

Tyr Asp Asn Asp Lys Ala Asn Thr Met Asp Tyr Thr Asn Trp Lys Glu
465                 470                 475                 480

Ile Tyr Val Ile Val Cys Pro Ala Ser Ile Pro Ser Asp Glu Ile Ser
                485                 490                 495

Thr Glu Glu Ala Asp His Ile Asp Tyr Trp Lys Ala Ile Arg Gln Glu
            500                 505                 510

Asn Ala Ile Phe Phe Ala Ala Arg His Gln Val Val Pro Ala Leu Asn
        515                 520                 525

Ile Cys Lys Ala Lys Ala Cys Lys Ala Ile Glu Trp Asn Thr Glu Pro
    530                 535                 540

Lys His Cys Phe Lys Lys Gly Gln His Ile Glu Val Trp Phe Asp
545                 550                 555                 560

Tyr Val Ala Trp Asp Ser Val Tyr Tyr Cys Gly Asp Asp Gly Trp Cys
                565                 570                 575

Lys Thr Glu Ala Glu Lys Tyr Gly Cys Lys Gly Thr Trp Glu Val His
            580                 585                 590

Phe Gly Asn Ser Ile Asp Cys Asn Asp Ser Met Cys Ser Thr Phe Asp
        595                 600                 605

Asp Asn Val Ser Ala Thr Glu Leu Val Lys Asp His Ile Asp Tyr Trp
    610                 615                 620

Lys Leu Ile Arg Leu Glu Cys Ala Ile Phe Tyr Lys Ala Arg Arg Arg
625                 630                 635                 640
```

```
Leu Ser Ser Asp Gln Asp Gln Ser Gln Leu Val Thr Lys Tyr Pro Leu
                645                 650                 655
Leu Lys Leu Leu Ser Thr Gln Thr Thr Thr Pro Glu Asn Thr Ser Leu
            660                 665                 670
Val Glu Leu Arg Val Thr Thr Pro Lys Ser Thr Val Val Ile Arg Leu
            675                 680                 685
His Leu Thr Thr Arg Tyr Pro Leu Leu Ser Leu Leu Asn Ser Tyr Ser
690                 695                 700
Thr Pro Pro His Arg Ile Pro Ala Pro Cys Pro Trp Ala Pro Gln Arg
705                 710                 715                 720
Pro Pro Ile Pro Lys Pro Ser Pro Trp Ala Pro Arg Ile Pro Ala Pro
                725                 730                 735
Cys Pro Trp Ala Pro Pro Arg Pro Pro His Cys Pro Trp Val Pro Cys
            740                 745                 750
Phe Leu Leu Cys Phe Cys Val Leu Leu Cys Val Cys Leu Leu Ile Arg
            755                 760                 765
Pro Leu Leu Leu Ser Val Ser Thr Tyr Leu Arg Pro Leu Leu Leu Ser
770                 775                 780
Ile Ser Val Tyr Ala Gln Val Leu Val Leu Val Leu Leu Leu Trp Val
785                 790                 795                 800
Ser Ile Gly Ser Leu Leu Pro Ser Val Cys Met Cys Ala Tyr Ala Trp
            805                 810                 815
Val Leu Val Phe Val Tyr Ile Val Val Ile Thr Ser Pro Ala Thr Ala
            820                 825                 830
Ile Val Tyr Arg Asp Gly Asn Pro Tyr Ala Val Cys Asp Lys Cys Leu
            835                 840                 845
Lys Phe Tyr Ser Lys Ile Ser Glu Tyr Arg His Tyr Cys Tyr Ser Leu
850                 855                 860
Tyr Gly Thr Thr Leu Glu Gln Gln Tyr Asn Lys Pro Leu Cys Asp Leu
865                 870                 875                 880
Leu Ile Arg Cys Ile Asn Val Val Tyr Arg Asp Ser Ile Pro His Ala
                885                 890                 895
Ala Cys His Lys Cys Ile Asp Phe Tyr Ser Arg Ile Arg Glu Leu Arg
            900                 905                 910
His Tyr Ser Asp Ser Val Tyr Gly Asp Thr Leu Glu Lys Leu Thr Asn
            915                 920                 925
Thr Gly Leu Tyr Asn Leu Leu Ile Arg Cys Leu Arg Val Tyr Cys Lys
            930                 935                 940
Gly Gln Leu Thr Glu Thr Glu Val Leu Asp Phe Ala Phe Thr Asp Leu
945                 950                 955                 960
Thr Ile Val Tyr Arg Asp Ser Lys Val Ser Glu Phe Arg Trp Tyr Arg
                965                 970                 975
Tyr Ser Val Tyr Gly Thr Thr Leu Cys Val Glu Cys Lys Lys Thr Leu
            980                 985                 990
Gln Arg Ser Glu Val Tyr Asp Cys Gln Arg Pro Leu Cys Pro Gln Glu
            995                 1000                1005
Lys Lys Arg His Val Asp Leu Asn Lys Arg Phe His Thr Leu His
        1010                1015                1020
Glu Tyr Met Leu Asp Leu Gln Pro Glu Thr Thr Asp Leu Tyr Cys
        1025                1030                1035
Tyr Glu Gln Pro Glu Thr Thr Asp Leu His Cys Tyr Glu Gln Leu
        1040                1045                1050
Gly Asp Ser Ser Asp Glu Glu Asp Thr Gly Gly Leu Asp Gly Glu
```

-continued

|  |  |  |
|---|---|---|
| 1055 | 1060 | 1065 |

Glu Asn Asp Glu Ile Asp Gly Val Asn His Gln His Leu Pro Ala
         1070             1075             1080

Arg Arg Ala Glu Pro Gln Arg His Thr Met Leu Cys Met Cys Cys
         1085             1090             1095

Lys Cys Glu Ala Arg Ile Ala
         1100             1105

<210> SEQ ID NO 75
<211> LENGTH: 4470
<212> TYPE: DNA
<213> ORGANISM: Artificial Sequence
<220> FEATURE:
<223> OTHER INFORMATION: vaccine construct

<400> SEQUENCE: 75

```
atggatgcta tgaagagggg cctgtgctgc gtgctgctgc tgtgtggcgc cgtgtttgtg      60
tcccccagcc aggaaatcca cgcccggttc agaagaggca gcaagctggc cgacgaggac     120
gagacagcct acgacagcgg caccgacctg atcgacttca tcgacgatag cgccgctgcc     180
gacgagaatg agaacgacag cgataccggc gaggacatgg tggatttcat cgacaacgct     240
gccgccgacg aaaccgacga agagagcacc gagagcgacc tggacggctt tatcgacaac     300
agcgcagccg cccagctggc tgacagcgac tctaatgcct cgccttcct gaaggccgct      360 gctcagctgg cagacgtgaa cagcaatgcc gccgctttcc tgaaggctgc cgccaactgc     420
atcctgctgt acggcgctgc caacaccggc aagagcctgt cggcatgtc tctggccgca     480 gccaactgcc tggtgctgtg cggacctgcc aatactggca aaagctactt cggcatgagc     540
ctggcagccg ccaattgtct cgtgatctac ggccctccta taccggcaa gtcctgcttt     600 gccatgagtc tggccgctgc ctggccctac ctgcactcta actggtggt gttcaccttc     660 cccaacccct cgctgccgc ttggccttac ctggaaagcc ggatcaccgt gttcgagttc     720
cccaatgcct cgccgcagc cctgagatac ctgcacagca gaatccacgt gctgcagttt     780 ctgaaccccct tgccgccgc aaacgtgtgt caggacaaga tcctggaaca ctacgagaac     840
gactccaagg atgccgctgc cattctggaa cattatgaga tgatagcaa ggacctgtgc     900 gaccacattg ctgccgcctg cgatcacatc gactactgga agcacatccg gctggaatgc     960
gccatcatgt acaaggccag agccgccgct atcagactgg aatgtgctat tatgtataag    1020
gctcgcgaga tgggcttcca cgctgctgcc cagttcgacg gcgacatctg caacaccatg    1080
cactacacca actgggctgc cgctatctac atctgcgagg acgcccagtg caccgtggtg    1140
gaaggacagg tggacgccgc tgctaagaaa tgggaggtgc acgctggcgg ccaagtgatc    1200
ctgtgtccag agtctgctgc cgcaggccag cggagaatca gaggcctag aagcgaggca    1260 gccgctaact gccacccaa caaactgctg gctgctgcca tcctgaagtg cctgcggtac    1320
agattcaaga agcactgcaa actggctgca gctagcagca cctggcactg gacctgtcac    1380
gacggcaagc acaaagccgc cgcatggcat tggacatgcc acgatggaaa acacaagaac    1440
gccatcgtga ccctgaccta tgcagccgcc tacgaggccg acaagaacga cctgaacgcc    1500
cagatcgagc actggaagct gatcaggatg gaatgtgcaa tcttctataa ggccaaagag    1560
ctgggcatca gcgctgccgc aatctgccac caggtggtgc ctccactggc cgcctctaaa    1620
gccaaagcct gccaggccat cgaactgcag ctggccctgg aagccctgaa tgccagccct    1680
tatgccgcag ccgatgagtg gacctgcag cagaccagcc tggaaatgtg gctggccgaa    1740
```

-continued

```
cctcaggccg cagcttttaa gaagcacggc atcaccatca ccgtgcagta cgacaacgac      1800
aaggccaata ccatggatta caccaattgg aaagagatct acgccgcagc tgtgatcgtg      1860
tgccccgcca gcatccctag cgacgagatc agcacagagg aagcagccgc cgaccacatc      1920
gattattgga aagccatcag acaggaaaac gccatcttct cgccgctag agccgctgcc       1980 caccaggtgg tgccagccct gaatatctgc aaggccaagg cctgtaaagc catcgaagcc      2040
gctgcttgga acaccgagcc caagcactgc ttcaagaagg gcggccagca catcgaagtg      2100
tggttcgacg ctgcagccta cgtggcctgg gacagcgtgt actactgtgg cgacgacggc      2160
tggtgcaaga ccgccgctgc agaggccgag aagtatggct gcaagggcac ctgggaagtg      2220
catttcggcg cagctgccaa ctccatcgac tgcaacgaca gcatgtgcag caccttcgac      2280
gacaacgtgt ccgccaccga gctcgtgaaa gctgccgctg accatattga ttactggaaa      2340
ctgattcgcc tggaatgcgc tattttctac aaagccaggg ccgcagcacg gcggctgtcc      2400
tcagatcagg atcagagcca ggctgctgca ctcgtgacca agtacccct gctgaagctg       2460 ctgagcgccg cagcaagacc ccccaacatg ggagtgaagg cccacggcaa gtgcatctgg      2520
gagaacaagg tgttcatcgt gccccaccctg tgccccgtgc ctctggatcc aacatatcct    2580
ctgctgaaac tgctgaccgc tgccgccacc cagaccacca cacctgagaa tacctccctg      2640
gtggaactga gagtgaccac ccccaagagc acagtcgtga tcaggctgca cctggctgcc      2700
gcaaccacca gatacctct gctgtccctg ctgaacagct acagcacccc ccctcatcgg       2760
atccctgccc cttgtccttg ggctcctcag aggcctgccg ctgcacctat ccctaagcct      2820
tctccatggg cccctgccgc agctagaatc ccagctccat gtccatgggc accagctgct      2880
gctcccagac ctcctcattg cccttgggtg ccagcagccg ctcctccacc tcctcctaga      2940
ccttgggccc cagccgccgc ttgtttcctg ctgtgcttct gtgtgctgct gtgcgtgtgc      3000
ctgctgatca gaccctgct gctgagtgtg tccacctacg cagctgctct gcggccactg       3060
ctgctgtcca tctctgtgta cgcacaggtg ctggtgctgg tgctgctgct gtgggtgtcc      3120
atcggatctg ccgcagcact gctgccctcc gtgtgcatgt gtgcctatgc ctgggtgctg      3180
gtgttcgtgt acatcgtcgt gattaccagc cccgccaccg cagccgcaat cgtgtacagg      3240
gacggcaacc cttacgccgt gtgcgacaag tgcctgaagt tctacagcaa gatcagcgag      3300
taccgccact actgctacag cctgtacggc accaccctgg aacagcagta caacaagccc      3360
ctgtgcgatc tgctgatccg gtgcatcaac gcagccgctg tggtgtacag agacagcatc      3420
ccacacgccg cctgccacaa gtgtatcgac ttctactccc ggatcagaga gctgagacac      3480
tactccgact ccgtgtacgg cgatacctg gaaaagctga ccaataccgg cctgtacaac       3540
ctgctgatta gatgcctgcg ggcagccgca gtgttctgca gaaaagccct gaccgccagc      3600
gaggtgtaca cttcgccta caccgatctg cgggtggtgt accgggatgc tgctgcctcc      3660
aaagtgcgga agctgcggta ctacaactgc tctgtgtatg cgcctccct ggcagctgcc       3720 gtgtattgca agggacagct gaccgagaca gaggtgctga tttcgccttt cacagacctg     3780
accatcgtgt atagagatgc agctgctagc aaggtgtccg agttccggtg gtacagatat     3840
agcgtgtacg aacaacact ggcagcagct tgcgtggaat gcaagaaaac actgcagcgg       3900
agcgaagtgt acgatgctgc agcttgccag aggccgctgt gtcctcagga aagaaaaga     3960 cacgtggacc tgaacaagcg gttccacgca gcagctaccc tgcacgagta catgctggac     4020
ctgcagcccg agacaaccga cctgtactgc tacgagcagg cagctgcacc cgaaaaccaca    4080 gatctgcact gttatgagca gctgggagac agctccgatg aagaggacac cggcggactg     4140
```

```
gatgctgccg ctggggatga ggacgaggat gaggtggacc atctgcagga acagccccag    4200
caggccagaa gggatgagca gcaccctgc tatctgatcg agacacagtg ctgcagatgc      4260
gagagcctgg tggccgctgc tgaggaaaac gacgagatcg acggcgtgaa ccaccagcat    4320
ctgcccgcta aagggccga gcctcagaga cacaccatgc tgtgtatgtg ttgcaagtgc     4380
gaggcccgga tcgccggatc tggacctggc gctagcggaa agcccatccc caatccactg    4440
ctgggcctgg actccacccg gacctgataa                                       4470
```

<210> SEQ ID NO 76
<211> LENGTH: 1488
<212> TYPE: PRT
<213> ORGANISM: Artificial Sequence
<220> FEATURE:
<223> OTHER INFORMATION: vaccine construct

<400> SEQUENCE: 76

```
Met Asp Ala Met Lys Arg Gly Leu Cys Cys Val Leu Leu Cys Gly
1               5                   10                  15

Ala Val Phe Val Ser Pro Ser Gln Glu Ile His Ala Arg Phe Arg Arg
            20                  25                  30

Gly Ser Lys Leu Ala Asp Glu Asp Glu Thr Ala Tyr Asp Ser Gly Thr
        35                  40                  45

Asp Leu Ile Asp Phe Ile Asp Asp Ser Ala Ala Asp Glu Asn Glu
    50                  55                  60

Asn Asp Ser Asp Thr Gly Glu Asp Met Val Asp Phe Ile Asp Asn Ala
65                  70                  75                  80

Ala Ala Asp Glu Thr Asp Glu Glu Ser Thr Glu Ser Asp Leu Asp Gly
            85                  90                  95

Phe Ile Asp Asn Ser Ala Ala Gln Leu Ala Asp Ser Asp Ser Asn
            100                 105                 110

Ala Cys Ala Phe Leu Lys Ala Ala Ala Gln Leu Ala Asp Val Asn Ser
        115                 120                 125

Asn Ala Ala Ala Phe Leu Lys Ala Ala Ala Asn Cys Ile Leu Leu Tyr
    130                 135                 140

Gly Ala Ala Asn Thr Gly Lys Ser Leu Phe Gly Met Ser Leu Ala Ala
145                 150                 155                 160

Ala Asn Cys Leu Val Leu Cys Gly Pro Ala Asn Thr Gly Lys Ser Tyr
                165                 170                 175

Phe Gly Met Ser Leu Ala Ala Ala Asn Cys Leu Val Ile Tyr Gly Pro
            180                 185                 190

Pro Asn Thr Gly Lys Ser Cys Phe Ala Met Ser Leu Ala Ala Ala Trp
        195                 200                 205

Pro Tyr Leu His Ser Arg Leu Val Val Phe Thr Phe Pro Asn Pro Phe
    210                 215                 220

Ala Ala Ala Trp Pro Tyr Leu Glu Ser Arg Ile Thr Val Phe Glu Phe
225                 230                 235                 240

Pro Asn Ala Phe Ala Ala Ala Leu Arg Tyr Leu His Ser Arg Ile His
                245                 250                 255

Val Leu Gln Phe Leu Asn Pro Phe Ala Ala Ala Asn Val Cys Gln Asp
            260                 265                 270

Lys Ile Leu Glu His Tyr Glu Asn Asp Ser Lys Asp Ala Ala Ala Ile
        275                 280                 285

Leu Glu His Tyr Glu Asn Asp Ser Lys Asp Leu Cys Asp His Ile Ala
    290                 295                 300
```

```
Ala Ala Cys Asp His Ile Asp Tyr Trp Lys His Ile Arg Leu Glu Cys
305                 310                 315                 320

Ala Ile Met Tyr Lys Ala Arg Ala Ala Ala Ile Arg Leu Glu Cys Ala
                325                 330                 335

Ile Met Tyr Lys Ala Arg Glu Met Gly Phe His Ala Ala Ala Gln Phe
            340                 345                 350

Asp Gly Asp Ile Cys Asn Thr Met His Tyr Thr Asn Trp Ala Ala Ala
        355                 360                 365

Ile Tyr Ile Cys Glu Asp Ala Gln Cys Thr Val Val Glu Gly Gln Val
    370                 375                 380

Asp Ala Ala Lys Lys Trp Glu Val His Ala Gly Gln Val Ile
385                 390                 395                 400

Leu Cys Pro Glu Ser Ala Ala Ala Gly Gln Arg Arg Ile Lys Arg Pro
                405                 410                 415

Arg Ser Glu Ala Ala Ala Asn Cys His Pro Asn Lys Leu Leu Ala Ala
                420                 425                 430

Ala Ile Leu Lys Cys Leu Arg Tyr Arg Phe Lys Lys His Cys Lys Leu
        435                 440                 445

Ala Ala Ala Ser Ser Thr Trp His Trp Thr Cys His Asp Gly Lys His
        450                 455                 460

Lys Ala Ala Ala Trp His Trp Thr Cys His Asp Gly Lys His Lys Asn
465                 470                 475                 480

Ala Ile Val Thr Leu Thr Tyr Ala Ala Ala Tyr Glu Ala Asp Lys Asn
                485                 490                 495

Asp Leu Asn Ala Gln Ile Glu His Trp Lys Leu Ile Arg Met Glu Cys
            500                 505                 510

Ala Ile Phe Tyr Lys Ala Lys Glu Leu Gly Ile Ser Ala Ala Ala Ile
        515                 520                 525

Cys His Gln Val Val Pro Pro Leu Ala Ser Lys Ala Lys Ala Cys
    530                 535                 540

Gln Ala Ile Glu Leu Gln Leu Ala Leu Glu Ala Leu Asn Ala Ser Pro
545                 550                 555                 560

Tyr Ala Ala Ala Asp Glu Trp Thr Leu Gln Gln Thr Ser Leu Glu Met
                565                 570                 575

Trp Leu Ala Glu Pro Gln Ala Ala Ala Phe Lys Lys His Gly Ile Thr
            580                 585                 590

Ile Thr Val Gln Tyr Asp Asn Asp Lys Ala Asn Thr Met Asp Tyr Thr
        595                 600                 605

Asn Trp Lys Glu Ile Tyr Ala Ala Val Ile Val Cys Pro Ala Ser
610                 615                 620

Ile Pro Ser Asp Glu Ile Ser Thr Glu Glu Ala Ala Asp His Ile
625                 630                 635                 640

Asp Tyr Trp Lys Ala Ile Arg Gln Glu Asn Ala Ile Phe Phe Ala Ala
                645                 650                 655

Arg Ala Ala Ala His Gln Val Val Pro Ala Leu Asn Ile Cys Lys Ala
                660                 665                 670

Lys Ala Cys Lys Ala Ile Glu Ala Ala Trp Asn Thr Glu Pro Lys
                675                 680                 685

His Cys Phe Lys Lys Gly Gly Gln His Ile Glu Val Trp Phe Asp Ala
            690                 695                 700

Ala Ala Tyr Val Ala Trp Asp Ser Val Tyr Tyr Cys Gly Asp Asp Gly
705                 710                 715                 720
```

-continued

Trp Cys Lys Thr Ala Ala Glu Ala Glu Lys Tyr Gly Cys Lys Gly
        725                 730                 735

Thr Trp Glu Val His Phe Gly Ala Ala Ala Asn Ser Ile Asp Cys Asn
        740                 745                 750

Asp Ser Met Cys Ser Thr Phe Asp Asp Asn Val Ser Ala Thr Glu Leu
        755                 760                 765

Val Lys Ala Ala Ala Asp His Ile Asp Tyr Trp Lys Leu Ile Arg Leu
        770                 775                 780

Glu Cys Ala Ile Phe Tyr Lys Ala Arg Ala Ala Arg Arg Leu Ser
785                 790                 795                 800

Ser Asp Gln Asp Gln Ser Gln Ala Ala Ala Leu Val Thr Lys Tyr Pro
                805                 810                 815

Leu Leu Lys Leu Leu Ser Ala Ala Ala Arg Pro Pro Asn Met Gly Val
                820                 825                 830

Lys Ala His Gly Lys Cys Ile Trp Glu Asn Lys Val Phe Ile Val Pro
                835                 840                 845

Thr Leu Cys Pro Val Pro Leu Asp Pro Thr Tyr Pro Leu Leu Lys Leu
        850                 855                 860

Leu Thr Ala Ala Ala Thr Gln Thr Thr Thr Pro Glu Asn Thr Ser Leu
865                 870                 875                 880

Val Glu Leu Arg Val Thr Thr Pro Lys Ser Thr Val Val Ile Arg Leu
                885                 890                 895

His Leu Ala Ala Ala Thr Thr Arg Tyr Pro Leu Leu Ser Leu Leu Asn
                900                 905                 910

Ser Tyr Ser Thr Pro Pro His Arg Ile Pro Ala Pro Cys Pro Trp Ala
        915                 920                 925

Pro Gln Arg Pro Ala Ala Pro Ile Pro Lys Pro Ser Pro Trp Ala
        930                 935                 940

Pro Ala Ala Ala Arg Ile Pro Ala Pro Cys Pro Trp Ala Pro Ala Ala
945                 950                 955                 960

Ala Pro Arg Pro Pro His Cys Pro Trp Val Pro Ala Ala Ala Pro Pro
                965                 970                 975

Pro Pro Pro Arg Pro Trp Ala Pro Ala Ala Ala Cys Phe Leu Leu Cys
                980                 985                 990

Phe Cys Val Leu Leu Cys Val Cys Leu Leu Ile Arg Pro Leu Leu Leu
        995                 1000                1005

Ser Val Ser Thr Tyr Ala Ala Ala Leu Arg Pro Leu Leu Leu Ser
        1010                1015                1020

Ile Ser Val Tyr Ala Gln Val Leu Val Leu Val Leu Leu Leu Trp
        1025                1030                1035

Val Ser Ile Gly Ser Ala Ala Ala Leu Leu Pro Ser Val Cys Met
        1040                1045                1050

Cys Ala Tyr Ala Trp Val Leu Val Phe Val Tyr Ile Val Val Ile
        1055                1060                1065

Thr Ser Pro Ala Thr Ala Ala Ala Ile Val Tyr Arg Asp Gly Asn
        1070                1075                1080

Pro Tyr Ala Val Cys Asp Lys Cys Leu Lys Phe Tyr Ser Lys Ile
        1085                1090                1095

Ser Glu Tyr Arg His Tyr Cys Tyr Ser Leu Tyr Gly Thr Thr Leu
        1100                1105                1110

Glu Gln Gln Tyr Asn Lys Pro Leu Cys Asp Leu Leu Ile Arg Cys
        1115                1120                1125

Ile Asn Ala Ala Ala Val Val Tyr Arg Asp Ser Ile Pro His Ala

```
                    1130              1135              1140

Ala Cys His Lys Cys Ile Asp Phe Tyr Ser Arg Ile Arg Glu Leu
    1145              1150              1155

Arg His Tyr Ser Asp Ser Val Tyr Gly Asp Thr Leu Glu Lys Leu
    1160              1165              1170

Thr Asn Thr Gly Leu Tyr Asn Leu Leu Ile Arg Cys Leu Arg Ala
    1175              1180              1185

Ala Ala Val Phe Cys Lys Lys Ala Leu Thr Ala Ser Glu Val Tyr
    1190              1195              1200

Asn Phe Ala Tyr Thr Asp Leu Arg Val Val Tyr Arg Asp Ala Ala
    1205              1210              1215

Ala Ser Lys Val Arg Lys Leu Arg Tyr Tyr Asn Cys Ser Val Tyr
    1220              1225              1230

Gly Ala Ser Leu Ala Ala Ala Val Tyr Cys Lys Gly Gln Leu Thr
    1235              1240              1245

Glu Thr Glu Val Leu Asp Phe Ala Phe Thr Asp Leu Thr Ile Val
    1250              1255              1260

Tyr Arg Asp Ala Ala Ala Ser Lys Val Ser Glu Phe Arg Trp Tyr
    1265              1270              1275

Arg Tyr Ser Val Tyr Gly Thr Thr Leu Ala Ala Ala Cys Val Glu
    1280              1285              1290

Cys Lys Lys Thr Leu Gln Arg Ser Glu Val Tyr Asp Ala Ala Ala
    1295              1300              1305

Cys Gln Arg Pro Leu Cys Pro Gln Glu Lys Lys Arg His Val Asp
    1310              1315              1320

Leu Asn Lys Arg Phe His Ala Ala Ala Thr Leu His Glu Tyr Met
    1325              1330              1335

Leu Asp Leu Gln Pro Glu Thr Thr Asp Leu Tyr Cys Tyr Glu Gln
    1340              1345              1350

Ala Ala Ala Pro Glu Thr Thr Asp Leu His Cys Tyr Glu Gln Leu
    1355              1360              1365

Gly Asp Ser Ser Asp Glu Glu Asp Thr Gly Gly Leu Asp Ala Ala
    1370              1375              1380

Ala Gly Asp Glu Asp Glu Asp Glu Val Asp His Leu Gln Glu Gln
    1385              1390              1395

Pro Gln Gln Ala Arg Arg Asp Glu Gln His Pro Cys Tyr Leu Ile
    1400              1405              1410

Glu Thr Gln Cys Cys Arg Cys Glu Ser Leu Val Ala Ala Ala Glu
    1415              1420              1425

Glu Asn Asp Glu Ile Asp Gly Val Asn His Gln His Leu Pro Ala
    1430              1435              1440

Arg Arg Ala Glu Pro Gln Arg His Thr Met Leu Cys Met Cys Cys
    1445              1450              1455

Lys Cys Glu Ala Arg Ile Ala Gly Ser Gly Pro Ala Ser Gly
    1460              1465              1470

Lys Pro Ile Pro Asn Pro Leu Leu Gly Leu Asp Ser Thr Arg Thr
    1475              1480              1485

<210> SEQ ID NO 77
<211> LENGTH: 20
<212> TYPE: PRT
<213> ORGANISM: Artificial Sequence
<220> FEATURE:
<223> OTHER INFORMATION: consensus sequence
<220> FEATURE:
```

```
<221> NAME/KEY: misc_feature
<222> LOCATION: (11)..(11)
<223> OTHER INFORMATION: Xaa can be any naturally occurring amino acid

<400> SEQUENCE: 77

Asp Glu Asp Glu Asn Ala Ser Asp Thr Gly Xaa Asp Leu Val Asp Phe
1               5                   10                  15

Ile Asp Asn Ser
            20

<210> SEQ ID NO 78
<211> LENGTH: 19
<212> TYPE: PRT
<213> ORGANISM: Human papillomavirus type 16

<400> SEQUENCE: 78

Asp Glu Asn Glu Asn Asp Ser Thr Gly Glu Asp Leu Val Asp Phe Ile
1               5                   10                  15

Val Asn Asp

<210> SEQ ID NO 79
<211> LENGTH: 20
<212> TYPE: PRT
<213> ORGANISM: Human papillomavirus type 18

<400> SEQUENCE: 79

Asp Glu Asp Glu Asn Ala Thr Asp Thr Gly Ser Asp Met Val Asp Phe
1               5                   10                  15

Ile Asp Thr Gln
            20

<210> SEQ ID NO 80
<211> LENGTH: 20
<212> TYPE: PRT
<213> ORGANISM: Human papillomavirus type 31

<400> SEQUENCE: 80

Asp Glu Asn Glu Asp Ser Ser Asp Thr Gly Glu Asp Met Val Asp Phe
1               5                   10                  15

Ile Asp Asn Cys
            20

<210> SEQ ID NO 81
<211> LENGTH: 20
<212> TYPE: PRT
<213> ORGANISM: Human papillomavirus type 52

<400> SEQUENCE: 81

Asp Glu Asp Glu Asn Ala Tyr Asp Ser Gly Thr Asp Leu Ile Asp Phe
1               5                   10                  15

Ile Asp Asp Ser
            20

<210> SEQ ID NO 82
<211> LENGTH: 19
<212> TYPE: PRT
<213> ORGANISM: Human papillomavirus type 53

<400> SEQUENCE: 82

Asp Glu Thr Asp Glu Glu Ser Thr Glu Ser Asp Leu Asp Gly Phe Ile
1               5                   10                  15

Asp Asn Ser
```

<210> SEQ ID NO 83
<211> LENGTH: 20
<212> TYPE: PRT
<213> ORGANISM: Human papillomavirus type 58

<400> SEQUENCE: 83

Asp Glu Asp Glu Thr Ala Asp Asp Ser Gly Thr Asp Leu Ile Glu Phe
1               5                   10                  15

Ile Asp Asp Ser
            20

<210> SEQ ID NO 84
<211> LENGTH: 15
<212> TYPE: PRT
<213> ORGANISM: Artificial Sequence
<220> FEATURE:
<223> OTHER INFORMATION: concensus sequence

<400> SEQUENCE: 84

Ala Gln Leu Ala Asp Val Asn Ser Asn Ala Ala Ala Phe Leu Lys
1               5                   10                  15

<210> SEQ ID NO 85
<211> LENGTH: 15
<212> TYPE: PRT
<213> ORGANISM: Human papillomavirus type 16

<400> SEQUENCE: 85

Ala Gln Leu Ala Asp Thr Asn Ser Asn Ala Ser Ala Phe Leu Lys
1               5                   10                  15

<210> SEQ ID NO 86
<211> LENGTH: 15
<212> TYPE: PRT
<213> ORGANISM: Human papillomavirus type 18

<400> SEQUENCE: 86

Ala Leu Leu Ala Asp Ser Asn Ser Asn Ala Ala Ala Phe Leu Lys
1               5                   10                  15

<210> SEQ ID NO 87
<211> LENGTH: 15
<212> TYPE: PRT
<213> ORGANISM: Human papillomavirus type 31

<400> SEQUENCE: 87

Ala Gln Leu Ala Asp Ser Asp Ser Asn Ala Cys Ala Phe Leu Lys
1               5                   10                  15

<210> SEQ ID NO 88
<211> LENGTH: 15
<212> TYPE: PRT
<213> ORGANISM: Human papillomavirus type 52

<400> SEQUENCE: 88

Ala Gln Leu Ala Asp Val Asn Ser Asn Ala Ala Ala Phe Leu Lys
1               5                   10                  15

<210> SEQ ID NO 89
<211> LENGTH: 15
<212> TYPE: PRT
<213> ORGANISM: Human papillomavirus type 53

<400> SEQUENCE: 89

Ala Gln Leu Ala Asp Val Asp Ser Asn Ala Gln Ala Phe Leu Lys
1               5                   10                  15

<210> SEQ ID NO 90
<211> LENGTH: 15
<212> TYPE: PRT
<213> ORGANISM: Human papillomavirus type 58

<400> SEQUENCE: 90

Ala Gln Leu Ala Asp Val Asn Ser Asn Ala Ala Ala Phe Leu Arg
1               5                   10                  15

<210> SEQ ID NO 91
<211> LENGTH: 20
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 91

Asn Cys Leu Xaa Leu Tyr Gly Pro Ala Asn Thr Gly Lys Ser Tyr Phe
1               5                   10                  15

Gly Met Ser Leu
            20

<210> SEQ ID NO 92
<211> LENGTH: 20
<212> TYPE: PRT
<213> ORGANISM: Human papillomavirus type 16

<400> SEQUENCE: 92

Asn Cys Ile Leu Leu Tyr Gly Ala Ala Asn Thr Gly Lys Ser Leu Phe
1               5                   10                  15

Gly Met Ser Leu
            20

<210> SEQ ID NO 93
<211> LENGTH: 20
<212> TYPE: PRT
<213> ORGANISM: Human papillomavirus type 18

<400> SEQUENCE: 93

Asn Cys Leu Val Phe Cys Gly Pro Ala Asn Thr Gly Lys Ser Tyr Phe
1               5                   10                  15

Gly Met Ser Phe
            20

<210> SEQ ID NO 94
<211> LENGTH: 20
<212> TYPE: PRT
<213> ORGANISM: Human papillomavirus type 31

<400> SEQUENCE: 94

Asn Cys Ile Leu Ile His Gly Ala Pro Asn Thr Gly Lys Ser Tyr Phe
1               5                   10                  15

Gly Met Ser Leu
            20

<210> SEQ ID NO 95

```
<211> LENGTH: 20
<212> TYPE: PRT
<213> ORGANISM: Human papillomavirus type 52

<400> SEQUENCE: 95

Asn Cys Leu Val Leu Tyr Gly Pro Ala Asn Thr Gly Lys Ser Tyr Phe
1               5                   10                  15

Gly Met Ser Leu
            20

<210> SEQ ID NO 96
<211> LENGTH: 20
<212> TYPE: PRT
<213> ORGANISM: Human papillomavirus type 53

<400> SEQUENCE: 96

Asn Cys Leu Val Ile Tyr Gly Pro Pro Asn Thr Gly Lys Ser Cys Gly
1               5                   10                  15

Ala Met Ser Leu
            20

<210> SEQ ID NO 97
<211> LENGTH: 20
<212> TYPE: PRT
<213> ORGANISM: Human papillomavirus type 58

<400> SEQUENCE: 97

Ser Cys Met Leu Leu Cys Gly Pro Ala Asn Thr Gly Lys Ser Tyr Phe
1               5                   10                  15

Gly Met Ser Leu
            20

<210> SEQ ID NO 98
<211> LENGTH: 20
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (11)..(11)
<223> OTHER INFORMATION: Xaa can be any naturally occurring amino acid

<400> SEQUENCE: 98

Asp Glu Asp Glu Asn Ala Ser Asp Thr Gly Xaa Asp Leu Val Asp Phe
1               5                   10                  15

Ile Asp Asn Ser
            20

<210> SEQ ID NO 99
<211> LENGTH: 20
<212> TYPE: PRT
<213> ORGANISM: Human papillomavirus type 16

<400> SEQUENCE: 99

Asp Glu Asn Glu Asn Asp Ser Asp Thr Gly Glu Asp Leu Val Asp Phe
1               5                   10                  15

Ile Val Asn Asp
            20

<210> SEQ ID NO 100
<211> LENGTH: 20
<212> TYPE: PRT
<213> ORGANISM: Human papillomavirus type 18
```

<400> SEQUENCE: 100

Asp Glu Asp Glu Asn Ala Thr Asp Thr Gly Ser Asp Met Val Asp Phe
1               5                   10                  15

Ile Asp Thr Gln
            20

<210> SEQ ID NO 101
<211> LENGTH: 20
<212> TYPE: PRT
<213> ORGANISM: Human papillomavirus type 31

<400> SEQUENCE: 101

Asp Glu Asn Glu Asp Ser Ser Asp Thr Gly Glu Asp Met Val Asp Phe
1               5                   10                  15

Ile Asp Asn Cys
            20

<210> SEQ ID NO 102
<211> LENGTH: 20
<212> TYPE: PRT
<213> ORGANISM: Human papillomavirus type 52

<400> SEQUENCE: 102

Asp Glu Asp Glu Asn Ala Tyr Asp Ser Gly Thr Asp Leu Ile Asp Phe
1               5                   10                  15

Ile Asp Asp Ser
            20

<210> SEQ ID NO 103
<211> LENGTH: 19
<212> TYPE: PRT
<213> ORGANISM: Human papillomavirus type 53

<400> SEQUENCE: 103

Asp Glu Thr Asp Glu Glu Ser Thr Glu Ser Asp Leu Asp Gly Phe Ile
1               5                   10                  15

Asp Asn Ser

<210> SEQ ID NO 104
<211> LENGTH: 20
<212> TYPE: PRT
<213> ORGANISM: Human papillomavirus type 58

<400> SEQUENCE: 104

Asp Glu Asp Glu Thr Ala Asp Asp Ser Gly Thr Asp Leu Ile Glu Phe
1               5                   10                  15

Ile Asp Asp Ser
            20

<210> SEQ ID NO 105
<211> LENGTH: 20
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

```
<220> FEATURE:
<221> NAME/KEY: misc_feature
<222> LOCATION: (15)..(15)
<223> OTHER INFORMATION: Xaa can be any naturally occurring amino acid

<400> SEQUENCE: 105

Asp Glu Asp Glu Xaa Ala Xaa Asp Ser Gly Thr Asp Leu Ile Xaa Phe
1               5                   10                  15

Ile Asp Asp Ser
            20

<210> SEQ ID NO 106
<211> LENGTH: 20
<212> TYPE: PRT
<213> ORGANISM: Human papillomavirus type 52

<400> SEQUENCE: 106

Asp Glu Asp Glu Asn Ala Tyr Asp Ser Gly Thr Asp Leu Ile Asp Phe
1               5                   10                  15

Ile Asp Asp Ser
            20

<210> SEQ ID NO 107
<211> LENGTH: 20
<212> TYPE: PRT
<213> ORGANISM: Human papillomavirus type 58

<400> SEQUENCE: 107

Asp Glu Asp Glu Thr Ala Asp Asp Ser Gly Thr Asp Leu Ile Glu Phe
1               5                   10                  15

Ile Asp Asp Ser
            20

<210> SEQ ID NO 108
<211> LENGTH: 15
<212> TYPE: PRT
<213> ORGANISM: Artificial Sequence
<220> FEATURE:
<223> OTHER INFORMATION: consensus sequence

<400> SEQUENCE: 108

Ala Gln Leu Ala Asp Ser Asp Ser Asn Ala Cys Ala Phe Leu Lys
1               5                   10                  15

<210> SEQ ID NO 109
<211> LENGTH: 15
<212> TYPE: PRT
<213> ORGANISM: Human papillomavirus type 31

<400> SEQUENCE: 109

Ala Gln Leu Ala Asp Ser Asp Ser Asn Ala Cys Ala Phe Leu Lys
1               5                   10                  15

<210> SEQ ID NO 110
<211> LENGTH: 15
<212> TYPE: PRT
<213> ORGANISM: Human papillomavirus type 53

<400> SEQUENCE: 110

Ala Gln Leu Ala Asp Val Asp Ser Asn Ala Gln Ala Phe Leu Lys
1               5                   10                  15

<210> SEQ ID NO 111
<211> LENGTH: 20
```

```
<212> TYPE: PRT
<213> ORGANISM: Artificial Sequence
<220> FEATURE:
<223> OTHER INFORMATION: consensus sequence

<400> SEQUENCE: 111

Asn Cys Ile Leu Leu Tyr Gly Ala Ala Asn Thr Gly Lys Ser Leu Phe
1               5                   10                  15

Gly Met Ser Leu
            20

<210> SEQ ID NO 112
<211> LENGTH: 20
<212> TYPE: PRT
<213> ORGANISM: Human papillomavirus type 16

<400> SEQUENCE: 112

Asn Cys Ile Leu Leu Tyr Gly Ala Ala Asn Thr Gly Lys Ser Leu Phe
1               5                   10                  15

Gly Met Ser Leu
            20

<210> SEQ ID NO 113
<211> LENGTH: 20
<212> TYPE: PRT
<213> ORGANISM: Human papillomavirus type 31

<400> SEQUENCE: 113

Asn Cys Ile Leu Ile His Gly Ala Pro Asn Thr Gly Lys Ser Tyr Phe
1               5                   10                  15

Gly Met Ser Leu
            20

<210> SEQ ID NO 114
<211> LENGTH: 17
<212> TYPE: PRT
<213> ORGANISM: Artificial Sequence
<220> FEATURE:
<223> OTHER INFORMATION: consensus sequence

<400> SEQUENCE: 114

Trp Pro Tyr Leu His Ser Arg Leu Val Val Phe Thr Phe Pro Asn Pro
1               5                   10                  15

Phe

<210> SEQ ID NO 115
<211> LENGTH: 17
<212> TYPE: PRT
<213> ORGANISM: Human papillomavirus type 16

<400> SEQUENCE: 115

Trp Pro Tyr Leu His Asn Arg Leu Val Val Phe Thr Phe Pro Asn Glu
1               5                   10                  15

Phe

<210> SEQ ID NO 116
<211> LENGTH: 17
<212> TYPE: PRT
<213> ORGANISM: Human papillomavirus type 31

<400> SEQUENCE: 116

Trp Pro Tyr Leu His Ser Arg Leu Val Val Phe Thr Phe Pro Asn Pro
1               5                   10                  15
```

Phe

<210> SEQ ID NO 117
<211> LENGTH: 17
<212> TYPE: PRT
<213> ORGANISM: Human papillomavirus type 52

<400> SEQUENCE: 117

Trp Pro Tyr Leu His Ser Arg Leu Val Val Phe His Phe Lys Asn Pro
1               5                   10                  15

Phe

<210> SEQ ID NO 118
<211> LENGTH: 19
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (6)..(6)
<223> OTHER INFORMATION: Xaa can be any naturally occurring amino acid

<400> SEQUENCE: 118

Asp Glu Asn Glu Asn Xaa Ser Asp Thr Gly Glu Asp Met Val Asp Phe
1               5                   10                  15

Ile Asp Asn

<210> SEQ ID NO 119
<211> LENGTH: 19
<212> TYPE: PRT
<213> ORGANISM: Human papillomavirus type 31

<400> SEQUENCE: 119

Asp Glu Asn Glu Asp Ser Ser Asp Thr Gly Glu Asp Met Val Asp Phe
1               5                   10                  15

Ile Asp Asn

<210> SEQ ID NO 120
<211> LENGTH: 19
<212> TYPE: PRT
<213> ORGANISM: Human papillomavirus type 16

<400> SEQUENCE: 120

Asp Glu Asn Glu Asn Asp Ser Asp Thr Gly Glu Asp Leu Val Asp Phe
1               5                   10                  15

Ile Val Asn

<210> SEQ ID NO 121
<211> LENGTH: 19
<212> TYPE: PRT
<213> ORGANISM: Human papillomavirus type 18

<400> SEQUENCE: 121

Asp Glu Asp Glu Asn Ala Thr Asp Thr Gly Ser Asp Met Val Asp Phe
1               5                   10                  15

Ile Asp Thr

<210> SEQ ID NO 122
<211> LENGTH: 19
<212> TYPE: PRT
<213> ORGANISM: Human papillomavirus type 53

-continued

```
<400> SEQUENCE: 122

Asp Glu Thr Asp Glu Glu Ser Thr Glu Ser Asp Leu Asp Gly Phe Ile
1               5                   10                  15

Asp Asn Ser

<210> SEQ ID NO 123
<211> LENGTH: 15
<212> TYPE: PRT
<213> ORGANISM: Artificial Sequence
<220> FEATURE:
<223> OTHER INFORMATION: consensus sequence

<400> SEQUENCE: 123

Ala Gln Leu Ala Asp Val Asn Ser Asn Ala Ala Ala Phe Leu Lys
1               5                   10                  15

<210> SEQ ID NO 124
<211> LENGTH: 15
<212> TYPE: PRT
<213> ORGANISM: Human papillomavirus type 52

<400> SEQUENCE: 124

Ala Gln Leu Ala Asp Val Asn Ser Asn Ala Ala Ala Phe Leu Lys
1               5                   10                  15

<210> SEQ ID NO 125
<211> LENGTH: 15
<212> TYPE: PRT
<213> ORGANISM: Human papillomavirus type 58

<400> SEQUENCE: 125

Ala Gln Leu Ala Asp Val Asn Ser Asn Ala Ala Ala Phe Leu Arg
1               5                   10                  15

<210> SEQ ID NO 126
<211> LENGTH: 15
<212> TYPE: PRT
<213> ORGANISM: Human papillomavirus type 18

<400> SEQUENCE: 126

Ala Leu Leu Ala Asp Ser Asn Ser Asn Ala Ala Ala Phe Leu Lys
1               5                   10                  15

<210> SEQ ID NO 127
<211> LENGTH: 15
<212> TYPE: PRT
<213> ORGANISM: Human papillomavirus type 16

<400> SEQUENCE: 127

Ala Gln Leu Ala Asp Thr Asn Ser Asn Ala Ser Ala Phe Leu Lys
1               5                   10                  15

<210> SEQ ID NO 128
<211> LENGTH: 20
<212> TYPE: PRT
<213> ORGANISM: Artificial Sequence
<220> FEATURE:
<223> OTHER INFORMATION: consensus sequence

<400> SEQUENCE: 128

Asn Cys Leu Val Leu Cys Gly Pro Ala Asn Thr Gly Lys Ser Tyr Phe
1               5                   10                  15

Gly Met Ser Leu
```

```
<210> SEQ ID NO 129
<211> LENGTH: 20
<212> TYPE: PRT
<213> ORGANISM: Human papillomavirus type 18

<400> SEQUENCE: 129

Asn Cys Leu Val Phe Cys Gly Pro Ala Asn Thr Gly Lys Ser Tyr Phe
1               5                   10                  15

Gly Met Ser Phe
            20

<210> SEQ ID NO 130
<211> LENGTH: 20
<212> TYPE: PRT
<213> ORGANISM: Human papillomavirus type 52

<400> SEQUENCE: 130

Asn Cys Leu Val Leu Tyr Gly Pro Ala Asn Thr Gly Lys Ser Tyr Phe
1               5                   10                  15

Gly Met Ser Leu
            20

<210> SEQ ID NO 131
<211> LENGTH: 20
<212> TYPE: PRT
<213> ORGANISM: Human papillomavirus type 58

<400> SEQUENCE: 131

Ser Cys Met Leu Leu Cys Gly Pro Ala Asn Thr Gly Lys Ser Tyr Phe
1               5                   10                  15

Gly Met Ser Leu
            20

<210> SEQ ID NO 132
<211> LENGTH: 20
<212> TYPE: PRT
<213> ORGANISM: Human papillomavirus type 53

<400> SEQUENCE: 132

Asn Cys Leu Val Ile Tyr Gly Pro Pro Asn Thr Gly Lys Ser Cys Phe
1               5                   10                  15

Ala Met Ser Leu
            20

<210> SEQ ID NO 133
<211> LENGTH: 16
<212> TYPE: PRT
<213> ORGANISM: Artificial Sequence
<220> FEATURE:
<223> OTHER INFORMATION: consensus sequence

<400> SEQUENCE: 133

Trp Pro Tyr Leu Glu Ser Arg Thr Val Phe Glu Phe Pro Asn Ala Phe
1               5                   10                  15

<210> SEQ ID NO 134
<211> LENGTH: 17
<212> TYPE: PRT
<213> ORGANISM: Human papillomavirus type 18

<400> SEQUENCE: 134
```

```
Trp Pro Tyr Leu Glu Ser Arg Ile Thr Val Phe Glu Phe Pro Asn Ala
1               5                   10                  15

Phe

<210> SEQ ID NO 135
<211> LENGTH: 17
<212> TYPE: PRT
<213> ORGANISM: Human papillomavirus type 58

<400> SEQUENCE: 135

Trp Pro Tyr Leu His Ser Arg Leu Thr Val Phe Glu Phe Asn Asn Pro
1               5                   10                  15

Phe

<210> SEQ ID NO 136
<211> LENGTH: 17
<212> TYPE: PRT
<213> ORGANISM: Human papillomavirus type 53

<400> SEQUENCE: 136

Leu Arg Tyr Leu His Ser Arg Ile His Val Leu Gln Phe Leu Asn Pro
1               5                   10                  15

Phe

<210> SEQ ID NO 137
<211> LENGTH: 20
<212> TYPE: PRT
<213> ORGANISM: Artificial Sequence
<220> FEATURE:
<223> OTHER INFORMATION: consensus sequence

<400> SEQUENCE: 137

Asp His Ile Asp Tyr Trp Lys His Met Arg Leu Glu Cys Ala Ile Tyr
1               5                   10                  15

Tyr Lys Ala Arg
            20

<210> SEQ ID NO 138
<211> LENGTH: 20
<212> TYPE: PRT
<213> ORGANISM: Human papillomavirus type 16

<400> SEQUENCE: 138

Asp His Ile Asp Tyr Trp Lys His Met Arg Leu Glu Cys Ala Ile Tyr
1               5                   10                  15

Tyr Lys Ala Arg
            20

<210> SEQ ID NO 139
<211> LENGTH: 20
<212> TYPE: PRT
<213> ORGANISM: Human papillomavirus type 18

<400> SEQUENCE: 139

Ser Gln Ile Gln Tyr Trp Gln Leu Ile Arg Trp Glu Asn Ala Ile Phe
1               5                   10                  15

Phe Ala Ala Arg
            20

<210> SEQ ID NO 140
<211> LENGTH: 20
<212> TYPE: PRT
```

<213> ORGANISM: Human papillomavirus type 31

<400> SEQUENCE: 140

Asp His Ile Asp Tyr Trp Lys His Ile Arg Leu Glu Cys Val Leu Met
1               5                   10                  15

Tyr Lys Ala Arg
            20

<210> SEQ ID NO 141
<211> LENGTH: 20
<212> TYPE: PRT
<213> ORGANISM: Human papillomavirus type 52

<400> SEQUENCE: 141

Ala Gln Ile Glu His Trp Lys Leu Thr Arg Met Glu Cys Val Leu Phe
1               5                   10                  15

Tyr Lys Ala Lys
            20

<210> SEQ ID NO 142
<211> LENGTH: 20
<212> TYPE: PRT
<213> ORGANISM: Human papillomavirus type 53

<400> SEQUENCE: 142

Asp His Ile Asp Tyr Trp Lys Ala Val Arg Gln Glu Asn Val Ile Tyr
1               5                   10                  15

Tyr Lys Ala Arg
            20

<210> SEQ ID NO 143
<211> LENGTH: 20
<212> TYPE: PRT
<213> ORGANISM: Human papillomavirus type 58

<400> SEQUENCE: 143

Ser Gln Ile Glu His Trp Lys Leu Ile Arg Met Glu Cys Ala Ile Met
1               5                   10                  15

Tyr Thr Ala Arg
            20

<210> SEQ ID NO 144
<211> LENGTH: 20
<212> TYPE: PRT
<213> ORGANISM: Artificial Sequence
<220> FEATURE:
<223> OTHER INFORMATION: consensus sequence

<400> SEQUENCE: 144

Asp His Ile Asp Tyr Trp Lys Leu Ile Arg Leu Glu Cys Ala Ile Phe
1               5                   10                  15

Tyr Lys Ala Arg
            20

<210> SEQ ID NO 145
<211> LENGTH: 15
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (1)..(3)
<223> OTHER INFORMATION: Xaa can be any naturally occurring amino acid

<400> SEQUENCE: 145

Xaa Xaa Xaa Pro Ile Pro Pro Pro Cys Pro Trp Ala Pro Lys Lys
1               5                   10                  15

<210> SEQ ID NO 146
<211> LENGTH: 16
<212> TYPE: PRT
<213> ORGANISM: Human papillomavirus type 16

<400> SEQUENCE: 146

Thr Pro Pro Arg Pro Ile Pro Lys Pro Ser Pro Trp Ala Pro Lys Lys
1               5                   10                  15

<210> SEQ ID NO 147
<211> LENGTH: 16
<212> TYPE: PRT
<213> ORGANISM: Human papillomavirus type 18

<400> SEQUENCE: 147

Thr Pro Pro His Arg Ile Pro Ala Pro Cys Pro Trp Ala Pro Gln Arg
1               5                   10                  15

<210> SEQ ID NO 148
<211> LENGTH: 16
<212> TYPE: PRT
<213> ORGANISM: Human papillomavirus type 31

<400> SEQUENCE: 148

Thr Pro Pro His Arg Ile Pro Lys Pro Ala Pro Trp Ala Pro Val Lys
1               5                   10                  15

<210> SEQ ID NO 149
<211> LENGTH: 12
<212> TYPE: PRT
<213> ORGANISM: Human papillomavirus type 52

<400> SEQUENCE: 149

Pro Arg Pro Pro His Cys Pro Trp Val Pro Lys Thr
1               5                   10

<210> SEQ ID NO 150
<211> LENGTH: 12
<212> TYPE: PRT
<213> ORGANISM: Human papillomavirus type 53

<400> SEQUENCE: 150

Pro Pro Pro Pro Pro Arg Pro Trp Ala Pro Thr Lys
1               5                   10

<210> SEQ ID NO 151
<211> LENGTH: 5
<212> TYPE: PRT
<213> ORGANISM: Human papillomavirus type 58

<400> SEQUENCE: 151

Pro Pro Thr Thr Lys
1               5

<210> SEQ ID NO 152
<211> LENGTH: 10
<212> TYPE: PRT
<213> ORGANISM: Artificial Sequence
<220> FEATURE:
<223> OTHER INFORMATION: consensus sequence -continued

<400> SEQUENCE: 152

Pro Ile Pro Lys Pro Ser Pro Trp Ala Pro
1               5                   10

<210> SEQ ID NO 153
<211> LENGTH: 10
<212> TYPE: PRT
<213> ORGANISM: Human papillomavirus type 16

<400> SEQUENCE: 153

Pro Ile Pro Lys Pro Ser Pro Trp Ala Pro
1               5                   10

<210> SEQ ID NO 154
<211> LENGTH: 10
<212> TYPE: PRT
<213> ORGANISM: Human papillomavirus type 31

<400> SEQUENCE: 154

Arg Ile Pro Lys Pro Ala Pro Trp Ala Pro
1               5                   10

<210> SEQ ID NO 155
<211> LENGTH: 10
<212> TYPE: PRT
<213> ORGANISM: Human papillomavirus type 18

<400> SEQUENCE: 155

Arg Ile Pro Ala Pro Cys Pro Trp Ala Pro
1               5                   10

<210> SEQ ID NO 156
<211> LENGTH: 10
<212> TYPE: PRT
<213> ORGANISM: Human papillomavirus type 52

<400> SEQUENCE: 156

Pro Arg Pro Pro His Cys Pro Trp Val Pro
1               5                   10

<210> SEQ ID NO 157
<211> LENGTH: 10
<212> TYPE: PRT
<213> ORGANISM: Human papillomavirus type 53

<400> SEQUENCE: 157

Pro Pro Pro Pro Pro Arg Pro Trp Ala Pro
1               5                   10

<210> SEQ ID NO 158
<211> LENGTH: 9713
<212> TYPE: DNA
<213> ORGANISM: Artificial Sequence
<220> FEATURE:
<223> OTHER INFORMATION: Plasmid construct

<400> SEQUENCE: 158
agcgcccaat acgcaaaccg cctctccccg cgcgttggcc gattcattaa tgcagctggc    60
acgacaggtt tcccgactgg aaagcgggca gtgagcgcaa cgcaattaat gtgagttagc   120
tcactcatta ggcaccccag gctttacact ttatgcttcc ggctcgtatg ttgtgtggaa   180
ttgtgagcgg ataacaattt cacacaggaa acagctatga ccatgattac gccaagcttg   240

```
catgcatctg gaaacgggca tctccattta agactagatg ccacggggtt taaaatacta    300
atcatgacat tttgtagagc gtaattactt agtaaatccg ccgtactagg ttcatttcct    360
cctcgtttgg atctcacatc agaaattaaa ataatcttag aaggatgcag ttgttttttg    420
atggatcgta gatattcctc atcaacgaac cgagtcacta gagtcacatc acgcaatcca    480
tttaaaatag gatcatgatg gcggccgtca attagcatcc atttgatgat cactcctaaa    540
ttatagaaat gatctctcaa ataacgtata tgtgtaccgg gagcagatcc tatatacact    600
acggtggcac catctaatat accgtgtcgc tgtaacttac taagaaaaaa taattctcct    660
agtaatagtt ttaactgtcc ttgatacggt agttttttg cgacctcatt tgcactttct      720
ggttcgtaat ctaactcatt atcaatttcc tcaaaataca taaacggttt atctaacgac    780
acaacatcca tttttaagta ttatattaaa atttaatcaa tgtttatttt tagttttttta   840
gataaaaaat ataatattat gagtcgatgt aacactttct acacaccgat tgatacatat    900
cattacctcc tattatctct atctcggttt cctcacccaa tcgtttagaa aaggaagcct    960
ccttaaagca tttcatacac acagcagtta gttttaccac catttcagat aatggaataa    1020
gattcaaaat attattaaac ggtttacgtt gaaatgtccc atcgagtgcg gctactataa    1080
ctattttttcc ttcgtttgcc atacagatcc tacgtactcg agcggccgct tatcaggtcc  1140
gggtggagtc caggcccagc agtggattgg ggataggctt gccagaggcg ccaggtccag    1200
agccggcgat tctggcctcg cacttgcagc acatacacag catggtgtgt ctctgaggct    1260
cggcccttct agcgggcaga tgctggtggt tcacgccgtc gatctcgtcg ttctcttcca    1320
ccagagattc gcatctgcag cactgtgtct cgatcagata gcaagggtgc tgttcgtccc    1380
gtctagcctg ctggggctgt tcctgcagat ggtccacttc gtcctcatcc tcgtccccat    1440
ccaggccgcc agtgtcctct tcatcggagc tgtctcccag ctgctcataa cagtgcagat    1500
cagtggtttc aggctgctcg tagcagtaca ggtcggttgt ctcgggctgc agatccagca    1560
tgtactcgtg cagggtgtgg aaccgcttgt tcaggtccac gtgtcttttc ttttcctgcg    1620
gacacagtgg ccgctggcag tcgtacacct cagatctctg cagggttttc ttgcattcca    1680
cgcacagtgt ggtgccatac acggaatatc tgtaccaccg gaactcggac accttggagt    1740
cgcgatacac gattgtcagg tctgtgaagg cgaaatccag cacctctgtc tcggtcagct    1800
gtcccttgca ataccaggg ctggcgccat acacagagca gttgtagtac ctcagcttcc     1860
gcactttgct gtcccgatac accacccgca gatcggtgta ggcgaagttg tacacctcgc    1920
tggctgtcag ggccttcttg cagaacaccc gcaggcatct aatcagcagg ttgtacaggc    1980
cagtgttggt cagcttttcc agggtatcgc cgtacacgga gtcgctgtag tgccgcagct    2040
ctctgattct ggagtagaag tcgatacact tgtggcaggc ggcgtggggg atggagtctc    2100
tgtacaccac gttgatgcac cgaatcagca gatcgcacag gggcttgttg tactgctgtt    2160
ccagggtggt gccgtacagg ctgtagcagt agtgccggta ctcgctgatc ttgctgtaga    2220
acttcaggca cttgtcgcac acggcgtaag gattgccatc ccggtacacg atggcggtgg    2280
cggggctggt aatcacgacg atgtacacga acaccagcac ccaggcatag gcacacatgc    2340
acacgctggg cagcaggctt ccgatggaca cccacagcag cagcaccagc accagcacct    2400
gagcgtacac gctgatagac agcagcagag gcctcaggta ggtggacaca ctcagcagca    2460
ggggtctgat cagcaggcac acgcacagca gcacacaaaa gcagcagcagg aagcaagggg   2520
cccaaggtct tggaggaggt ggaggggca cccatggaca gtgtggaggt ctaggaggtg     2580
cccaggggca aggggcaggg attctagggg cccatggaga aggcttaggg atgggggcc    2640
```

```
tctgaggagc ccaaggacat ggagcaggga tccggtgagg gggggtgctg tagctgttca  2700
gcagtgacag cagtgggtat ctggtggtca ggtgcagcct gatcacgact gtgctcttgg  2760
gggtggtcac tctcagttcc accagggagg tattctcggg ggtggtggtc tgggtggtca  2820
gcagtttcag cagaggatat gttggatcca gaggcacggg gcacagggtg ggcacgatga  2880
acaccttgtt ctcccagatg cacttgccgt gggccttcac gcccatgttg ggggtctgg   2940
acagcagctt cagcaggggg tacttggtca cgagctgaga ctgatcctgg tcgctggaca  3000
gccgccgtct ggccttgtaa aaaatggcac attccaggcg aatcagcttc caatagtcga  3060
tatggtcctt cacgagctcg gtggcggaca cgttgtcgtc gaaggtgctg cacatggagt  3120
cgttgcagtc gatgctgttg ccgaaatgca cttcccaggt gcccttgcag ccgtacttct  3180
cggcctcggt cttgcaccag ccatcgtcgc cgcagtagta cacgctgtcc caggccacgt  3240
agtcgaacca cacttcgatg tgctggccgc ccttcttgaa gcagtgcttg ggctcggtgt  3300
tccactcgat ggctttacag gccttggcct tgcagatatt cagggcgggc accacctggt  3360
gtctggcggc gaagaagatg gcgttttcct gcctgatggc tttccaataa tcaatgtggt  3420
cggcttcctc ggtgctgatc tcatcggagg ggatgctggc ggggcacacg atcacgtaga  3480
tttctttcca atttgtgtaa tccatggtat tggccttgtc attgtcgtac tgcacggtga  3540
tggtgatgcc gtgcttctta aactgggct cggccagcca catttccagg ctggtctgct   3600
gcagggtcca ctcatcgtag gggctggcat tcagggcttc cagggccagc tgcagttcga  3660
tggcctggca ggctttggct ttagaggcgg ccagtggagg caccacctgg tggcagatgc  3720
tgatgcccag ctctttggcc ttatagaaga ttgcacattc catccggatc agtttccagt  3780
gctcgatctg ggcgttcagg tcgttcttgt cggcctcgta gtaggtcagg gtcacaatgg  3840
cgttcttgtg tttcccatcg tgacatgtcc aatgccactt gtgcttgccg tcgtggcagg  3900
tccagtgcca ggtgctgctc agcttgcagt gcttcttgaa tctgtaccgc aggcacttca  3960
ggatcagcag cttgttgggg tggcagttct cgcttctggg cctcttgatc cgccgctggc  4020
cgctctcagg acacaggatc acttggccgc cagcgtgcac ctcccatttc ttgtccacct  4080
ggccttccac cacggtgcac tgggcgtcct cgcagatata gatccagttg gtgtagtgca  4140
tggtgttgca gatgtcgccg tcgaactggt ggaagcccat ctcgcgagcc ttatacataa  4200
tagcacattc cagtctgatc cgggccttgt acatgatggc gcattccagc cggatgtgct  4260
tccagtagtc gatgtgatcg cagatgtggt cgcacaggtc cttggaatca ttctcataat  4320
gttccagaat gtccttgctg tcgttctcgt agtgttccag gatcttgtcc tggcacacgt  4380
tgaaggggtt cagaaactgc agcacgtgga tccgggagtg caggtatctc agaaaggcat  4440
tggggaactc gaacacggtg atccggcttt ccaggtaagg ccagaagggg ttggggaagg  4500
taaacaccac cagtctgctg tgcaggtagg gccacagaga catggcaaag caggacttgc  4560
ctgtgttagg tgggccgtag atcacgagac aattcaggga catgccgaag taggactttc  4620
cggtattggc tgggccgcac agcaccaggc agttcaggct catgccgaac aggctcttgc  4680
cggtgttggc agcgccgtac agcaggatgc agttcttcag aaaagcagcg gcgttgctgt  4740
tcacgtctgc cagctgagcc ttcaggaagg cgcaggcatt gctgtcgctg tcagccagct  4800
gggcggagtt gtcgataaag ccgtccaggt cgctctcggt gctctcttcg tcggtttcgt  4860
cgttgtcgat gaaatccacc atgtcctcgc cggtgtcgga gtcgttctca ttctcgtcgc  4920
tgtcgtcgat gaagtcgatc aggtcggtgc cgctgtcgta ggctgtctcg tcctcgtcgg  4980
```

```
ccagcttgct gcctcttctg aaccgggcgt ggatttcctg gctgggggac acaaacacgg    5040
cgccacacag cagcagcacg cagcacaggc ccctcttcat agcatccatg gtggcggcgc    5100
ggctagcggt accggatcta gatggggatc cgtcactgtt ctttatgatt ctacttcctt    5160
accgtgcaat aaattagaat atattttcta cttttacgag aaattaatta ttgtattat    5220 tatttatggg tgaaaaactt actataaaaa gcgggtgggt ttggaattag tgatcagttt    5280
atgtatatcg caactaccgg gcatatggct atcgacatcg agaacattac ccacatgata    5340
agagattgta tcagtttcgt agtcttgagt attggtatta ctatatagta tatagatgtc    5400
gacctgcagg tcgacgaagt tcctatactt tctagagaat aggaacttcg cagccaagct    5460
ggaattcatc cactttggat aagaaatctg catgataaat atattgatat cctaccacct    5520
attaaagtac cattatctaa tagcaataag atagataaac aaatgttttt tgatgaagtt    5580
attacgtgga taaatatata tcttcaggaa aagggtatta tgttaccaga tgatataaga    5640
gaactcagag atgctattat tccttaacta gttacgtctc tttaggtact tattttgata    5700
cgttacaagt aaaaaactat caaatataaa tggaatctga ttctaatata gcgattgaag    5760
aggatccacc ggtcgccacc atggtgagca agggcgagga gctgttcacc ggggtggtgc    5820
ccatcctggt cgagctggac ggcgacgtaa acggccacaa gttcagcgtg tccggcgagg    5880
gcgagggcga tgccacctac ggcaagctga ccctgaagtt catctgcacc accggcaagc    5940
tgcccgtgcc ctggcccacc ctcgtgacca ccctgaccta cggcgtgcag tgcttcagcc    6000
gctaccccga ccacatgaag cagcacgact tcttcaagtc cgccatgccc gaaggctacg    6060
tccaggagcg caccatcttc ttcaaggacg acggcaacta caagacccgc gccgaggtga    6120
agttcgaggg cgacaccctg gtgaaccgca tcgagctgaa gggcatcgac ttcaaggagg    6180
acggcaacat cctggggcac aagctggagt acaactacaa cagccacaac gtctatatca    6240
tggccgacaa gcagaagaac ggcatcaagg tgaacttcaa gatccgccac aacatcgagg    6300
acggcagcgt gcagctcgcc gaccactacc agcagaacac ccccatcggc gacggccccg    6360
tgctgctgcc cgacaaccac tacctgagca cccagtccgc cctgagcaaa gaccccaacg    6420
agaagcgcga tcacatggtc ctgctggagt tcgtgaccgc cgccgggatc actctcggca    6480
tggacgagct gtacaagtaa agcggccgcg aagttcctat actttctaga aataggaac    6540 ttcaacaatg tctggaaaga actgtccttc atcgatacct atcacggaga aatctgtaat    6600
tgattccaag acatcacata gtttagttgc ttccaatgct tcaaaattat tcttatcatg    6660
cgtccatagt cccgttccgt atctattatc gttagaatat tttatagtca cgcatttata    6720
ttgagctatt tgataacgtc taactcgtct aattaattct gtactttac ctgaaaacat    6780 ggggccgatt atcaactgaa tatgtccgcc gttcatgatg acaataaaga attaattatt    6840 gttcactta ttcgacttta atatatccat cacgttagaa aatgcgatat cgcgacgagg    6900
atctatgtat ctaacaggat ctattgcggt ggtagctaga gctgattctt ttttgaatcg    6960
catcaaacta atcacaaagt cgaacaaata tcctttatta agtttgaccc ttccatctgt    7020
aacaataggg accttgttaa acagtttttt aaaatcttga gagtctgtga attttgtcaa    7080
ttgtctgtat tcctctgaaa gagattcata acaatgaccc acggcttcta atttattttt    7140
tgattggatc aataataata acagaaagtc tagatattga gtgatttgca atatatcaga    7200
taatgaagat tcatcatctt gactagccaa atacttaaaa aatgaatcat catctgcgaa    7260
gaacatcgtt aagagatact ggttgtgatc catttatgag ctcgcgaaag cttggcactg    7320
gccgtcgttt tacaacgtcg tgactgggaa aaccctggcg ttacccaact taatcgcctt    7380
```

```
gcagcacatc cccctttcgc cagctggcgt aatagcgaag aggcccgcac cgatcgccct    7440
tcccaacagt tgcgcagcct gaatggcgaa tggcgcctga tgcggtattt tctccttacg    7500
catctgtgcg gtatttcaca ccgcatatgg tgcactctca gtacaatctg ctctgatgcc    7560
gcatagttaa gccagccccg acacccgcca cacccgctg acgcgccctg acgggcttgt     7620
ctgctcccgg catccgctta cagacaagct gtgaccgtct ccgggagctg catgtgtcag    7680
aggttttcac cgtcatcacc gaaacgcgcg agacgaaagg gcctcgtgat acgcctattt    7740
ttataggtta atgtcatgat aataatggtt tcttagacgt caggtggcac ttttcgggga    7800
aatgtgcgcg gaaccccat ttgtttattt ttctaaatac attcaaatat gtatccgctc      7860
atgagacaat aaccctgata aatgcttcaa taatattgaa aaggaagag tatgagtatt      7920 caacatttcc gtgtcgccct tattccctt tttgcggcat tttgccttcc tgttttgct      7980 cacccagaaa cgctggtgaa agtaaaagat gctgaagatc agttgggtgc acgagtgggt     8040
tacatcgaac tggatctcaa cagcggtaag atccttgaga gttttcgccc cgaagaacgt     8100
tttccaatga tgagcacttt taaagttctg ctatgtggcg cggtattatc ccgtattgac     8160
gccgggcaag agcaactcgg tcgccgcata cactattctc agaatgactt ggttgagtac     8220
tcaccagtca cagaaaagca tcttacggat ggcatgacag taagagaatt atgcagtgct     8280
gccataacca tgagtgataa cactgcggcc aacttacttc tgacaacgat cggaggaccg     8340
aaggagctaa ccgcttttt gcacaacatg ggggatcatg taactcgcct tgatcgttgg      8400
gaaccggagc tgaatgaagc cataccaaac gacgagcgtg acaccacgat gcctgtagca    8460
atggcaacaa cgttgcgcaa actattaact ggcgaactac ttactctagc ttcccggcaa    8520
caattaatag actggatgga ggcggataaa gttgcaggac cacttctgcg ctcggccctt    8580
ccggctggct ggtttattgc tgataaatct ggagccggtg agcgtgggtc tcgcggtatc    8640
attgcagcac tggggccaga tggtaagccc tcccgtatcg tagttatcta cacgacgggg    8700
agtcaggcaa ctatggatga acgaaataga cagatcgctg agataggtgc ctcactgatt    8760
aagcattggt aactgtcaga ccaagtttac tcatatatac tttagattga tttaaaactt    8820 cattttaat ttaaaaggat ctaggtgaag atccttttg ataatctcat gaccaaaatc       8880
ccttaacgtg agttttcgtt ccactgagcg tcagacccg tagaaaagat caaaggatct      8940
tcttgagatc ctttttttct gcgcgtaatc tgctgcttgc aaacaaaaaa accaccgcta    9000
ccagcggtgg tttgtttgcc ggatcaagag ctaccaactc ttttttccgaa ggtaactggc    9060 ttcagcagag cgcagatacc aaatactgtt cttctagtgt agccgtagtt aggccaccac    9120
ttcaagaact ctgtagcacc gcctacatac ctcgctctgc taatcctgtt accagtggct    9180
gctgccagtg gcgataagtc gtgtcttacc gggttggact caagacgata gttaccggat    9240
aaggcgcagc ggtcgggctg aacggggggt tcgtgcacac agcccagctt ggagcgaacg    9300
acctacaccg aactgagata cctacagcgt gagctatgag aaagcgccac gcttcccgaa    9360
gggagaaagg cggacaggta tccggtaagc ggcagggtcg aacaggaga gcgcacgagg      9420 gagcttccag ggggaaacgc ctggtatctt tatagtcctg tcgggtttcg ccacctctga    9480
cttgagcgtc gatttttgtg atgctcgtca gggggcgga gcctatggaa aaacgccagc      9540
aacgcggcct ttttacggtt cctggccttt tgctggcctt tgctcacat gttctttcct      9600 gcgttatccc ctgattctgt ggataaccgt attaccgcct tgagtgagc tgataccgct      9660 cgccgcagcc gaacgaccga gcgcagcgag tcagtgagcg aggaagcgga aga           9713
```

<210> SEQ ID NO 159
<211> LENGTH: 10405
<212> TYPE: DNA
<213> ORGANISM: Artificial Sequence
<220> FEATURE:
<223> OTHER INFORMATION: Plasmid construct

<400> SEQUENCE: 159

| | | | | | |
|---|---|---|---|---|---|
| agcgcccaat | acgcaaaccg | cctctccccg | cgcgttggcc | gattcattaa tgcagctggc | 60 |
| acgacaggtt | tcccgactgg | aaagcgggca | gtgagcgcaa | cgcaattaat gtgagttagc | 120 |
| tcactcatta | ggcaccccag | gctttacact | ttatgcttcc | ggctcgtatg ttgtgtggaa | 180 |
| ttgtgagcgg | ataacaattt | cacacaggaa | acagctatga | ccatgattac gccaagctat | 240 |
| ttaggtgaca | ctatagaata | ctcaagctat | gcatcaagct | tggtaccgag ctcggatcca | 300 |
| ctagtaacgg | ccgccagtgt | gctggaattc | gcccttgtaa | tctattcgat ataccgttgc | 360 |
| taacagtata | ctggcccaat | aactgtggat | ggaaaatcta | ataatacatt aatatcat | 420 |
| ccgatggtgc | tagggttatt | tggatggatg | cgtataaatt | tcttgcggt ttatctttac | 480 |
| aagactattg | ttatcattgg | ggtagcaaac | cagagagccg | accattcgat ttaataaaaa | 540 |
| aatcagatgc | taaacgcaat | tctaaatcgt | tggtcaaaga | atctatggca tccttgaaat | 600 |
| ccttgtacga | ggcattcgag | acacaatcag | gagcgttaga | agttttaatg agtccatgta | 660 |
| ggatgttttc | gttttctaga | atagaagaca | tgttcttaac | tagtgtcatt aatagagtat | 720 |
| ccgagaatac | tggaatgggg | atgtattatc | ctaccaacga | tataccttct ctatttatcg | 780 |
| aatcatctat | ctgtctagat | tatattatag | taaataatca | ggaatccaac aaatatcgta | 840 |
| tcaaatctgt | tctcgatatc | atttcttcaa | acaataccc | tgcaggacgt cccaactacg | 900 |
| ttaaaaatgg | tacaaaagga | agtaatata | tcgcgttgtg | taaagttacc gtacctacta | 960 |
| acgaccatat | tccagtagtt | tatcacgatg | atgacaatac | taccacctt attacagtat | 1020 |
| tgacgtccgt | cgatattgaa | actgctatca | gagcaggata | ttcgatagtc gaattagggg | 1080 |
| ctttacaatg | ggataataat | attccagaac | ttaaaaacgg | tttactggat agtatcaaga | 1140 |
| tgatttatga | cttgaacgca | gttacaacaa | ataatttatt | ggaacagctc atagaaaata | 1200 |
| ttaactttaa | caactctagt | ataatttcgt | tgttttatac | atttgccatt agttattgcc | 1260 |
| gagcattcat | ttactcaatt | atggaaacca | tagatccggt | gtatatatct cagttcagtt | 1320 |
| ataaagaatt | atacgttagt | agctcttata | aagatattaa | tgaatccatg agtcagatgg | 1380 |
| taaaattata | aaaagtgaaa | aacaatatta | tttttatcgt | tggttgttac actatggatg | 1440 |
| ctatgaagag | gggcctgtgc | tgcgtgctgc | tgctgtgtgg | cgccgtgttt gtgtccccca | 1500 |
| gccaggaaat | ccacgcccgg | ttcagaagag | gcagcaagct | ggccgacgag gacgagacag | 1560 |
| cctacgacag | cggcaccgac | ctgatcgact | tcatcgacga | cagcgacgag aatgagaacg | 1620 |
| actccgacac | cggcgaggac | atggtggatt | tcatcgacaa | cgacgaaacc gacgaagaga | 1680 |
| gcaccgagag | cgacctggac | ggctttatcg | acaactccgc | ccagctggct gacagcgaca | 1740 |
| gcaatgcctg | cgccttcctg | aaggctcagc | tggcagacgt | gaacagcaac gccgctgctt | 1800 |
| ttctgaagaa | ctgcatcctg | ctgtacgcg | ctgccaacac | cggcaagagc ctgttcggca | 1860 |
| tgagcctgaa | ctgcctggtg | ctgtgcggcc | cagccaatac | cggaaagtcc tacttcggca | 1920 |
| tgtccctgaa | ttgtctcgtg | atctacggcc | cacctaacac | aggcaagtcc tgctttgcca | 1980 |
| tgtctctgtg | gccctacctg | cacagcagac | tggtggtgtt | taccttcccc aacccccttc t | 2040 |
| ggccttacct | ggaaagccgg | atcaccgtgt | tcgagttccc | caatgccttt ctgagatacc | 2100 |

```
tgcactcccg gatccacgtg ctgcagtttc tgaacccctt caacgtgtgc caggacaaga    2160
tcctggaaca ctacgagaac gacagcaagg acattctgga acattatgag aatgattcca    2220
aggacctgtg cgaccacatc tgcgatcaca tcgactactg gaagcacatc cggctggaat    2280
gcgccatcat gtacaaggcc cggatcgac tggaatgtgc tattatgtat aaggctcgcg     2340
agatgggctt ccaccagttc gacggcgaca tctgcaacac catgcactac accaactgga    2400
tctatatctg cgaggacgcc cagtgcaccg tggtggaagg ccaggtggac aagaaatggg    2460
aggtgcacgc tggcggccaa gtgatcctgt gtcctgagag cggccagcgg cggatcaaga    2520
ggcccagaag cgagaactgc cacccaaca agctgctgat cctgaagtgc ctgcggtaca     2580
gattcaagaa gcactgcaag ctgagcagca cctggcactg gacctgccac gacggcaagc    2640
acaagtggca ttggacatgt cacgatggga acacaagaa cgccattgtg accctgacct     2700
actacgaggc cgacaagaac gacctgaacg cccagatcga gcactggaaa ctgatccgga    2760
tggaatgtgc aatcttctat aaggccaaag agctgggcat cagcatcgc caccaggtgg     2820
tgcctccact ggccgcctct aaagccaaag cctgccaggc catcgaactg cagctggccc    2880
tggaagccct gaatgccagc ccctacgatg agtggaccct gcagcagacc agcctggaaa    2940
tgtggctggc cgagccccag tttaagaagc acggcatcac catcaccgtg cagtacgaca    3000
atgacaaggc caataccatg gattacacaa attggaaaga atctacgtg atcgtgtgcc     3060
ccgccagcat ccctccgat gagatcagca ccgaggaagc cgaccacatt gattattgga     3120
aagccatcag gcaggaaaac gccatcttct tcgccgccag acaccaggtg gtgcccgccc    3180
tgaatatctg caaggccaag gcctgtaaag ccatcgagtg gaacaccgag cccaagcact    3240
gcttcaagaa gggcggccag cacatcgaag tgtggttcga ctacgtggcc tgggacagcg    3300
tgtactactg cggcgacgat ggctggtgca agaccgaggc cgagaagtac ggctgcaagg    3360
gcacctggga agtgcatttc ggcaacagca tcgactgcaa cgactccatg tgcagcacct    3420
tcgacgacaa cgtgtccgcc accgagctcg tgaaggacca tatcgactat tggaagctga    3480
ttcgcctgga atgtgccatt ttttacaagg ccagacggcg gctgtccagc gaccaggatc    3540
agtctcagct cgtgaccaag tacccctgc tgaagctgct gtccagaccc ccaacatgg     3600
gcgtgaaggc ccacggcaag tgcatctggg agaacaaggt gttcatcgtg cccacctgt    3660
gccccgtgcc tctggatcca acatatcctc tgctgaaact gctgaccacc agaccacca     3720
cccccgagaa tacctccctg gtggaactga gagtgaccac ccccaagagc acagtcgtga    3780
tcaggctgca cctgaccacc agatacccac tgctgtcact gctgaacagc tacagcaccc    3840
cccctcaccg gatccctgct ccatgtcctt gggctcctca gaggcccccc atccctaagc    3900
cttctccatg ggcccctaga atccctgccc cttgcccctg ggcacctcct agacctccac    3960
actgtccatg ggtgcccct ccacctcctc caagaccttg ggcccttgc ttcctgctgt     4020
gcttttgtgt gctgctgtgc gtgtgcctgc tgatcagacc cctgctgctg agtgtgtcca    4080
cctacctgag gcctctgctg ctgtctatca gcgtgtacgc tcaggtgctg gtgctggtgc    4140
tgctgctgtg ggtgtccatc ggaagcctgc tgcccagcgt gtgcatgtgt gcctatgcct    4200
gggtgctggt gttcgtgtac atcgtcgtga ttaccagccc cgccaccgcc atcgtgtacc    4260
gggatggcaa tccttacgcc gtgtgcgaca gtgcctgaa gttctacagc aagatcagcg     4320
agtaccggca ctactgctac agcctgtacg gcaccaccct ggaacagcag tacaacaagc    4380
ccctgtgcga tctgctgatt cggtgcatca acgtggtgta cagagactcc atcccccacg    4440
```

```
ccgcctgcca caagtgtatc gacttctact ccagaatcag agagctgcgg cactacagcg    4500
actccgtgta cggcgatacc ctggaaaagc tgaccaacac tggcctgtac aacctgctga    4560
ttagatgcct gcgggtgttc tgcaagaagg ccctgacagc cagcgaggtg tacaacttcg    4620
cctacaccga tctgcgggtg gtgtatcggg acagcaaagt gcggaagctg aggtactaca    4680
actgctctgt gtatggcgcc agcctggtgt attgcaaggg acagctgacc gagacagagg    4740
tgctggattt cgccttcaca gacctgacaa tcgtgtatcg cgactccaag gtgtccgagt    4800
tccggtggta cagatattcc gtgtatggca ccacactgtg cgtggaatgc aagaaaaccc    4860
tgcagagatc tgaggtgtac gactgccagc ggccactgtg tccgcaggaa aagaaaagac    4920
acgtggacct gaacaagcgg ttccacaccc tgcacgagta catgctggat ctgcagcccg    4980
agacaaccga cctgtactgc tacgagcagc tgaaaccac tgatctgcac tgttatgagc    5040
agctgggaga cagctccgat gaagaggaca ctggcggcct ggatggggac gaggatgagg    5100
acgaagtgga ccatctgcag gaacagcccc agcaggctag acgggacgaa cagcacccctt    5160
gctatctgat cgagacacag tgctgcagat gcgaatctct ggtggaagag aacgacgaga    5220
tcgacggcgt gaaccaccag catctgcccg ctagaagggc cgagcctcag agacacacca    5280
tgctgtgtat gtgctgcaag tgcgaggcca gaatcgccgg ctaattttta taaccgagtt    5340
tctgcattat tgtaattcgt atgctggcac catcaaagaa tcacttctaa agatatcaa    5400
tatcacacat acaaatatta ctaccctatt gaatgagaca gccaaggtta tcaagttagt    5460
aaaatctctg gtagataaag aagatactga tattgtgaat aatttcatta ccaaagaaat    5520
taaaaacaga gacaaaatag ttaatagttt gtctctatca aacctggact ttcgtttgta    5580
aattggggct ttttgtacaa taaatgggtg ttgccaatga ttcatcccct gaatatcaat    5640
ggatgtctcc ccatagatta tcagatactg ttatattagg agactgtttg tatttttaaca    5700
atataatgtc ccaattagat ttacaccaaa attgggctcc atcagttaga ttgttaaatt    5760
atttttaagaa ttttaataag gaaacactac taaagataga agagaatgat tacattaatt    5820
catccttttt ccaacaaaag gataaacgat tttatcctat aaacgacgat ttttatcaca    5880
tatctacagg aggatatggt atagtcttta agatagataa ctatgtagta aaatttgtat    5940
tcgaggccac aaaattatat agtcccatgg aaactacggc ggagttcaca gtacccaaat    6000
ttctatacaa caatcaaag ggagatgaaa aaaaattaat cgtgtgtgcg tgggccatgg    6060
gattaaacta taaattaaca tttttacata ctctgtataa acgtgttctt catatgttgc    6120
tattattgat acaaactatg gatggtcagg aactatcatt gagatattct tctaaagttt    6180
ttttaaaggc gtttaacgag agaaaggaca gtatcaaatt cgtgaaatta ctatcccact    6240
tttatccggc agttattaac agtaatatta atgttataaa ctattttaac cgcatgtttc    6300
acttttcga acatgaaaag agaactaact acgaatacga aagaggaaat attataattt    6360
ttcccctagc actgtattcg gcagataaag tagataccga gctagctatc aaattaggat    6420
ttaaatcttt ggtacaatac ataaagttta tcttttaca gatggctctg ttatacatta    6480
aaatttacga actaccatgc tgcgacaact ttttacacgc agatcttaaa cccgataata    6540
tcttactttt tgattccaat gaaccaataa taattcatct aaaggataaa agtttgttt    6600
ttaatgaacg tattaaatcg gcattaaacg actttgactt ttcccaagaa gggcgaattc    6660
tgcagatatc catcacactg gcggccgctt acttgtacag ctcgtccatg ccgagagtga    6720
tcccggcggc ggtcacgaac tccagcagga ccatgtgatc gcgcttctcg ttggggtctt    6780
tgctcagggc ggactgggtg ctcaggtagt ggttgtcggg cagcagcacg ggccgtcgc    6840
```

```
cgatggggt gttctgctgg tagtggtcgg cgagctgcac gctgccgtcc tcgatgttgt   6900
ggcggatctt gaagttcacc ttgatgccgt tcttctgctt gtcggccatg atatagacgt   6960
tgtggctgtt gtagttgtac tccagcttgt gccccaggat gttgccgtcc tccttgaagt   7020
cgatgcccct cagctcgatg cggttcacca gggtatcgcc ctcgaacttc acctcggcgc   7080
gggtcttgta gttgccgtcg tccttgaaga agatggtgcg ctcctggacg tagccttcgg   7140
gcatggcgga cttgaagaag tcgtgctgct tcatgtggtc ggggtagcgg ctgaagcact   7200
gcacgccgta ggtcagggtg gtcacgaggg tcggccaggg cacgggcagc ttgccggtgg   7260
tgcagatgaa cttcagggtc agcttgccgt aggtggcatc gccctcgccc tcgccggaca   7320
cgctgaactt gtggccgttt acgtcgccgt ccagctcgac caggatgggc accaccccgg   7380
taaacagctc ctcgcccttg ctcaccatgt ttaaacttta tattccaaaa aaaaaaaata   7440
aaatttcaat ttttgtttaa acgttgtacg gcagtttaag gtttacacct ataaagaga   7500
gagccgttat cgtctgtttg tggatgtaca gagtgatatt attgacacgc cggggcgacg   7560
gatggtgatc cccctggcca gtgcacgtct gctgtcagat aaagtctccc gtgaacttta   7620
cccggtggtg catatcgggg atgaaagctg gcgcatgatg accaccgata tggccagtgt   7680
gccggtctcc gttatcgggg aagaagtggc tgatctcagc caccgcgaaa atgacatcaa   7740
aaacgccatt aacctgatgt tctggggaat ataaatgtca ggcatgagat tatcaaaaag   7800
gatcttcacc tagatccttt tcacgtagaa agccagtccg cagaaacggt gctgaccccg   7860
gatgaatgtc agctactggg ctatctggac aagggaaaac gcaagcgcaa agagaaagca   7920
ggtagcttgc agtgggctta catggcgata gctagactgg gcggttttat ggacagcaag   7980
cgaaccggaa ttgccagctg gggcgccctc tggtaaggtt gggaagccct gcaaagtaaa   8040
ctggatggct ttctcgccgc caaggatctg atggcgcagg gatcaagct ctgatcaaga   8100
gacaggatga ggatcgtttc gcatgattga acaagatgga ttgcacgcag gttctccggc   8160
cgcttgggtg gagaggctat tcggctatga ctgggcacaa cagacaatcg gctgctctga   8220
tgccgccgtg ttccggctgt cagcgcaggg gcgcccggtt ctttttgtca agaccgacct   8280
gtccggtgcc ctgaatgaac tgcaagacga ggcagcgcgg ctatcgtggc tggccacgac   8340
gggcgttcct tgcgcagctg tgctcgacgt tgtcactgaa gcgggaaggg actggctgct   8400
attgggcgaa gtgccggggc aggatctcct gtcatctcac cttgctcctg ccgagaaagt   8460
atccatcatg gctgatgcaa tgcggcggct gcatacgctt gatccggcta cctgcccatt   8520
cgaccaccaa gcgaaacatc gcatcgagcg agcacgtact cggatggaag ccggtcttgt   8580
cgatcaggat gatctggacg aagagcatca ggggctcgcg ccagccgaac tgttcgccag   8640
gctcaaggcg agcatgcccg acggcgagga tctcgtcgtg acccatggcg atgcctgctt   8700
gccgaatatc atggtggaaa atggccgctt ttctggattc atcgactgtg gccggctggg   8760
tgtggcggac cgctatcagg acatagcgtt ggctacccgt gatattgctg aagagcttgg   8820
cggcgaatgg gctgaccgct tcctcgtgct ttacggtatc gccgctcccg attcgcagcg   8880
catcgccttc tatcgccttc ttgacgagtt cttctgaatt attaacgctt acaatttcct   8940
gatgcggtat tttctcctta cgcatctgtg cggtatttca caccgcatac aggtggcact   9000
tttcggggaa atgtgcgcgg aaccccattt tgtttatttt tctaaataca ttcaaatatg   9060
tatccgctca tgagacaata accctgataa atgcttcaat aatagcacgt gaggagggcc   9120
accatggcca agttgaccag tgccgttccg gtgctcaccg cgcgcgacgt cgccggagcg   9180
```

```
gtcgagttct ggaccgaccg gctcgggttc tcccgggact tcgtggagga cgacttcgcc    9240
ggtgtggtcc gggacgacgt gaccctgttc atcagcgcgg tccaggacca ggtggtgccg    9300
gacaacaccc tggcctgggt gtgggtgcgc ggcctggacg agctgtacgc cgagtggtcg    9360
gaggtcgtgt ccacgaactt ccgggacgcc tccgggccgg ccatgaccga gatcggcgag    9420
cagccgtggg ggcgggagtt cgccctgcgc gacccggccg gcaactgcgt gcacttcgtg    9480
gccgaggagc aggactgaca cgtgctaaaa cttcattttt aatttaaaag gatctaggtg    9540
aagatccttt ttgataatct catgaccaaa atcccttaac gtgagttttc gttccactga    9600
gcgtcagacc ccgtagaaaa gatcaaagga tcttcttgag atcctttttt tctgcgcgta    9660
atctgctgct tgcaaacaaa aaaaccaccg ctaccagcgg tggtttgttt gccggatcaa    9720
gagctaccaa ctcttttttcc gaaggtaact ggcttcagca gagcgcagat accaaatact    9780
gtccttctag tgtagccgta gttaggccac cacttcaaga actctgtagc accgcctaca    9840
tacctcgctc tgctaatcct gttaccagtg gctgctgcca gtggcgataa gtcgtgtctt    9900
accgggttgg actcaagacg atagttaccg gataaggcgc agcggtcggg ctgaacgggg    9960
ggttcgtgca cacagcccag cttggagcga acgacctaca ccgaactgag atacctacag   10020
cgtgagctat gagaaagcgc cacgcttccc gaagggagaa aggcggacag gtatccggta   10080
agcggcaggg tcggaacagg agagcgcacg agggagcttc cagggggaaa cgcctggtat   10140
ctttatagtc ctgtcgggtt tcgccacctc tgacttgagc gtcgattttt gtgatgctcg   10200 tcagggggc ggagcctatg gaaaaacgcc agcaacgcgg cctttttacg gttcctgggc    10260
ttttgctggc cttttgctca catgttcttt cctgcgttat cccctgattc tgtggataac   10320
cgtattaccg cctttgagtg agctgatacc gctcgccgca gccgaacgac cgagcgcagc   10380
gagtcagtga gcgaggaagc ggaag                                         10405
```

<210> SEQ ID NO 160
<211> LENGTH: 20
<212> TYPE: PRT
<213> ORGANISM: Artificial Sequence
<220> FEATURE:
<223> OTHER INFORMATION: conserved region 1
<220> FEATURE:
<221> NAME/KEY: misc_feature
<222> LOCATION: (11)..(11)
<223> OTHER INFORMATION: Xaa can be any naturally occurring amino acid

<400> SEQUENCE: 160

Asp Glu Asp Glu Asn Ala Ser Asp Thr Gly Xaa Asp Leu Val Asp Phe
1               5                   10                  15

Ile Asp Asn Ser
            20

<210> SEQ ID NO 161
<211> LENGTH: 20
<212> TYPE: PRT
<213> ORGANISM: Artificial Sequence
<220> FEATURE:
<223> OTHER INFORMATION: conserved region 1

<400> SEQUENCE: 161

Asp Glu Asn Glu Asn Asp Ser Asp Thr Gly Glu Asp Leu Val Asp Phe
1               5                   10                  15

Ile Val Asn Asp
            20

```
<210> SEQ ID NO 162
<211> LENGTH: 20
<212> TYPE: PRT
<213> ORGANISM: Artificial Sequence
<220> FEATURE:
<223> OTHER INFORMATION: conserved region 1

<400> SEQUENCE: 162

Asp Glu Asp Glu Asn Ala Thr Asp Thr Gly Ser Asp Met Val Asp Phe
1               5                   10                  15

Ile Asp Thr Gln
            20

<210> SEQ ID NO 163
<211> LENGTH: 20
<212> TYPE: PRT
<213> ORGANISM: Artificial Sequence
<220> FEATURE:
<223> OTHER INFORMATION: conserved region 1

<400> SEQUENCE: 163

Asp Glu Asn Glu Asp Ser Ser Asp Thr Gly Glu Asp Met Val Asp Phe
1               5                   10                  15

Ile Asp Asn Cys
            20

<210> SEQ ID NO 164
<211> LENGTH: 20
<212> TYPE: PRT
<213> ORGANISM: Artificial Sequence
<220> FEATURE:
<223> OTHER INFORMATION: conserved region 1

<400> SEQUENCE: 164

Asp Glu Asp Glu Asn Ala Tyr Asp Ser Gly Thr Asp Leu Ile Asp Phe
1               5                   10                  15

Ile Asp Asp Ser
            20

<210> SEQ ID NO 165
<211> LENGTH: 20
<212> TYPE: PRT
<213> ORGANISM: Artificial Sequence
<220> FEATURE:
<223> OTHER INFORMATION: conserved region 1

<400> SEQUENCE: 165

Asp Glu Asp Glu Thr Ala Asp Asp Ser Gly Thr Asp Leu Ile Glu Phe
1               5                   10                  15

Ile Asp Asp Ser
            20

<210> SEQ ID NO 166
<211> LENGTH: 20
<212> TYPE: PRT
<213> ORGANISM: Artificial Sequence
<220> FEATURE:
<223> OTHER INFORMATION: conserved region 1
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
```

-continued

```
<221> NAME/KEY: misc_feature
<222> LOCATION: (15)..(15)
<223> OTHER INFORMATION: Xaa can be any naturally occurring amino acid

<400> SEQUENCE: 166

Asp Glu Asp Glu Xaa Ala Xaa Asp Ser Gly Thr Asp Leu Ile Xaa Phe
1               5                   10                  15

Ile Asp Asp Ser
            20

<210> SEQ ID NO 167
<211> LENGTH: 20
<212> TYPE: PRT
<213> ORGANISM: Artificial Sequence
<220> FEATURE:
<223> OTHER INFORMATION: conserved region 1

<400> SEQUENCE: 167

Asp Glu Asp Glu Asn Ala Tyr Asp Ser Gly Thr Asp Leu Ile Asp Phe
1               5                   10                  15

Ile Asp Asp Ser
            20

<210> SEQ ID NO 168
<211> LENGTH: 20
<212> TYPE: PRT
<213> ORGANISM: Artificial Sequence
<220> FEATURE:
<223> OTHER INFORMATION: conserved region 1

<400> SEQUENCE: 168

Asp Glu Asp Glu Thr Ala Asp Ser Gly Thr Asp Leu Ile Glu Phe
1               5                   10                  15

Ile Asp Asp Ser
            20

<210> SEQ ID NO 169
<211> LENGTH: 19
<212> TYPE: PRT
<213> ORGANISM: Artificial Sequence
<220> FEATURE:
<223> OTHER INFORMATION: conserved region 1
<220> FEATURE:
<221> NAME/KEY: misc_feature
<222> LOCATION: (6)..(6)
<223> OTHER INFORMATION: Xaa can be any naturally occurring amino acid

<400> SEQUENCE: 169

Asp Glu Asn Glu Asn Xaa Ser Asp Thr Gly Glu Asp Met Val Asp Phe
1               5                   10                  15

Ile Asp Asn

<210> SEQ ID NO 170
<211> LENGTH: 19
<212> TYPE: PRT
<213> ORGANISM: Artificial Sequence
<220> FEATURE:
<223> OTHER INFORMATION: conserved region 1

<400> SEQUENCE: 170

Asp Glu Asn Glu Asp Ser Ser Asp Thr Gly Glu Asp Met Val Asp Phe
1               5                   10                  15

Ile Asp Asn
```

```
<210> SEQ ID NO 171
<211> LENGTH: 19
<212> TYPE: PRT
<213> ORGANISM: Artificial Sequence
<220> FEATURE:
<223> OTHER INFORMATION: conserved region 1

<400> SEQUENCE: 171

Asp Glu Asn Glu Asn Asp Ser Asp Thr Gly Glu Asp Leu Val Asp Phe
1               5                   10                  15

Ile Val Asn

<210> SEQ ID NO 172
<211> LENGTH: 19
<212> TYPE: PRT
<213> ORGANISM: Artificial Sequence
<220> FEATURE:
<223> OTHER INFORMATION: conserved region 1

<400> SEQUENCE: 172

Asp Glu Asp Glu Asn Ala Thr Asp Thr Gly Ser Asp Met Val Asp Phe
1               5                   10                  15

Ile Asp Thr

<210> SEQ ID NO 173
<211> LENGTH: 15
<212> TYPE: PRT
<213> ORGANISM: Artificial Sequence
<220> FEATURE:
<223> OTHER INFORMATION: conserved region 2

<400> SEQUENCE: 173

Ala Gln Leu Ala Asp Thr Asn Ser Asn Ala Ser Ala Phe Leu Lys
1               5                   10                  15

<210> SEQ ID NO 174
<211> LENGTH: 15
<212> TYPE: PRT
<213> ORGANISM: Artificial Sequence
<220> FEATURE:
<223> OTHER INFORMATION: conserved region 2

<400> SEQUENCE: 174

Ala Leu Leu Ala Asp Ser Asn Ser Asn Ala Ala Ala Phe Leu Lys
1               5                   10                  15

<210> SEQ ID NO 175
<211> LENGTH: 15
<212> TYPE: PRT
<213> ORGANISM: Artificial Sequence
<220> FEATURE:
<223> OTHER INFORMATION: conserved region 2

<400> SEQUENCE: 175

Ala Gln Leu Ala Asp Ser Asp Ser Asn Ala Cys Ala Phe Leu Lys
1               5                   10                  15

<210> SEQ ID NO 176
<211> LENGTH: 15
<212> TYPE: PRT
<213> ORGANISM: Artificial Sequence
<220> FEATURE:
<223> OTHER INFORMATION: conserved region 2

<400> SEQUENCE: 176

Ala Gln Leu Ala Asp Val Asp Ser Asn Ala Gln Ala Phe Leu Lys
```

```
1               5                  10                  15

<210> SEQ ID NO 177
<211> LENGTH: 15
<212> TYPE: PRT
<213> ORGANISM: Artificial Sequence
<220> FEATURE:
<223> OTHER INFORMATION: conserved region 2

<400> SEQUENCE: 177

Ala Gln Leu Ala Asp Val Asn Ser Asn Ala Ala Ala Phe Leu Arg
1               5                  10                  15

<210> SEQ ID NO 178
<211> LENGTH: 15
<212> TYPE: PRT
<213> ORGANISM: Artificial Sequence
<220> FEATURE:
<223> OTHER INFORMATION: conserved region 2

<400> SEQUENCE: 178

Ala Gln Leu Ala Asp Val Asp Ser Asn Ala Gln Ala Phe Leu Lys
1               5                  10                  15

<210> SEQ ID NO 179
<211> LENGTH: 15
<212> TYPE: PRT
<213> ORGANISM: Artificial Sequence
<220> FEATURE:
<223> OTHER INFORMATION: conserved region 2

<400> SEQUENCE: 179

Ala Gln Leu Ala Asp Val Asn Ser Asn Ala Ala Ala Phe Leu Arg
1               5                  10                  15

<210> SEQ ID NO 180
<211> LENGTH: 15
<212> TYPE: PRT
<213> ORGANISM: Artificial Sequence
<220> FEATURE:
<223> OTHER INFORMATION: conserved region 2

<400> SEQUENCE: 180

Ala Leu Leu Ala Asp Ser Asn Ser Asn Ala Ala Ala Phe Leu Lys
1               5                  10                  15

<210> SEQ ID NO 181
<211> LENGTH: 15
<212> TYPE: PRT
<213> ORGANISM: Artificial Sequence
<220> FEATURE:
<223> OTHER INFORMATION: conserved region 2

<400> SEQUENCE: 181

Ala Gln Leu Ala Asp Thr Asn Ser Asn Ala Ser Ala Phe Leu Lys
1               5                  10                  15

<210> SEQ ID NO 182
<211> LENGTH: 20
<212> TYPE: PRT
<213> ORGANISM: Artificial Sequence
<220> FEATURE:
<223> OTHER INFORMATION: conserved region 3
<220> FEATURE:
<221> NAME/KEY: misc_feature
<222> LOCATION: (4)..(4)
<223> OTHER INFORMATION: Xaa can be any naturally occurring amino acid
```

```
<400> SEQUENCE: 182

Asn Cys Leu Xaa Leu Tyr Gly Pro Ala Asn Thr Gly Lys Ser Tyr Phe
1               5                   10                  15

Gly Met Ser Leu
            20

<210> SEQ ID NO 183
<211> LENGTH: 20
<212> TYPE: PRT
<213> ORGANISM: Artificial Sequence
<220> FEATURE:
<223> OTHER INFORMATION: conserved region 3

<400> SEQUENCE: 183

Asn Cys Leu Val Phe Cys Gly Pro Ala Asn Thr Gly Lys Ser Tyr Phe
1               5                   10                  15

Gly Met Ser Phe
            20

<210> SEQ ID NO 184
<211> LENGTH: 20
<212> TYPE: PRT
<213> ORGANISM: Artificial Sequence
<220> FEATURE:
<223> OTHER INFORMATION: conserved region 3

<400> SEQUENCE: 184

Asn Cys Ile Leu Ile His Gly Ala Pro Asn Thr Gly Lys Ser Tyr Phe
1               5                   10                  15

Gly Met Ser Leu
            20

<210> SEQ ID NO 185
<211> LENGTH: 20
<212> TYPE: PRT
<213> ORGANISM: Artificial Sequence
<220> FEATURE:
<223> OTHER INFORMATION: conserved region 3

<400> SEQUENCE: 185

Asn Cys Leu Val Leu Tyr Gly Pro Ala Asn Thr Gly Lys Ser Tyr Phe
1               5                   10                  15

Gly Met Ser Leu
            20

<210> SEQ ID NO 186
<211> LENGTH: 20
<212> TYPE: PRT
<213> ORGANISM: Artificial Sequence
<220> FEATURE:
<223> OTHER INFORMATION: conserved region 3

<400> SEQUENCE: 186

Ser Cys Met Leu Leu Cys Gly Pro Ala Asn Thr Gly Lys Ser Tyr Phe
1               5                   10                  15

Gly Met Ser Leu
            20

<210> SEQ ID NO 187
<211> LENGTH: 20
<212> TYPE: PRT
<213> ORGANISM: Artificial Sequence
<220> FEATURE:
<223> OTHER INFORMATION: conserved region 3; note "X" should be "J"
```

```
      meaning leucine or isoleucine
<220> FEATURE:
<221> NAME/KEY: misc_feature
<222> LOCATION: (5)..(5)
<223> OTHER INFORMATION: Xaa can be any naturally occurring amino acid

<400> SEQUENCE: 187

Asn Cys Ile Leu Xaa Tyr Gly Ala Ala Asn Thr Gly Lys Ser Leu Phe
1               5                   10                  15

Gly Met Ser Leu
            20

<210> SEQ ID NO 188
<211> LENGTH: 20
<212> TYPE: PRT
<213> ORGANISM: Artificial Sequence
<220> FEATURE:
<223> OTHER INFORMATION: conserved region 3

<400> SEQUENCE: 188

Asn Cys Ile Leu Ile His Gly Ala Pro Asn Thr Gly Lys Ser Tyr Phe
1               5                   10                  15

Gly Met Ser Leu
            20

<210> SEQ ID NO 189
<211> LENGTH: 20
<212> TYPE: PRT
<213> ORGANISM: Artificial Sequence
<220> FEATURE:
<223> OTHER INFORMATION: conserved region 3

<400> SEQUENCE: 189

Asn Cys Leu Val Phe Cys Gly Pro Ala Asn Thr Gly Lys Ser Tyr Phe
1               5                   10                  15

Gly Met Ser Phe
            20

<210> SEQ ID NO 190
<211> LENGTH: 20
<212> TYPE: PRT
<213> ORGANISM: Artificial Sequence
<220> FEATURE:
<223> OTHER INFORMATION: conserved region 3

<400> SEQUENCE: 190

Asn Cys Leu Val Leu Tyr Gly Pro Ala Asn Thr Gly Lys Ser Tyr Phe
1               5                   10                  15

Gly Met Ser Leu
            20

<210> SEQ ID NO 191
<211> LENGTH: 20
<212> TYPE: PRT
<213> ORGANISM: Artificial Sequence
<220> FEATURE:
<223> OTHER INFORMATION: conserved region 3

<400> SEQUENCE: 191

Ser Cys Met Leu Leu Cys Gly Pro Ala Asn Thr Gly Lys Ser Tyr Phe
1               5                   10                  15

Gly Met Ser Leu
            20
```

```
<210> SEQ ID NO 192
<211> LENGTH: 20
<212> TYPE: PRT
<213> ORGANISM: Artificial Sequence
<220> FEATURE:
<223> OTHER INFORMATION: conserved region 4
<220> FEATURE:
<221> NAME/KEY: misc_feature
<222> LOCATION: (11)..(11)
<223> OTHER INFORMATION: Xaa can be any naturally occurring amino acid

<400> SEQUENCE: 192

Asp Glu Asp Glu Asn Ala Ser Asp Thr Gly Xaa Asp Leu Val Asp Phe
1               5                   10                  15

Ile Asp Asn Ser
            20

<210> SEQ ID NO 193
<211> LENGTH: 20
<212> TYPE: PRT
<213> ORGANISM: Artificial Sequence
<220> FEATURE:
<223> OTHER INFORMATION: conserved region 4

<400> SEQUENCE: 193

Asp Glu Asn Glu Asn Asp Ser Asp Thr Gly Glu Asp Leu Val Asp Phe
1               5                   10                  15

Ile Val Asn Asp
            20

<210> SEQ ID NO 194
<211> LENGTH: 20
<212> TYPE: PRT
<213> ORGANISM: Artificial Sequence
<220> FEATURE:
<223> OTHER INFORMATION: conserved region 4

<400> SEQUENCE: 194

Asp Glu Asp Glu Asn Ala Thr Asp Thr Gly Ser Asp Met Val Asp Phe
1               5                   10                  15

Ile Asp Thr Gln
            20

<210> SEQ ID NO 195
<211> LENGTH: 20
<212> TYPE: PRT
<213> ORGANISM: Artificial Sequence
<220> FEATURE:
<223> OTHER INFORMATION: conserved region 4

<400> SEQUENCE: 195

Asp Glu Asn Glu Asp Ser Ser Asp Thr Gly Glu Asp Met Val Asp Phe
1               5                   10                  15

Ile Asp Asn Cys
            20

<210> SEQ ID NO 196
<211> LENGTH: 20
<212> TYPE: PRT
<213> ORGANISM: Artificial Sequence
<220> FEATURE:
<223> OTHER INFORMATION: conserved region 4

<400> SEQUENCE: 196

Asp Glu Asp Glu Asn Ala Tyr Asp Ser Gly Thr Asp Leu Ile Asp Phe
1               5                   10                  15
```

Ile Asp Asp Ser
            20

<210> SEQ ID NO 197
<211> LENGTH: 20
<212> TYPE: PRT
<213> ORGANISM: Artificial Sequence
<220> FEATURE:
<223> OTHER INFORMATION: conserved region 4

<400> SEQUENCE: 197

Asp Glu Asp Glu Thr Ala Asp Asp Ser Gly Thr Asp Leu Ile Glu Phe
1               5                   10                  15

Ile Asp Asp Ser
            20

<210> SEQ ID NO 198
<211> LENGTH: 17
<212> TYPE: PRT
<213> ORGANISM: Artificial Sequence
<220> FEATURE:
<223> OTHER INFORMATION: conserved region 4

<400> SEQUENCE: 198

Trp Pro Tyr Leu His Asn Arg Leu Val Val Phe Thr Phe Pro Asn Glu
1               5                   10                  15

Phe

<210> SEQ ID NO 199
<211> LENGTH: 17
<212> TYPE: PRT
<213> ORGANISM: Artificial Sequence
<220> FEATURE:
<223> OTHER INFORMATION: conserved region 4

<400> SEQUENCE: 199

Trp Pro Tyr Leu His Ser Arg Leu Val Val Phe His Phe Lys Asn Pro
1               5                   10                  15

Phe

<210> SEQ ID NO 200
<211> LENGTH: 17
<212> TYPE: PRT
<213> ORGANISM: Artificial Sequence
<220> FEATURE:
<223> OTHER INFORMATION: conserved region 4; note"X" should be "J"
      meaning leucine or isoleucine
<220> FEATURE:
<221> NAME/KEY: misc_feature
<222> LOCATION: (8)..(8)
<223> OTHER INFORMATION: Xaa can be any naturally occurring amino acid

<400> SEQUENCE: 200

Trp Pro Tyr Leu Glu Ser Arg Xaa Thr Val Phe Glu Phe Pro Asn Ala
1               5                   10                  15

Phe

<210> SEQ ID NO 201
<211> LENGTH: 17
<212> TYPE: PRT
<213> ORGANISM: Artificial Sequence
<220> FEATURE:
<223> OTHER INFORMATION: conserved region 4

<400> SEQUENCE: 201

```
Trp Pro Tyr Leu His Ser Arg Leu Thr Val Phe Glu Phe Asn Asn Pro
1               5                   10                  15

Phe

<210> SEQ ID NO 202
<211> LENGTH: 20
<212> TYPE: PRT
<213> ORGANISM: Artificial Sequence
<220> FEATURE:
<223> OTHER INFORMATION: conserved region 1

<400> SEQUENCE: 202

Asp His Ile Asp Tyr Trp Lys His Met Arg Leu Glu Cys Ala Ile Tyr
1               5                   10                  15

Tyr Lys Ala Arg
            20

<210> SEQ ID NO 203
<211> LENGTH: 20
<212> TYPE: PRT
<213> ORGANISM: Artificial Sequence
<220> FEATURE:
<223> OTHER INFORMATION: conserved region 1

<400> SEQUENCE: 203

Ser Gln Ile Gln Tyr Trp Gln Leu Ile Arg Trp Glu Asn Ala Ile Phe
1               5                   10                  15

Phe Ala Ala Arg
            20

<210> SEQ ID NO 204
<211> LENGTH: 20
<212> TYPE: PRT
<213> ORGANISM: Artificial Sequence
<220> FEATURE:
<223> OTHER INFORMATION: conserved region 1

<400> SEQUENCE: 204

Asp His Ile Asp Tyr Trp Lys His Ile Arg Leu Glu Cys Val Leu Met
1               5                   10                  15

Tyr Lys Ala Arg
            20

<210> SEQ ID NO 205
<211> LENGTH: 20
<212> TYPE: PRT
<213> ORGANISM: Artificial Sequence
<220> FEATURE:
<223> OTHER INFORMATION: conserved region 1

<400> SEQUENCE: 205

Ala Gln Ile Glu His Trp Lys Leu Thr Arg Met Glu Cys Val Leu Phe
1               5                   10                  15

Tyr Lys Ala Lys
            20

<210> SEQ ID NO 206
<211> LENGTH: 20
<212> TYPE: PRT
<213> ORGANISM: Artificial Sequence
<220> FEATURE:
<223> OTHER INFORMATION: conserved region 1

<400> SEQUENCE: 206
```

Asp His Ile Asp Tyr Trp Lys Ala Val Arg Gln Glu Asn Val Ile Tyr
1               5                   10                  15

Tyr Lys Ala Arg
            20

<210> SEQ ID NO 207
<211> LENGTH: 20
<212> TYPE: PRT
<213> ORGANISM: Artificial Sequence
<220> FEATURE:
<223> OTHER INFORMATION: conserved region 1

<400> SEQUENCE: 207

Ser Gln Ile Glu His Trp Lys Leu Ile Arg Met Glu Cys Ala Ile Met
1               5                   10                  15

Tyr Thr Ala Arg
            20

<210> SEQ ID NO 208
<211> LENGTH: 12
<212> TYPE: PRT
<213> ORGANISM: Artificial Sequence
<220> FEATURE:
<223> OTHER INFORMATION: conserved region 1

<400> SEQUENCE: 208

Pro Ile Pro Pro Pro Cys Pro Trp Ala Pro Lys Lys
1               5                   10

<210> SEQ ID NO 209
<211> LENGTH: 18
<212> TYPE: PRT
<213> ORGANISM: Artificial Sequence
<220> FEATURE:
<223> OTHER INFORMATION: conserved region 1

<400> SEQUENCE: 209

Thr Pro Pro His Arg Pro Ile Pro Lys Pro Ser Pro Trp Ala Pro Lys
1               5                   10                  15

Lys Glu

<210> SEQ ID NO 210
<211> LENGTH: 17
<212> TYPE: PRT
<213> ORGANISM: Artificial Sequence
<220> FEATURE:
<223> OTHER INFORMATION: conserved region 1

<400> SEQUENCE: 210

Thr Pro Pro His Arg Ile Pro Ala Pro Cys Pro Trp Ala Pro Gln Arg
1               5                   10                  15

Pro

<210> SEQ ID NO 211
<211> LENGTH: 17
<212> TYPE: PRT
<213> ORGANISM: Artificial Sequence
<220> FEATURE:
<223> OTHER INFORMATION: conserved region 1

<400> SEQUENCE: 211

Thr Pro Pro His Arg Ile Pro Lys Pro Ala Pro Trp Ala Pro Val Lys
1               5                   10                  15

```
Val

<210> SEQ ID NO 212
<211> LENGTH: 13
<212> TYPE: PRT
<213> ORGANISM: Artificial Sequence
<220> FEATURE:
<223> OTHER INFORMATION: conserved region 1

<400> SEQUENCE: 212

Pro Arg Pro Pro His Cys Pro Trp Val Pro Lys Thr Glu
1               5                   10

<210> SEQ ID NO 213
<211> LENGTH: 13
<212> TYPE: PRT
<213> ORGANISM: Artificial Sequence
<220> FEATURE:
<223> OTHER INFORMATION: conserved region 1

<400> SEQUENCE: 213

Pro Pro Pro Pro Pro Arg Pro Trp Ala Pro Thr Lys Pro
1               5                   10

<210> SEQ ID NO 214
<211> LENGTH: 10
<212> TYPE: PRT
<213> ORGANISM: Artificial Sequence
<220> FEATURE:
<223> OTHER INFORMATION: conserved region 1

<400> SEQUENCE: 214

Arg Ile Pro Lys Pro Ala Pro Trp Ala Pro
1               5                   10
```

The invention claimed is:

1. A vaccine comprising a nucleic acid encoding a polypeptide comprising a plurality of conserved peptide sequences:
   wherein the conserved sequences are conserved across one or more HPV genotypes 16, 18, 31, 52, 53, and 58;
   wherein the polypeptide comprises a conserved peptide sequence of each of the HPV proteins E1, E2, E4, E5, E6, and E7; and further wherein
   the nucleic acid comprises or consists of the sequence of SEQ ID NO: 60 or 62, with a different peptide adjuvant encoded than the TPA lead sequence; or
   the nucleic acid comprises or consists of the sequence of SEQ ID NO: 71, 73 or 75, not encoding the TPA lead sequence.

2. A vaccine comprising a nucleic acid encoding a polypeptide comprising a plurality of conserved peptide sequences:
   wherein the conserved sequences are conserved across one or more HPV genotypes 16, 18, 31, 52, 53, and 58;
   wherein the polypeptide comprises a conserved peptide sequence of each of the HPV proteins E1, E2, E4, E5, E6, and E7; and further wherein
   the polypeptide comprises or consists of the sequence of SEQ ID NO: 61, with a different peptide adjuvant than the TPA lead sequence; or
   the polypeptide comprises or consists of the sequence of SEQ ID NO: 72, 74 or 76, with a different peptide adjuvant than the TPA lead sequence.

3. The vaccine according to claim 1, further comprising another therapeutically or prophylactically active ingredient, or an adjuvant, or both.

4. A composition comprising a plurality of different vaccines according to claim 1, optionally wherein the composition is a pharmaceutically acceptable composition.

5. A method of treatment or prophylaxis of HPV infection comprising the administration of the vaccine according to claim 1.

6. A prime boost vaccination kit comprising:
   a prime vaccination comprising the vaccine according to claim 1; and
   a boost vaccination comprising the vaccine according to claim 1,
   wherein the prime and boost vaccination are different,
   wherein the prime and boost vaccination differ in the encoded polypeptide sequence, and/or
   wherein the prime and boost vaccination comprise different viral vectors.

7. A vaccine according to claim 2, further comprising another therapeutically or prophylactically active ingredient, or an adjuvant, or both.

8. A composition comprising a plurality of different vaccines according to claim 2, optionally wherein the composition is a pharmaceutically acceptable composition.

9. A method of treatment or prophylaxis of HPV infection comprising the administration of the vaccine according to claim 2.

10. A method of treatment or prophylaxis of HPV infection comprising the administration of the composition of claim 4.

11. A prime boost vaccination kit comprising:
    a prime vaccination comprising the vaccine according to claim 2; and a boost vaccination comprising the vaccine according to claim 2,
wherein the prime and boost vaccination are different,
wherein the prime and boost vaccination differ in the encoded polypeptide sequence, and/or
wherein the prime and boost vaccination comprise different viral vectors.

\* \* \* \* \*